US012723048B2

(12) United States Patent
Li et al.

(10) Patent No.: US 12,723,048 B2
(45) Date of Patent: Sep. 1, 2026

(54) 5-AMINO-6,8-DIHYDRO-1H-FURO[3,4-D]PYRROLO[3,2-B]PYRIDINE-2-CARBOXAMIDE DERIVATIVES AS MTA-COOPERATIVE INHIBITORS OF PRMT5

(71) Applicant: BeiGene Switzerland GmbH, Basel (CH)

(72) Inventors: Jing Li, Beijing (CN); Sanjia Xu, Beijing (CN); Yian Guo, Beijing (CN); Zhiwei Wang, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 245 days.

(21) Appl. No.: 18/617,913

(22) Filed: Mar. 27, 2024

(65) Prior Publication Data

US 2024/0368177 A1 Nov. 7, 2024

(30) Foreign Application Priority Data

| | | |
|---|---|---|
| Mar. 30, 2023 | (WO) | PCT/CN2023/085078 |
| Aug. 2, 2023 | (WO) | PCT/CN2023/110807 |
| Mar. 7, 2024 | (WO) | PCT/CN2024/080582 |

(51) Int. Cl.

| | |
|---|---|
| ***C07D 491/147*** | (2006.01) |
| ***A61K 31/437*** | (2006.01) |
| ***A61K 31/444*** | (2006.01) |
| ***A61K 31/4709*** | (2006.01) |
| ***A61K 31/4725*** | (2006.01) |
| ***A61K 31/497*** | (2006.01) |
| ***A61K 31/501*** | (2006.01) |
| ***A61K 31/506*** | (2006.01) |
| ***A61K 31/5377*** | (2006.01) |
| ***A61P 35/00*** | (2006.01) |
| ***C07D 519/00*** | (2006.01) |

(52) U.S. Cl.

CPC ........ *C07D 491/147* (2013.01); *A61K 31/437* (2013.01); *A61K 31/444* (2013.01); *A61K 31/4709* (2013.01); *A61K 31/4725* (2013.01); *A61K 31/497* (2013.01); *A61K 31/501* (2013.01); *A61K 31/506* (2013.01); *A61K 31/5377* (2013.01); *A61P 35/00* (2018.01); *C07D 519/00* (2013.01)

(58) Field of Classification Search

CPC .................................................. C07D 491/147

See application file for complete search history.

(56) References Cited

U.S. PATENT DOCUMENTS

2025/0320202 A1 10/2025 Haibing

FOREIGN PATENT DOCUMENTS

| | | | | |
|---|---|---|---|---|
| WO | 2021163344 A1 | 8/2021 | | |
| WO | 2022115377 A1 | 6/2022 | | |
| WO | WO-2022132914 A1 * | 6/2022 | ........... C07D 491/04 | |
| WO | 2022169948 A1 | 8/2022 | | |
| WO | 2024012308 A1 | 1/2024 | | |

OTHER PUBLICATIONS

Schuemacher, A., International Search Report and Written Opinion issued in App. No. PCT/CN2024/083980, dated Jun. 24, 2024, 11 pages.

Karkhanis, Vrajesh, et al. "Versatility of PRMT5-induced methylation in growth control and development." Trends in biochemical sciences 36.12 (2011): 633-641.

Gerhart, Sarah V., et al. "Activation of the p53-MDM4 regulatory axis defines the anti-tumour response to PRMT5 inhibition through its role in regulating cellular splicing." Scientific reports 8.1 (2018): 9711.

Jansson, Martin, et al. "Arginine methylation regulates the p53 response." Nature cell biology 10.12 (2008): 1431-1439.

Hsu, Jung-Mao, et al. "Crosstalk between Arg 1175 methylation and Tyr 1173 phosphorylation negatively modulates EGFR-mediated ERK activation." Nature cell biology 13.2 (2011): 174-181.

Wei, Tong-You Wade, et al. "Methylosome protein 50 promotes androgen-and estrogen-independent tumorigenesis." Cellular signalling 26.12 (2014): 2940-2950.

Rodon Ahnert, Jordi, et al. "PF-06939999, a potent and selective PRMT5 inhibitor, in patients with advanced or metastatic solid tumors: A phase 1 dose escalation study." (2021): 3019-3019.

Firestone, Ross S., and Vern L. Schramm. "The transition-state structure for human MAT2A from isotope effects." Journal of the American Chemical Society 139.39 (2017): 13754-13760.

Lochmüller, Charles H., and Rex W. Souter. "Chromatographic resolution of enantiomers: Selective review." Journal of Chromatography A 113.3 (1975): 283-302.

Morton Bradbury, E. "Reversible histone modification and the chromosome cell cycle." Bioessays 14.1 (1992): 9-16.

Copeland, R. A., M. P. Moyer, and V. M. Richon. "Targeting genetic alterations in protein methyltransferases for personalized cancer therapeutics." Oncogene 32.8 (2013): 939-946.

Bedford, Mark T., and Stéphane Richard. "Arginine methylation: an emerging regulatorof protein function." Molecular cell 18.3 (2005): 263-272.

Yang, Yanzhong, and Mark T. Bedford. "Protein arginine methyltransferases and cancer." Nature Reviews Cancer 13.1 (2013): 37-50.

Dhar, Surbhi, et al. "Loss of the major Type I arginine methyltransferase PRMT1 causes substrate scavenging by other PRMTs." Scientific reports 3.1 (2013): 1311.

Gao, Guozhen, et al. "PRMT1 loss sensitizes cells to PRMT5 inhibition." Nucleic acids research 47.10 (2019): 5038-5048.

* cited by examiner

*Primary Examiner* — Nizal S Chandrakumar

(74) *Attorney, Agent, or Firm* — McNeill PLLC

(57) ABSTRACT

This disclosure provides 5-amino-6,8-dihydro-1H-furo[3,4-d]pyrrolo[3,2-b]pyridine-2-carboxamide derivatives, the use thereof for selectively inhibiting the activity of PRMT5 in cooperation with MTA in tumors bearing $MTAP^{DEL}$ mutation, and pharmaceutical compositions comprising the compounds, e.g., for treatment of various diseases including cancer.

28 Claims, No Drawings

5-AMINO-6,8-DIHYDRO-1H-FURO[3,4-D] PYRROLO[3,2-B]PYRIDINE-2-CARBOXAMIDE DERIVATIVES AS MTA-COOPERATIVE INHIBITORS OF PRMT5

CROSS-REFERENCE TO RELATED APPLICATIONS

This application claims the benefit of priority of International Application No. PCT/CN2023/085078, filed Mar. 30, 2023, International Application No. PCT/CN2023/110807, filed Aug. 2, 2023, and International Application No. PCT/CN2024/080582, filed Mar. 7, 2024, the contents of which are hereby incorporated by reference in their entireties.

FIELD OF THE INVENTION

This disclosure provides 5-AMINO-6,8-DIHYDRO-1H-FURO[3,4-d]PYRROLO[3,2-b]PYRIDINE-2-CARBOXAMIDE derivatives, the use thereof, e.g., for selectively inhibiting the activity of PRMT5 in cooperation with methylthioadenosine (MTA) in tumors bearing $MTAP^{DEL}$ mutations, and pharmaceutical compositions comprising the compounds.

BACKGROUND OF THE INVENTION

Epigenetic modification is a process that can modify genetic output changing the primary DNA sequence. Epigenetic modification plays an important role in gene expression and regulation, protein production and cell differentiation in multiple dimensions. Typically, this process is reversible and selective, on DNA, its regulatory proteins such as histones and other proteins such as transcription factors [Bradbury, E. M., *BioEssays,* 1992, 14 (1): pp. 9-16]. PMTs (protein methyltransferases) are central players on epigenetic modifications, consisting of two sub-families named PKMTs (protein lysine methyltransferases) and PRMTs (protein arginine methyltransferases) [Copeland, R. A., et al., *Oncogene,* 2012. 32 (8): pp. 939-46]. PMTs are associated with various human diseases and considered as potential therapeutic targets [Copeland. R. A., et al., *Oncogene,* 2012, 32 (8): pp. 939-46].

As the name implies, PRMTs catalyze the methylation of the arginine residues of proteins. Besides their primary functions of methylating the histone tails, PRMTs also target other cellular proteins such as NAB2p, FOXO1, PABP1, Sm D1, etc. [Bedford. M. T., et al., *Molecular Cell.* 2005. 18 (3): pp. 263-72]. Divided by the products, the 9 mammalian PRMTs can be classified into 3 subtypes: type I (PRMT1, PRMT2, PRMT3, PRMT4, PRMT6 and PRMT8) catalyzes aDMA (asymmetrical dimethylated arginine) formation; type II (PRMT5, PRMT9) catalyzes sDMA (symmetrical dimethylated arginine); and type III (PRMT7) catalyzes MMA (monomethylated arginine) formation [Yang. Y., et al., *Nature Reviews Cancer,* 2012, 13 (1): pp. 37-50]. In addition, type I/II PRMTs can also catalyze MMA formation as an intermediate to aDMA and sDMA. The PRMTs comprise a pocket to interact with its cofactor SAM (S-adenosyl methionine), and an adjacent pocket to interact with the arginine residue on a protein, namely SAM-pocket and substrate-pocket. The methylation process involves an $S_N2$-like mechanism of transferring an activated methyl group from cofactor SAM to the guanidino group on the arginine residue. [Bedford. M. T., et al., *Molecular Cell.* 2005, 18 (3): pp. 263-72]. The side product of the process is SAH (S-adenosyl-L-homocysteine).

The overall arginine level in cells is roughly 1500:3:2:1 for Arg:aDMA:MMA:sDMA, and PRMT5 accounts for the vast majority of sDMA formation [Dhar. S. et al., *Scientific Reports.* 2013, 3: 1311]. In contrast with PRMT1, the major type I PRMT which functions on its own in cells, PRMT5 binds to MEP50 (methylosome protein 50) to form a heterocomplex that is often elevated in cancer cells and correlates to poor patient survival [Gao, G., et al., *Nucleic Acids Research,* 2019, 47 (10): pp. 5038-48]. PRMT5 promotes tumorigenesis by varied mechanisms. PRMT5 is a strong repressor of numerous genes, when PRMT5 methylates histones H2a and H4 on Arg3 and histone H3 on Arg8, it represses gene transcripts involved in differentiation, transformation, cell-cycle progression and tumor suppression [Karkhanis, V., et al., *Trends in Biochemical Sciences,* 2011, 36 (12): pp. 633-41]. Besides its epigenetic roles, PRMT5 may also regulate RNA-binding proteins such as splicing factors. For instance, a reproducible event was observed in PRMT5 knockout mice, in which exon 6 skipping of MDM4 (murine double minute 4) occurred and p53 was released to upregulate p53 pathway [Gerhart, S. V., et al., *Scientific Reports,* 2018, 8: 9711]. In addition, PRMT5 could directly influence key proliferation pathways by direct methylation of p53 [Jansson, M., et al., *Nature Cell Biology,* 2008, 10 (12): pp. 1431-9], EGFR [Hsu. J.-M. et al., *Nature Cell Biology* 2011, 13 (2): pp. 174-81], PI3K [Wei, T.-Y. W. et al., *Cellular Signaling,* 2014, 26 (12): pp. 2940-50], etc. Thus, PRMT5 has a good potential to become a clinically relevant target.

On the other hand, PRMT5 is an essential gene in normal tissues, and the systemic inhibition of PRMT5 may result in significant liabilities, especially hematologic toxicity [Ahnert, J. R. et al., *Journal of Clinical Oncology,* 2021, 39 (15-suppl): p. 3019]. Therefore, strategies to selectively block the PRMT5 activities in tumor cells are required for a safer therapy.

Homozygous deletion of tumor depressor CDKN2A (cyclin dependent kinase inhibitor 2A) occurs in about 15% of all tumor types. Interestingly, the mutation frequently involves the co-deletion of proximate genes existing in 9p21, including the gene that encodes MTAP (methylthioadenosine phosphorylase) [Firestone. R. S. et al., *Journal of American Chemical Society,* 2017, 139 (39): p. 13754-60]. As a result of MTAP deletion, MTA (methylthioadenosine), the substrate of MTAP, accumulates. MTA is structurally related to SAM, and is a weak ligand/inhibitor of PRMT5 that occupies the same pocket with SAM. The formation of MTA-PRMT5 complex provides chances for further PRMT5 inhibition by formation of a tertiary complex. In such way, a correlation of MTAP null status and dependency of PRMT5 is established through MTA concentration level, to provide a precise oncological therapy.

Currently, most of the clinical-stage PRMT5 inhibitors are unable to differentiate normal cells and cancer cells, based on a SAM/MTA competitive mechanism (JNJ64619178, PF06939999, PRT543, and PRT811) or a non-MTA cooperative mechanism (GSK3326595). There thus remain unmet and continuous medical needs for potent and selective MTA-cooperative PRMT5 inhibitors.

SUMMARY OF THE INVENTION

One objective of the present invention is to provide PRMT5 inhibitory compounds, and methods of preparation and uses thereof.

Aspect 1. A compound of Formula (I):

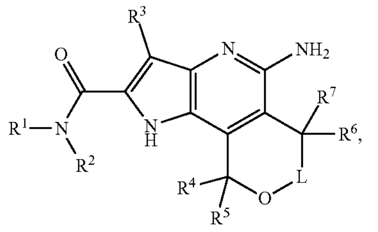

(I)

or an N-oxide thereof, or a pharmaceutically acceptable salt, stereoisomer, tautomer, or a deuterated analog thereof, wherein:

L is a single bond or —C($R^8R^9$)—;

$R^1$ and $R^2$ are each independently selected from hydrogen, —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl and 5- to 12-membered heteroaryl, wherein each of said —$C_{1-8}$alkyl, —$C_3$-$C_8$cycloalkyl, 3- to 12-membered heterocyclyl, —$C_6$-$C_{12}$aryl and 5- to 12-membered heteroaryl is optionally substituted with at least one substituent $R^{1a}$; or $R^1$ and $R^2$ together with the nitrogen atom to which they are attached, form a 3- to 8-membered unsaturated or saturated ring, said ring comprising 0-3 additional heteroatoms independently selected from nitrogen, oxygen or sulfur and said ring is optionally substituted with at least one substituent $R^{1a}$;

$R^{1a}$ is independently hydrogen, halogen, deuterium, —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl, 5- to 12-membered heteroaryl, —$OR^{1b}$, —$SO_2R^{1b}$, —$SO_2NR^{1b}R^{1c}$, —$COR^{1b}$, —$CO_2R^{1b}$, —$CONR^{1b}R^{1c}$, —$NR^{1b}R^{1c}$, —$NR^{1b}COR^{1c}$, —$NR^{1b}CO_2R^{1c}$, —$NR^{1b}SO_2R^{1c}$, oxo, or —CN, wherein each of said —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl and 5- to 12-membered heteroaryl is optionally substituted with at least one substituent $R^{1d}$; or two $R^{1a}$ together with the atom(s) to which they are attached, form a 3- to 8-membered unsaturated or saturated ring, said ring comprising 0-3 heteroatoms independently selected from nitrogen, oxygen or sulfur and said ring is optionally substituted with at least one substituent $R^{1d}$;

$R^{1b}$ and $R^{1c}$ are each independently selected from hydrogen, —$C_{1-8}$alkyl, —$C_3$-$C_8$cycloalkyl, 3- to 12-membered heterocyclyl, —$C_6$-$C_{12}$aryl and 5- to 12-membered heteroaryl, wherein each of said —$C_{1-8}$alkyl, —$C_3$-$C_8$cycloalkyl, 3- to 12-membered heterocyclyl, —$C_6$-$C_{12}$aryl and 5- to 12-membered heteroaryl is optionally substituted with at least one substituent $R^{1e}$;

$R^{1d}$ and $R^{1c}$ are each independently hydrogen, halogen, —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl, 5- to 12-membered heteroaryl, —$OR^{1f}$, —$SO_2R^{1f}$, —$SO_2NR^{1f}R^{1g}$, —$COR^{1f}$, —$CO_2R^{1f}$, —$CONR^{1f}R^{1g}$, —$NR^{1f}R^{1g}$, —$NR^{1f}COR^{1g}$, —$NR^{1f}CO_2R^{1g}$, —$NR^{1f}SO_2R^{1g}$, oxo, or —CN, wherein each of said —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl and 5- to 12-membered heteroaryl is optionally substituted with at least one substituent $R^{1h}$;

$R^{1f}$ and $R^{1g}$ are each independently selected from hydrogen, —$C_{1-8}$alkyl, —$C_3$-$C_8$cycloalkyl, 3- to 12-membered heterocyclyl, —$C_6$-$C_{12}$aryl and 5- to 12-membered heteroaryl, wherein each of said —$C_{1-8}$alkyl, —$C_3$-$C_8$cycloalkyl, 3- to 12-membered heterocyclyl, —$C_6$-$C_{12}$aryl and 5- to 12-membered heteroaryl is optionally substituted with at least one substituent $R^{1i}$;

$R^{1h}$ and $R^{1i}$ are each independently hydrogen, halogen, —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl, 5- to 12-membered heteroaryl, —$OR^{1j}$, —$SO_2R^{1j}$, —$SO_2NR^{1j}R^{1k}$, —$COR^{1j}$, —$CO_2R^{1j}$, —$CONR^{1j}R^{1k}$, —$NR^{1j}R^{1k}$, —$NR^{1j}COR^{1k}$, —$NR^{1j}CO_2R^{1k}$, —$NR^{1j}SO_2R^{1k}$, oxo, or —CN, wherein each of said —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl and 5- to 12-membered heteroaryl is optionally substituted with at least one substituent selected from the group consisting of halogen, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl, —CN, —OH, —$NH_2$ or oxo;

$R^{1j}$ and $R^{1k}$ are each independently selected from hydrogen, —$C_{1-8}$alkyl, —$C_3$-$C_8$cycloalkyl, 3- to 12-membered heterocyclyl, —$C_6$-$C_{12}$aryl and 5- to 12-membered heteroaryl, wherein each of said —$C_{1-8}$alkyl, —$C_3$-$C_8$cycloalkyl, 3- to 12-membered heterocyclyl, —$C_6$-$C_{12}$aryl and 5- to 12-membered heteroaryl is optionally substituted with at least one substituent selected from the group consisting of halogen, —$C_{1-8}$alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl, —CN, —OH, —$NH_2$ or oxo;

$R^3$ is selected from hydrogen, halogen, —$C_{1-8}$alkyl, —$C_3$-$C_8$cycloalkyl, —CN, —OH, or —$NH_2$, wherein each of said —$C_{1-8}$alkyl and —$C_3$-$C_8$cycloalkyl is optionally substituted with at least one substituent selected from the group consisting of halogen, —$C_{1-8}$alkoxy, —$C_{1-8}$alkyl, —$C_3$ -$C_8$cycloalkyl, and 3- to 8-membered heterocyclyl;

$R^4$, $R^5$, $R^6$, $R^7$, $R^8$ and $R^9$ are each independently selected from hydrogen, halogen, —$C_{1-8}$ alkyl or —$C_3$-$C_8$cycloalkyl, wherein each of said —$C_{1-8}$alkyl and —$C_3$-$C_8$cycloalkyl is optionally substituted with at least one substituent selected from the group consisting of halogen, —$C_{1-8}$alkoxy, —$C_{1-8}$alkyl, —$C_3$-$C_8$cycloalkyl, 3- to 8-membered heterocyclyl, $C_6$-$C_{12}$aryl, 5- to 12-membered heteroaryl, oxo, —CN, —$OR^{4a}$, —$SO_2R^{4a}$, —$SO_2N^{4a}R^{4b}$, —$COR^{4a}$, —$CO_2R^{4a}$, —$CONR^{4a}R^{4b}$, —$NR^{4a}R^{4b}$, —$NR^{4a}COR^{4b}$, —$NR^{4a}CO_2R^{4b}$, or —$NR^{4a}SO_2R^{4b}$;

$R^{4a}$ and $R^{4b}$ are each independently hydrogen, —$C_{1-8}$alkyl, $C_3$-$C_8$cycloalkyl, 3- to 8-membered heterocyclyl, —$C_6$-$C_{12}$aryl, or 5- to 12-membered heteroaryl; each of said —$C_{1-8}$alkyl, $C_3$-$C_8$cycloalkyl, 3- to 8-membered heterocyclyl, —$C_6$-$C_{12}$aryl, or 5- to 12-membered heteroaryl is optionally substituted with at least one halogen, —OH, —$C_{1-8}$alkyl, —$C_{1-8}$alkoxy, $C_{1-8}$alkoxy-$C_{1-8}$alkyl-, —$C_{2-8}$alkenyl, —$C_{2-8}$alkynyl, —$C_3$-$C_8$cycloalkyl, 3- to 8-membered heterocyclyl, —$C_6$-$C_{12}$aryl, or 5- to 12-membered heteroaryl.

In one embodiment, $R^1$ and $R^2$ are each independently selected from —$C_{1-8}$alkyl, —$C_3$-$C_8$cycloalkyl, —$C_3$-$C_{12}$cycloalkenyl and 3- to 12-membered heterocyclyl, wherein each of said —$C_{1-8}$alkyl, —$C_3$-$C_8$cycloalkyl, —$C_3$-

$C_{12}$cycloalkenyl and 3- to 12-membered heterocyclyl is optionally substituted with at least one substituent $R^{1a}$. $R^{1a}$ is defined as previously.

In one embodiment, $R^1$ and $R^2$ are each independently selected from —$C_{1-8}$alkyl, wherein said —$C_{1-8}$alkyl is optionally substituted with at least one substituent $R^{1a}$. $R^{1a}$ is defined as previously. Preferably, $R^1$ and $R^2$ are each independently selected from —$C_{1-4}$alkyl, wherein said —$C_{1-8}$alkyl is optionally substituted with at least one substituent $R^{1a}$. $R^{1a}$ is defined as previously. More preferably, $R^1$ and $R^2$ are each independently selected from methyl, ethyl and propyl (iso-propyl or n-propyl), wherein each of said methyl, ethyl and propyl (iso-propyl or n-propyl) is optionally substituted with at least one substituent $R^{1a}$. $R^{1a}$ is defined as previously. In one embodiment, $R^1$ is methyl, ethyl, propyl (iso-propyl or n-propyl), butyl (n-butyl, sec-butyl, iso-butyl or tert-butyl), each of said methyl, ethyl, propyl (iso-propyl or n-propyl), butyl (n-butyl, sec-butyl, iso-butyl or tert-butyl) is optionally substituted with at least one substituent $R^{1a}$, $R^{1a}$ is defined as previously. In one embodiment, $R^{1a}$ is phenyl, pyrimidinyl, tetrahydro-2H-pyranyl, pyridazinyl, pyrazinyl, triazolyl (preferably, 1H-1,2,4-triazolyl, 4H-1,2,4-triazolyl), pyridinyl, pyrazolyl, imidazolyl, thiazolyl, tetrahydropyranyl, dihydrofuropyridinyl or tetrahydrofuropyridinyl; each of said phenyl, pyrimidinyl, tetrahydro-2H-pyranyl, pyridazinyl, pyrazinyl, triazolyl (preferably, 1H-1,2,4-triazolyl, 4H-1,2,4-triazolyl), pyridinyl, pyrazolyl, imidazolyl, thiazolyl, tetrahydropyranyl, dihydrofuropyridinyl or tetrahydrofuropyridinyl is optionally substituted with at least one substituent $R^{1d}$, $R^{1d}$ is defined as previously. In one embodiment, $R^1$ is

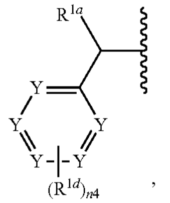
,

Y is N or CH; n4 is 0, 1, 2, 3 or 4; preferably, n4 is 1, 2 or 3. In one embodiment $R^1$ is

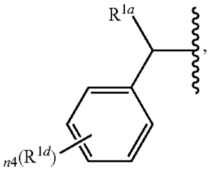
,
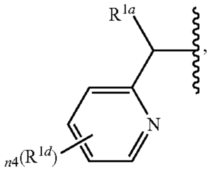
,
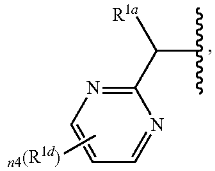
,
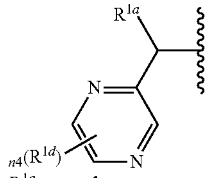
or
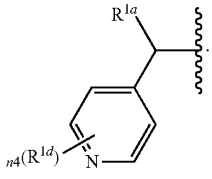
.

In one embodiment, $R^1$ is

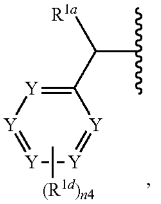
,

Y is N or CH; preferably, zero, one, or two occurrences of Y are N and the rest are CH; more preferably, zero or one occurrence of Y is N and the rest are CH; $R^{1a}$ is hydrogen or $C_{1-8}$alkyl; preferably, $R^{1a}$ is hydrogen, methyl, ethyl, propyl (iso-propyl or n-propyl), or butyl (n-butyl, sec-butyl, iso-butyl or tert-butyl); more preferably, $R^{1a}$ is hydrogen, methyl, ethyl, or propyl (iso-propyl or n-propyl); $R^{1d}$ is independently selected from halo, methyl substituted with one or more halo, $C_{3-5}$cycloalkyl optionally substituted with fluoro, or —CN; preferably, $R^{1d}$ is independently selected from —F, —Br, —I, —$CF_3$, cyclopropyl, fluorocyclopropyl, cyclobutyl or —CN; n4 is 0, 1, 2, 3 or 4; preferably, n4 is 1, 2 or 3. In a further embodiment, $R^1$ is

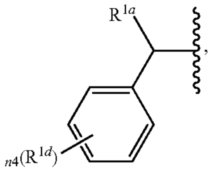
,
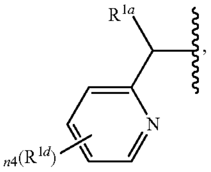
,
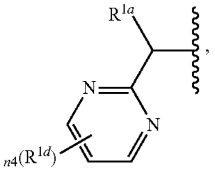
,
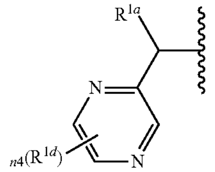
or
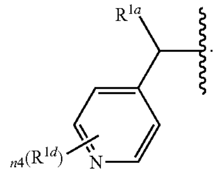
.

In one embodiment, $R^1$ and $R^2$ are each independently selected from methyl, ethyl, propyl (iso-propyl or n-propyl), butyl (n-butyl, sec-butyl, iso-butyl or tert-butyl), cyclopropyl, cyclobutyl, cyclopentyl, cyclohexyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl (iso-propyl or n-propyl), butyl (n-butyl, sec-butyl, iso-butyl or tert-butyl), cyclopropyl, cyclobutyl, cyclopentyl, cyclohexyl, chromanyl, isochromanyl, dihydropyranopyridinyl (preferably, 5,8-dihydro-6H-pyrano[3,4-b]pyridinyl, 3,4-dihydro-2H-pyrano

[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b] pyridinyl), tetrahydronaphthalenyl (preferably, 1,2,3,4-tetrahydronaphthalenyl), benzo[d]thiazolyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1a}$. $R^{1a}$ is defined as previously.

In one embodiment, $R^1$ is 3- to 12-membered heterocyclyl, said 3- to 12-membered heterocyclyl is optionally substituted with at least one substituent $R^{1a}$, $R^{1a}$ is defined as previously. Preferably, $R^1$ is 6- to 10-membered heterocyclyl, said 6- to 10-membered heterocyclyl is optionally substituted with at least one substituent $R^{1a}$, $R^{1a}$ is defined as previously. In one embodiment, $R^1$ is 3- to 12-membered heterocyclyl, said 3- to 12-membered heterocyclyl is optionally substituted with at least one substituent $R^{1a}$; and $R^2$ is —$C_{1-8}$alkyl which is further substituted with 3- to 12-membered heterocyclyl, —$C_6$-$C_{12}$aryl, 5- to 12-membered heteroaryl, and each of said 3- to 12-membered heterocyclyl, —$C_6$-$C_{12}$aryl and 5- to 12-membered heteroaryl is optionally substituted with at least one substituent $R^{1d}$. Preferably, $R^2$ is —$C_{1-4}$alkyl which is further substituted with 5- to 10-membered heterocyclyl, phenyl or 5- to 6-membered heteroaryl, and each of said 5- to 10-membered heterocyclyl, phenyl and 5- to 6-membered heteroaryl is optionally substituted with at least one substituent $R^{1d}$.

In one embodiment, $R^1$ is 3- to 12-membered heterocyclyl, said 3- to 12-membered heterocyclyl is optionally substituted with at least one substituent $R^{1a}$, $R^{1a}$ is defined as previously. In one embodiment, $R^1$ is tetrahydropyranyl, said tetrahydropyranyl is optionally substituted with at least one substituent $R^{1a}$, $R^{1a}$ is defined as previously. Preferably, $R^{1a}$ is —$C_{1-8}$ alkoxy, more preferably, $R^{1a}$ is methoxy or ethoxy. In one embodiment, $R^1$ is

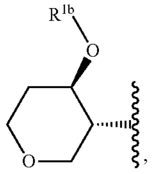

$R^{1b}$ is —$C_{1-8}$alkyl, preferably, $R^{1b}$ is methyl or ethyl.

In one embodiment, $R^1$ is 3- to 12-membered heterocyclyl; preferably, $R^1$ is tetrahydroquinolinyl, said tetrahydroquinolinyl is optionally substituted with at least one substituent $R^{1a}$, $R^{1a}$ is defined as previously. In one embodiment, $R^{1a}$ is H. In one embodiment, $R^1$ is

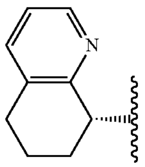
or
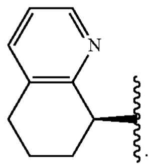

In one embodiment, $R^1$ is 3- to 12-membered heterocyclyl; preferably, $R^1$ is chromanyl or isochromanyl, each of said chromanyl or isochromanyl is optionally substituted with at least one substituent $R^{1a}$, $R^{1a}$ is defined as previously. In one embodiment, $R^{1a}$ is H. In one embodiment, $R^{1a}$ is —F, —$CH_3$, or —$CF_3$. In one embodiment, $R^1$ is

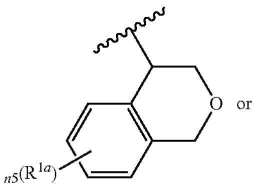
or
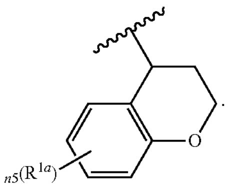

In one embodiment, $R^1$ is

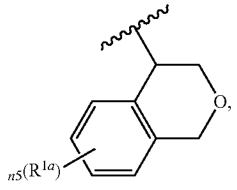

$R^{1a}$ is independently selected from methyl, ethyl, propyl, halo, methyl substituted with one or more halo, $C_{3-5}$cycloalkyl, or —CN, or two $R^{1a}$ attached to the same atom form $C_{3-5}$cycloalkyl; preferably, $R^{1a}$ is hydrogen, methyl, ethyl, —F, —Cl, —Br, —I, —$CF_3$, cyclopropyl, or —CN, or two $R^{1a}$ attached to the same atom form cyclopropyl; n5 is 0, 1, 2, 3, 4 or 5; preferably, n5 is 1, 2, 3, 4, or 5; more preferably, n5 is 1, 2, 3, or 4; yet more preferably, n5 is 1, 2, or 3.

$R^{1a}$ can be the substituent group(s) on the

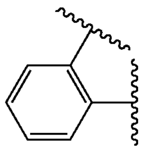 [SMILES: *c1ccccc1*]

moiety of

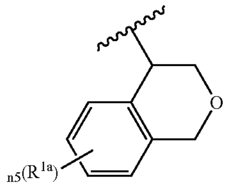

or on the

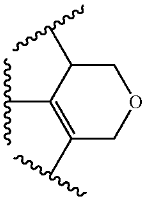 [SMILES: *C1=C(*)C(*)COC1]

moiety of

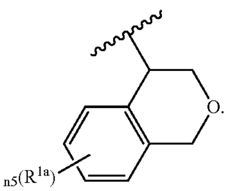

In one embodiment, $R^1$ is benzyl, pyridylmethyl, pyridazinylmethyl, pyrimidinylmethyl, pyrazinylmethyl, 1-pyridylethyl, 1-pyridazinylethyl, 1-pyrimidinylethyl or 1-pyrazinylethyl, each of said benzyl, pyridylmethyl, pyridazinylmethyl, pyrimidinylmethyl, pyrazinylmethyl, 1-pyridylethyl, 1-pyridazinylethyl, 1-pyrimidinylethyl or 1-pyrazinylethyl is optionally substituted with at least one substituent $R^{1d}$, $R^{1d}$ is defined as previously. In one embodiment, $R^{1d}$ is each independently hydrogen, —F, —Cl, —Br, —I, methyl, ethyl, propyl (iso-propyl or n-propyl), butyl (n-butyl, sec-butyl, iso-butyl or tert-butyl), phenyl, pyrimidinyl, tetrahydro-2H-pyranyl, pyridazinyl, pyrazinyl, triazolyl (preferably, 1H-1,2,4-triazolyl, 4H-1,2,4-triazolyl), pyridinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, —$OR^{1f}$, —$SO_2R^{1f}$ or —CN, wherein each of said methyl, ethyl, propyl (iso-propyl or n-propyl), butyl (n-butyl, sec-butyl, iso-butyl or tert-butyl), phenyl, pyrimidinyl, tetrahydro-2H-pyranyl, pyridazinyl, pyrazinyl, triazolyl (preferably, 1H-1,2,4-triazolyl, 4H-1,2,4-triazolyl), pyridinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1h}$; $R^{1f}$ is each independently selected from hydrogen, methyl, ethyl, propyl (iso-propyl or n-propyl), cyclopropyl, cyclobutyl, cyclopentyl, cyclohexyl or phenyl, wherein each of said methyl, ethyl, propyl (iso-propyl or n-propyl), cyclopropyl, cyclobutyl, cyclopentyl, cyclohexyl or phenyl is optionally substituted with at least one substituent $R^{1i}$; $R^{1h}$ and $R^{1i}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, —OH, or —CN.

In one embodiment, $R^2$ is $C_{1-8}$alkyl. In one embodiment, $R^2$ is methyl, ethyl, propyl (iso-propyl or n-propyl), or butyl (n-butyl, sec-butyl, iso-butyl or tert-butyl). In one embodiment, $R^2$ is methyl, ethyl, or propyl (iso-propyl or n-propyl). In one embodiment, $R^2$ is methyl.

Aspect 2. The compound of aspect 1, wherein the compound is of formula (IIa) or (IIb):

(IIa)

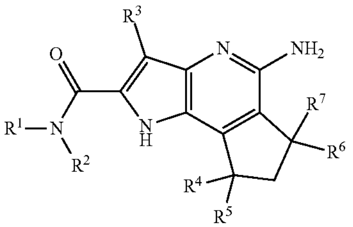

-continued (IIb)

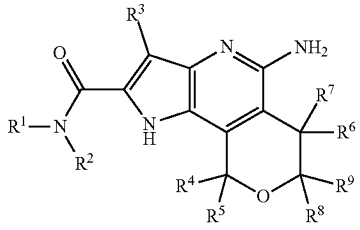

preferably, the compound is of formula (IIc) or (IId):

(IIc)

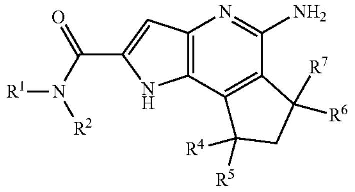

(IId)

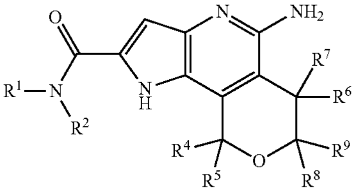

or preferably, the compound is of formula (IIe), (IIf), (IIg) or (IIh):

(IIe)

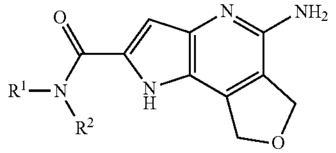

(IIf)

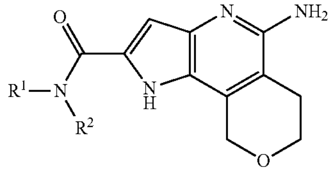

(IIg)

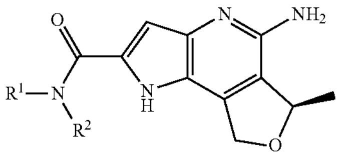

(IIh)

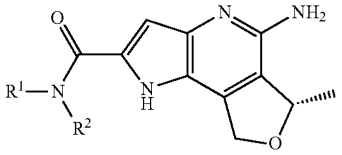

wherein $R^1$, $R^2$, $R^3$, $R^4$, $R^5$, $R^6$, $R^7$, $R^8$ and $R^9$ are as defined in aspect 1.

Aspect 3. The compound of aspect 1, wherein the compound is of formula (IIIa):

(IIIa)

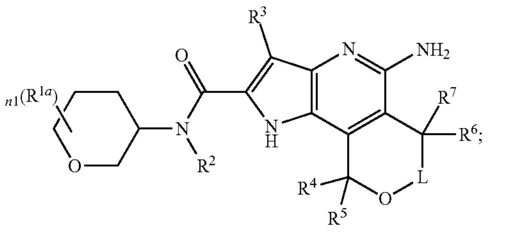

preferably, the compound is of formula (IIIb):

(IIIb)

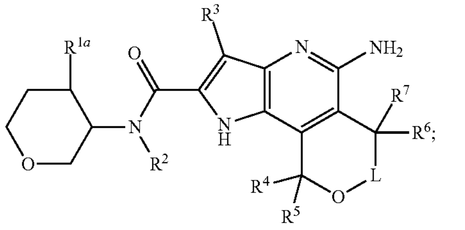

more preferably, the compound is of formula (IIIc):

(IIIc)

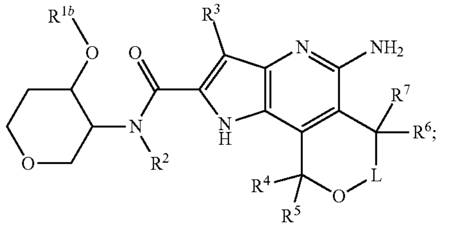

even more preferably, the compound is of formula (IIId), (IIIe), (IIIf) or (IIIg):

(IIId)

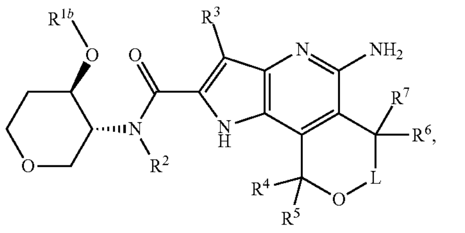

(IIIe)

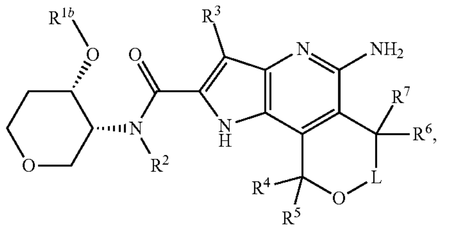

-continued (IIIf)

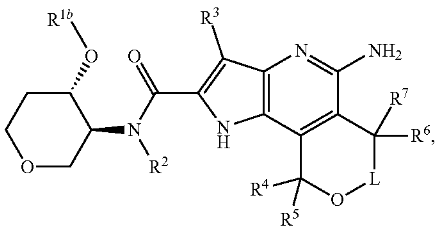

(IIIg)

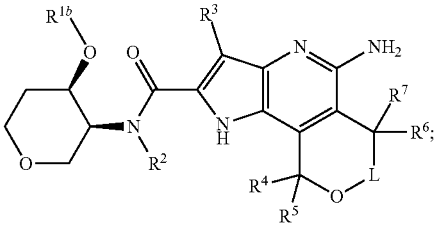

even more preferably, the compound is of formula (IIIh), (IIIi), (IIIj) or (IIIk):

(IIIh)

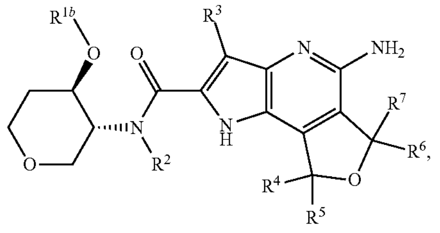

(IIIi)

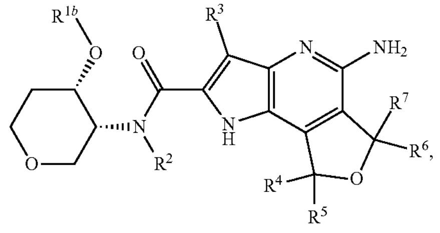

(IIIj)

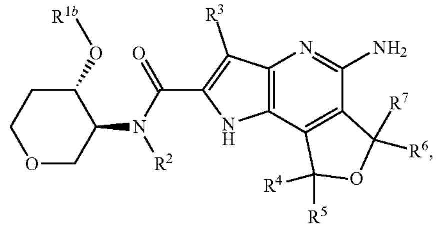

(IIIk)

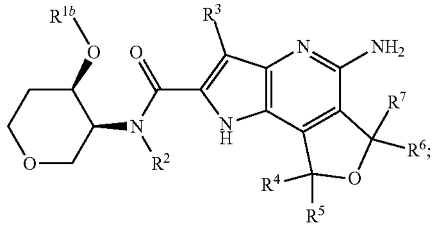

wherein, n1 is 0, 1, 2 or 3; preferably, n1 is 1 or 2; more preferably, n1 is 1;

$R^{1a}$, $R^{1b}$, $R^2$, $R^3$, $R^4$, $R^5$, $R^6$, $R^7$ and L are as defined in aspect 1.
Aspect 4. The compound of aspect 1, wherein the compound is of formula (IVa), (IVb), (IVc), (IVd), (IVe), (IVf), (IVg) or (IVh):
(IVa)
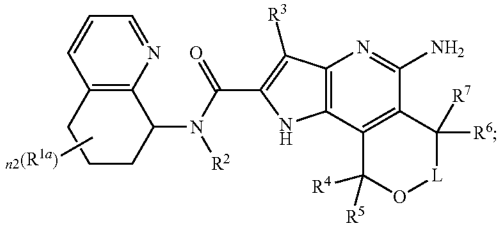
(IVb)
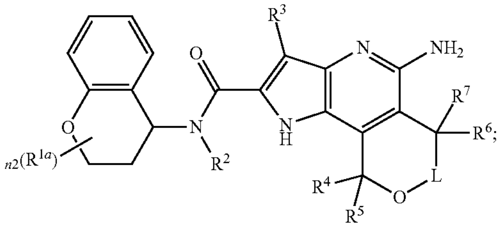
(IVc)
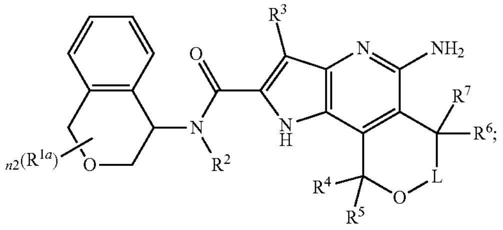
(IVd)
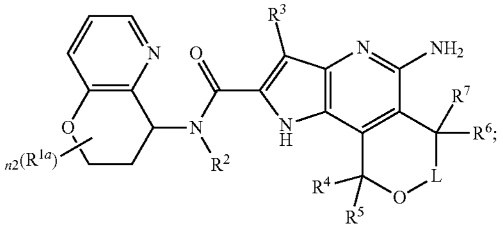
(IVe)
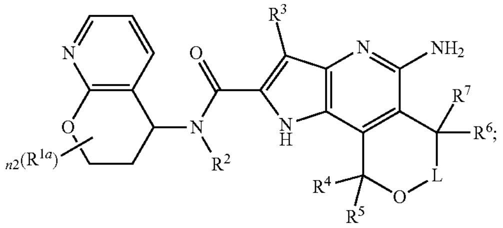
(IVf)
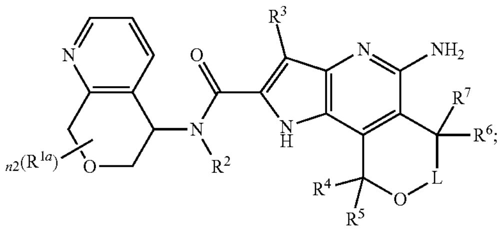
-continued
(IVh)
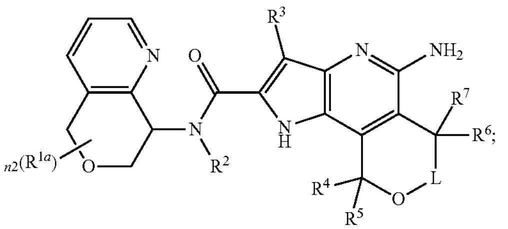
preferably, the compound is of formula (IVi), (IVj), (IVk), (IVl), (IVm), (IVn), (IVo), (IVp), (IVq), (IVr), (IVs), (IVt), (IVu) or (IVv):
(IVi)
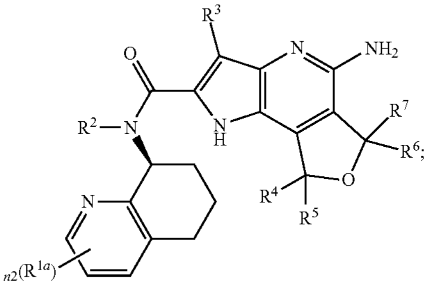
(IVj)
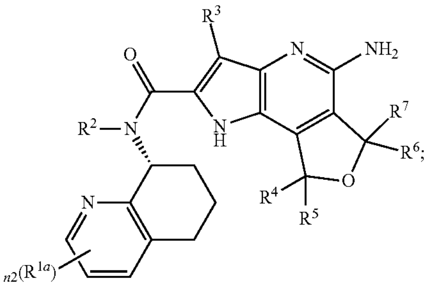
(IVk)
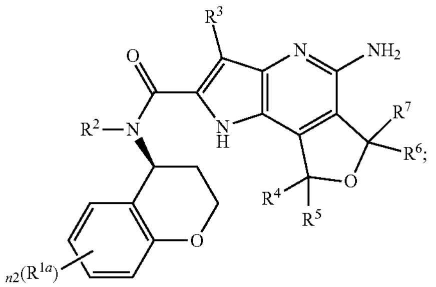
(IVl)
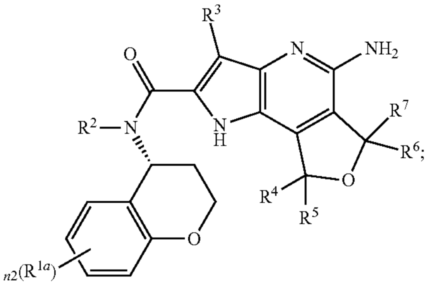

-continued
(IVm)
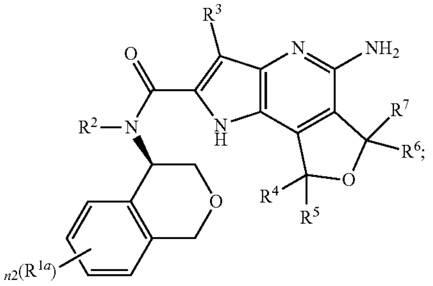
(IVn)
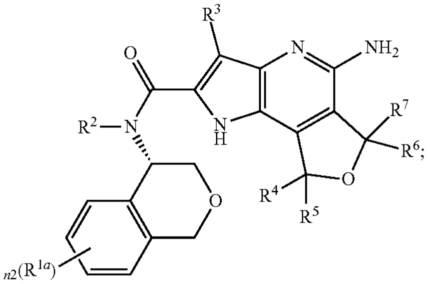
(IVo)
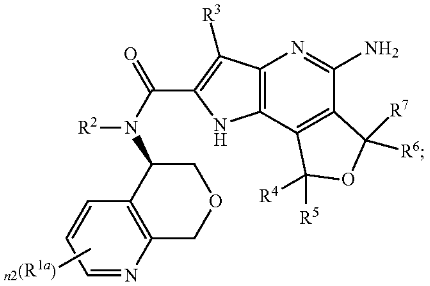
(IVp)
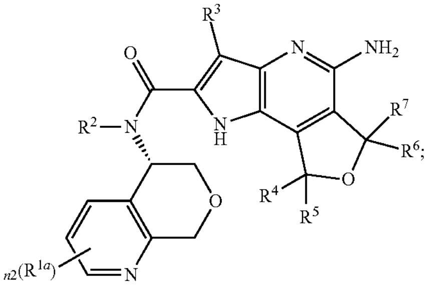
(IVq)
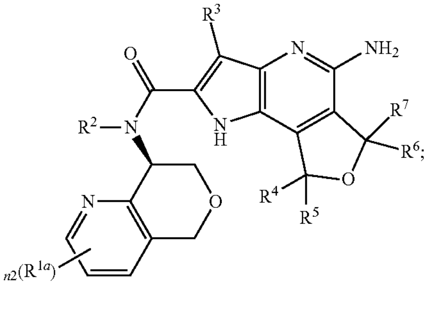
-continued
(IVr)
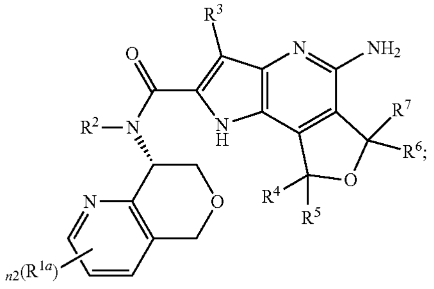
(IVs)
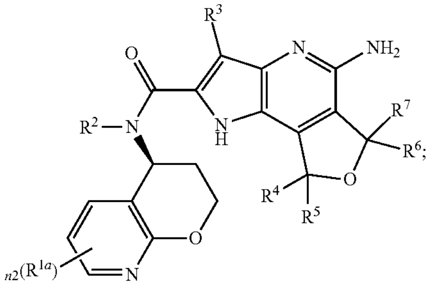
(IVt)
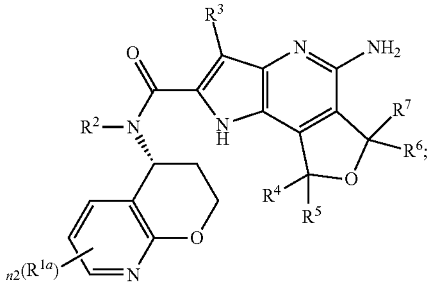
(IVu)
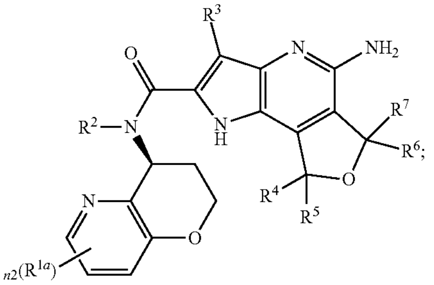
(IVv)
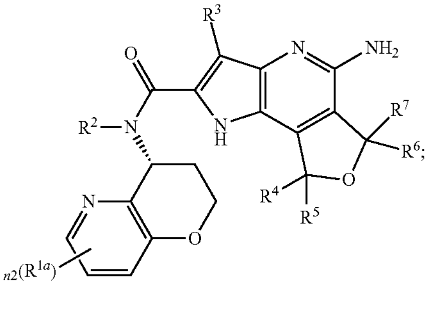
wherein, n2 is 0, 1, 2 or 3; preferably, n2 is 0, 1 or 2; $R^{1a}$, $R^2$, $R^3$, $R^4$, $R^5$, $R^6$, $R^7$ and L are as defined in aspect 1.

$R^{1a}$ can be substituted on any position of

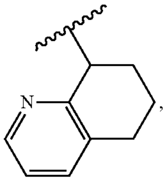,
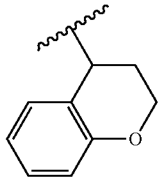,
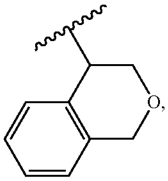
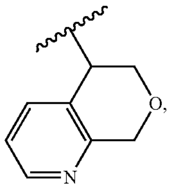
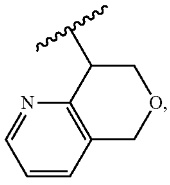
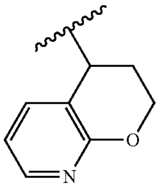
or
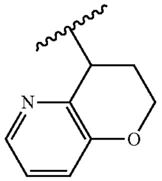

that can fulfill the valency theory.

Aspect 5. The compound of aspect 1, wherein the compound is of formula (Va):

(Va)

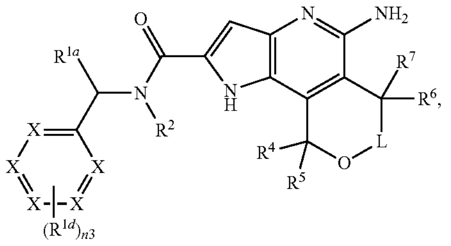

wherein, n3 is 0, 1, 2, 3 or 4, preferably, n3 is 1, 2 or 3;

each occurrence of X is independently N or CH, preferably, zero, one or two occurrences of X are N, and the rest are CH;

$R^{1a}$, $R^{1d}$, $R^2$, $R^3$, $R^4$, $R^5$, $R^6$, $R^7$ and L are as defined in aspect 1;

preferably, the compound is of formula (Vb), (Vc), (Vd), (Ve) or (Vf):

(Vb)

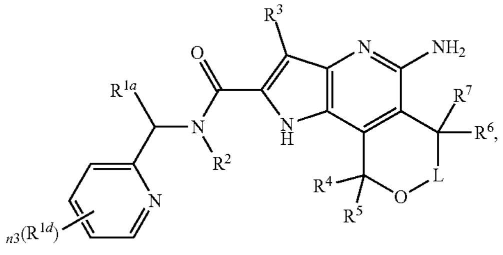

-continued (Vc)

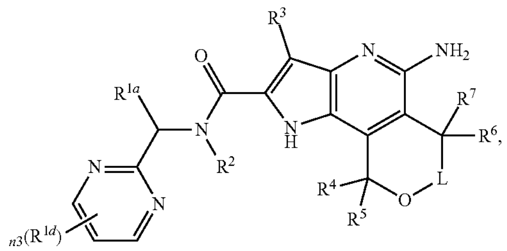

(Vd)

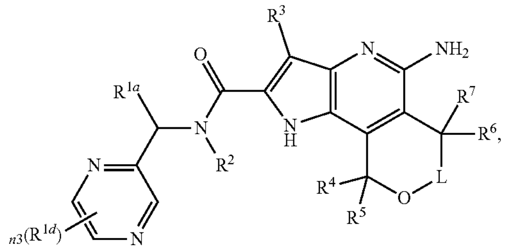

(Ve)

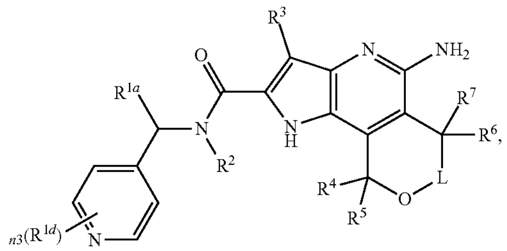

(Vf)

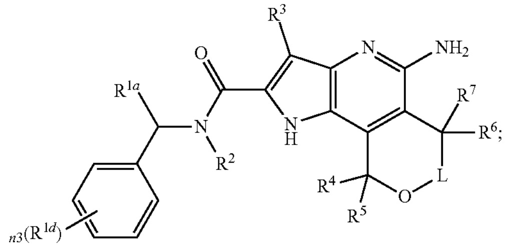

wherein, n3 is 0, 1, 2 or 3; preferably, n3 is 1 or 2; more preferably, n3 is 1;

$R^{1a}$, $R^{1d}$, $R^2$, $R^3$, $R^4$, $R^5$, $R^6$, $R^7$ and L are as defined in aspect 1;

more preferably, the compound is of formula (Vg), (Vh), (Vi), (Vj), (Vk), (Vl), (Vm), (Vn) or (Vo):

(Vg)

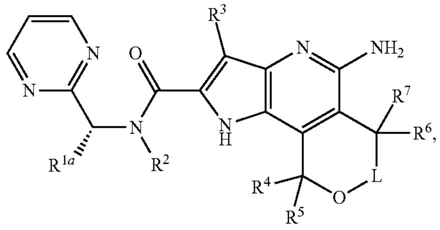

-continued
(Vh)
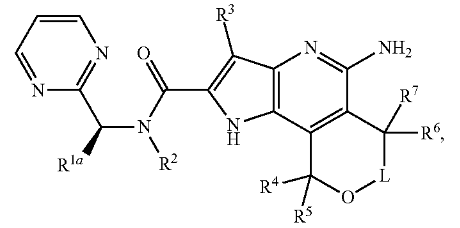
(Vi)
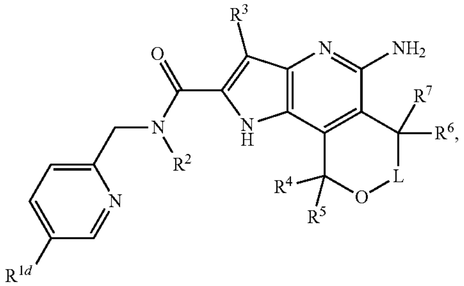
(Vj)
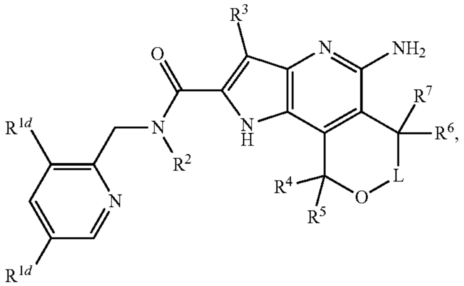
(Vk)
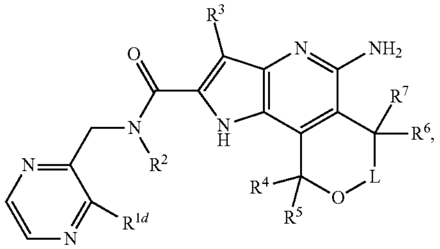
(Vl)
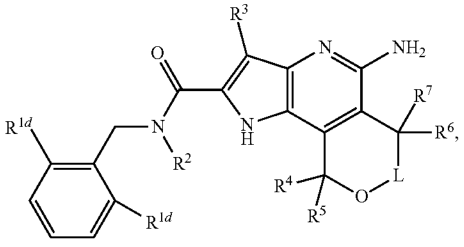
(Vm)
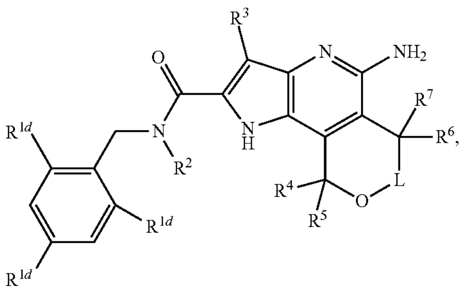
-continued
(Vn)
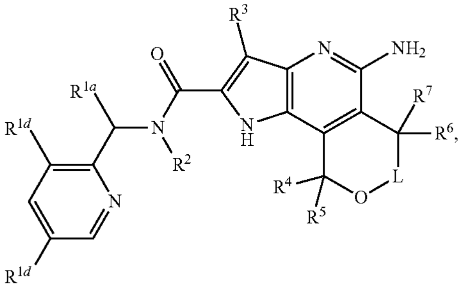
(Vo)
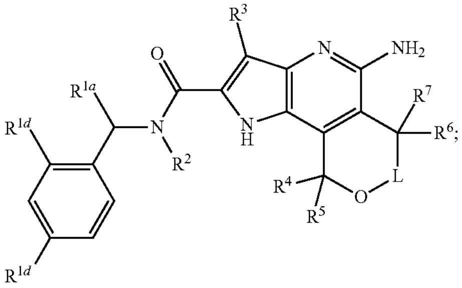
even more preferably, the compound is of formula (Vp), (Vq), (Vr), (Vs), (Vt), (Vu), (Vv), (Vw), (Vx), (Vy) or (Vz):
(Vp)
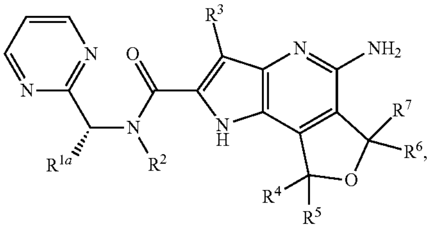
(Vq)
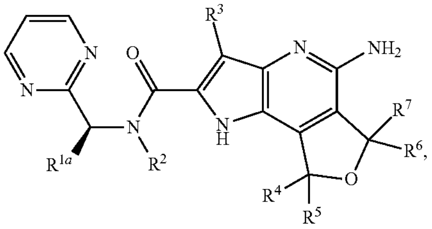
(Vr)
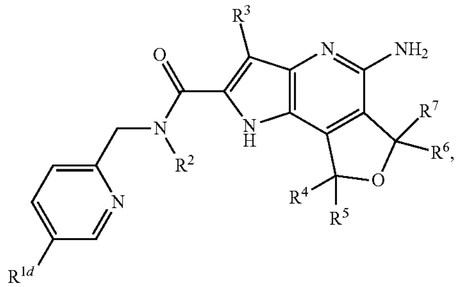

-continued (Vs)

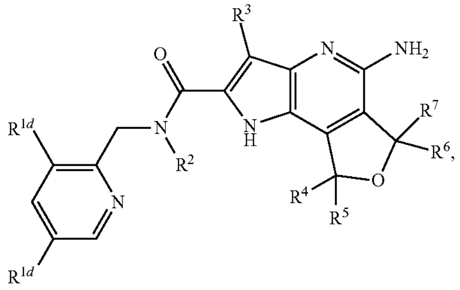

(Vt)

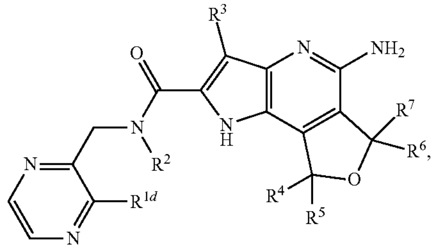

(Vu)

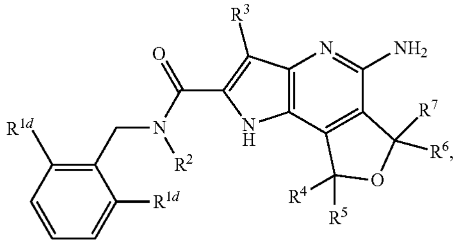

(Vv)

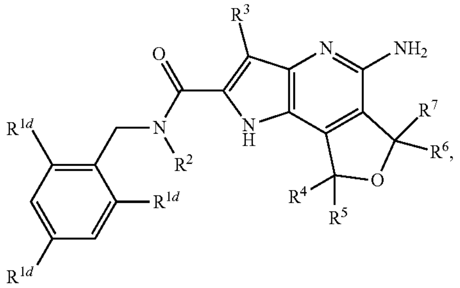

(Vw)

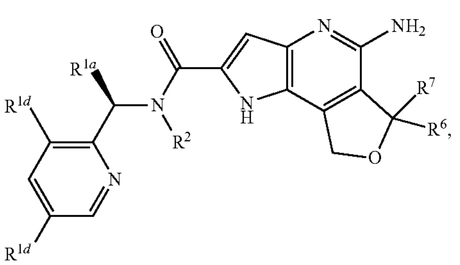

-continued (Vx)

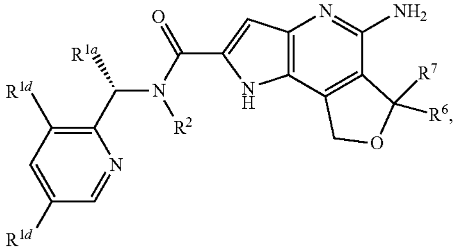

(Vy)

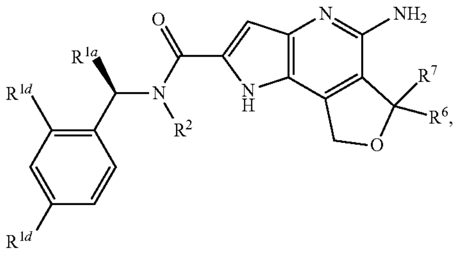

(Vz)

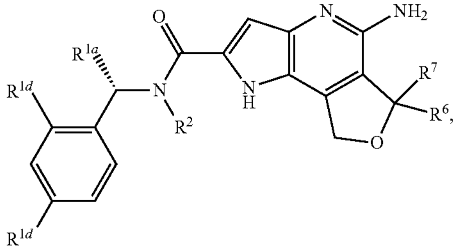

wherein, $R^{1a}$, $R^{1d}$, $R^2$, $R^3$, $R^4$, $R^5$, $R^6$, $R^7$ and L are as defined in aspect 1.

Aspect 6. A compound of Formula (VI):

(VI)

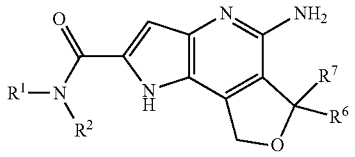

or an N-oxide thereof, or a pharmaceutically acceptable salt, stereoisomer, tautomer, or a deuterated analog thereof, wherein:

$R^1$ and $R^2$ are each independently selected from hydrogen, —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl and 5- to 12-membered heteroaryl, wherein each of said —$C_{1-8}$alkyl, —$C_3$-$C_8$cycloalkyl, 3- to 12-membered heterocyclyl, —$C_6$-$C_2$aryl and 5- to 12-membered heteroaryl is optionally substituted with at least one substituent $R^{1a}$; or $R^1$ and $R^2$ together with the nitrogen atom to which they are attached, form a 3- to 8-membered unsaturated or saturated ring, said ring comprising 0-3 additional heteroatoms independently selected from nitrogen, oxygen or sulfur and said ring is optionally substituted with at least one substituent $R^{1a}$;

$R^{1a}$ is independently hydrogen, halogen, deuterium, —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl, 5- to 12-membered heteroaryl, —$OR^{1b}$, —$SO_2R^{1b}$, —$SO_2NR^{1b}R^{1c}$, —$COR^{1b}$, —$CO_2R^{1b}$, —$CONR^{1b}R^{1c}$, —$NR^{1b}R^{1c}$, —$NR^{1b}COR^{1c}$, —$NR^{1b}CO_2R^{1c}$, —$NR^{1b}SO_2R^{1c}$, oxo, or —CN, wherein each of said —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl and 5- to 12-membered heteroaryl is optionally substituted with at least one substituent $R^{1d}$; or two $R^{1a}$ together with the atom(s) to which they are attached, form a 3- to 8-membered unsaturated or saturated ring, said ring comprising 0-3 heteroatoms independently selected from nitrogen, oxygen or sulfur and said ring is optionally substituted with at least one substituent $R^{1d}$;

$R^{1b}$ and $R^{1c}$ are each independently selected from hydrogen, —$C_{1-8}$alkyl, —$C_3$-$C_8$cycloalkyl, 3- to 12-membered heterocyclyl, —$C_6$-$C_{12}$aryl and 5- to 12-membered heteroaryl, wherein each of said —$C_{1-8}$alkyl, —$C_3$-$C_8$cycloalkyl, 3- to 12-membered heterocyclyl, —$C_6$-$C_{12}$aryl and 5- to 12-membered heteroaryl is optionally substituted with at least one substituent $R^{1c}$;

$R^{1d}$ and $R^{1e}$ are each independently hydrogen, halogen, —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl, 5- to 12-membered heteroaryl, —$OR^{1f}$, —$SO_2R^{1f}$, —$SO_2NR^{1f}R^{1g}$, —$COR^{1f}$, —$CO_2R^{1f}$, —$CONR^{1f}R^{1g}$—, —$NR^{1f}R^{1g}$, —$NR^{1f}COR^{1g}$, —$NR^{1f}CO_2R^{1g}$, —$NR^{1f}SO_2R^{1g}$, oxo, or —CN, wherein each of said —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl and 5- to 12-membered heteroaryl is optionally substituted with at least one substituent $R^{1h}$;

$R^{1f}$ and $R^{1g}$ are each independently selected from hydrogen, —$C_{1-8}$alkyl, —$C_3$-$C_8$cycloalkyl, 3- to 12-membered heterocyclyl, —$C_6$-$C_{12}$aryl and 5- to 12-membered heteroaryl, wherein each of said —$C_{1-8}$alkyl, —$C_3$-$C_8$cycloalkyl, 3- to 12-membered heterocyclyl, —$C_6$-$C_{12}$aryl and 5- to 12-membered heteroaryl is optionally substituted with at least one substituent $R^{1i}$;

$R^{1h}$ and $R^{1i}$ are each independently hydrogen, halogen, —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl, 5- to 12-membered heteroaryl, —$OR^{1j}$, —$SO_2R^{1j}$, —$SO_2NR^{1j}R^{1k}$, —$COR^{1j}$, —$CO_2R^{1j}$, —$CONR^{1j}R^{1k}$, —$NR^{1j}R^{1k}$, —$NR^{1j}COR^{1k}$, —$NR^{1j}CO_2R^{1k}$, —$NR^{1j}SO_2R^{1k}$, oxo, or —CN, wherein each of said —$C_{1-8}$alkyl, —$C_3$-$C_8$cycloalkyl, —$C_3$-$C_{12}$cycloalkenyl, 3- to 12-membered heterocyclyl, —$C_6$-$C_{12}$aryl and 5- to 12-membered heteroaryl is optionally substituted with at least one substituent selected from the group consisting of halogen, —$C_{1-8}$ alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl, —CN, —OH, —$NH_2$ or oxo;

$R^{1j}$ and $R^{1k}$ are each independently selected from hydrogen, —$C_{1-8}$alkyl, —$C_3$-$C_8$cycloalkyl, 3- to 12-membered heterocyclyl, —$C_6$-$C_{12}$aryl and 5- to 12-membered heteroaryl, wherein each of said —$C_{1-8}$alkyl, —$C_3$-$C_8$cycloalkyl, 3- to 12-membered heterocyclyl, —$C_6$-$C_{12}$aryl and 5- to 12-membered heteroaryl is optionally substituted with at least one substituent selected from the group consisting of halogen, —$C_{1-8}$ alkyl, —$C_{1-8}$alkoxy, —$C_{2-8}$alkenyl, —$C_{2-8}$alkynyl, —$C_3$-$C_8$cycloalkyl, 3- to 8-membered heterocyclyl, —$C_6$-$C_{12}$aryl, 5- to 12-membered heteroaryl, —CN, —OH, —$NH_2$ or oxo;

$R^6$ and $R^7$ are each independently selected from hydrogen or methyl.

Aspect 7. The compound of aspect 6, wherein the compound is formula (VIIa):

(VIIa)

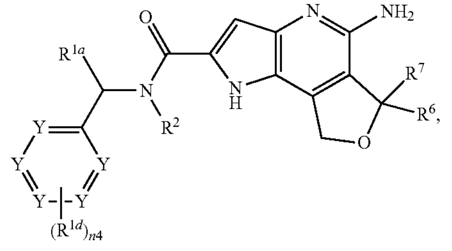

wherein, n4 is 0, 1, 2, 3 or 4; preferably, n4 is 1, 2 or 3;

each occurrence of Y is independently N or CH, preferably, zero, one or two occurrences of Y are N, and the rest are CH;

$R^{1a}$, $R^{1d}$, $R^2$, $R^6$ and $R^7$ are as defined in aspect 6;

preferably, the compound is formula (VIIb), (VIIc), (VIId), (VIIe) or (VIIf):

(VIIb)

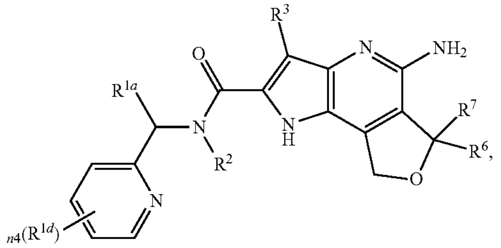

(VIIc)

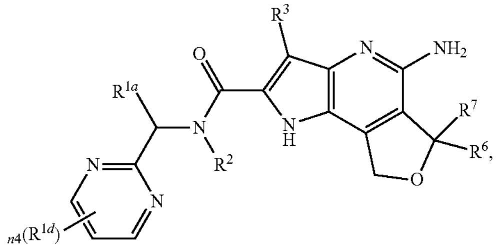

(VIId)

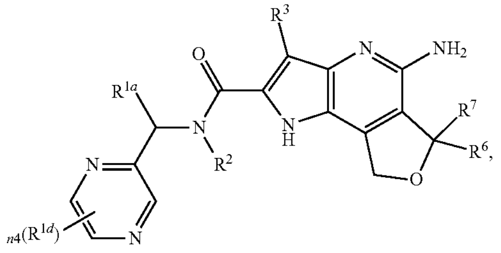

-continued
(VIIe)
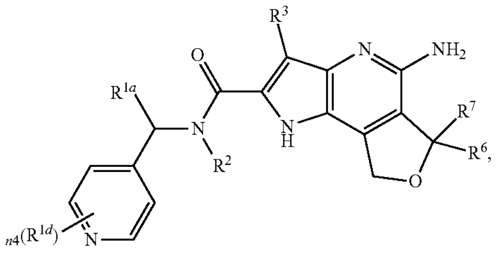
(VIIf)
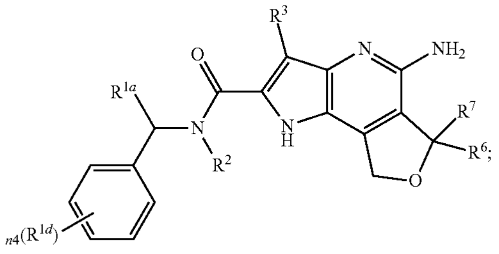
wherein, n4 is 0, 1, 2 or 3; preferably, n4 is 1 or 2; more preferably, n4 is 1;
$R^{1a}$, $R^{1d}$, $R^2$, $R^6$ and $R^7$ are as defined in aspect 6;
even more preferably, the compound is formula (VIIg), (VIIh), (VIIi), (VIIj), (VIIk), (VIIl), (VIIm), (VIIn), (VIIo), (VIIp) or (VIIq):
(VIIg)
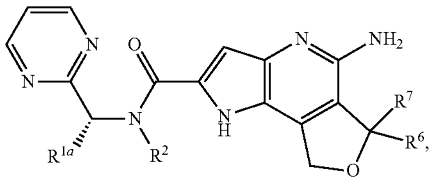
(VIIh)
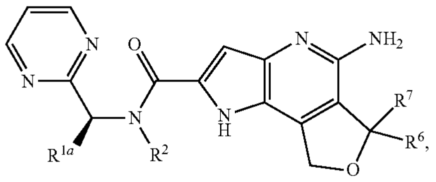
(VIIi)
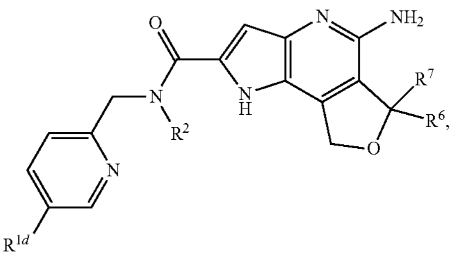
-continued
(VIIj)
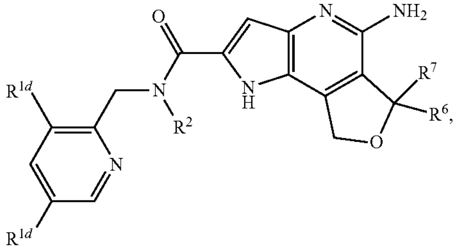
(VIIk)
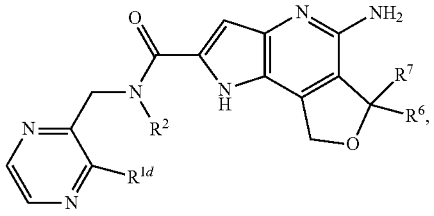
(VIIl)
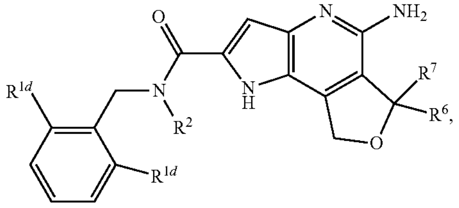
(VIIm)
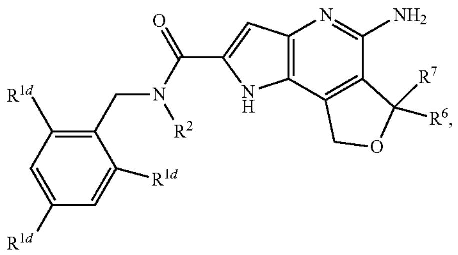
(VIIn)
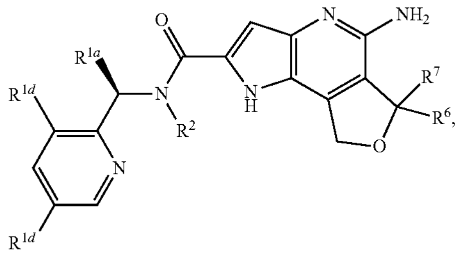
(VIIo)
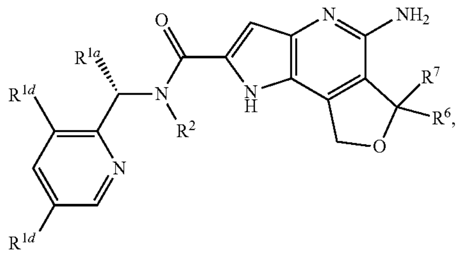

-continued (VIIp)

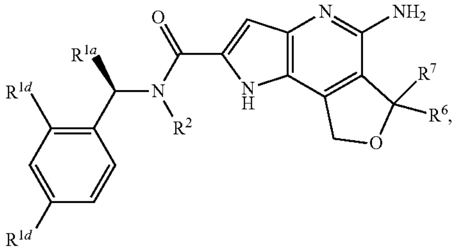

(VIIq)

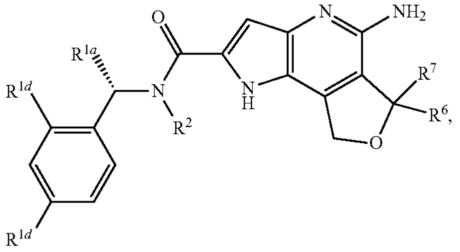

wherein, $R^{1a}$, $R^{1d}$, $R^2$, $R^6$ and $R^7$ are as defined in aspect 6.

Aspect 8. The compound of aspect 6, wherein the compound is formula (VIIIa):

(VIIIa)

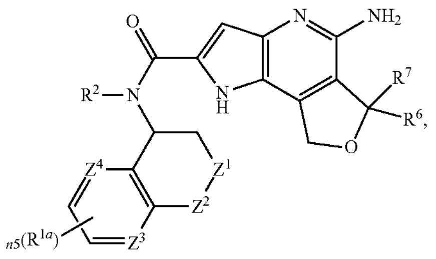

wherein, n5 is 0, 1, 2, 3 or 4; preferably, n5 is 1, 2 or 3; $Z^1$ and $Z^2$ are each independently selected from O or $CH_2$; $Z^3$ and $Z^4$ are each independently selected from N or CH; $R^{1a}$, $R^6$ and $R^7$ are as defined in aspect 6;

preferably, the compound is formula (VIIIb), (VIIIc), (VIIId), (VIIIe), (VIIIf), (VIIIg), (VIIIh), (VIIIi), (VIIIj), (VIIIk), (VIIIl), (VIIIm), (VIIIn) or (VIIIo):

(VIIIb)

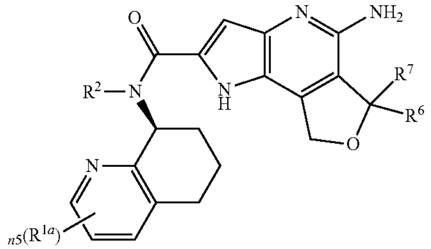

-continued (VIIIc)

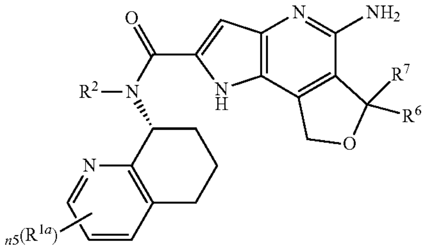

(VIIId)

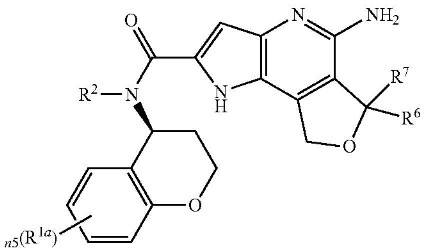

(VIIIe)

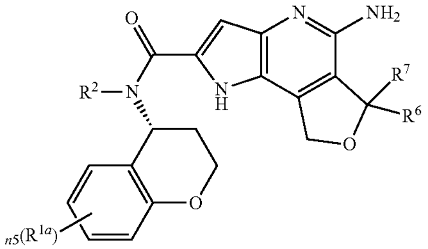

(VIIIf)

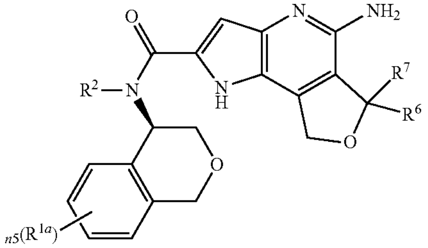

(VIIIg)

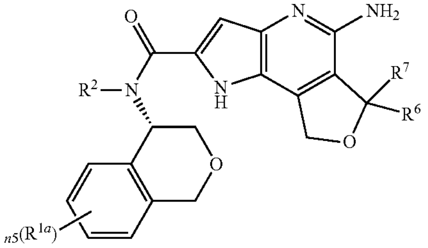

(VIIIh)

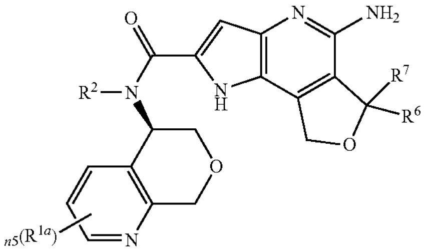

-continued (VIIIi)

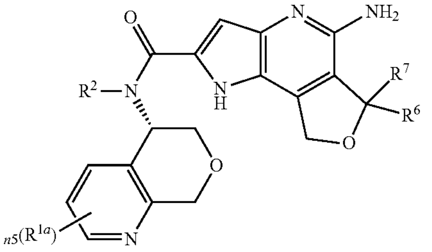

(VIIIj)

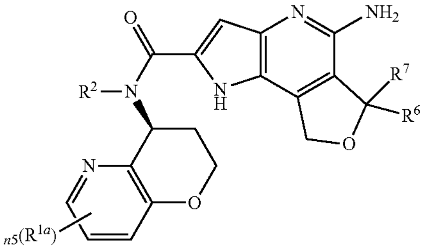

(VIIIk)

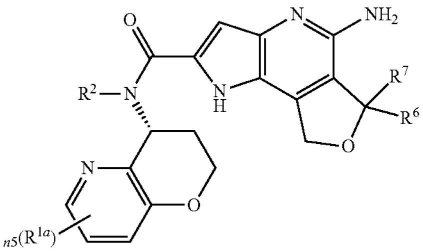

(VIIIl)

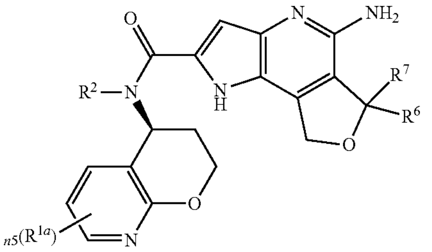

(VIIIm)

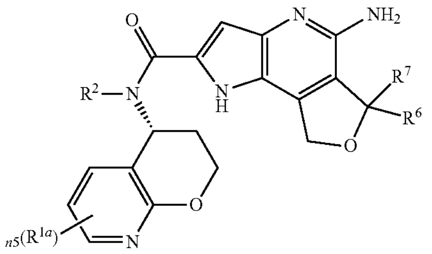

(VIIIn)

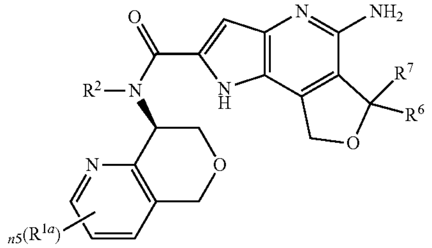

-continued (VIIIo)

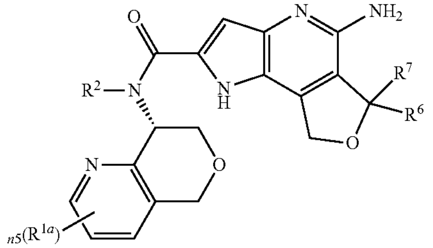

wherein, n5 is 0, 1, 2 or 3; preferably, n5 is 1 or 2; $R^{1a}$, $R^{1d}$, $R^2$, $R^6$ and $R^7$ are as defined in aspect 6; $R^{1a}$ can be substituted on any position of

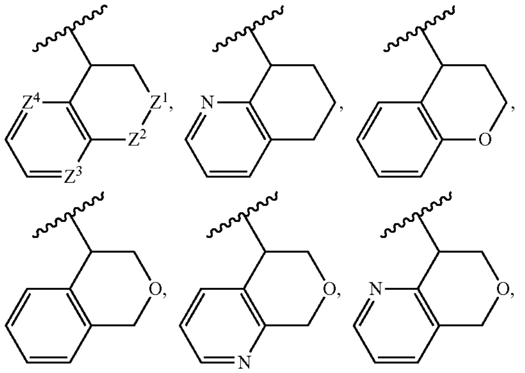

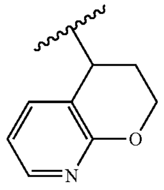

or

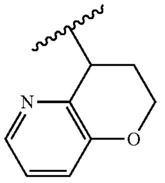

that can fulfill the valency theory.

Aspect 9. The compound of any one of the preceding aspects, wherein $R^1$ and $R^2$ are each independently selected from hydrogen, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —$C_3$-$C_{12}$cycloalkenyl, 3- to 12-membered heterocyclyl, phenyl and 5- to 12-membered heteroaryl, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, 3- to 12-membered heterocyclyl, phenyl and 5- to 12-membered heteroaryl is optionally substituted with at least one substituent $R^{1a}$; or $R^1$ and $R^2$ together with the nitrogen atom to which they are attached, form a 3-, 4-, 5-, 6-, 7- or 8-membered unsaturated or saturated ring, said ring comprising 0, 1, 2 or 3 additional heteroatoms independently selected from nitrogen, oxygen or sulfur and said ring is optionally substituted with at least one substituent $R^{1a}$;

$R^{1a}$ is independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —$C_3$-$C_{12}$cycloalkenyl, 3- to 12-membered heterocyclyl, phenyl, 5- to 12-membered heteroaryl, —$OR^{1b}$, —$SO_2R^{1b}$, —$SO_2NR^{1b}R^{1c}$, —$COR^{1b}$, —$CO_2R^{1b}$, —$CONR^{1b}R^{1c}$, —$NR^{1b}R^{1c}$, —$NR^{1b}COR^{1c}$, —$NR^{1b}CO_2R^{1c}$, —$NR^{1b}SO_2R^{1c}$, oxo, or —CN, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —$C_3$-$C_{12}$cycloalkenyl, 3- to 12-membered heterocyclyl, phenyl or 5- to 12-membered heteroaryl is optionally substituted with at least one substituent $R^{1d}$; or two $R^{1a}$ together with the atom(s) to which they are attached, form a 3-, 4-, 5-, 6-, 7- or 8-membered unsaturated or saturated ring, said ring comprising 0, 1, 2 or 3 heteroatoms independently selected from nitrogen, oxygen or sulfur and said ring is optionally substituted with at least one substituent $R^{1d}$;

$R^{1b}$ and $R^{1c}$ are each independently selected from hydrogen, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, 3- to 12-membered heterocyclyl, phenyl or 5- to 12-membered heteroaryl, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, 3- to 12-membered heterocyclyl, phenyl or 5- to 12-membered heteroaryl is optionally substituted with at least one substituent $R^{1c}$;

$R^{1d}$ and $R^{1e}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —$C_3$-$C_{12}$cycloalkenyl, 3- to 12-membered heterocyclyl, phenyl, 5- to 12-membered heteroaryl, —$OR^{1f}$, —$SO_2R^{1f}$, —$SO_2NR^{1f}R^{1g}$, —$COR^{1f}$, —$CO_2R^{1f}$, —$CONR^{1f}R^{1g}$, —$NR^{1f}R^{1g}$, —$NR^{1f}COR^{1g}$, —$NR^{1f}CO_2R^{1g}$, —$NR^{1f}SO_2R^{1g}$, oxo, or —CN, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —$C_3$-$C_{12}$cycloalkenyl, 3- to 12-membered heterocyclyl, phenyl, and 5- to 12-membered heteroaryl is optionally substituted with at least one substituent $R^{1h}$;

$R^{1f}$ and $R^{1g}$ are each independently selected from hydrogen, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, 3- to 12-membered heterocyclyl, phenyl or 5- to 12-membered heteroaryl, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, 3- to 12-membered heterocyclyl, phenyl or 5- to 12-membered heteroaryl is optionally substituted with at least one substituent $R^{1i}$;

$R^{1h}$ and $R^{1i}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —$C_3$-$C_{12}$cycloalkenyl, 3- to 12-membered heterocyclyl, phenyl, 5- to 12-membered heteroaryl, —$OR^{1j}$, —$SO_2R^{1j}$, —$SO_2NR^{1j}R^{1k}$, —$COR^{1j}$, —$CO_2R^{1j}$, —$CONR^{1j}R^{1k}$, —$NR^{1j}R^{1k}$, —$NR^{1j}COR^{1k}$, —$NR^{1j}CO_2R^{1k}$, —$NR^{1j}SO_2R^{1k}$, oxo, or —CN, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —$C_3$-$C_{12}$cycloalkenyl, 3- to 12-membered heterocyclyl, phenyl and 5- to 12-membered heteroaryl is optionally substituted with at least one substituent —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, methoxy, ethoxy, propoxy, butoxy, pentoxy, hexoxy, hepthoxy, octoxy, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl, 5- to 12-membered heteroaryl, —CN, —OH, —$NH_2$ or oxo;

$R^{1j}$ and $R^{1k}$ are each independently selected from hydrogen, methyl, ethyl, propyl, butyl, pentyl, hexyl, heptyl, octyl, cyclopropyl, cyclobutyl, cyclopentyl, cyclohexyl, cycloheptyl, cyclooctyl, 3- to 12-membered heterocyclyl, phenyl and 5- to 12-membered heteroaryl, wherein each of said methyl, ethyl, propyl, butyl, pentyl, hexyl, heptyl, octyl, cyclopropyl, cyclobutyl, cyclopentyl, cyclohexyl, cycloheptyl, cyclooctyl, 3- to 12-membered heterocyclyl, phenyl and 5- to 12-membered heteroaryl is optionally substituted with at least one substituent —F, —Cl, —Br, —I, methyl, ethyl, propyl, butyl, pentyl, hexyl, heptyl, octyl, methoxy, ethoxy, propoxy, butoxy, pentoxy, hexoxy, hepthoxy, octoxy, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl, 5- to 12-membered heteroaryl, —CN, —OH, —$NH_2$ or oxo.

Aspect 10. The compound of any one of the preceding aspects, wherein $R^1$ and $R^2$ are each independently selected from hydrogen, methyl, ethyl, propyl (iso-propyl or n-propyl), butyl (n-butyl, sec-butyl, iso-butyl or tert-butyl), cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl (iso-propyl or n-propyl), butyl (n-butyl, sec-butyl, iso-butyl or tert-butyl), cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl(preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1a}$; or $R^1$ and $R^2$ together with the nitrogen atom to which they are attached, form a 3-, 4-, 5-, 6-, 7- or 8-membered unsaturated or saturated ring, said ring comprising 0, 1, 2 or 3 additional heteroatoms independently selected from nitrogen, oxygen or sulfur; said ring is optionally substituted with at least one substituent $R^{1a}$;

$R^{1a}$ is independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, tetrahydrofuropyridinyl —$OR^{1b}$, —$SO_2R^{1b}$, —$SO_2NR^{1b}R^{1c}$, —$COR^{1b}$, —$CO_2R^{1b}$, —$CONR^{1b}R^{1c}$, —$NR^{1b}R^{1c}$, —$NR^{1b}COR^{1c}$, —$NR^{1b}CO_2R^{1c}$, —$NR^{1b}SO_2R^{1c}$, oxo, or —CN, wherein each of said methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1d}$; or two $R^{1a}$ together with the atom(s) to which they are attached, form a 3-, 4-, 5- or 6-membered unsaturated or saturated ring, said ring comprising 0, 1, 2 or 3 heteroatoms independently selected from nitrogen, oxygen or sulfur; said ring is optionally substituted with at least one substituent $R^{1d}$;

$R^{1b}$ and $R^{1c}$ are each independently selected from hydrogen, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, phenyl, chromanyl, isochromanyl, dihydropyranopyridinyl (preferably, 5,8-dihydro-6H-pyrano[3,4-b]pyridinyl, 3,4 -dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1e}$;

$R^{1d}$ and $R^{1e}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, —$OR^{1f}$, —$SO_2R^{1f}$, —$COR^{1f}$, —$CO_2R^{1f}$, —$CONR^{1f}R^{1g}$, —$NR^{1f}R^{1g}$, —$NR^{1f}COR^{1g}$, —$NR^{1f}CO_2R^{1g}$, oxo, or —CN, wherein each of said methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1h}$;

$R^{1f}$ and $R^{1g}$ are each independently selected from hydrogen, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1i}$;

$R^{1h}$ and $R^{1i}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, $—OR^{1j}$, $—COR^{1j}$, $—CO_2R^{1j}$, $—CONR^{1j}R^{1k}$, $—NR^{1j}R^{1k}$, $—NR^{1j}COR^{1k}$, $—NR^{1j}CO_2R^{1k}$, oxo, or —CN, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, methoxy, ethoxy, propoxy, butoxy, pentoxy, hexoxy, hepthoxy, octoxy, $—C_{2-8}$alkenyl, $—C_{2-8}$alkynyl, cyclopropyl, cyclobutyl, cyclopentyl, cyclohexyl, cycloheptyl, cyclooctyl, phenyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, —CN, —OH, $—NH_2$ or oxo;

$R^{1j}$ and $R^{1k}$ are each independently selected from hydrogen, methyl, ethyl, propyl, butyl, pentyl, hexyl, heptyl, octyl, cyclopropyl, cyclobutyl, cyclopentyl, cyclohexyl, cycloheptyl, cyclooctyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl, butyl, pentyl, hexyl, heptyl, octyl, cyclopropyl, cyclobutyl, cyclopentyl, cyclohexyl, cycloheptyl, cyclooctyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent —F, —Cl, —Br, —I, methyl, ethyl, propyl, butyl, pentyl, hexyl, heptyl, octyl, methoxy, ethoxy, propoxy, butoxy, pentoxy, hexoxy, hepthoxy, octoxy, $—C_{2-8}$alkenyl, $—C_{2-8}$alkynyl, cyclopropyl, cyclobutyl, cyclopentyl, cyclohexyl, cycloheptyl, cyclooctyl, phenyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, —CN, —OH, $—NH_2$ or oxo;

preferably, $R^1$ and $R^2$ are each independently selected from hydrogen, methyl, ethyl, propyl (iso-propyl or n-propyl), butyl (n-butyl, sec-butyl, iso-butyl or tert-butyl), cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl (iso-propyl or n-propyl), butyl (n-butyl, sec-butyl, iso-butyl or tert-butyl), cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3- b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1a}$; or $R^1$ and $R^2$ together with the nitrogen atom to which they are attached, form a 3-, 4-, 5-, 6-, 7- or 8-membered unsaturated or saturated ring, said ring comprising 0, 1, 2 or 3 additional heteroatoms independently selected from nitrogen, oxygen or sulfur; said ring is optionally substituted with at least one substituent $R^{1a}$;

$R^{1a}$ is independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl (preferably, 2,3-dihydrofuro[2,3-b]pyridinyl), tetrahydrofuropyridinyl, —$OR^{1b}$ or —CN, wherein each of said methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1d}$; or two $R^{1a}$ together with the atom(s) to which they are attached, form a 3-, 4-, 5- or 6-membered unsaturated or saturated ring, said ring comprising 0, 1, 2 or 3 heteroatoms independently selected from nitrogen, oxygen or sulfur; said ring is optionally substituted with at least one substituent $R^{1d}$;

$R^{1b}$ is each independently hydrogen, methyl, ethyl, propyl (iso-propyl or n-propyl), cyclopropyl or cyclobutyl;

$R^{1d}$ is each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, —$OR^{1f}$, —$NR^{1f}R^{1g}$, —$NR^{1f}COR^{1g}$, oxo, —$SO_2R^{1f}$ or —CN, wherein each of said methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3 -dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1h}$;

$R^{1f}$ and $R^{1g}$ are each independently selected from hydrogen, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1i}$;

$R^{1h}$ and $R^{1i}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b] pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, triazolyl (preferably, 1H-1,2,4-triazolyl, 4H-1,2,4-triazolyl), pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, —OH, or —CN;

more preferably, $R^1$ and $R^2$ are each independently selected from hydrogen, methyl, ethyl, propyl (iso-propyl or n-propyl), cyclopropyl, cyclobutyl, cyclopentyl, cyclohexyl, phenyl, chromanyl, isochromanyl, dihydropyranopyridinyl (preferably, 5,8-dihydro-6H-pyrano[3,4-b]pyridinyl, 3,4-dihydro-2H-pyrano[3,2-b] pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl (iso-propyl or n-propyl), phenyl, chromanyl, isochromanyl, dihydropyranopyridinyl (preferably, 5,8-dihydro-6H-pyrano[3,4-b]pyridinyl, 3,4-dihydro-2H-pyrano[3,2-b]pyridine or 7,8-dihydro-5H-pyrano[4,3-b]pyridinyl), pyrimidinyl, tetrahydro-2H-pyranyl, pyridazinyl, pyrazinyl, dihydrofuropyridinyl (preferably, 2,3-dihydrofuro[2,3-b]pyridinyl), tetrahydronaphthalenyl (preferably, 1,2,3,4-tetrahydronaphthalenyl), benzo[d]thiazolyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1a}$; or $R^1$ and $R^2$ together with the nitrogen atom to which they are attached, form a 6-membered unsaturated or saturated ring, said ring is optionally substituted with at least one substituent $R^{1a}$;

$R^{1a}$ is independently hydrogen, —F, —Cl, —Br, —I, methyl, ethyl, propyl (iso-propyl or n-propyl), cyclopropyl, cyclobutyl, cyclopentyl, cyclohexyl, phenyl, pyrimidinyl, pyridazinyl, pyrazinyl, dihydrofuropyridinyl (preferably, 2,3-dihydrofuro[2,3-b]pyridinyl), benzo[d]thiazolyl, pyridinyl, quinolinyl, isoquinolinyl, thiazolyl, —$OR^{1b}$ or —CN wherein each of said methyl, ethyl, propyl (iso-propyl or n-propyl), phenyl, pyrimidinyl, pyridazinyl, pyrazinyl, dihydrofuropyridinyl (preferably, 2,3-dihydrofuro[2,3-b]pyridinyl), benzo[d] thiazolyl, pyridinyl, quinolinyl, isoquinolinyl or thiazolyl is optionally substituted with at least one substituent $R^{1d}$;

$R^{1b}$ is each independently hydrogen, methyl, ethyl, propyl (iso-propyl or n-propyl), cyclopropyl or cyclobutyl;

$R^{1d}$ is each independently hydrogen, —F, —Cl, —Br, —I, methyl, ethyl, propyl (iso-propyl or n-propyl), butyl (n-butyl, sec-butyl, iso-butyl or tert-butyl), phenyl, pyrimidinyl, tetrahydro-2H-pyranyl, pyridazinyl, pyrazinyl, triazolyl (preferably, 1H-1,2,4-triazolyl, 4H-1,2,4-triazolyl), pyridinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, —$OR^{1f}$, —$SO_2R^{1f}$ or —CN, wherein each of said methyl, ethyl, propyl (iso-propyl or n-propyl), butyl (n-butyl, sec-butyl, iso-butyl or tert-butyl), phenyl, pyrimidinyl, tetrahydro-2H-pyranyl, pyridazinyl, pyrazinyl, triazolyl (preferably, 1H-1,2,4-triazolyl, 4H-1,2,4-triazolyl), pyridinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1h}$;

$R^{1f}$ is each independently selected from hydrogen, methyl, ethyl, propyl (iso-propyl or n-propyl), cyclopropyl, cyclobutyl, cyclopentyl, cyclohexyl or phenyl, wherein each of said methyl, ethyl, propyl (iso-propyl or n-propyl), cyclopropyl, cyclobutyl, cyclopentyl, cyclohexyl or phenyl is optionally substituted with at least one substituent $R^{1i}$;

$R^{1h}$ and $R^{1i}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, —OH, or —CN.

Aspect 11. The compound of any one of preceding aspects, wherein $R^1$ and $R^2$ are each independently selected from —$C_{1-8}$alkyl, —$C_3$-$C_8$cycloalkyl, —$C_3$-$C_{12}$cycloalkenyl and 3- to 12-membered heterocyclyl, wherein each of said —$C_{1-8}$alkyl, —$C_3$-$C_8$cycloalkyl, —$C_3$-$C_{12}$cycloalkenyl and 3- to 12-membered heterocyclyl is optionally substituted with at least one substituent $R^{1a}$; or $R^1$ and $R^2$ together with the nitrogen atom to which they are attached, form a 3- to 8-membered unsaturated or saturated ring, said ring comprising 0-3 additional heteroatoms independently selected from nitrogen, oxygen or sulfur and said ring is optionally substituted with at least one substituent $R^{1a}$;

$R^{1a}$ is independently hydrogen, halogen, deuterium, —$C_{1-8}$alkyl, —$C_3$-$C_8$cycloalkyl, —$C_6$-$C_{12}$aryl, 5- to 12-membered heteroaryl, —$OR^{1b}$ or —CN, wherein each of said —$C_{1-8}$alkyl, —$C_3$-$C_8$cycloalkyl, —$C_6$-$C_{12}$aryl and 5- to 12-membered heteroaryl is optionally substituted with at least one substituent $R^{1d}$; or two $R^{1a}$ together with the atom(s) to which they are attached, form a 3- to 8-membered unsaturated or saturated ring, said ring comprising 0-3 heteroatoms independently selected from nitrogen, oxygen or sulfur and said ring is optionally substituted with at least one substituent $R^{1d}$;

$R^{1b}$ is each independently selected from hydrogen, —$C_{1-8}$alkyl, wherein said —$C_{1-8}$alkyl is optionally substituted with at least one substituent $R^{1e}$;

$R^{1d}$ and $R^{1e}$ are each independently hydrogen, halogen, —$C_{1-8}$alkyl, —$C_3$-$C_8$cycloalkyl, —$C_6$-$C_{12}$aryl, 5- to 12-membered heteroaryl, —$OR^{1f}$, —$SO_2R^{1f}$ or —CN, wherein each of said —$C_{1-8}$alkyl, —$C_6$-$C_{12}$aryl and 5- to 12-membered heteroaryl is optionally substituted with at least one substituent $R^{1h}$;

$R^{1f}$ is each independently selected from hydrogen. —$C_{1-8}$alkyl and —$C_3$-$C_8$cycloalkyl, wherein each of said —$C_{1-8}$alkyl and —$C_3$-$C_8$cycloalkyl is optionally substituted with at least one substituent $R^{1i}$;

$R^{1h}$ and $R^{1i}$ are each independently hydrogen, halogen, —$C_{1-8}$alkyl or —CN;

preferably, $R^1$ and $R^2$ are each independently selected from methyl, ethyl, propyl (iso-propyl or n-propyl), butyl (n-butyl, sec-butyl, iso-butyl or tert-butyl), cyclopropyl, cyclobutyl, cyclopentyl, cyclohexyl, chromanyl, isochromanyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl, wherein each of said methyl, ethyl, propyl (iso-propyl or n-propyl), butyl (n-butyl, sec-butyl, iso-butyl or tert-butyl), cyclopropyl, cyclobutyl, cyclopentyl, cyclohexyl, chromanyl, isochromanyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1a}$; or $R^1$ and $R^2$ together with the nitrogen atom to which they are attached, form a 3-, 4-, 5-, 6-, 7- or 8-membered unsaturated or saturated ring, said ring comprising 0, 1, 2 or 3 additional heteroatoms independently selected from nitrogen, oxygen or sulfur; said ring is optionally substituted with at least one substituent $R^{1a}$;

$R^{1a}$ is independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, pyridinyl, pyrimidinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl (preferably, 2,3-dihydrofuro[2,3-b]pyridinyl), tetrahydrofuropyridinyl —$OR^{1b}$ or —CN, wherein each of said methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, pyridinyl, pyrimidinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1d}$; or two $R^{1a}$ together with the atom(s) to which they are attached, form a 3-, 4-, 5- or 6-membered unsaturated or saturated ring, said ring comprising 0, 1, 2 or 3 heteroatoms independently selected from nitrogen, oxygen or sulfur; said ring is optionally substituted with at least one substituent $R^{1d}$;

$R^{1b}$ is each independently selected from hydrogen, methyl, ethyl, propyl (iso-propyl or n-propyl), butyl (n-butyl, sec-butyl, iso-butyl or tert-butyl), pentyl, hexyl, heptyl and octyl, wherein each of said methyl, ethyl, propyl (iso-propyl or n-propyl), butyl (n-butyl, sec-butyl, iso-butyl or tert-butyl), pentyl, hexyl, heptyl and octyl is optionally substituted with at least one substituent $R^{1e}$;

$R^{1d}$ and $R^{1e}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, cyclopropyl, cyclobutyl, cyclopentyl, cyclohexyl, phenyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl, tetrahydrofuropyridinyl, —$OR^{1f}$, —$SO_2R^{1f}$ or —CN, wherein each of said methyl, ethyl, propyl (iso-propyl or n-propyl), butyl (n-butyl, sec-butyl, iso-butyl or tert-butyl), pentyl, hexyl, phenyl, pyridinyl, quinolinyl, isoquinolinyl, pyrazolyl, imidazolyl, thiazolyl, tetrahydropyranyl, tetrahydroquinolinyl, tetrahydronaphthyl, dihydrofuropyridinyl or tetrahydrofuropyridinyl is optionally substituted with at least one substituent $R^{1h}$;

$R^{1f}$ is each independently selected from hydrogen, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl or cyclooctyl, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl or cyclooctyl is optionally substituted with at least one substituent $R^{1i}$;

$R^{1h}$ and $R^{1i}$ are each independently hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl or —CN.

Aspect 12. The compound of any one of preceding aspects, wherein $R^1$ and $R^2$ are each independently selected from -Me, -Et, —Pr (-nPr or -isoPr), -Bu (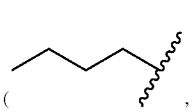, 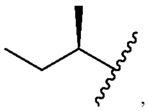, 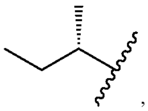,

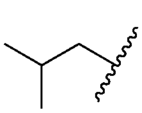 or 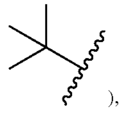), pentyl (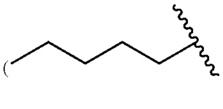, 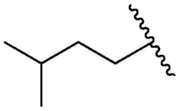,

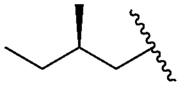, 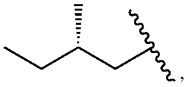,

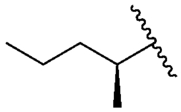, 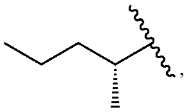,

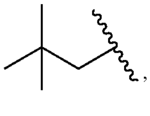, 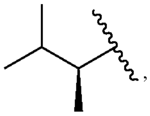, 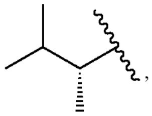,

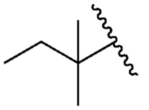 or 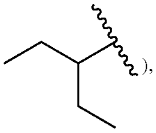), —$CF_3$, —$CH_2CF_3$,

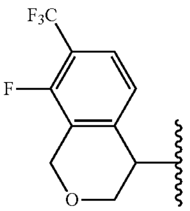 (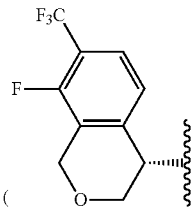 or

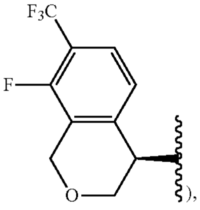), 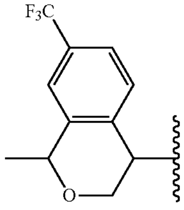

-continued
( 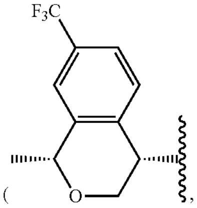 , 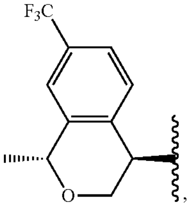 ,
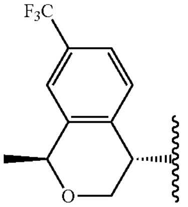 or 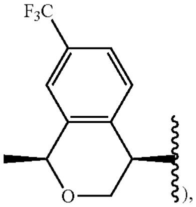 ),
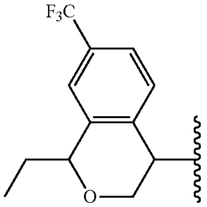 ( 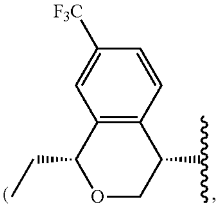 ,
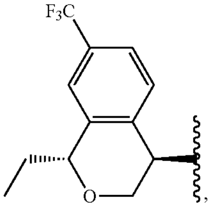 , 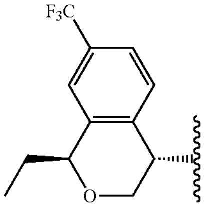 or
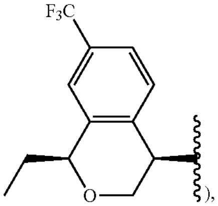 ), 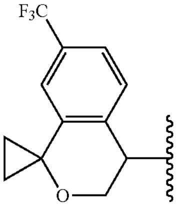
( 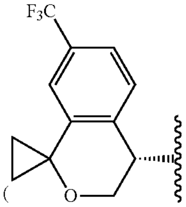 or 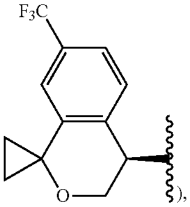 ),
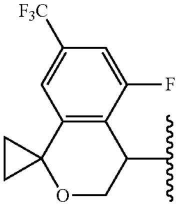 ( 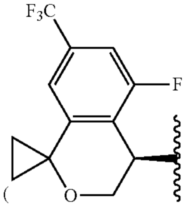 or
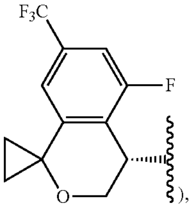 ), 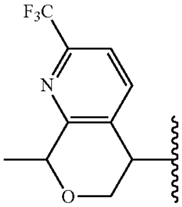
-continued
( 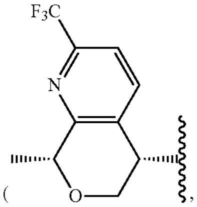 , 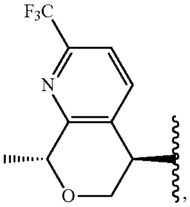 ,
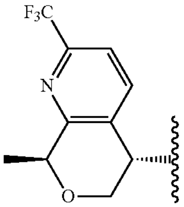 or 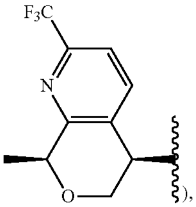 ),
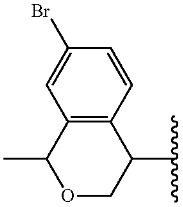 ( 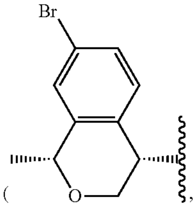 , 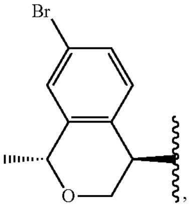 ,
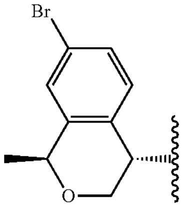 or 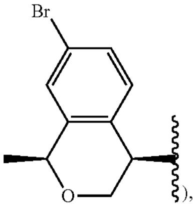 ),
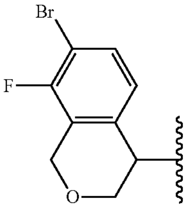 ( 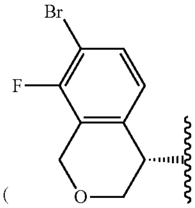 or
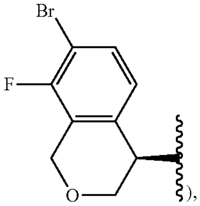 ), 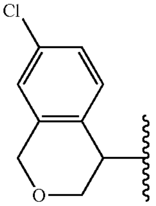 ( 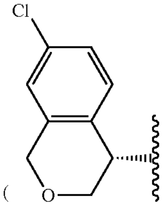 or
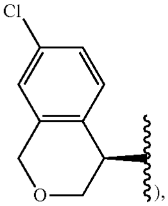 ), 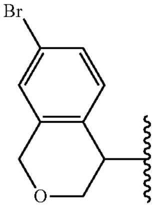 ( 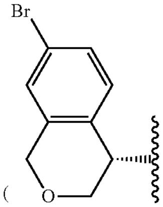 or
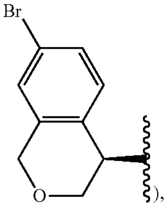 ), 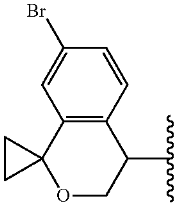 ( 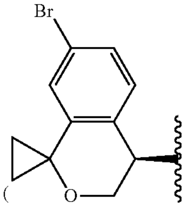 or -continued
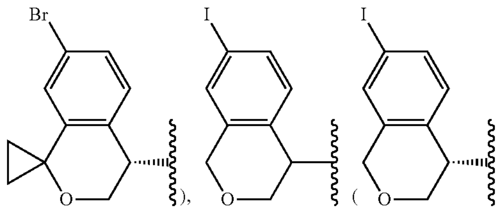
or
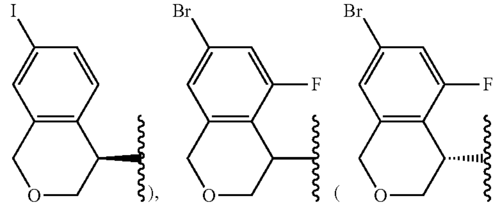
or
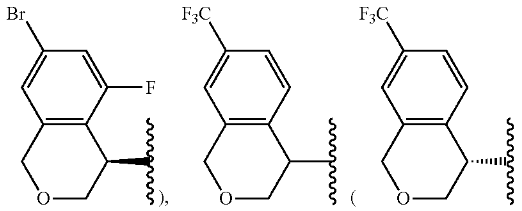
or
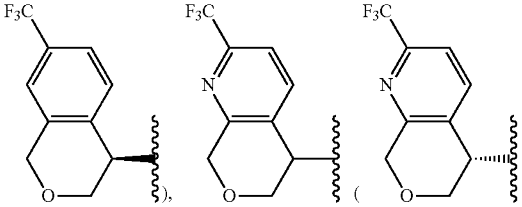
or
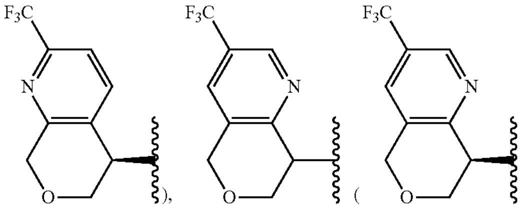
or
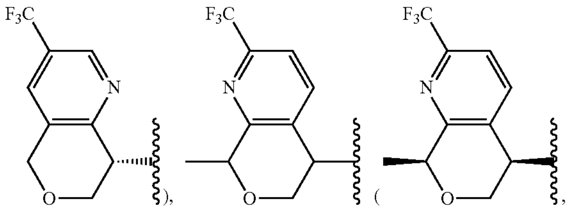
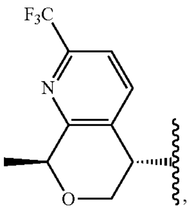
or
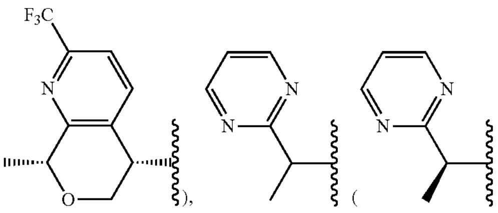
or
-continued
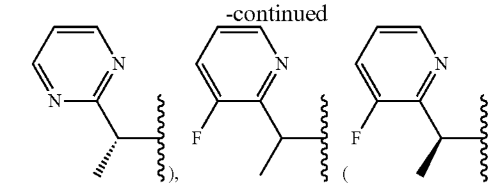
or
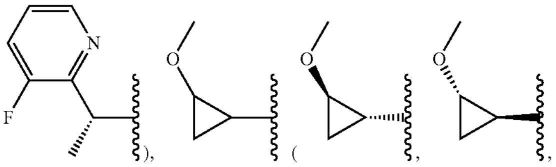
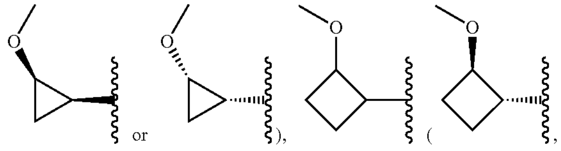
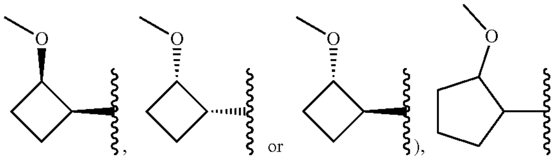
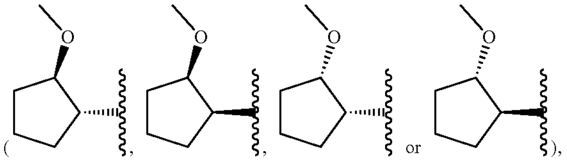
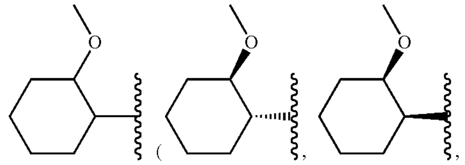
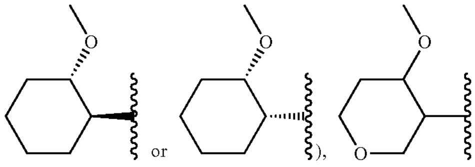
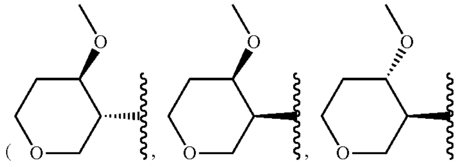
or
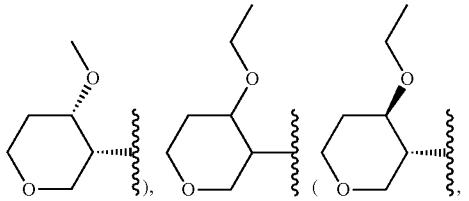
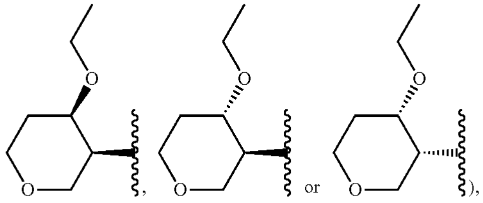

-continued
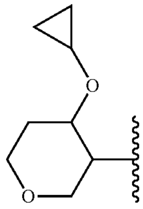 ( 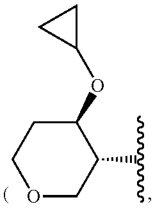, 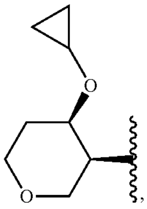,
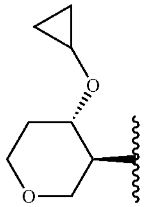 or 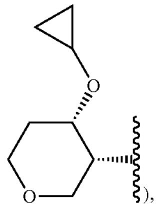), 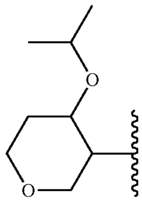
( 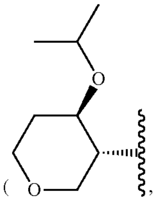, 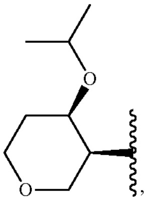, 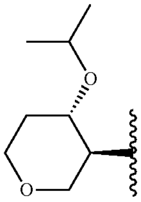 or
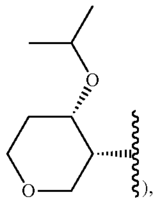), 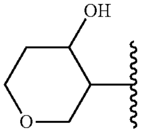 ( 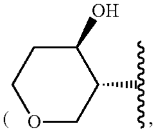,
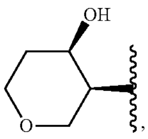, 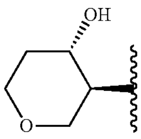 or 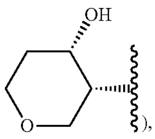),
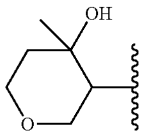 ( 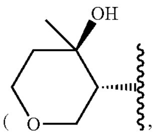, 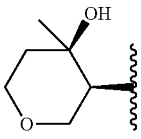,
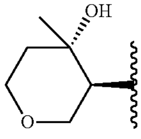 or 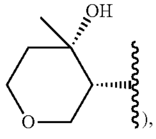),
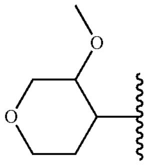 ( 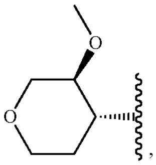, 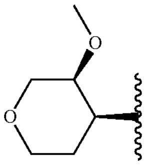,
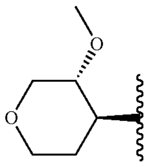 or 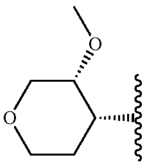),
-continued
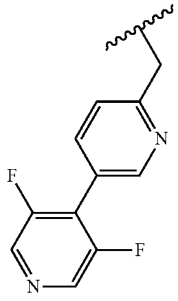, 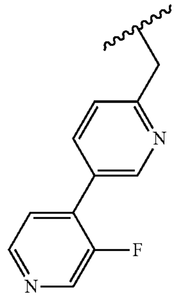,
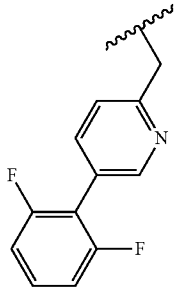, 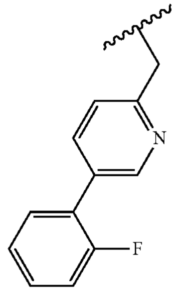,
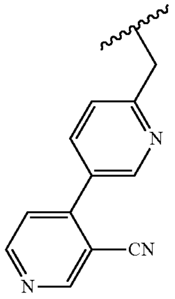, 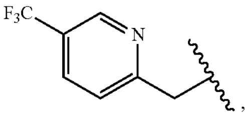,
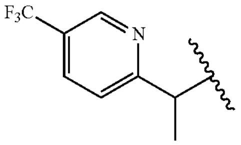 ( 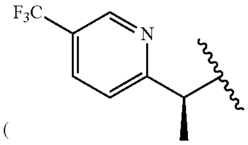 or
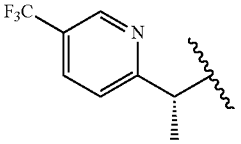), 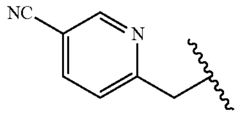,
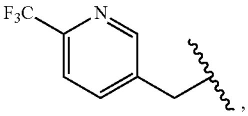, 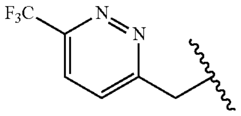,
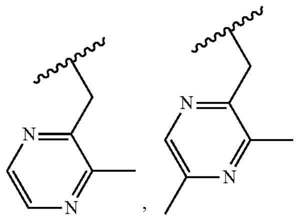, 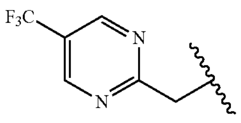,
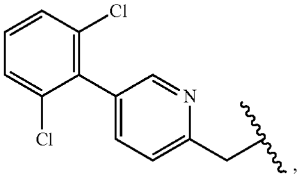, -continued
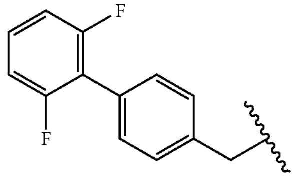,
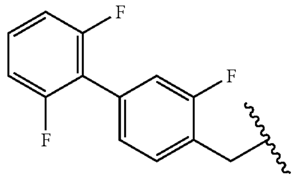,
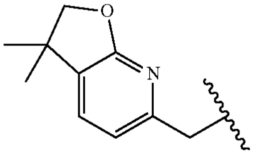, 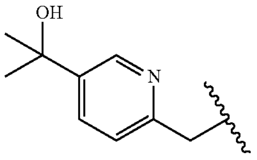,
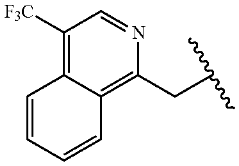, 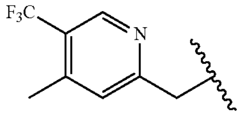,
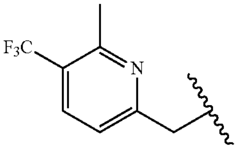, 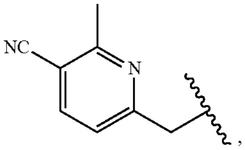,
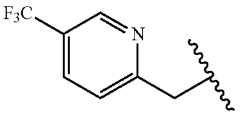, 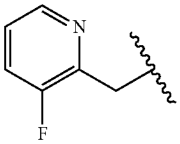,
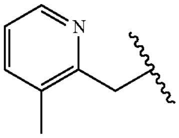, 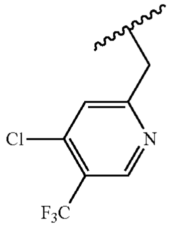,
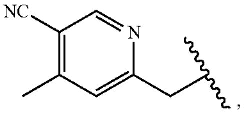, 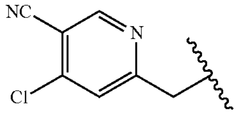,
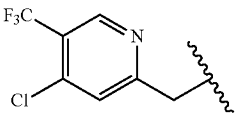, 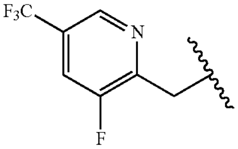,
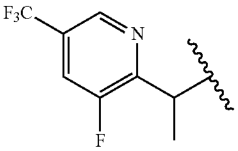 ( 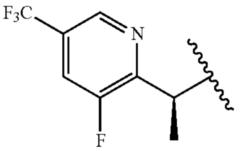 or
-continued
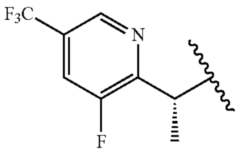 ),
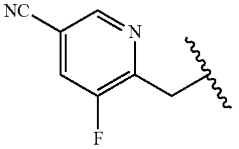, 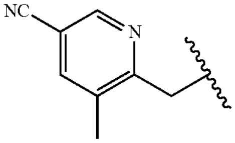,
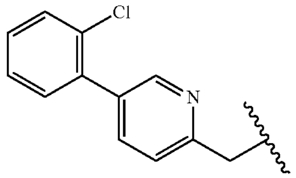,
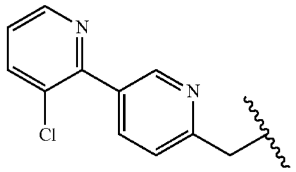,
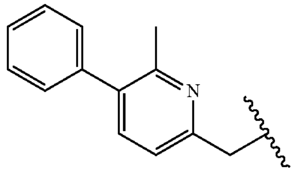,
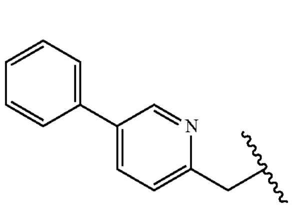, 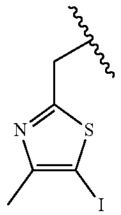,
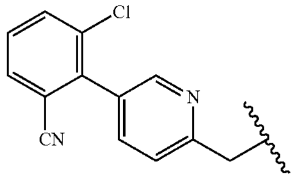,
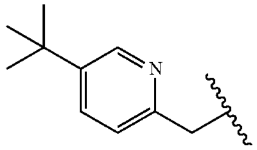,
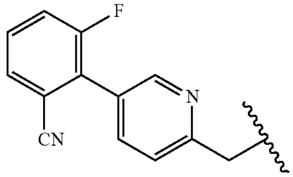, 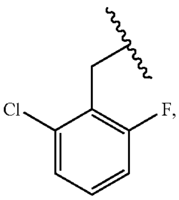

-continued
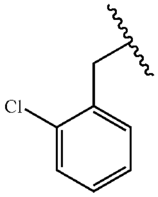,
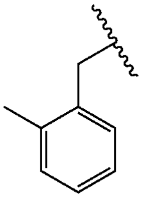,
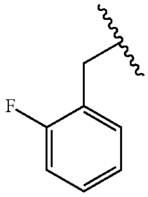,
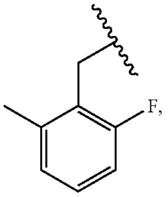
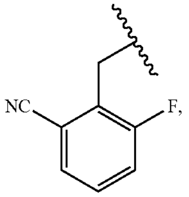
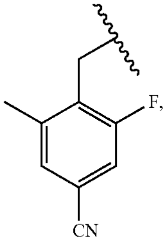
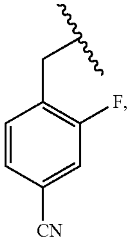
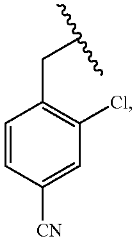
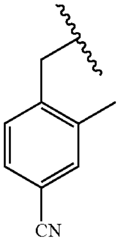,
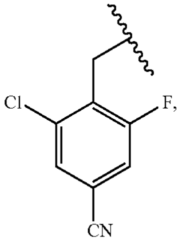
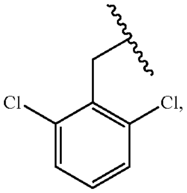
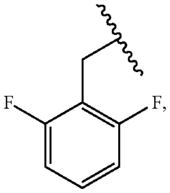
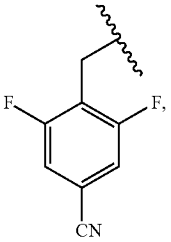
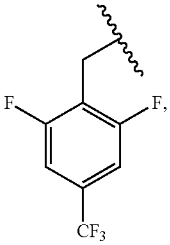
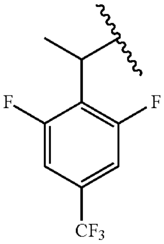
(
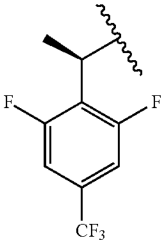
or
-continued
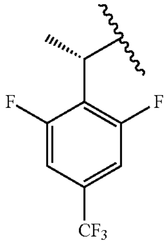
),
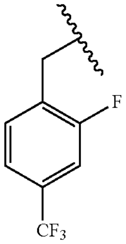,
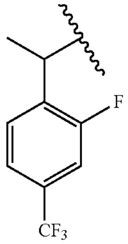
(
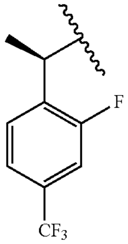
or
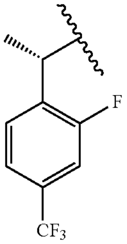
),
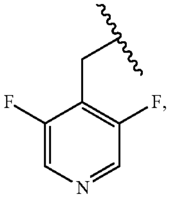
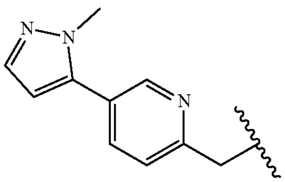,
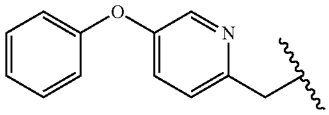,
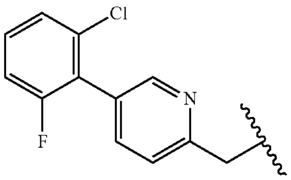,
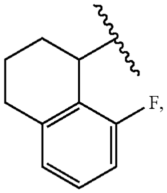
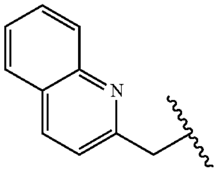,
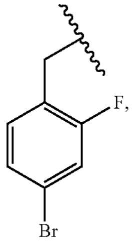
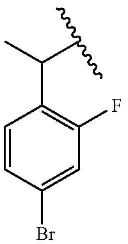
(
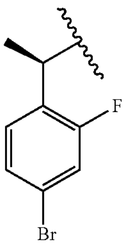
or -continued
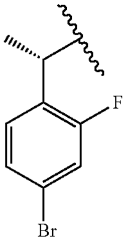
),
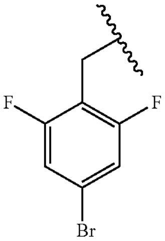
,
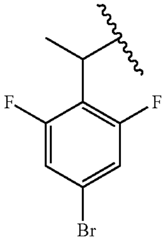
(
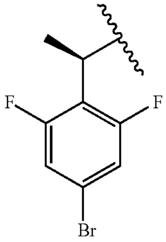
or
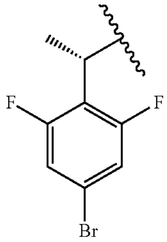
),
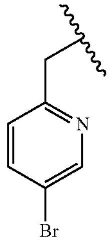
,
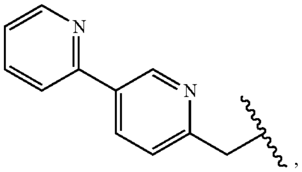
,
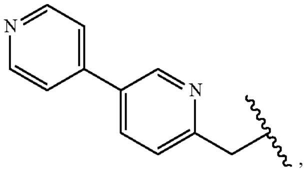
,
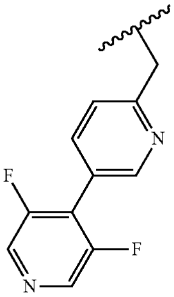
,
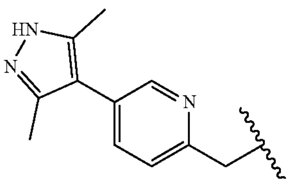
,
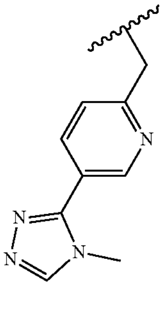
,
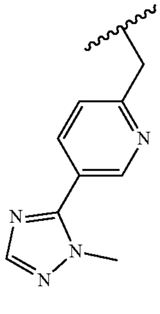
,
-continued
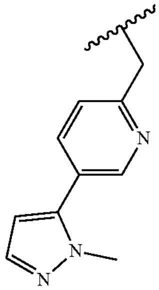
,
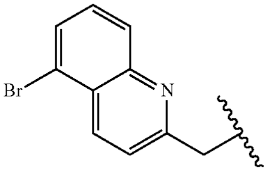
,
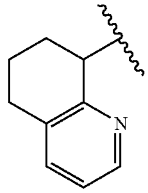
(
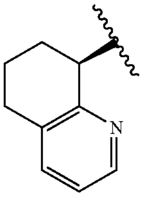
or
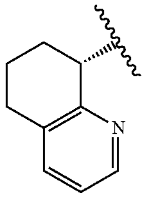
),
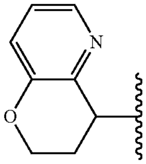
(
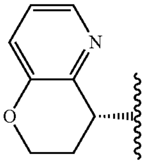
or
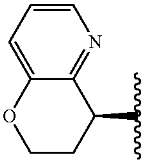
),
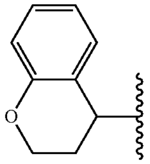
(
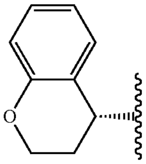
or
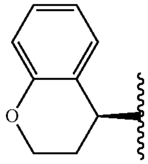
),
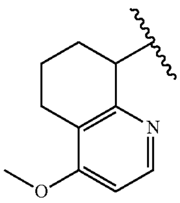
,
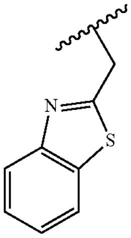
,
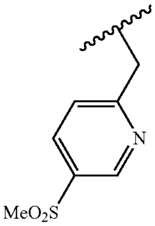
,
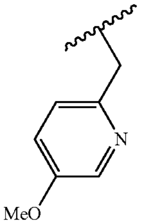
,
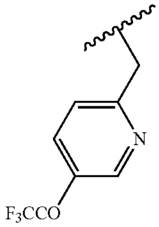
, -continued
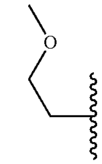, 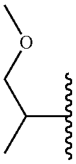, 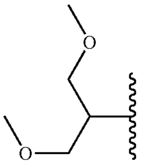,
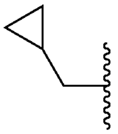, 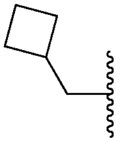, 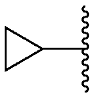,
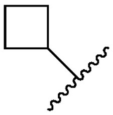, 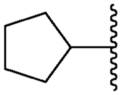, 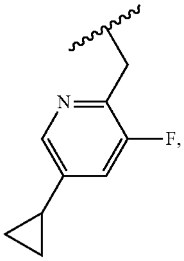
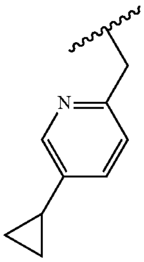, 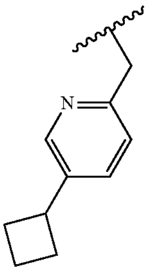, 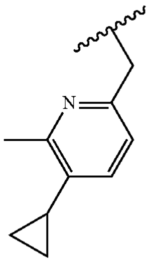,
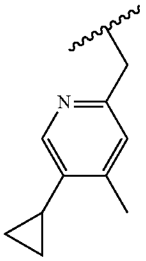, 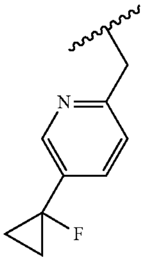, 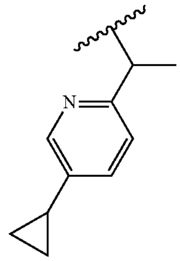
( 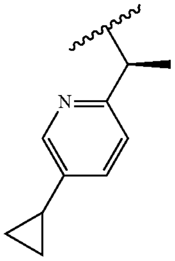 or 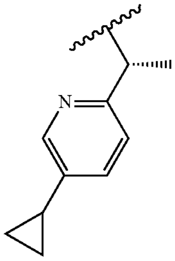 ),
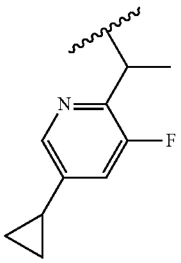 ( 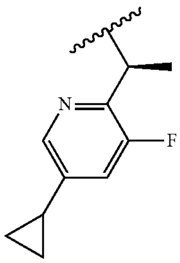 or
-continued
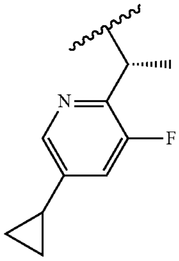 ), 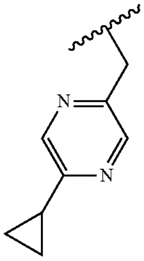,
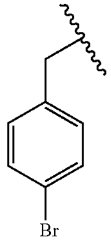, 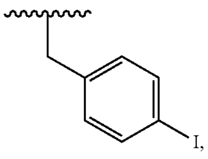 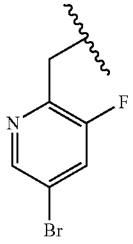,
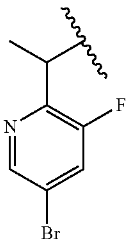 ( 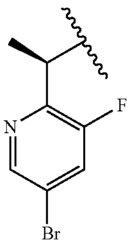 or 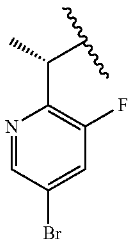 ),
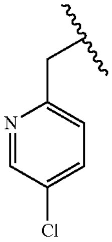, 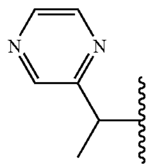 ( 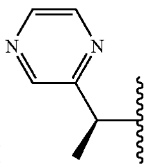 or
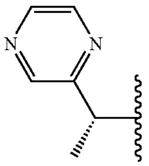 ), 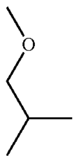 ( 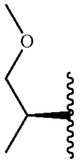 or 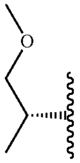 ),
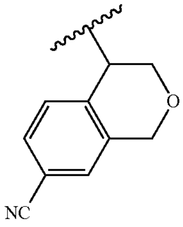 ( 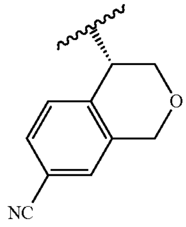 or
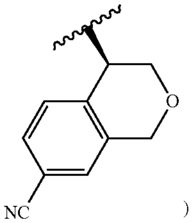 ), 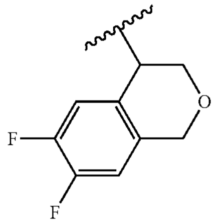

-continued
(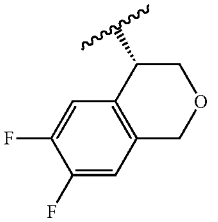
or
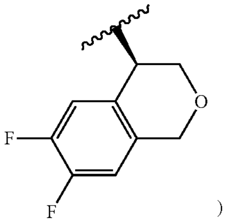
),
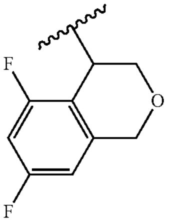
(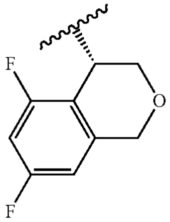
or
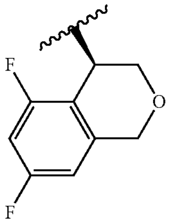
),
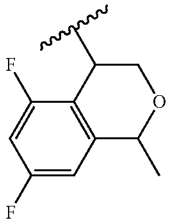
(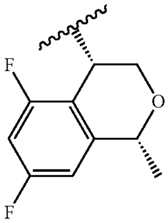
,
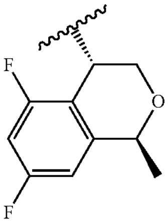
,
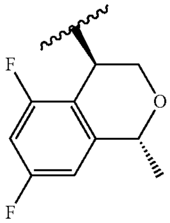
or
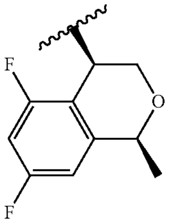
),
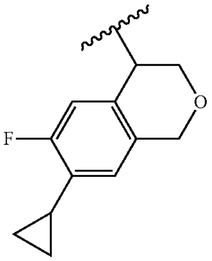
(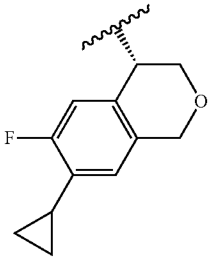
or
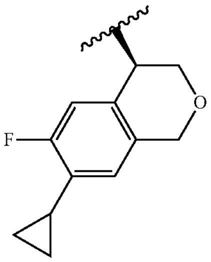
),
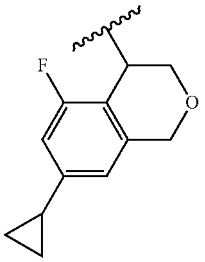
(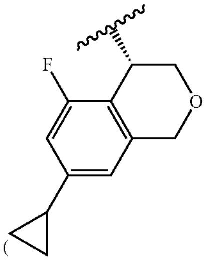
or
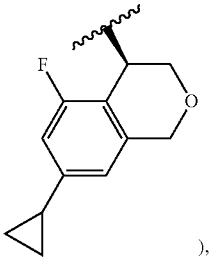
),
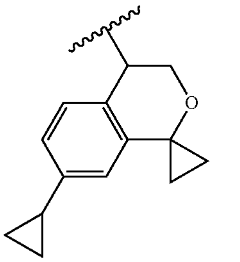
(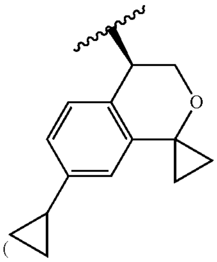
or
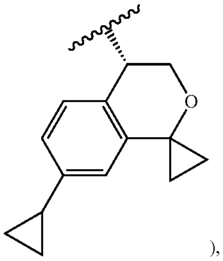
),
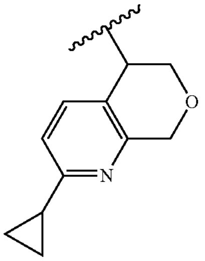
(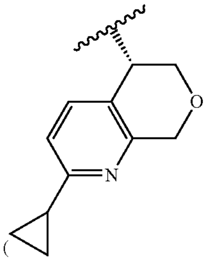
or
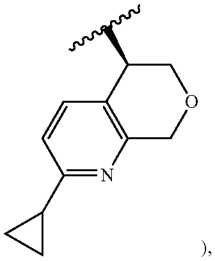
),
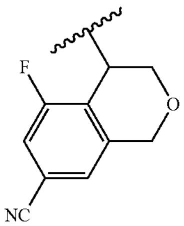
(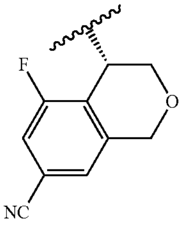
or
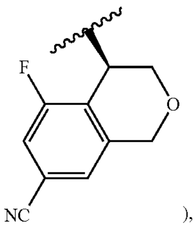
),
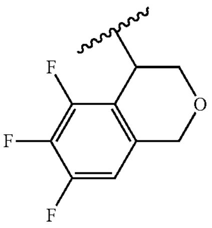

-continued
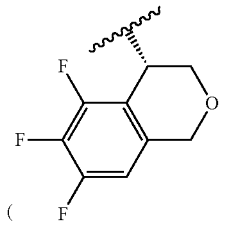
or
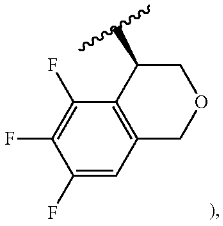
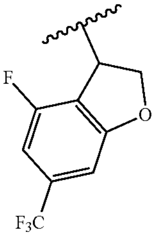
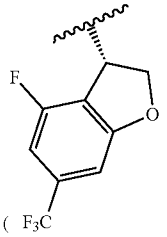
or
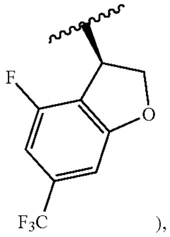
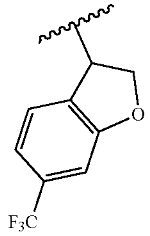
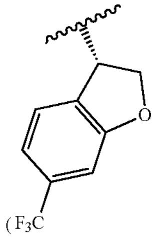
or
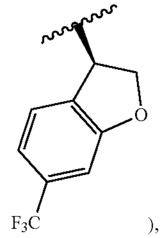
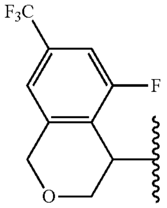
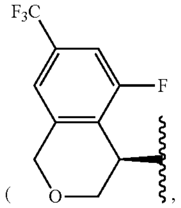
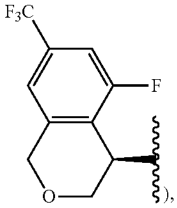
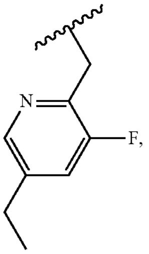
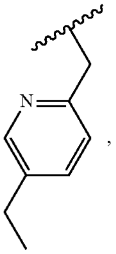
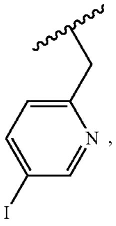
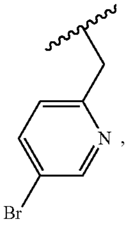
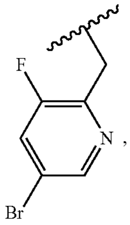
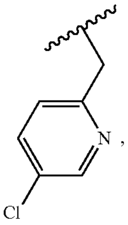
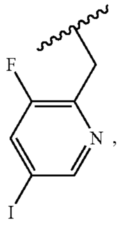
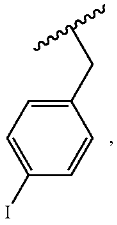
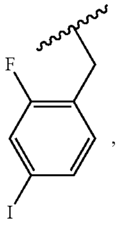
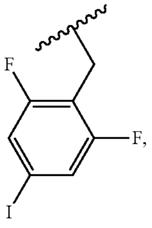
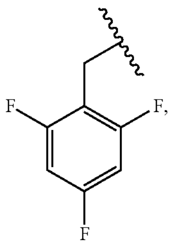
-continued
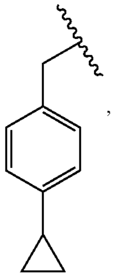
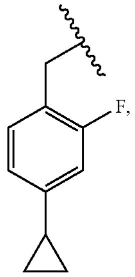
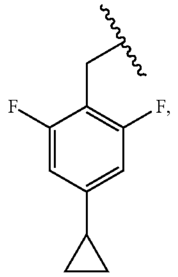
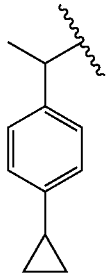
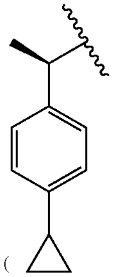
or
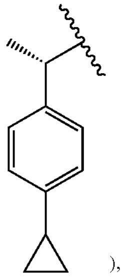
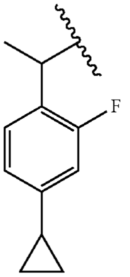
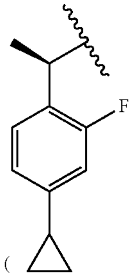
or
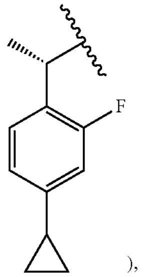
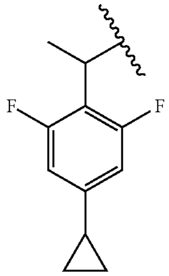
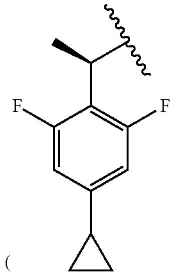
or
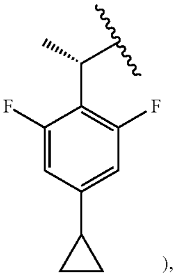
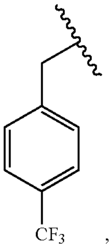
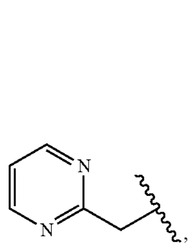
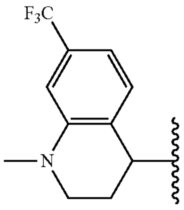
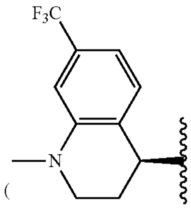
or -continued
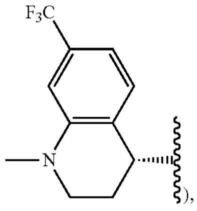
),
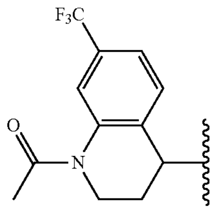
(
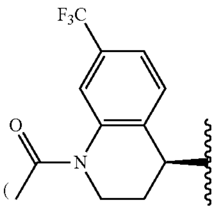
or
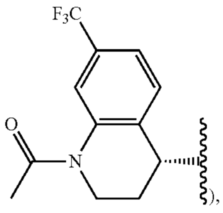
),
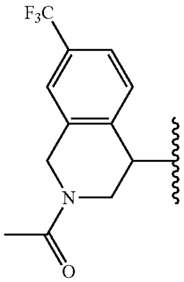
(
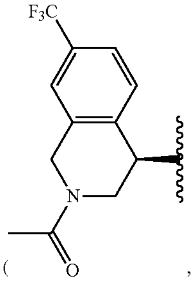
,
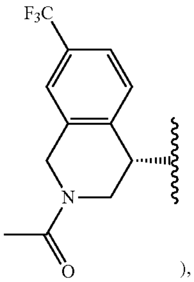
),
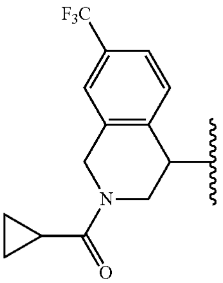
(
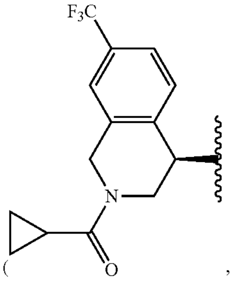
,
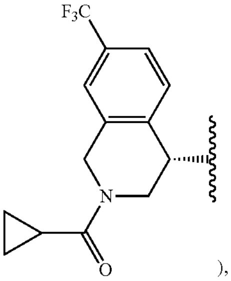
),
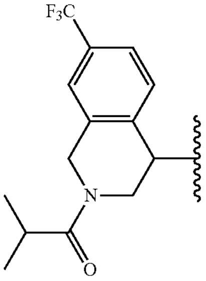
(
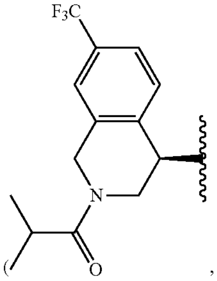
,
-continued
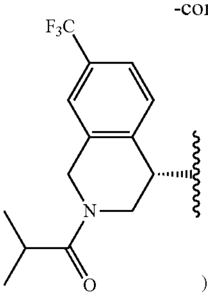
),
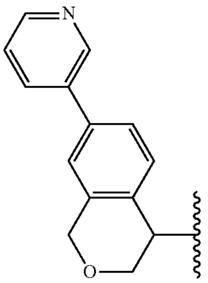
(
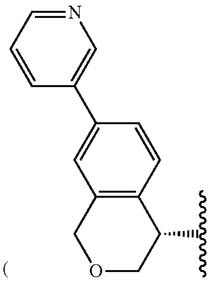
or
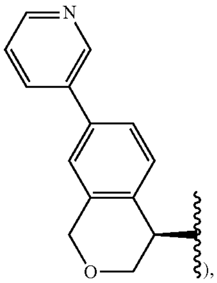
),
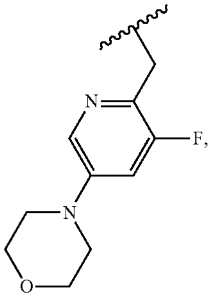
,
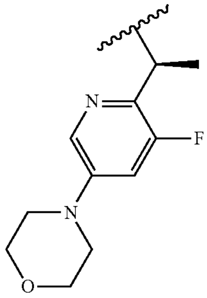
(
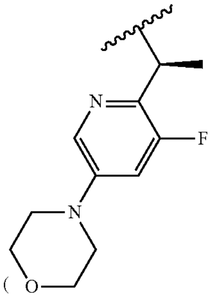
or
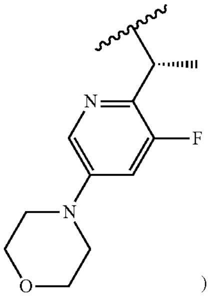
) or
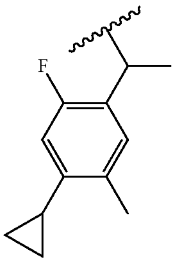
(
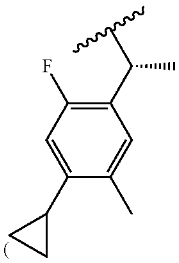
or
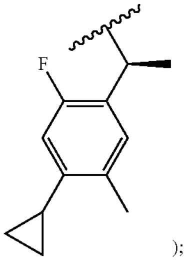
);

or $R^1$ and $R^2$ together with the nitrogen atom to which they are attached, form

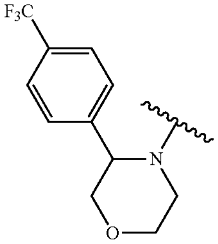
,
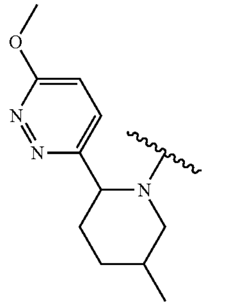

(
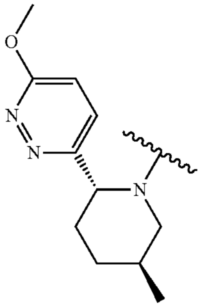
,
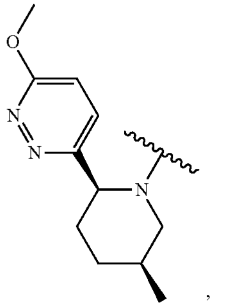
,
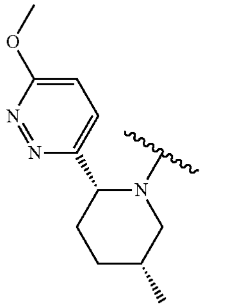
or
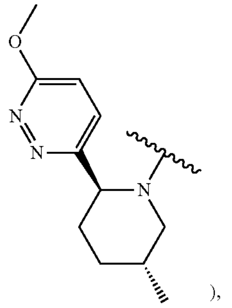
),

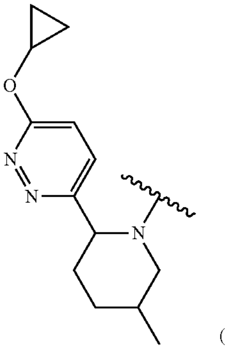
(
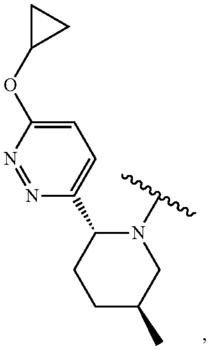
,
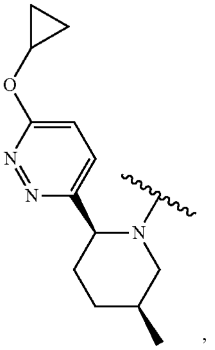
,
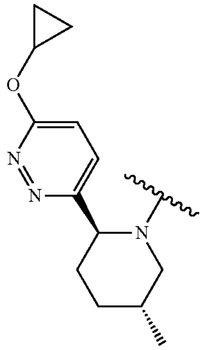
or

-continued

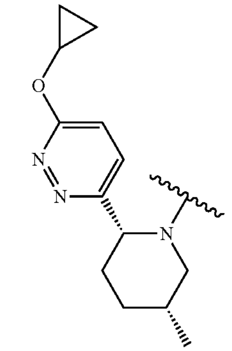
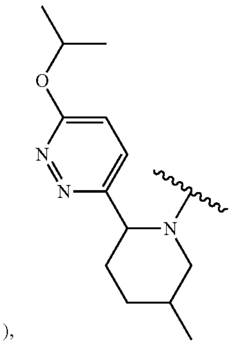
), (
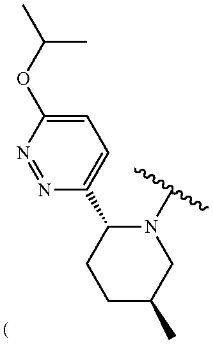
,
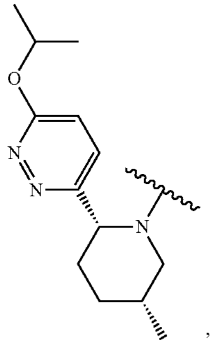
,
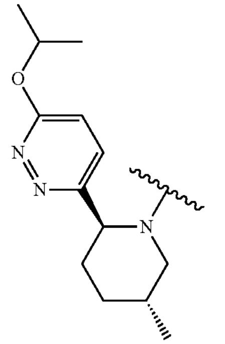
or
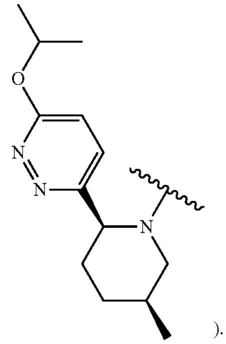
).

Aspect 13. The compound of any one of the preceding aspects, wherein L is a single bond.

Aspect 13'. The compound of any one of the preceding aspects, wherein $R^{1a}$ is independently selected from hydrogen, methyl, ethyl, propyl, halo, methyl substituted with one or more halo, $C_{3-5}$cycloalkyl, or —CN, or two $R^{1a}$ attached to the same atom form $C_{3-5}$cycloalkyl; preferably, $R^{1a}$ is independently selected from hydrogen, methyl, ethyl, —F, —Cl, —Br, —I, —$CF_3$, cyclopropyl, or —CN, or two $R^{1a}$ attached to the same atom form cyclopropyl.

Aspect 13". The compound of any one of the preceding aspects, wherein $R^{1d}$ is independently selected from hydrogen, halo, $C_{1-4}$alkyl, $C_{1-4}$alkyl substituted with one or more halo, $C_{1-4}$alkyl substituted with —OH, —O—$C_{1-4}$alkyl, —O—$C_{1-4}$alkyl substituted with one or more halo, $C_{3-5}$cycloalkyl optionally substituted with fluoro, —$SO_2$—$C_{1-4}$alkyl, or —CN; preferably, $R^{1d}$ is selected from hydrogen, —F, —Br, —Cl, —I, methyl, ethyl, propyl, butyl, —$CF_3$, hydroxypropyl, methoxy, trifluoromethoxy, cyclopropyl, fluorocyclopropyl, cyclobutyl, —$SO_2CH_3$, or —CN.

Aspect 13'". The compound of any one of the preceding aspects, wherein $R^2$ is $C_{1-8}$ alkyl; preferably, $R^2$ is methyl, ethyl, propyl (iso-propyl or n-propyl), or butyl (n-butyl, sec-butyl, iso-butyl or tert-butyl); more preferably, $R^2$ is methyl, ethyl, or propyl (iso-propyl or n-propyl); yet more preferably, $R^2$ is methyl.

Aspect 14. The compound of any one of the preceding aspects, wherein $R^3$ is selected from hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —CN, —OH or —$NH_2$, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl or cyclooctyl is optionally substituted with at least one substituent selected from —F, —Cl, —Br, —I, methoxy, ethoxy, propoxy, butoxy, pentoxy, hexoxy, hepthoxy, octoxy, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl or 3- to 8-membered heterocyclyl;

preferably, $R^3$ is selected from hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —CN, —OH or —$NH_2$;

more preferably, $R^3$ is selected from hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, —CN, —OH;

even more preferably, $R^3$ is selected from hydrogen, —F, —Cl, methyl, ethyl, propyl (iso-propyl or n-propyl), butyl (n-butyl, sec-butyl, iso-butyl or tert-butyl);

even more preferably, $R^3$ is selected from hydrogen.

Aspect 15. The compound of any one of preceding aspects, wherein $R^4$, $R^5$, $R^6$, $R^7$, $R^8$ and $R^9$ are each independently selected from hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl or cyclooctyl, wherein each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl or cyclooctyl is optionally substituted with at least one substituent selected from —F, —Cl, —Br, —I, methoxy, ethoxy, propoxy, butoxy, pentoxy, hexoxy, hepthoxy, octoxy, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, 3- to 8-membered heterocyclyl, phenyl, 5- to 12-membered heteroaryl, oxo, —CN, —$OR^{4a}$, —$SO_2R^{4a}$, —$SO_2NR^{4a}R^{4b}$, —$COR^{4a}$, —$CO_2R^{4a}$, —$CONR^{4a}R^{4b}$, —$NR^{4a}R^{4b}$, —$NR^{4a}COR^{4b}$, —$NR^{4a}CO_2R^{4b}$, or —$NR^{4a}SO_2R^{4b}$;

$R^{4a}$ and $R^{4b}$ are each independently hydrogen, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl; each of said methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl, cyclooctyl, 3- to 8-membered heterocyclyl, phenyl, or 5- to 12-membered heteroaryl is optionally substituted with at least one —F, —Cl, —Br, —I, —OH, methyl, ethyl, propyl (iso-propyl or n-propyl), butyl (n-butyl, sec-butyl, iso-butyl or tert-butyl), pentyl, hexyl, heptyl, octyl, methoxy, ethoxy, propoxy, butoxy, pentoxy, hexoxy, hepthoxy, octoxy, $C_{1-8}$alkoxy-$C_{1-8}$alkyl-, —$C_{2-8}$alkenyl, —$C_{2-8}$alkynyl, cyclopropyl, cyclobutyl, cyclopentyl, cyclohexyl, cycloheptyl, cyclooctyl, 3- to 8-membered heterocyclyl, phenyl, or 5- to 12-membered heteroaryl;

preferably, $R^4$, $R^5$, $R^6$, $R^7$, $R^8$ and $R^9$ are each independently selected from hydrogen, —F, —Cl, —Br, —I, methyl, ethyl, propyl (iso-propyl or n-propyl), butyl (n-butyl, sec-butyl, iso-butyl or tert-butyl), pentyl, hexyl, heptyl, octyl, cyclopropyl, cyclobutyl, cyclopentyl, cyclohexyl, cycloheptyl or cyclooctyl;

more preferably, $R^4$, $R^5$, $R^6$, $R^7$, $R^8$ and $R^9$ are each independently selected from hydrogen, —F, —Cl, —Br, —I, methyl, ethyl, propyl (iso-propyl or n-propyl), cyclopropyl, cyclobutyl, even more preferably, $R^4$, $R^5$, $R^6$, $R^7$, $R^8$ and $R^9$ are each independently selected from hydrogen, —F, —Cl, —Br, —I, methyl.

Aspect 15'. A compound of formula (VIIIp):

(VIIIp)

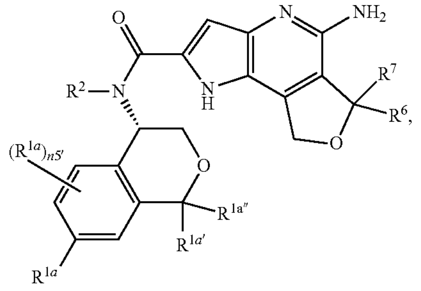

or an N-oxide thereof, or a pharmaceutically acceptable salt, stereoisomer, tautomer, or a deuterated analog therefor an N-oxide thereof, or a pharmaceutically acceptable salt thereof, or a stereoisomer thereof, or a tautomer thereof, or a deuterated analog thereof, wherein:

$R^{1a'}$ is independently selected from hydrogen, methyl or ethyl: $R^{1a''}$ is hydrogen; or $R^{1a'}$ and $R^{1a''}$ together with the atom to which they are attached, form a $C_{3-5}$cycloalkyl;

n5' is 0, 1 or 2; and $R^{1a}$, $R^2$, $R^6$, and $R^7$ are as defined in any one of the preceding aspects.

In one embodiment:

$R^{1a}$ is independently selected from halo, methyl substituted with one or more halo, $C_{3-5}$cycloalkyl or —CN; preferably, —F, —Cl, —Br, —I, —$CF_3$, cyclopropyl or —CN;

$R^2$ is $C_{1-8}$alkyl; preferably, methyl;

$R^6$ is hydrogen or methyl; preferably, hydrogen; and $R^7$ is hydrogen.

Aspect 15". A compound of formula (VIIr):

(VIIr)

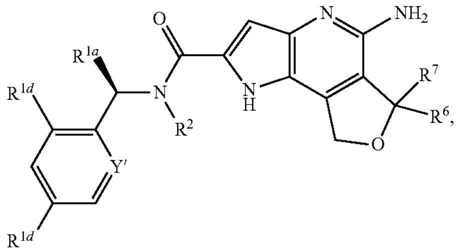

or an N-oxide thereof, or a pharmaceutically acceptable salt thereof, or a stereoisomer thereof, or a tautomer thereof, or a deuterated analog thereof, wherein Y' is N or $C(R^{1d})$, and $R^{1a}$, $R^{1d}$, $R^2$, $R^6$, and $R^7$ are as defined in any one of the preceding aspects.

In one embodiment:

$R^{1a}$ is hydrogen or methyl;

$R^{1d}$ is independently selected from hydrogen, halo, methyl substituted with one or more halo, $C_{3-5}$cycloalkyl optionally substituted with fluoro, or —CN; preferably, hydrogen, —F, —Br, —I, —$CF_3$, cyclopropyl, fluorocyclopropyl, cyclobutyl or —CN;

$R^2$ is $C_{1-8}$alkyl; preferably, methyl, ethyl, or propyl;

$R^6$ is hydrogen or methyl; and $R^7$ is hydrogen.

In one embodiment, Y' is N. In one embodiment, Y' is $C(R^{1d})$.

Aspect 16. The compound of any one of the preceding aspects, wherein the compound is selected from:

Example 1

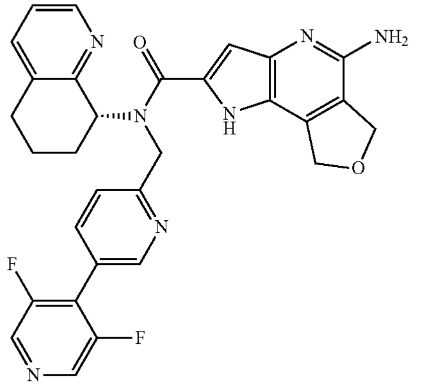

Example 2

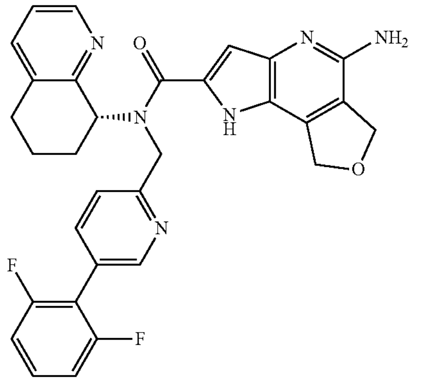

-continued

Example 3

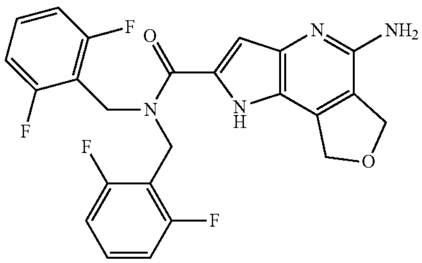

Example 4

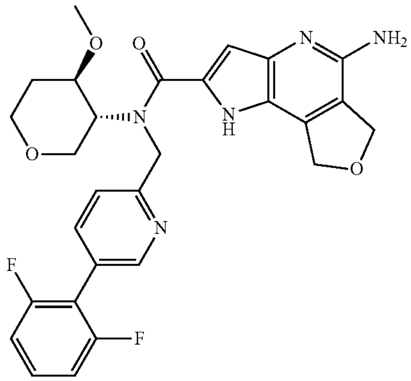

Example 5

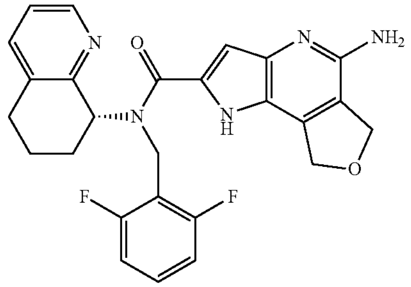

Example 6

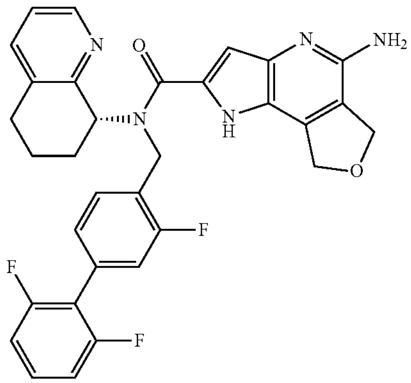

Example 7

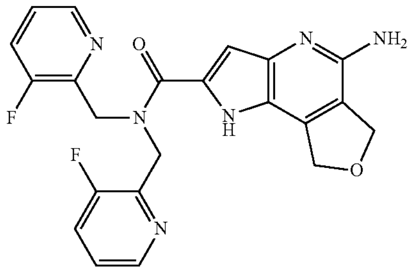

-continued
Example 8
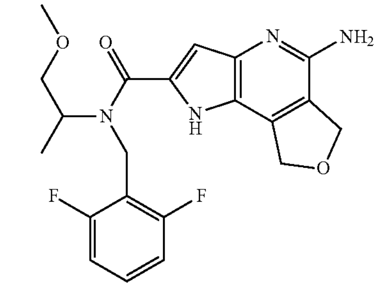
Example 9
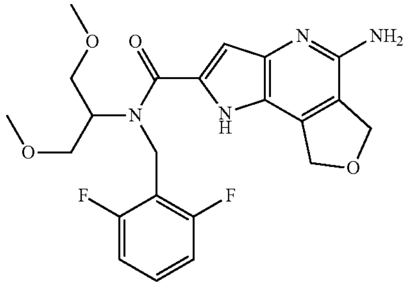
Example 10
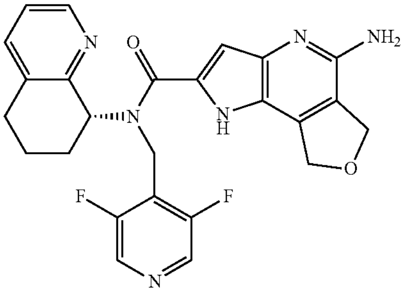
Example 11
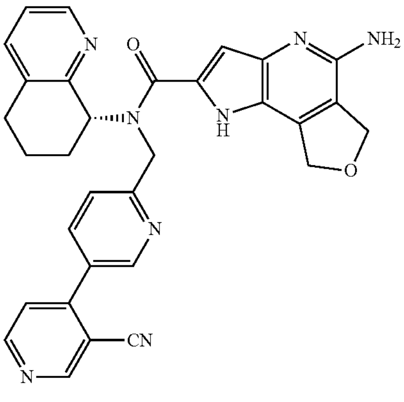
-continued
Example 12
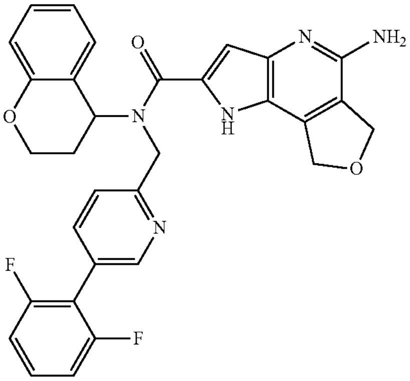
Example 13
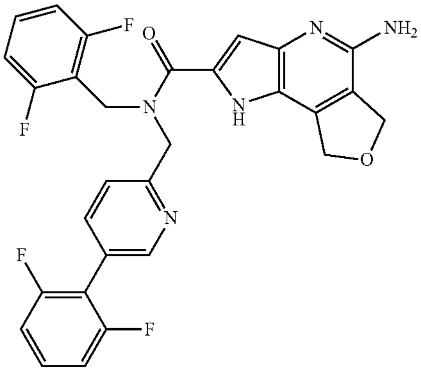
Example 14
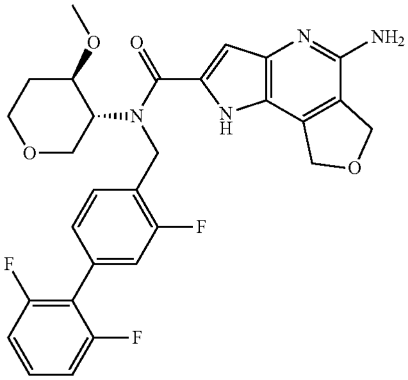
Example 15
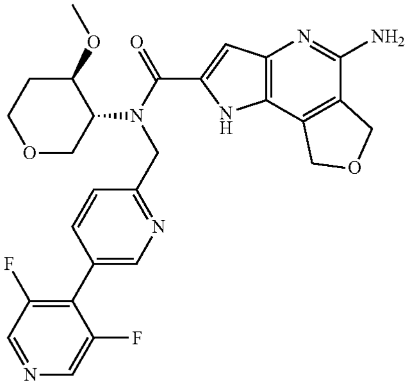

-continued
Example 16
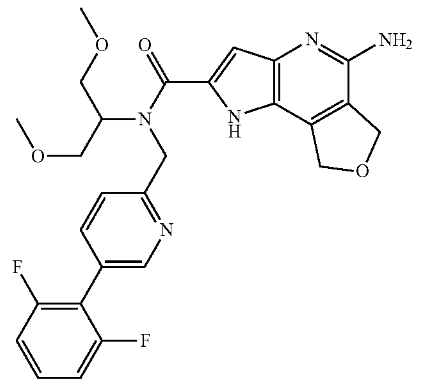
Example 17
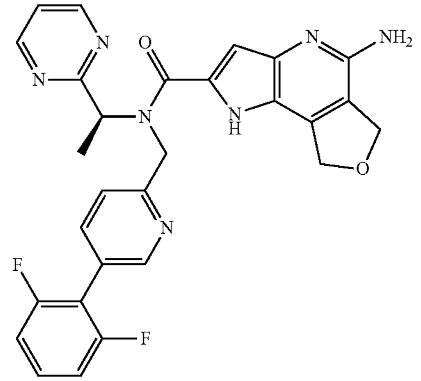
Example 18
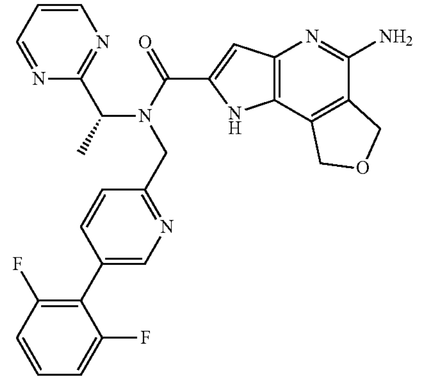
Example 19
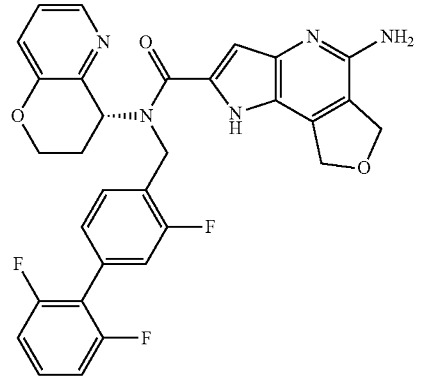
-continued
Example 20
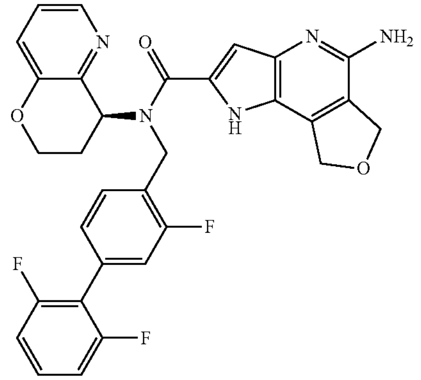
Example 21
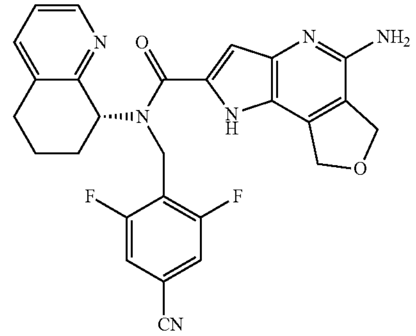
Example 22
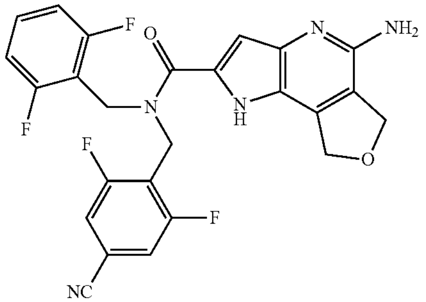
Example 23
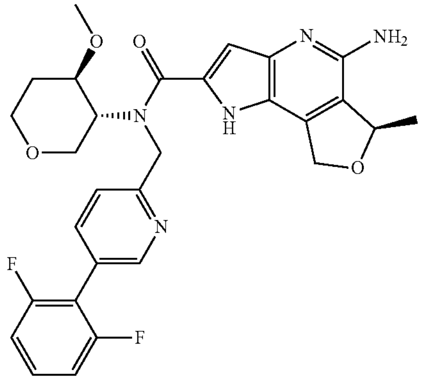

-continued
Example 24
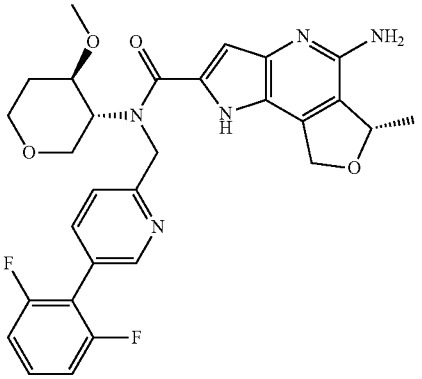
Example 25
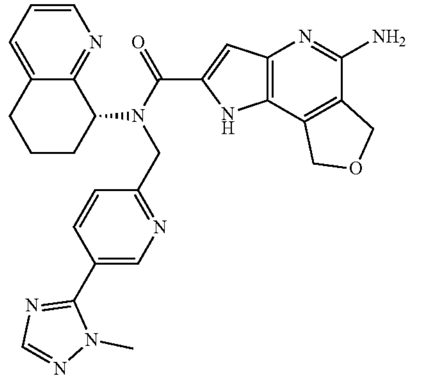
Example 26
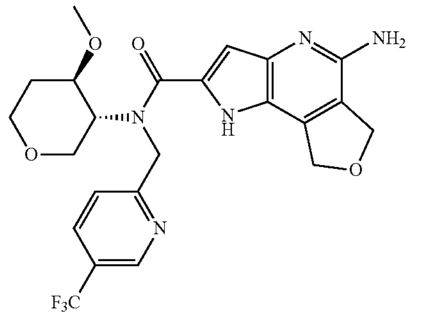
Example 27
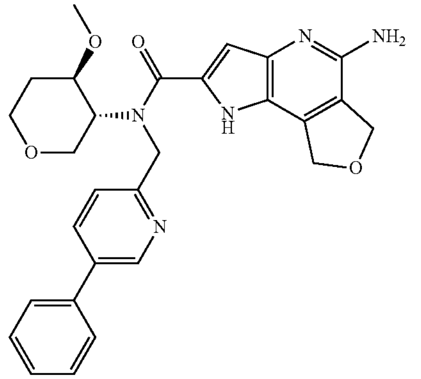
Example 28
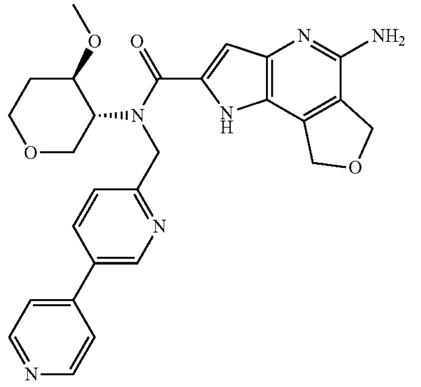
Example 29
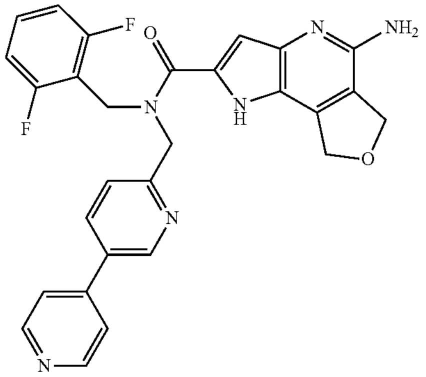
Example 30
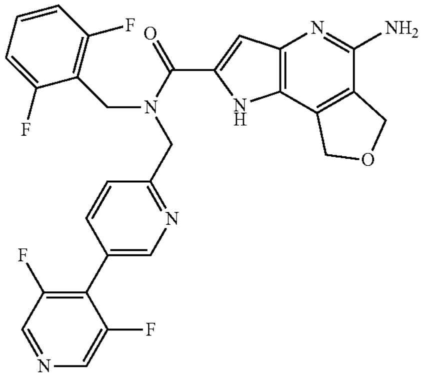
Example 31
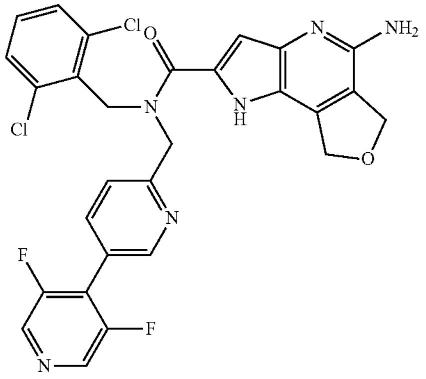

-continued
Example 32
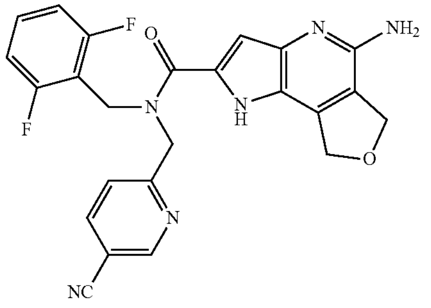
Example 33
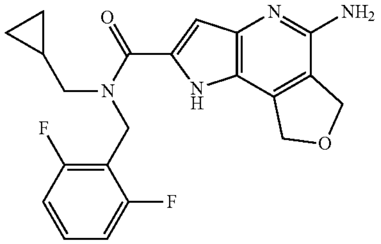
Example 34
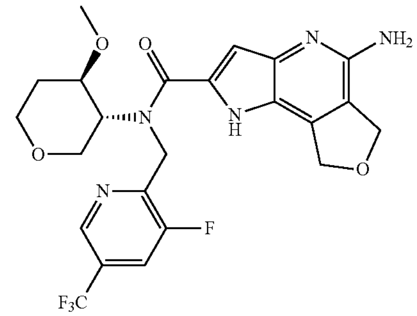
Example 35
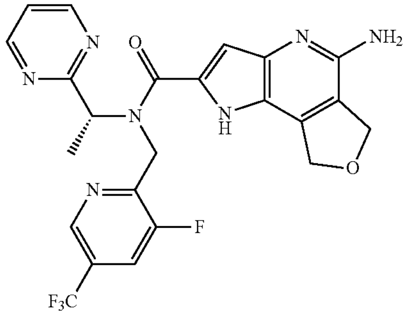
Example 36
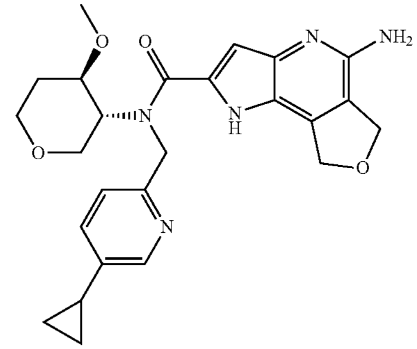
-continued
Example 37
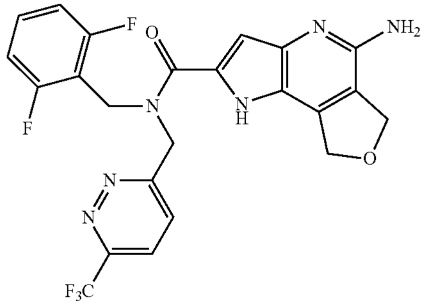
Example 38
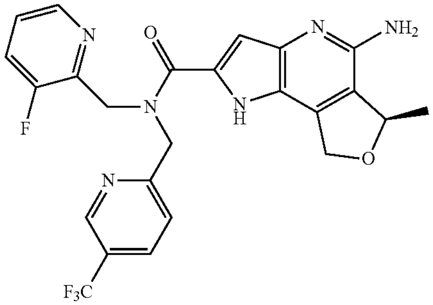
Example 39
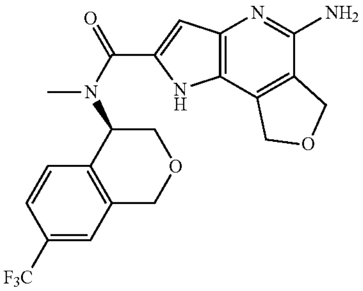
Example 40
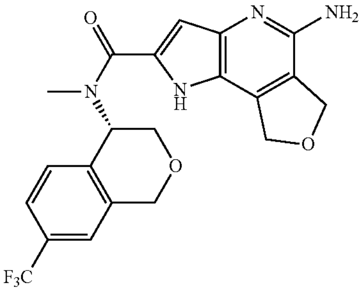
Example 41
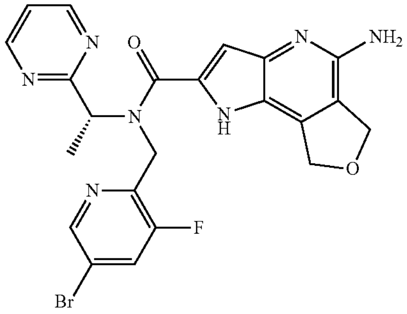

-continued
Example 42
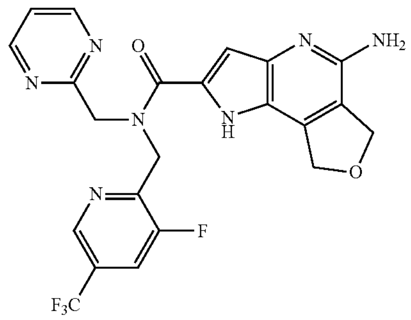
Example 43
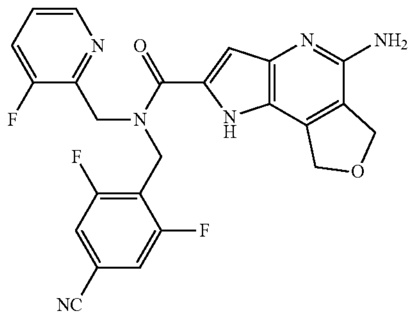
Example 44
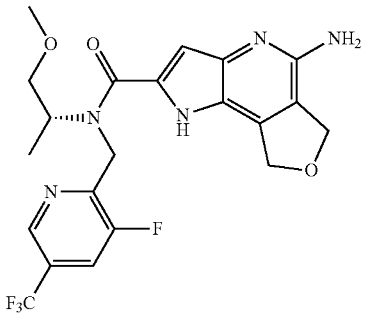
Example 45
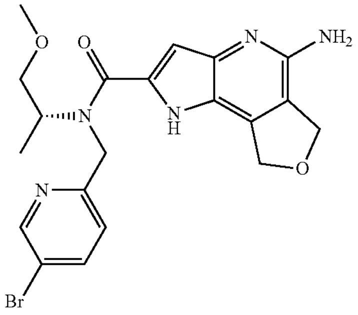
Example 46
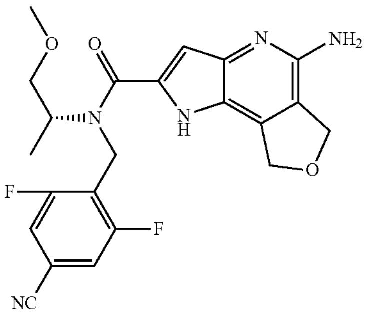
-continued
Example 47
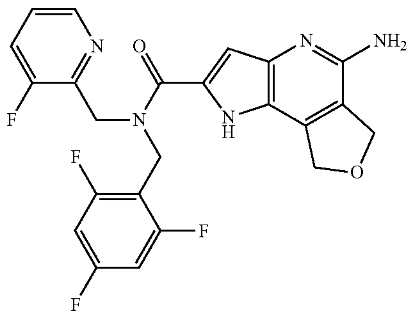
Example 48
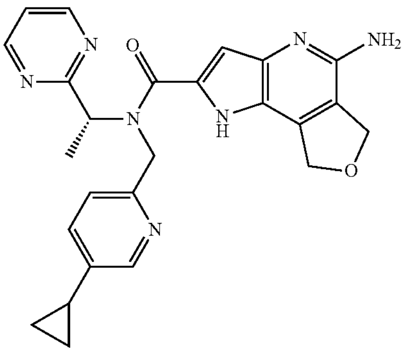
Example 49
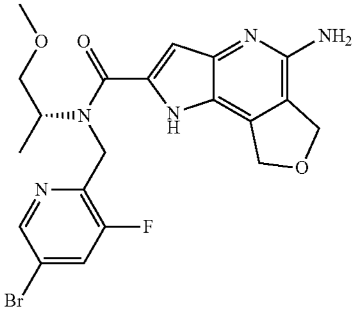
Example 50
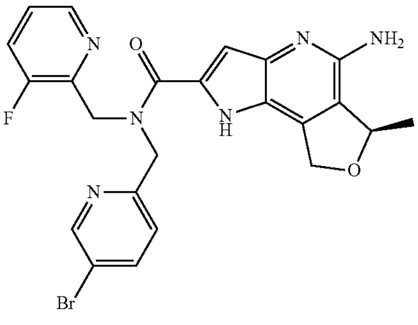
Example 51
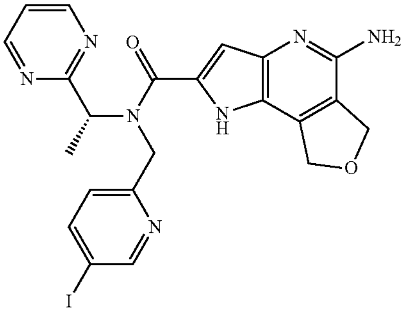

-continued
Example 52
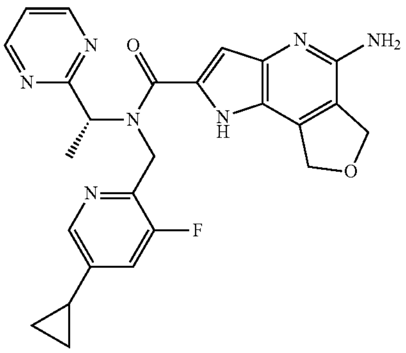
Example 53
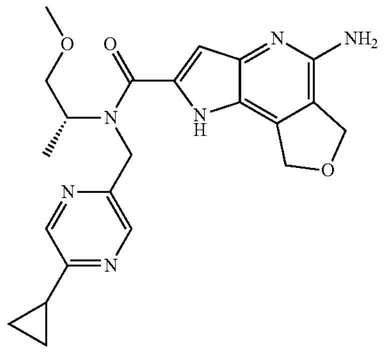
Example 54
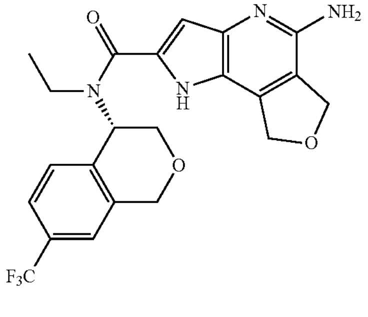
Example 55
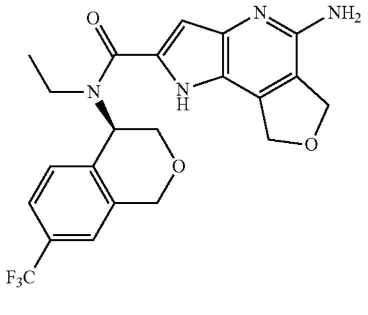
-continued
Example 56
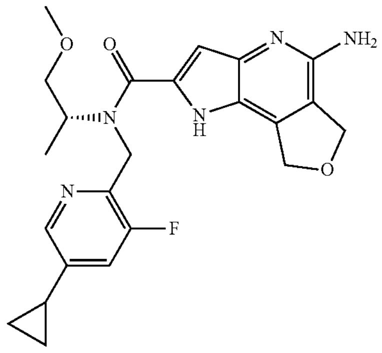
Example 57
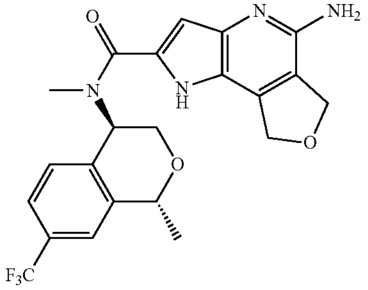
Example 58
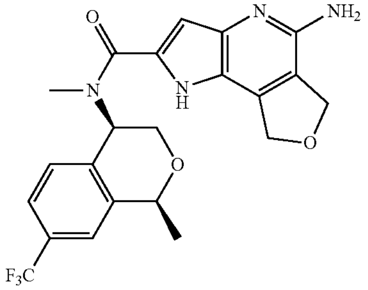
Example 59
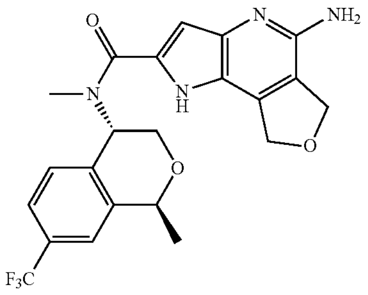
Example 60
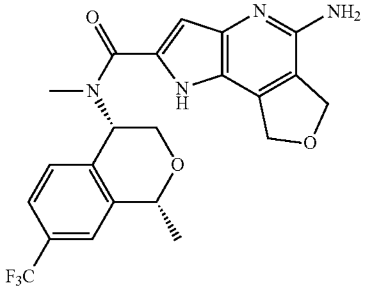

-continued
Example 61
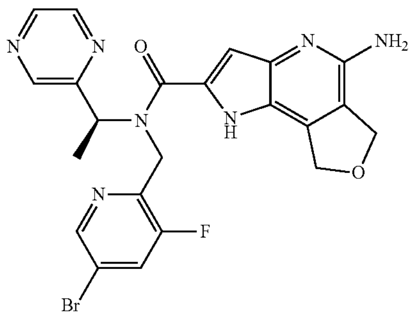
Example 62
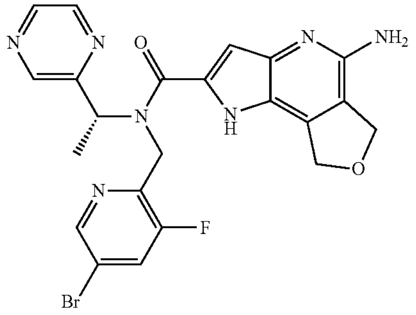
Example 63
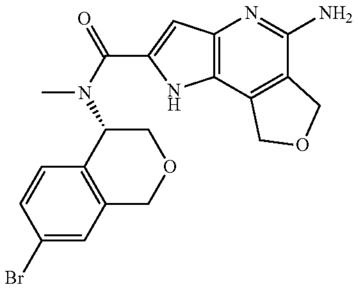
Example 64
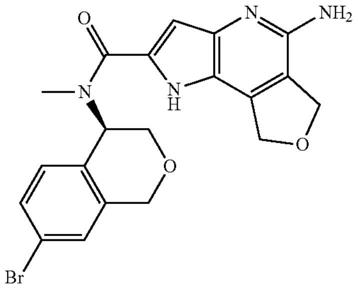
Example 65
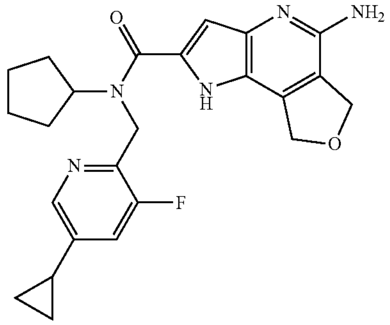
-continued
Example 66
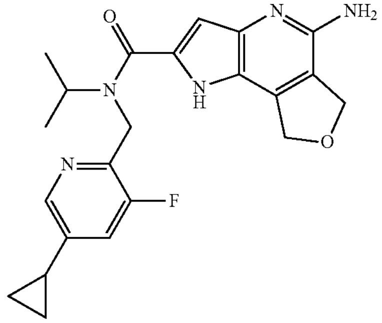
Example 67
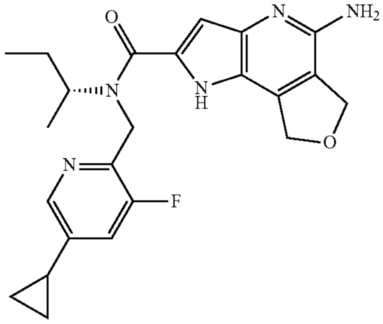
Example 68
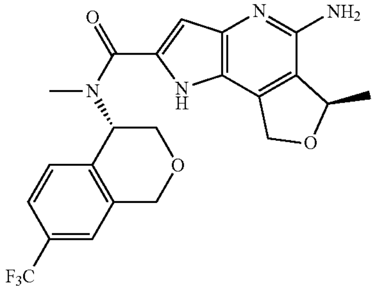
Example 69
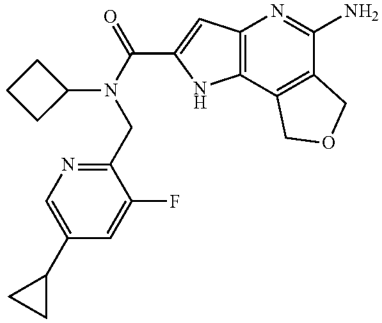
Example 70
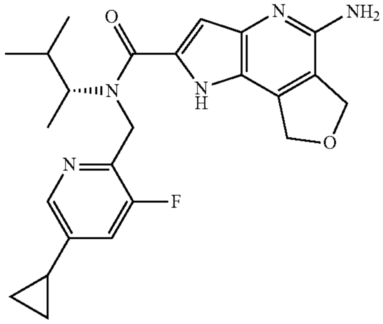

-continued
Example 71
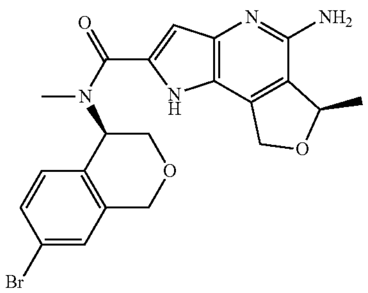
Example 72
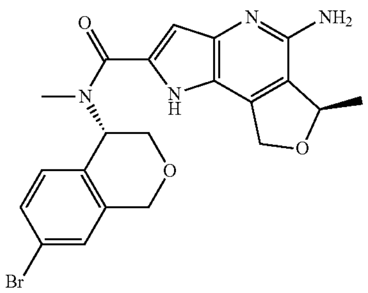
Example 73
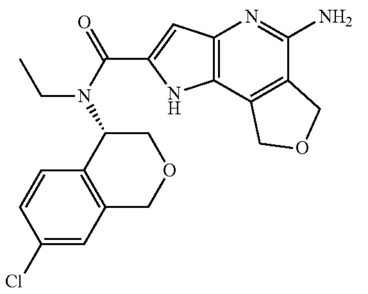
Example 74
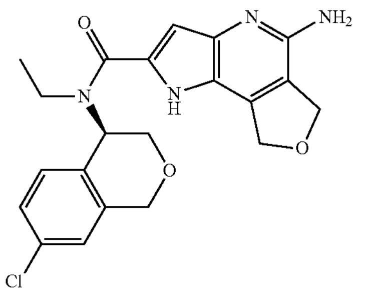
Example 75
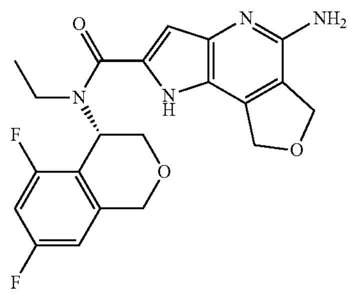
-continued
Example 76
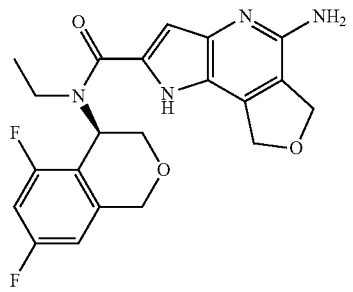
Example 77
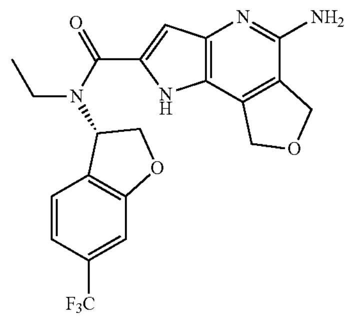
Example 78
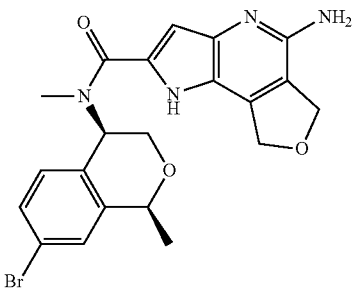
Example 79
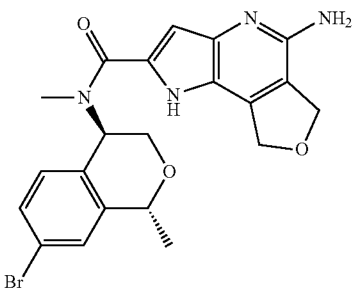
Example 80
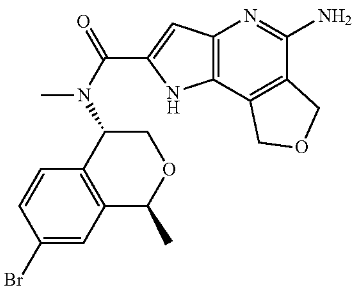

-continued
Example 81
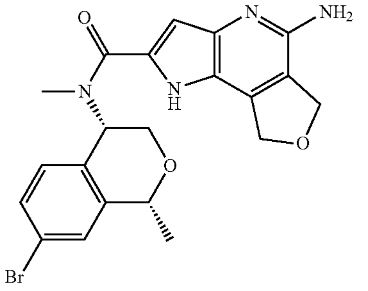
Example 82
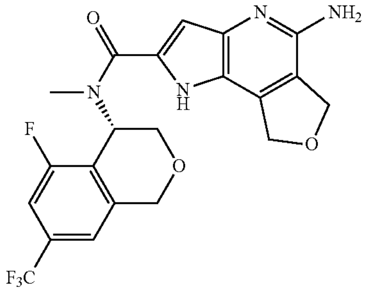
Example 83
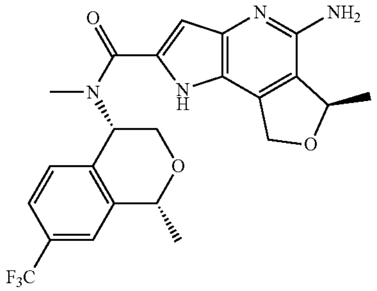
Example 84
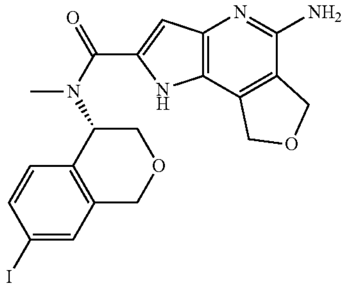
Example 85
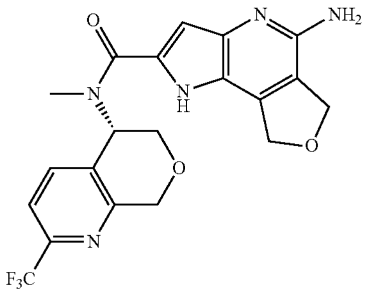
-continued
Example 86
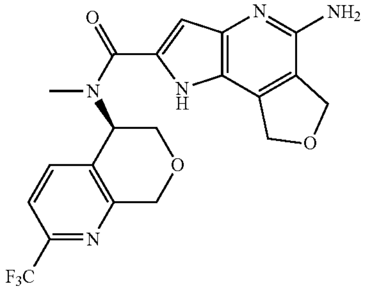
Example 87
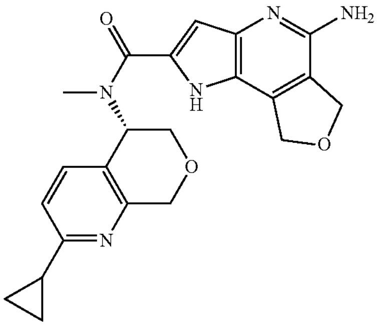
Example 88
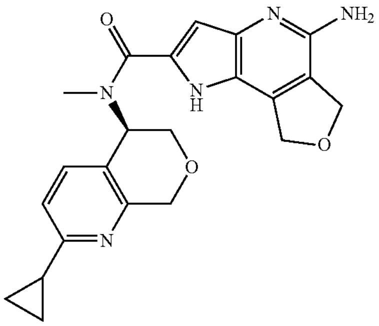
Example 89
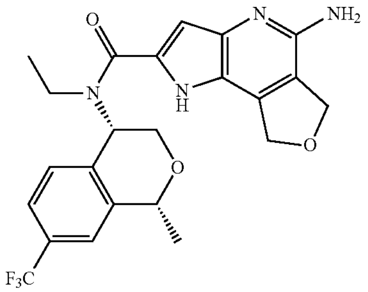
Example 90
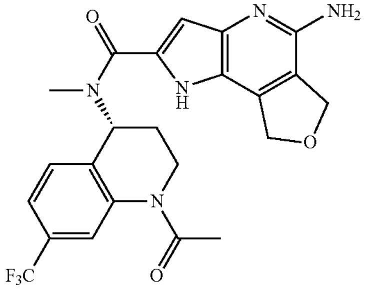

-continued
Example 91
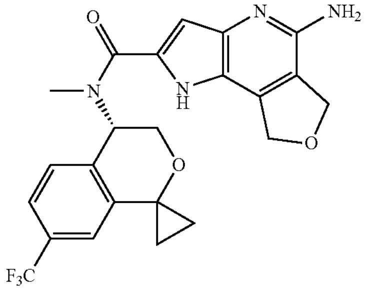
Example 92
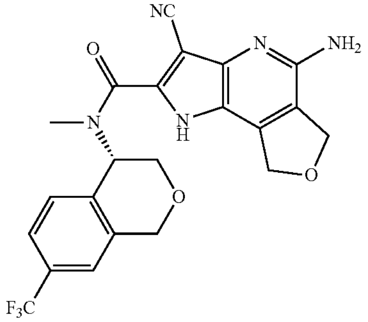
Example 93
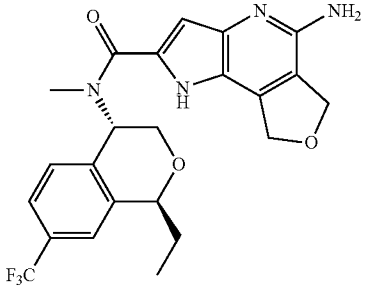
Example 94
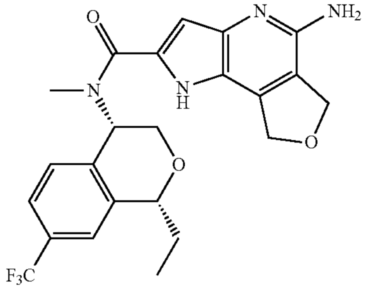
Example 95
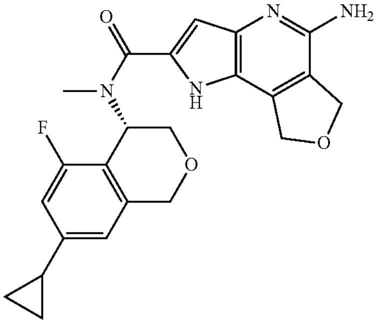
-continued
Example 96
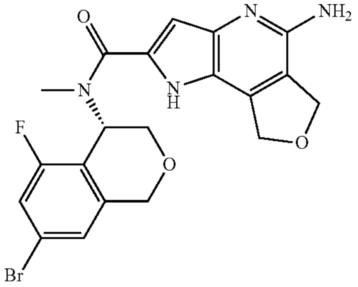
Example 97
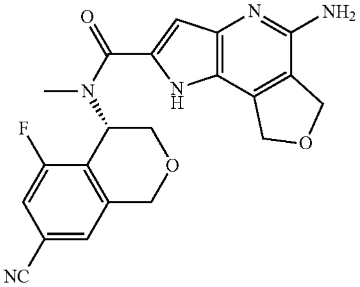
Example 98
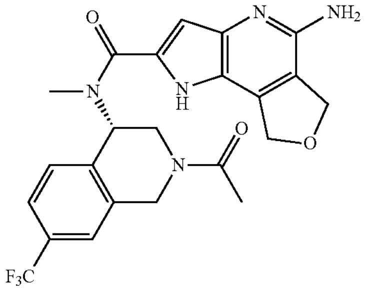
Example 99
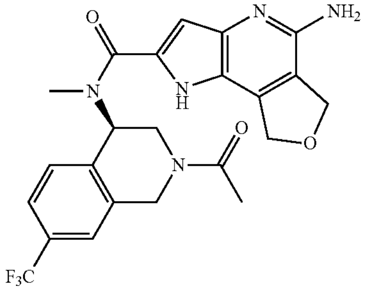
Example 100
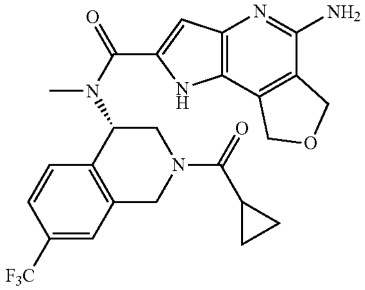

-continued
Example 101
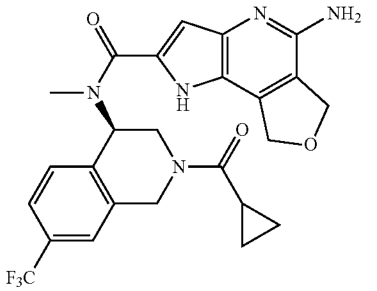
Example 102
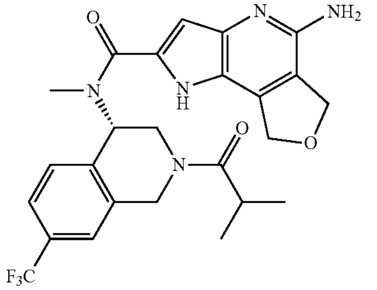
Example 103
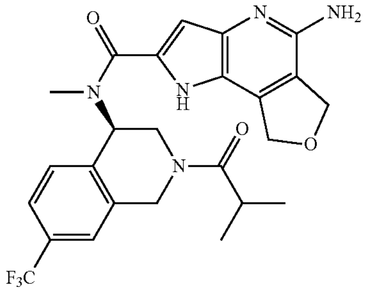
Example 104
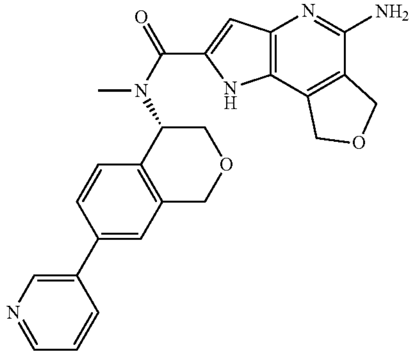
Example 105
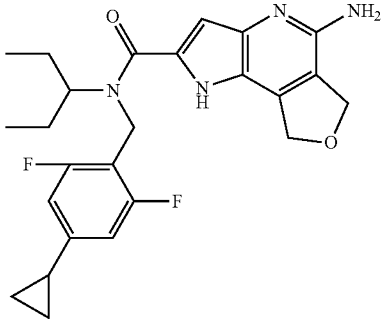
-continued
Example 106
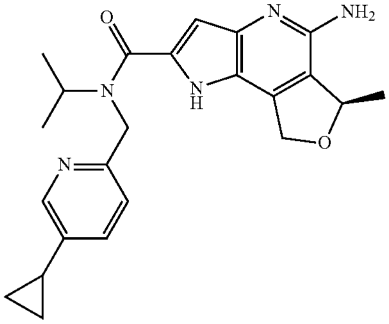
Example 107
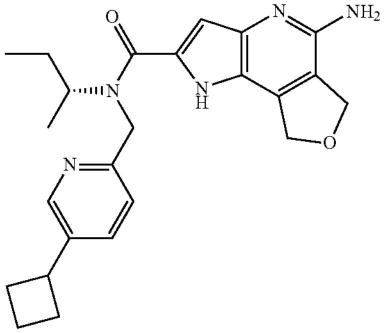
Example 108
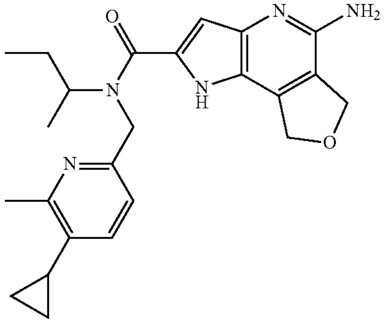
Example 109
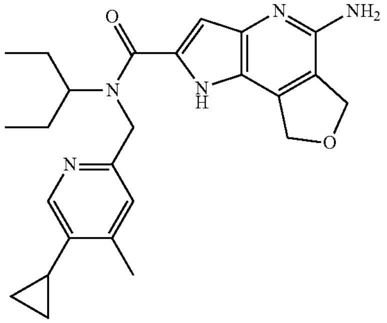
Example 110
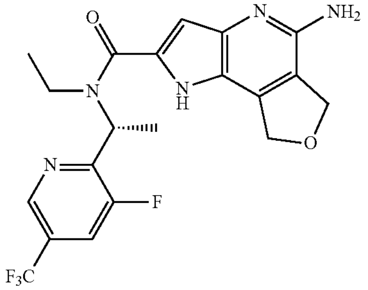

-continued
Example 111
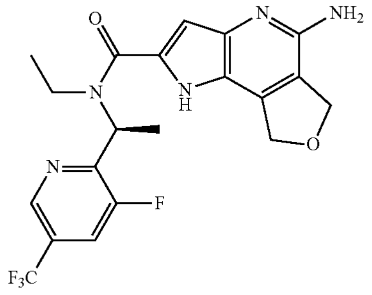
Example 112
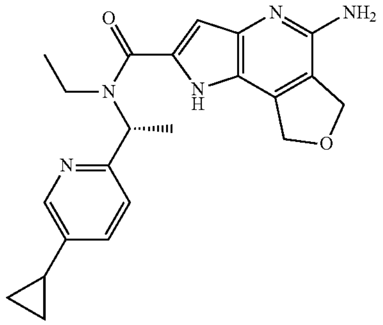
Example 113
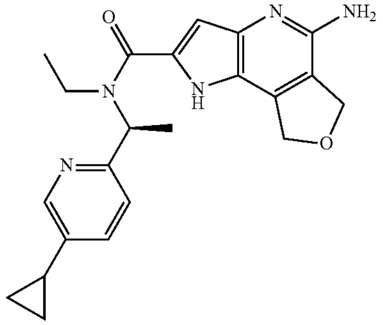
Example 114
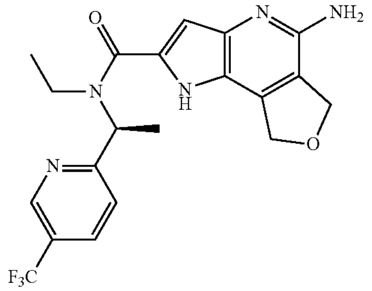
Example 115
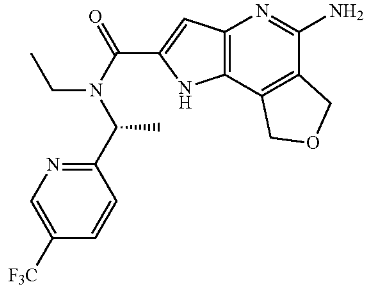
-continued
Example 116
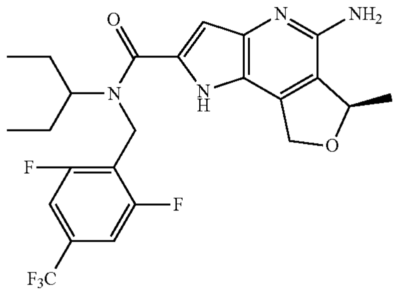
Example 117
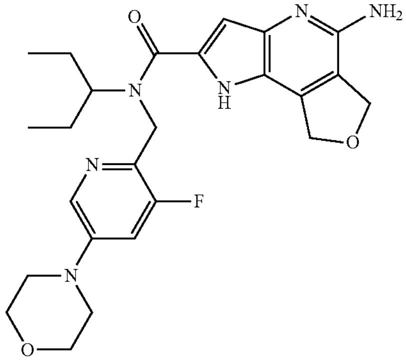
Example 118
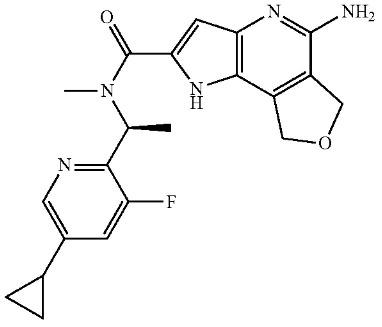
Example 119
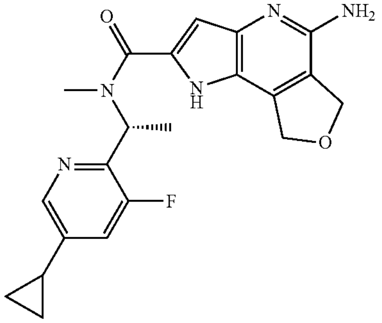
Example 120
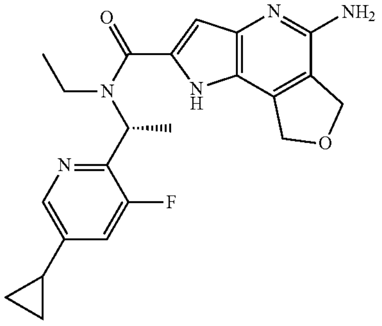

Example 121
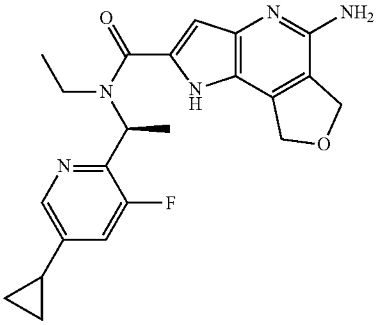
Example 122
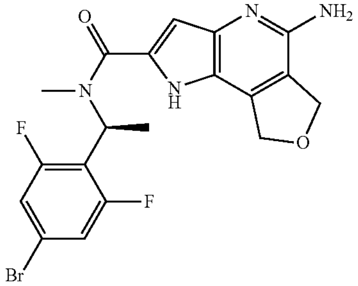
Example 123
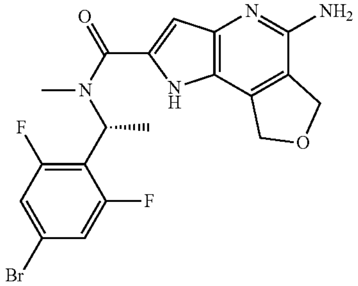
Example 124
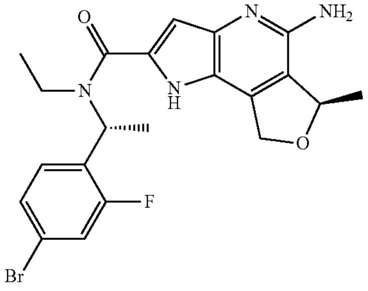
Example 125
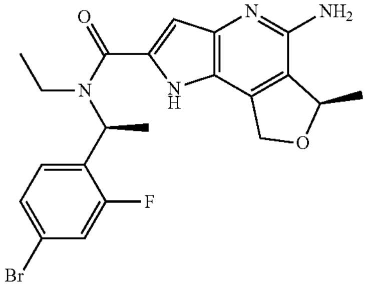
Example 126
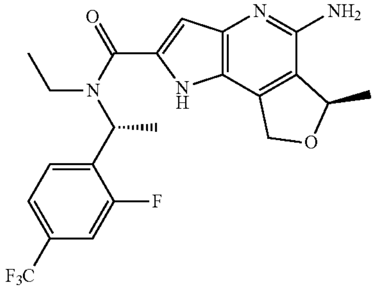
Example 127
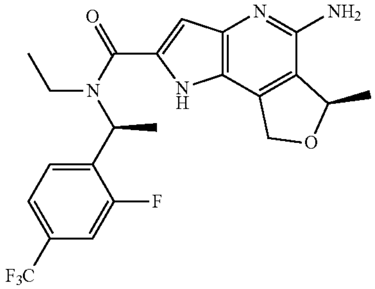
Example 128
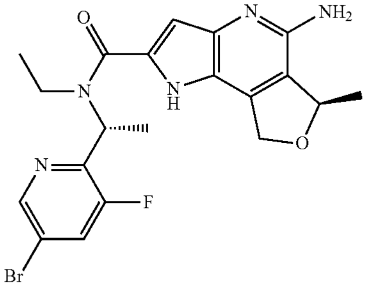
Example 129
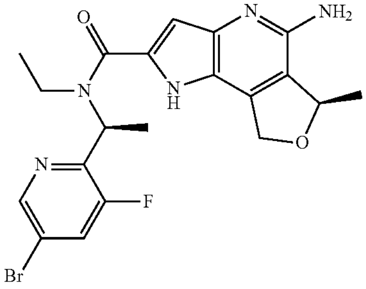
Example 130
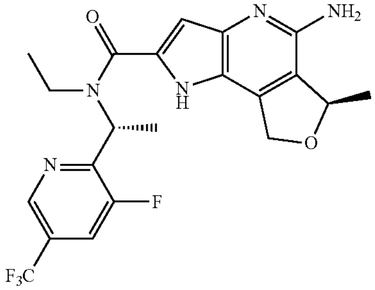

-continued
Example 131
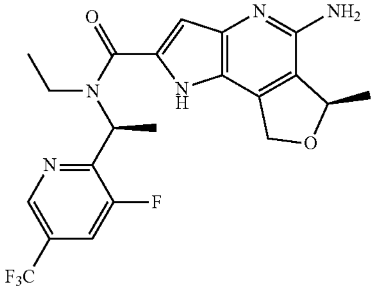
Example 132
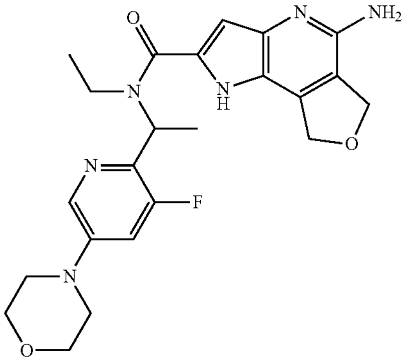
Example 133
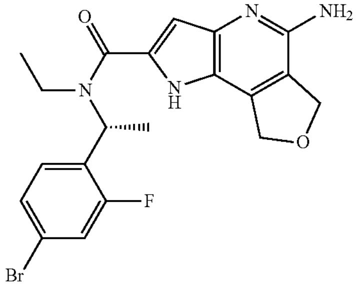
Example 134
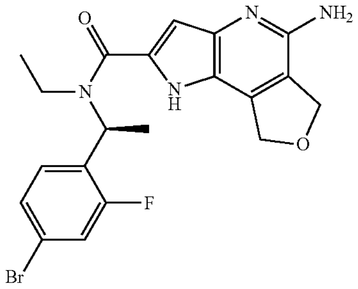
Example 135
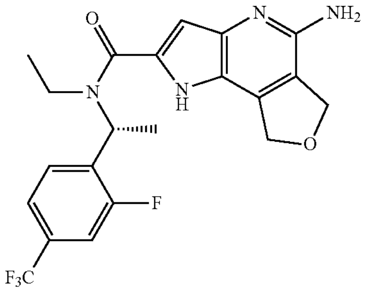
-continued
Example 136
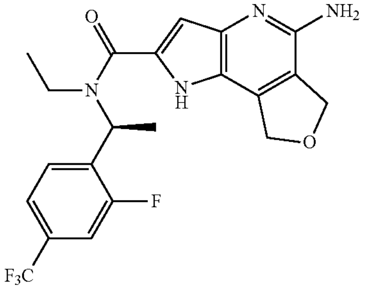
Example 137
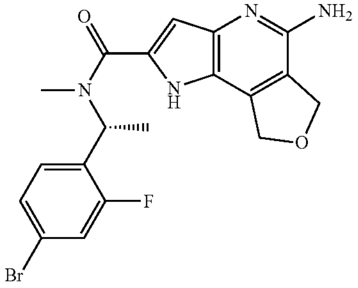
Example 138
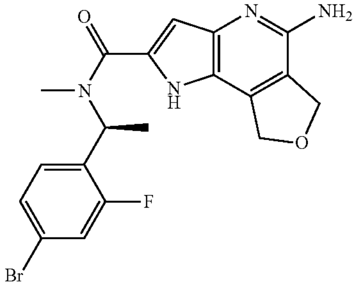
Example 139
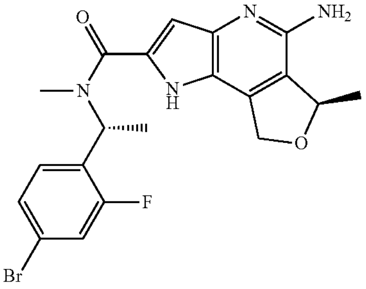
Example 140
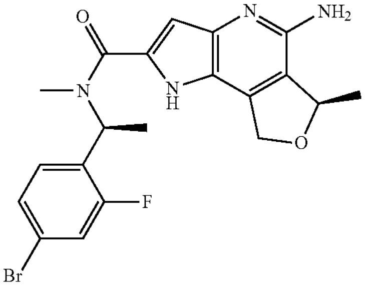

-continued
Example 141
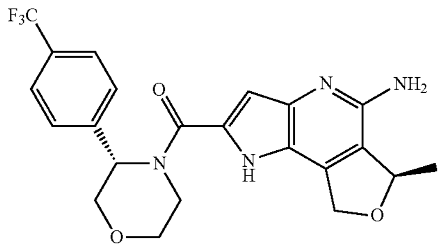
Example 142
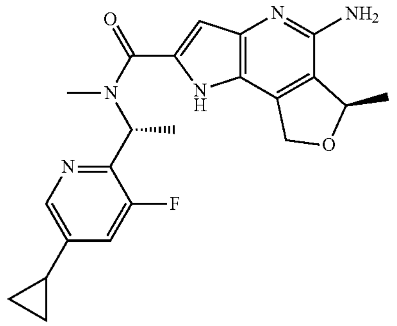
Example 143
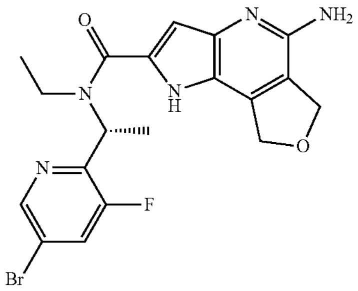
Example 144
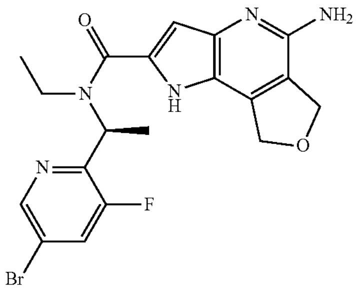
Example 145
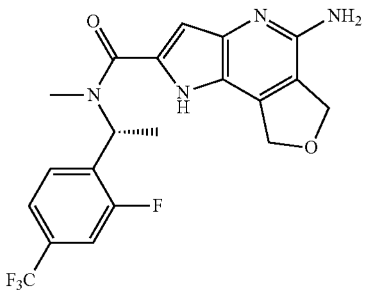
-continued
Example 146
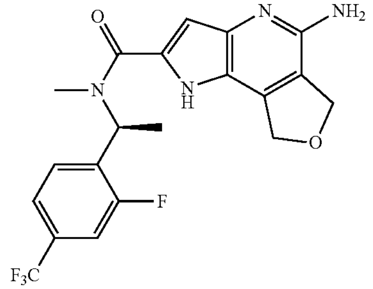
Example 147
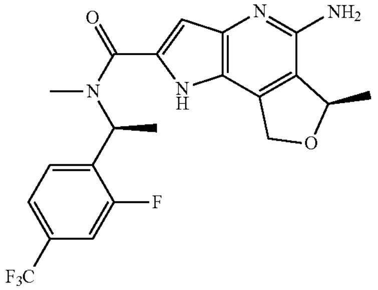
Example 148
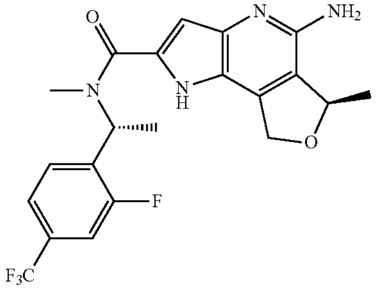
Example 149
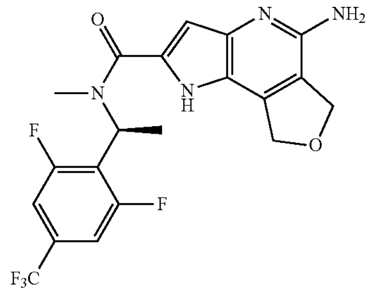
Example 150
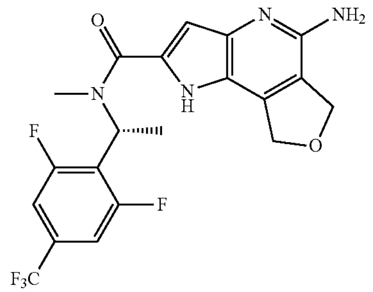

Example 151
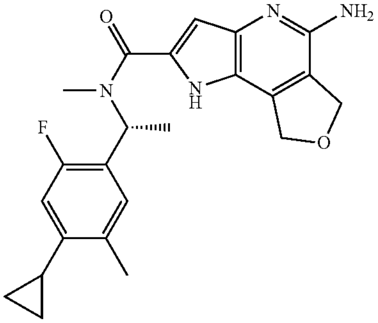
Example 152
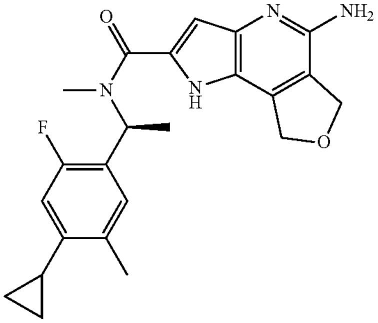
Example 153
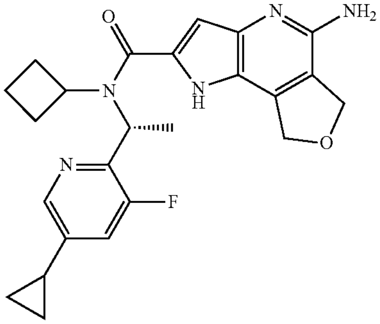
Example 154
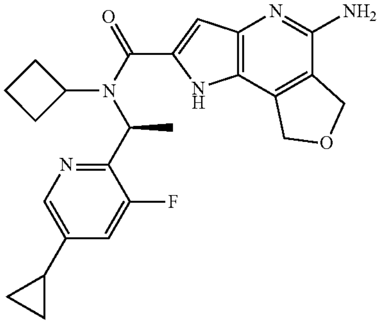
Example 155
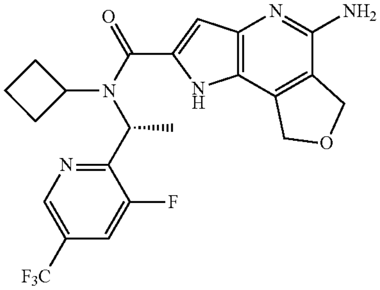
Example 156
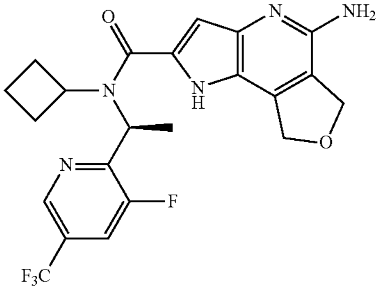
Example 157
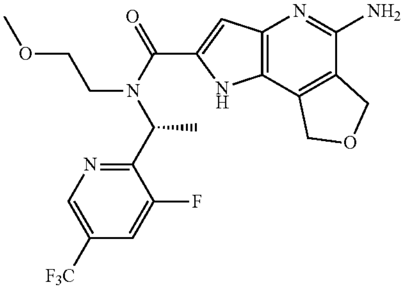
Example 158
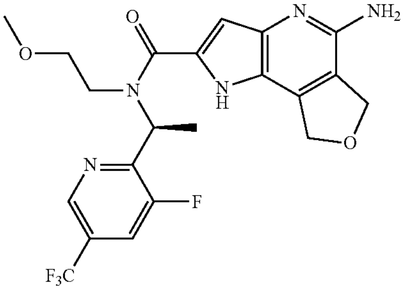
Example 159
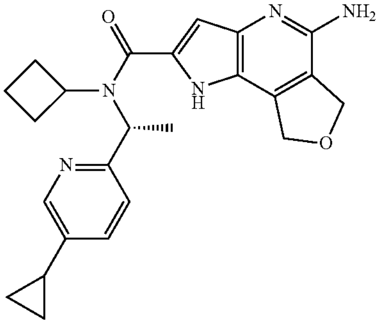
Example 160
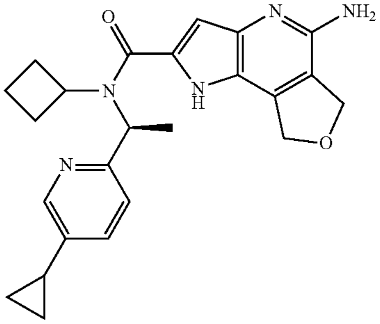

Example 161
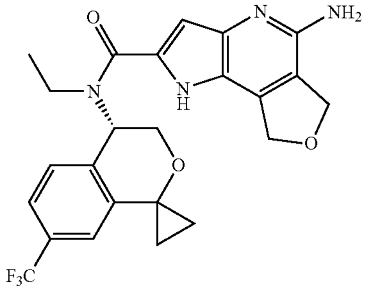
Example 162
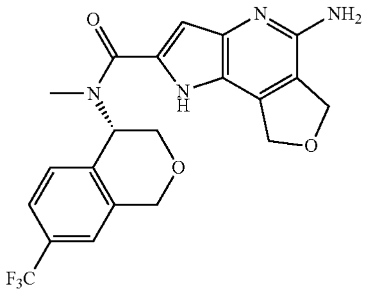
Example 163
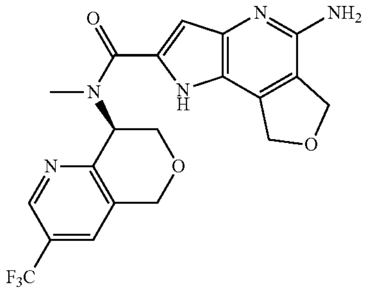
Example 164
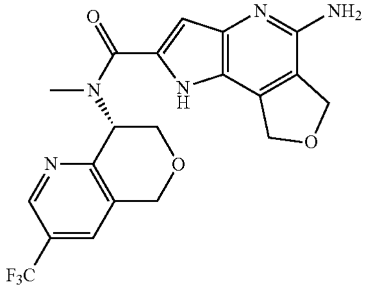
Example 165
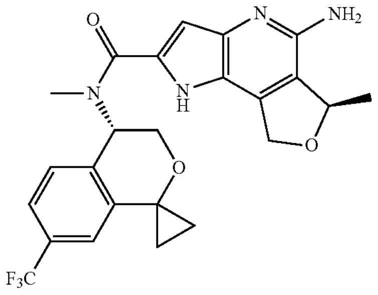
Example 166
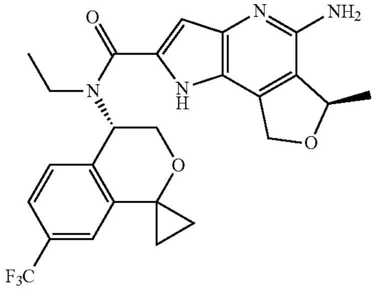
Example 167
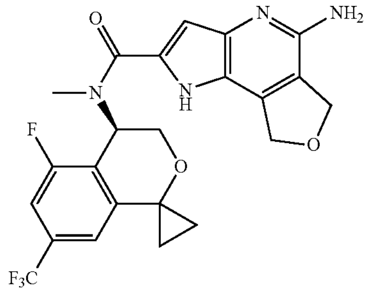
Example 168
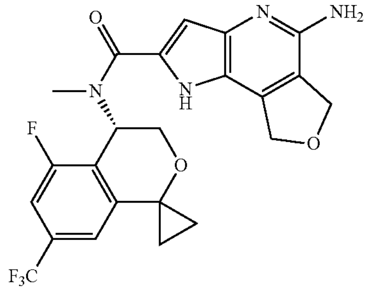
Example 169
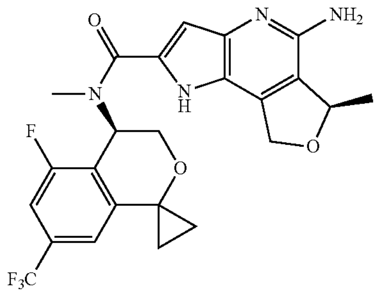
Example 170
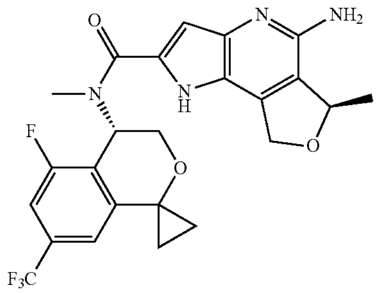

-continued
Example 171
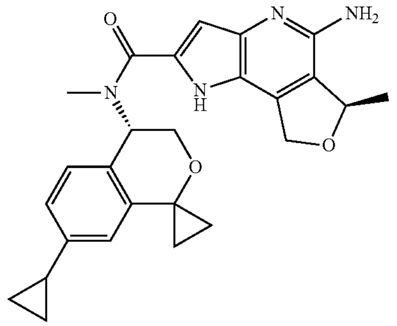
Example 172
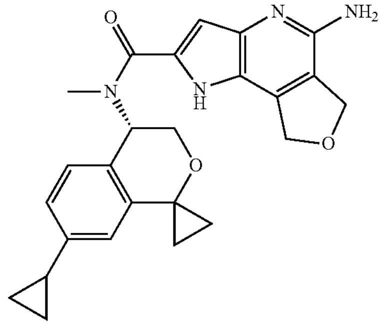
Example 173
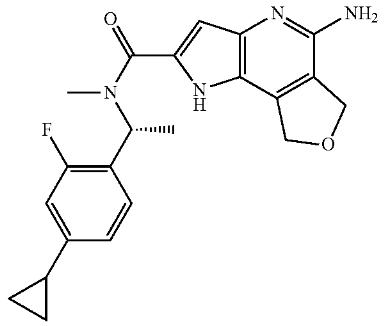
Example 174
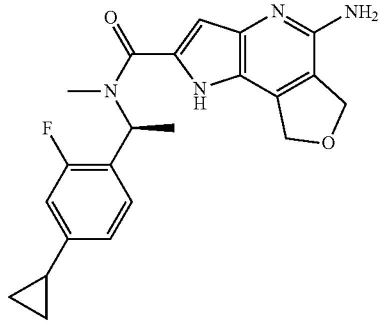
Example 175
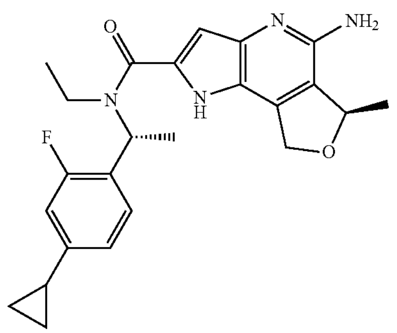
-continued
Example 176
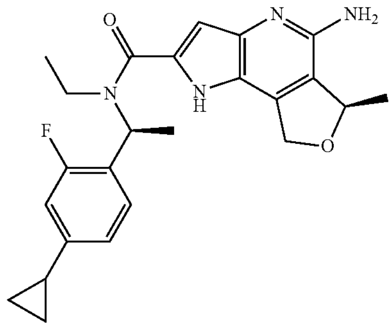
Example 177
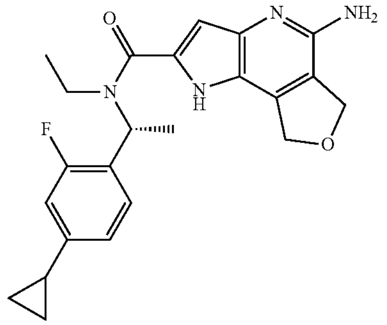
Example 178
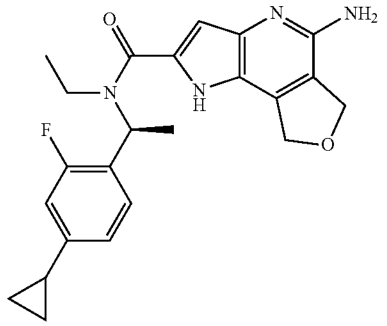
Example 179
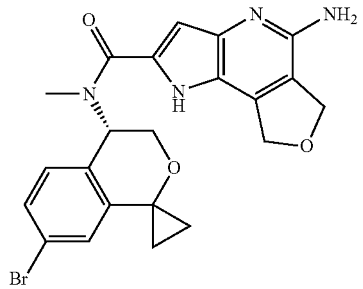
Example 180
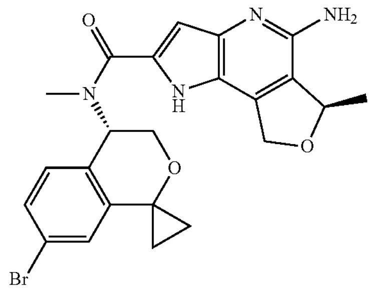

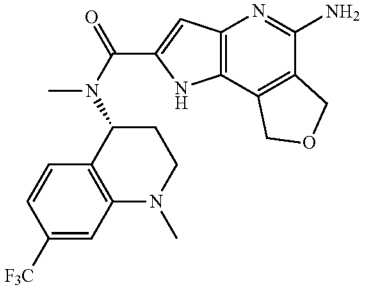
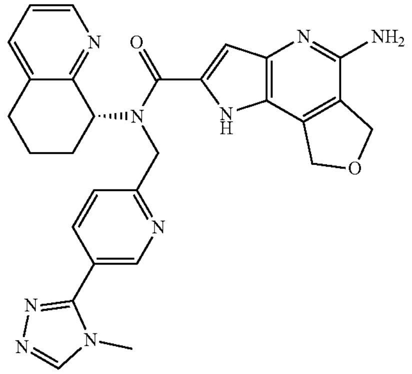
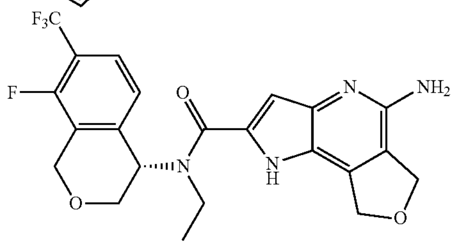
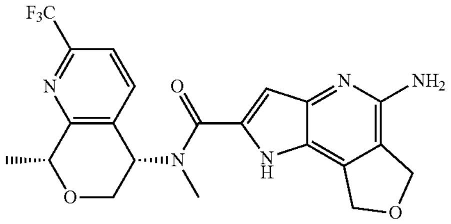
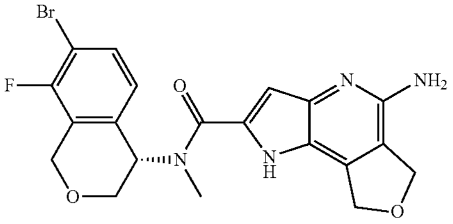
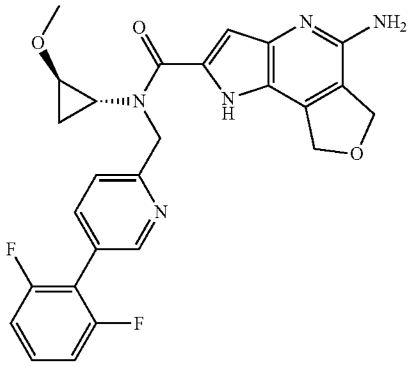
Example 181
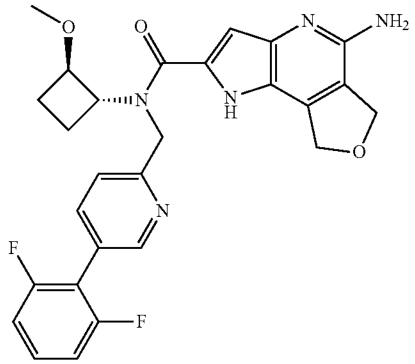
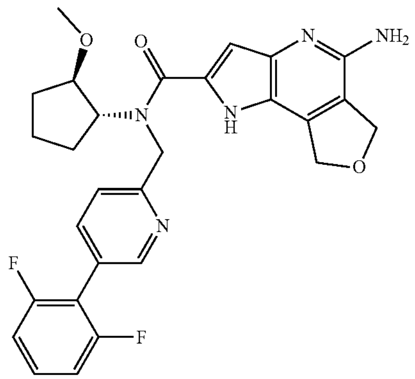
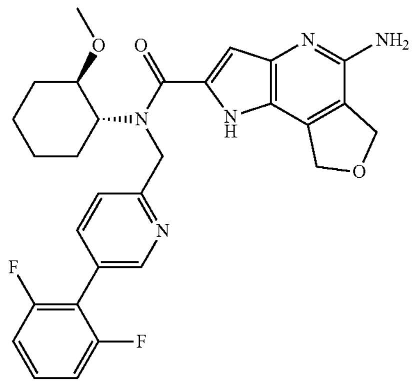
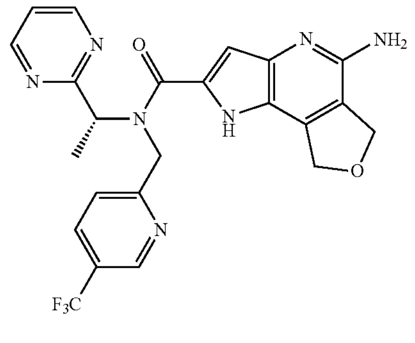 [SMILES: C[C@H](c1ncccn1)N(Cc1ccc(C(F)(F)F)cn1)C(=O)c1cc2nc(N)c3c(c2[nH]1)COC3]

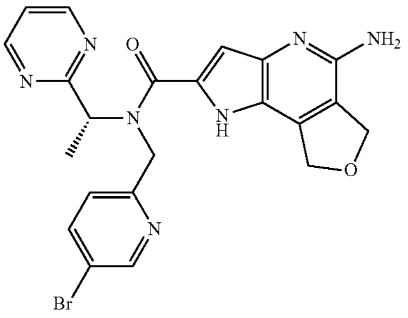
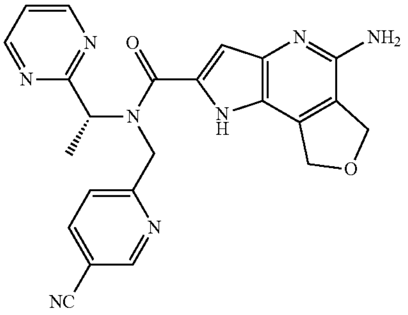
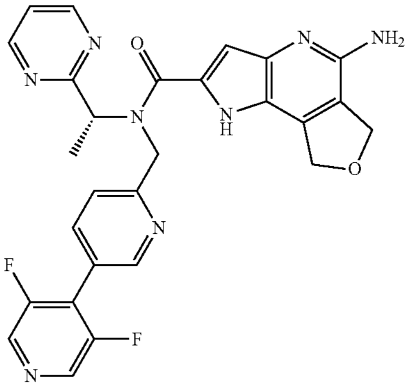
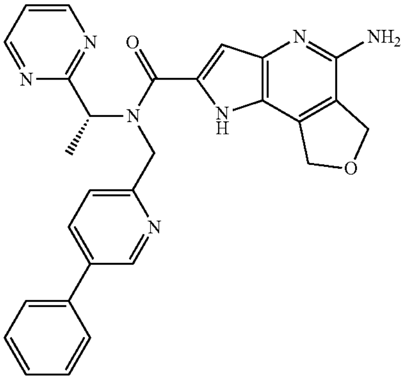
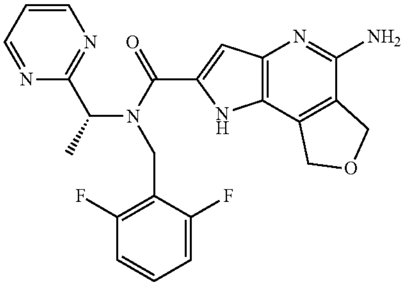
-continued
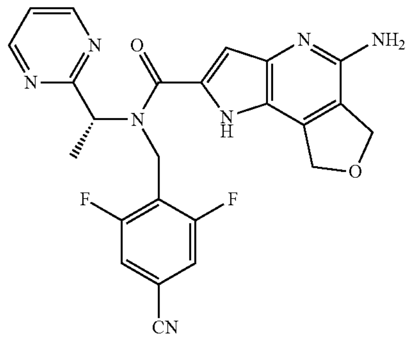
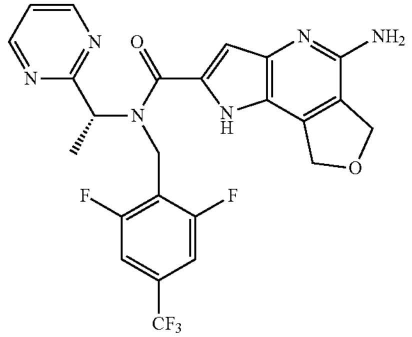
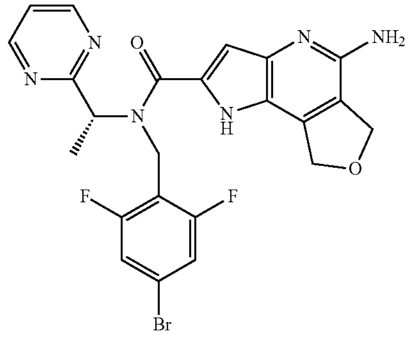
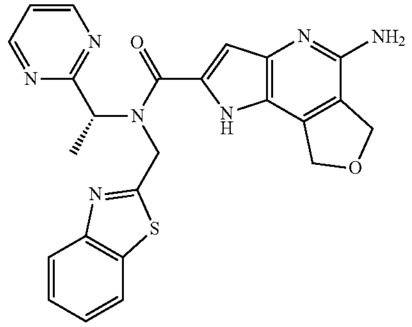
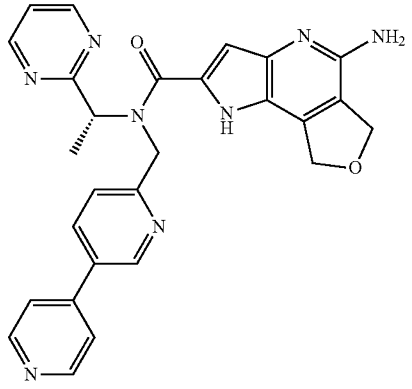

-continued
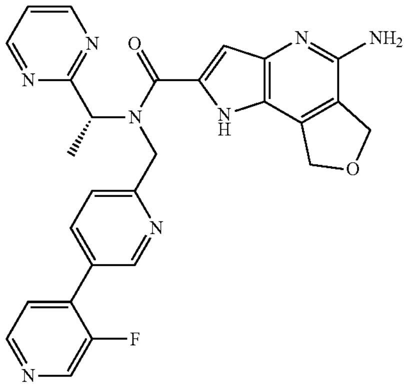
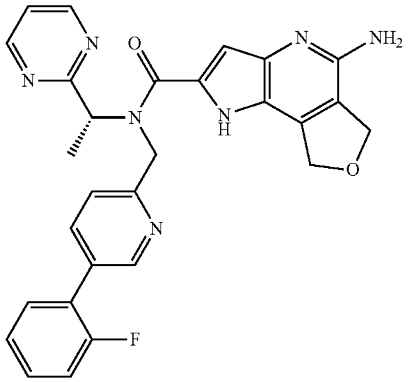
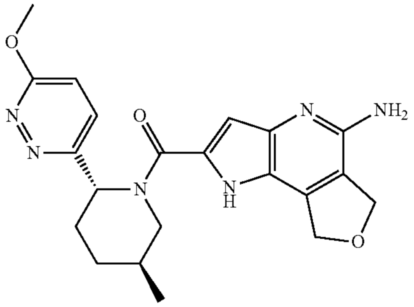
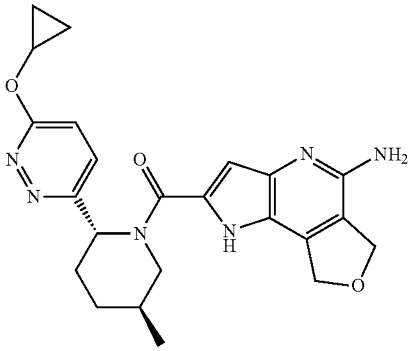
-continued
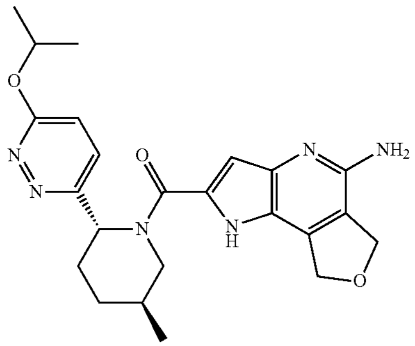
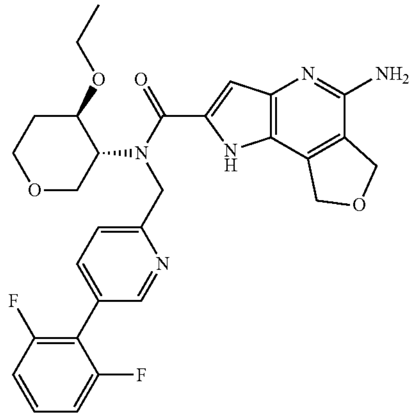
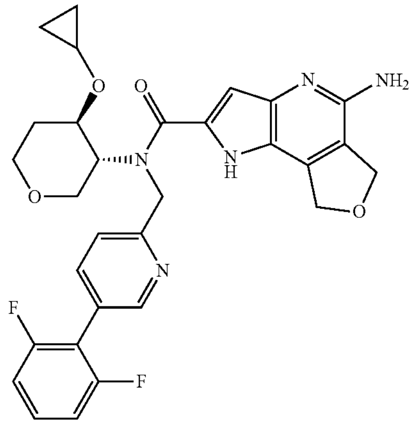
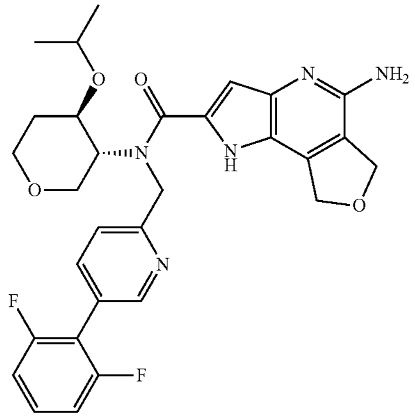

-continued
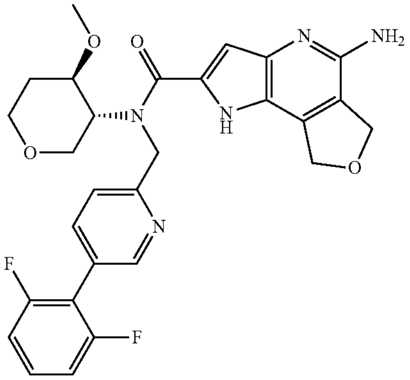
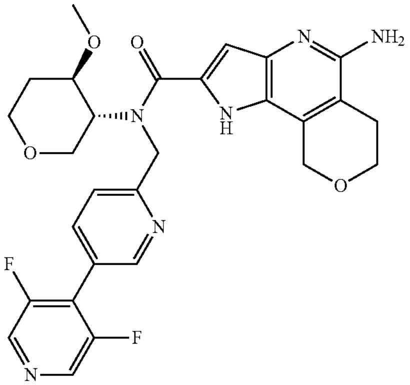
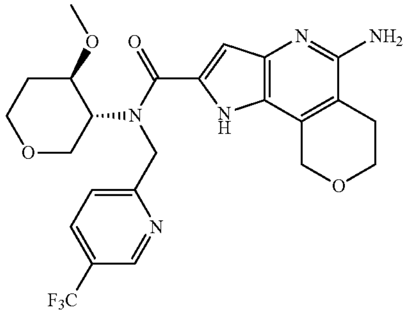
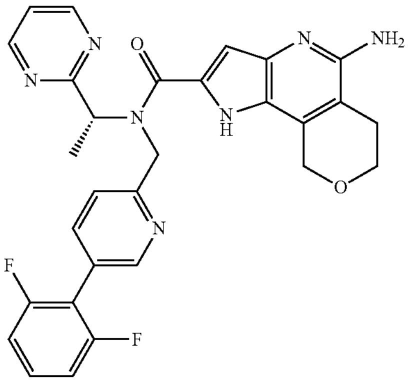
-continued
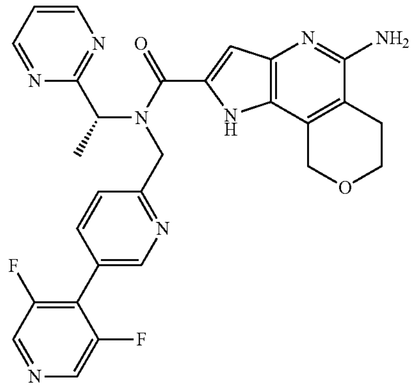
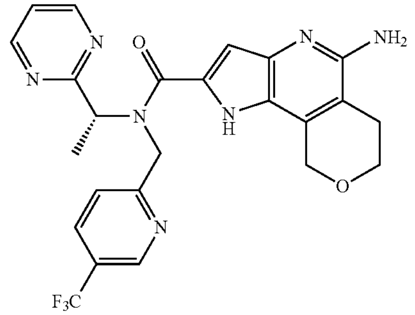
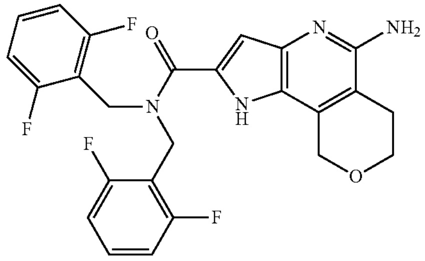
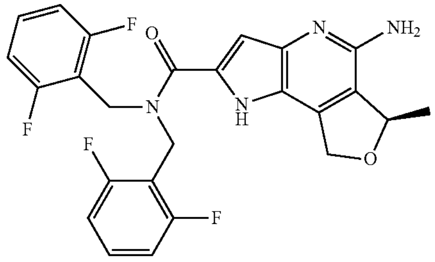
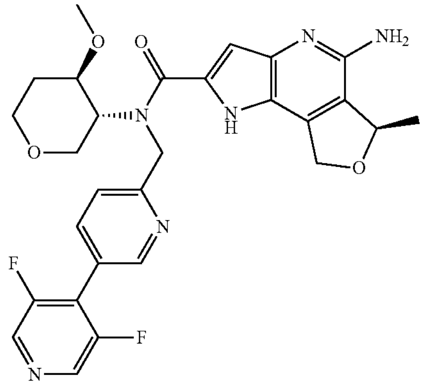

-continued
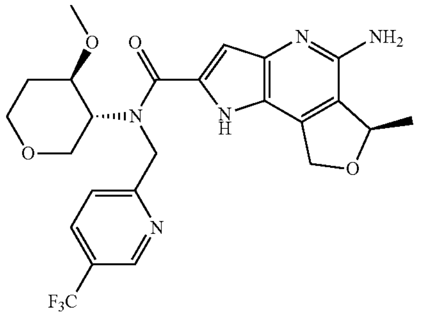
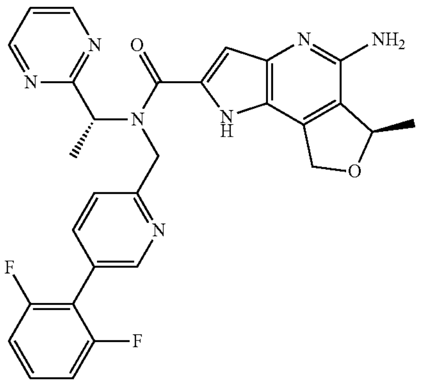
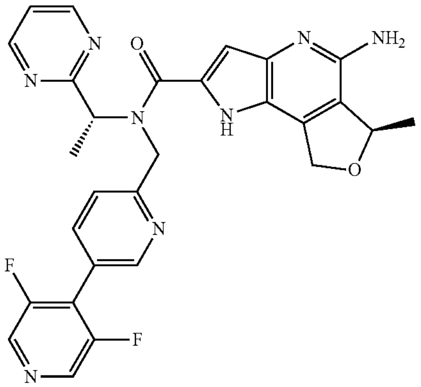
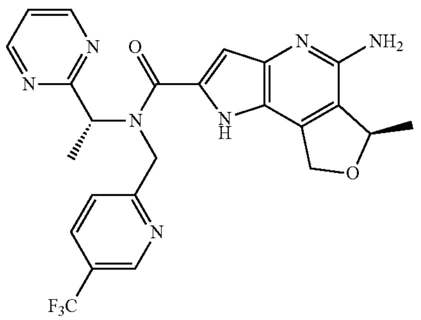
-continued
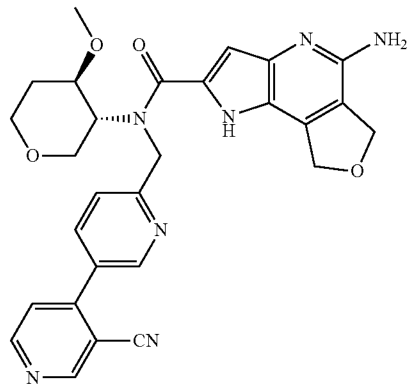
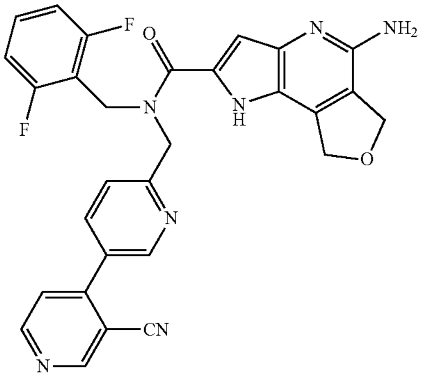
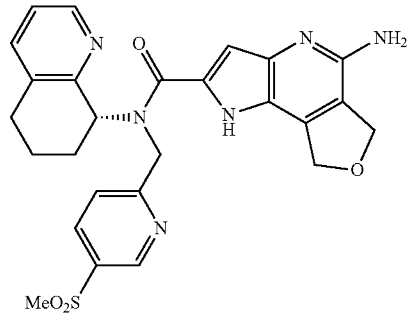
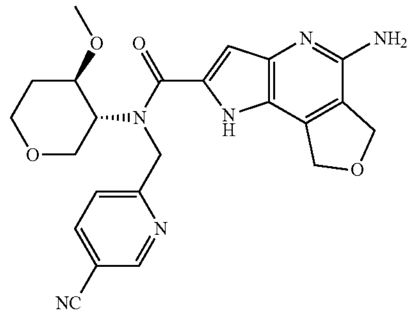
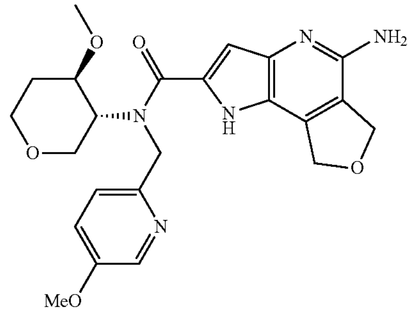

-continued
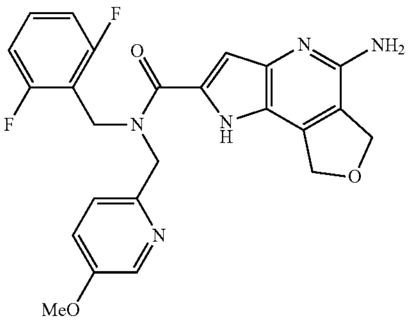
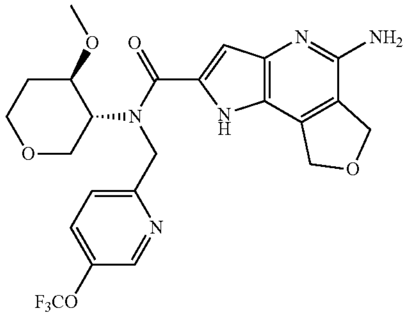
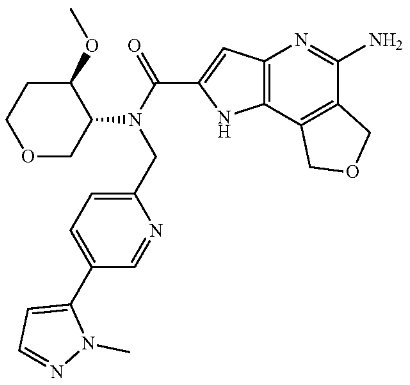
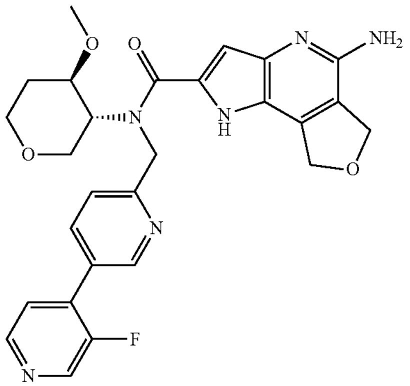
-continued
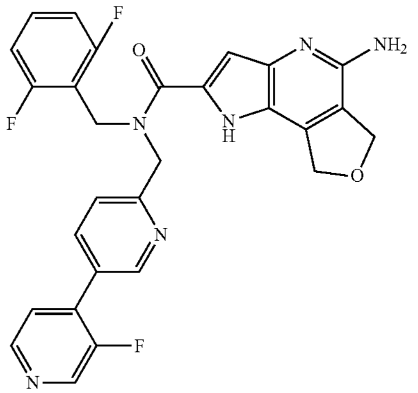
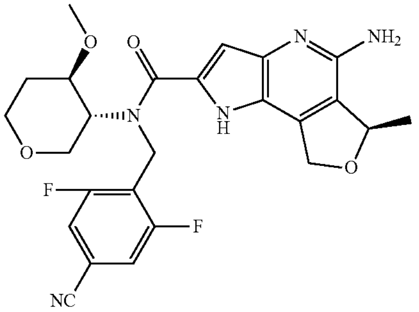
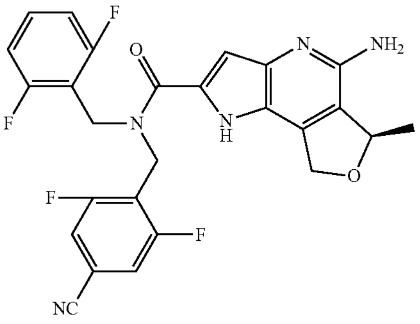
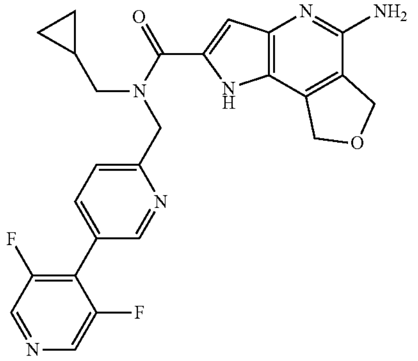

-continued
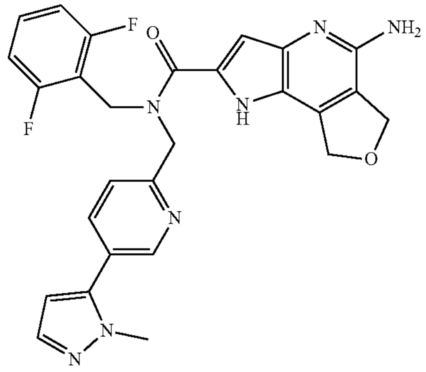
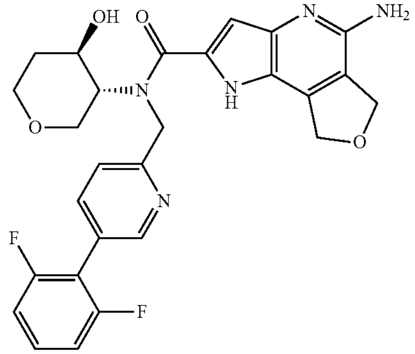
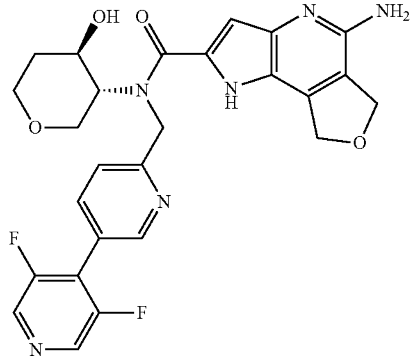
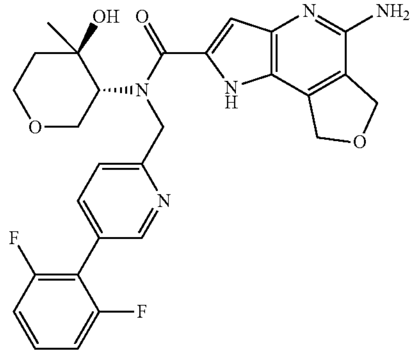
-continued
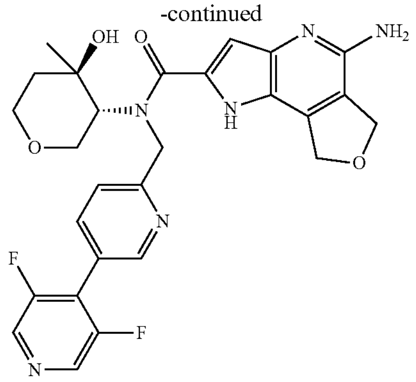
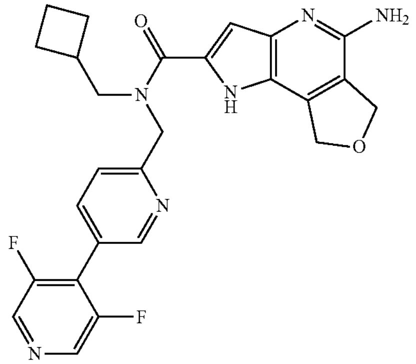
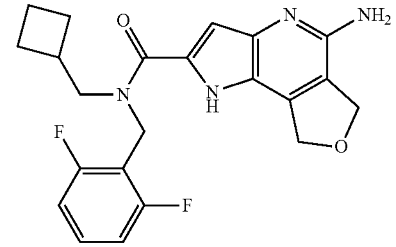
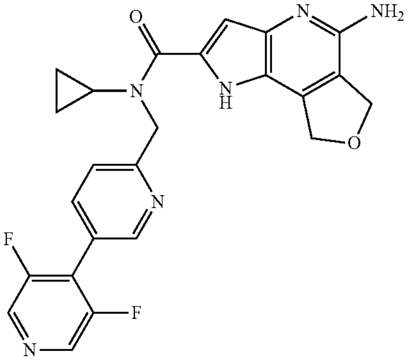
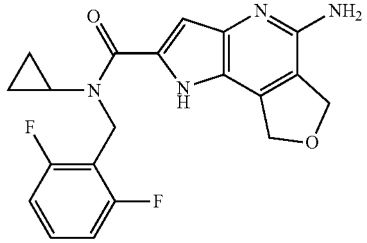

-continued
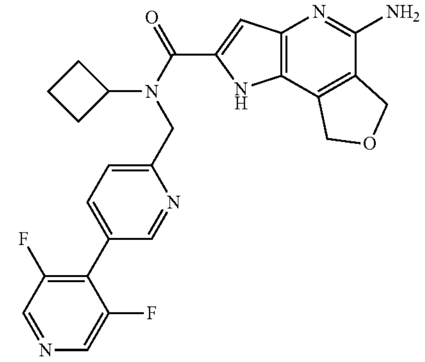
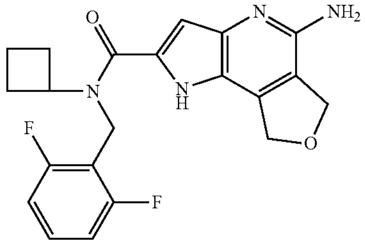
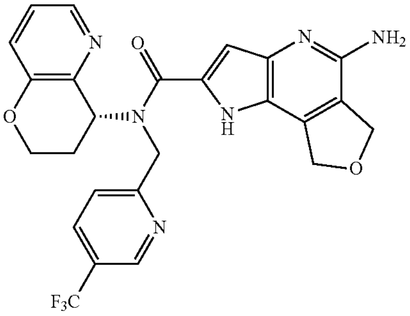
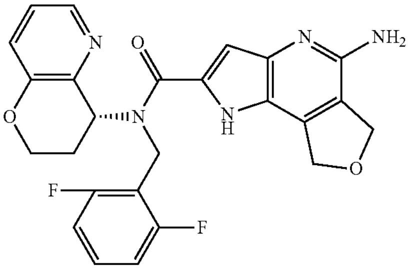
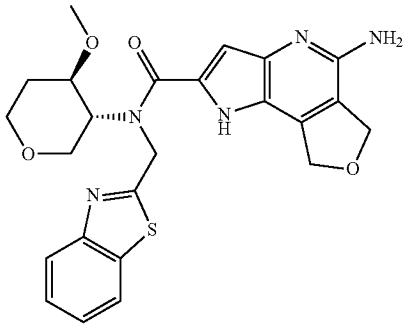
-continued
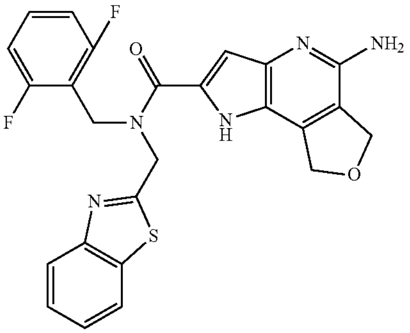
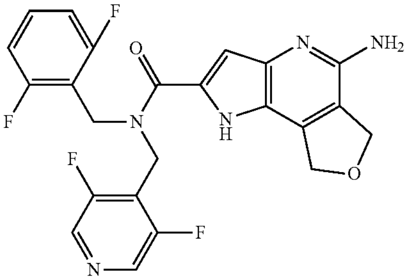
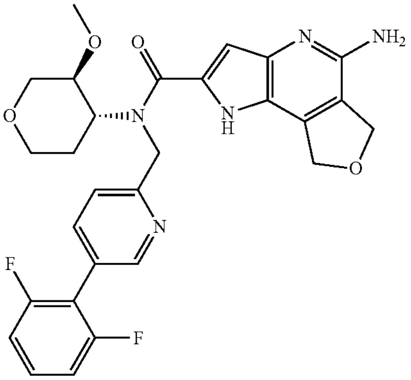
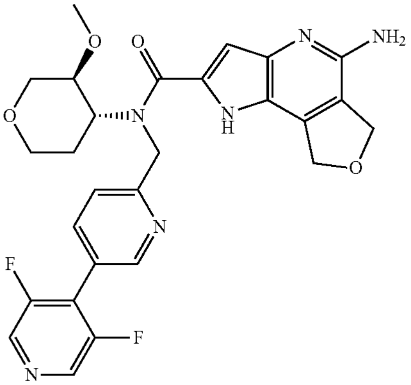
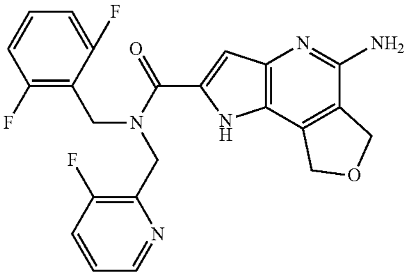

-continued
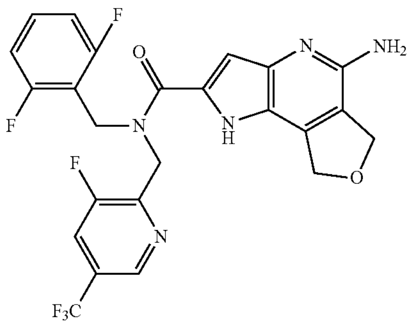
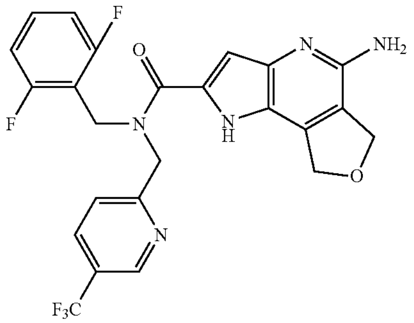
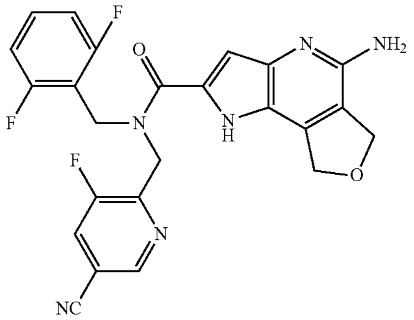
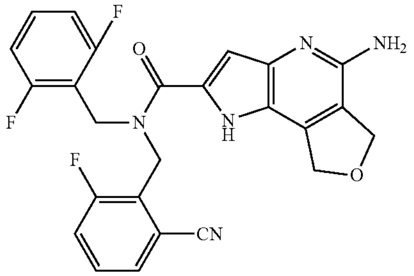
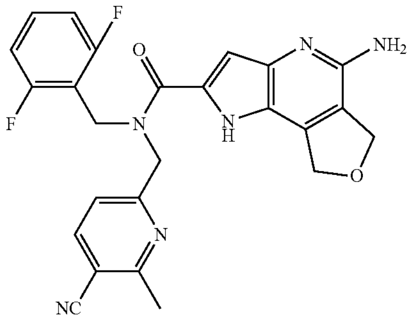
-continued
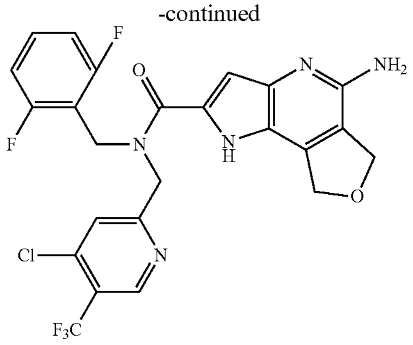
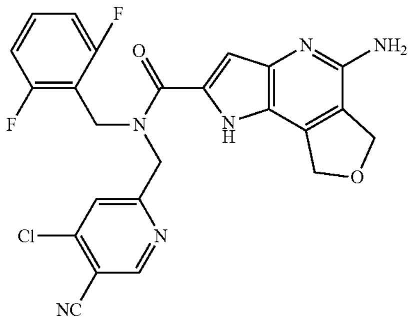
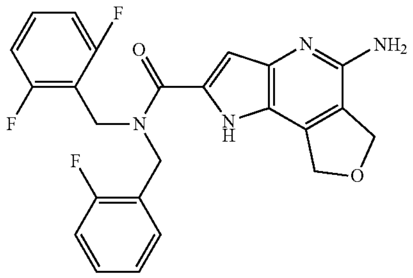
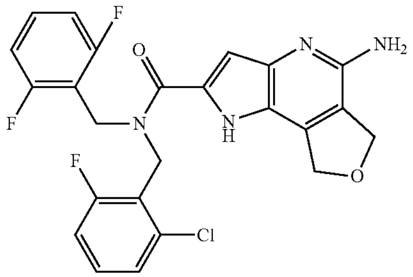
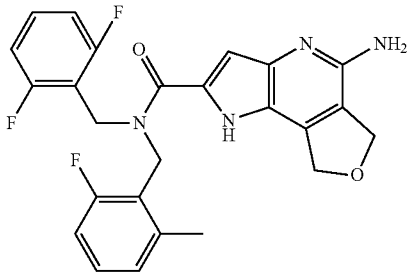

-continued
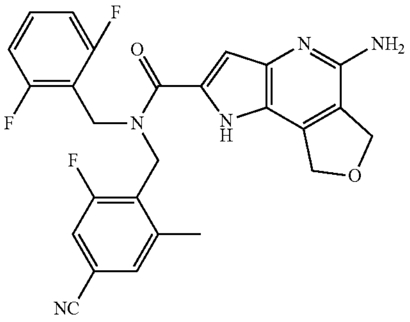
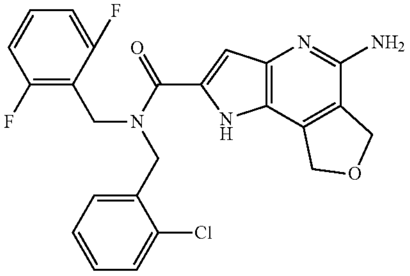
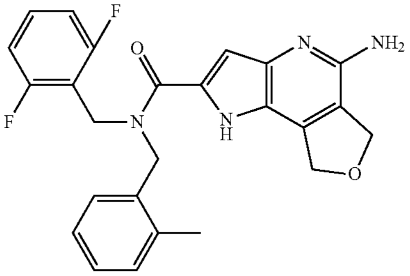
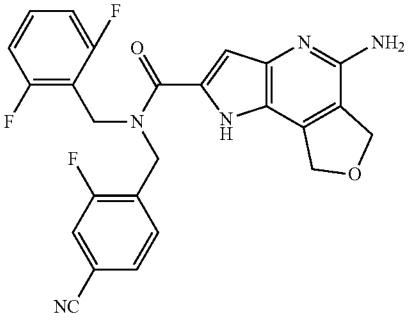
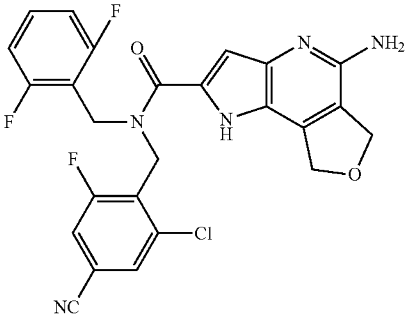
-continued
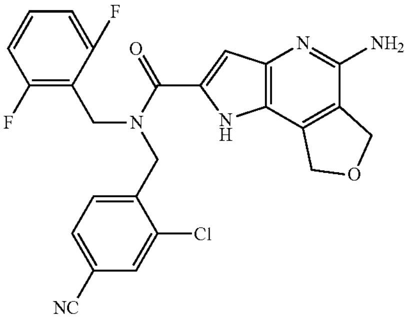
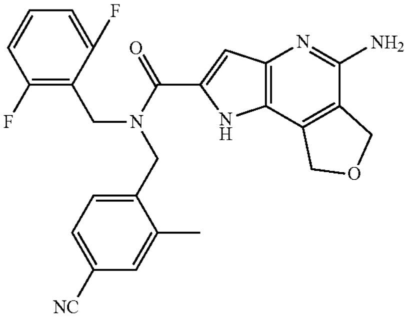
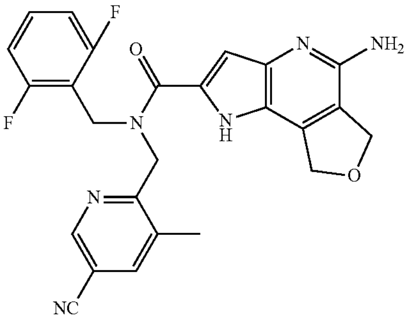
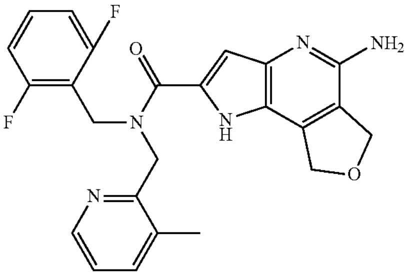
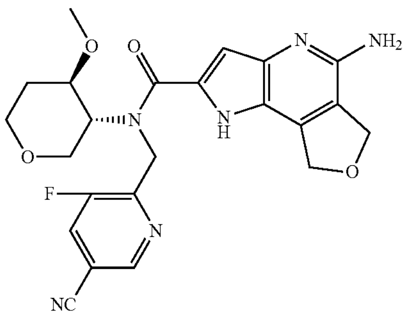

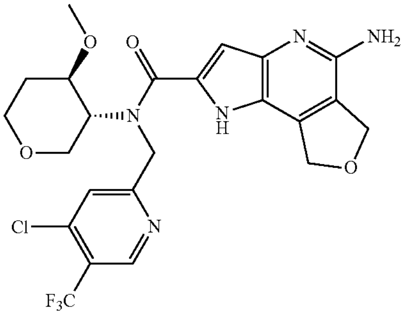
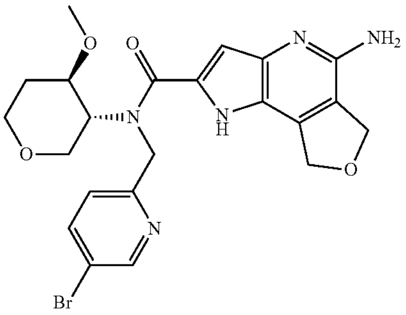
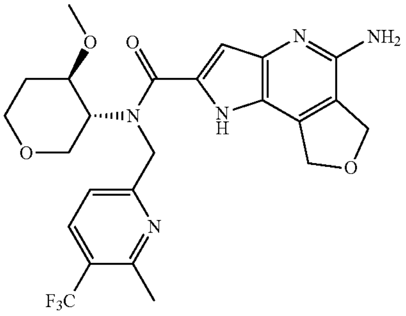
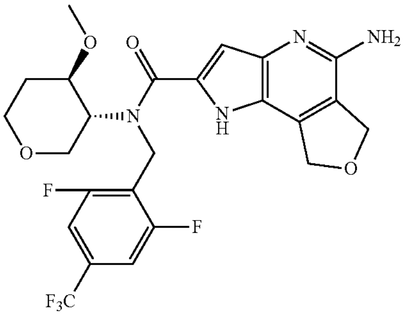
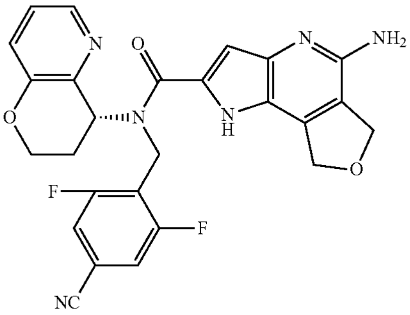
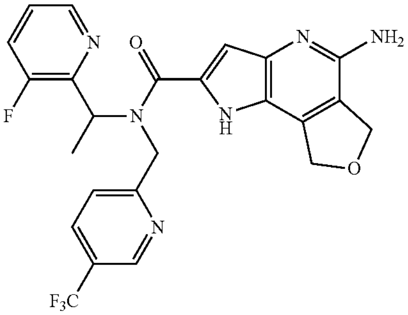
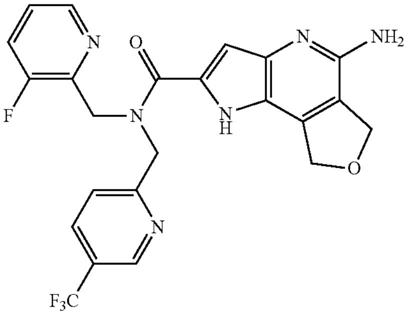
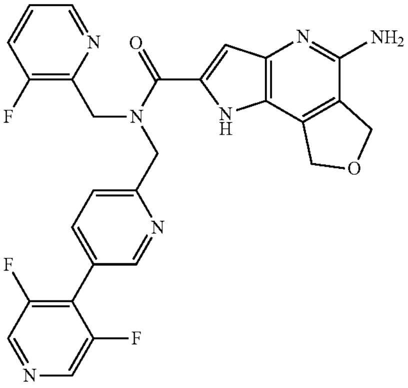
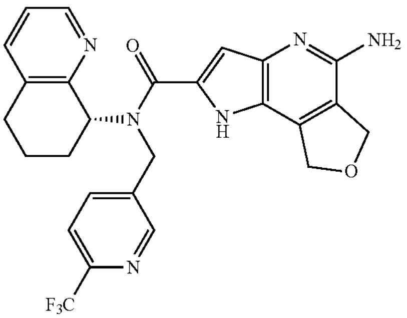
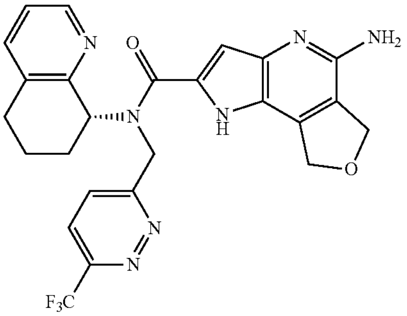

-continued
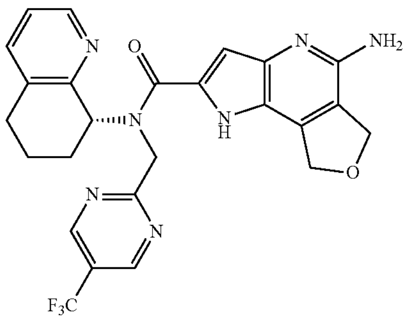
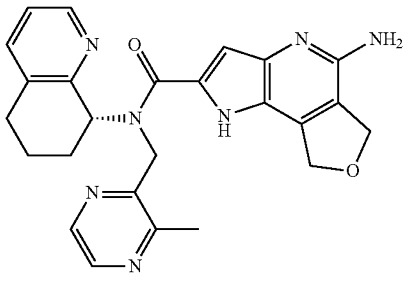
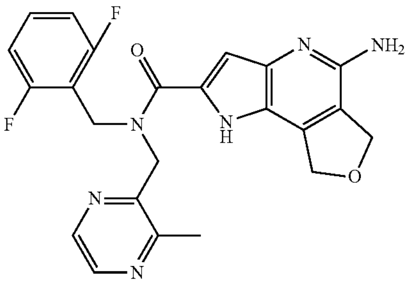
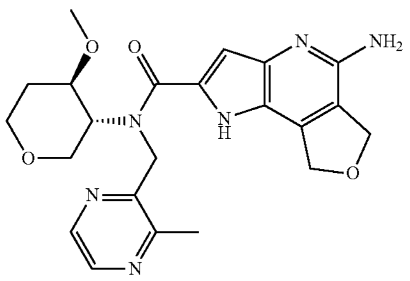
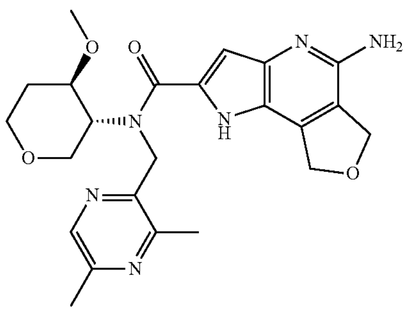
-continued
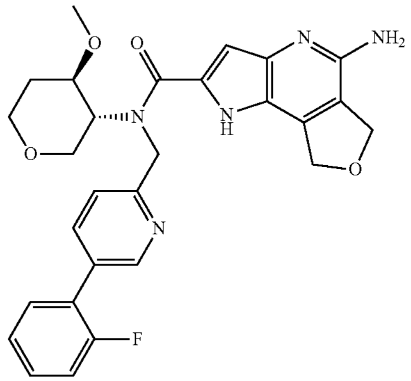
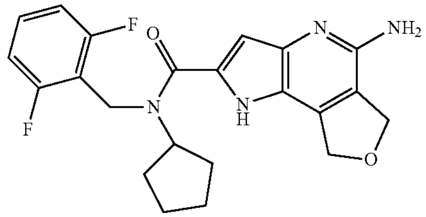
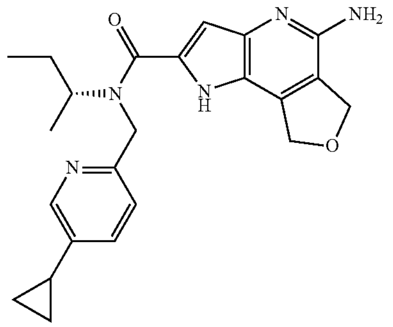
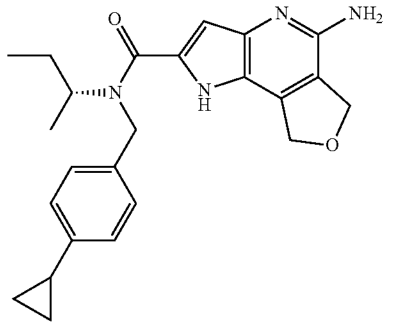
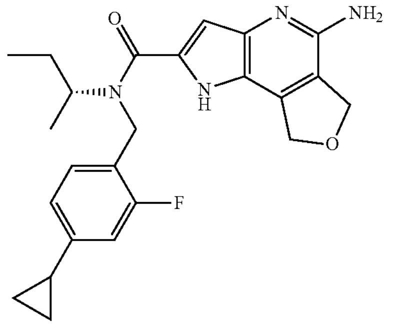

-continued
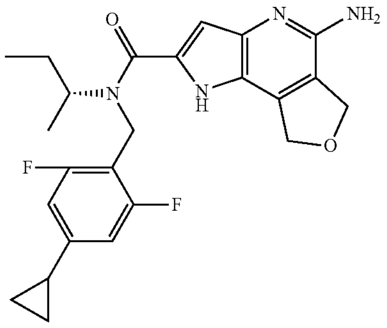
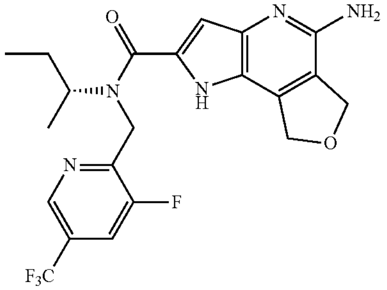
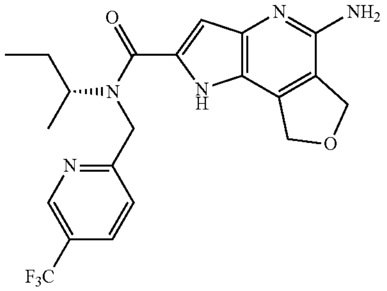
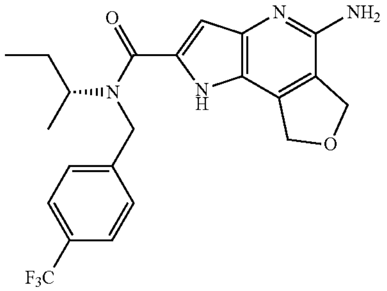
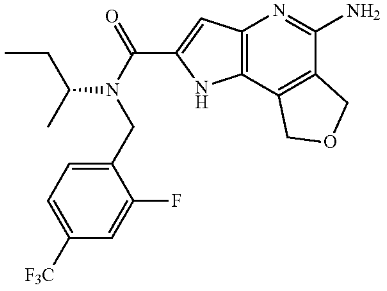
-continued
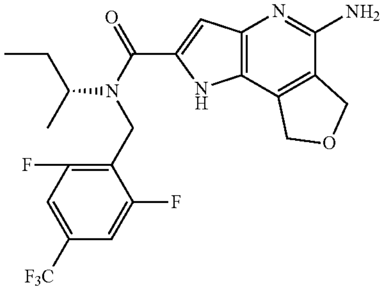
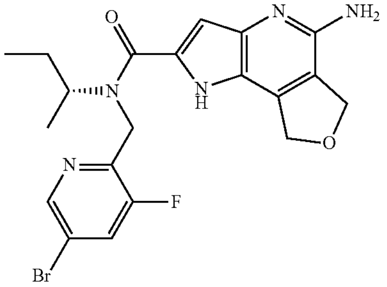
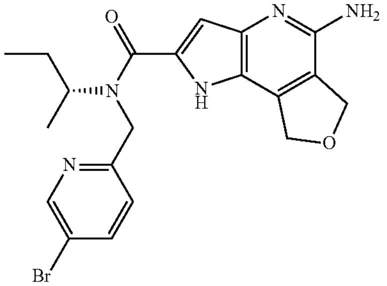
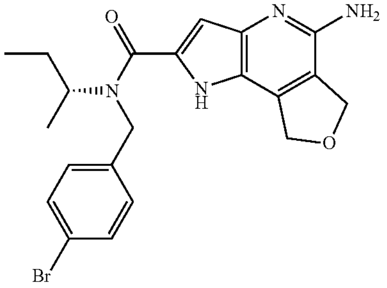
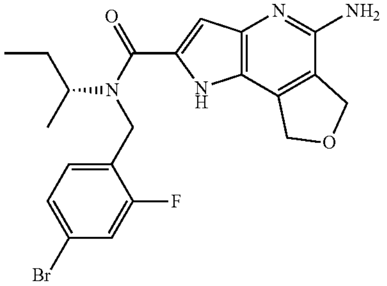
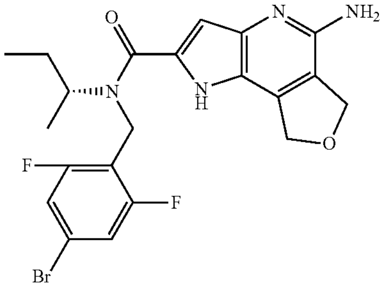

-continued
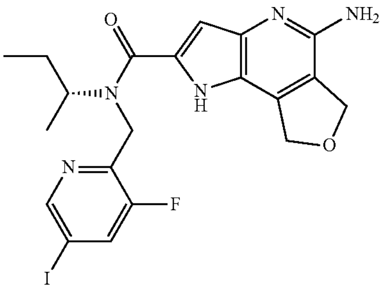
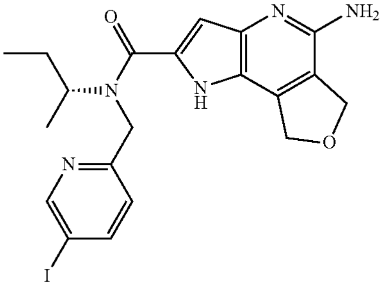
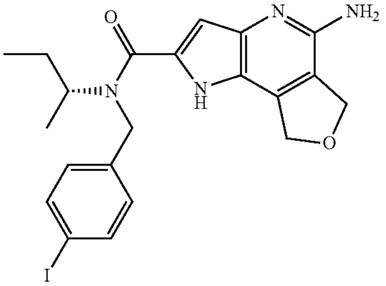
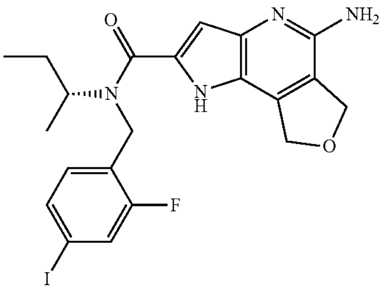
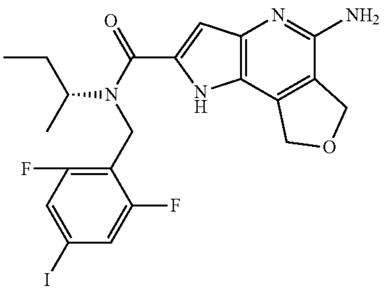
-continued
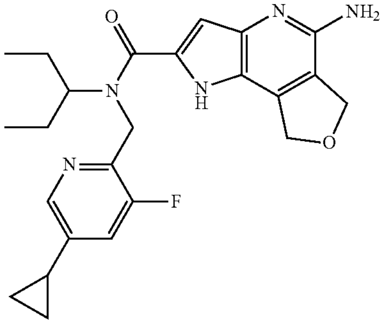
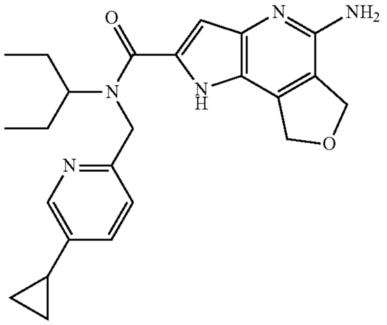
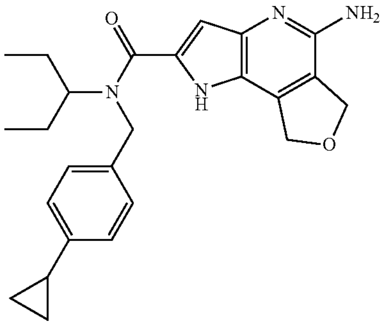
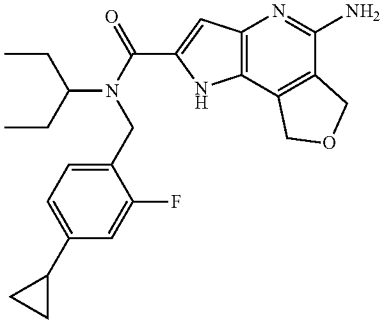
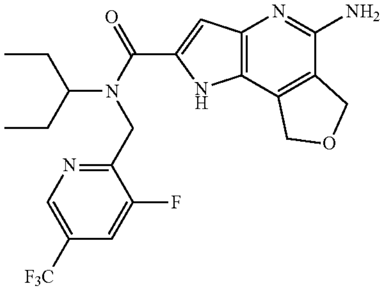

-continued
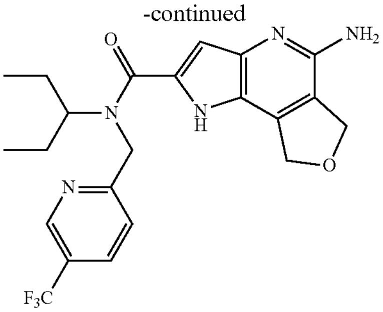
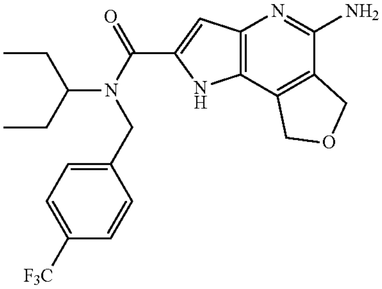
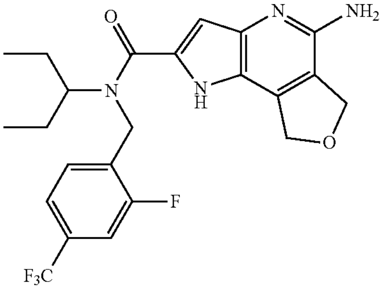
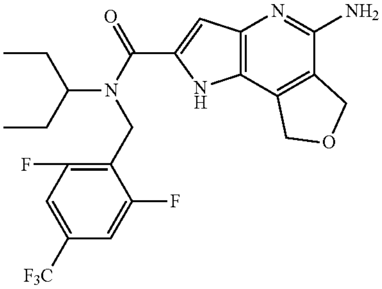
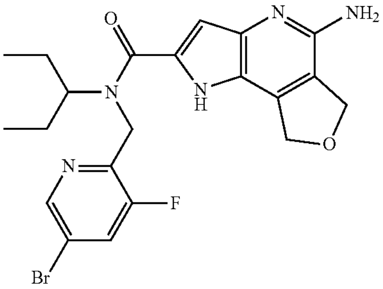
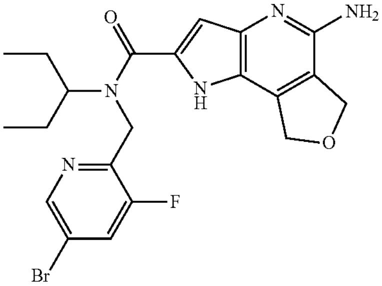
-continued
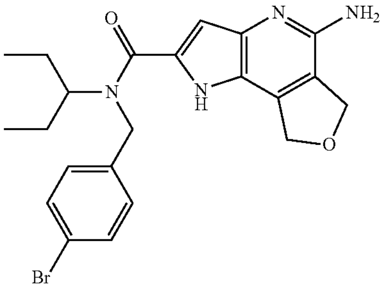
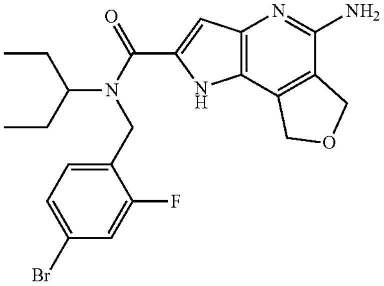
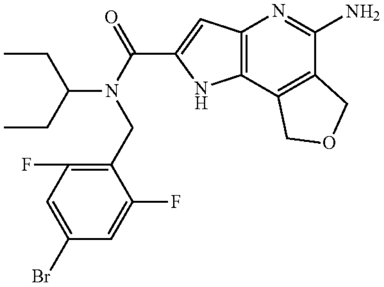
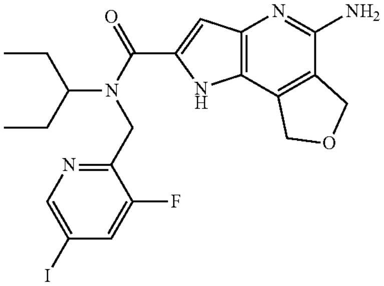
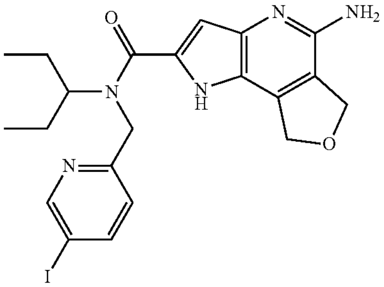
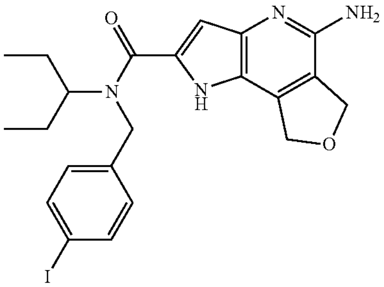

-continued
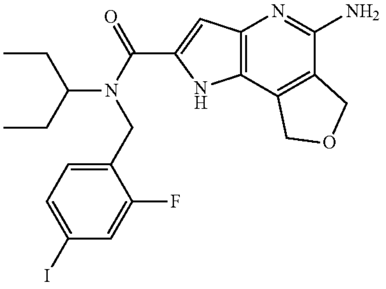
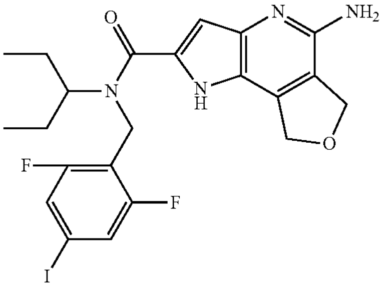
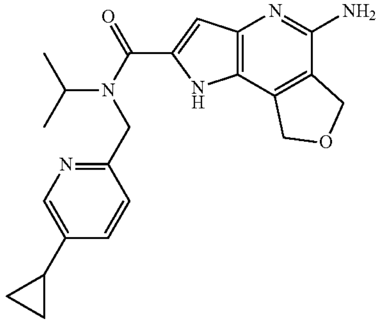
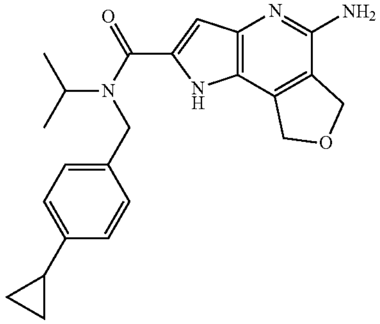
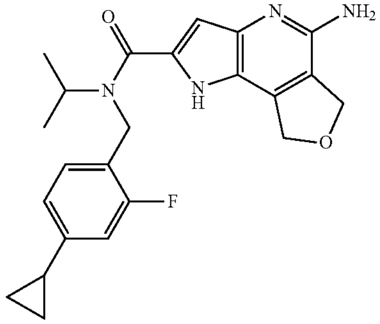
-continued
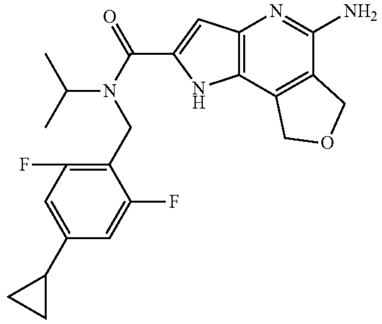
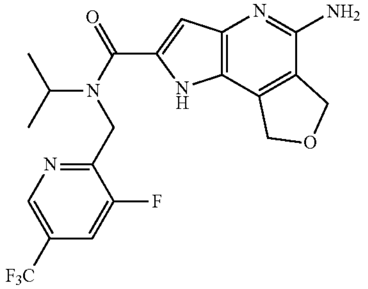
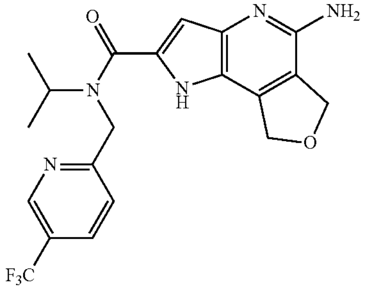
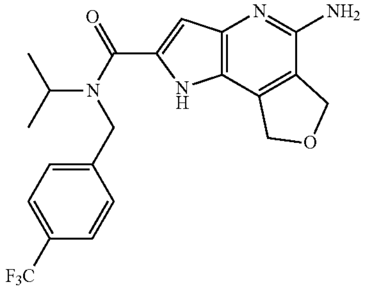
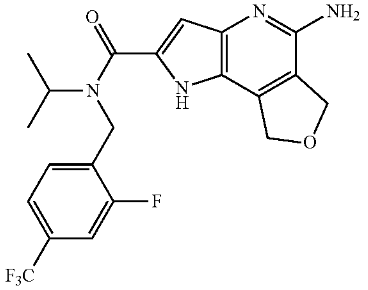

-continued
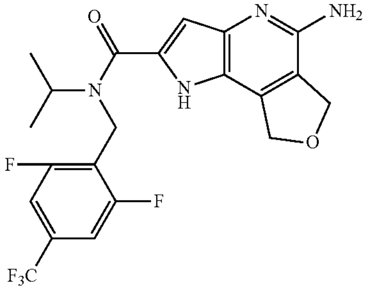
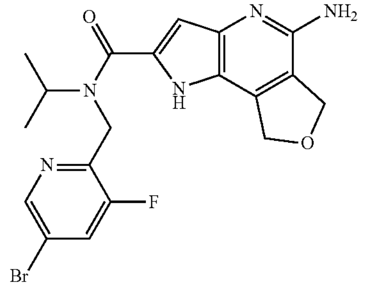
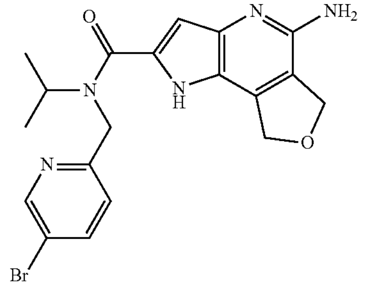
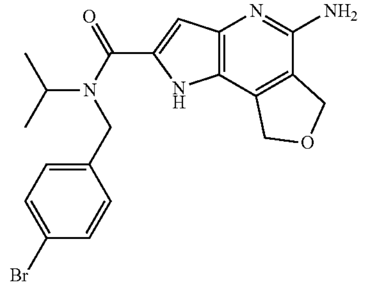
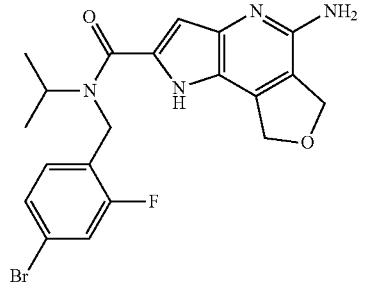
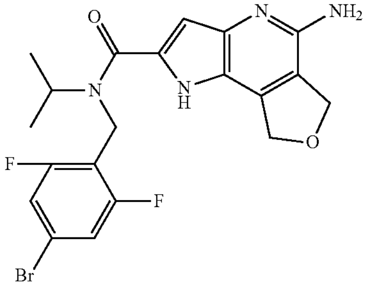
-continued
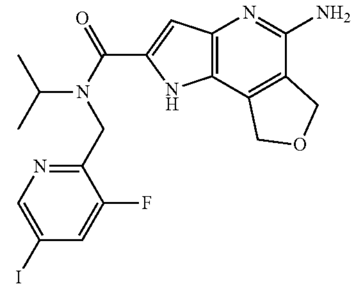
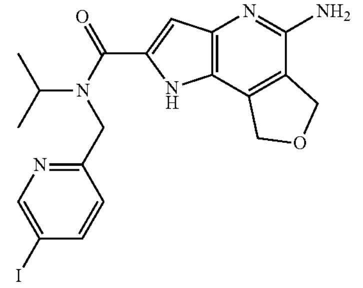
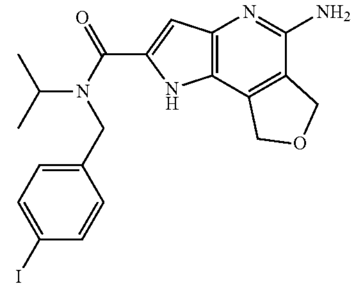
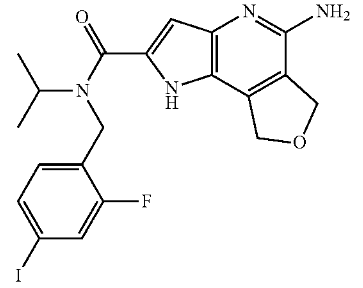
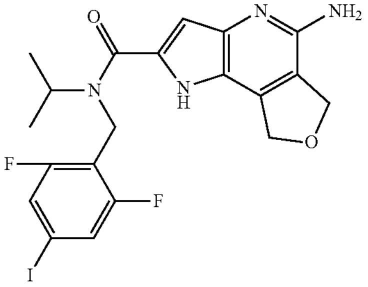

-continued
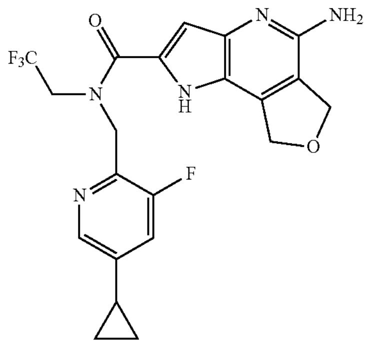
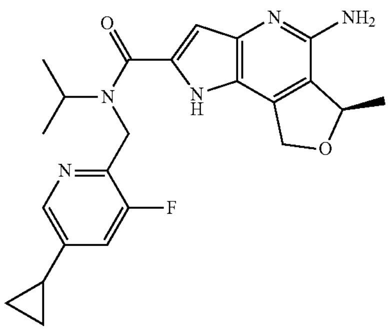
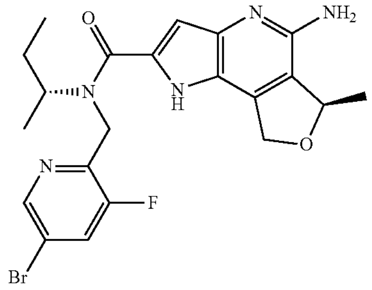
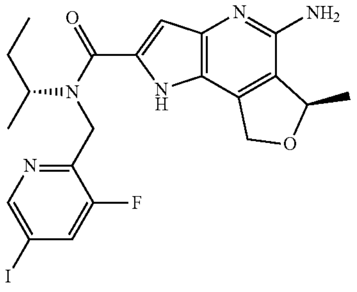
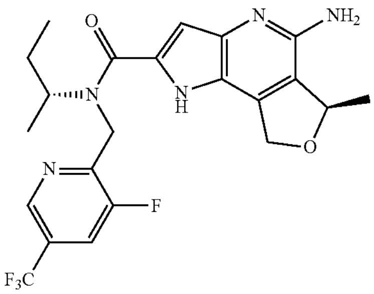
-continued
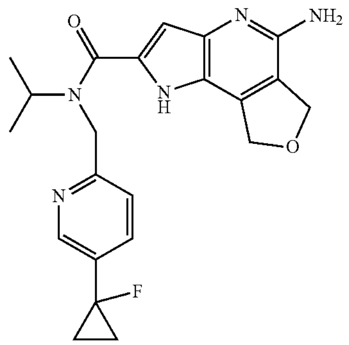
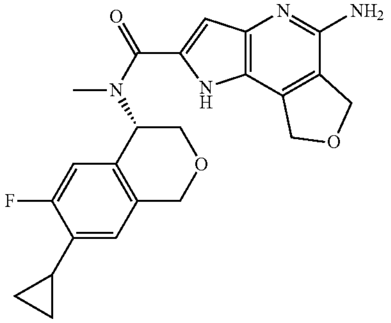
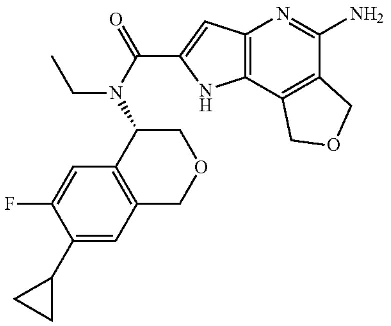
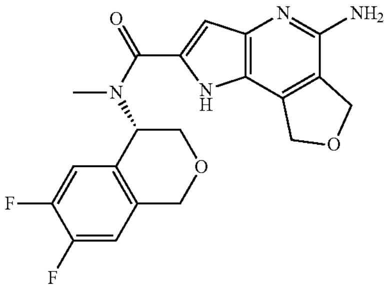
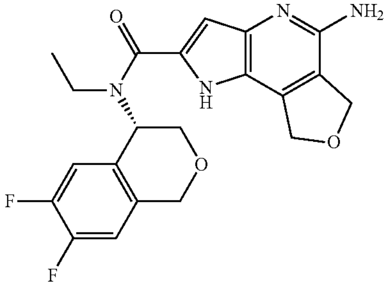

-continued

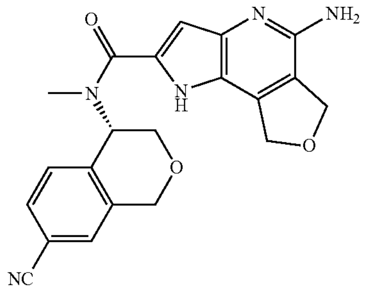

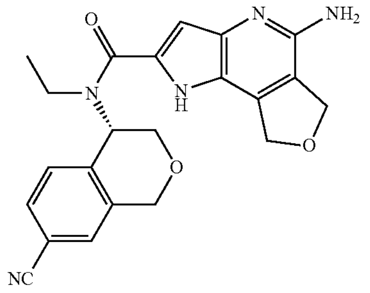

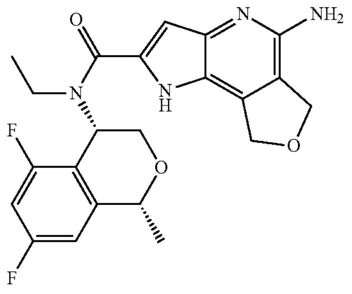

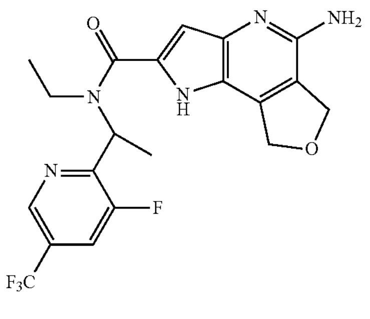

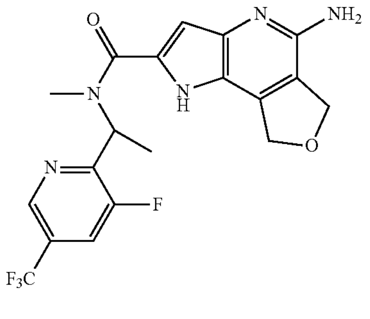

-continued

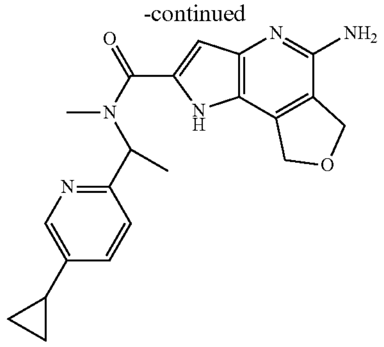

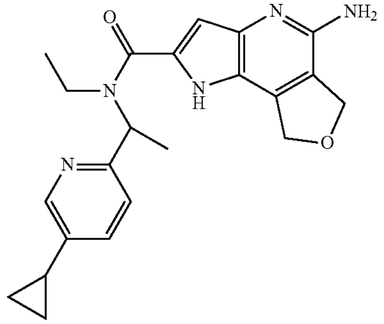

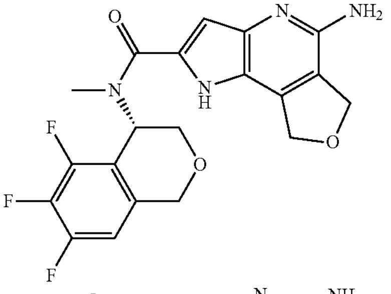

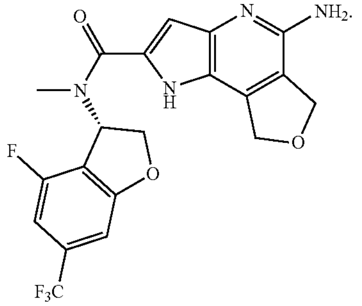

Aspect 17. A pharmaceutical composition comprising a compound of any one of aspects 1-16 or an N-oxide thereof, or a pharmaceutically acceptable salt, stereoisomer, tautomer, or a deuterated analog thereof, and a pharmaceutically acceptable excipient.

In one embodiment, the pharmaceutical composition is for use as described herein, e.g., in any one of Aspects 18-22.

Aspect 18. A method of decreasing or inhibiting PRMT5 activity, comprising administering to a subject in need thereof an effective amount of the compound according to any one of aspects 1-16, or an N-oxide thereof, or a pharmaceutically acceptable salt, stereoisomer, tautomer, or a deuterated analog thereof, including the compound of formula (I) or any specific compound exemplified herein.

Aspect 19. A method of treating a disease modulated by PRMT5, comprising administering to a subject in need thereof an effective amount of the compound according to any one of aspects 1-16, or an N-oxide thereof, or a pharmaceutically acceptable salt, stereoisomer, tautomer, or a deuterated analog thereof, including the compound of formula (I) or any specific compound exemplified herein.

Aspect 20. Use of a compound of any one of aspects 1-16 or an N-oxide thereof, or a pharmaceutically acceptable salt, stereoisomer, tautomer, or a deuterated analog thereof in the preparation of a medicament for treating a disease modulated by PRMT5.

Aspect 21. The method of aspect 19 or the use of aspect 20, wherein the disease is cancer.

Aspect 22. The method of aspect 19 or the use of aspect 20, wherein the disease is MTAP-null solid tumor, including lung cancer, bladder cancer, melanoma, pancreatic cancer, esophageal cancer, gastric adenocarcinoma, breast cancer, and glioblastoma.

DETAILED DESCRIPTION OF THE INVENTION

The following terms have the indicated meanings throughout the specification:

Unless specifically defined elsewhere in this document, all other technical and scientific terms used herein have the meaning commonly understood by one of ordinary skill in the art to which this invention belongs.

The following terms have the indicated meanings throughout the specification.

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" includes a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. If there is no opposite definition, "$C_{1-8}$alkyl" includes a hydrocarbon group selected from linear and branched, saturated hydrocarbon groups comprising from 1 to 8 carbon atoms, "$C_{1-8}$alkyl" also includes a hydrocarbon group selected from linear and branched, saturated hydrocarbon groups comprising from 1 to 6 carbon atoms ($C_{1-6}$alkyl) or 1 to 4 carbon atoms ($C_{1-4}$alkyl).

The term "propyl" includes 1-propyl or n-propyl ("n-Pr"), 2-propyl or isopropyl ("i-Pr").

The term "butyl" includes 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu").

The term "pentyl" includes 1-pentyl, 2-pentyl, 3-pentyl, 2-methyl-2-butyl, 3-methyl-2-butyl, 3-methyl-1-butyl, 2-methyl-1-butyl. The term "pentyl" further comprises

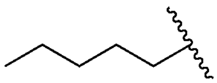,
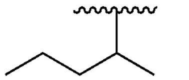

( 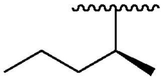 or 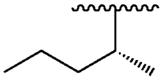 ),

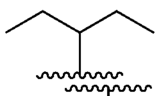, 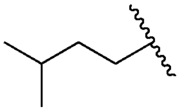, 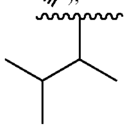, ( 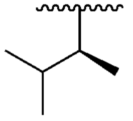 or 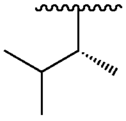 ), 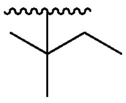,

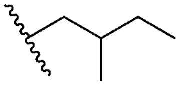 and 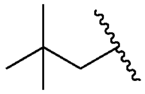.

The term "hexyl" includes 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "alkylene" refers to a divalent alkyl group by removing two hydrogen from alkane. Alkylene includes but not limited to methylene, ethylene, propylene, and so on.

The term "halogen" includes fluoro (F), chloro (Cl), bromo (Br) and iodo (I).

The term "H" or "hydrogen" disclosed herein includes Hydrogen and the non-radioisotope deuterium.

The term "alkenyl" includes a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkenylene" refers to a divalent alkenyl group by removing two hydrogen from alkene. Alkenylene includes but not limited to, vinylidene, butenylene, and so on.

The term "alkynyl" includes a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "alkynylene" refers to a divalent alkynyl group by removing two hydrogen from alkyne. Alkenylene includes but not limited to ethynylene and so on.

The term "cycloalkyl" includes a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "spiro cycloalkyl" includes a cyclic structure which contains carbon atoms and is formed by at least two rings sharing one atom.

The term "fused cycloalkyl" includes a bicyclic cycloalkyl group as defined herein which is saturated and is formed by two or more rings sharing two adjacent atoms.

The term "bridged cycloalkyl" includes a cyclic structure which contains carbon atoms and is formed by two rings sharing two atoms which are not adjacent to each other. The term "7 to 10 membered bridged cycloalkyl" includes a cyclic structure which contains 7 to 12 carbon atoms and is formed by two rings sharing two atoms which are not adjacent to each other.

Examples of fused cycloalkyl, fused cycloalkenyl, or fused cycloalkynyl include but are not limited to bicyclo [1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2,3-dihydro-1H-indenyl, 1H-indenyl, 1, 2, 3,4-tetralyl, 1,4-dihydronaphthyl, etc. Preferred embodiments are 8 to 9 membered fused rings, which refer to cyclic structures containing 8 to 9 ring atoms within the above examples.

The term "aryl" used alone or in combination with other terms includes a group selected from:

- 5- and 6-membered carbocyclic aromatic rings, e.g., phenyl;
- bicyclic ring systems such as 7 to 12 membered bicyclic ring systems, wherein at least one ring is carbocyclic and aromatic, e.g., naphthyl and indanyl; and,
- tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" includes a bicyclic aryl ring as defined herein. The typical bicyclic fused aryl is naphthalene.

The term "heteroaryl" includes a group selected from:

- 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
- 7- to 12-membered bicyclic rings comprising at least one heteroatom, for example, from 1 to 4, or, in some embodiments, from 1 to 3, or, in other embodiments. 1 or 2, heteroatoms, selected from N, O, and S, with the remaining ring atoms being carbon and wherein at least one ring is aromatic and at least one heteroatom is present in the aromatic ring; and
- 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" includes a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

"Heterocyclyl", "heterocycle" or "heterocyclic" are interchangeable and include anon-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "at least one substituent" disclosed herein includes, for example, from 1 to 4, such as from 1 to 3, further as 1 or 2, substituents, provided that the theory of valence is met. For example, "at least one substituent F" disclosed herein includes from 1 to 4, such as from 1 to 3, further as 1 or 2, substituents F.

The term "divalent" refers to a linking group capable of forming covalent bonds with two other moieties. For example, "a divalent cycloalkyl group" refers to a cycloalkyl group obtained by removing two hydrogen from the corresponding cycloalkane to form a linking group, the term "divalent aryl group", "divalent heterocyclyl group" or "divalent heteroaryl group" should be understood in a similar manner.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art could select and apply the techniques most likely to achieve the desired separation.

"Diastereomers" refer to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel. E. and Wilen, S. *Stereochemistry of Organic Compounds*. New York: John Wiley & Sons, Inc., 1994; Lochmuller, C. H., et al. "*Chromatographic resolution of enantiomers: Selective review.*" *J. Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker. Inc., 1993.

Some of the compounds disclosed herein may exist with different points of attachment of hydrogen, referred to as tautomers. For example, compounds including carbonyl $—CH_2C(O)—$ groups (keto forms) may undergo tautomerism to form hydroxyl $—CH=C(OH)—$ groups (enol forms). Both keto and enol forms, individually as well as mixtures thereof, are also intended to be included where applicable.

"Prodrug" refers to a derivative of an active agent that requires a transformation within the body to release the active agent. In some embodiments, the transformation is an enzymatic transformation. Prodrugs are frequently, although not necessarily, pharmacologically inactive until converted to the active agent.

"Pharmaceutically acceptable salts" refer to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base. The term also includes salts of the stereoisomers (such as enantiomers and/or diastereomers), tautomers and prodrugs of the compound of the invention.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds Those skilled in the art will recognize various synthetic methodologies that may be used without undue experimentation to prepare non-toxic pharmaceutically acceptable addition salts.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The term "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer, tautomer or prodrug thereof, and/or at least one pharmaceutically acceptable salt thereof disclosed herein effective to “treat” as defined herein, a disease or disorder in a subject. In the case of combination therapy, the term “therapeutically effective amount” refers to the total amount of the combination objects for the effective treatment of a disease, a disorder or a condition.

The term “disease” refers to any disease, discomfort, illness, symptoms or indications, and can be interchangeable with the term “disorder” or “condition”.

Throughout this specification and the claims which follow, unless the context requires otherwise, the term “comprise”, and variations such as “comprises” and “comprising” are intended to specify the presence of the features thereafter, but do not exclude the presence or addition of one or more other features. When used herein the term “comprising” can be substituted with the term “containing”, “including” or sometimes “having”.

Throughout this specification and the claims which follow, the term “$C_{n-m}$” indicates a range which includes the endpoints, wherein n and m are integers and indicate the number of carbons. Examples include $C_{1-8}$, $C_{1-6}$, and the like.

Illustrations herein showing a substituent(s) bonded to a cyclic group (e.g., aryl, heteroaryl, cycloalkyl, fused cyclic group, spiro cyclic group) through a bond between ring atoms are meant to indicate, unless specified otherwise, that the substituent(s) may be bonded to the cyclic group at any ring position of any ring in the cyclic group (e.g., any ring in a fused cyclic group), so long as such substitution results in a stable compound.

Unless specifically defined elsewhere in this document, all other technical and scientific terms used herein have the meaning commonly understood by one of ordinary skill in the art to which this invention belongs.

EXAMPLES

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from the solvent’s boiling temperature. A given reaction can be carried out in one solvent or mixture of solvents.

The selection of appropriate protecting group, can be readily determined by one skilled in the art. In the synthesis schemes, some protection/deprotection steps are not shown and can be incorporated before, after or in between any steps. The protecting group shown in the synthesis schemes may or may not be used based on reaction conditions. The sequences of reactions may vary and provide similar results.

Reactions can be monitored according to any suitable method known in the art, such as NMR, UV, HPLC, LC-MS and TLC. Compounds can be purified by a variety of methods, including prep-HPLC and silica gel chromatography. Unless specified, prep-HPLC uses a buffered acetonitrile/water systems and silica gel chromatography (including column chromatography and prep-TLC) uses PE/EtOAc or DCM/MeOH systems as mobile phases. NMR spectra are recorded using a Bruker or Varian instrument with preset pulse sequences.

Scheme I

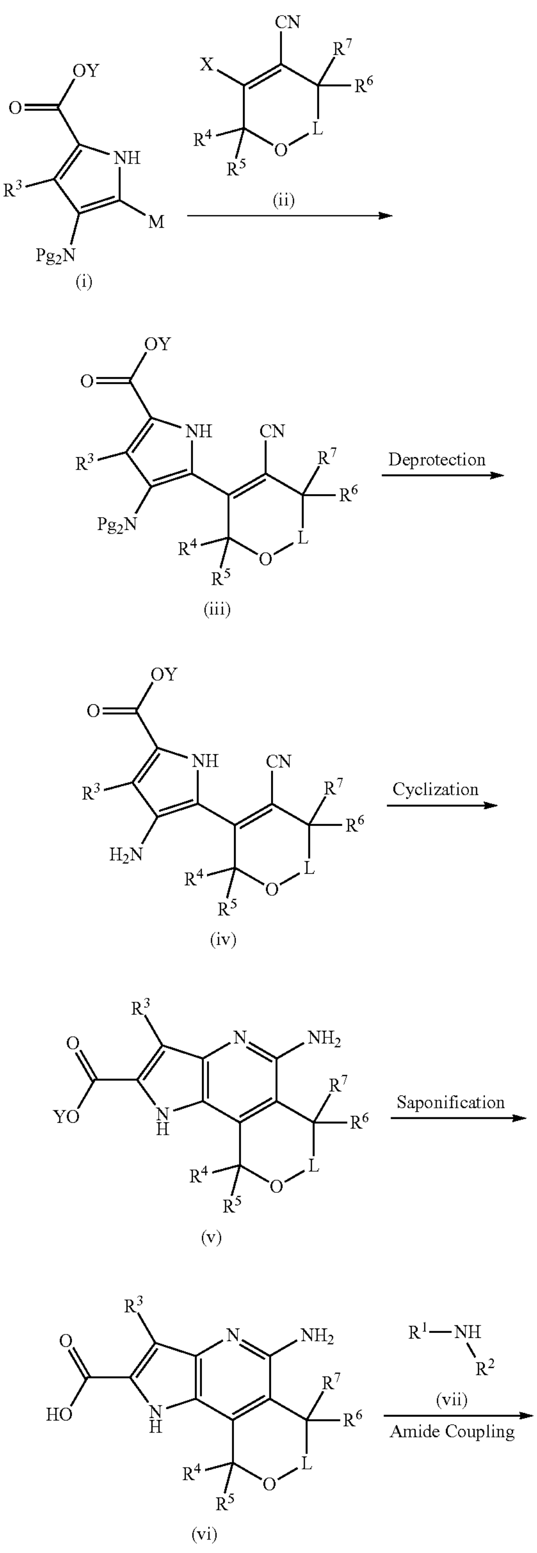

-continued

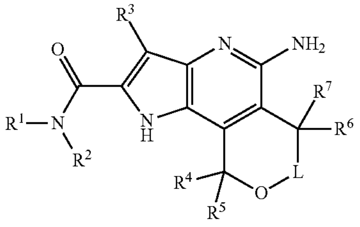

(viii)

M = hydrogen, boronic acid, boronic ester or metals
X = halogens or pseudohalogens
Y = alkyl or substituted alkyl
Pg = optional protective groups For example, compounds of Formula (I) can be formed as shown in Scheme I. Compound (i) and compound (ii) can be coupled together by transition metal catalyzed coupling to give compound (iii). Compound (iii) can be deprotected to give compound (iv). Compound (iv) can intramolecularly cyclize to give compound (v). Compound (v) can be saponified to give compound (vi). Compound (vi) can be coupled with compound (vii) to give compound (viii) [i.e., Formula (I)].

Scheme II

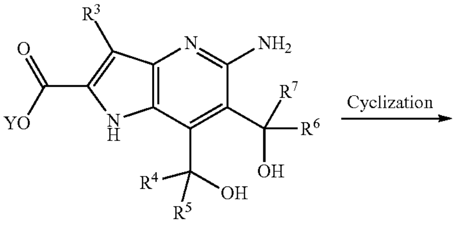

(i)

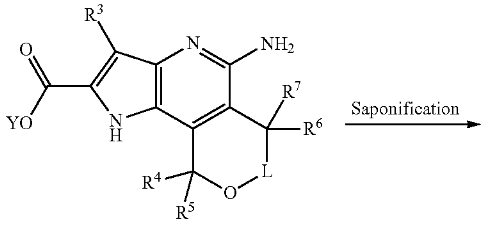

(ii)

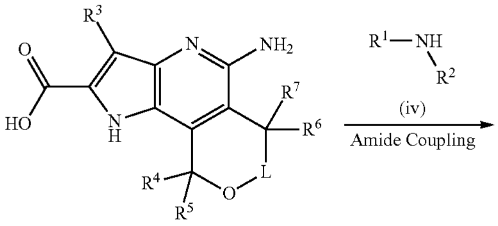

(iii)

-continued

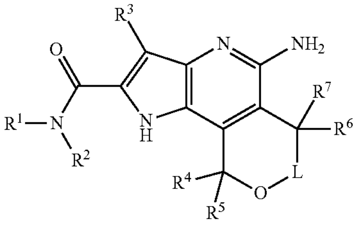

(v)

Y = alkyl or substituted alkyl

For example, compounds of Formula (I) can be formed as shown in Scheme II. Compound (i) can go through a dehydrative cyclization to give compound (ii). Compound (ii) can be saponified to give compound (iii). Compound (iii) can be coupled with compound (iv) to give compound (v) [i.e., Formula (I)].

Scheme III

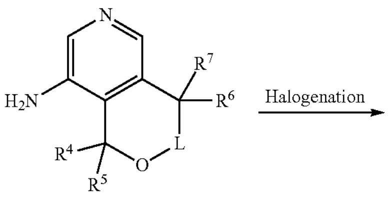

(i)

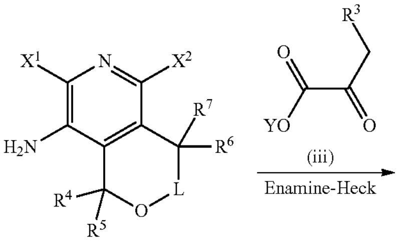

(ii)

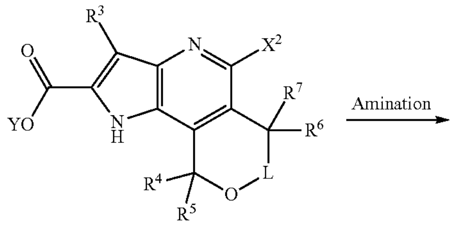

(iv)

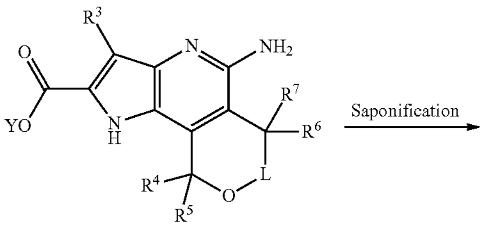

(v)

-continued

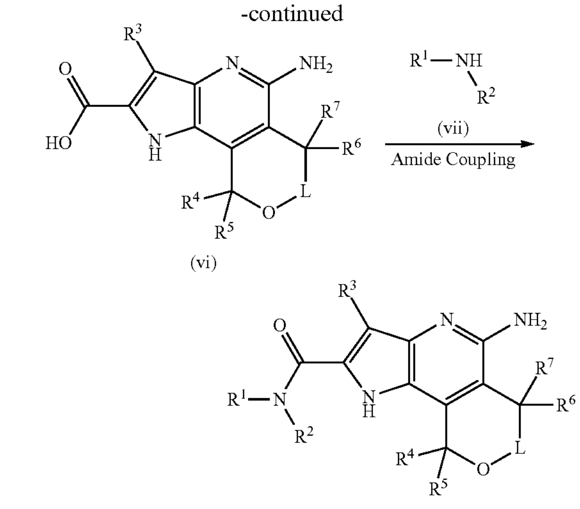

(vi)

(viii)

$X^1$, $X^2$ = halogens or pseudohalogens
Y = alkyl or substituted alkyl

For example, compounds of Formula (I) can be formed as shown in Scheme III. Compound (i) can be halogenated to give compound (ii). Compound (ii) can react with compound (iii) through an enamine-Heck reaction to give compound (iv). Compound (iv) can be aminated to give compound (v). Compound (v) can be saponified to give compound (vi). Compound (vi) can be coupled with compound (vii) to give compound (viii) [i.e., Formula (I)].

Scheme IV

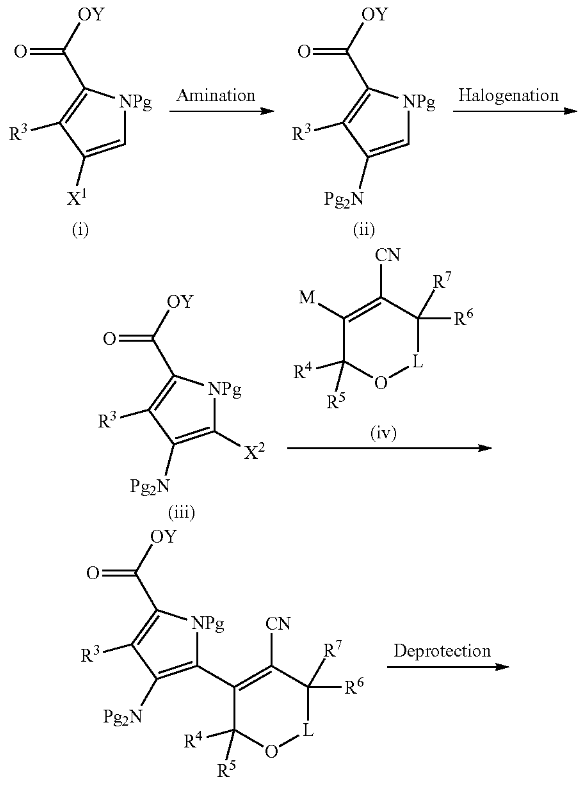

(i) (ii) (iii) (iv) (v)

-continued

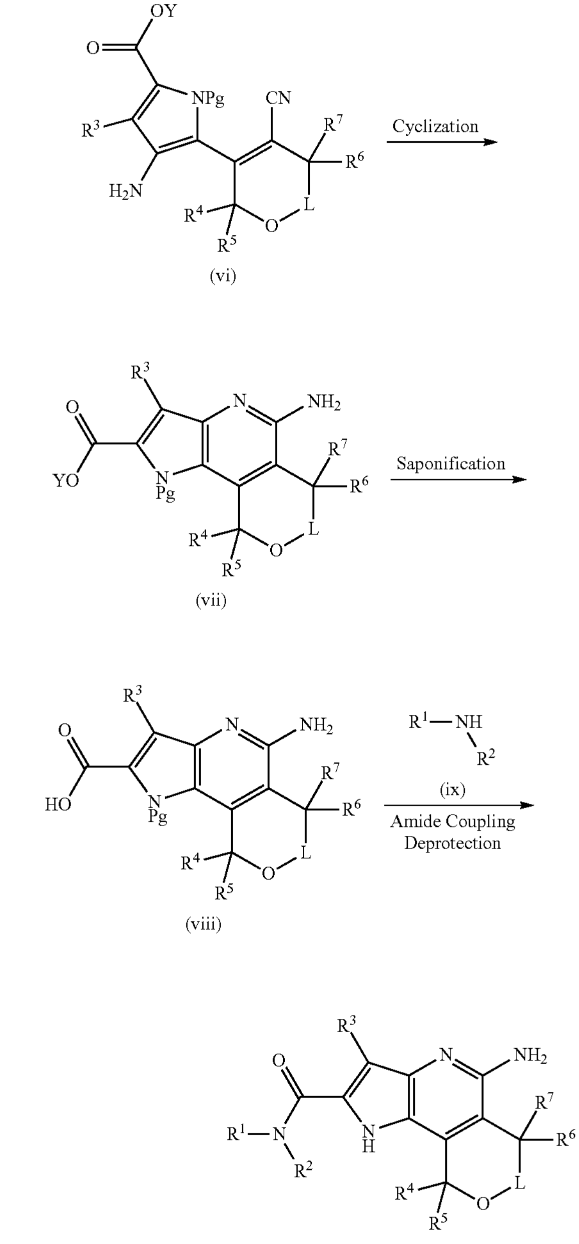

(vi) (vii) (viii) (x)

M = hydrogen, boronic acid, boronic ester or metals
$X^1$, $X^2$ = halogens or pseudohalogens
Y = alkyl or substituted alkyl
Pg = optional protective groups For example, compounds of Formula (I) can be formed as shown in Scheme IV. Compound (i) can be aminated, for example, via metal-catalyzed coupling reactions, to give compound (ii). Compound (ii) can be halogenated to give compound (iii). Compound (iii) and compound (iv) can be couple together by transition metal catalyzed coupling to give compound (v). Compound (v) can be deprotected to give compound (vi). Compound (vi) can intramolecularly cyclize to give compound (vii). Compound (vii) can be saponified to give compound (viii). Compound (viii) can be coupled with compound (ix) followed by optional deprotection to give compound (x) [i.e., Formula (I)].

Scheme V

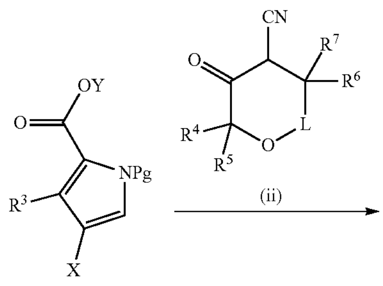

(i)

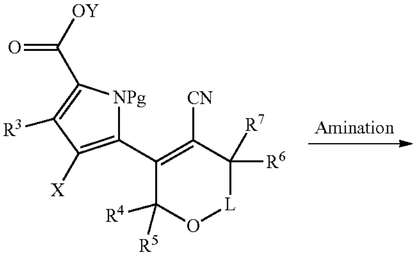

(iii)

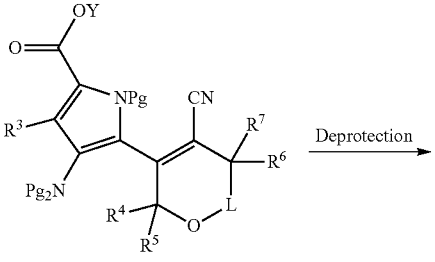

(ivi)

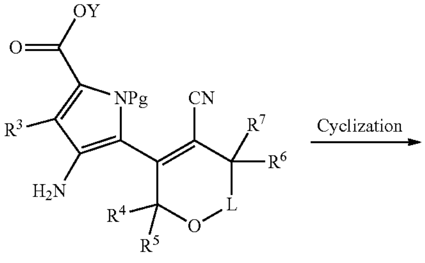

(v)

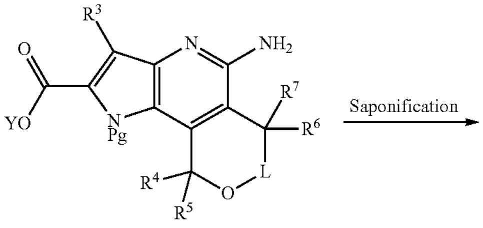

(vi)

-continued

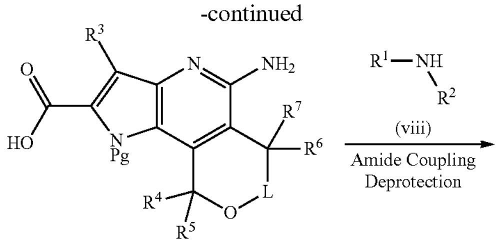

(vii)

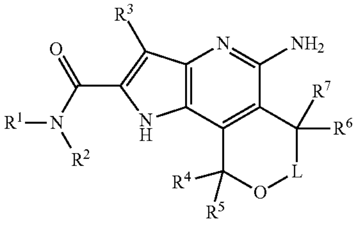

(ix)

X = halogens or pseudohalogens
Y = alkyl or substituted alkyl
Pg = optional protective groups For example, compounds of Formula (I) can be formed as shown in Scheme V. Compound (i) can be condensed with compound (ii) to give compound (iii). Compound (iii) can be aminated, for example, via metal-catalyzed coupling reactions, to give compound (iv). Compound (iv) can be deprotected to give compound (v). Compound (v) can intramolecularly cyclize to give compound (vi). Compound (vi) can be saponified to give compound (vii). Compound (vii) can be coupled with compound (viii) followed by optional deprotection to give compound (ix) [i.e., Formula (I)].

Scheme VI

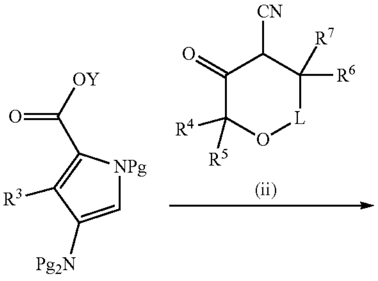

(i)

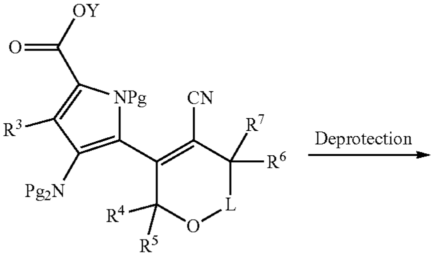

(iii)

-continued

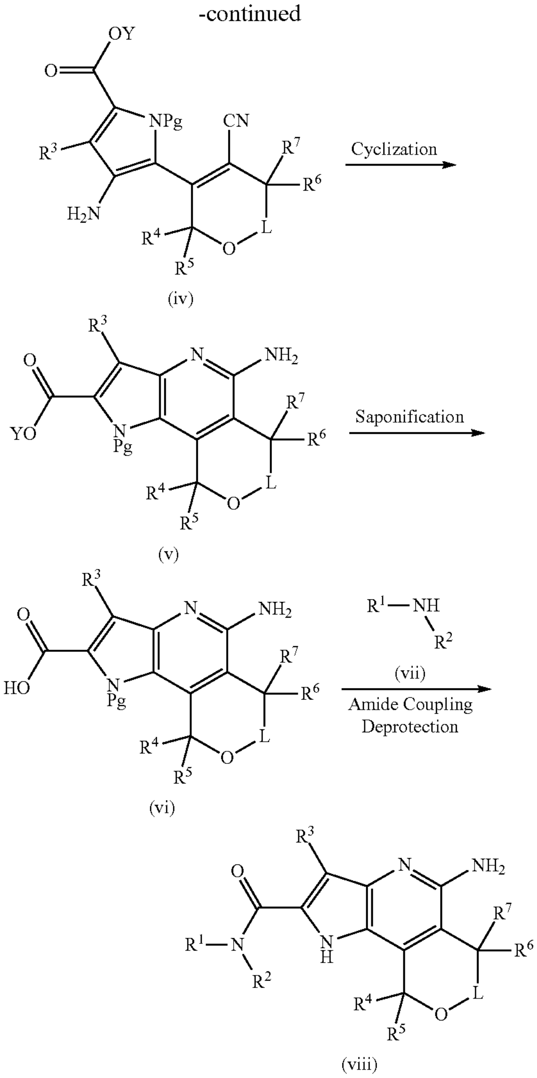

Y = alkyl or substituted alkyl
Pg = optional protective groups

For example, compounds of Formula (I) can be formed as shown in Scheme VI. Compound (i) can be condensed with compound (ii) to give compound (iii). Compound (iii) can be deprotected to give compound (iv). Compound (iv) can intramolecularly cyclize to give compound (v). Compound (v) can be saponified to give compound (vi). Compound (vi) can be coupled with compound (vii) followed by optional deprotection to give compound (viii) [i.e., Formula (I)].

| ABBREVIATIONS | |
|---|---|
| NMR | nuclear magnetic resonance |
| UV | ultraviolet |
| HPLC | high performance liquid chromatography |
| prep | preparation/preparative |
| LC-MS | liquid chromatograph mass spectrometer |
| TLC | thin layer chromatography |
| PE | petroleum ether |
| Et | ethyl |
| Ac | acetyl |
| dppf | 1,1'-bis(diphenylphosphino)ferrocene |
| Me | methyl |
| DCM | dichloromethane |
| Boc | tert-butyloxycarbonyl |
| NBS | N-bromosuccinimide |
| Bu | butyl |
| Tf | trifluoromethanesulfonyl |
| dba | dibenzylideneacetone |
| BPD | bis(pinacolato)diboron |
| DMSO | dimethyl sulfoxide |
| XPhos | 2-(dicyclohexylphosphino)-2',4',6'-triisopropylbiphenyl |
| THF | tetrahydrofuran |
| Ph | phenyl |
| DMF | N,N-dimethylformamide |
| DIPEA | diisopropylethylamine |
| HATU | 1-[bis (dimethylamino)methylene]-1H-1,2,3-triazolo [4,5-b]pyridinium 3-oxid hexafluorophosphate |
| BOPCl | bis(2-oxo-3-oxazolidinyl)phosphinic chloride |
| DMAP | 4-dimethylaminopyridine |
| MTBE | methyl tert-butyl ether |
| DIBAL-H | diisobutyl aluminium hydride |
| SEM | 2-(trimethylsilyl)ethoxymethyl |
| DMAC | dimethylacetamide |
| tR | retention time |
| AIBN | 2,2'-azobis(isobutyronitrile) |
| SFC | supercritical fluid chromatography |
| DPPA | diphenyl phosphoryl azide |
| DBU | 1,8-diazabicyclo[5.4.0]undec-7-ene |
| BINAP | 2,2'-bis(diphenylphosphino)-1,1'-binaphthalene |
| DIAD | diisopropyl azodicarboxylate |
| TFA | trifluoroacetic acid |
| DIBAD | di-tert-butyl azodicarboxylate |
| Ns | nitrosulfonyl |
| T3P | propylphosphonic anhydride |
| SPhos | 2-dicyclohexylphosphino-2',6'-dimethoxybiphenyl |
| NIS | N-iodosuccinimide |
| mCPBA | meta-chloroperbenzoic acid |
| NMP | N-methyl-2-pyrrolidone |
| Bn | benzyl |
| DMA | N,N-dimethylacetamide |
| CMPI | 2-chloro-1-methylpyridinium iodide |
| Xantphos | 4,5-bis(diphenylphosphino)-9,9-dimethylxanthene |
| CMPI | 2-Chloro-1-methylpyridinium iodide |

Example 1; (R)-5-amino-N-((3',5'-difluoro-[3,4'-bipyridin]-6-yl)methyl)-N-(5,6,7,8-tetrahydroquinolin-8-yl)-6,8-dihydro-1H-furo[3,4-d]pyrrolo[3,2-b]pyridine-2-carboxamide

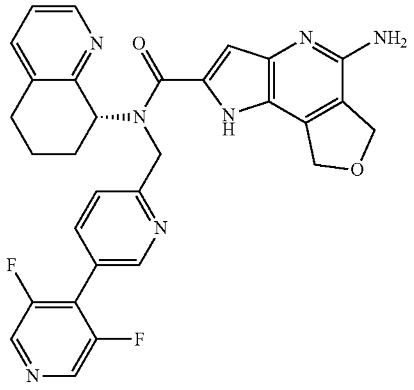 [SMILES: Nc1nc2cc(C(=O)N(Cc3ccc(-c4c(F)cncc4F)cn3)[C@@H]3CCCc4cccnc43)[nH]c2c2c1COC2]

Step 1: 3',5'-difluoro-[3,4'-bipyridine]-6-carbaldehyde

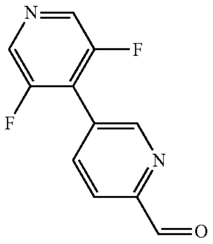 [SMILES: O=Cc1ccc(-c2c(F)cncc2F)cn1]

To a mixture of 3,5-difluoro-4-iodopyridine (0.85 g, 3.53 mmol) in dioxane (17 mL), toluene (8.5 mL) and water (8.5 mL) was added 5-(4,4,5,5-tetramethyl-1,3,2-dioxaborolan-2-yl)picolinaldehyde (1.64 g, 7.05 mmol), $K_3PO_4$ (2.25 g, 10.6 mmol) and $Pd(dppf)Cl_2$ (258 mg, 0.35 mmol) at 20° C. The mixture was stirred at 85° C. for 3 h. The mixture was cooled to room temperature and filtered. The filtrate was concentrated under reduced pressure. The residue was purified by silica gel chromatograph (PE:EtOAc=1:0 to 1:1) to give the title compound (0.70 g, 90%). LC-MS $(M+H)^+$=221.2.

Step 2: (R)—N-((3',5'-difluoro-[3,4'-bipyridin]-6-yl)methyl)-5,6,7,8-tetrahydroquinolin-8-amine

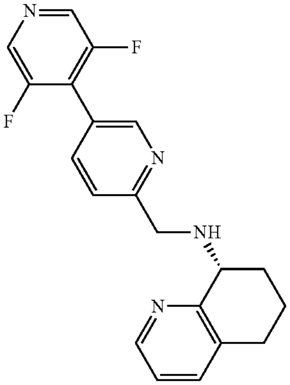 [SMILES: Fc1cncc(F)c1-c1ccc(CN[C@@H]2CCCc3cccnc32)nc1]

To a solution of (R)-5,6,7,8-tetrahydroquinolin-8-amine (525 mg, 3.54 mmol) in DCM (13 mL) was added $NaBH(OAc)_3$ (939 mg, 4.43 mmol), MeOH (0.13 mL) and 3',5'-difluoro-[3,4'-bipyridine]-6-carbaldehyde (0.65 g, 2.95 mmol). The mixture was stirred at 20° C. for 1 h and then poured into saturated $NaHCO_3$ (50 mL). The mixture was extracted with DCM (50 mL×3). The combined organic layer was washed with brine (50 mL), dried over $Na_2SO_4$, filtered and concentrated under vacuum. The residue was purified by prep-HPLC to give the title compound (216 mg, 21%). LC-MS $(M+H)^+$=353.2.

Step 3: ethyl 4-amino-1H-pyrrole-2-carboxylate

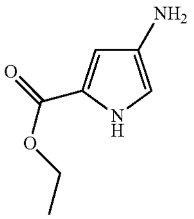

To a solution of ethyl 4-nitro-1H-pyrrole-2-carboxylate (9.0 g, 48.9 mmol) in MeOH (100 mL) was added Pd/C (10%, 5.2 g, 4.89 mmol). The mixture was stirred under hydrogen (15 psi) at 25° C. for 12 h. The mixture was filtered through a short pad of celite. The filtrate was concentrated under vacuum to give the title compound (7 g, 93%). LCMS $(M+H)^+$=155.2.

Step 4: ethyl 4-((tert-butoxycarbonyl)amino)-1H-pyrrole-2-carboxylate

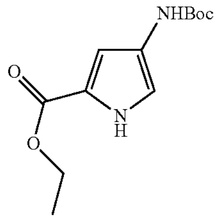 [SMILES: CCOC(=O)c1cc(NC(=O)OC(C)(C)C)c[nH]1]

To a solution of ethyl 4-amino-1H-pyrrole-2-carboxylate (7.0 g, 45.4 mmol) in DCM (80 mL) was added $Boc_2O$ (14.9 g, 68.1 mmol) and $Et_3N$ (13.8 g, 136 mmol). The mixture was stirred at 25° C. for 1 h. The mixture was diluted with water (100 mL) and then extracted with DCM (50 mL×3). The combined organic layer was washed with brine (50 mL×2), dried over $Na_2SO_4$, filtered and concentrated under reduced pressure. The residue was purified by silica gel chromatography (PE:EtOAc=1:0 to 1:1) to give the title compound (8.0 g, 69%). LCMS $(M+H\text{-}t\text{-}Bu)^+$=199.2.

Step 5: ethyl 5-bromo-4-((tert-butoxycarbonyl)amino)-1H-pyrrole-2-carboxylate

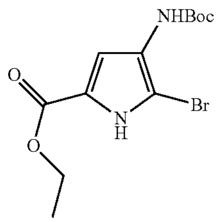 [SMILES: CCOC(=O)c1cc(NC(=O)OC(C)(C)C)c(Br)[nH]1]

To a solution of ethyl 4-((tert-butoxycarbonyl)amino)-1H-pyrrole-2-carboxylate (7.0 g, 27.5 mmol) in DCM (35 mL) was added NBS (4.90 g, 27.5 mmol). The mixture was stirred at 25° C. for 2 h. The mixture was diluted with water (50 mL) and then extracted with DCM (30 mL×3). The combined organic layer was washed with brine (30 mL×2), dried over $Na_2SO_4$, filtered and concentrated under reduced pressure. The residue was purified by silica gel chromatography (PE:EtOAc=5:1) to give the title compound (6.0 g, 65%). LCMS $(M+H-tBu)^+$=277.1.

Step 6: 4-cyano-2,5-dihydrofuran-3-yl trifluoromethanesulfonate

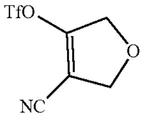 [SMILES: N#CC1=C(OS(=O)(=O)C(F)(F)F)COC1]

To a solution of 4-oxotetrahydrofuran-3-carbonitrile (10.0 g, 90.0 mmol) in DCM (100 mL) was added DIPEA (14.0 g, 108 mmol) and $Tf_2O$ (25.4 g, 90.0 mmol) at −78° C. and the mixture was stirred at −78° C. for 1 h. The reaction mixture was diluted with water (100 mL), warmed to room temperature and then extracted with DCM (50 mL×3). The combined organic layer was washed with brine (50 mL×2), dried over $Na_2SO_4$, filtered and concentrated under reduced pressure. The residue was purified by silica gel chromatography (PE:EtOAc=1:0 to 3:1) to give the title compound (10.0 g, 46%). $^1$H NMR (400 MHz, $CDCl_3$) δ 4.95-4.60 (m, 4H).

Step 7: ethyl 4-((tert-butoxycarbonyl)amino)-5-(4-cyano-2,5-dihydrofuran-3-yl)-1H-pyrrole-2-carboxylate & ethyl 5-amino-6,8-dihydro-1H-furo[3,4-d]pyrrolo[3,2-b]pyridine-2-carboxylate

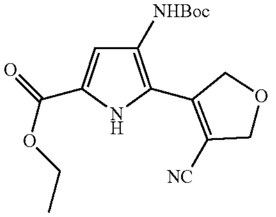
&
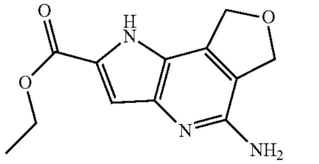

To a solution of ethyl 5-bromo-4-((tert-butoxycarbonyl)amino)-1H-pyrrole-2-carboxylate (13.0 g, 39.0 mmol) and BPD (19.8 g, 78.0 mmol) in THF (200 mL) was added $Pd_2(dba)_3$ (1.79 g, 1.95 mmol), KOAc (11.5 g, 117 mmol) and XPhos (1.86 g, 3.9 mmol). The mixture was stirred at 75° C. for 3 h and cooled to room temperature. Solid was filtered off and the filtrate was concentrated under vacuum. The crude was re-dissolved in dioxane (150 mL) and water (30 mL), then 4-cyano-2,5-dihydrofuran-3-yl trifluoromethanesulfonate (17.9 g, 73.6 mmol), Pd(dppf)$Cl_2$ (2.69 g 3.68 mmol) and $K_2CO_3$ (12.7 g, 92.0 mmol) was added. The mixture was degassed and purged with nitrogen for 3 times, and then stirred at 80° C. for 12 h. The mixture was cooled to room temperature, diluted with water (400 mL), and extracted with EtOAc (300 mL×3). The combined organic layer was washed with brine (100 mL×2), dried over $Na_2SO_4$, filtered and concentrated under vacuum. The residue was purified by silica gel chromatography (PE/EtOAc=1/0 to 3/1) to give the following compounds:

Ethyl 4-((tert-butoxycarbonyl)amino)-5-(4-cyano-2,5-dihydrofuran-3-yl)-1H-pyrrole-2-carboxylate (7.0 g, 52%). LCMS $(M+H-t-Bu)^+$=292.1.

Ethyl 5-amino-6,8-dihydro-1H-furo[3,4-d]pyrrolo[3,2-b]pyridine-2-carboxylate (2.0 g, 21%). LCMS $(M+H)^+$=248.2.

Step 8: methyl 5-amino-6,8-dihydro-1H-furo[3,4-d]pyrrolo[3,2-b]pyridine-2-carboxylate

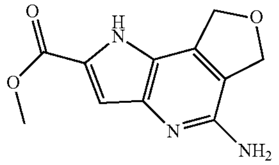 [SMILES: COC(=O)c1cc2nc(N)c3c(c2[nH]1)COC3]

To ethyl 4-((tert-butoxycarbonyl)amino)-5-(4-cyano-2,5-dihydrofuran-3-yl)-1H-pyrrole-2-carboxylate (0.70 g, 2.02 mmol) was added HCl in MeOH (3 M, 10 mL) at 25° C. and stirred for 1 h. The mixture was concentrated under vacuum. The residue was re-dissolved in MeOH (5 mL), and $K_2CO_3$ (1.28 g, 9.27 mmol) was added. The mixture was stirred at 50° C. for 2 h, cooled to room temperature and the solid was filtered off. The filtrate was concentrated under vacuum. The residue was purified by silica gel chromatography (PE/EtOAc=2/1 to 3/1, then EtOAc/MeOH=5/1) to give the title compound (0.40 g, 85%). $^1$H NMR (400 MHz, DMSO-d6) δ 11.84 (br s, 1H), 6.85 (s, 1H), 5.70 (s, 2H), 5.19-5.09 (m, 2H), 4.97-4.88 (m, 2H), 3.85 (s, 3H). LCMS $(M+H)^+$=234.2.

Step 9: 5-amino-6,8-dihydro-1H-furo[3,4-d]pyrrolo[3,2-b]pyridine-2-carboxylic Acid

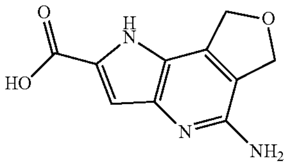 [SMILES: Nc1nc2cc(C(=O)O)[nH]c2c2c1COC2]

To a solution of methyl 5-amino-6,8-dihydro-1H-furo[3,4-d]pyrrolo[3,2-b]pyridine-2-carboxylate (0.40 g, 1.72 mmol) in THF (4 mL), MeOH (0.8 mL) and water (0.8 mL) was added LiOH·$H_2O$ (108 mg, 2.57 mmol). The mixture was stirred at 45° C. for 4 h and then cooled to room temperature. The mixture was diluted with $H_2O$ (10 mL) and then washed with EtOAc (15 mL×3). The aqueous phase was lyophilized to give a residue. The residue was purified prep-HPLC to give the title compound (80 mg, 21%). LCMS $(M+H)^+$=220.1.

Step 10: (R)-5-amino-N-((3',5'-difluoro-[3,4'-bipyridin]-6-yl)methyl)-N-(5,6,7,8-tetrahydroquinolin-8-yl)-6,8-dihydro-1H-furo[3,4-d]pyrrolo[3,2-b]pyridine-2-carboxamide To a solution of 5-amino-6,8-dihydro-1H-furo[3,4-d]pyrrolo[3,2-b]pyridine-2-carboxylic acid (100 mg, 0.45 mmol)

and (R)—N-((3',5'-difluoro-[3,4'-bipyridin]-6-yl)methyl)-5,6,7,8-tetrahydroquinolin-8-amine (158 mg, 0.45 mmol) in DMF (2 mL) was added DIPEA (0.25 mL, 1.35 mmol) and HATU (171 mg, 0.45 mmol). The mixture was stirred at 25° C. for 12 h. The reaction mixture was diluted with water (5 mL) and then extracted with EtOAc (20 mL×3). The combined organic layer was washed with brine (5 mL×2), dried over $Na_2SO_4$, filtered and concentrated under reduced pressure. The residue was purified by prep-HPLC to give Example 1 (15 mg, 6%). $^1$H NMR (500 MHz, DMSO-d6) δ 11.68-11.62 (m, 1H), 8.82-8.65 (m, 3H), 8.36-8.34 (m, 1H), 8.13-7.98 (m, 2H), 7.56-7.52 (m, 2H), 7.25-7.16 (m, 1H), 6.74 (s, 1H), 5.53-5.56 (m, 2H), 5.11-5.08 (m, 2H), 4.93-4.82 (m, 3H), 3.93-3.90 (m, 1H), 2.85-2.36 (m, 3H), 2.07-1.79 (m, 3H). LC-MS $(M+H)^+$=554.3.

Example 2: (R)-5-amino-N-((5-(2,6-difluorophenyl)pyridin-2-yl)methyl)-N-(5,6,7,8-tetrahydroquinolin-8-yl)-6,8-dihydro-1H-furo[3,4-d]pyrrolo[3,2-b]pyridine-2-carboxamide

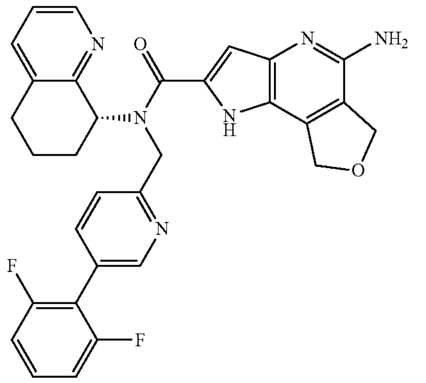 [SMILES: Nc1nc2cc(C(=O)N(Cc3ccc(-c4c(F)cccc4F)cn3)[C@@H]3CCCc4cccnc43)[nH]c2c2c1COC2]

Step 1: 5-(2,6-difluorophenyl)picolinaldehyde

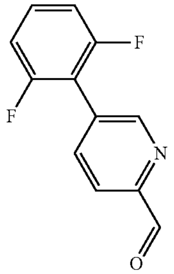 [SMILES: O=Cc1ccc(-c2c(F)cccc2F)cn1]

To a mixture of 5-(4,4,5,5-tetramethyl-1,3,2-dioxaborolan-2-yl)picolinaldehyde (62 g, 266 mmol) and 1,3-difluoro-2-iodobenzene (95.8 g, 399 mmol) in dioxane (600 mL), toluene (300 mL) and water (300 mL) was added Pd(dppf)$Cl_2$ (9.73 g, 13.3 mmol) and $K_3PO_4$ (141 g, 665 mmol). The mixture was stirred at 85° C. for 16 h, cooled to room temperature and poured into water (1000 mL). The organic layer was separated. The aqueous phase was extracted with EtOAc (800 mL×2). The combined organic layer was washed with brine (500 mL), dried with $Na_2SO_4$, filtered and concentrated under vacuum. The residue was purified by silica gel chromatography (PE:EtOAc=50:1 to 5:1) to give the title compound (30 g, 51%). LC-MS $(M+H)^+$=220.2.

Step 2: (R)—N-((5-(2,6-difluorophenyl)pyridin-2-yl)methyl)-5,6,7,8-tetrahydroquinolin-8-amine

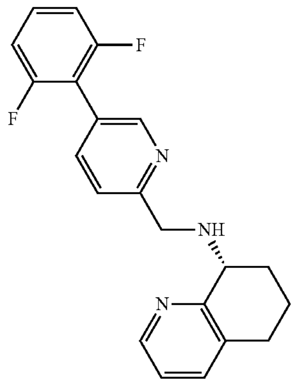 [SMILES: Fc1cccc(F)c1-c1ccc(CN[C@@H]2CCCc3cccnc32)nc1]

To a solution (R)-5,6,7,8-tetrahydroquinolin-8-amine (1.35 g, 9.12 mmol) in DCM (20 mL) was added 5-(2,6-difluorophenyl)picolinaldehyde (2.0 g, 9.12 mmol), MeOH (2 mL) and $NaBH(OAc)_3$ (5.80 g, 27.4 mmol). The mixture was stirred at room temperature for 1 h and quenched with saturated $NaHCO_3$ (50 mL). The organic layer was separated, and the aqueous layer was extracted with DCM (50 mL×3). The combined organic layer was washed with brine (50 mL), dried with $Na_2SO_4$, filtered, and concentrated under vacuum. The residue was purified by silica gel chromatography (PE:EtOAc=1:0 to 0:1) to give the title compound (582 mg, 18%). LC-MS $(M+H)^+$=352.1.

Step 3: (R)-5-amino-N-((5-(2,6-difluorophenyl)pyridin-2-yl)methyl)-N-(5,6,7,8-tetrahydroquinolin-8-yl)-6,8-dihydro-1H-furo[3,4-d]pyrrolo[3,2-b]pyridine-2-carboxamide To a solution of 5-amino-6,8-dihydro-1H-furo[3,4-d]pyrrolo[3,2-b]pyridine-2-carboxylic acid (30 mg, 0.14 mmol) and (R)—N-((5-(2,6-difluorophenyl)pyridin-2-yl)methyl)-5,6,7,8-tetrahydroquinolin-8-amine (48 mg, 0.14 mmol) in THF (1 mL) was added DIPEA (53 mg, 0.41 mmol) and BOPCl (52 mg, 0.20 mmol). The mixture was stirred at 25° C. for 12 h. The mixture was diluted with water (5 mL) and extracted with EtOAc (5 mL×3). The combined organic layer was washed with brine (5 mL×2), dried over $Na_2SO_4$, filtered and concentrated under reduced pressure. The crude was purified by prep-HPLC to give Example 2 (13 mg, 17%). $^1$H NMR (400 MHz, DMSO-d6) 11.71-11.61 (m, 1H), 8.71-8.34 (m, 2H), 7.97-7.85 (m, 1H), 7.58-7.15 (m, 5H), 6.73-6.21 (m, 1H), 5.99-5.32 (m, 3H), 5.25-5.11 (m, 2H), 4.92-4.86 (m, 2H), 4.84-3.82 (m, 1H), 2.92-2.66 (m, 3H), 2.20-1.95 (m, 2H), 1.82-1.75 (m, 1H). LC-MS $(M+H)^+$= 553.0.

Example 3: 5-amino-N,N-bis(2,6-difluorobenzyl)-6,8-dihydro-1H-furo[3,4-d]pyrrolo[3,2-b]pyridine-2-carboxamide

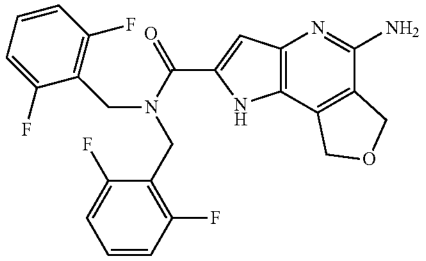 [SMILES: Nc1nc2cc(C(=O)N(Cc3c(F)cccc3F)Cc3c(F)cccc3F)[nH]c2c2c1COC2]

Step 1: bis(2,6-difluorobenzyl)amine

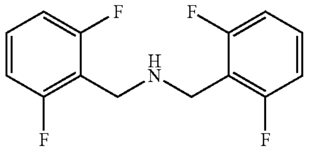 [SMILES: Fc1cccc(F)c1CNCc1c(F)cccc1F]

To a solution of 2,6-difluorobenzaldehyde (142 mg, 1.0 mmol) and (2,6-difluorophenyl)methanamine (143 mg, 1.0 mmol) in DCM (15 mL) was added $NaBH(OAc)_3$ (2 mmol, 422 mg) in portions at 0° C. The mixture was warmed to room temperature and stirred for 1 h. The reaction was quenched by saturated $NaHCO_3$ (10 mL). The organic layer was separated and the aqueous layer was extracted with EtOAc (30 mL×2). The combine organic layer was concentrated under reduced pressure to give the title compound (256 mg, 95%). LC-MS $(M+H)^+$=270.1.

Step 2: 5-amino-N,N-bis(2,6-difluorobenzyl)-6,8-dihydro-1H-furo[3,4-d]pyrrolo[3,2-b]pyridine-2-carboxamide To a solution of 5-amino-6,8-dihydro-1H-furo[3,4-d]pyrrolo[3,2-b]pyridine-2-carboxylic acid (100 mg, 0.45 mmol) and bis(2,6-difluorobenzyl)amine (121 mg, 0.45 mmol) in THF (4 mL) was added DIPEA (0.4 mL, 2.25 mmol) and BOPCl (171 mg, 0.67 mmol). The mixture was stirred at 25° C. for 12 h. The reaction mixture was diluted with water (5 mL) and then extracted with EtOAc (20 mL×3). The combined organic layer was washed with brine (5 mL×2), dried over $Na_2SO_4$, filtered and concentrated under reduced pressure. The residue was purified by prep-HPLC to give the title compound (17 mg, 8%). $^1$HNMR (500 MHz, DMSO-d6) δ 11.60 (s, 1H), 7.50-7.34 (m, 2H), 7.17-6.96 (m, 4H), 6.72-6.53 (m, 1H), 5.58 (s, 2H), 5.20-5.10 (m, 2H), 4.95-4.91 (m, 2H), 4.85 (s, 4H). LC-MS $(M+H)^+$=471.2.

Example 4: 5-amino-N-((5-(2,6-difluorophenyl)pyridin-2-yl)methyl)-N-((3R,4R)-4-methoxytetrahydro-2H-pyran-3-yl)-6,8-dihydro-1H-furo[3,4-d]pyrrolo[3,2-b]pyridine-2-carboxamide

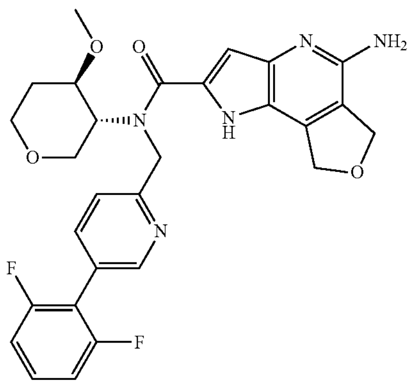 [SMILES: CO[C@@H]1CCOC[C@H]1N(Cc1ccc(-c2c(F)cccc2F)cn1)C(=O)c1cc2nc(N)c3c(c2[nH]1)COC3]

Step 1: (3R,4R)-3-(((5-(2,6-difluorophenyl)pyridin-2-yl)methyl)amino)tetrahydro-2H-pyran-4-ol

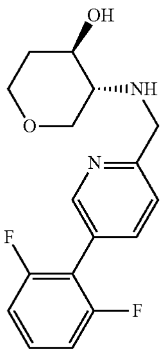 [SMILES: O[C@@H]1CCOC[C@H]1NCc1ccc(-c2c(F)cccc2F)cn1]

To a solution of (3R,4R)-3-aminotetrahydro-2H-pyran-4-ol (120 mg, 1.02 mmol) and 5-(2,6-difluorophenyl)picolinaldehyde (224 mg, 1.02 mmol) in DCM (10 mL) was added $NaBH(OAc)_3$ (430 mg, 2.03 mmol) at 0° C. The mixture was warmed to room temperature and stirred for 2 h. The mixture was concentrated under reduced pressure and the residue was purified by silica gel chromatograph (PE/EtOAc=1/1) to give the title compound (200 mg, 61%). LCMS $(M+H)^+$=321.1.

Step 2: tert-butyl ((5-(2,6-difluorophenyl)pyridin-2-yl)methyl)((3R,4R)-4-hydroxytetrahydro-2H-pyran-3-yl)carbamate

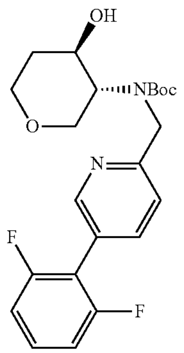

To a solution of (3R,4R)-3-(((5-(2,6-difluorophenyl)pyridin-2-yl)methyl)amino)tetrahydro-2H-pyran-4-ol (200 mg, 0.62 mmol) in DCM (10 mL) was added $Boc_2O$ (164 mg, 0.75 mmol) and $Et_3N$ (188 mg, 1.86 mmol). The mixture was stirred at room temperature for overnight. The mixture was concentrated under reduced pressure and the residue was purified by silica gel chromatograph (PE/EtOAc=2/1) to give the title compound (230 mg, 88%). LCMS $(M+H)^+$=421.1.

Step 3: tert-butyl ((5-(2,6-difluorophenyl)pyridin-2-yl)methyl)((3R,4R)-4-methoxytetrahydro-2H-pyran-3-yl)carbamate

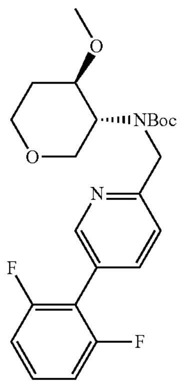

To a mixture of tert-butyl ((5-(2,6-difluorophenyl)pyridin-2-yl)methyl)((3R,4R)-4-hydroxytetrahydro-2H-pyran-3-yl)carbamate (230 mg, 0.55 mmol) and MeI (78 mg, 0.55 mmol) in DMF (10 mL) was added NaH (60%, 29 mg, 0.72 mmol) at 0° C. The mixture was stirred at room temperature under nitrogen for 5 h. The mixture was diluted with iced water (20 mL) and extracted with EtOAc (20 mL×2), The combined organic layer was washed with brine (20 mL), dried over $Na_2SO_4$, filtered and concentrated under reduced pressure. The residue was purified by silica gel chromatograph (PE/EtOAc=2/1) to give the title compound (230 mg, 96%). LCMS $(M+H)^+$=435.1.

Step 4: (3R,4R)—N-((5-(2,6-difluorophenyl)pyridin-2-yl)methyl)-4-methoxytetrahydro-2H-pyran-3-anine Hydrochloride

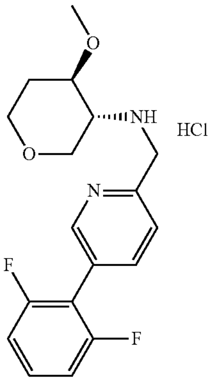 [SMILES: CO[C@@H]1CCOC[C@H]1NCc1ccc(-c2c(F)cccc2F)cn1 ; Cl]

A mixture of tert-butyl ((5-(2,6-difluorophenyl)pyridin-2-yl)methyl)((3R,4R)-4-methoxytetrahydro-2H-pyran-3-yl) carbamate (230 mg, 0.53 mmol) in HCl (4 M in MeOH, 5 mL) was stirred at room temperature for 2 h. The mixture was concentrated under reduced pressure to give the title compound (180 mg, 92%). LCMS $(M+H)^+$=335.1.

Step 5: 5-amino-N-((5-(2,6-difluorophenyl)pyridin-2-yl)methyl)-N-((3R,4R)-4-methoxytetrahydro-2H-pyran-3-yl)-6,8-dihydro-1H-furo[3,4-d]pyrrolo[3,2-b]pyridine-2-carboxamide A mixture of 5-amino-6,8-dihydro-1H-furo[3,4-d]pyrrolo[3,2-b]pyridine-2-carboxylic acid (90 mg, 0.40 mmol) in $SOCl_2$ (5 mL) was stirred at 50° C. for 3 h. Volatiles were removed in vacuo, and the residue was redissolved in DCM (10 mL). To the mixture was added (3R,4R)—N-((5-(2,6-difluorophenyl)pyridin-2-yl)methyl)-4-methoxytetrahydro-2H-pyran-3-amine hydrochloride (150 mg, 0.4 mmol) and DIPEA (154 mg, 1.2 mmol) at 0° C. The mixture was stirred for 1 h then diluted with DCM (20 mL). The mixture was successively washed with water (10 mL) and brine (10 mL). The organic laver was dried over $Na_2SO_4$, filtered and concentrated under reduced pressure. The residue was purified by silica gel chromatography (DCM/MeOH=20/1) and then prep-HPLC to give Example 4 (11 mg, 5%). $^1H$ NMR (500 MHz, DMSO-d6) δ 11.58 (s, 1H), 8.84-8.48 (m, 1H), 8.10-7.82 (m, 1H), 7.72-7.43 (m, 2H), 7.37-7.18 (m, 2H), 6.81-6.29 (m, 1H), 5.79-4.18 (m, 9H), 4.14-3.34 (m, 5H), 3.21-3.03 (m, 3H), 2.26-2.13 (m, 1H), 1.47-1.19 (m, 1H). LCMS $(M+H)^+$=536.4.

Example 5: (R)-5-amino-N-(2,6-difluorobenzyl)-N-(5,6,7,8-tetrahydroquinolin-8-yl)-6,8-dihydro-1H-furo[3,4-d]pyrrolo[3,2-b]pyridine-2-carboxamide

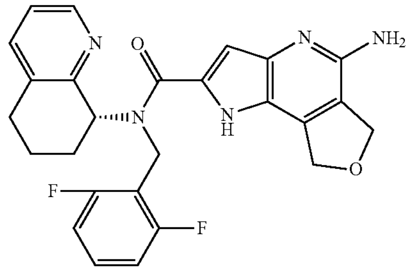 [SMILES: Nc1nc2cc(C(=O)N(Cc3c(F)cccc3F)[C@@H]3CCCc4cccnc43)[nH]c2c2c1COC2]

Step 1: (R)—N-(2,6-difluorobenzyl)-5,6,7,8-tetrahydroquinolin-8-amine

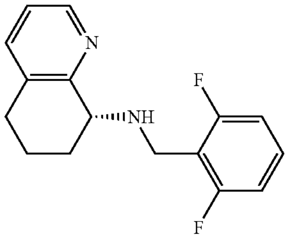 [SMILES: Fc1cccc(F)c1CN[C@@H]1CCCc2cccnc21]

To a mixture of (R)-5,6,7,8-tetrahydroquinolin-8-amine (355 mg, 2.4 mmol) and 2,6-difluorobenzaldehyde (284 mg, 2.0 mmol) in DCM (10 mL) was added $NaBH(OAc)_3$ (848 mg, 4.0 mmol) and the mixture was stirred at room temperature for 2 h. The mixture was diluted with DCM (30 mL) and carefully washed with saturated $NaHCO_3$ (30 mL) and brine (30 mL). The organic layer was dried over $Na_2SO_4$, filtered and concentrated under reduced pressure. The residue was purified by silica gel chromatography (DCM/MeOH=20/1) to give the title compound (500 mg, 91%). LC-MS $(M+H)^+$=275.2.

Step 2: (R)-5-amino-N-(2,6-difluorobenzyl)-N-(5,6,7,8-tetrahydroquinolin-8-yl)-6,8-dihydro-1H-furo[3,4-d]pyrrolo[3,2-b]pyridine-2-carboxamide Example 5 (2 mg, 2%) was prepared in a manner similar to that in Example 2 step 3 from 5-amino-6,8-dihydro-1H-furo[3,4-d]pyrrolo[3,2-b]pyridine-2-carboxylic acid and (R)—N-(2,6-difluorobenzyl)-5,6,7,8-tetrahydroquinolin-8-amine. $^1$H NMR (500 MHz, DMSO-d6) δ 11.61 (s, 1H), 8.33 (s, 1H), 7.50 (s, 1H), 7.30 (s, 1H), 7.16 (s, 1H), 6.98 (s, 2H), 6.59 (s, 1H), 5.52 (s, 2H), 5.23-5.04 (m, 2H), 4.91 (s, 2H), 4.74 (s, 1H), 2.79-2.64 (m, 3H), 2.24-1.71 (m, 3H). LC-MS $(M+H)^+$=476.2.

Example 6: (R)-5-amino-N-(5,6,7,8-tetrahydroquinolin-8-yl)-N-((2',3,6'-trifluoro-[1,1'-biphenyl]-4-yl)methyl)-6,8-dihydro-1H-furo[3,4-d]pyrrolo[3,2-b]pyridine-2-carboxamide

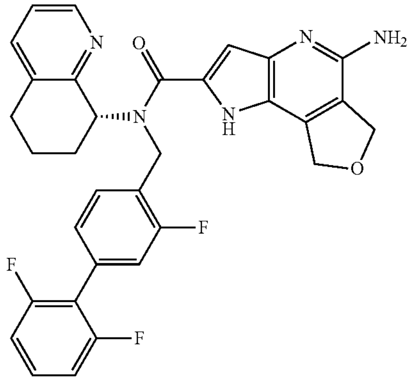 [SMILES: Nc1nc2cc(C(=O)N(Cc3ccc(-c4c(F)cccc4F)cc3F)[C@@H]3CCCc4cccnc43)[nH]c2c2c1COC2]

Step 1: 2',3,6'-trifluoro-[1,1'-biphenyl]-4-carbaldehyde

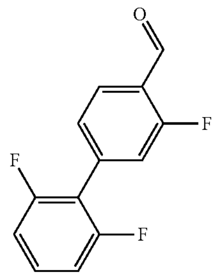 [SMILES: O=Cc1ccc(-c2c(F)cccc2F)cc1F]

A mixture of 4-bromo-2-fluorobenzaldehyde (60) mg, 3.0 mmol), (2,6-difluorophenyl)boronic acid (948 mg, 6.0 mmol), $Pd(dppf)Cl_2$ (196 mg, 0.3 mmol) and $K_3PO_4$ (1.9 g, 9.0 mmol) in dioxane (15 mL) and water (3 mL) was stirred at 100° C. overnight under nitrogen and then cooled to room temperature. The mixture was extracted with EtOAc (50 mL×3). The combined organic layer was concentrated under reduced pressure. The residue was purified by silica gel column chromatography (PE/EtOAc=10/1) to give the title compound (520 mg, 73%). LC-MS $(M+H)^+$=237.1.

Step 2: (R)—N-((2',3,6'-trifluoro-[1,1'-biphenyl]-4-yl)methyl)-5,6,7,8-tetrahydroquinolin-8-amine

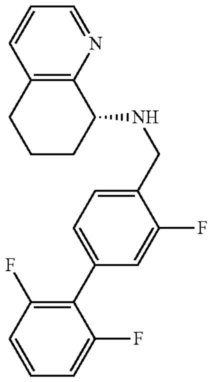

The title compound (282 mg, 76%) was prepared in a manner similar to that in Example 5 step 1 from 2',3,6'-trifluoro-[1,1'-biphenyl]-4-carbaldehyde and (R)-5,6,7,8-tetrahydroquinolin-8-amine. LC-MS $(M+H)^+$=369.3.

Step 3: (R)-5-amino-N-(5,6,7,8-tetrahydroquinolin-8-yl)-N-((2',3,6'-trifluoro-[1,1'-biphenyl]-4-yl)methyl)-6,8-dihydro-1H-furo[3,4-d]pyrrolo[3,2-b]pyridine-2-carboxamide Example 6 (2 mg, 4%) was prepared in a manner similar to that in Example 2 step 3 from 5-amino-6,8-dihydro-1H-furo[3,4-d]pyrrolo[3,2-b]pyridine-2-carboxylic acid and (R)—N-((2',3,6'-trifluoro-[1,1'-biphenyl]-4-yl)methyl)-5,6,7,8-tetrahydroquinolin-8-amine. $^1$H NMR (500 MHz, DMSO-d6) δ 11.72-11.55 (m, 1H), 8.47-8.32 (m, 1H), 7.65-7.11 (m, 8H), 6.81-6.53 (m, 1H), 6.25-5.45 (m, 3H), 5.25-3.70 (m, 6H), 2.95-2.81 (m, 1H), 2.78-2.67 (m, 1H), 2.37-1.72 (m, 4H). LC-MS $(M+H)^+$=570.5.

Example 7: 5-amino-N,N-bis((3-fluoropyridin-2-yl)methyl)-6,8-dihydro-1H-furo[3,4-d]pyrrolo[3,2-b]pyridine-2-carboxamide

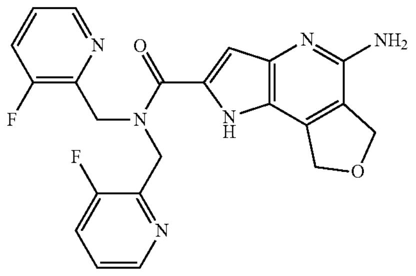 [SMILES: Nc1nc2cc(C(=O)N(Cc3ncccc3F)Cc3ncccc3F)[nH]c2c2c1COC2]

Step 1: bis((3-fluoropyridin-2-yl)methyl)amine

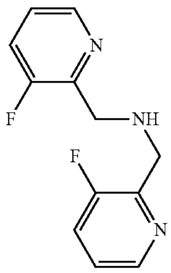 [SMILES: Fc1cccnc1CNCc1ncccc1F]

The title compound (200 mg, 87%) was prepared in a manner similar to that in Example 5 step 1 from 3-fluoropicolinaldehyde and (3-fluoropyridin-2-yl)methanamine. LC-MS $(M+H)^+$=236.2.

Step 2: 5-amino-N,N-bis((3-fluoropyridin-2-yl)methyl)-6,8-dihydro-1H-furo[3,4-d]pyrrolo[3,2-b]pyridine-2-carboxamide Example 7 (5 mg, 11%) was prepared in a manner similar to that in Example 2 step 3 from 5-amino-6,8-dihydro-1H-furo[3,4-d]pyrrolo[3,2-b]pyridine-2-carboxylic acid and bis((3-fluoropyridin-2-yl)methyl)amine. $^1$H NMR (500 MHz, DMSO-d6) δ 11.62 (s, 1H), 8.41 (s, 2H), 7.72 (s, 2H), 7.43 (s, 2H), 6.43 (d, J=2.4 Hz, 1H), 5.52 (s, 2H), 5.35-4.76 (m, 8H). LC-MS $(M+H)^+$=437.4.

Example 8: 5-amino-N-(2,6-difluorobenzyl)-N-(1-methoxypropan-2-yl)-6,8-dihydro-1H-furo[3,4-d]pyrrolo[3,2-b]pyridine-2-carboxamide

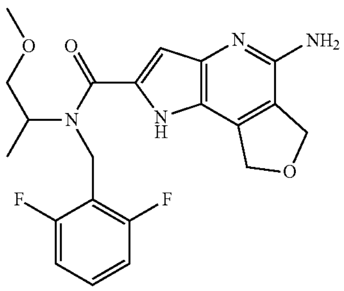 [SMILES: COCC(C)N(Cc1c(F)cccc1F)C(=O)c1cc2nc(N)c3c(c2[nH]1)COC3]

Step 1: N-(2,6-difluorobenzyl)-1-methoxypropan-2-amine

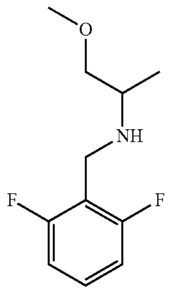

The title compound (150 mg, 49%) was prepared in a manner similar to that in Example 5 step 1 from 2,6-difluorobenzaldehyde and 1-methoxypropan-2-amine. LC-MS $(M+H)^+$=216.1.

Step 2: 5-amino-N-(2,6-difluorobenzyl)-N-(1-methoxypropan-2-yl)-6,8-dihydro-1H-furo[3,4-d]pyrrolo[3,2-b]pyridine-2-carboxamide Example 8 (4 mg, 7%) was prepared in a manner similar to that in Example 2 step 3 from 5-amino-6,8-dihydro-1H-furo[3,4-d]pyrrolo[3,2-b]pyridine-2-carboxylic acid and N-(2,6-difluorobenzyl)-1-methoxypropan-2-amine. $^1H$ NMR (500 MHz, DMSO-d6) δ 11.49 (s, 1H), 8.16 (s, 1H), 7.36 (t, J=7.4 Hz, 1H), 7.06 (t, J=8.2 Hz, 2H), 6.53 (d, J=1.9 Hz, 1H), 5.54 (s, 2H), 5.11 (d, J=2.7 Hz, 2H), 4.92 (t, J=2.7 Hz, 2H), 4.84 (s, 1H), 3.56-3.49 (m, 1H), 3.15 (s, 3H), 1.19 (d, J=6.7 Hz, 3H). LC-MS $(M+H)^+$=417.2.

Example 9: 5-amino-N-(2,6-difluorobenzyl)-N-(1,3-dimethoxypropan-2-yl)-6,8-dihydro-1H-furo[3,4-d]pyrrolo[3,2-b]pyridine-2-carboxamide

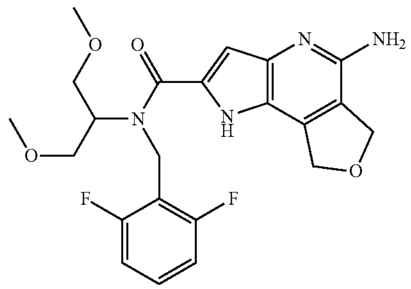 [SMILES: COCC(COC)N(Cc1c(F)cccc1F)C(=O)c1cc2nc(N)c3c(c2[nH]1)COC3]

Example 9 (2 mg, 4%) was prepared in a manner similar to that in Example 2 step 3. $^1H$ NMR (500 MHz, DMSO-d6) δ 11.49 (s, 1H), 8.29 (s, 1H), 7.41-7.33 (m, 1H), 7.06 (t, J=8.1 Hz, 2H), 6.62 (d, J=2.0 Hz, 1H), 5.55 (s, 2H), 5.11 (s, 2H), 4.92 (d, J=2.7 Hz, 2H), 4.80 (s, 2H), 3.64-3.58 (m, 2H), 3.49-3.44 (m, 2H), 3.15 (s, 6H). LC-MS $(M+H)^+$=447.1.

Example 10: (R)-5-amino-N-((3,5-difluoropyridin-4-yl)methyl)-N-(5,6,7,8-tetrahydroquinolin-8-yl)-6,8-dihydro-1H-furo[3,4-d]pyrrolo[3,2-b]pyridine-2-carboxamide

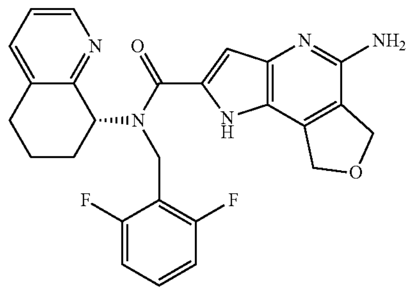 [SMILES: Nc1nc2cc(C(=O)N(Cc3c(F)cccc3F)[C@@H]3CCCc4cccnc43)[nH]c2c2c1COC2]

Example 10 (1 mg, 1%) was prepared in a manner similar to that in Example 2 step 3. $^1H$ NMR (500 MHz, DMSO-d6) δ 11.64 (s, 1H), 8.55-8.16 (m, 3H), 7.54 (s, 1H), 7.19 (s, 1H), 6.61 (s, 1H), 5.80 (s, 1H), 5.53 (s, 2H), 5.11 (s, 2H), 4.91 (s, 2H), 4.60 (s, 1H), 4.10 (s, 1H), 2.89-2.87 (m, 1H), 2.75-2.72 (m, 1H), 2.36 (s, 2H), 2.12-1.80 (m, 2H). LC-MS $(M+H)^+$=477.5.

Example 11: (R)-5-amino-N-((3'-cyano-[3,4'-bipyridin]-6-yl)methyl)-N-(5,6,7,8-tetrahydroquinolin-8-yl)-6,8-dihydro-1H-furo[3,4-d]pyrrolo[3,2-b]pyridine-2-carboxamide

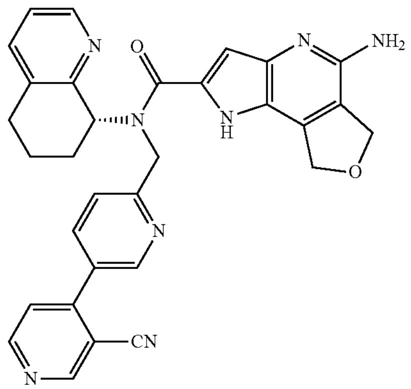 [SMILES: N#Cc1cnccc1-c1ccc(CN(C(=O)c2cc3nc(N)c4c(c3[nH]2)COC4)[C@@H]2CCCc3cccnc32)nc1]

Step 1: 6-formyl-[3,4'-bipyridine]-3'-carbonitrile

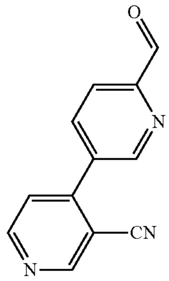 [SMILES: N#Cc1cnccc1-c1ccc(C=O)nc1]

The title compound (160 mg, 26%) was prepared in a manner similar to that in Example 6 step 1 from 5-bromopicolinaldehyde and 4-(4,4,5,5-tetramethyl-1,3,2-dioxaborolan-2-yl)nicotinonitrile. LC-MS $(M+H)^+$=210.1.

Step 2: (R)-6-(((5,6,7,8-tetrahydroquinolin-8-yl)amino)methyl)-[3,4'-bipyridine]-3'-carbonitrile

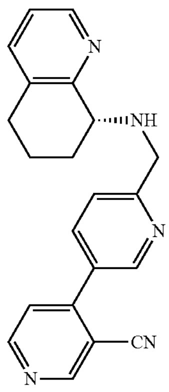 [SMILES: N#Cc1cnccc1-c1ccc(CN[C@@H]2CCCc3cccnc32)nc1]

The title compound (88 mg, 64%) was prepared in a manner similar to that in Example 5 step 1 from 6-formyl-[3,4'-bipyridine]-3'-carbonitrile and (R)-5,6,7,8-tetrahydroquinolin-8-amine. LC-MS $(M+H)^+$=342.2.

Step 3: (R)-5-amino-N-((3'-cyano-[3,4'-bipyridin]-6-yl)methyl)-N-(5,6,7,8-tetrahydroquinolin-8-yl)-6,8-dihydro-1H-furo[3,4-d]pyrrolo[3,2-b]pyridine-2-carboxamide Example 11 (8 mg, 14%) was prepared in a manner similar to that in Example 2 step 3 from 5-amino-6,8-dihydro-1H-furo[3,4-d]pyrrolo[3,2-b]pyridine-2-carboxylic acid and (R)-6-(((5,6,7,8-tetrahydroquinolin-8-yl)amino)methyl)-[3,4'-bipyridine]-3'-carbonitrile. $^1$H NMR (500 MHz, DMSO-d6) δ 11.78-11.55 (m, 1H), 9.21-9.11 (m, 1H), 9.03-8.72 (m, 2H), 8.47-8.32 (m, 1H), 8.25-8.01 (m, 1H), 7.92-7.75 (m, 1H), 7.70-7.47 (m, 2H), 7.32-7.11 (m, 1H), 6.82-6.22 (m, 1H), 6.03-3.91 (m, 9H), 2.92-2.71 (m, 2H), 2.32-1.68 (m, 4H). LC-MS $(M+H)^+$=543.6.

Example 12: 5-amino-N-(chroman-4-yl)-N-((5-(2,6-difluorophenyl)pyridin-2-yl)methyl)-6,8-dihydro-1H-furo[3,4-d]pyrrolo[3,2-b]pyridine-2-carboxamide

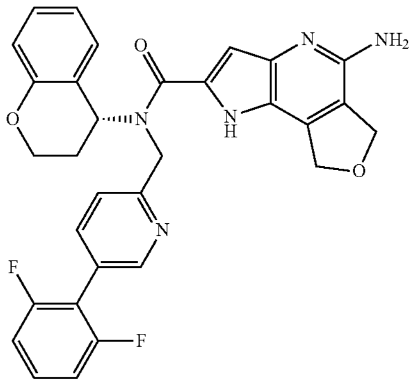 [SMILES: Nc1nc2cc(C(=O)N(Cc3ccc(-c4c(F)cccc4F)cn3)[C@@H]3CCOc4ccccc43)[nH]c2c2c1COC2]

Step 1: N-((5-(2,6-difluorophenyl)pyridin-2-yl)methyl)chroman-4-amine

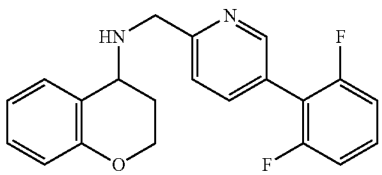 [SMILES: Fc1cccc(F)c1-c1ccc(CNC2CCOc3ccccc32)nc1]

The title compound (400 mg, 85%) was prepared in a manner similar to that in Example 5 step 1 from chroman-4-amine and 5-(2,6-difluorophenyl)picolinaldehyde. LC-MS $(M+H)^+$=353.2.

Step 2: 5-amino-N-(chroman-4-yl)-N-((5-(2,6-difluorophenyl)pyridin-2-yl)methyl)-6,8-dihydro-1H-furo[3,4-d]pyrrolo[3,2-b]pyridine-2-carboxamide Example 12 (7 mg, 8%) was prepared in a manner similar to that in Example 2 step 3 from 5-amino-6,8-dihydro-1H-furo[3,4-d]pyrrolo[3,2-b]pyridine-2-carboxylic acid and N-((5-(2,6-difluorophenyl)pyridin-2-yl)methyl)chroman-4-anine. $^1$H NMR (400 MHz, DMSO-d6) δ 11.73 (br s, 1H), 8.67-8.56 (m, 1H), 7.91-7.88 (m, 1H), 7.57-7.49 (m, 2H), 7.29-7.05 (m, 4H), 6.97-6.36 (m, 3H), 6.11-6.01 (m, 1H), 5.55 (br s, 2H), 5.22-4.85 (m, 5H), 4.64-3.92 (m, 3H), 2.37-2.04 (m, 2H). LC-MS $(M+H)^+$=554.2.

Example 13: 5-amino-N-(2,6-difluorobenzyl)-N-((5-(2,6-difluorophenyl)pyridin-2-yl)methyl)-6,8-dihydro-1H-furo[3,4-d]pyrrolo[3,2-b]pyridine-2-carboxamide

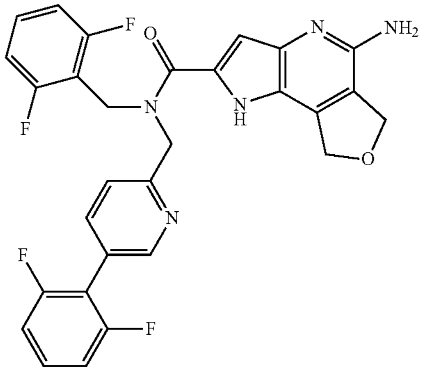 [SMILES: Nc1nc2cc(C(=O)N(Cc3ccc(-c4c(F)cccc4F)cn3)Cc3c(F)cccc3F)[nH]c2c2c1COC2]

Step 1: 1-(tert-butyl) 2-ethyl 5-(bis(tert-butoxycarbonyl)amino)-6,8-dihydro-1H-furo[3,4-d]pyrrolo[3,2-b]pyridine-1,2-dicarboxylate

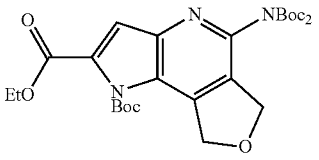

To a solution of ethyl 5-amino-6,8-dihydro-1H-furo[3,4-d]pyrrolo[3,2-b]pyridine-2-carboxylate (2.0 g, 8.09 mmol) in THF (40 mL) was added $Boc_2O$ (5.3 g, 24.3 mmol), DMAP (99 mg, 0.81 mmol) and $Et_3N$ (3.28 g, 16.2 mmol). The mixture was stirred at 45° C. for 12 h then cooled to room temperature. The mixture was diluted with water (30 mL) and then extracted with EtOAc (15 mL×3). The combined organic layer was washed with brine (15 mL×2), dried over $Na_2SO_4$, filtered and concentrated under reduced pressure. The residue was purified by silica gel chromatography (PE/EtOAc=1:0 to 3:1) to give the title compound (2.4 g, 54%). LC-MS $(M+H)^+$=548.4.

Step 2: 5-((tert-butoxycarbonyl)amino)-6,8-dihydro-1H-furo[3,4-d]pyrrolo[3,2-b]pyridine-2-carboxylic Acid

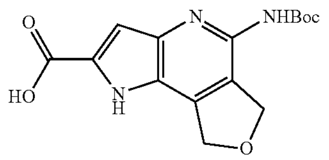 [SMILES: CC(C)(C)OC(=O)Nc1nc2cc(C(=O)O)[nH]c2c2c1COC2]

To a solution of 1-(tert-butyl) 2-ethyl 5-(bis(tert-butoxycarbonyl)amino)-6,8-dihydro-1H-furo[3,4-d]pyrrolo[3,2-b]pyridine-1,2-dicarboxylate (2.4 g, 4.38 mmol) in THF (20 mL), MeOH (4 mL) and water (4 mL) was added LiOH—$H_2O$ (221 mg, 5.26 mmol). The mixture was stirred at 45° C. for 12 h. The mixture was cooled to room temperature and diluted with water (10 mL). The mixture was washed with EtOAc (15 mL×3). To the aqueous phase was carefully added aqueous HCl (0.5 M) until its pH reached 4-5. Solid was collected by filtration to give the title compound (0.90 g, 49%). LC-MS $(M+H)^+$=320.2.

Step 3: N-(2,6-difluorobenzyl)-1-(5-(2,6-difluorophenyl)pyridin-2-yl)methanamine

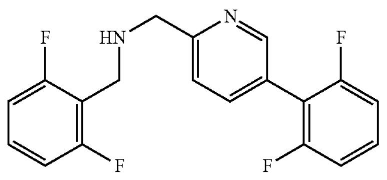 [SMILES: Fc1cccc(F)c1CNCc1ccc(-c2c(F)cccc2F)cn1]

The title compound (260 mg, 55%) was prepared in a manner similar to that in Example 5 step 1 from 5-(2,6-difluorophenyl)picolinaldehyde and (2,6-difluorophenyl) methanamine. LC-MS $(M+H)^+$=347.2.

Step 4: tert-butyl (2-((2,6-difluorobenzyl)((5-(2,6-difluorophenyl)pyridin-2-yl)methyl)carbamoyl)-6,8-dihydro-1H-furo[3,4-d]pyrrolo[3,2-b]pyridin-5-yl) carbamate

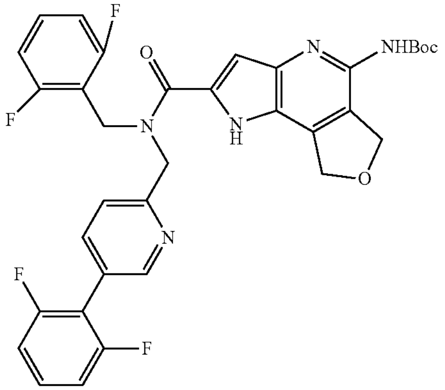 [SMILES: CC(C)(C)OC(=O)Nc1nc2cc(C(=O)N(Cc3ccc(-c4c(F)cccc4F)cn3)Cc3c(F)cccc3F)[nH]c2c2c1COC2]

To a solution of N-(2,6-difluorobenzyl)-1-(5-(2,6-difluorophenyl)pyridin-2-yl)methanamine (70 mg, 0.20 mmol) and 5-((tert-butoxycarbonyl)amino)-6,8-dihydro-1H-furo[3,4-d]pyrrolo[3,2-b]pyridine-2-carboxylic acid (65 mg, 0.20 mmol) in THF (3 mL) was added BOPCl (62 mg, 0.24 mmol) and DIPEA (78 mg, 0.61 mmol) at 25° C. The mixture was stirred at 40° C. for 1 h. The mixture was cooled to room temperature and diluted with water (5 mL). The mixture was extracted with EtOAc (5 mL×4). The combined organic layer was washed with brine (5 mL×2), dried over $Na_2SO_4$, filtered, and concentrated under vacuum to give the title compound (85 mg, 66%). LC-MS $(M+H)^+$=648.3.

Step 5: 5-amino-N-(2,6-difluorobenzyl)-N-((5-(2,6-difluorophenyl)pyridin-2-yl)methyl)-6,8-dihydro-1H-furo[3,4-d]pyrrolo[3,2-b]pyridine-2-carboxamide A mixture of tert-butyl (2-((2,6-difluorobenzyl)((5-(2,6-difluorophenyl)pyridin-2-yl)methyl)carbamoyl)-6,8-dihydro-1H-furo[3,4-d]pyrrolo[3,2-b]pyridin-5-yl)carbamate (85 mg, 0.13 mmol) in methanolic HCl (3 M, 3 mL) was stirred at 25° C. for 1 h and then concentrated under reduced pressure. The residue was purified by prep-HPLC to give Example 13 (31 mg, 44%). $^1H$ NMR (400 MHz, $CD_3OD$) δ 11.67 (s, 1H), 8.60 (br s, 1H), 7.89 (br d, J=7.9 Hz, 1H), 7.59-7.49 (m, 1H), 7.45 (d, J=8.1 Hz, 1H), 7.40-7.32 (m, 1H), 7.31-7.23 (m, 2H), 7.09-7.00 (m, 2H), 6.65-6.26 (m, 1H), 5.55 (s, 2H), 5.13 (br s, 2H), 5.00 (br s, 3H), 4.91 (br s, 3H). LC-MS $(M+H)^+$=548.2.

Example 14: 5-amino-N-((3R,4R)-4-methoxytetrahydro-2H-pyran-3-yl)-N-((2',3,6'-trifluoro-[1,1'-biphenyl]-4-yl)methyl)-6,8-dihydro-1H-furo[3,4-d]pyrrolo[3,2-b]pyridine-2-carboxamide

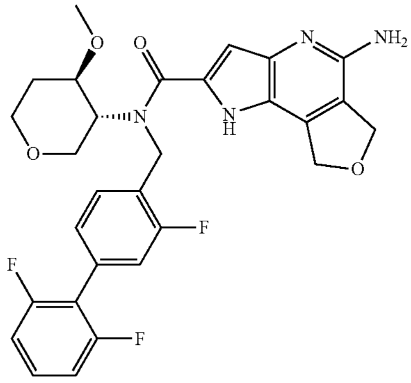 [SMILES: CO[C@@H]1CCOC[C@H]1N(Cc1ccc(-c2c(F)cccc2F)cc1F)C(=O)c1cc2nc(N)c3c(c2[nH]1)COC3]

Step 1: (3R,4R)-3-(((2',3,6'-trifluoro-[1,1'-biphenyl]-4-yl)methyl)amino)tetrahydro-2H-pyran-4-ol

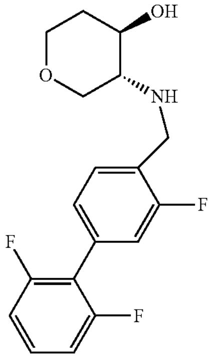 [SMILES: O[C@@H]1CCOC[C@H]1NCc1ccc(-c2c(F)cccc2F)cc1F]

The title compound (680 mg, 99%) was prepared in a manner similar to that in Example 4 step 1 from (3R,4R)-3-aminotetrahydro-2H-pyran-4-ol hydrochloride and 2',3,6'-trifluoro-[1,1'-biphenyl]-4-carbaldehyde. LC-MS $(M+H)^+$=338.2.

Step 2: tert-butyl ((3R,4R)-4-hydroxytetrahydro-2H-pyran-3-yl)((2',3,6'-trifluoro-[1,1'-biphenyl]-4-yl)methyl)carbamate

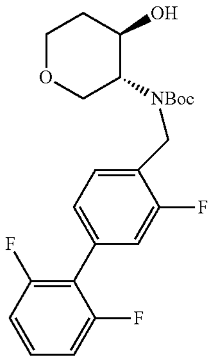 [SMILES: CC(C)(C)OC(=O)N(Cc1ccc(-c2c(F)cccc2F)cc1F)[C@@H]1COCC[C@H]1O]

The title compound (850 mg, 97%) was prepared in a manner similar to that in Example 4 step 2 from (3R,4R)-3-(((2',3,6'-trifluoro-[1,1'-biphenyl]-4-yl)methyl)amino)tetrahydro-2H-pyran-4-ol. LC-MS $(M+H)^+$=438.3.

Step 3: tert-butyl ((3R,4R)-4-methoxytetrahydro-2H-pyran-3-yl)((2',3,6'-trifluoro-[1,1'-biphenyl]-4-yl)methyl)carbamate

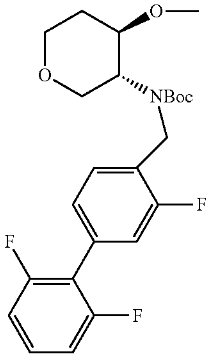 [SMILES: CO[C@@H]1CCOC[C@H]1N(Cc1ccc(-c2c(F)cccc2F)cc1F)C(=O)OC(C)(C)C]

The title compound (600 mg, 68%) was prepared in a manner similar to that in Example 4 step 3 from tert-butyl ((3R,4R)-4-hydroxytetrahydro-2H-pyran-3-yl)((2',3,6'-trifluoro-[1,1'-biphenyl]-4-yl)methyl)carbamate. LC-MS $(M+H)^+$=452.3.

Step 4: (3R,4R)-4-methoxy-N-((2',3,6'-trifluoro-[1,1'-biphenyl]-4-yl)methyl)tetrahydro-2H-pyran-3-anine hydrochloride

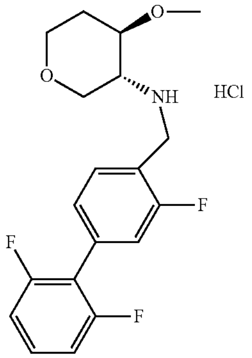 [SMILES: CO[C@@H]1CCOC[C@H]1NCc1ccc(-c2c(F)cccc2F)cc1F ; Cl]

The title compound (510 mg, 99%) was prepared in a manner similar to that in Example 4 step 4 from tert-butyl ((3R,4R)-4-methoxytetrahydro-2H-pyran-3-yl)((2',3,6'-trifluoro-[1,1'-biphenyl]-4-yl)methyl)carbamate. LC-MS $(M+H)^+$=352.2.

Step 5: tert-butyl (2-(((3R,4R)-4-methoxytetrahydro-2H-pyran-3-yl)((2',3,6'-trifluoro-[1,1'-biphenyl]-4-yl)methyl)carbamoyl)-6,8-dihydro-1H-furo[3,4-d]pyrrolo[3,2-b]pyridin-5-yl)carbamate

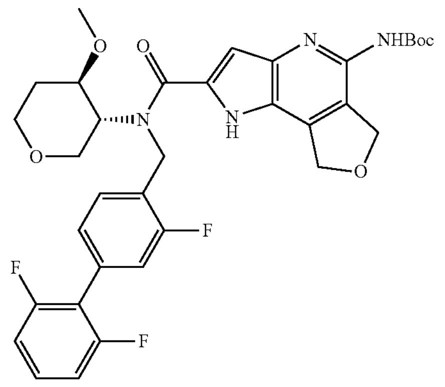 [SMILES: CO[C@@H]1CCOC[C@H]1N(Cc1ccc(-c2c(F)cccc2F)cc1F)C(=O)c1cc2nc(NC(=O)OC(C)(C)C)c3c(c2[nH]1)COC3]

The title compound (15 mg, 52%) was prepared in a manner similar to that in Example 13 step 4 from (3R,4R)-4-methoxy-N-((2',3,6'-trifluoro-[1,1'-biphenyl]-4-yl)methyl)tetrahydro-2H-pyran-3-amine hydrochloride and 5-((tert-butoxycarbonyl)amino)-6,8-dihydro-1H-furo[3,4-d]pyrrolo[3,2-b]pyridine-2-carboxylic acid. LC-MS $(M+H)^+$= 653.4.

Step 6: 5-amino-N-((3R,4R)-4-methoxytetrahydro-2H-pyran-3-yl)-N-((2',3,6'-trifluoro-[1,1'-biphenyl]-4-yl)methyl)-6,8-dihydro-1H-furo[3,4-d]pyrrolo[3,2-b]pyridine-2-carboxamide A mixture of tert-butyl (2-(((3R,4R)-4-methoxytetrahydro-2H-pyran-3-yl)((2',3,6'-trifluoro-[1,1'-biphenyl]-4-yl)methyl)carbamoyl)-6,8-dihydro-1H-furo[3,4-d]pyrrolo[3,2-b]pyridin-5-yl)carbamate (15 mg, 0.020 mmol) in HCl in dioxane (4 M, 2 mL) was stirred for 1 h at room temperature then concentrated under vacuum. The residue was purified by prep-HPLC to give Example 14 (2 mg, 19%). $^1$H NMR (500 MHz, DMSO-d6) δ 11.57 (s, 1H), 7.54-7.45 (m, 2H), 7.38-7.31 (m, 1H), 7.27-7.21 (m, 3H), 6.76 (s, 1H), 5.57 (s, 2H), 5.13 (s, 2H), 4.93 (s, 2H), 4.87-4.76 (m, 1H), 4.75-4.64 (m, 1H), 4.63-4.49 (m, 1H), 4.17-4.04 (m, 1H), 3.86-3.82 (m, 1H), 3.73-3.60 (m, 1H), 3.58-3.50 (m, 1H), 3.41-3.35 (m, 1H), 3.15 (s, 3H), 2.24-2.18 (m, 1H), 1.38-1.27 (m, 1H). LC-MS $(M+H)^+$=553.4.

Example 15: 5-amino-N-((3',5'-difluoro-[3,4'-bipyridin]-6-yl)methyl)-N-((3R,4R)-4-methoxytetrahydro-2H-pyran-3-yl)-6,8-dihydro-1H-furo[3,4-d]pyrrolo[3,2-b]pyridine-2-carboxamide

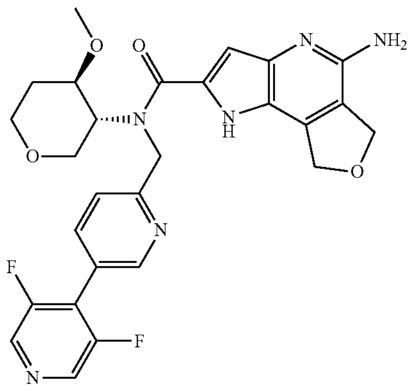 [SMILES: CO[C@@H]1CCOC[C@H]1N(Cc1ccc(-c2c(F)cncc2F)cn1)C(=O)c1cc2nc(N)c3c(c2[nH]1)COC3]

Step 1: (3R,4R)—N-((3',5'-difluoro-[3,4'-bipyridin]-6-yl)methyl)-4-methoxytetrahydro-2H-pyran-3-amine

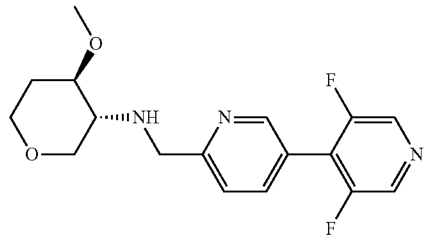 [SMILES: CO[C@@H]1CCOC[C@H]1NCc1ccc(-c2c(F)cncc2F)cn1]

The title compound (150 mg, 85%) was prepared in a manner similar to that in Example 4 step 1 from (3R,4R)-4-methoxytetrahydro-2H-pyran-3-amine and 3',5'-difluoro-[3,4'-bipyridine]-6-carbaldehyde. LC-MS $(M+H)^+$=336.2.

Step 2: 5-amino-N-((3',5'-difluoro-[3,4'-bipyridin]-6-yl)methyl)-N-((3R,4R)-4-methoxytetrahydro-2H-pyran-3-yl)-6,8-dihydro-1H-furo[3,4-d]pyrrolo[3,2-b]pyridine-2-carboxamide Example 15 (1 mg, 5%) was prepared in a manner similar to that in Example 2 step 3 from 5-amino-6,8-dihydro-1H-furo[3,4-d]pyrrolo[3,2-b]pyridine-2-carboxylic acid and (3R,4R)—N-((3',5'-difluoro-[3,4'-bipyridin]-6-yl)methyl)-4-methoxytetrahydro-2H-pyran-3-amine. $^1$H NMR (500 MHz, DMSO-d6) δ 11.82-11.39 (m, 1H), 9.03-8.56 (m, 3H), 8.18-7.93 (nm, 1H), 7.83-7.50 (m, 1H), 6.85-6.22 (m, 1H), 5.79-4.17 (m, 9H), 4.17-3.43 (m, 5H), 3.21-3.05 (m, 3H), 2.28-2.11 (m, 1H), 1.44-1.27 (m, 1H). LCMS $(M+H)^+$= 537.4.

Example 16: 5-amino-N-((5-(2,6-difluorophenyl) pyridin-2-yl)methyl)-N-(1,3-dimethoxypropan-2-yl)-6,8-dihydro-1H-furo[3,4-d]pyrrolo[3,2-b]pyridine-2-carboxamide

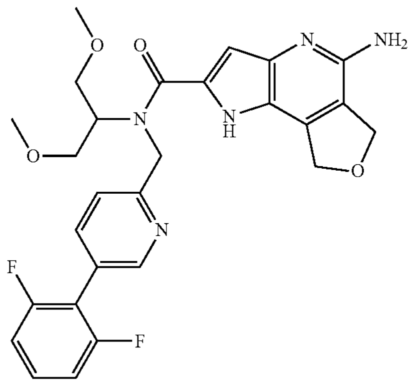 [SMILES: COCC(COC)N(Cc1ccc(-c2c(F)cccc2F)cn1)C(=O)c1cc2nc(N)c3c(c2[nH]1)COC3]

Step 1: N-((5-(2,6-difluorophenyl)pyridin-2-yl) methyl)-1,3-dimethoxypropan-2-amine

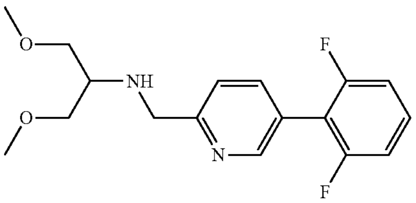 [SMILES: COCC(COC)NCc1ccc(-c2c(F)cccc2F)cn1]

The title compound (0.20 g, 76%) was prepared in a manner similar to that in Example 5 step 1 from 1,3-dimethoxypropan-2-one and (5-(2,6-difluorophenyl)pyridin-2-yl)methanamine. $^1$H NMR (400 MHz, DMSO-d6) δ 8.57 (s, 1H), 7.87 (d, J=8.4 Hz, 1H), 7.60-7.48 (m, 2H), 7.32-7.22 (m, 2H), 3.94 (s, 2H), 3.34 (d, J=5.6 Hz, 4H), 3.24 (s, 6H), 2.89 (quin, J=5.6 Hz, 1H). LC-MS $(M+H)^+$=323.2.

Step 2: tert-butyl (2-(((5-(2,6-difluorophenyl)pyridin-2-yl)methyl(1,3-dimethoxypropan-2-yl)carbamoyl)-6,8-dihydro-1H-furo[3,4-d]pyrrolo[3,2-b]pyridin-5-yl)carbamate

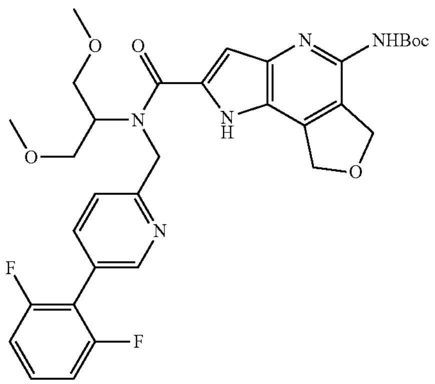 [SMILES: COCC(COC)N(Cc1ccc(-c2c(F)cccc2F)cn1)C(=O)c1cc2nc(NC(=O)OC(C)(C)C)c3c(c2[nH]1)COC3]

The title compound (40 mg, 30%) was prepared in a manner similar to that in Example 13 step 4 from 5-((tert-butoxycarbonyl)amino)-6,8-dihydro-1H-furo[3,4-d]pyrrolo[3,2-b]pyridine-2-carboxylic acid and N-((5-(2,6-difluorophenyl)pyridin-2-yl)methyl)-1,3-dimethoxypropan-2-amine. LC-MS $(M+H)^+$=624.3.

Step 3: 5-amino-N-((5-(2,6-difluorophenyl)pyridin-2-yl)methyl)-N-(1,3-dimethoxypropan-2-yl)-6,8-dihydro-1H-furo[3,4-d]pyrrolo[3,2-b]pyridine-2-carboxamide Example 16 (1 mg, 5%) was prepared in a manner similar to that in Example 14 step 6 from tert-butyl (2-(((5-(2,6-difluorophenyl)pyridin-2-yl)methyl)(1,3-dimethoxypropan-2-yl)carbamoyl)-6,8-dihydro-1H-furo[3,4-d]pyrrolo[3,2-b]pyridin-5-yl)carbamate. 1H NMR (400 MHz, DMSO-d6) δ 11.52 (s, 1H), 8.59 (brs, 1H), 7.89 (br s, 1H), 7.59-7.49 (m, 2H), 7.32-7.23 (m, 2H), 6.80-6.32 (m, 1H), 5.54 (s, 2H), 5.12-4.91 (m, 7H), 3.65-3.47 (m, 4H), 3.16 (s, 6H). LC-MS (M+H)+=524.2.

Example 17 & 18: (S)-5-amino-N-((5-(2,6-difluorophenyl)pyridin-2-yl)methyl)-N-(1-(pyrimidin-2-yl)ethyl)-6,8-dihydro-1H-furo[3,4-d]pyrrolo[3,2-b]pyridine-2-carboxamide & (R)- 5-amino-N-((5-(2,6-difluorophenyl)pyridin-2-yl)methyl)-N-(1-(pyrimidin-2-yl)ethyl)-6,8-dihydro-1H-furo[3,4-d]pyrrolo[3,2-b]pyridine-2-carboxamide

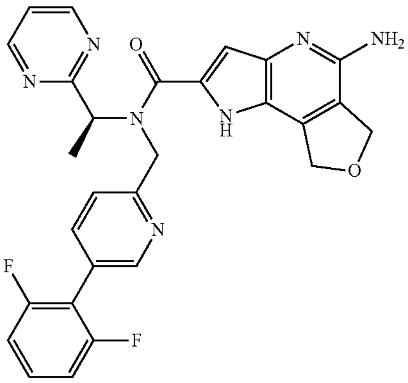

&

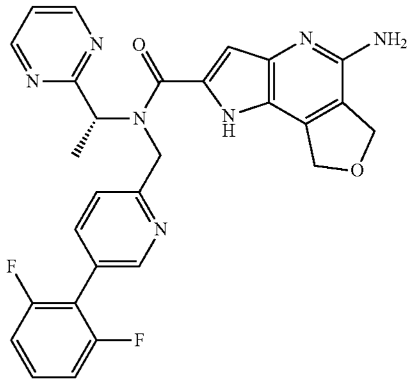

Step 1: N-((5-(2,6-difluorophenyl)pyridin-2-yl)methyl)-1-(pyrimidin-2-yl)ethan-1-amine

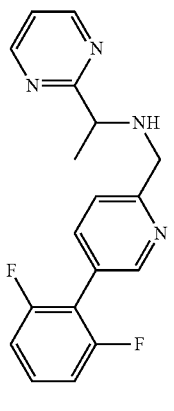 [SMILES: CC(NCc1ccc(-c2c(F)cccc2F)cn1)c1ncccn1]

To a solution of (5-(2,6-difluorophenyl)pyridin-2-yl)methanamine (0.10 g, 0.45 mmol) and 1-(pyrimidin-2-yl)ethan-1-one (55 mg, 0.45 mmol) in DCM (2.7 mL) and MeOH (0.9 mL) was added $NaBH(OAc)_3$ (192 mg, 0.91 mmol). The mixture was stirred at 20° C. for 1 h. Saturated $NaHCO_3$ (10 mL) was added, and the mixture was extracted with DCM (2 mL×4). The combined organic layer was washed with brine (5 mL), dried over $Na_2SO_4$, filtered and concentrated under vacuum. The residue was purified by silica gel chromatography (PE/EtOAc=1/0 to 0/1) to give the title compound (70 mg, 47%). LC-MS $(M+H)^+$=327.3.

Step 2: tert-butyl (2-(((5-(2,6-difluorophenyl)pyridin-2-yl)methyl)(1-(pyrimidin-2-yl)ethyl)carbamoyl)-6,8-dihydro-1H-furo[3,4-d]pyrrolo[3,2-b]pyridin-5-yl)carbamate

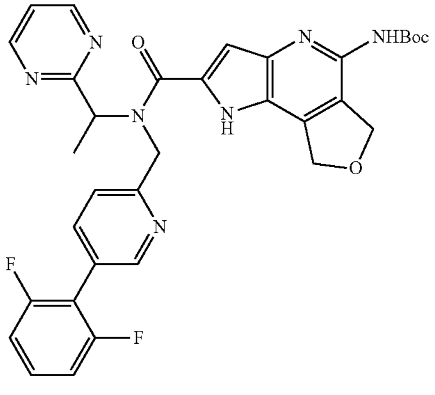 [SMILES: CC(c1ncccn1)N(Cc1ccc(-c2c(F)cccc2F)cn1)C(=O)c1cc2nc(NC(=O)OC(C)(C)C)c3c(c2[nH]1)COC3]

To a solution of N-((5-(2,6-difluorophenyl)pyridin-2-yl)methyl)-1-(pyrimidin-2-yl)ethan-1-amine (70 mg, 0.21 mmol) and 5-((tert-butoxycarbonyl)amino)-6,8-dihydro-1H-furo[3,4-d]pyrrolo[3,2-b]pyridine-2-carboxylic acid (72 mg, 0.23 mmol) in THF (1 mL) and DMF (0.5 mL) was added BOPCl (82 mg, 0.32 mmol) and DIPEA (139 mg, 1.07 mmol). The mixture was stirred at 40° C. for 1 h. The mixture was cooled to room temperature and concentrated under vacuum. The residue was purified by silica gel chromatography (PE/EtOAc=3/1 to 0/1) to give the title compound (50 mg, 37%). LC-MS $(M+H)^+$=628.3.

Step 3: (S)-5-amino-N-((5-(2,6-difluorophenyl)pyridin-2-yl)methyl)-N-(1-(pyrimidin-2-yl)ethyl)-6,8-dihydro-1H-furo[3,4-d]pyrrolo[3,2-b]pyridine-2-carboxamide & (R)-5-amino-N-((5-(2,6-difluorophenyl)pyridin-2-yl)methyl)-N-(1-(pyrimidin-2-yl)ethyl)-6,8-dihydro-1H-furo[3,4-d]pyrrolo[3,2-b]pyridine-2-carboxamide A solution of tert-butyl (2-(((5-(2,6-difluorophenyl)pyridin-2-yl)methyl)(1-(pyrimidin-2-yl)ethyl)carbamoyl)-6,8-dihydro-1H-furo[3,4-d]pyrrolo[3,2-b]pyridin-5-yl)carbamate (50 mg, 0.080 mol) in methanolic HCl (4 M, 0.50 mL) was stirred at 20° C. for 12 h then concentrated under vacuum. The residue was purified by prep-HPLC and then by prep-SFC to give Example 17 (10 mg, 24%) and Example 18 (7 mg, 17%).

Analytical chiral-SFC condition as below. Column: Chiralcel OJ-3; Column size: 4.6×50 mm, 3 μm; Mobile phase: A: $CO_2$, B: 14 mM $NH_3$ in MeOH; Gradient: A:B=95:5 (0.2 min), A:B=95:5 to 50:50 (1 min), A:B=50:50 (1 min), A:B=50:50 to 95:5 (0.4 min), A:B=95:5 (0.4 min); Flow: 3.4 mL/min; Temperature: 35° C.

Example 17: Analytical chiral-SFC tR=1.23 mm. $^1$H NMR (400 MHz, DMSO-d6) δ 11.74-11.59 (m, 1H), 8.92-8.46 (m, 3H), 8.01-7.22 (m, 6H), 6.81-6.23 (m, 1H), 6.21-5.48 (m, 3H), 5.40-4.52 (m, 6H), 1.78-1.59 (m, 3H). LC-MS $(M+H)^+$=528.2.

Example 18: Analytical chiral-SFC tR=1.47 min. $^1$H NMR (40 MHz, DMSO-d6) δ 11.75-11.59 (m, 1H), 8.92-8.44 (m, 3H), 8.01-7.22 (m, 6H), 6.81-6.23 (m, 1H), 6.21-5.49 (m, 3H), 5.40-4.52 (m, 6H), 1.78-1.58 (m, 3H). LC-MS $(M+H)^+$=528.2.

Example 19 & Example 20: (R)-5-amino-N-(3,4-dihydro-2H-pyrano[3,2-b]pyridin-4-yl)-N-((2',3,6'-trifluoro-[1,1'-biphenyl]-4-yl)methyl)-6,8-dihydro-1H-furo[3,4-d]pyrrolo[3,2-b]pyridine-2-carboxamide & (S)-5-amino-N-(3,4-dihydro-2H-pyrano[3,2-b]pyridin-4-yl)-N-((2',3,6'-trifluoro-[1,1'-biphenyl]-4-yl)methyl)-6,8-dihydro-1H-furo[3,4-d]pyrrolo[3,2-b]pyridine-2-carboxamide

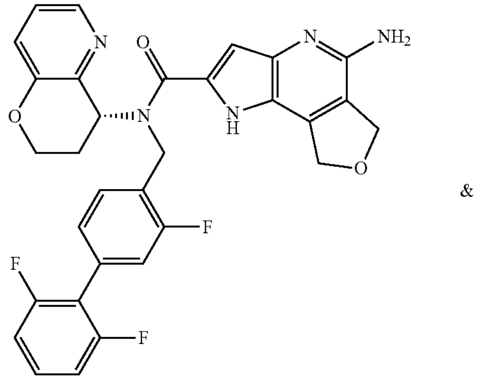

&

-continued

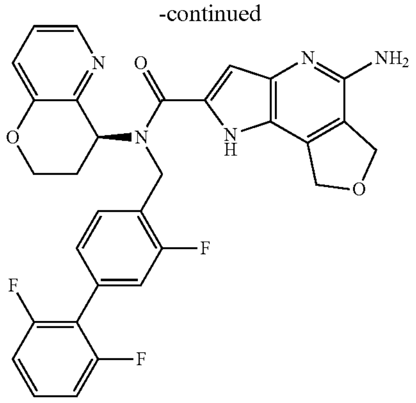

Step 1: N-((2',3,6'-trifluoro-[1,1'-biphenyl]-4-yl)methyl)-3,4-dihydro-2H-pyrano[3,2-b]pyridin-4-amine

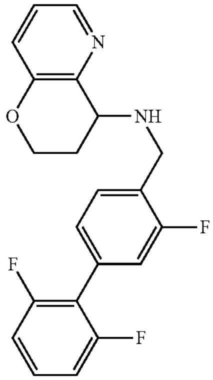 [SMILES: Fc1cc(-c2c(F)cccc2F)ccc1CNC1CCOc2cccnc21]

To a mixture of 3,4-dihydro-2H-pyrano[3,2-b]pyridin-4-amine (330 mg, 2.2 mmol) and 2',3,6'-trifluoro-[1,1'-biphenyl]-4-carbaldehyde (470 mg, 2.0 mmol) in DCM (20 mL) was added $NaBH(OAc)_3$ (848 mg, 4.0 mmol) and the mixture was stirred at room temperature for 2 h. The mixture was diluted with DCM (30 mL) and washed with saturated $NaHCO_3$ (10 mL) and brine (10 mL), dried over $Na_2SO_4$, filtered and concentrated under reduced pressure. The residue was purified by silica gel chromatography (DCM/MeOH=20/1) to give the title compound (620 mg, 83%). LC-MS $(M+H)^+$=371.4.

Step 2: tert-butyl (2-((3,4-dihydro-2H-pyrano[3,2-b]pyridin-4-yl)((2',3,6'-trifluoro-[1,1'-biphenyl]-4-yl)methyl)carbamoyl)-6,8-dihydro-1H-furo[3,4-d]pyrrolo[3,2-b]pyridin-5-yl)carbamate

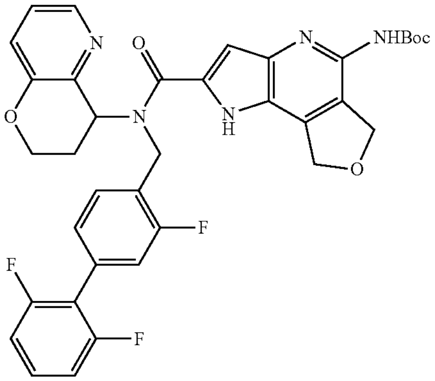 [SMILES: CC(C)(C)OC(=O)Nc1nc2cc(C(=O)N(Cc3ccc(-c4c(F)cccc4F)cc3F)C3CCOc4cccnc43)[nH]c2c2c1COC2]

The title compound (140 mg, 83%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and N-((2',3,6'-trifluoro-[1,1'-biphenyl]-4-yl)methyl)-3,4-dihydro-2H-pyrano[3,2-b]pyridin-4-amine. LC-MS $(M+H)^+$=672.4.

Step 3: (R)-5-amino-N-(3,4-dihydro-2H-pyrano[3,2-b]pyridin-4-yl)-N-((2',3,6'-trifluoro-[1,1'-biphenyl]-4-yl)methyl)-6,8-dihydro-1H-furo[3,4-d]pyrrolo[3,2-b]pyridine-2-carboxamide & (S)-5-amino-N-(3,4-dihydro-2H-pyrano[3,2-b]pyridin-4-yl)-N-((2',3,6'-trifluoro-[1,1'-biphenyl]-4-yl)methyl)-6,8-dihydro-1H-furo[3,4-d]pyrrolo[3,2-b]pyridine-2-carboxamide To a solution of tert-butyl (2-((3,4-dihydro-2H-pyrano[3,2-b]pyridin-4-yl)((2',3,6'-trifluoro-[1,1'-biphenyl]-4-yl)methyl)carbamoyl)-6,8-dihydro-1H-furo[3,4-d]pyrrolo[3,2-b]pyridin-5-yl)carbamate (140 mg, 0.21 mmol) in DCM (3 mL) was added HCl in dioxane (4 M, 8 mL) and the mixture was stirred at room temperature for overnight. The mixture was concentrated under reduced pressure. The residue was purified by prep-TLC followed by chiral prep-HPLC to give Example 19 (19 mg, 16%) and Example 20 (18 mg, 15%).

Analytical chiral-HPLC condition as below. Column: CHIRALPAK OD-H; Column size: 4.6×150 mm, 5 μm; Mobile phase: hexane:(0.1% diethylamine in EtOH)=9:1 isocratic; Flow: 1.0 mL/min; Temperature: 25° C.

Example 19: Analytical chiral-HPLC tR=18.65 min. $^1H$ NMR (500 MHz, DMSO-d6) δ 13.02-12.68 (m, 1H), 8.29-7.04 (m, 9H), 7.01-6.42 (m, 2H), 6.04-3.86 (m, 11H), 2.44-2.10 (m, 2H). LC-MS $(M+H)^+$=572.4.

Example 20: Analytical chiral-HPLC tR=22.16 min. $^1H$ NMR (500 MHz, DMSO-d6) δ 13.02-12.68 (m, 1H), 8.29-7.04 (m, 9H), 7.01-6.42 (m, 2H), 6.04-3.86 (m, 11H), 2.44-2.10 (m, 2H). LC-MS $(M+H)^+$=572.4.

Example 21: (R)-5-amino-N-(4-cyano-2,6-difluorobenzyl)-N-(5,6,7,8-tetrahydroquinolin-8-yl)-6,8-dihydro-1H-furo[3,4-d]pyrrolo[3,2-b]pyridine-2-carboxamide

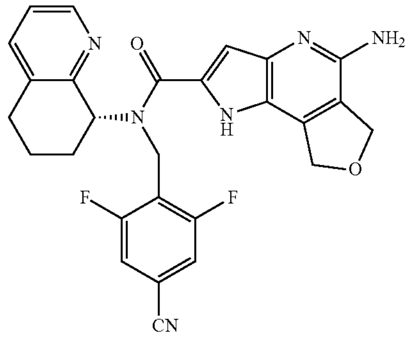 [SMILES: N#Cc1cc(F)c(CN(C(=O)c2cc3nc(N)c4c(c3[nH]2)COC4)[C@@H]2CCCc3cccnc32)c(F)c1]

Step 1: (R)-3,5-difluoro-4-(((5,6,7,8-tetrahydroquinolin-8-yl)amino)methyl)benzonitrile

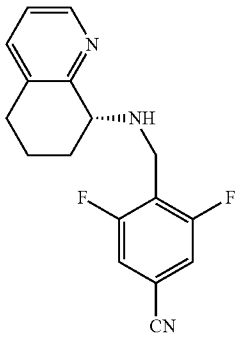 [SMILES: N#Cc1cc(F)c(CN[C@@H]2CCCc3cccnc32)c(F)c1]

The title compound (200 mg, 56%) was prepared in a manner similar to that in Example 5 step 1 from (R)-5,6,7,8-tetrahydroquinolin-8-amine and 3,5-difluoro-4-formylbenzonitrile. LC-MS $(M+H)^+$=300.1.

Step 2: tert-butyl (R)-(2-((4-cyano-2,6-difluorobenzyl)(5,6,7,8-tetrahydroquinolin-8-yl)carbamoyl)-6,8-dihydro-1H-furo[3,4-d]pyrrolo[3,2-b]pyridin-5-yl) carbamate

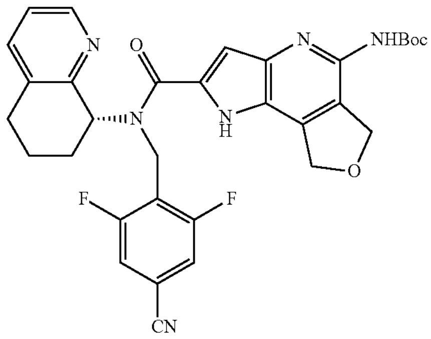 [SMILES: CC(C)(C)OC(=O)Nc1nc2cc(C(=O)N(Cc3c(F)cc(C#N)cc3F)[C@@H]3CCCc4cccnc43)[nH]c2c2c1COC2]

The title compound (30 mg, 30%) was prepared in a manner similar to that in Example 17 & 18 step 2 from 5-((tert-butoxycarbonyl)amino)-6,8-dihydro-1H-furo[3,4-d] pyrrolo[3,2 -b]pyridine-2-carboxylic acid and (R)-3,5-difluoro-4-(((5,6,7,8-tetrahydroquinolin-8-yl)amino)methyl) benzonitrile. LC-MS $(M+H)^+$=601.3.

Step 3: (R)-5-amino-N-(4-cyano-2,6-difluorobenzyl)-N-(5,6,7,8-tetrahydroquinolin-8-yl)-6,8-dihydro-1H-furo[3,4-d]pyrrolo[3,2-b]pyridine-2-carboxamide Example 21 (17 mg, 68%) was prepared in a manner similar to that in Example 14 step 6 from tert-butyl (R)-(2-((4-cyano-2,6-difluorobenzyl)(5,6,7,8-tetrahydroquinolin-8-yl)carbamoyl)-6,8-dihydro-1H-furo[3,4-d]pyrrolo[3,2-b] pyridin-5-yl)carbamate. $^1H$ NMR (500 MHz, DMSO-d6) δ 12.21 (s, 1H), 8.33 (s, 1H), 7.82-7.61 (m, 2H), 7.53 (s, 1H), 7.19 (s, 1H), 6.89-5.62 (m, 3H), 5.31-5.05 (m, 2H), 5.05-4.80 (m, 2H), 4.71-4.44 (m, 1H), 4.31-4.08 (m, 1H), 2.97-2.66 (m, 2H), 2.44-2.23 (m, 2H), 2.11-1.92 (m, 1H), 1.83-1.63 (m, 1H). LC-MS $(M+H)^+$=501.3.

Example 22: 5-amino-N-(4-cyano-2,6-difluorobenzyl)-N-(2,6-difluorobenzyl)-6,8-dihydro-1H-furo[3,4-d]pyrrolo[3,2-b]pyridine-2-carboxamide

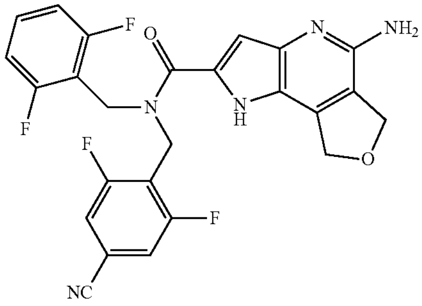 [SMILES: N#Cc1cc(F)c(CN(Cc2c(F)cccc2F)C(=O)c2cc3nc(N)c4c(c3[nH]2)COC4)c(F)c1]

Step 1: 4-(((2,6-difluorobenzyl)amino)methyl)-3,5-difluorobenzonitrile

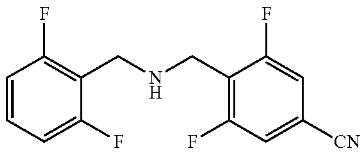 [SMILES: N#Cc1cc(F)c(CNCc2c(F)cccc2F)c(F)c1]

To a mixture of 3,5-difluoro-4-formylbenzonitrile (350 mg, 2.09 mmol) and (2,6-difluorophenyl)methanamine (300 mg, 2.09 mmol) in DCM (10 mL) was added $NaBH(OAc)_3$ (889 mg, 4.09 mmol) and the mixture was stirred at room temperature for 3 h. The mixture was diluted with DCM (30 mL) and washed with saturated $NaHCO_3$ (10 mL) and brine (10 mL), dried over $Na_2SO_4$, filtered and concentrated under reduced pressure. The residue was purified by silica gel chromatography (DCM/MeOH=20/1) to give the title compound (370 mg, 60%). LC-MS $(M+H)^+$=295.2.

Step 2: tert-butyl (2-((4-cyano-2,6-difluorobenzyl) (2,6-difluorobenzyl)carbamoyl)-6,8-dihydro-1H-furo [3,4-d]pyrrolo[3,2-b]pyridin-5-yl)carbamate

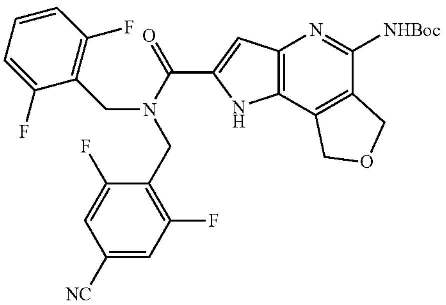 [SMILES: CC(C)(C)OC(=O)Nc1nc2cc(C(=O)N(Cc3c(F)cccc3F)Cc3c(F)cc(C#N)cc3F)[nH]c2c2c1COC2]

The title compound (50 mg, 93%) was prepared in a manner similar to that in Example 17 & 18 step 2 from 5-((tert-butoxycarbonyl)amino)-6,8-dihydro-1H-furo[3,4-d] pyrrolo[3,2-b]pyridine-2-carboxylic acid and 4-(((2,6-difluorobenzyl)amino)methyl)-3,5-difluorobenzonitrile. LC-MS $(M+H)^+$=596.3.

Step 3: 5-amino-N-(4-cyano-2,6-difluorobenzyl)-N-(2,6-difluorobenzyl)-6,8-dihydro-1H-furo[3,4-d]pyrrolo[3,2-b]pyridine-2-carboxamide A solution of tert-butyl (2-((4-cyano-2,6-difluorobenzyl)(2,6-difluorobenzyl)carbamoyl)-6,8-dihydro-1H-furo[3,4-d]pyrrolo[3,2-b]pyridin-5-yl)carbamate (50 mg, 0.084 mmol) in HCl in dioxane (4 M, 2 mL) was stirred for 3 h at room temperature. The mixture was concentrated under vacuum. The residue was purified by prep-HPLC to give Example 22 (24 mg, 58%). $^1$H NMR (500 MHz, DMSO-d6) δ 11.62 (s, 1H), 7.89-7.67 (m, 2H), 7.53-7.34 (m, 1H), 7.17-6.98 (m, 2H), 6.66 (d, J=1.7 Hz, 1H), 5.60 (s, 2H), 5.24-5.07 (m, 2H), 5.08-4.67 (m, 6H). LC-MS $(M+H)^+$= 496.3.

Example 23 & Example 24: (R)-5-amino-N-((5-(2,6-difluorophenyl)pyridin-2-yl)methyl)-N-((3R,4R)-4-methoxytetrahydro-2H-pyran-3-yl)-6-methyl-6,8-dihydro-1H-furo[3,4-d]pyrrolo[3,2-b]pyridine-2-carboxamide & (S)-5-amino-N-((5-(2,6-difluorophenyl)pyridin-2-yl)methyl)-N-((3R,4R)-4-methoxytetrahydro-2H-pyran-3-yl)-6-methyl-6,8-dihydro-1H-furo[3,4-d]pyrrolo[3,2-b]pyridine-2-carboxamide

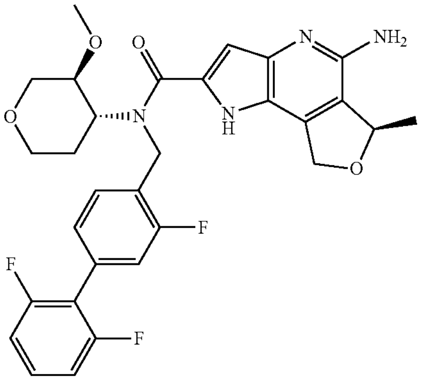

&

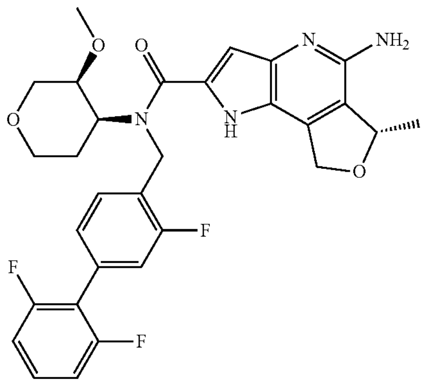

Step 1: 2-methyl-4-oxotetrahydrofuran-3-carbonitrile

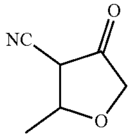

To a suspension of NaH (60%, 4.44 g, 0.11 mol) in THF (150 mL) was added methyl glycolate (20.0 g, 0.222 mol) at 0° C. The mixture was stirred at 60° C. for 30 min. Crotononitrile (17.8 g, 0.266 mmol) in THF (50 mL) was added dropwise at 60° C. The mixture was stirred at 70° C. for 2 h. The mixture was cooled to 0° C. and acidified with aqueous HCl (1 M) until its pH reached 4-5. The mixture was extracted with EtOAc (300 mL). The organic layer washed with water (100 mL) and brine (100 mL), dried over $Na_2SO_4$, filtered and concentrated under reduced pressure. The residue was purified by silica gel chromatography (PE/EtOAc=1/1) to give the title compound (10.0 g, 36%). $^1$H NMR (500 MHz, $CDCl_3$) δ 4.42-4.27 (m, 2H), 4.26-4.18 (m, 2H), 3.23-2.98 (m, 1H), 1.63-1.27 (m, 3H).

Step 2: 4-cyano-5-methyl-2,5-dihydrofuran-3-yl trifluoromethanesulfonate

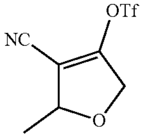

To a mixture of 2-methyl-4-oxotetrahydrofuran-3-carbonitrile (5.0 g, 40 mmol) and DIPEA (6.7 g, 52 mmol) in DCM (100 mL) was added $Tf_2O$ (13.5 g, 48 mmol) dropwise at −78° C. and the mixture was stirred at −78° C. for 2 h. The mixture was diluted with DCM (100 mL), successively washed with saturated $NaHCO_3$ (50 mL) and brine (50 mL), dried over $Na_2SO_4$, filtered and concentrated under reduced pressure. The residue was purified by silica gel chromatography (PE/EtOAc=3/1) to give the title compound (8.5 g, 83%). $^1$HNMR (500 MHz, $CDCl_3$) δ 5.13-5.06 (m, 1H), 4.94-4.76 (m, 2H), 1.49 (d, J=6.3 Hz, 3H).

Step 3: ethyl 4-((tert-butoxy carbonyl)amino)-5-(4-cyano-5-methyl-2,5-dihydrofuran-3-yl)-1H-pyrrole-2-carboxylate

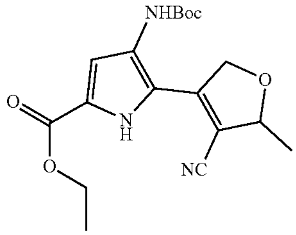 [SMILES: CCOC(=O)c1cc(NC(=O)OC(C)(C)C)c(C2=C(C#N)C(C)OC2)[nH]1]

To a solution of ethyl 5-bromo-4-((tert-butoxycarbonyl)amino)-1H-pyrrole-2-carboxylate (3.0 g, 9.0 mmol) and BPD (4.6 g, 18.0 mmol) in THF (50 mL) was added $Pd_2(dba)_3$ (0.41 g, 0.45 mmol), KOAc (2.65 g, 27.0 mmol) and XPhos (0.43 g, 0.90 mmol). The mixture was stirred at 75° C. for 3 h and cooled to room temperature. Solid was filtered off and the filtrate was concentrated under vacuum. The crude was re-dissolved in dioxane (100 mL) and water (20 mL), followed by addition of 4-cyano-5-methyl-2,5-dihydrofuran-3-yl trifluoromethanesulfonate (3.0 g, 11.7 mmol) $Pd(dppf)Cl_2$ (83 mg, 0.58 mmol) and $NaHCO_3$ (1.96 g, 23.4 mmol). The mixture was stirred at 80° C. for 5 h. The mixture was cooled to room temperature and diluted with EtOAc (100 mL). The mixture was washed with brine (50 mL), and the aqueous layer was back-extracted with EtOAc (50 mL). The combined organic layer was dried over $Na_2SO_4$, filtered and concentrated under reduced pressure. The residue was purified by silica gel chromatograph (PE/EtOAc=3/1) to give the title compound (2.0 g, 62%). LC-MS (M+H)+=362.1.

Step 4: ethyl 5-amino-6-methyl-6,8-dihydro-1H-furo[3,4-d]pyrrolo[3,2-b]pyridine-2-carboxylate

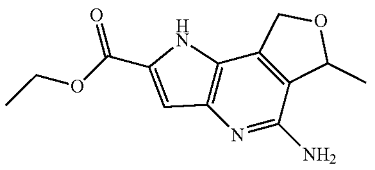 [SMILES: CCOC(=O)c1cc2nc(N)c3c(c2[nH]1)COC3C]

To a solution of ethyl 4-((tert-butoxycarbonyl)amino)-5-(4-cyano-5-methyl-2,5-dihydrofuran-3-yl)-1H-pyrrole-2-carboxylate (2.0 g, 5.5 mmol) in dioxane (10 mL) was added HCl in dioxane (4 M, 10 mL) and the mixture was stirred at room temperature for 5 h. The mixture was concentrated under reduced pressure, and the crude was re-dissolved in EtOH (60 mL) followed by addition of $K_2CO_3$ (3.44 g, 25 mmol). The mixture was stirred at 70° C. for 4 h then cooled to room temperature. Solid was filtered off and the filtrate was concentrated under reduced pressure. The residue was purified by silica gel chromatography (DCM/MeOH=10/1) to give the title compound (1.0 g, 69%). LC-MS $(M+H)^+$=262.1.

Step 5: 5-amino-6-methyl-6,8-dihydro-1H-furo[3,4-d]pyrrolo[3,2-b]pyridine-2-carboxylic acid

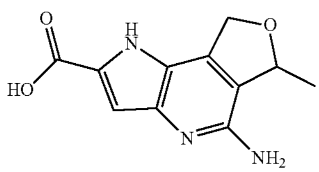 [SMILES: CC1OCc2c1c(N)nc1cc(C(=O)O)[nH]c21]

A mixture of ethyl 5-amino-6-methyl-6,8-dihydro-1H-furo[3,4-d]pyrrolo[3,2-b]pyridine-2-carboxylate (1.0 g, 3.8 mmol) and $LiOH{\cdot}H_2O$ (0.32 g, 7.6 mmol) in MeOH (20 mL) and water (10 mL) was stirred at 50° C. for 3 h. The mixture was cooled to room temperature and concentrated under reduced pressure. The residue was purified by prep-HPLC to give the title compound (500 mg, 56%). LCMS $(M+H)^+$=234.1.

Step 6: (R)-5-amino-N-((5-(2,6-difluorophenyl)pyridin-2-yl)methyl)-N-((3R,4R)-4-methoxytetrahydro-2H-pyran-3-yl)-6-methyl-6,8-dihydro-1H-furo[3,4-d]pyrrolo[3,2-b]pyridine-2-carboxamide & (S)-5-amino-N-((5-(2,6-difluorophenyl)pyridin-2-yl)methyl)-N-((3R,4R)-4-methoxytetrahydro-2H-pyran-3-yl)-6-methyl-6,8-dihydro-1H-furo[34-d]pyrrolo[3,2-b]pyridine-2-carboxamide To a mixture of 5-amino-6-methyl-6,8-dihydro-1H-furo[3,4-d]pyrrolo[3,2-b]pyridine-2-carboxylic acid (170 mg, 0.73 mmol), (3R,4R)—N-((5-(2,6-difluorophenyl)pyridin-2-yl)methyl)-4-methoxytetrahydro-2H-pyran-3-amine hydrochloride (270 mg, 0.73 mmol) and DIPEA (471 mg, 3.65 mmol) in anhydrous DMF (5 mL) under nitrogen was added HATU (832 mg, 2.19 mmol) and the mixture was stirred at 70° C. for 2 h. The mixture cooled to room temperature and diluted with EtOAc (20 mL). The mixture was washed with water (20 mL) and brine (20 mL). The aqueous layer was back-extracted with EtOAc (20 mL). The combined organic layer was dried over $Na_2SO_4$, filtered and concentrated under reduced pressure. The crude was purified by prep-HPLC and chiral-SFC to give Example 23 (47 mg, 12%) and Example 24 (45 mg, 11%).

Analytical chiral-HPLC condition as below. Column: CHIRALPAK IE-3; Column size: 4.6×50 mm, 3 μm; Mobile phase: (0.1% diethylamine in MTBE):MeOH:DCM=3:1:1 isocratic; Flow: 1.0 mL/min; Temperature: 25° C.

Example 23: Analytical chiral-HPLC tR=2.26 min. $^1H$ NMR (500 MHz, DMSO-d6) δ 11.92-11.42 (m, 1H), 8.90-8.46 (m, 1H), 8.06-7.80 (m, 1H), 7.76-7.46 (m, 2H), 7.40-7.14 (m, 2H), 6.85-6.24 (m, 1H), 5.88-4.72 (m, 7H), 4.61-3.35 (m, 6H), 3.20-3.10 (m, 3H), 2.24-2.14 (m, 1H), 1.41-1.29 (m, 4H). LCMS $(M+H)^+$=550.4.

Example 24: Analytical chiral-HPLC tR=2.97 min. $^1H$ NMR (500 MHz, DMSO-d6) δ 11.90-11.46 (m, 1H), 8.82-8.48 (m, 1H), 8.03-7.76 (m, 1H), 7.74-7.46 (m, 2H), 7.38-7.19 (m, 2H), 6.85-6.26 (m, 1H), 5.81-4.70 (m, 7H), 4.67-3.61 (m, 4H), 3.59-3.35 (m, 2H), 3.20-3.06 (m, 3H), 2.27-2.15 (m, 1H), 1.43-1.27 (m, 4H). LCMS $(M+H)^+$=550.4.

Example 25: (R)-5-amino-N-((5-(1-methyl-1H-1,2,4-triazol-5-yl)pyridin-2-yl)methyl)-N-(5,6,7,8-tetrahydroquinolin-8-yl)-6,8-dihydro-1H-furo[3,4-d]pyrrolo[3,2-b]pyridine-2-carboxamide

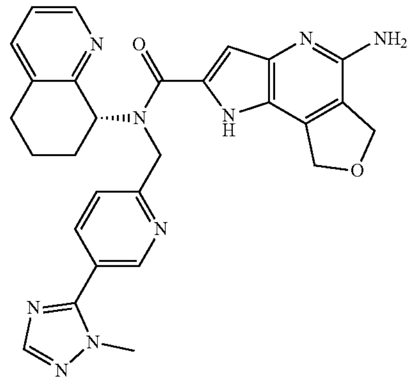 [SMILES: Cn1ncnc1-c1ccc(CN(C(=O)c2cc3nc(N)c4c(c3[nH]2)COC4)[C@@H]2CCCc3cccnc32)nc1]

Step 1: 2-(1,3-dioxolan-2-yl)-5-(1-methyl-1H-1,2,4-triazol-5-yl)pyridine

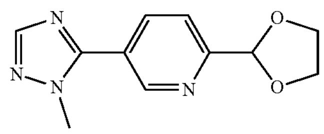 [SMILES: Cn1ncnc1-c1ccc(C2OCCO2)nc1]

To a mixture of (6-(1,3-dioxolan-2-yl)pyridin-3-yl)boronic acid (2.0 g, 10.3 mmol) in dioxane (20 mL), toluene (10 mL) and water (10 mL) was added 5-bromo-1-methyl-1H-1,2,4-triazole (1.66 g, 10.3 mmol), $K_3PO_4$ (6.53 g, 30.8 mmol) and $Pd(dppf)Cl_2$ (751 mg, 1.0 mmol). The mixture was stirred at 80° C. for 12 h and cooled to room temperature. Solid was filtered off and the filtrate was concentrated under reduced pressure. The residue was purified by silica gel chromatograph (PE:EtOAc=5:1 to 0:1) to give the title compound (1.3 g, 55%). LC-MS $(M+H)^+$=233.3.

Step 2: 541-methyl-1H-1,2,4-triazol-5-yl)picolinaldehyde

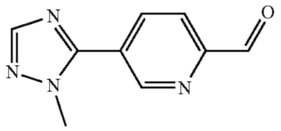

To a mixture of 2-(1,3-dioxolan-2-yl)-5-(1-methyl-1H-1,2,4-triazol-5-yl)pyridine (1.2 g, 5.17 mmol) in water (6 mL) and dioxane (12 mL) was added concentrated HCl (6.5 mL) and the mixture was stirred at 60° C. for 3 h. The mixture was cooled to room temperature and neutralized with saturated $NaHCO_3$ until pH reached 7-8. The mixture was diluted with water (100 mL) and extracted with EtOAc (100 mL×3). The combined organic layer was dried with $Na_2SO_4$, filtered and concentrated in vacuum to give the title compound (0.60 g, 62%). LC-MS $(M+H)^+$=189.3.

Step 3: (R)—N-((5-(1-methyl-1H-1,2,4-triazol-5-yl)pyridin-2-yl)methyl)-5,6,7,8-tetrahydroquinolin-8-amine

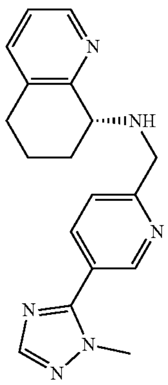 [SMILES: Cn1ncnc1-c1ccc(CN[C@@H]2CCCc3cccnc32)nc1]

The title compound (0.28 g, 25%) was prepared in a manner similar to that in Example 5 step 1 from (R)-5,6,7,8-tetrahydroquinolin-8-amine and 5-(1-methyl-1H-1,2,4-triazol-5-yl)picolinaldehyde. LC-MS $(M+H)^+$=321.1.

Step 4: tert-butyl (R)-(2-(((5-(1-methyl-1H-1,2,4-triazol-5-yl)pyridin-2-yl)methyl(5,6,7,8-tetrahydroquinolin-8-yl)carbamoyl)-6,8-dihydro-1H-furo[3,4-d]pyrrolo[3,2-b]pyridin-5-yl)carbamate

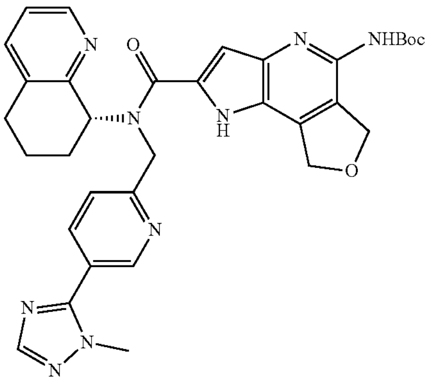 [SMILES: Cn1ncnc1-c1ccc(CN(C(=O)c2cc3nc(NC(=O)OC(C)(C)C)c4c(c3[nH]2)COC4)[C@@H]2CCCc3cccnc32)nc1]

The title compound (30 mg, 32%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and (R)—N-((5-(1-methyl-1H-1,2,4-triazol-5-yl)pyridin-2-yl)methyl)-5,6,7,8-tetrahydroquinolin-8-amine. LC-MS $(M+H)^+$=622.1.

Step 5: (R)-5-amino-N-((5-(1-methyl-1H-1,2,4-triazol-5-yl)pyridin-2-yl)methyl)-N-(5,6,7,8-tetrahydroquinolin-8-yl)-6,8-dihydro-1H-furo[3,4-d]pyrrolo[3,2-b]pyridine-2-carboxamide Example 25 (8 mg, 30%) was prepared in a manner similar to that in Example 22 step 3 from tert-butyl (R)-(2-(((5-(1-methyl-1H-1,2,4-triazol-5-yl)pyridin-2-yl)methyl)(5,6,7,8-tetrahydroquinolin-8-yl)carbamoyl)-6,8-dihydro-1H-furo[3,4-d]pyrrolo[3,2-b]pyridin-5-yl)carbamate. $^1H$ NMR (500 MHz, DMSO-d6) δ 11.75-11.53 (m, 1H), 9.10-8.75 (m, 1H), 8.50- 7.90 (m, 6H), 6.81-6.17 (m, 1H), 6.00-4.76 (m, 8H), 4.10-3.87 (m, 4H), 3.05-2.39 (m, 4H), 2.30-1.68 (m, 4H). LC-MS $(M+H)^+$=522.4.

Example 26: 5-amino-N-((3R,4R)-4-methoxytetrahydro-2H-pyran-3-yl)-N-((5-(trifluoromethyl)pyridin-2-yl)methyl)-6,8-dihydro-1H-furo[3,4-d]pyrrolo[3,2-b]pyridine-2-carboxamide

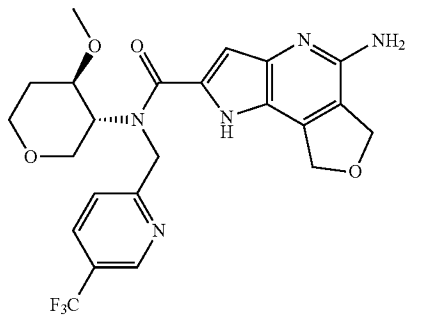 [SMILES: CO[C@@H]1CCOC[C@H]1N(Cc1ccc(C(F)(F)F)cn1)C(=O)c1cc2nc(N)c3c(c2[nH]1)COC3]

Step 1: (3R,4R)-4-methoxy-N-((5-(trifluoromethyl) pyridin-2-yl)methyl)tetrahydro-2H-pyran-3-amine

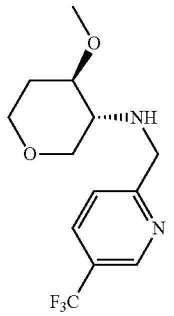 [SMILES: CO[C@@H]1CCOC[C@H]1NCc1ccc(C(F)(F)F)cn1]

The title compound (50 mg, 55%) was prepared in a manner similar to that in Example 4 step 1 from (3R,4R)-4-methoxytetrahydro-2H-pyran-3-amine and 5-(trifluoromethyl)picolinaldehyde. LC-MS $(M+H)^+$=291.3.

Step 2: tert-butyl (2-(((3R,4R)-4-methoxytetrahydro-2H-pyran-3-yl)((5-(trifluoromethyl)pyridin-2-yl)methyl)carbamoyl)-6,8-dihydro-1H-furo[3,4-d] pyrrolo[3,2-b]pyridin-5-yl)carbamate

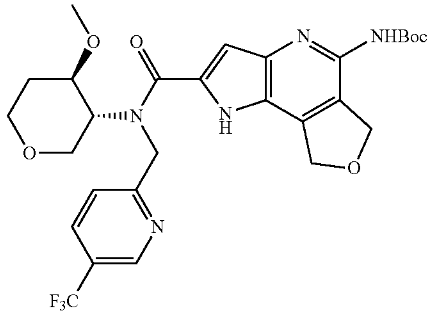 [SMILES: CO[C@@H]1CCOC[C@H]1N(Cc1ccc(C(F)(F)F)cn1)C(=O)c1cc2nc(NC(=O)OC(C)(C)C)c3c(c2[nH]1)COC3]

The title compound (60 mg, 59%) was prepared in a manner similar to that in Example 17 & 18 step 2 from 5-((tert-butoxycarbonyl)amino)-6,8-dihydro-1H-furo[3,4-d] pyrrolo[3,2-b]pyridine-2-carboxylic acid and (3R,4R)-4-methoxy-N-((5-(trifluoromethyl)pyridin-2-yl)methyl)tetrahydro-2H-pyran-3-amine. LC-MS $(M+H)^+$=592.4.

Step 3: 5-amino-N-((3R,4R)-4-methoxytetrahydro-2H-pyran-3-yl)-N-((5-(trifluoromethylpyridin-2-yl) methyl)-6,8-dihydro-1H-furo[3,4-d]pyrrolo[3,2-b] pyridine-2-carboxamide Example 26 (31 mg, 63%) was prepared in a manner similar to that in Example 22 step 3 from tert-butyl (2-(((3R, 4R)-4-methoxytetrahydro-2H-pyran-3-yl)((5-(trifluoromethyl)pyridin-2-yl)methyl)carbamoyl)-6,8-dihydro-1H-furo [3,4-d]pyrrolo[3,2-b]pyridin-5-yl)carbamate. $^1$H NMR (500 MHz, DMSO-d6) δ 11.73-11.39 (m, 1H), 9.10-8.79 (m, 1H), 8.30-8.07 (m, 1H), 7.86-7.54 (m, 1H), 6.82-6.08 (m, 1H), 5.57 (s, 2H), 5.26-4.73 (m, 6H), 4.67-3.44 (m, 5H), 3.21-3.04 (m, 3H), 2.32-2.06 (m, 1H), 1.41-1.20 (m, 1H). LC-MS $(M+H)^+$=492.4.

Example 27: 5-amino-N-((3R,4R)-4-methoxytetrahydro-2H-pyran-3-yl)-N-((5-phenylpyridin-2-yl) methyl)-6,8-dihydro-1H-furo[3,4-d]pyrrolo[3,2-b] pyridine-2-carboxamide

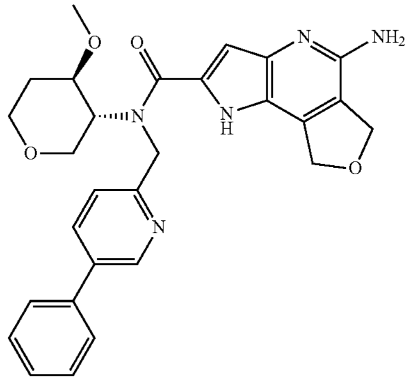 [SMILES: CO[C@@H]1CCOC[C@H]1N(Cc1ccc(-c2ccccc2)cn1)C(=O)c1cc2nc(N)c3c(c2[nH]1)COC3]

Step 1: (3R,4R)-4-methoxy-N-((5-phenylpyridin-2-yl)methyl)tetrahydro-2H-pyran-3-amine

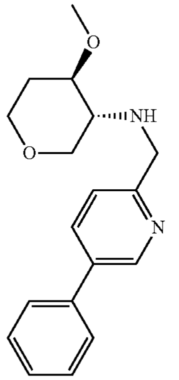 [SMILES: CO[C@@H]1CCOC[C@H]1NCc1ccc(-c2ccccc2)cn1]

The title compound (0.050 g, 58%) was prepared in a manner similar to that in Example 4 step 1 from 5-phenylpicolinaldehyde and (3R,4R)-4-methoxytetrahydro-2H-pyran-3-amine. LC-MS $(M+H)^+$=299.1.

Step 2: tert-butyl (2-(((3R,4R)-4-methoxytetrahydro-2H-pyran-3-yl)((5-phenylpyridin-2-yl)methyl)carbamoyl)-6,8-dihydro-1H-furo[3,4-d]pyrrolo[3,2-b]pyridin-5-yl)carbamate

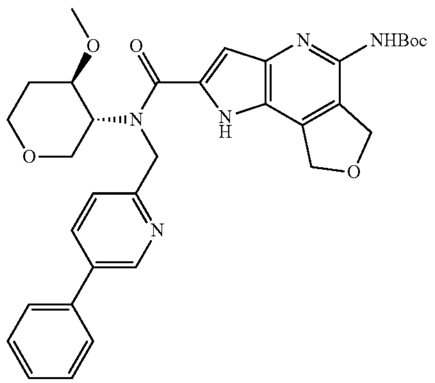 [SMILES: CO[C@@H]1CCOC[C@H]1N(Cc1ccc(-c2ccccc2)cn1)C(=O)c1cc2nc(NC(=O)OC(C)(C)C)c3c(c2[nH]1)COC3]

The title compound (60 mg, 57%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and (3R,4R)-4-methoxy-N-((5-phenylpyridin-2-yl)methyl)tetrahydro-2H-pyran-3-amine. LC-MS $(M+H)^+$=600.2.

Step 3: 5-amino-N-((3R,4R)-4-methoxytetrahydro-2H-pyran-3-yl)-N-((5-phenylpyridin-2-yl)methyl)-6,8-dihydro-1H-furo[3,4-d]pyrrolo[3,2-b]pyridine-2-carboxamide Example 27 (23 mg, 46%) was prepared in a manner similar to that in Example 22 step 3 from tert-butyl (2-(((3R,4R)-4-methoxytetrahydro-2H-pyran-3-yl)((5-phenylpyridin-2-yl)methyl)carbamoyl)-6,8-dihydro-1H-furo[3,4-d]pyrrolo[3,2-b]pyridin-5-yl)carbamate. 1H NMR (500 MHz, DMSO-d6) δ 11.57 (s, 1H), 8.82 (s, 1H), 8.04 (s, 1H), 7.72 (s, 2H), 7.59-7.35 (m, 4H), 6.74 (s, 1H), 5.58-5.51 (m, 2H), 5.13 (s, 2H), 4.93 (s, 3H), 4.77-4.55 (m, 1H), 4.05 (s, 1H), 3.84 (d, J=7.9 Hz, 2H), 3.51-3.26 (m, 6H), 2.20 (d, J=10.1 Hz, 1H), 1.33 (s, 1H). LC-MS $(M+H)^+$=500.2.

Example 28: N-([3,4'-bipyridin]-6-ylmethyl)-5-amino-N-((3R,4R)-4-methoxytetrahydro-2H-pyran-3-yl)-6,8-dihydro-1H-furo[3,4-d]pyrrolo[3,2-b]pyridine-2-carboxamide

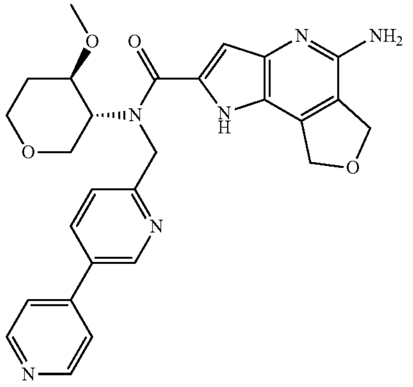 [SMILES: CO[C@@H]1CCOC[C@H]1N(Cc1ccc(-c2ccncc2)cn1)C(=O)c1cc2nc(N)c3c(c2[nH]1)COC3]

Step 1: [3,4'-bipyridine]-6-carbaldehyde

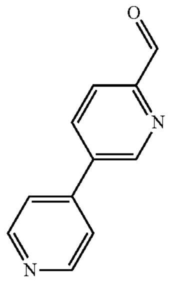 [SMILES: O=Cc1ccc(-c2ccncc2)cn1]

The title compound (1.0 g, 100%) was prepared in a manner similar to that in Example 6 step 1 from 5-bromopicolinaldehyde and pyridin-4-ylboronic acid. LC-MS $(M+H)^+$=185.0.

Step 2: (3R,4R)—N-([3,4'-bipyridin]-6-ylmethyl)-4-methoxytetrahydro-2H-pyran-3-amine

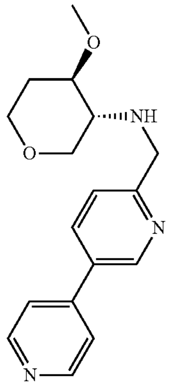 [SMILES: CO[C@@H]1CCOC[C@H]1NCc1ccc(-c2ccncc2)cn1]

The title compound (40 mg, 29%) was prepared in a manner similar to that in Example 4 step 1 from [3,4'-bipyridine]-6-carbaldehyde and (3R,4R)-4-methoxytetrahydro-2H-pyran-3-amine. LC-MS $(M+H)^+$=300.1.

Step 3: tert-butyl (2-(([3,4'-bipyridin]-6-ylmethyl)((3R,4R)-4-methoxytetrahydro-2H-pyran-3-yl)carbamoyl)-6,8-dihydro-1H-furo[3,4-d]pyrrolo[3,2-b]pyridin-5-yl)carbamate

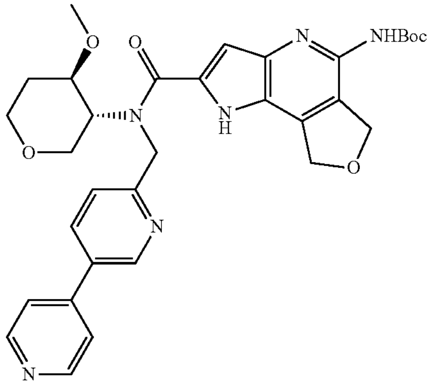 [SMILES: CO[C@@H]1CCOC[C@H]1N(Cc1ccc(-c2ccncc2)cn1)C(=O)c1cc2nc(NC(=O)OC(C)(C)C)c3c(c2[nH]1)COC3]

The title compound (35 mg, 29%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and (3R,4R)—N-([3,4'-bipyridin]-6-ylmethyl)-4-methoxytetrahydro-2H-pyran-3-amine. LC-MS $(M+H)^+$=601.2.

Step 4: N-([3,4'-bipyridin]-6-ylmethyl)-5-amino-N-((3R,4R)-4-methoxytetrahydro-2H-pyran-3-yl)-6,8-dihydro-1H-furo[3,4-d]pyrrolo[3,2-b]pyridine-2-carboxamide Example 28 (2 mg, 7%) was prepared in a manner similar to that in Example 22 step 3 from tert-butyl (2-(([3,4'-bipyridin]-6-ylmethyl)((3R,4R)-4-methoxytetrahydro-2H-pyran-3-yl)carbamoyl)-6,8-dihydro-1H-furo[3,4-d]pyrrolo[3,2-b]pyridin-5-yl)carbamate. $^1$H NMR (500 MHz, DMSO-d6) δ 11.56 (s, 1H), 9.01 (d, J=46.7 Hz, 1H), 8.67 (d, J=5.2 Hz, 2H), 8.17 (s, 1H), 7.79 (s, 2H), 7.65-7.53 (m, 1H), 6.74 (s, 1H), 5.57-5.50 (m, 2H), 5.13 (s, 2H), 4.93 (s, 2H), 4.82-4.50 (m, 1H), 4.06 (s, 1H), 3.84 (d, J=9.7 Hz, 2H), 3.68 (s, 1H), 3.50 (s, 1H), 3.17 (s, 3H), 2.20 (d, J=10.0 Hz, 1H), 1.34 (s, 1H). LC-MS $(M+H)^+$=501.2.

Example 29: N-([3,4'-bipyridin]-6-ylmethyl)-5-amino-N-(2,6-difluorobenzyl)-6,8-dihydro-1H-furo[3,4-d]pyrrolo[3,2-b]pyridine-2-carboxamide

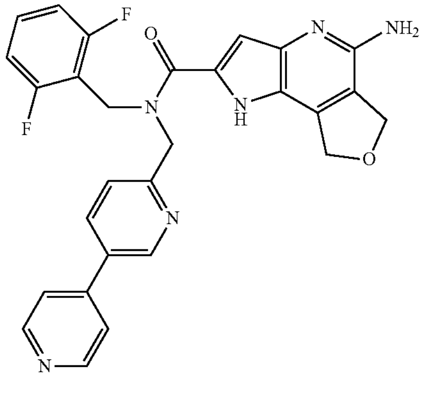 [SMILES: Nc1nc2cc(C(=O)N(Cc3ccc(-c4ccncc4)cn3)Cc3c(F)cccc3F)[nH]c2c2c1COC2]

Step 1: 1-([3,4'-bipyridin]-6-yl)-N-(2,6-difluorobenzyl)methanamine

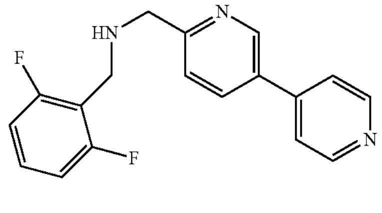 [SMILES: Fc1cccc(F)c1CNCc1ccc(-c2ccncc2)cn1]

The title compound (40 mg, 23%) was prepared in a manner similar to that in Example 3 step 1 from [3,4'-bipyridine]-6-carbaldehyde and (2,6-difluorophenyl)methanamine. LC-MS $(M+H)^+$=312.1.

Step 2: tert-butyl (2-(([3,4'-bipyridin]-6-ylmethyl)(2,6-difluorobenzyl)carbamoyl)-6,8-dihydro-1H-furo[3,4-d]pyrrolo[3,2-b]pyridin-5-yl)carbamate

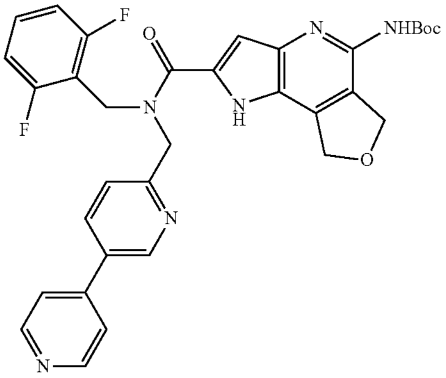 [SMILES: CC(C)(C)OC(=O)Nc1nc2cc(C(=O)N(Cc3ccc(-c4ccncc4)cn3)Cc3c(F)cccc3F)[nH]c2c2c1COC2]

The title compound (20 mg, 26%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and 1-([3,4'-bipyridin]-6-yl)-N-(2,6-difluorobenzyl)methanamine. LC-MS $(M+H)^+$=613.2.

Step 3: N-([3,4'-bipyridin]-6-ylmethyl)-5-amino-N-(2,6-difluorobenzyl)-6,8-dihydro-1H-furo[3,4-d]pyrrolo[3,2-b]pyridine-2-carboxamide Example 29 (4 mg, 25%) was prepared in a manner similar to that in Example 22 step 3 from tert-butyl (2-(([3,4'-bipyridin]-6-ylmethyl)(2,6-difluorobenzyl)carbamoyl)-6,8-dihydro-1H-furo[3,4-d]pyrrolo[3,2-b]pyridin-5-yl)carbamate. $^1$H NMR (500 MHz, DMSO-d6) δ 11.67 (s, 1H), 8.98 (s, 1H), 8.68 (dd, J=4.6, 1.5 Hz, 2H), 8.20 (d, J=7.3 Hz, 1H), 7.78 (d, J=5.9 Hz, 2H), 7.45 (d, J=8.2 Hz, 1H), 7.44-7.32 (m, 1H), 7.05 (t, J=8.0 Hz, 2H), 6.46 (s, 1H), 5.55 (s, 2H), 5.13 (s, 2H), 5.00 (s, 2H), 4.91 (s, 2H). LC-MS $(M+H)^+$=513.1.

Example 30: 5-amino-N-((3',5'-difluoro-[3,4'-bipyridin]-6-yl)methyl)-N-(2,6-difluorobenzyl)-6,8-dihydro-1H-furo[3,4-d]pyrrolo[3,2-b]pyridine-2-carboxamide

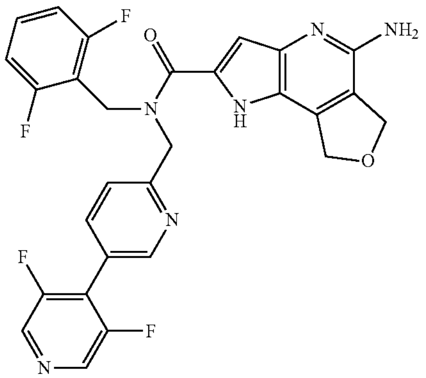 [SMILES: Nc1nc2cc(C(=O)N(Cc3ccc(-c4c(F)cncc4F)cn3)Cc3c(F)cccc3F)[nH]c2c2c1COC2]

Step 1: 1-(3',5'-difluoro-[3,4'-bipyridin]-6-yl)-N-(2,6-difluorobenzyl)methanamine

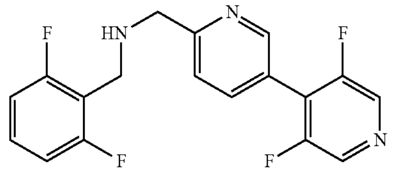 [SMILES: Fc1cccc(F)c1CNCc1ccc(-c2c(F)cncc2F)cn1]

The title compound (130 mg, 75%) was prepared in a manner similar to that in Example 3 step 1 from 3',5'-difluoro-[3,4'-bipyridine]-6-carbaldehyde and (2,6-difluorophenyl)methanamine. LC-MS $(M+H)^+$=348.2.

Step 2: 5-amino-N-((3',5'-difluoro-[3,4'-bipyridin]-6-yl)methyl)-N-(2,6-difluorobenzyl)-6,8-dihydro-1H-furo[3,4-d]pyrrolo[3,2-b]pyridine-2-carboxamide Example 30 (15 mg, 27%) was prepared in a manner similar to that in Example 2 step 3 from 5-amino-6,8-dihydro-1H-furo[3,4-d]pyrrolo[3,2-b]pyridine-2-carboxylic acid and 1-(3',5'-difluoro-[3,4'-bipyridin]-6-yl)-N-(2,6-difluorobenzyl)methanamine. $^1H$ NMR (500 MHz, DMSO-d6) δ 11.72 (s, 1H), 8.78-8.62 (m, 3H), 8.05-7.95 (m, 1H), 7.55-7.30 (m, 2H), 7.04 (t, J=8.0 Hz, 2H), 6.52 (s, 1H), 5.85-4.75 (m, 10H). LC-MS $(M+H)^+$=549.3.

Example 31: 5-amino-N-(2,6-dichlorobenzyl)-N-((3',5'-difluoro-[3,4'-bipyridin]-6-yl)methyl)-6,8-dihydro-1H-furo[3,4-d]pyrrolo[3,2-b]pyridine-2-carboxamide

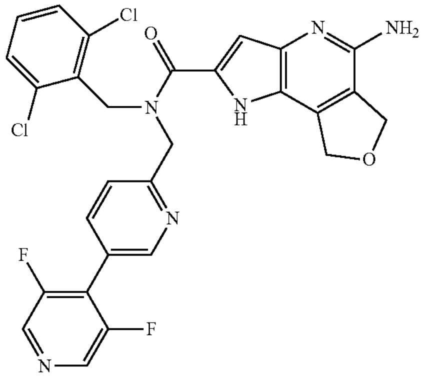 [SMILES: Nc1nc2cc(C(=O)N(Cc3ccc(-c4c(F)cncc4F)cn3)Cc3c(Cl)cccc3Cl)[nH]c2c2c1COC2]

Step 1: N-(2,6-dichlorobenzyl-1-(3',5'-difluoro-[3,4'-bipyridin]-6-yl)methanamine

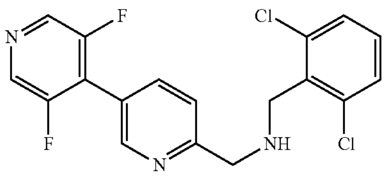 [SMILES: Fc1cncc(F)c1-c1ccc(CNCc2c(Cl)cccc2Cl)nc1]

The title compound (140 mg, 74%) was prepared in a manner similar to that in Example 5 step 1 from 3',5'-difluoro-[3,4'-bipyridine]-6-carbaldehyde and (2,6-dichlorophenyl)methanamine. LC-MS $(M+H)^+$=380.1

Step 2: 5-amino-N-(2,6-dichlorobenzyl)-N-((3',5'-difluoro-[3,4'-bipyridin]-6-yl)methyl)-6,8-dihydro-1H-furo[3,4-d]pyrrolo[3,2-b]pyridine-2-carboxamide Example 31 (14 mg, 24%) was prepared in a manner similar to that in Example 2 step 3 from 5-amino-6,8-dihydro-1H-furo[3,4-d]pyrrolo[3,2-b]pyridine-2-carboxylic acid and N-(2,6-dichlorobenzyl)-1-(3',5'-difluoro-[3,4'-bipyridin]-6-yl)methanamine. $^1H$ NMR (500 MHz. DMSO-d6) δ 11.69 (s, 1H), 8.72-8.53 (m, 3H), 7.94 (d, J=8.0 Hz, 1H), 7.51-7.35 (m, 3H), 7.28 (t, J=8.0 Hz, 1H), 6.52 (s, 1H), 5.56 (s, 2H), 5.47-4.62 (m, 8H). LC-MS $(M+H)^+$=581.3.

Example 32: 5-amino-N-((5-cyanopyridin-2-yl)methyl)-N-(2,6-difluorobenzyl)-6,8-dihydro-1H-furo[3,4-d]pyrrolo[3,2-b]pyridine-2-carboxamide

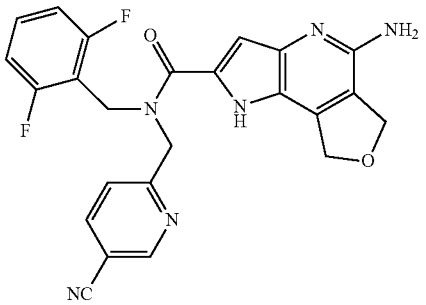 [SMILES: N#Cc1ccc(CN(Cc2c(F)cccc2F)C(=O)c2cc3nc(N)c4c(c3[nH]2)COC4)nc1]

Step 1: 6-(((2,6-difluorobenzyl)amino)methyl)nicotinonitrile

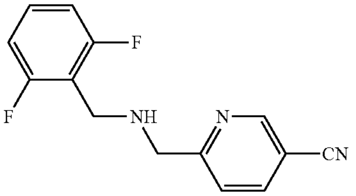 [SMILES: N#Cc1ccc(CNCc2c(F)cccc2F)nc1]

The title compound (260 mg, 100%) was prepared in a manner similar to that in Example 3 step 1 from (2,6-difluorophenyl)methanamine and 6-formylnicotinonitrile. LC-MS $(M+H)^+$=260.2.

Step 2: 5-amino-N-((5-cyanopyridin-2-yl)methyl)-N-(2,6-difluorobenzyl)-6,8-dihydro-1H-furo[3,4-d]pyrrolo[3,2-b]pyridine-2-carboxamide Example 32 (8 mg, 9%) was prepared in a manner similar to that in Example 2 step 3 from 6-(((2,6-difluorobenzyl)amino)methyl)nicotinonitrile and 5-amino-6,8-dihydro-1H-furo[3,4-d]pyrrolo[3,2-b]pyridine-2-carboxylic acid. $^1H$ NMR (500 MHz, DMSO-d6) δ 11.64 (s, 1H), 8.95 (s, 1H), 8.27 (d, J=7.2 Hz, 1H), 7.51 (d, J=7.8 Hz, 1H), 7.40-7.30 (m, 1H), 7.13-6.96 (m, 2H), 6.87-6.11 (m, 1H), 5.55 (s, 2H), 5.27-4.71 (m, 8H). LC-MS $(M+H)^+$=461.4.

Example 33: 5-amino-N-(cyclopropylmethyl)-N-(2,6-difluorobenzyl)-6,8-dihydro-1H-furo[3,4-d]pyrrolo[3,2-b]pyridine-2-carboxamide

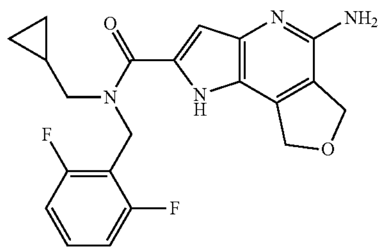 [SMILES: Nc1nc2cc(C(=O)N(Cc3c(F)cccc3F)CC3CC3)[nH]c2c2c1COC2]

Step 1: 1-cyclopropyl-N-(2,6-difluorobenzyl)methanamine

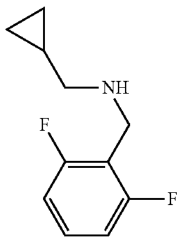 [SMILES: Fc1cccc(F)c1CNCC1CC1]

The title compound (80 mg, 58%) was prepared in a manner similar to that in Example 3 step 1 from (2,6-difluorophenyl)methanamine and cyclopropanecarbaldehyde. LC-MS $(M+H)^+$=198.3.

Step 2: 5-amino-N-(cyclopropylmethyl)-N-(2,6-difluorobenzyl)-6,8-dihydro-1H-furo[3,4-d]pyrrolo[3,2-b]pyridine-2-carboxamide Example 33 (9 mg, 16%) was prepared in a manner similar to that in Example 2 step 3 from 5-amino-6,8-dihydro-1H-furo[3,4-d]pyrrolo[3,2-b]pyridine-2-carboxylic acid and 1-cyclopropyl-N-(2,6-difluorobenzyl)methanamine. 1H NMR (500 MHz, DMSO-d6) δ 11.75-11.47 (m, 1H), 7.51-7.36 (m, 1H), 7.21-7.00 (m, 2H), 6.71-6.57 (m, 1H), 5.74-5.47 (m, 2H), 5.25-4.84 (m, 6H), 3.57-3.39 (m, 2H), 1.11-0.97 (m, 1H), 0.60-0.33 (m, 2H), 0.27-0.03 (m, 2H). LC-MS $(M+H)^+$=399.3.

Example 34: 5-amino-N-((3-fluoro-5-(trifluoromethyl)pyridin-2-yl)methyl)-N-((3R,4R)-4-methoxytetrahydro-2H-pyran-3-yl)-6,8-dihydro-1H-furo[3,4-d]pyrrolo[3,2-b]pyridine-2-carboxamide

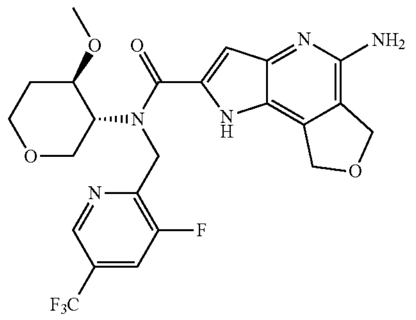 [SMILES: CO[C@@H]1CCOC[C@H]1N(Cc1ncc(C(F)(F)F)cc1F)C(=O)c1cc2nc(N)c3c(c2[nH]1)COC3]

Step 1: (3R,4R)—N-((3-fluoro-5-(trifluoromethyl)pyridin-2-yl)methyl)-4-methoxytetrahydro-2H-pyran-3-amine

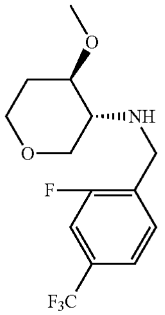 [SMILES: CO[C@@H]1CCOC[C@H]1NCc1ccc(C(F)(F)F)cc1F]

To a mixture of 3-fluoro-5-(trifluoromethyl)picolinaldehyde (1.0 g, 5.18 mmol) and (3R,4R)-4-methoxytetrahydro-2H-pyran-3-amine (747 mg, 5.7 mmol) in DCM (50 mL) was added triethylamine (575 mg, 5.7 mmol) and then the mixture was stirred for 10 min at room temperature. $NaBH(OAc)_3$ (2.2 g, 10.36 mmol) was added and the mixture was stirred for another 2 h at room temperature. The mixture was quenched with saturated $NaHCO_3$, diluted with DCM (40 mL), successively washed with water (40 mL) and brine (40 mL), dried over $Na_2SO_4$, filtered and concentrated under reduced pressure. The residue was purified by silica gel chromatograph to give the title compound (1.3 g, 82%). LC-MS $(M+H)^+$=309.2.

Step 2: tert-butyl (2-(((3-fluoro-5-(trifluoromethyl) pyridin-2-yl)methyl)(3R,4R)-4-methoxytetrahydro-2H-pyran-3-yl)carbamoyl)-6,8-dihydro-1H-furo[3,4-d]pyrrolo[3,2-b]pyridin-5-yl)carbamate

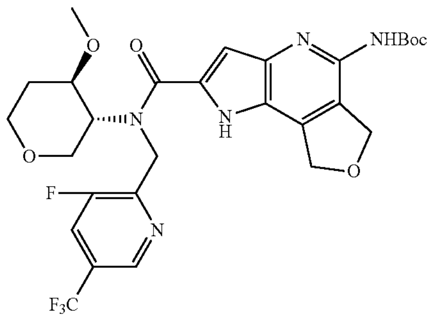 [SMILES: CO[C@@H]1CCOC[C@H]1N(Cc1ncc(C(F)(F)F)cc1F)C(=O)c1cc2nc(NC(=O)OC(C)(C)C)c3c(c2[nH]1)COC3]

The title compound (1.5 g, 58%) was prepared in a manner similar to that in Example 13 step 4 from 5-((tert-butoxycarbonyl)amino)-6,8-dihydro-1H-furo[3,4-d]pyrrolo[3,2-b]pyridine-2-carboxylic acid and (3R,4R)—N-((3-fluoro-5-(trifluoromethyl)pyridin-2-yl)methyl)-4-methoxytetrahydro-2H-pyran-3-amine. LC-MS $(M+H)^+=$ 610.3.

Step 3: 5-amino-N-((3-fluoro-5-(trifluoromethyl) pyridin-2-yl)methyl)-N-((3R,4R)-4-methoxytetrahydro-2H-pyran-3-yl)-6,8-dihydro-1H-furo[3,4-d] pyrrolo[3,2-b]pyridine-2-carboxamide Example 34 (970 mg, 77%) was prepared in a manner similar to that in Example 14 step 6 from tert-butyl (2-(((3-fluoro-5-(trifluoromethyl)pyridin-2-yl)methyl)((3R,4R)-4-methoxytetrahydro-2H-pyran-3-yl)carbamoyl)-6,8-dihydro-1H-furo[3,4-d]pyrrolo[3,2-b]pyridin-5-yl)carbamate. $^1$H NMR (400 MHz, DMSO-d6) δ 11.48 (s, 1H), 8.76 (s, 1H), 8.27 (s, 1H), 6.65 (s, 1H), 5.55 (s, 2H), 5.31-4.98 (m, 3H), 4.89 (s, 2H), 4.76-4.64 (m, 1H), 4.60-4.68 (m, 1H), 4.19-4.02 (m, 1H), 3.89-3.69 (m, 2H), 3.55-3.44 (m, 1H), 3.38-3.35 (m, 1H), 3.34 (s, 3H), 2.25-2.11 (m, 1H), 1.43-1.30 (m, 1H). LC-MS $(M+H)^+=510.3$.

Example 35: (R)-5-amino-N-((3-fluoro-5-(trifluoromethyl)pyridin-2-yl)methyl)-N-(1-(pyrimidin-2-yl) ethyl)-6,8-dihydro-1H-furo[3,4-d]pyrrolo[3,2-b] pyridine-2-carboxamide

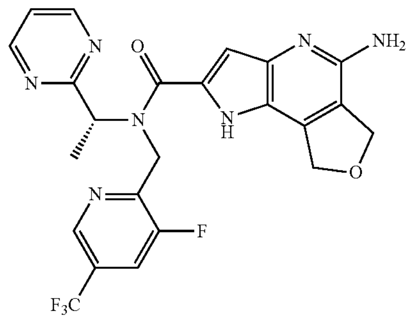 [SMILES: C[C@H](c1ncccn1)N(Cc1ncc(C(F)(F)F)cc1F)C(=O)c1cc2nc(N)c3c(c2[nH]1)COC3]

Step 1: (R)—N-((3-fluoro-5-(trifluoromethyl)pyridin-2-yl)methyl)-1-(pyrimidin-2-yl)ethan-1-amine

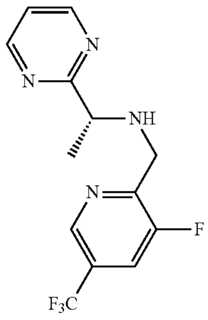 [SMILES: C[C@@H](NCc1ncc(C(F)(F)F)cc1F)c1ncccn1]

To a mixture of 3-fluoro-5-(trifluoromethyl)picolinaldehyde (100 mg, 0.52 mmol) and (R)-1-(pyrimidin-2-yl)ethan-1-amine dihydrochloride (122 mg, 0.62 mmol) in DCM (2 mL) and MeOH (0.2 mL) was added $NaBH(OAc)_3$ (220 mg, 1.04 mmol). The mixture was stirred at 25° C. for 1 h then quenched with a mixture of saturated $NaHCO_3$ (5 mL) and water (5 mL). The mixture was extracted with EtOAc (5 mL×3). The combined organic layer was washed with brine (5 mL), dried with $Na_2SO_4$, filtered and concentrated under reduced pressure to give the title compound (100 mg, 64%). LC-MS $(M+H)^+=301.1$.

Step 2: tert-butyl (R)-(2-(((3-fluoro-5-(trifluoromethyl)pyridin-2-yl)methyl)(1-(pyrimidin-2-yl)ethyl) carbamoyl)-6,8-dihydro-1H-furo[3,4-d]pyrrolo[3,2-b]pyridin-5-yl)carbamate

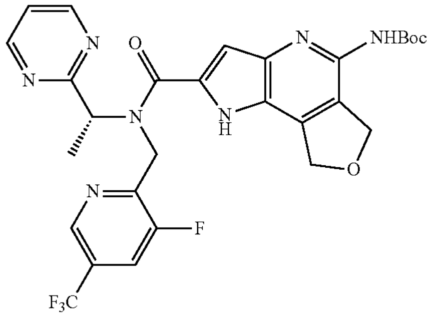 [SMILES: C[C@H](c1ncccn1)N(Cc1ncc(C(F)(F)F)cc1F)C(=O)c1cc2nc(NC(=O)OC(C)(C)C)c3c(c2[nH]1)COC3]

To a mixture of (R)—N-((3-fluoro-5-(trifluoromethyl) pyridin-2-yl)methyl)-1-(pyrimidin-2-yl)ethan-1-amine (100 mg, 0.33 mmol) and 5-((tert-butoxycarbonyl)amino)-6,8-dihydro-1H-furo[3,4-d]pyrrolo[3,2-b]pyridine-2-carboxylic acid (106 mg, 0.33 mmol) in THF (5 mL) was added BOPCl (170 mg, 0.67 mmol) and DIPEA (129 mg, 1.0 mmol). The mixture was stirred at 40° C. for 1 h and cooled to room temperature. The mixture was diluted with water (15 mL) and extracted with EtOAc (5 mL×3). The combined organic layer was washed with brine (5 mL), dried with $Na_2SO_4$, filtered and concentrated under reduced pressure to give the title compound (100 mg, 50%). LC-MS $(M+H\text{-}Boc)^+=$ 502.3.

Step 3: (R)-5-amino-N-((3-fluoro-5-(trifluoromethyl)pyridin-2-yl)methyl)-N-(1-(pyrimidin-2-yl)ethyl)-6,8-dihydro-1H-furo[3,4-d]pyrrolo[3,2-b]pyridine-2-carboxamide To a solution tert-butyl (R)-(2-(((3-fluoro-5-(trifluoromethyl)pyridin-2-yl)methyl)(1-(pyrimidin-2-yl)ethyl)carbamoyl)-6,8-dihydro-1H-furo[3,4-d]pyrrolo[3,2-b]pyridin-5-yl) carbamate (100 mg, 0.167 mmol) in MeOH (1 mL) was added HCl (4 M in MeOH, 1 mL, 4.0 mmol). The mixture was stirred at 40° C. for 1 h and cooled to room temperature. The mixture was concentrated under reduced. The residue was purified by prep-HPLC to give Example 35 (15 mg, 18%). $^1$H NMR (400 MHz, DMSO-d6) δ 11.69-11.47 (m, 1H), 8.98-8.53 (m, 3H), 8.42-8.05 (m, 1H), 7.62-7.17 (m, 1H), 6.77-6.20 (m, 1H), 6.20-5.63 (m, 1H), 5.63-5.18 (m, 3H), 5.18-4.98 (m, 3H), 4.95-4.61 (m, 3H), 1.86-1.34 (m, 3H). LC-MS $(M+H)^+$=502.1.

Example 36: 5-amino-N-((5-cyclopropylpyridin-2-yl)methyl)-N-((3R,4R)-4-methoxytetrahydro-2H-pyran-3-yl)-6,8-dihydro-1H-furo[3,4-d]pyrrolo[3,2-b]pyridine-2-carboxamide

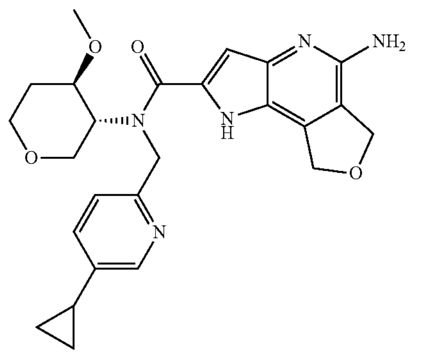 [SMILES: CO[C@@H]1CCOC[C@H]1N(Cc1ccc(C2CC2)cn1)C(=O)c1cc2nc(N)c3c(c2[nH]1)COC3]

Step 1: 5-cyclopropylpicolinaldehyde

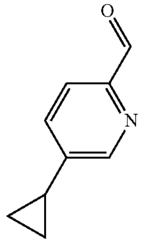 [SMILES: O=Cc1ccc(C2CC2)cn1]

To a mixture of 5-bromopicolinaldehyde (1.0 g, 5.38 mmol), $K_3PO_4$ (2.28 g, 10.8 mmol), $Pd(OAc)_2$ (120 mg, 0.54 mmol) and SPhos (440 mg, 1.08 mmol) in toluene (15 mL) and water (1.5 mL) was added cyclopropylboronic acid (550 mg, 6.46 mmol). The mixture was stirred for 3 h at 100° C. under nitrogen, then cooled to room temperature. The mixture was diluted with EtOAc (100 mL), successively washed with water (40 mL) and brine (40 mL), dried over $Na_2SO_4$, filtered and concentrated under reduced pressure. The residue was purified by silica gel chromatograph to give the title compound (450 mg, 57%). LC-MS $(M+H)^+$=148.2.

Step 2: (3R,4R)—N-((5-cyclopropylpyridin-2-yl)methyl)-4-methoxytetrahydro-2H-pyran-3-amine

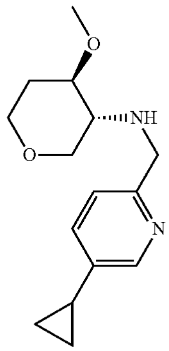 [SMILES: CO[C@@H]1CCOC[C@H]1NCc1ccc(C2CC2)cn1]

The title compound (280 mg, 87%) was prepared in a manner similar to that in Example 34 step 1 from 5-cyclopropylpicolinaldehyde and (3R,4R)-4-methoxytetrahydro-2H-pyran-3-amine. LC-MS $(M+H)^+$=263.3.

Step 3: tert-butyl (2-(((5-cyclopropylpyridin-2-yl)methyl)((3R,4R)-4-methoxytetrahydro-2H-pyran-3-yl)carbamoyl)-6,8-dihydro-1H-furo[3,4-d]pyrrolo[3,2-b]pyridin-5-yl)carbamate

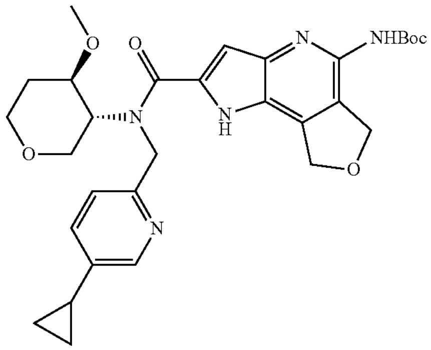 [SMILES: CO[C@@H]1CCOC[C@H]1N(Cc1ccc(C2CC2)cn1)C(=O)c1cc2nc(NC(=O)OC(C)(C)C)c3c(c2[nH]1)COC3]

The title compound (90 mg, 42%) was prepared in a manner similar to that in Example 13 step 4 from 5-((tert-butoxycarbonyl)amino)-6,8-dihydro-1H-furo[3,4-d]pyrrolo[3,2-b]pyridine-2-carboxylic acid and (3R,4R)—N-((5-cyclopropylpyridin-2-yl)methyl)-4-methoxytetrahydro-2H-pyran-3-amine. LC-MS $(M+H)^+$=564.4.

Step 4: 5-amino-N-((5-cyclopropylpyridin-2-yl)methyl)-N-((3R,4R)-4-methoxytetrahydro-2H-pyran-3-yl)-6,8-dihydro-1H-furo[3,4-d]pyrrolo[3,2-b]pyridine-2-carboxamide Example 36 (43 mg, 58%) was prepared in a manner similar to that in Example 14 step 6 from tert-butyl (2-(((5-cyclopropylpyridin-2-yl)methyl)((3R,4R)-4-methoxytetrahydro-2H-pyran-3-yl)carbamoyl)-6,8-dihydro-1H-furo[3,4-d]pyrrolo[3,2-b]pyridin-5-yl)carbamate. $^1$H NMR (400 MHz, DMSO-d6) δ 11.51 (s, 1H), 8.30 (s, 1H), 7.34-7.23 (m, 2H), 6.66 (s, 1H), 5.53 (s, 2H), 5.10 (s, 2H), 5.01-4.75 (m, 4H), 4.61-4.45 (m, 1H), 3.98-3.91 (m, 1H), 3.84- 3.70

(m, 2H), 3.65-3.56 (m, 1H), 3.44-3.35 (m, 1H), 3.11 (s, 3H), 2.14 (s, 1H), 1.91 (s, 1H), 1.29 (s, 1H), 0.95 (s, 2H), 0.68 (s, 2H). LC-MS $(M+H)^+$=464.3.

Example 37: 5-amino-N-(2,6-difluorobenzyl)-N-((6-(trifluoromethyl)pyridazin-3-yl)methyl)-6,8-dihydro-1H-furo[3,4-d]pyrrolo[3,2-b]pyridine-2-carboxamide

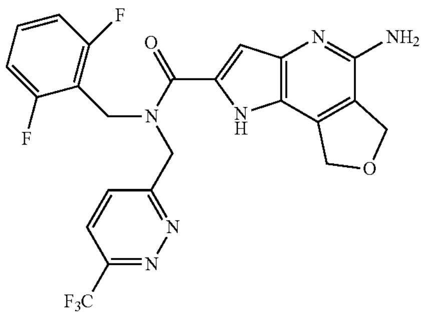 [SMILES: Nc1nc2cc(C(=O)N(Cc3ccc(C(F)(F)F)nn3)Cc3c(F)cccc3F)[nH]c2c2c1COC2]

Step 1: 6-(trifluoromethyl)pyridazine-3-carbaldehyde

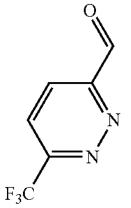 [SMILES: O=Cc1ccc(C(F)(F)F)nn1]

To a solution of ethyl 6-(trifluoromethyl)pyridazine-3-carboxylate (920 mg, 4.18 mmol) in DCM (10 mL) was added DIBAL-H (5.57 mL, 8.36 mmol) at −78° C. under nitrogen. The mixture was stirred for 3 h at −78° C. The mixture was poured into saturated $NH_4Cl$ solution (100 mL) and then extracted with DCM (100 mL×2). The combined organic layer was washed with brine (100 mL), dried over $Na_2SO_4$, filtered and concentrated under reduced pressure to give the title compound (350 mg, 48%). LC-MS $(M+H)^+$=177.1.

Step 2: N-(2,6-difluorobenzyl)-1-(6-(trifluoromethyl)pyridazin-3-yl)methanamine

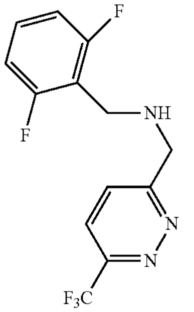 [SMILES: Fc1cccc(F)c1CNCc1ccc(C(F)(F)F)nn1]

The title compound (38 mg, 35%) was prepared in a manner similar to that in Example 5 step 1 from 6-(trifluoromethyl)pyridazine-3-carbaldehyde and (2,6-difluorophenyl)methanamine. LC-MS $(M+H)^+$=304.3.

Step 3: 5-amino-N-(2,6-difluorobenzyl)-N-((6-trifluoromethyl)pyridazin-3-yl)methyl)-6,8-dihydro-1H-furo[3,4-d]pyrrolo[3,2-b]pyridine-2-carboxamide Example 37 (18 mg, 28%) was prepared in a manner similar to that in Example 2 step 3 from 5-amino-6,8-dihydro-1H-furo[3,4-d]pyrrolo[3,2-b]pyridine-2-carboxylic acid and N-(2,6-difluorobenzyl)-1-(6-(trifluoromethyl) pyridazin-3-yl)methanamine. $^1$H NMR (500 MHz, DMSO-d6) δ 11.66 (s, 1H), 8.32-8.06 (m, 1H), 8.01-7.76 (m, 1H), 7.42-7.23 (m, 1H), 7.14-6.92 (m, 2H), 6.80-6.26 (m, 1H), 5.74-5.47 (m, 2H), 5.40-4.65 (m, 8H). LC-MS $(M+H)^+$=505.2.

Example 38: (R)-5-amino-N-((3-fluoropyridin-2-yl)methyl)-6-methyl-N-((5-(trifluoromethyl)pyridin-2-yl)methyl)-6,8-dihydro-1H-furo[3,4-d]pyrrolo[3,2-b]pyridine-2-carboxamide

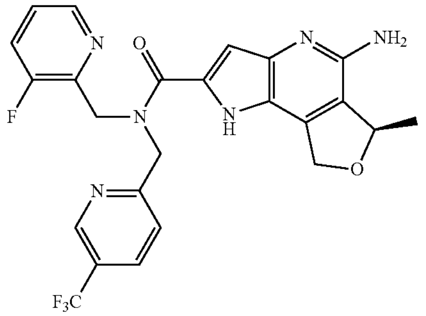 [SMILES: C[C@H]1OCc2c1c(N)nc1cc(C(=O)N(Cc3ccc(C(F)(F)F)cn3)Cc3ncccc3F)[nH]c21]

Step 1: ethyl (S)-5-amino-6-methyl-6,8-dihydro-1H-furo[3,4-d]pyrrolo[3,2-b]pyridine-2-carboxylate and ethyl (R)-5-amino-6-methyl-6,8-dihydro-1H-furo[3,4-d]pyrrolo[3,2-b]pyridine-2-carboxylate

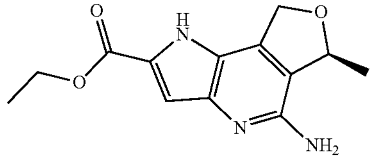

&

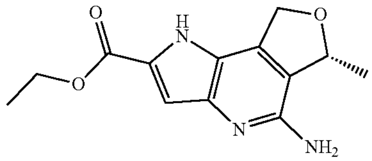 [SMILES: CCOC(=O)c1cc2nc(N)c3c(c2[nH]1)CO[C@@H]3C]

To the solution of ethyl 4-((tert-butoxycarbonyl)amino)-5-(4-cyano-5-methyl-2,5-dihydrofuran-3-yl)-1H-pyrrole-2-carboxylate (20 g, 55 mmol) in dioxane (100 mL) was added a solution of HCl in dioxane (100 mL, 4M) and the mixture was stirred at room temperature for 5 h. The mixture was concentrated under reduced pressure. The crude was redissolved in EtOH (200 mL) followed by addition of $K_2CO_3$ (27.6 g, 2(0) mmol). The mixture was stirred at 70° C. for 4 h then cooled to room temperature. Solid was filtered off and the filtrate was concentrated under reduced pressure. The residue was purified by silica gel chromatography (DCM:MeOH=10:1) to give a racemate (5.0 g). The material was separated by SFC to give ethyl (S)-5-amino-6-methyl-6,8-dihydro-1H-furo[3,4-d]pyrrolo[3,2-b]pyridine-2-carboxylate (2.25 g, 16%) and ethyl (R)-5-amino-6-methyl-6,8-dihydro-1H-furo[3,4-d]pyrrolo[3,2-b]pyridine-2-carboxylate (2.34 g, 16%).

Analytical chiral-SFC condition as below. Column: CHIRALPAK IC-3; Column size: 3.0×100 mm, 3 μm; Mobile phase: 10 μM $NH_3$ in methanol:$CO_2$1:9 to 1:1 in 2 min, 1:1 for 1 min; Flow: 2.0 mL/min; Temperature: 35° C.; back pressure: 1500 psi.

ethyl (S)-5-amino-6-methyl-6,8-dihydro-1H-furo[3,4-d]pyrrolo[3,2-b]pyridine-2-carboxylate: Analytical SFC tR=2.01 min. LC-MS $(M+H)^+$=262.1.

ethyl (R)-5-amino-6-methyl-6,8-dihydro-1H-furo[3,4-d]pyrrolo[3,2-b]pyridine-2-carboxylate: Analytical SFC tR=2.36 min. LC-MS $(M+H)^+$=262.1.

Step 2: (R)-5-amino-6-methyl-6,8-dihydro-1H-furo[3,4-d]pyrrolo[3,2-b]pyridine-2-carboxylic Acid

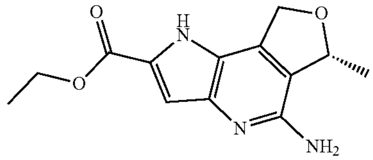

A mixture of ethyl (R)-5-amino-6-methyl-6,8-dihydro-1H-furo[3,4-d]pyrrolo[3,2-b]pyridine-2-carboxylate (1.5 g, 5.7 mmol) and $LiOH{\cdot}H_2O$ (0.32 g 7.6 mmol) in MeOH (20 mL) and water (10 mL) was stirred at 50° C. for 3 h. The mixture was cooled to room temperature and concentrated under reduced pressure. The residue was purified by prep-HPLC to give the title compound (1.2 g, 90%). LC-MS $(M+H)^+$=234.1.

Step 3: 1-(3-fluoropyridin-2-yl)-N-((5-(trifluoromethyl)pyridin-2-yl)methyl)methanamine

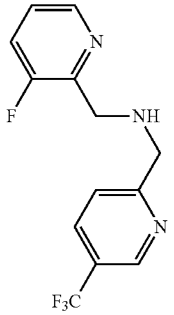 [SMILES: Fc1cccnc1CNCc1ccc(C(F)(F)F)cn1]

The title compound (100 mg, 60%) was prepared in a manner similar to that in Example 5 step 1 from 5-(trifluoromethyl)picolinaldehyde and (3-fluoropyridin-2-yl)methanamine. LC-MS $(M+H)^+$=286.2.

Step 4: (R)-5-amino-N-((3-fluoropyridin-2-yl)methyl)-6-methyl-N-((5-(trifluoromethyl)pyridin-2-yl)methyl)-6,8-dihydro-1H-furo[3,4-d]pyrrolo[3,2-b]pyridine-2-carboxamide Example 38 (18 mg, 43%) was prepared in a manner similar to that in Example 2 step 3 from 1-(3-fluoropyridin-2-yl)-N-((5-(trifluoromethyl)pyridin-2-yl)methyl)methanamine and (R)-5-amino-6-methyl-6,8-dihydro-1H-furo[3,4-d]pyrrolo[3,2-b]pyridine-2-carboxylic acid. $^1$H NMR (400 MHz, DMSO-d6) δ 11.63 (s, 1H), 9.1-8.75 (m, 1H), 8.5-8.1 (m, 2H), 7.8-7.56 (m, 2H), 7.42 (s, 1H), 6.6-6.1 (m, 1H), 5.44 (s, 2H), 5.37-4.69 (m, 7H), 1.32 (d, J=6.1 Hz, 3H). LC-MS $(M+H)^+$=501.1.

Example 39 & Example 40: (R)-5-amino-N-methyl-N-(7-(trifluoromethyl)isochroman-4-yl)-6,8-dihydro-1H-furo[3,4-d]pyrrolo[3,2-b]pyridine-2-carboxamide & (S)-5-amino-N-methyl-N-(7-(trifluoromethyl)isochroman-4-yl)-6,8-dihydro-1H-furo[3,4-d]pyrrolo[3,2-b]pyridine-2-carboxamide

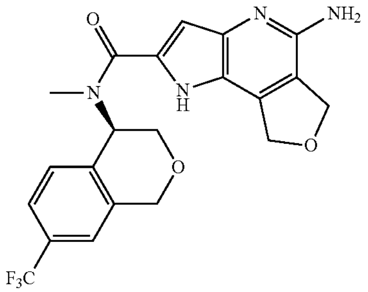

&

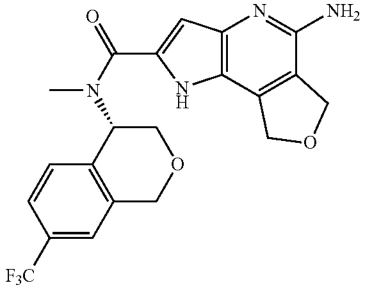

Step 1: 2-((allyloxy)methyl)-1-bromo-4-(trifluoromethyl)benzene

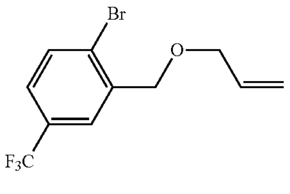 [SMILES: C=CCOCc1cc(C(F)(F)F)ccc1Br]

To a solution of (2-bromo-5-(trifluoromethyl)phenyl)methanol (5.0 g, 19.6 mmol) in THF (100 mL) was added NaH (60%, 941 mg, 23.5 mmol) at 0° C. over a 1-hour period. Allyl bromide (3.08 g, 25.5 mmol) was added dropwise at 0° C. The mixture was stirred at room temperature for 11 h. The mixture was diluted with water (100 mL).

The mixture was extracted with ethyl acetate (100 mL×2). The combined organic layer was washed with brine (50 mL), dried over $Na_2SO_4$, filtered and concentrated under reduced pressure. The residue was purified by silica gel chromatography (PE/EtOAc=1/0 to 10/1) to give the title compound (8.0 g, 69%). $^1$H NMR (400 MHz, DMSO-d6) δ 7.84 (d, J=8.0 Hz, 1H), 7.76 (s, 1H), 7.58 (d, J=8.0 Hz, 1H), 6.04-5.88 (m, 1H), 5.37-5.28 (m, 1H), 5.23-5.16 (m, 1H), 4.55 (s, 2H), 4.16-4.07 (m, 2H).

Step 2: 4-methylene-7-(trifluoromethyl)isochromane

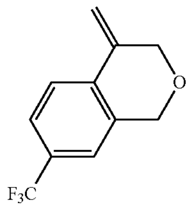

A mixture of 2-((allyloxy)methyl)-1-bromo-4-(trifluoromethyl)benzene (8.0 g, 27.1 mmol), $Pd(OAc)_2$ (913 mg, 4.07 mmol), $Cs_2CO_3$ (10.6 g, 32.5 mmol) and $PPh_3$ (3.20 g, 12.2 mmol) in DMF (80 mL) was degassed and purged with nitrogen for 3 times, and the mixture was stirred at 90° C. for 12 h. The mixture was cooled to room temperature and diluted with water (100 mL). The mixture was extracted with EtOAc (100 mL×2). The combined organic layer was washed with brine (50 mL), dried with $Na_2SO_4$, filtered and concentrated under reduced pressure. The residue was purified by silica gel chromatograph (PE/EtOAc=1/0 to 5/1) to give the title compound (5.0 g, 86%). $^1$H NMR (400 MHz, DMSO-d6) δ 7.97 (d, J=8.4 Hz, 1H), 7.56 (d, J=8.4 Hz, 1H), 7.52 (s, 1H), 5.87-5.83 (m, 1H), 5.24-5.18 (m, 1H), 4.80 (s, 2H), 4.41 (s, 2H).

Step 3: 7-(trifluoromethyl)isochroman-4-one

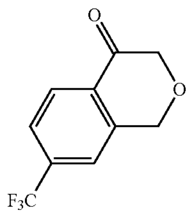

To a solution of 4-methylene-7-(trifluoromethyl)isochromane (4.9 g, 22.9 mmol) in dioxane (100 mL) and water (20 mL) was added potassium osmate (VI) dihydrate (843 mg, 2.29 mmol), 2,6-lutidine (4.90 g, 45.8 mmol) and sodium periodate (19.6 g, 91.5 mmol). The mixture was stirred at 25° C. for 2 h. The mixture was diluted with water (100 mL) and extracted with EtOAc (100 mL×3). The combined organic layer was washed with brine (50 mL), dried over $Na_2SO_4$, filtered and concentrated under reduced pressure. The residue was purified by silica gel chromatography (PE/EtOAc=1/0 to 5/1) to give the title compound (3.0 g, 61%). $^1$H NMR (400 MHz, DMSO-d6) δ 8.13-8.06 (m, 1H), 7.93-7.78 (m, 2H), 4.99 (s, 2H), 4.44 (s, 2H).

Step 4: 7-(trifluoromethyl)isochroman-4-one Oxime

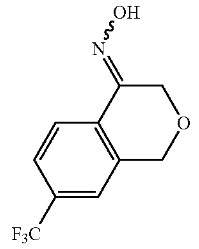

To a solution of 7-(trifluoromethyl)isochroman-4-one (500 mg, 2.32 mmol) in MeOH (10 mL) was added hydroxylamine hydrochloride (804 mg, 11.6 mmol) and pyridine (5.4 mL). The mixture was stirred at 65° C. for 1 h then cooled to room temperature. The mixture was concentrated under reduced pressure and diluted with water (10 mL). Aqueous HCl (1 M) was added to until the pH reached 5. The mixture was extracted with EtOAc (10 mL×3). The combined organic layers were washed with brine (10 mL), dried over $Na_2SO_4$, filtered and concentrated under reduced pressure. The residue was purified by silica gel chromatography (PE/EtOAc=1/0 to 3/1) to give the title compound (500 mg, 94%). $^1$H NMR (400 MHz, DMSO-d6) δ 11.76 (s, 1H), 8.07-8.00 (m, 1H), 7.68-7.62 (m, 2H), 4.77-4.68 (m, 4H).

Step 5: 7-trifluoromethyl)isochroman-4-amine

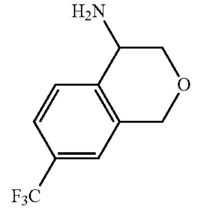 [SMILES: NC1COCc2cc(C(F)(F)F)ccc21]

To a solution of 7-(trifluoromethyl)isochroman-4-one oxime (500 mg, 2.16 mmol) in MeOH (10 mL) was added Raney-Ni (371 mg) under nitrogen. The suspension was degassed and purged with hydrogen for 3 times. The mixture was stirred under hydrogen (30 psi) at 40° C. for 1 h then cooled to room temperature. The solid was filtered off and the filtrate was concentrated under reduced pressure to give the title compound (400 mg, 85%). LCMS $(M+H)^+$=218.1.

Step 6: tert-butyl (7-(trifluoromethyl)isochroman-4-yl)carbamate

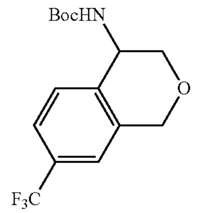 [SMILES: CC(C)(C)OC(=O)NC1COCc2cc(C(F)(F)F)ccc21]

To a solution of 7-(trifluoromethyl)isochroman-4-amine (350 mg, 1.61 mmol) in THF (4 mL) was added $Boc_2O$ (352 mg, 1.61 mmol) and DIPEA (417 mg, 3.22 mmol). The mixture was stirred at room temperature for 1 h and then diluted with water (10 mL). The mixture was extracted with EtOAc (5 mL×3). The combined organic layer was washed with brine (5 mL), dried with $Na_2SO_4$, filtered and concentrated under reduced pressure. The residue was purified by silica gel chromatography (PE/EtOAc=1/0 to 10/1) to give the title compound (400 mg, 78%). LCMS $(M+H-tBu)^+$=262.0.

Step 7: tert-butyl methyl(7-(trifluoromethyl)isochroman-4-yl)carbamate

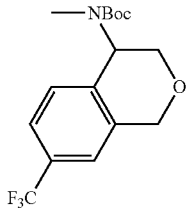 [SMILES: CN(C(=O)OC(C)(C)C)C1COCc2cc(C(F)(F)F)ccc21]

A solution of tert-butyl (7-(trifluoromethyl)isochroman-4-yl)carbamate (350 mg, 1.10 mmol) in THF (5 mL) was added dropwise to a suspension of NaH (60%, 49 mg, 1.21 mmol) in THF (5 mL) at 0° C. The resulting mixture was stirred for 10 min and MeI (172 mg, 1.21 mmol) was added dropwise at 0° C. The mixture was warmed to room temperature and stirred for 12 h. The mixture was diluted with water (30 mL) and extracted with EtOAc (15 mL×3). The combined organic layer was washed with brine (5 mL), dried over $Na_2SO_4$, filtered and concentrated under reduced pressure. The residue was purified by silica gel chromatography (PE/EtOAc=1/0 to 10/1) to give the title compound (300 mg, 82%). LCMS $(M+H-tBu)^+$=276.2.

Step 8: N-methyl-7-(trifluoromethyl)isochroman-4-amine Hydrochloride

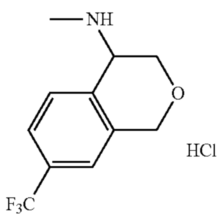 [SMILES: CNC1COCc2cc(C(F)(F)F)ccc21 ; Cl]

To a solution of tert-butyl methyl(7-(trifluoromethyl)isochroman-4-yl)carbamate (300 mg, 0.91 mmol) in MeOH (3 mL) was added HCl (4 M in MeOH, 3 mL). The mixture was stirred at room temperature for 12 h. The mixture was concentrated under reduced pressure to give the title compound (200 mg, 82%). LC-MS $(M+H)^+$=232.2.

Step 9: tert-butyl (2-(methyl(7-(trifluoromethyl)isochroman-4-yl)carbamoyl)-6,8-dihydro-1H-furo[3,4-d]pyrrolo[3,2-b]pyridin-5-yl)carbamate

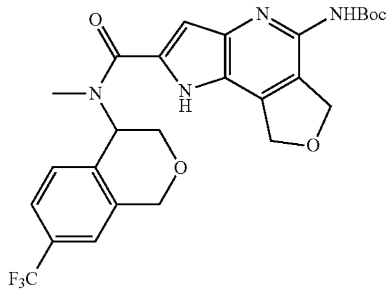 [SMILES: CN(C(=O)c1cc2nc(NC(=O)OC(C)(C)C)c3c(c2[nH]1)COC3)C1COCc2cc(C(F)(F)F)ccc21]

To a solution of N-methyl-7-(trifluoromethyl)isochroman-4-amine hydrochloride (200 mg, 0.75 mmol) and 5-((tert-butoxycarbonyl)amino)-6,8-dihydro-1H-furo[3,4-d]pyrrolo[3,2-b]pyridine-2-carboxylic acid (276 mg, 0.87 mmol) in THF (5 mL) was added DIPEA (559 mg, 4.33 mmol) and BOPCl (440 mg, 1.73 mmol). The mixture was stirred at room temperature for 1 h and then diluted with water (5 mL). The mixture was extracted with EtOAc (5.0 mL×3). The combined organic layer was washed with brine (5.0 mL), dried over $Na_2SO_4$, filtered and concentrated under reduced pressure to give the title compound (3(0) mg, 75%). LC-MS (M+H)+=533.1.

Step 10: (R)-5-amino-N-methyl-N-(7-(trifluoromethyl)isochroman-4-yl)-6,8-dihydro-1H-furo[3,4-d]pyrrolo[3,2-b]pyridine-2-carboxamide & (S)-5-amino-N-methyl-N-(7-(trifluoromethyl)isochroman-4-yl)-6,8-dihydro-1H-furo[3,4-d]pyrrolo[3,2-b]pyridine-2-carboxamide To a solution of tert-butyl (2-(methyl(7-(trifluoromethyl)isochroman-4-yl)carbamoyl)-6,8-dihydro-1H-furo[3,4-d]pyrrolo[3,2-b]pyridin-5-yl)carbamate (300 mg, 0.56 mmol) in MeOH (4 mL) was added HCl (4 M in MeOH, 4 mL). The mixture was stirred at 25° C. for 1 h and concentrated under reduced pressure. The residue was purified by prep-HPLC and further separated by SFC to give Example 39 (21 mg, 9%) and Example 40 (20 mg, 8%).

Analytical chiral-SFC condition as below. Column: CHIRALPAK AD-3; Column size: 4.6×50 mm, 3 μm; Mobile phase: 14 mM $NH_3$ in methanol:$CO_2$ 1:1 isocratic; Flow: 4.0 mL/min; Temperature: 35° C.; back pressure: 1800 psi.

Example 39: Analytical SFC tR=1.11 min. $^1H$ NMR (400 MHz, DMSO-d6) δ 11.86-11.51 (m, 1H), 7.69-7.62 (m, 1H), 7.61 (s, 1H), 7.53-7.35 (m, 1H), 6.84-6.45 (m, 1H), 5.96-5.65 (m, 1H), 5.59 (s, 2H), 5.25-5.10 (m, 2H), 4.99-4.84 (m, 3H), 4.75 (d, J=15.4 Hz, 1H), 4.27-3.99 (m, 2H), 3.18-2.58 (m, 3H). LC-MS $(M+H)^+$=433.1.

Example 40: Analytical SFC tR=2.14 min. $^1H$ NMR (400 MHz, DMSO-d6) δ 11.88-11.51 (m, 1H), 7.69-7.62 (m, 1H), 7.61 (s, 1H), 7.53-7.35 (m, 1H), 6.85-6.45 (m, 1H), 5.97-5.67 (m, 1H), 5.59 (s, 2H), 5.23-5.09 (m, 2H), 4.99-4.84 (m, 3H), 4.75 (d, J=15.4 Hz, 1H), 4.27-3.99 (m, 2H), 3.17-2.59 (m, 3H). LC-MS $(M+H)^+$=433.1.

Example 41: (R)-5-amino-N-((5-bromo-3-fluoropyridin-2-yl)methyl)-N-(1-(pyrimidin-2-yl)ethyl)-6,8-dihydro-1H-furo[3,4-d]pyrrolo[3,2-b]pyridine-2-carboxamide

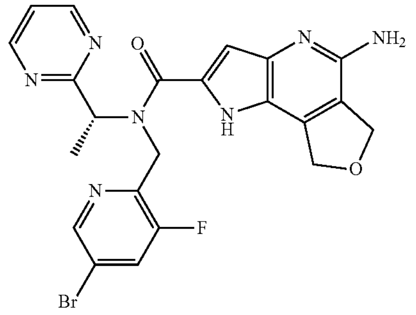 [SMILES: C[C@H](c1ncccn1)N(Cc1ncc(Br)cc1F)C(=O)c1cc2nc(N)c3c(c2[nH]1)COC3]

Step 1: (R)—N-((5-bromo-3-fluoropyridin-2-yl)methyl)-1-(pyrimidin-2-yl)ethan-1-amine

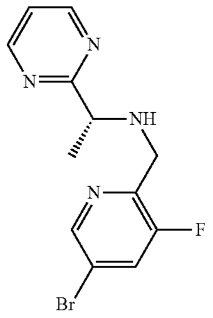 [SMILES: C[C@@H](NCc1ncc(Br)cc1F)c1ncccn1]

The title compound (90 mg, 59%) was prepared in a manner similar to that in Example 35 step 1 from of 5-bromo-3-fluoropicolinaldehyde and (R)-1-(pyrimidin-2-yl)ethan-1-amine dihydrochloride. LC-MS $(M+H)^+$=311.1.

Step 2: tert-butyl (R)-(2-(((5-bromo-3-fluoropyridin-2-yl)methyl)(1-(pyrimidin-2-yl)ethyl)carbamoyl)-6,8-dihydro-1H-furo[3,4-d]pyrrolo[3,2-b]pyridin-5-yl)carbamate

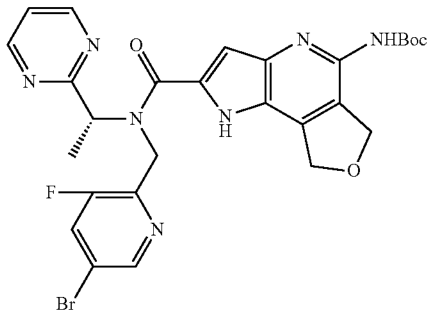 [SMILES: C[C@H](c1ncccn1)N(Cc1ncc(Br)cc1F)C(=O)c1cc2nc(NC(=O)OC(C)(C)C)c3c(c2[nH]1)COC3]

The title compound (90 mg, 57%) was prepared in a manner similar to that in Example 35 step 2 from 5-((tert-butoxycarbonyl)amino)-6,8-dihydro-1H-furo[3,4-d]pyrrolo[3,2-b]pyridine-2-carboxylic acid and (R)—N-((5-bromo-3-fluoropyridin-2-yl)methyl)-1-(pyrimidin-2-yl)ethan-1-amine. LC-MS $(M+H)^+$=612.2.

Step 3: (R)-5-amino-N-((5-bromo-3-fluoropyridin-2-yl)methyl)-N-(1-(pyrimidin-2-yl)ethyl)-6,8-dihydro-1H-furo[3,4-d]pyrrolo[3,2-b]pyridine-2-carboxamide Example 41 (30 mg, 40%) was prepared in a manner similar to that in Example 35 step 3 from tert-butyl (R)-(2-(((5-bromo-3-fluoropyridin-2-yl)methyl)(1-(pyrimidin-2-yl)ethyl)carbamoyl)-6,8-dihydro-1H-furo[3,4-d]pyrrolo[3,2-b]pyridin-5-yl)carbamate. $^1$H NMR (400 MHz, DMSO-d6) δ 11.35 (s, 1H), 8.76-8.75 (m, 2H), 8.42 (s, 1H), 8.01-7.98 (m, 1H), 7.34-7.38 (m, 1H), 6.55 (s, 1H), 5.97-5.87 (m, 1H), 5.29 (s, 2H), 5.14-5.04 (m, 3H), 4.93-4.78 (m, 3H), 1.66 (d, 3H). LC-MS $(M+H)^+$=512.2.

Example 42: 5-amino-N-((3-fluoro-5-(trifluoromethyl)pyridin-2-yl)methyl)-N-(pyrimidin-2-ylmethyl)-6,8-dihydro-1H-furo[3,4-d]pyrrolo[3,2-b]pyridine-2-carboxamide

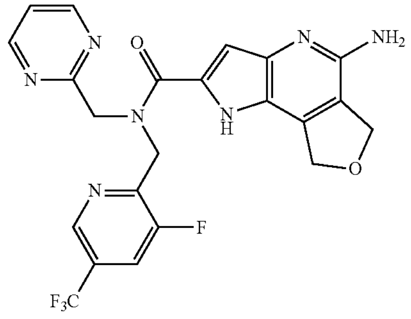 [SMILES: Nc1nc2cc(C(=O)N(Cc3ncccn3)Cc3ncc(C(F)(F)F)cc3F)[nH]c2c2c1COC2]

Step 1: 1-(3-fluoro-5-(trifluoromethyl)pyridin-2-yl)-N-(pyrimidin-2-ylmethyl)methanamine

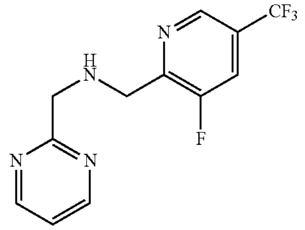 [SMILES: Fc1cc(C(F)(F)F)cnc1CNCc1ncccn1]

The title compound (45 mg, 17%) was prepared in a manner similar to that in Example 3 step 1 from pyrimidin-2-ylmethanamine and 3-fluoro-5-(trifluoromethyl)picolinaldehyde. LC-MS $(M+H)^+$=287.0.

Step 2: tert-butyl (2-(((3-fluoro-5-(trifluoromethyl)pyridin-2-yl)methyl)(pyrimidin-2-ylmethyl)carbamoyl)-6,8-dihydro-1H-furo[3,4-d]pyrrolo[3,2-b]pyridin-5-yl)carbamate

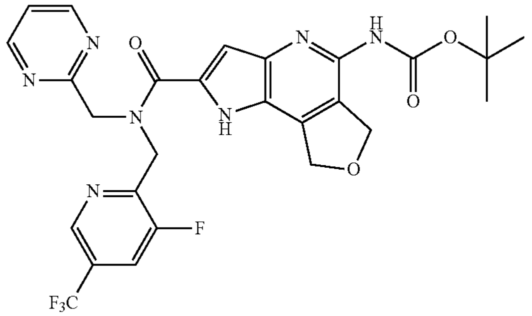 [SMILES: CC(C)(C)OC(=O)Nc1nc2cc(C(=O)N(Cc3ncccn3)Cc3ncc(C(F)(F)F)cc3F)[nH]c2c2c1COC2]

The title compound (60 mg, 58%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and 1-(3-fluoro-5-(trifluoromethyl)pyridin-2-yl)-N-(pyrimidin-2-ylmethyl)methanamine. LC-MS $(M+H)^+$=588.1.

Step 3: 5-amino-N-((3-fluoro-5-(trifluoromethyl)pyridin-2-yl)methyl)-N-(pyrimidin-2-ylmethyl)-6,8-dihydro-1H-furo[3,4-d]pyrrolo[3,2-b]pyridine-2-carboxamide Example 42 (30 mg, 35%) was prepared in a manner similar to that in Example 22 step 3 from tert-butyl (2-(((3-fluoro-5-(trifluoromethyl)pyridin-2-yl)methyl)(pyrimidin-2-ylmethyl)carbamoyl)-6,8-dihydro-1H-furo[3,4-d]pyrrolo[3,2-b]pyridin-5-yl)carbamate. $^1$H NMR (400 MHz, DMSO-d6) δ 11.59 (s, 1H), 8.87-8.78 (m, 3H), 8.28 (d, J=9.4 Hz, 1H), 7.48 (s, 1H), 6.33 (s, 1H), 5.54 (s, 2H), 5.38-5.52 (m, 2H), 5.08 (s, 4H), 4.88 (s, 2H). LC-MS $(M+H)^+$=488.1.

Example 43: 5-amino-N-(4-cyano-2,6-difluorobenzyl)-N-((3-fluoropyridin-2-yl)methyl)-6,8-dihydro-1H-furo[3,4-d]pyrrolo[3,2-b]pyridine-2-carboxamide

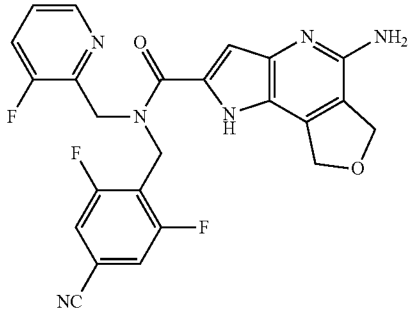 [SMILES: N#Cc1cc(F)c(CN(Cc2ncccc2F)C(=O)c2cc3nc(N)c4c(c3[nH]2)COC4)c(F)c1]

Step 1: 3,5-difluoro-4-((((3-fluoropyridin-2-yl)methyl)amino)methyl)benzonitrile

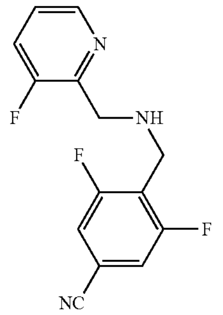 [SMILES: N#Cc1cc(F)c(CNCc2ncccc2F)c(F)c1]

The title compound (70 mg, 25%) was prepared in a manner similar to that in Example 3 step 1 from (3-fluoropyridin-2-yl)methanamine hydrochloride and 3,5-difluoro-4-formylbenzonitrile. LC-MS $(M+H)^+$=278.2.

Step 2: tert-butyl (2-((4-cyano-2,6-difluorobenzyl)((3-fluoropyridin-2-yl)methyl)carbamoyl)-6,8-dihydro-1H-furo[3,4-d]pyrrolo[3,2-b]pyridin-5-yl)carbamate

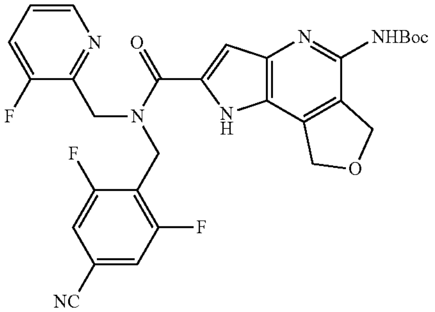 [SMILES: CC(C)(C)OC(=O)Nc1nc2cc(C(=O)N(Cc3ncccc3F)Cc3c(F)cc(C#N)cc3F)[nH]c2c2c1COC2]

The title compound (35 mg, 24%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and 3,5-difluoro-4-((((3-fluoropyridin-2-yl)methyl)amino)methyl)benzonitrile. LC-MS $(M+H)^+$=579.3.

Step 3: 5-amino-N-(4-cyano-2,6-difluorobenzyl)-N-((3-fluoropyridin-2-yl)methyl)-6,8-dihydro-1H-furo[3,4-d]pyrrolo[3,2-b]pyridine-2-carboxamide Example 43 (8 mg, 27%) was prepared in a manner similar to that in Example 22 step 3 from tert-butyl (2-((4-cyano-2,6-difluorobenzyl)((3-fluoropyridin-2-yl)methyl)carbamoyl)-6,8-dihydro-1H-furo[3,4-d]pyrrolo[3,2-b]pyridin-5-yl)carbamate. $^1$H NMR (400 MHz, DMSO) δ 11.61 (s, 1H), 8.36-8.35 (m, 1H), 7.75-7.69 (m, 3H), 7.43-7.38 (m, 1H), 6.42 (s, 1H), 5.54 (s, 2H), 5.25-4.99 (m, 4H), 4.97-4.78 (m, 4H). LC-MS $(M+H)^+$=479.2.

Example 44: (R)-5-amino-N-((3-fluoro-5-(trifluoromethyl)pyridin-2-yl)methyl)-N-(1-methoxypropan-2-yl)-6,8-dihydro-1H-furo[3,4-d]pyrrolo[3,2-b]pyridine-2-carboxamide

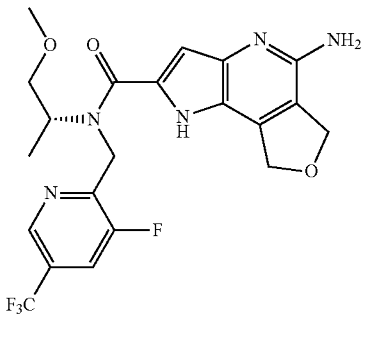 [SMILES: COC[C@@H](C)N(Cc1ncc(C(F)(F)F)cc1F)C(=O)c1cc2nc(N)c3c(c2[nH]1)COC3]

Step 1: ethyl 5-bromo-4-((tert-butoxycarbonyl)amino)-1-((2-(trimethylsilyl)ethoxy)methyl)-1H-pyrrole-2-carboxylate

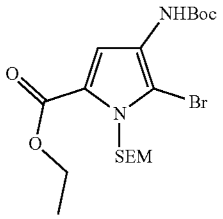 [SMILES: CCOC(=O)c1cc(NC(=O)OC(C)(C)C)c(Br)n1COCC[Si](C)(C)C]

To a solution of ethyl 5-bromo-4-((tert-butoxycarbonyl)amino)-1H-pyrrole-2-carboxylate (320 g, 960 mmol) in DMF (4000 mL) was added $K_2CO_3$ (332 g, 2.40 mol) and SEMCl (400 g, 2.40 mol). The mixture was stirred at 45° C. for 12 h and cooled to room temperature. Most of DMF was removed under reduced pressure. Water (1500 mL) was added, and the mixture was extracted with EtOAc (800 mL×3). The combined organic layer was washed with brine (500 mL×2), dried over $Na_2SO_4$, filtered and concentrated under reduced pressure. The residue was purified by silica gel chromatograph (PE:EtOAc=1:0 to 5:1) to give the title compound (310 g, 70%). LC-MS $(M+Na)^+$=485.2.

Step 2: ethyl 4-((tert-butoxycarbonyl)amino)-5-(4,4,5,5-tetramethyl-1,3,2-dioxaborolan-2-yl)-1-((2-(trimethylsilyl)ethoxy)methyl)-1H-pyrrole-2-carboxylate

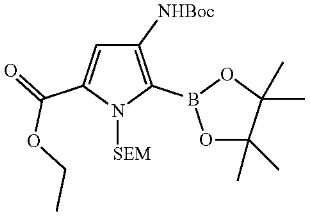 [SMILES: CCOC(=O)c1cc(NC(=O)OC(C)(C)C)c(B2OC(C)(C)C(C)(C)O2)n1COCC[Si](C)(C)C]

To a mixture of ethyl 5-bromo-4-((tert-butoxycarbonyl)amino)-1-((2-(trimethylsilyl)ethoxy)methyl)-1H-pyrrole-2-carboxylate (276 g, 596 mmol) and 4,4,5,5-tetramethyl-1,3,2-dioxaborolane (152 g, 1.19 mol) in dioxane (450 mL) was added allylpalladium chloride dimer (13.1 g, 35.7 mmol), triethylamine (301 g, 2.98 mol) and XPhos (56.8 g, 119 mmol). The mixture was stirred at 80° C. under nitrogen for 12 h. The mixture was cooled to room temperature, and the solid was filtered off. The filtrate was concentrated under reduced pressure to give the title compound (300 g, crude). The material was used in Example 44 step 3 directly. LC-MS $(M+Na)^+$=533.3.

Step 3: ethyl 5-amino-1-((2-(trimethylsilyl)ethoxy)methyl)-6,8-dihydro-1H-furo[3,4-d]pyrrolo[3,2-b]pyridine-2-carboxylate

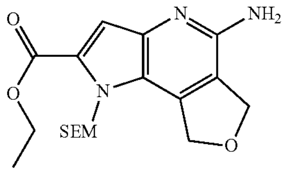 [SMILES: CCOC(=O)c1cc2nc(N)c3c(c2n1COCC[Si](C)(C)C)COC3]

To a solution of ethyl 4-((tert-butoxycarbonyl)amino)-5-(4,4,5,5-tetramethyl-1,3,2-dioxaborolan-2-yl)-1-((2-(trimethylsilyl)ethoxy)methyl)-1H-pyrrole-2-carboxylate (300 g crude) and 4-cyano-2,5-dihydrofuran-3-yl trifluoromethanesulfonate (214 g, 881 mmol) in dioxane (3900 mL) and water (780 mL) was added $K_2CO_3$ (244 g, 1.76 mol) and $Pd(dppf)Cl_2—CH_2Cl_2$ (24.0 g, 29.4 mmol). The mixture was stirred at 80° C. under nitrogen for 12 h. The mixture was cooled to room temperature, and most of dioxane was removed under reduced pressure. The remainder was diluted with water (1500 mL) and extracted with EtOAc (500 mL×3). The combined organic layer was washed with brine (500 mL×2), dried over $Na_2SO_4$, filtered and concentrated under reduced pressure. The residue was purified by silica gel chromatograph (PE:EtOAc=1:0 to 0:1) to give the title compound (100 g, 44% over 2 steps). $^1H$ NMR (400 MHz, DMSO-d6) δ 6.99 (s, 1H), 5.87 (s, 2H), 5.76 (s, 2H), 5.37-5.32 (m, 2H), 4.97-4.90 (m, 2H), 4.31 (q, J=7.0 Hz, 2H), 3.39 (t, J=7.8 Hz, 2H), 1.32 (t, J=7.0 Hz, 3H), 0.76 (t, J=7.8 Hz, 2H), −0.12 (s, 9H). LC-MS $(M+H)^+$=378.2.

Step 4: 5-amino-1-((2-(trimethylsilyl)ethoxy)methyl)-6,8-dihydro-1H-furo[3,4-d]pyrrolo[3,2-b]pyridine-2-carboxylic Acid

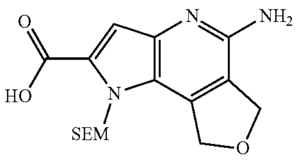 [SMILES: C[Si](C)(C)CCOCn1c(C(=O)O)cc2nc(N)c3c(c21)COC3]

To a solution of ethyl 5-amino-1-((2-(trimethylsilyl)ethoxy)methyl)-6,8-dihydro-1H-furo[3,4-d]pyrrolo[3,2-b]pyridine-2-carboxylate (65 g, 172 mmol) in MeOH (150 mL), THF (450 mL) and water (150 mL) was added LiOH—$H_2O$ (14.5 g, 344 mmol). The mixture was stirred at 45° C. for 12 h. Most of organic solvents were removed under reduced pressure, and the remainder was diluted with water (200 mL). The mixture was washed with MTBE (100 mL×3). To the aqueous phase was added aqueous HCl (1 M) until its pH reached 2-3. The solid was collected by filtration and then triturated with MTBE (500 mL) for 1 h. The solid was collected by filtration and dried under vacuum to give the title compound (49.4 g, 82%). $^1$H NMR (400 MHz, DMSO-d6) δ 6.95 (s, 1H), 5.94 (br s, 2H), 5.80 (s, 2H), 5.36-5.32 (m, 2H), 4.96-4.91 (m, 2H), 3.40 (t, J=8.0 Hz, 2H), 0.76 (t, J=8.0 Hz, 2H), −0.12 (s, 9H); (—COOH not apparent). LC-MS (M+H)$^+$=350.2.

Step 5: (R)—N-((3-fluoro-5-(trifluoromethylpyridin-2-yl)methyl)-1-methoxypropan-2-amine

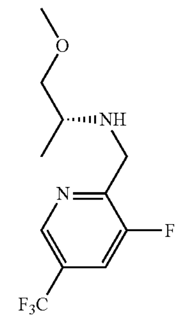 [SMILES: COC[C@@H](C)NCc1ncc(C(F)(F)F)cc1F]

To a solution of (R)-1-methoxypropan-2-amine (691 mg, 7.7 mmol) in DCM (30 mL) was added 3-fluoro-5-(trifluoromethyl)picolinaldehyde (1.5 g, 7.7 mmol), and NaBH(OAc)$_3$ (3.29 g, 15.5 mmol). The mixture was stirred for 2 h at room temperature. The mixture was carefully added to into aqueous $NaHCO_3$ (100 mL, sat.) and extracted with DCM (100 mL). The organic layer was separated, washed with brine (100 mL), dried over $Na_2SO_4$, filtered and concentrated under reduced pressure. The residue was purified by silica gel chromatography (DCM:MeOH=20:1) to give the title compound (1.9 g, 91%). LC-MS (M+H)$^+$=267.3.

Step 6: (R)-5-amino-N-((3-fluoro-5-(trifluoromethyl)pyridin-2-yl)methyl)-N-(1-methoxypropan-2-yl)-1-((2-(trimethylsilyl)ethoxy)methyl)-6,8-dihydro-1H-furo[3,4-d]pyrrolo[3,2-b]pyridine-2-carboxamide

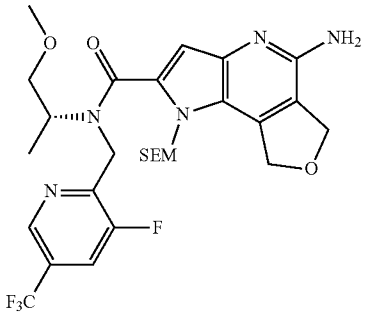 [SMILES: COC[C@@H](C)N(Cc1ncc(C(F)(F)F)cc1F)C(=O)c1cc2nc(N)c3c(c2n1COCC[Si](C)(C)C)COC3]

To a solution of (R)—N-((3-fluoro-5-(trifluoromethyl)pyridin-2-yl)methyl)-1-methoxypropan-2-amine (1.75 g, 6.6 mmol) in THF (30 mL) was added 5-amino-1-((2-(trimethylsilyl)ethoxy)methyl)-6,8-dihydro-1H-furo[3,4-d]pyrrolo[3,2-b]pyridine-2-carboxylic acid (2.3 g, 6.6 mmol), BOPCl (2.5 g, 9.9 mmol) and DIPEA (2.54 g, 19.7 mmol). The mixture was stirred for 16 h at 60° C. and then cooled to room temperature. The mixture was poured into water (100 mL) and extracted with EtOAc (100 mL×2). The combined organic layer was washed with brine (100 mL), dried over $Na_2SO_4$, filtered and concentrated under reduced pressure. The residue was purified by silica gel chromatography (DCM:MeOH=20:1) to give the title compound (3.0 g, 76%). LC-MS (M+H)$^+$=598.1.

Step 7: (R)-5-amino-N-((3-fluoro-5-(trifluoromethyl)pyridin-2-yl)methyl)-N-(1-methoxypropan-2-yl)-6,8-dihydro-1H-furo[3,4-d]pyrrolo[3,2-b]pyridine-2-carboxamide To a solution of (R)-5-amino-N-((3-fluoro-5-(trifluoromethyl)pyridin-2-yl)methyl)-N-(1-methoxypropan-2-yl)-1-((2-(trimethylsilyl)ethoxy)methyl)-6,8-dihydro-1H-furo[3,4-d]pyrrolo[3,2-b]pyridine-2-carboxamide (3.0 g, 5.0 mmol) in DCM (15 mL) was added TFA (15 mL). The mixture was stirred for 3 h at room temperature and then concentrated under reduced pressure. MeOH (30 mL) and ammonia in water (28%, 3 mL) was added, and the mixture was stirred for 3 h at room temperature. The mixture was poured into water (100 mL) and then extracted with EtOAc (100×2 mL). The combined organic layer was washed with brine (100 mL), dried over $Na_2SO_4$, filtered and concentrated under reduced pressure. The residue was purified by silica gel chromatography (DCM:MeOH=10:1) to give Example 44 (1.8 g, 77%). $^1$H NMR (400 MHz, DMSO-d6) δ 11.47 (s, 1H), 8.99-8.60 (m, 1H), 8.29-8.27 (m, 1H), 6.84-6.09 (m, 1H), 5.79-5.38 (m, 2H), 5.29-4.37 (m, 7H), 3.68-3.51 (m, 1H), 3.49-3.37 (m, 1H), 3.29-2.95 (m, 3H), 1.51-0.83 (m, 3H). LC-MS (M+H)$^+$=468.3.

Example 45: (R)-5-amino-N-((5-bromopyridin-2-yl)methyl)-N-(1-methoxypropan-2-yl)-6,8-dihydro-1H-furo[3,4-d]pyrrolo[3,2-b]pyridine-2-carboxamide

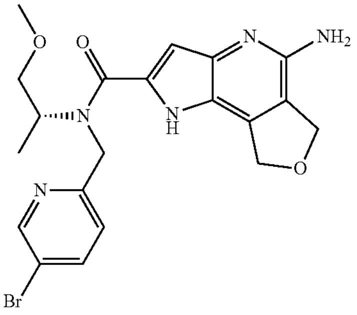 [SMILES: COC[C@@H](C)N(Cc1ccc(Br)cn1)C(=O)c1cc2nc(N)c3c(c2[nH]1)COC3]

Step 1: (R)—N-((5-bromopyridin-2-yl)methyl)-1-methoxypropan-2-amine

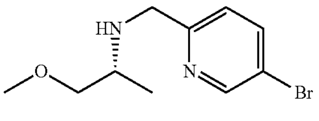

The title compound (130 mg, 94%) was prepared in a manner similar to that in Example 44 step 5 from (R)-1-methoxypropan-2-amine and 5-bromopicolinaldehyde. LC-MS $(M+H)^+$=259.1.

Step 2: tert-butyl (R)-(2-(((5-bromopyridin-2-yl) methyl)(1-methoxypropan-2-yl)carbamoyl)-6,8-dihydro-1H-furo[3,4-d]pyrrolo[3,2-b]pyridin-5-yl) carbamate

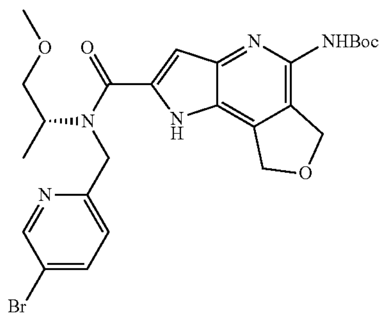 [SMILES: COC[C@@H](C)N(Cc1ccc(Br)cn1)C(=O)c1cc2nc(NC(=O)OC(C)(C)C)c3c(c2[nH]1)COC3]

The title compound (174 mg, 73%) was prepared in a manner similar to that in Example 17 & 18 step 2 from 5-((tert-butoxycarbonyl)amino)-6,8-dihydro-1H-furo[3,4-d] pyrrolo[3,2-b]pyridine-2-carboxylic acid and (R)—N-((5-bromopyridin-2-yl)methyl)-1-methoxypropan-2-amine. LC-MS $(M+H)^+$=560.2.

Step 3: (R)-5-amino-N-((5-bromopyridin-2-yl) methyl)-N-(1-methoxypropan-2-yl)-6,8-dihydro-1H-furo[3,4-d]pyrrolo[3,2-b]pyridine-2-carboxamide Example 45 (27 mg, 17%) was prepared in a manner similar to that in Example 22 step 3 from tert-butyl (R)-(2-(((5-bromopyridin-2-yl)methyl)(1-methoxypropan-2-yl)carbamoyl)-6,8-dihydro-1H-furo[3,4-d]pyrrolo[3,2-b]pyridin-5-yl)carbamate. $^1H$ NMR (400 MHz, DMSO-d6) δ 11.52 (s, 1H), 8.65 (s, 1H), 8.01 (d, J=6.8 Hz, 1H), 7.28-7.49 (m, 1H), 6.07-6.82 (m, 1H), 5.54 (s, 2H), 5.12 (s, 2H), 4.91 (s, 3H), 4.68 (s, 2H), 3.48 (brs, 1H), 3.34-3.39 (m, 1H), 3.13 (s, 3H), 1.18 (d, J=6.2 Hz, 3H). LC-MS $(M+H)^+$=460.1.

Example 46: (R)-5-amino-N-(4-cyano-2,6-difluorobenzyl)-N-(1-methoxypropan-2-yl)-6,8-dihydro-1H-furo[3,4-d]pyrrolo[3,2-b]pyridine-2-carboxamide

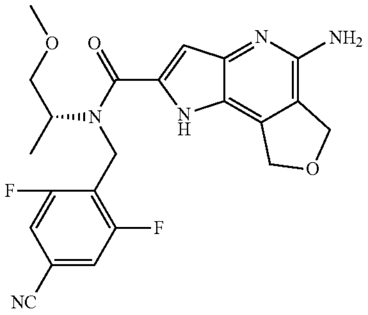 [SMILES: COC[C@@H](C)N(Cc1c(F)cc(C#N)cc1F)C(=O)c1cc2nc(N)c3c(c2[nH]1)COC3]

Step 1: (R)-3,5-difluoro-4-(((1-methoxypropan-2-yl) amino)methyl)benzonitrile

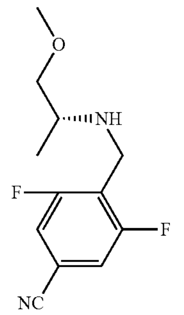 [SMILES: COC[C@@H](C)NCc1c(F)cc(C#N)cc1F]

The title compound (140 mg, 97%) was prepared in a manner similar to that in Example 44 step 5 from (R)-1-methoxypropan-2-amine and 3,5-difluoro-4-formylbenzonitrile. LC-MS $(M+H)^+$=241.2.

Step 2: tert-butyl (R)-(2-((4-cyano-2,6-difluorobenzyl)(1-methoxypropan-2-yl)carbamoyl)-6,8-dihydro-1H-furo[3,4-d]pyrrolo[3,2-b]pyridin-5-yl)carbamate

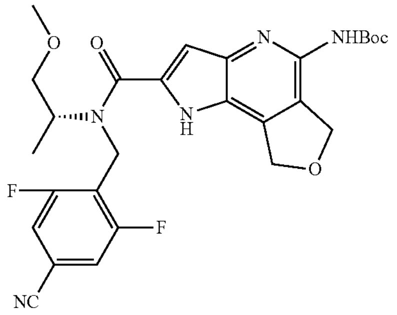 [SMILES: COC[C@@H](C)N(Cc1c(F)cc(C#N)cc1F)C(=O)c1cc2nc(NC(=O)OC(C)(C)C)c3c(c2[nH]1)COC3]

The title compound (33 mg, 15%) was prepared in a manner similar to that in Example 17 & 18 step 2 from 5-((tert-butoxycarbonyl)amino)-6,8-dihydro-1H-furo[3,4-d] pyrrolo[3,2-b]pyridine-2-carboxylic acid and (R)-3,5-difluoro-4-(((1-methoxypropan-2-yl)amino)methyl)benzonitrile. LC-MS $(M+H)^+$=542.2.

Step 3: (R)-5-amino-N-(4-cyano-2,6-difluorobenzyl)-N-(1-methoxypropan-2-yl)-6,8-dihydro-1H-furo [3,4-d]pyrrolo[3,2-b]pyridine-2-carboxamide Example 46 (4 mg, 15%) was prepared in a manner similar to that in Example 22 step 3 from tert-butyl (R)-(2-((4-cyano-2,6-difluorobenzyl)(1-methoxypropan-2-yl)carbamoyl)-6,8-dihydro-1H-furo[3,4-d]pyrrolo[3,2-b]pyridin-5-yl)carbamate. $^1H$ NMR (400 MHz, DMSO-d6) δ 11.44-11.58 (m, 1H), 7.68-7.83 (m, 2H), 6.58-6.50 (m, 1H), 5.57 (s, 2H) 5.10 (s, 2H), 4.91 (s, 2H), 4.51-4.85 (m, 3H) 3.60-3.49 (m, 1H), 3.36-3.40 (m, 1H), 3.16 (s, 3H) 1.27 (d, J=6.5 Hz, 3H). LC-MS $(M+H)^+$=442.1.

Example 47: 5-amino-N-((3-fluoropyridin-2-yl)methyl)-N-(2,4,6-trifluorobenzyl)-6,8-dihydro-1H-furo[3,4-d]pyrrolo[3,2-b]pyridine-2-carboxamide

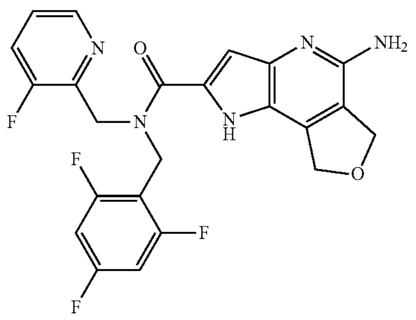 [SMILES: Nc1nc2cc(C(=O)N(Cc3ncccc3F)Cc3c(F)cc(F)cc3F)[nH]c2c2c1COC2]

Step 1: 1-(3-fluoropyridin-2-yl)-N-(2,4,6-trifluorobenzyl)methanamine

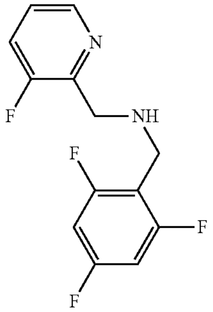 [SMILES: Fc1cc(F)c(CNCc2ncccc2F)c(F)c1]

The title compound (180 mg, 67%) was prepared in a manner similar to that in Example 3 step 1 from 2,4,6-trifluorobenzaldehyde and (3-fluoropyridin-2-yl)methanamine. LC-MS $(M+H)^+$=271.1.

Step 2: tert-butyl (2-(((3-fluoropyridin-2-yl)methyl)(2,4,6-trifluorobenzyl)carbamoyl)-6,8-dihydro-1H-furo[3,4-d]pyrrolo[3,2-b]pyridin-5-yl)carbamate

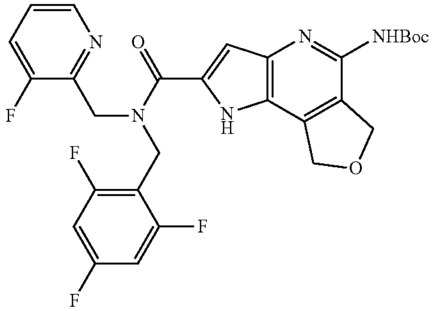 [SMILES: CC(C)(C)OC(=O)Nc1nc2cc(C(=O)N(Cc3ncccc3F)Cc3c(F)cc(F)cc3F)[nH]c2c2c1COC2]

The title compound (60 mg, 42%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and 1-(3-fluoropyridin-2-yl)-N-(2,4,6-trifluorobenzyl)methanamine. LC-MS $(M+H)^+$=572.3.

Step 3: 5-amino-N-((3-fluoropyridin-2-yl)methyl)-N-(2,4,6-trifluorobenzyl)-6,8-dihydro-1H-furo[3,4-d]pyrrolo[3,2-b]pyridine-2-carboxamide Example 47 (26 mg, 50%) was prepared in a manner similar to that in Example 22 step 3 from tert-butyl (2-(((3-fluoropyridin-2-yl)methyl)(2,4,6-trifluorobenzyl)carbamoyl)-6,8-dihydro-1H-furo[3,4-d]pyrrolo[3,2-b]pyridin-5-yl)carbamate. $^1$H NMR (400 MHz, DMSO-d6) δ 11.61 (s, 1H), 8.36 (d, J=4.4 Hz, 1H), 7.70 (t, J=9.3 Hz, 1H), 7.39 (dt, J=8.5, 4.4 Hz, 1H), 7.12 (t, J=8.7 Hz, 2H), 6.46 (s, 1H), 5.53 (s, 2H), 5.09 (s, 2H), 4.99 (s, 2H), 4.88 (s, 4H). LC-MS $(M+H)^+$=472.2.

Example 48: (R)-5-amino-N-((5-cyclopropylpyridin-2-yl)methyl)-N-(1-(pyrimidin-2-yl)ethyl)-6,8-dihydro-1H-furo[3,4-d]pyrrolo[3,2-b]pyridine-2-carboxamide

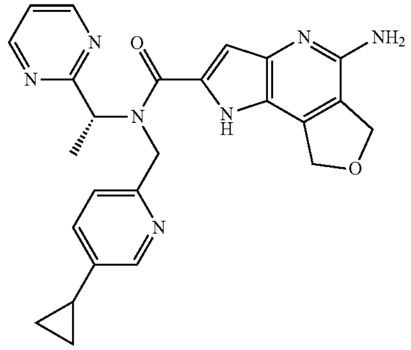 [SMILES: C[C@H](c1ncccn1)N(Cc1ccc(C2CC2)cn1)C(=O)c1cc2nc(N)c3c(c2[nH]1)COC3]

Step 1: (R)—N-((5-cyclopropylpyridin-2-yl)methyl)-1-(pyrimidin-2-yl)ethan-1-amine

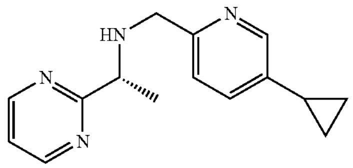 [SMILES: C[C@@H](NCc1ccc(C2CC2)cn1)c1ncccn1]

The title compound (60 mg, 35%) was prepared in a manner similar to that in Example 3 step 1 from 5-cyclopropylpicolinaldehyde and (R)-1-(pyrimidin-2-yl)ethan-1-amine dihydrochloride. LC-MS $(M+H)^+$=255.3.

Step 2: tert-butyl (R)-(2-(((5-cyclopropylpyridin-2-yl)methyl)(1-(pyrimidin-2-yl)ethyl)carbamoyl)-6,8-dihydro-1H-furo[3,4-d]pyrrolo[3,2-b]pyridin-5-yl) carbamate

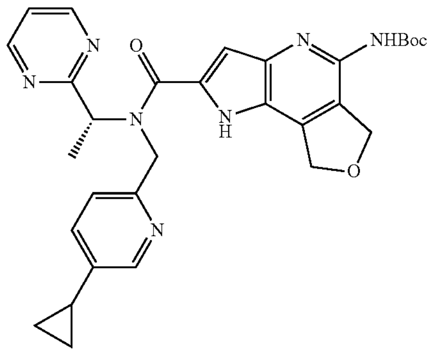 [SMILES: C[C@H](c1ncccn1)N(Cc1ccc(C2CC2)cn1)C(=O)c1cc2nc(NC(=O)OC(C)(C)C)c3c(c2[nH]1)COC3]

The title compound (60 mg, 45%) was prepared in a manner similar to that in Example 13 step 4 from 5-((tert-butoxycarbonyl)amino)-6,8-dihydro-1H-furo[3,4-d]pyrrolo [3,2-b]pyridine-2-carboxylic acid and (R)—N-((5-cyclopropylpyridin-2-yl)methyl)-1-(pyrimidin-2-yl)ethan-1-amine. LC-MS $(M+H)^+$=556.4.

Step 3: (R)-5-amino-N-((5-cyclopropylpyridin-2-yl) methyl)-N-(1-(pyrimidin-2-yl)ethyl)-6,8-dihydro-1H-furo[3,4-d]pyrrolo[3,2-b]pyridine-2-carboxamide Example 48 (20 mg, 40%) was prepared in a manner similar to that in Example 14 step 6 from tert-butyl (R)-(2-(((5-cyclopropylpyridin-2-yl)methyl)(1-(pyrimidin-2-yl) ethyl)carbamoyl)-6,8-dihydro-1H-furo[3,4-d]pyrrolo[3,2-b] pyridin-5-yl)carbamate. $^1$H NMR (400 MHz, DMSO-d6) δ 11.42 (s, 1H), 8.74-8.73 (m, 2H), 8.30 (s, 1H), 7.36-7.31 (m, 2H), 7.25-7.21 (m, 1H), 6.50 (s, 1H), 5.82 (brs, 1H), 5.25 (s, 2H), 5.12 (s, 2H), 5.05-4.97 (m, 1H), 4.91 (s, 2H), 4.79-4.68 (m, 1H), 1.97-1.89 (m, 1H), 1.61 (d, J=?? Hz, 3H), 0.99-0.93 (m, 2H), 0.71-0.67 (m, 2H). LC-MS $(M+H)^+$=456.3.

Example 49: (R)-5-amino-N-((5-bromo-3-fluoro-pyridin-2-yl)methyl)-N-(1-methoxypropan-2-yl)-6,8-dihydro-1H-furo[3,4-d]pyrrolo[3,2-b]pyridine-2-carboxamide

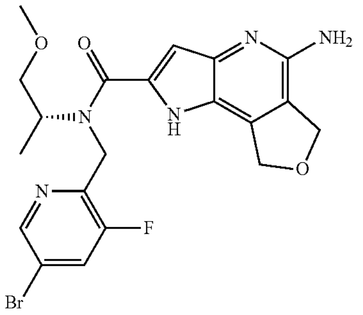 [SMILES: COC[C@@H](C)N(Cc1ncc(Br)cc1F)C(=O)c1cc2nc(N)c3c(c2[nH]1)COC3]

Step 1: (R)—N-((5-bromo-3-fluoropyridin-2-yl) methyl)-1-methoxypropan-2-amine

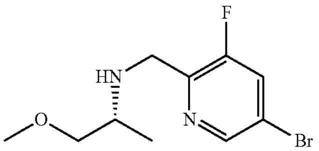

The title compound (231 mg, 57%) was prepared in a manner similar to that in Example 44 step 5 from (R)-1-methoxypropan-2-amine and 5-bromo-3-fluoropicolinaldehyde. LC-MS $(M+H)^+$=277.1.

Step 2: (R)-5-amino-N-((5-bromo-3-fluoropyridin-2-yl)methyl)-N-(1-methoxypropan-2-yl)-1-((2-(trimethylsilyl)ethoxy)methyl)-6,8-dihydro-1H-furo[3,4-d]pyrrolo[3,2-b]pyridine-2-carboxamide

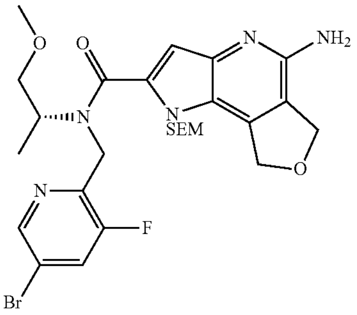 [SMILES: COC[C@@H](C)N(Cc1ncc(Br)cc1F)C(=O)c1cc2nc(N)c3c(c2n1COCC[Si](C)(C)C)COC3]

The title compound (234 mg, 43%) was prepared in a manner similar to that in Example 44 step 6 from 5-amino-1-((2-(trimethylsilyl)ethoxy)methyl)-6,8-dihydro-1H-furo [3,4-d]pyrrolo[3,2-b]pyridine-2-carboxylic acid and (R)—N-((5-bromo-3-fluoropyridin-2-yl)methyl)-1-methoxypropan-2-amine. LC-MS $(M+H)^+$=608.1.

Step 3: (R)-5-amino-N-((5-bromo-3-fluoropyridin-2-yl)methyl)-N-(1-methoxypropan-2-yl)-6,8-dihydro-1H-furo[3,4-d]pyrrolo[3,2-b]pyridine-2-carboxamide Example 49 (54 mg, 18%) was prepared in a manner similar to that in Example 44 step 7 from (R)-5-amino-N-((5-bromo-3-fluoropyridin-2-yl)methyl)-N-(1-methoxypropan-2-yl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ 11.55 (s, 1H), 8.53 (s, 1H), 8.15 (d, J=10.0 Hz, 1H), 6.75-6.23 (m, 1H), 5.82-5.54 (m, 2H), 5.11 (s, 2H), 5.00-4.39 (m, 5H), 3.56 (dd, J=7.8, 9.7 Hz, 1H), 3.39 (dd, J=5.2, 10.2 Hz, 1H), 3.17 (s, 3H), 1.23 (d, J=7.6 Hz, 3H). LC-MS $(M+H)^+$=478.2.

Example 50: (R)-5-amino-N-((5-bromopyridin-2-yl)methyl)-N-((3-fluoropyridin-2-yl)methyl)-6-methyl-6,8-dihydro-1H-furo[3,4-d]pyrrolo[3,2-b]pyridine-2-carboxamide

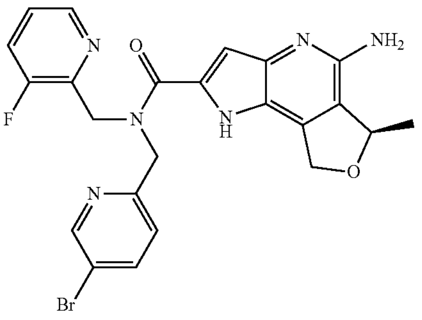 [SMILES: C[C@H]1OCc2c1c(N)nc1cc(C(=O)N(Cc3ccc(Br)cn3)Cc3ncccc3F)[nH]c21]

Step 1: 1-(5-bromopyridin-2-yl)-N-((3-fluoropyridin-2-yl)methyl)methanamine

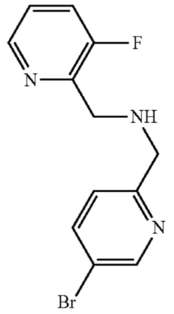 [SMILES: Fc1cccnc1CNCc1ccc(Br)cn1]

The title compound (100 mg, 65%) was prepared in a manner similar to that in Example 5 step 1 from 5-bromopicolinaldehyde and (3-fluoropyridin-2-yl)methanamine. LC-MS $(M+H)^+$=296.2.

Step 2: (R)-5-amino-N-((5-bromopyridin-2-yl)methyl)-N-((3-fluoropyridin-2-yl)methyl)-6-methyl-6,8-dihydro-1H-furo[3,4-d]pyrrolo[3,2-b]pyridine-2-carboxamide Example 50 (52 mg, 60%) was prepared in a manner similar to that in Example 2 step 3 from 1-(5-bromopyridin-2-yl)-N-((3-fluoropyridin-2-yl)methyl)methanamine and (R)-5-amino-6-methyl-6,8-dihydro-1H-furo[3,4-d]pyrrolo[3,2-b]pyridine-2-carboxylic acid. $^1H$ NMR (400 MHz, DMSO-d6) δ 11.58 (s, 1H), 8.8-8.53 (m, 1H), 8.34 (brs, 1H), 8.00 (brs, 1H), 7.67 (brs, 1H), 7.38 (brs, 2H), 6.5-6.1 (m, 1H), 5.40 (s, 2H), 5.32-4.56 (m, 7H), 1.28 (d, J=6.1 Hz, 3H). LC-MS $(M+H)^+$=511.4.

Example 51: (R)-5-amino-N-((5-iodopyridin-2-yl)methyl)-N-(1-(pyrimidin-2-yl)ethyl)-6,8-dihydro-1H-furo[3,4-d]pyrrolo[3,2-b]pyridine-2-carboxamide

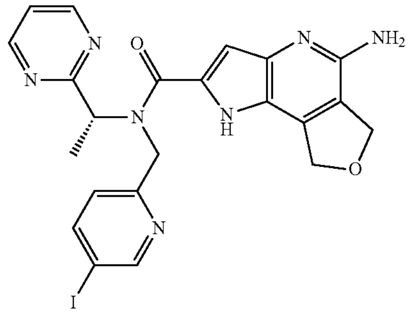 [SMILES: C[C@H](c1ncccn1)N(Cc1ccc(I)cn1)C(=O)c1cc2nc(N)c3c(c2[nH]1)COC3]

Step 1: 5-iodopicolinaldehyde

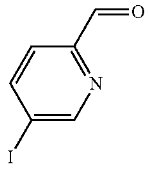

The title compound (136 mg, 77%) was prepared in a manner similar to that in Example 37 step 1 from methyl 5-iodopicolinate. LC-MS $(M+H)^+$=233.9.

Step 2: (R)—N-((5-iodopyridin-2-yl)methyl)-1-(pyrimidin-2-yl)ethan-1-amine

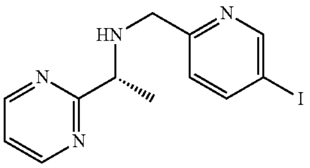 [SMILES: C[C@@H](NCc1ccc(I)cn1)c1ncccn1]

The title compound (84 mg, 67%) was prepared in a manner similar to that in Example 34 step 1 from 5-iodopicolinaldehyde and (R)-1-(pyrimidin-2-yl)ethan-1-amine dihydrochloride. LC-MS $(M+H)^+$=341.3.

Step 3: (R)-5-amino-N-((5-iodopyridin-2-yl)methyl)-N-(1-(pyrimidin-2-yl)ethyl)-1-((2-(trimethylsilyl)ethoxy)methyl)-6,8-dihydro-1H-furo[3,4-d]pyrrolo[3,2-b]pyridine-2-carboxamide

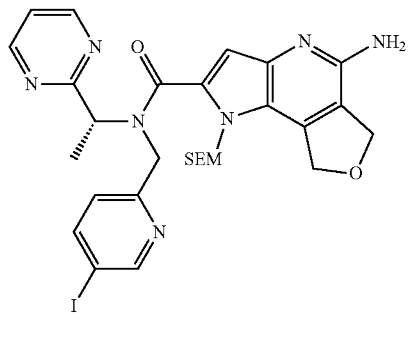 [SMILES: C[C@H](c1ncccn1)N(Cc1ccc(I)cn1)C(=O)c1cc2nc(N)c3c(c2n1COCC[Si](C)(C)C)COC3]

The title compound (80 mg, 48%) was prepared in a manner similar to that in Example 44 step 6 from 5-amino-1-((2-(trimethylsilyl)ethoxy)methyl)-6,8-dihydro-1H-furo[3,4-d]pyrrolo[3,2-b]pyridine-2-carboxylic acid and (R)—N-((5-iodopyridin-2-yl)methyl)-1-(pyrimidin-2-yl)ethan-1-amine. LC-MS $(M+H)^+$=672.3.

Step 4: (R)-5-amino-N-((5-iodopyridin-2-yl)methyl)-N-(1-(pyrimidin-2-yl)ethyl)-6,8-dihydro-1H-furo[3,4-d]pyrrolo[3,2-b]pyridine-2-carboxamide Example 51 (20 mg, 31%) was prepared in a manner similar to that in Example 44 step 7 from (R)-5-amino-N-((5-iodopyridin-2-yl)methyl)-N-(1-(pyrimidin-2-yl)ethyl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ: 11.63 (s, 1H), 8.98-8.46 (m, 3H), 8.25-7.95 (m, 1H), 7.55-7.00 (m, 2H), 6.30-6.05 (m, 1H), 5.71-4.42 (m, 9H), 1.76-1.48 (m, 3H). LC-MS $(M+H)^+$=542.2.

Example 52: (R)-5-amino-N-((5-cyclopropyl-3-fluoropyridin-2-yl)methyl)-N-(1-(pyrimidin-2-yl)ethyl)-6,8-dihydro-1H-furo[3,4-d]pyrrolo[3,2-b]pyridine-2-carboxamide

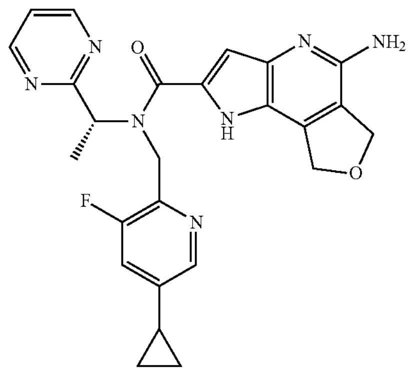 [SMILES: C[C@H](c1ncccn1)N(Cc1ncc(C2CC2)cc1F)C(=O)c1cc2nc(N)c3c(c2[nH]1)COC3]

Step 1: (R)—N-((5-cyclopropyl-3-fluoropyridin-2-yl)methyl)-1-(pyrimidin-2-yl)ethan-1-amine

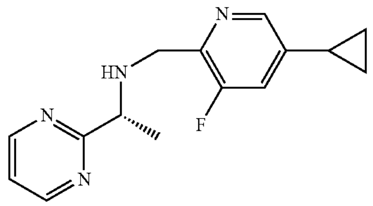 [SMILES: C[C@@H](NCc1ncc(C2CC2)cc1F)c1ncccn1]

To a solution of 5-cyclopropyl-3-fluoropicolinaldehyde (84 mg, 0.51 mmol) in DCM (3 mL) was added (R)-1-(pyrimidin-2-yl)ethan-1-amine dihydrochloride (100 mg, 0.51 mmol), triethylamine (103 mg, 1.02 mmol) and $NaBH(OAc)_3$ (217 mg, 1.02 mmol). The mixture was stirred for 3 h at room temperature. The mixture was carefully added into saturated $NaHCO_3$ (50 mL) and then extracted with DCM (50 mL). The organic layer was washed with brine (50 mL), dried over $Na_2SO_4$, filtered and concentrated under reduced pressure. The residue was purified by silica gel column chromatography (DCM:MeOH=20:1) to give the title compound (61 mg, 44%). LC-MS $(M+H)^+$=273.4.

Step 2: (R)-5-amino-N-((5-cyclopropyl-3-fluoropyridin-2-yl)methyl)-N-(1-(pyrimidin-2-yl)ethyl)-6,8-dihydro-1H-furo[3,4-d]pyrrolo[3,2-b]pyridine-2-carboxamide Example 52 (27 mg, 25%) was prepared in a manner similar to that in Example 2 step 3 from 5-amino-6,8-dihydro-1H-furo[3,4-d]pyrrolo[3,2-b]pyridine-2-carboxylic acid and (R)—N-((5-cyclopropyl-3-fluoropyridin-2-yl)methyl)-1-(pyrimidin-2-yl)ethan-1-amine. 1H NMR (500 MHz, DMSO) δ 11.71-11.39 (m, 1H), 9.02-8.58 (m, 2H), 8.46-7.86 (m, 1H), 7.61-7.08 (m, 2H), 6.74-6.23 (m, 1H), 6.19-4.36 (m, 9H), 2.12-1.85 (m, 1H), 1.85-1.43 (m, 3H), 1.05-0.89 (m, 2H), 0.89-0.64 (m, 2H). LC-MS $(M+H)^+$=474.4.

Example 53: (R)-5-amino-N-((5-cyclopropylpyrazin-2-yl)methyl)-N-(1-methoxypropan-2-yl)-6,8-dihydro-1H-furo[3,4-d]pyrrolo[3,2-b]pyridine-2-carboxamide

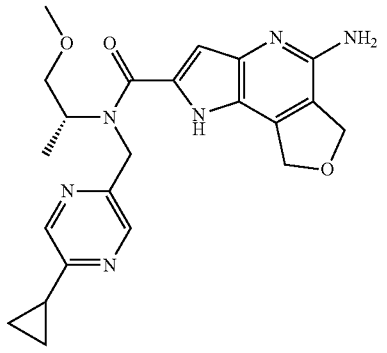 [SMILES: COC[C@@H](C)N(Cc1cnc(C2CC2)cn1)C(=O)c1cc2nc(N)c3c(c2[nH]1)COC3]

Step 1: 5-cyclopropylpyrazine-2-carbaldehyde

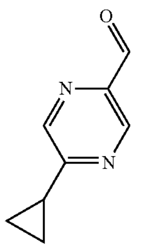 [SMILES: O=Cc1cnc(C2CC2)cn1]

The title compound (0.60 g, 29%) was prepared in a manner similar to that in Example 36 step 1 from 5-chloropyrazine-2-carbaldehyde and cyclopropylboronic acid. LC-MS $(M+H)^+$=149.1.

Step 2: (R)—N-((5-cyclopropylpyrazin-2-yl)methyl)-1-methoxypropan-2-amine

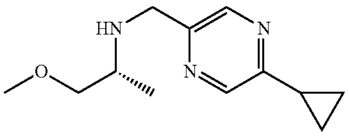 [SMILES: COC[C@@H](C)NCc1cnc(C2CC2)cn1]

The title compound (190 mg, 85%) was prepared in a manner similar to that in Example 44 step 5 from (R)-1-methoxypropan-2-amine and 5-cyclopropylpyrazine-2-carbaldehyde. LC-MS $(M+H)^+$=222.2.

Step 3: (R)-5-amino-N-((5-cyclopropylpyrazin-2-yl)methyl)-N-(1-methoxypropan-2-yl)-1-((2-(trimethylsilyl)ethoxy)methyl)-6,8-dihydro-1H-furo[3,4-d]pyrrolo[3,2-b]pyridine-2-carboxamide

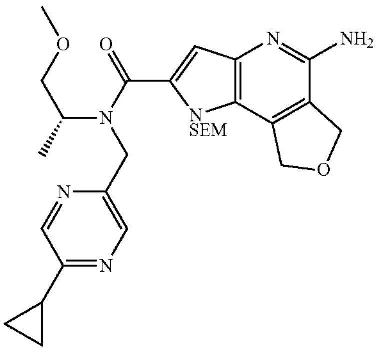 [SMILES: COC[C@@H](C)N(Cc1cnc(C2CC2)cn1)C(=O)c1cc2nc(N)c3c(c2n1COCC[Si](C)(C)C)COC3]

The title compound (234 mg, 43%) was prepared in a manner similar to that in Example 44 step 6 from 5-amino-1-((2-(trimethylsilyl)ethoxy)methyl)-6,8-dihydro-1H-furo[3,4-d]pyrrolo[3,2-b]pyridine-2-carboxylic acid and (R)—N-((5-cyclopropylpyrazin-2-yl)methyl)-1-methoxypropan-2-amine. LC-MS $(M+H)^+$=553.4.

Step 4: (R)-5-amino-N-((5-cyclopropylpyrazin-2-yl)methyl)-N-(1-methoxypropan-2-yl)-6,8-dihydro-1H-furo[3,4-d]pyrrolo[3,2-b]pyridine-2-carboxamide Example 53 (25 mg, 30%) was prepared in a manner similar to that in Example 44 step 7 from (R)-5-amino-N-((5-cyclopropylpyrazin-2-yl)methyl)-N-(1-methoxypropan-2-yl)-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.48 (s, 1H), 8.54 (s, 1H), 8.46 (s, 1H), 6.75-6.44 (m, 1H), 5.52 (s, 2H), 5.12 (s, 2H), 5.01-4.59 (m, 5H), 3.50 (t, J=9.3 Hz, 1H), 3.39-3.34 (m, 1H), 3.12 (s, 3H), 2.22-2.13 (m, 1H), 1.31-1.11 (m, 3H), 1.04-0.98 (m, 2H), 0.94-0.87 (m, 2H). LC-MS $(M+H)^+$=423.2.

Example 54 & Example 55: (S)-5-amino-N-ethyl-N-(7-(trifluoromethyl)isochroman-4-yl)-6,8-dihydro-1H-furo[3,4-d]pyrrolo[3,2-b]pyridine-2-carboxamide & (R)-5-amino-N-ethyl-N-(7-(trifluoromethyl)isochroman-4-yl)-6,8-dihydro-1H-furo[3,4-d]pyrrolo[3,2-b]pyridine-2-carboxamide

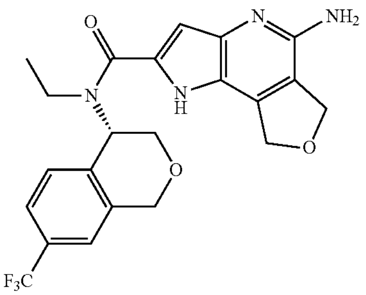

&

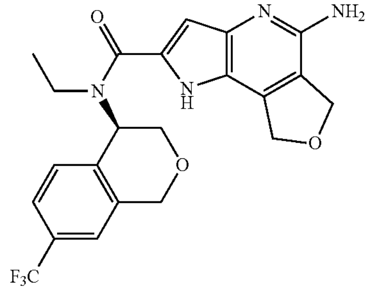

Step 1: tert-butyl ethyl(7-(trifluoromethyl)isochroman-4-yl)carbamate

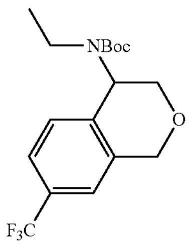 [SMILES: CCN(C(=O)OC(C)(C)C)C1COCc2cc(C(F)(F)F)ccc21]

The title compound (0.50 g, 92%) was prepared in a manner similar to that in Example 39&40 step 7 from tert-butyl (7-(trifluoromethyl)isochroman-4-yl)carbamate and EtI. LCMS $(M+H-tBu)^+$=290.1.

Step 2: N-ethyl-7-(trifluoromethyl)isochroman-4-amine Hydrochloride

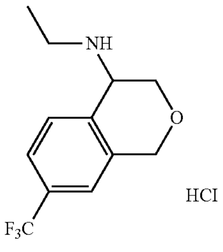

The title compound (0.20 g, 62%) was prepared in a manner similar to that in Example 39&40 step 8 from tert-butyl ethyl(7-(trifluoromethyl)isochroman-4-yl)carbamate. LC-MS $(M+H)^+$=246.1.

Step 3: tert-butyl (2-(ethyl(7-(trifluoromethyl)isochroman-4-yl)carbamoyl)-6,8-dihydro-1H-furo[3,4-d]pyrrolo[3,2-b]pyridin-5-yl)carbamate

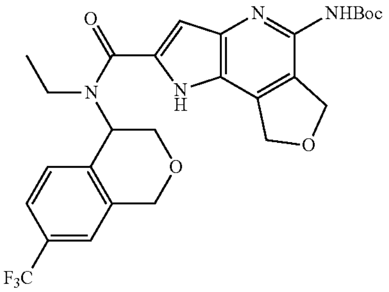 [SMILES: CCN(C(=O)c1cc2nc(NC(=O)OC(C)(C)C)c3c(c2[nH]1)COC3)C1COCc2cc(C(F)(F)F)ccc21]

The title compound (0.40 g, 90%) was prepared in a manner similar to that in Example 39&40 step 9 from 5-((tert-butoxycarbonyl)amino)-6,8-dihydro-1H-furo[3,4-d]pyrrolo[3,2-b]pyridine-2-carboxylic acid and N-ethyl-7-(trifluoromethyl)isochroman-4-amine hydrochloride. LC-MS $(M+H)^+$=547.2.

Step 4: (S)-5-amino-N-ethyl-N-(7-(trifluoromethyl)isochroman-4-yl)-6,8-dihydro-1H-furo[3,4-d]pyrrolo[3,2-b]pyridine-2-carboxamide & (R)-5-amino-N-ethyl-N-(7 -(trifluoromethyl)isochroman-4-yl)-6,8-dihydro-1H-furo[3,4-d]pyrrolo[3,2-b]pyridine-2-carboxamide Example 54 (22 mg, 14%) and Example 55 (23 mg, 14%) were prepared in a manner similar to that in Example 39 and 40 step 10 from tert-butyl (2-(ethyl(7-(trifluoromethyl)isochroman-4-yl)carbamoyl)-6,8-dihydro-1H-furo[3,4-d]pyrrolo[3,2-b]pyridin-5-yl)carbamate and N-ethyl-7-(trifluoromethyl)isochroman-4-amine hydrochloride.

Analytical chiral-SFC condition as below. Column: CHIRALPAK AD-3; Column size: 4.6×50 mm, 3 μm; Mobile phase: (ethanol containing 0.2% 7 M methanolic $NH_3$):$CO_2$, 1:19 for 0.2 min, 1:19 to 1:1 in 1.0 min, 1:1 for 1 min, 1:1 to 1:19 in 0.4 min; Flow: 3.4 mL/min; Temperature: 35° C.; back pressure: 1800 psi.

Example 54: Analytical SFC tR=1.70 min. $^1$H NMR (400 MHz, DMSO-d6) δ 11.68-11.52 (m, 1H), 7.62 (d, J=8.0 Hz, 1H), 7.58 (s, 1H), 7.44 (d, J=7.6 Hz, 1H), 6.62 (s, 1H), 5.61 (s, 1H), 5.56 (s, 2H), 5.14 (s, 2H), 4.93 (d, J=3.2 Hz, 2H), 4.90 (s, 1H), 4.81-4.73 (m, 1H), 4.10-4.21 (m, 2H), 3.72 (brs, 1H), 3.56-3.33 (m, 1H), 1.02-1.17 (m, 3H). LC-MS $(M+H)^+$=447.2.

Example 55: Analytical SFC tR=2.14 min. $^1$H NMR (400 MHz, DMSO-d6) δ 11.68-11.52 (m, 1H), 7.62 (d, J=8.0 Hz, 1H), 7.58 (s, 1H), 7.44 (d, J=7.6 Hz, 1H), 6.62 (s, 1H), 5.61 (s, 1H), 5.56 (s, 2H), 5.14 (s, 2H), 4.93 (d, J=3.2 Hz, 2H), 4.90 (s, 1H), 4.81-4.73 (m, 1H), 4.10-4.21 (m, 2H), 3.72 (brs, 1H), 3.56-3.33 (m, 1H), 1.02-1.17 (m, 3H). LC-MS $(M+H)^+$=447.2.

Example 56: (R)-5-amino-N-((5-cyclopropyl-3-fluoropyridin-2-yl)methyl)-N-(1-methoxypropan-2-yl)-6,8-dihydro-1H-furo[3,4-d]pyrrolo[3,2-b]pyridine-2-carboxamide

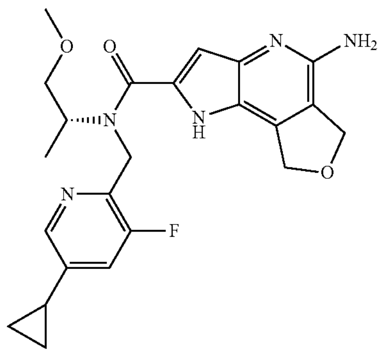 [SMILES: COC[C@@H](C)N(Cc1ncc(C2CC2)cc1F)C(=O)c1cc2nc(N)c3c(c2[nH]1)COC3]

Step 1: (R)—N-((5-cyclopropyl-3-fluoropyridin-2-yl)methyl)-1-methoxypropan-2-amine

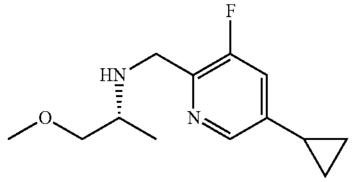 [SMILES: COC[C@@H](C)NCc1ncc(C2CC2)cc1F]

The title compound (110 mg, 51%) was prepared in a manner similar to that in Example 44 step 5 from (R)-1-methoxypropan-2-amine and 5-cyclopropyl-3-fluoropicolinaldehyde. LC-MS $(M+H)^+$=239.1.

Step 2: tert-butyl (R)-(2-(((5-cyclopropyl-3-fluoropyridin-2-yl)methyl)(1-methoxypropan-2-yl)carbamoyl)-6,8-dihydro-1H-furo[3,4-d]pyrrolo[3,2-b]pyridin-5-yl)carbamate

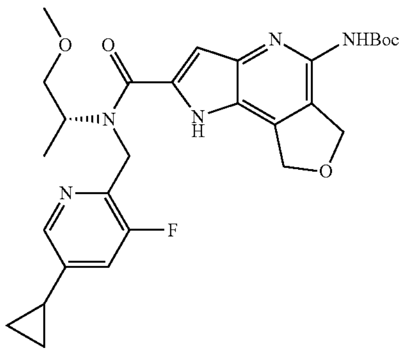 [SMILES: COC[C@@H](C)N(Cc1ncc(C2CC2)cc1F)C(=O)c1cc2nc(NC(=O)OC(C)(C)C)c3c(c2[nH]1)COC3]

The title compound (100 mg, 40%) was prepared in a manner similar to that in Example 13 step 4 from 5-((tert-butoxycarbonyl)amino)-6,8-dihydro-1H-furo[3,4-d]pyrrolo[3,2-b]pyridine-2-carboxylic acid and (R)—N-((5-cyclopropyl-3-fluoropyridin-2-yl)methyl)-1-methoxypropan-2-amine. LC-MS $(M+H)^+$=540.1.

Step 3: (R)-5-amino-N-((5-cyclopropyl-3-fluoropyridin-2-yl)methyl)-N-(1-methoxypropan-2-yl)-6,8-dihydro-1H-furo[3,4-d]pyrrolo[3,2-b]pyridine-2-carboxamide Example 56 (30 mg, 37%) was prepared in a manner similar to that in Example 14 step 5 from tert-butyl (R)-(2-(((5-cyclopropyl-3-fluoropyridin-2-yl)methyl)(l-methoxypropan-2-yl)carbamoyl)-6,8-dihydro-1H-furo[3,4-d]pyrrolo[3,2-b]pyridin-5-yl)carbamate. 1H NMR (400 MHz, DMSO-d6) δ 11.47 (s, 1H), 8.23 (s, 1H), 7.33 (d, J=11.6 Hz, 1H), 6.61-6.27 (m, 1H), 5.50 (s, 2H), 5.10 (br s, 2H), 5.05-4.41 (m, 5H), 3.56 (dd, J=7.4, 9.8 Hz, 1H), 3.37 (dd, J=5.4, 10.0 Hz, 1H), 3.17 (s, 3H), 2.03-1.94 (m, 1H), 1.07-1.27 (m, 3H), 1.05-0.96 (m, 2H), 0.77 (d, J=4.9 Hz, 2H). LC-MS $(M+H)^+$=440.2.

Example 57 & Example 58 & Example 59 & Example 60: 5-amino-N-methyl-N-((1R,4R)-1-methyl-7-(trifluoromethyl)isochroman-4-yl)-6,8-dihydro-1H-furo[3,4-d]pyrrolo[3,2-b]pyridine-2-carboxamide & 5-amino-N-methyl-N-((1S,4R)-1-methyl-7-(trifluoromethyl)isochroman-4-yl)-6,8-dihydro-1H-furo[3,4-d]pyrrolo[3,2-b]pyridine-2-carboxamide & 5-amino-N-methyl-N-((1S,4S)-1-methyl-7-(trifluoromethyl)isochroman-4-yl)-6,8-dihydro-1H-furo[3,4-d]pyrrolo[3,2-b]pyridine-2-carboxamide & 5-amino-N-methyl-N-((1R,4S)-1-methyl-7-(trifluoromethyl)isochroman-4-yl)-6,8-dihydro-1H-furo[3,4-d]pyrrolo[3,2-b]pyridine-2-carboxamide

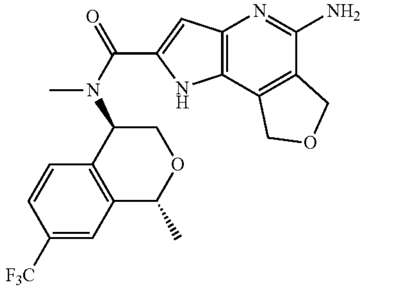

&

-continued

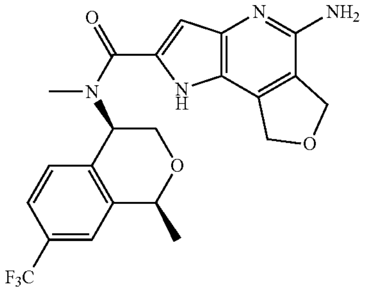

&

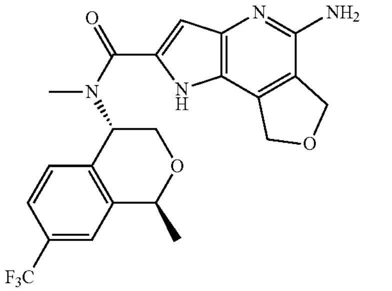

&

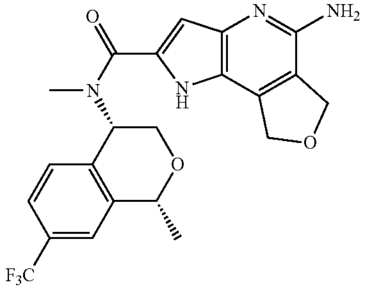

Step 1:
1-(2-bromo-5-(trifluoromethyl)phenyl)ethan-1-ol

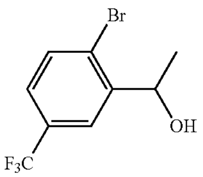

To a solution of 2-bromo-5-(trifluoromethyl)benzaldehyde (15.0 g, 59.3 mmol) in THF (150 mL) was added MeMgBr (3 M in $Et_2O$, 19.8 mL, 59.3 mmol) at 0° C. and the mixture was stirred at 0° C. for 1 h. The mixture was quenched with saturated $NH_4Cl$ (100 mL) and extracted with EtOAc (80 mL×3). The combined organic layer was washed with brine (100 mL), dried over $Na_2SO_4$, filtered and concentrated under reduced pressure. The residue was purified by silica gel chromatograph (PE/EtOAc=1/0 to 5/1) to give the title compound (12.0 g, 75% yield). $^1H$ NMR (400 MHz, $CDCl_3$) δ 7.90 (d, J=2.0 Hz, 1H), 7.65 (d, J=8.4 Hz, 1H), 7.39 (dd, J=8.4, 2.0 Hz, 1H), 5.32-5.23 (m, 1H), 2.03 (s, 1H), 1.51 (d, J=6.4 Hz, 3H).

Step 2: 2-(1-(allyloxy)ethyl)-1-bromo-4-(trifluoromethyl)benzene

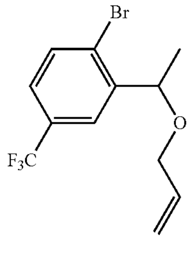 [SMILES: C=CCOC(C)c1cc(C(F)(F)F)ccc1Br]

The title compound (9.7 g, 70%) was prepared in a manner similar to that in Example 40 step 1 from 1-(2-bromo-5-(trifluoromethyl)phenyl)ethan-1-ol and allyl bromide. $^1$H NMR (400 MHz, $CDCl_3$) δ 7.81 (d, J=2.0 Hz, 1H), 7.65 (d, J=8.4 Hz, 1H), 7.39 (dd, J=8.4, 2.0 Hz, 1H), 5.98-5.85 (m, 1H), 5.33-5.17 (m, 2H), 4.93-4.85 (m, 1H), 3.97-3.77 (m, 2H), 1.44 (d, J=6.4 Hz, 3H).

Step 3: 1-methyl-4-methylene-7-(trifluoromethyl)isochromane

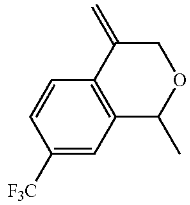 [SMILES: C=C1COC(C)c2cc(C(F)(F)F)ccc21]

The title compound (4.6 g, 64%) was prepared in a manner similar to that in Example 40 step 2 from 2-(1-(allyloxy)ethyl)-1-bromo-4-(trifluoromethyl)benzene. LC-MS $(M+H)^+$=229.1.

Step 4: 1-methyl-7-(trifluoromethyl)isochroman-4-one

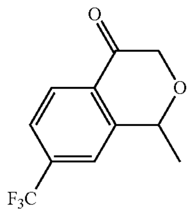 [SMILES: CC1OCC(=O)c2ccc(C(F)(F)F)cc21]

The title compound (3.3 g, 71%) was prepared in a manner similar to that in Example 40 step 3 from 1-methyl-4-methylene-7-(trifluoromethyl)isochromane. $^1$H NMR (400 MHz, $CDCl_3$) δ 8.17 (d, J=8.0 Hz, 1H), 7.69 (d, J=8.0 Hz, 1H), 7.53 (s, 1H), 5.03-4.94 (m, 1H), 4.57, 4.35 (ABq, J=17.2 Hz, 2H), 1.71 (d, J=6.8 Hz, 3H). LC-MS $(M+H)^+$=231.2.

Step 5: 1-methyl-7-(trifluoromethyl)isochroman-4-one Oxime

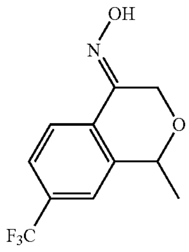

The title compound (0.75 g, 70%) was prepared in a manner similar to that in Example 40 step 4 from 1-methyl-7-(trifluoromethyl)isochroman-4-one. $^1$H NMR (400 MHz, $CDCl_3$) δ 8.03 (d, J=8.4 Hz, 1H), 7.56 (d, J=8.4 Hz, 1H), 7.44 (s, 1H), 5.13, 4.64 (ABq, J=17.0 Hz, 2H), 4.73 (q, J=6.5 Hz, 1H), 1.65 (d, J=6.4 Hz, 3H). LC-MS $(M+H)^+$=246.2.

Step 6: 1-methyl-7-(trifluoromethyl)isochroman-4-amine

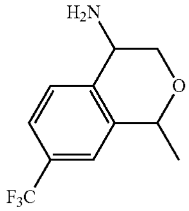 [SMILES: CC1OCC(N)c2ccc(C(F)(F)F)cc21]

The title compound (0.26 g, 79%) was prepared in a manner similar to that in Example 40 step 5 from 1-methyl-7-(trifluoromethyl)isochroman-4-one oxime. LC-MS $(M+H)^+$=232.1.

Step 7: tert-butyl (1-methyl-7-(trifluoromethyl)isochroman-4-yl)carbamate

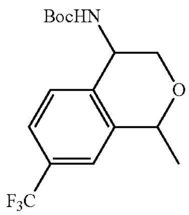 [SMILES: CC1OCC(NC(=O)OC(C)(C)C)c2ccc(C(F)(F)F)cc21]

The title compound (0.30 g, 87%) was prepared in a manner similar to that in Example 40 step 6 from 1-methyl-7-(trifluoromethyl)isochroman-4-amine. LCMS $(M+H-tBu)^+$=276.2.

Step 8: tert-butyl methyl(1-methyl-7-(trifluoromethyl)isochroman-4-yl)carbamate

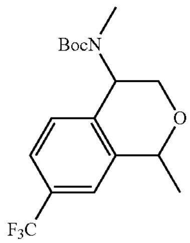 [SMILES: CC1OCC(N(C)C(=O)OC(C)(C)C)c2ccc(C(F)(F)F)cc21]

The title compound (0.30 g, 87%) was prepared in a manner similar to that in Example 40 step 7 from tert-butyl (1-methyl-7-(trifluoromethyl)isochroman-4-yl)carbamate. LCMS $(M+H-tBu)^+$=290.2.

Step 9: N,1-dimethyl-7-(trifluoromethyl)isochroman-4-amine Hydrochloride

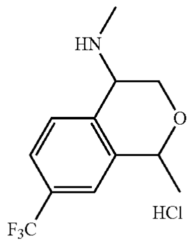 [SMILES: CNC1COC(C)c2cc(C(F)(F)F)ccc21 ; Cl]

The title compound (0.20 g, 94%) was prepared in a manner similar to that in Example 40 step 8 from tert-butyl methyl(1-methyl-7-(trifluoromethyl)isochroman-4-yl)carbamate. LC-MS $(M+H)^+$=246.1.

Step 10: tert-butyl (2-(methyl(1-methyl-7-(trifluoromethyl)isochroman-4-yl)carbamoyl)-6,8-dihydro-1H-furo[3,4-d]pyrrolo[3,2-b]pyridin-5-yl)carbamate

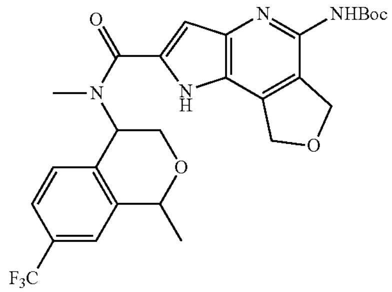 [SMILES: CC1OCC(N(C)C(=O)c2cc3nc(NC(=O)OC(C)(C)C)c4c(c3[nH]2)COC4)c2ccc(C(F)(F)F)cc21]

The title compound (0.15 g, 51%) was prepared in a manner similar to that in Example 40 step 9 from 5-((tert-butoxycarbonyl)amino)-6,8-dihydro-1H-furo[3,4-d]pyrrolo[3,2-b]pyridine-2-carboxylic acid and N,1-dimethyl-7-(trifluoromethyl)isochroman-4-amine hydrochloride. LC-MS $(M+H)^+$=547.4.

Step 11: 5-amino-N-methyl-N-((1R,4R)-1-methyl-7-(trifluoromethyl)isochroman-4-yl)-6,8-dihydro-1H-furo[3,4-d]pyrrolo[3,2-b]pyridine-2-carboxamide & 5-amino-N-methyl-N-((1S,4R)-1-methyl-7-(trifluoromethyl)isochroman-4-yl)-6,8-dihydro-1H-furo[3,4-d]pyrrolo[3,2-b]pyridine-2-carboxamide & 5-amino-N-methyl-N-((1S,4S)-1-methyl-7-(trifluoromethyl)isochroman-4-yl)-6,8-dihydro-1H-furo[3,4-d]pyrrolo[3,2-b]pyridine-2-carboxamide & 5-amino-N-methyl-N-((1R,4S)-1-methyl-7-(trifluoromethyl)isochroman-4-yl)-6,8-dihydro-1H-furo[3,4-d]pyrrolo[3,2-b]pyridine-2-carboxamide Example 57 (3 mg, 2%), Example 58 (13 mg, 8%). Example 59 (9 mg, 6%) and Example 60 (5 mg, 3%) were prepared in a manner similar to that in Example 40 step 10 from tert-butyl (2-(methyl(1-methyl-7-(trifluoromethyl)isochroman-4-yl)carbamoyl)-6,8-dihydro-1H-furo[3,4-d]pyrrolo[3,2-b]pyridin-5-yl)carbamate, and the isomers were separated by chiral SFC.

Analytical chiral-SFC condition 1: Column: CHIRALPAK AD-3; Column size: 4.6×50 mm, 3 μm; Mobile phase: (ethanol containing 0.2% 7 M methanolic $NH_3$):$CO_2$ 1:1 isocratic; Flow: 4 mL/min; Temperature: 35° C.; back pressure: 1800 psi.

Analytical chiral-SFC condition 2: Column: CHIRALPAK OJ-3; Column size: 4.6×50 mm, 3 μm; Mobile phase: Mobile phase: (ethanol containing 0.2% 7 M methanolic $NH_3$):$CO_2$, 1:19 for 0.2 min, 1:19 to 1:1 in 1.0 min, 1:1 for 1 min, 1:1 to 1:19 in 0.4 min; Flow: 3.4 mL/min; Temperature: 35° C.; back pressure: 1800 psi.

Example 57; Analytical SFC (Condition 1) tR=0.64 min. 1H NMR (400 MHz, DMSO-d6) δ 11.68 (s, 1H), 7.76-7.61 (m, 2H), 7.45 (d, J=8.0 Hz, 1H), 6.90-6.60 (m, 1H), 5.99-5.78 (m, 1H), 5.64 (br s, 2H), 5.22 (s, 2H), 5.10-4.92 (m, 3H), 4.36-4.17 (m, 1H), 4.08-3.93 (m, 1H), 3.24-2.76 (m, 3H), 1.57 (d, J=6.0 Hz, 3H). LC-MS $(M+H)^+$=447.2.

Example 58: Analytical SFC (Condition 2) tR=1.18 min. $^1$H NMR (400 MHz, DMSO-d6) δ 11.93 (s, 1H), 7.71-7.65 (m, 2H), 7.55-7.42 (m, 1H), 6.80-6.62 (m, 1H), 6.38-6.05 (m, 2H), 5.85-5.60 (m, 1H), 5.20 (br s, 2H), 4.95 (s, 2H), 4.86-4.78 (m, 1H), 4.29-4.17 (m, 1H), 4.13-4.02 (m, 1H), 3.17-2.76 (m, 3H), 1.59 (d, J=6.4 Hz, 3H). LC-MS $(M+H)^+$=447.2.

Example 59: Analytical SFC (Condition 2) tR=1.38 min. 1H NMR (400 MHz, DMSO-d6) δ 12.50 (s, 1H), 7.74-7.61 (m, 2H), 7.58-7.17 (m, 3H), 6.92-6.63 (m, 1H), 5.90-5.54 (m, 1H), 5.26 (s, 2H), 4.99 (s, 3H), 4.30-4.14 (m, 1H), 4.03-3.89 (m, 1H), 3.07-2.68 (m, 2H), 2.75-2.68 (m, 1H), 1.51 (d, J=5.6 Hz, 3H). LC-MS $(M+H)^+$=447.2.

Example 60: Analytical SFC (Condition 1) tR=1.32 min. $^1$H NMR (400 MHz, DMSO-d6) δ 11.69 (s, 1H), 7.71-7.64 (m, 2H), 7.48 (s, 1H), 6.72 (s, 1H), 5.89-5.60 (m, 3H), 5.21-5.13 (m, 2H), 4.98-4.90 (m, 2H), 4.86-4.78 (m, 1H), 4.30-4.01 (m, 2H), 3.19-2.80 (m, 3H), 1.59 (d, J=6.8 Hz, 3H). LC-MS $(M+H)^+$=447.2.

Example 61 & Example 62: (S)-5-amino-N-((5-bromo-3-fluoropyridin-2-yl)methyl)-N-(1-(pyrazin-2-yl)ethyl)-6,8-dihydro-1H-furo[3,4-d]pyrrolo[3,2-b]pyridine-2-carboxamide & (R)-5-amino-N-((5-bromo-3-fluoropyridin-2-yl)methyl)-N-(1-(pyrazin-2-yl)ethyl)-6,8-dihydro-1H-furo[3,4-d]pyrrolo[3,2-b]pyridine-2-carboxamide

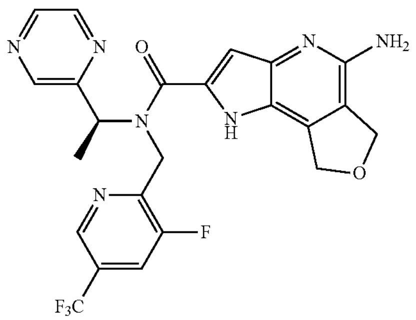

&

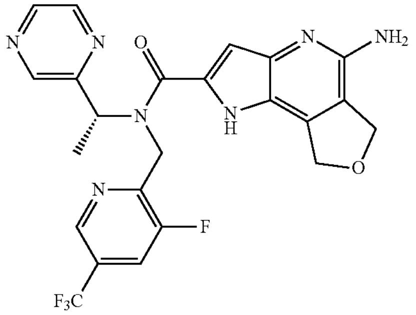

Step 1: N-((5-bromo-3-fluoropyridin-2-yl)methyl)-1-(pyrazin-2-yl)ethan-1-amine

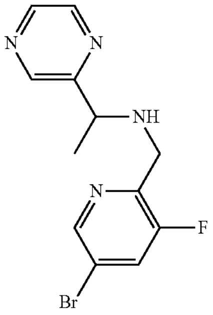 [SMILES: CC(NCc1ncc(Br)cc1F)c1cnccn1]

The title compound (90 mg, 40%) was prepared in a manner similar to that in Example 17 & 18 step 1 from (5-bromo-3-fluoropyridin-2-yl)methanamine and 1-(pyrazin-2-yl)ethan-1-one. LC-MS $(M+H)^+$=311.0.

Step 2: tert-butyl (2-(((5-bromo-3-fluoropyridin-2-yl)methyl)(1-(pyrazin-2-yl)ethyl)carbamoyl)-6,8-dihydro-1H-furo[3,4-d]pyrrolo[3,2-b]pyridin-5-yl)carbamate

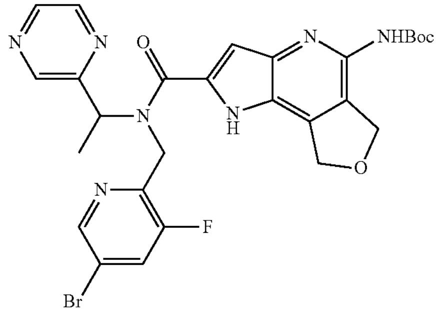 [SMILES: CC(c1cnccn1)N(Cc1ncc(Br)cc1F)C(=O)c1cc2nc(NC(=O)OC(C)(C)C)c3c(c2[nH]1)COC3]

The title compound (120 mg, 76%) was prepared in a manner similar to that in Example 17 & 18 step 2 from 5-((tert-butoxycarbonyl)amino)-6,8-dihydro-1H-furo[3,4-d]pyrrolo[3,2-b]pyridine-2-carboxylic acid and N-((5-bromo-3-fluoropyridin-2-yl)methyl)-1-(pyrazin-2-yl)ethan-1-amine. LC-MS $(M+H)^+$=612.2.

Step 3: (S)-5-amino-N-((5-bromo-3-fluoropyridin-2-yl)methyl)-N-(1-(pyrazin-2-yl)ethyl)-6,8-dihydro-1H-furo[3,4-d]pyrrolo[3,2-b]pyridine-2-carboxamide & (R)-5-amino-N-((5-bromo-3-fluoropyridin-2-yl)methyl)-N-(1-(pyrazin-2-yl)ethyl)-6,8-dihydro-1H-furo[3,4-d]pyrrolo[3,2-b]pyridine-2-carboxamide Example 61 (4 mg, 4%) and Example 62 (2 mg, 2%) were prepared in a manner similar to that in in Example 17 & 18 step 3 from tert-butyl (2-(((5-bromo-3-fluoropyridin-2-yl)methyl)(1-(pyrazin-2-yl)ethyl)carbamoyl)-6,8-dihydro-1H-furo[3,4-d]pyrrolo[3,2-b]pyridin-5-yl)carbamate, and the enantiomers were separated by chiral SFC.

Analytical chiral-SFC condition as below. Column: CHIRALPAK IG-3; Column size: 4.6×50 mm, 3 μm; Mobile phase: 14 mM $NH_3$ in isopropanol:$CO_2$ 3:2 isocratic; Flow: 4 mL/min; Temperature: 35° C.; back pressure: 1800 psi.

Example 61: Analytical SFC tR=1.28 min. $^1$H NMR (400 MHz, DMSO-d6) δ 11.55 (br s, 1H) 8.73 (s, 1H) 8.58-8.48 (m, 2H) 8.45 (s, 1H), 8.11 (d, J=9.5 Hz, 1H) 6.40 (br s, 1H) 5.90 (br s, 1H) 5.51 (s, 2H), 4.77-5.22 (m, 6H), 1.73-1.57 (m, 3H). LCMS $(M+H)^+$=512.0.

Example 62: Analytical SFC tR=2.17 min. $^1$H NMR (400 MHz, DMSO-d6) δ 11.55 (br s, 1H) 8.73 (s, 1H) 8.58-8.48 (m, 2H) 8.45 (s, 1H), 8.11 (d, J=9.5 Hz, 1H) 6.40 (br s, 1H) 5.90 (br s, 1H) 5.51 (s, 2H), 4.79-5.22 (m, 6H), 1.73-1.57 (m, 3H). LCMS $(M+H)^+$=512.0.

Example 63 & Example 64: (S)-5-amino-N-(7-bromoisochroman-4-yl)-N-methyl-6,8-dihydro-1H-furo[3,4-d]pyrrolo[3,2-b]pyridine-2-carboxamide & (R)-5-amino-N-(7-bromoisochroman-4-yl)-N-methyl-6,8-dihydro-1H-furo[3,4-d]pyrrolo[3,2-b]pyridine-2-carboxamide

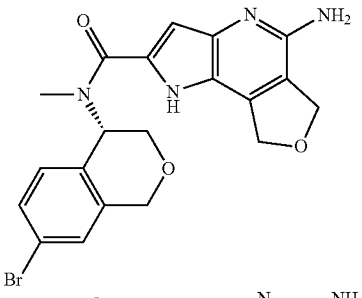

&

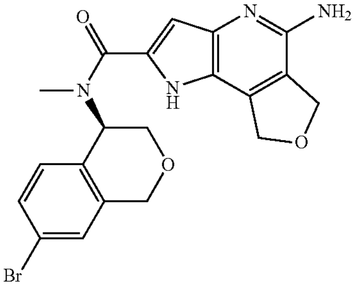

Step 1: 7-bromoisochroman-4-ol

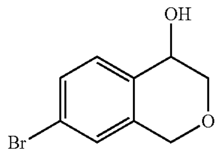

To a mixture of 7-bromoisochroman-4-one (500 mg, 2.2 mmol) in MeOH (20 mL) was added $NaBH_4$ (91 mg, 2.4 mmol) at 0° C. and the mixture was stirred at room temperature for 30 min. The mixture was diluted with water (10 mL) and MeOH was evaporated under reduced pressure. The mixture was extracted with EtOAc (20 mL). The organic layer was washed with brine (10 mL), dried over $Na_2SO_4$, filtered and concentrated to give the title compound (500 mg, 99%). LC-MS $(M+H)^+$=229.1.

Step 2:7-bromo-4-chloroisochromane

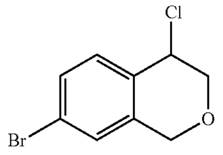

A mixture of 7-bromoisochroman-4-ol (500 mg, 2.2 mmol) and $SOCl_2$ (524 mg, 4.4 mmol) in THF (15 mL) was stirred at 60° C. for 2 h. The mixture was cooled to room temperature and concentrated under reduced pressure. The residue was purified by silica gel chromatograph (PE/EtOAc=20/1) to give the title compound (300 mg, 55%). LC-MS $(M+H)^+$=247.1.

Step 3: 7-bromo-N-methylisochroman-4-amine

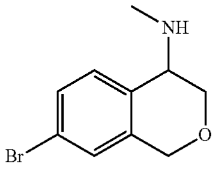

A mixture of 7-bromo-4-chloroisochromane (150 mg, 0.6 mmol), methylamine hydrochloride (122 mg, 1.8 mmol), $K_2CO_3$ (248 mg, 1.8 mmol) and KI (298.8 mg, 1.8 mmol) in DMAC (10 mL) was stirred at 100° C. for 15 hr and then cooled to room temperature. The mixture was diluted with EtOAc (20 mL) then successively washed with water (10 mL) and brine (10 mL), dried over $Na_2SO_4$, filtered and concentrated under reduced pressure. The residue was purified by silica gel chromatograph (DCM/MeOH=20/1) to give the title compound (80 mg, 55%). LC-MS $(M+H)^+$=242.1.

Step 4: 5-amino-N-(7-bromoisochroman-4-yl)-N-methyl-1-((2-(trimethylsilyl)ethoxy)methyl)-6,8-dihydro-1H-furo[3,4-d]pyrrolo[3,2-b]pyridine-2-carboxamide

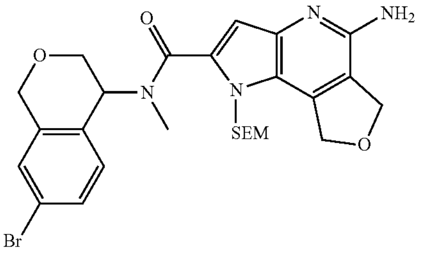 [SMILES: CN(C(=O)c1cc2nc(N)c3c(c2n1COCC[Si](C)(C)C)COC3)C1COCc2cc(Br)ccc21]

The title compound (110 mg, 58%) was prepared in a manner similar to that in Example 44 step 6 from 5-amino-1-((2-(trimethylsilyl)ethoxy)methyl)-6,8-dihydro-1H-furo[3,4-d]pyrrolo[3,2-b]pyridine-2-carboxylic acid and 7-bromo-N-methylisochroman-4-amine. LC-MS $(M+H)^+$=573.2.

Step 5: (S)-5-amino-N-(7-bromoisochroman-4-yl)-N-methyl-6,8-dihydro-1H-furo[3,4-d]pyrrolo[3,2-b]pyridine-2-carboxamide & (R)-5-amino-N-(7-bromoisochroman-4-yl)-N-methyl-6,8-dihydro-1H-furo[3,4-d]pyrrolo[3,2-b]pyridine-2-carboxamide Example 63 (20 mg, 24%) and Example 64 (31 mg, 37%) were prepared in a manner similar to that in Example 44 step 7 from 5-amino-N-(7-bromoisochroman-4-yl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: CHIRALPAK AS-H; Column size: 20×250 mm, 5 μm; Mobile phase: (0.1% $Et_2NH$ in MeOH):$CO_2$ 1:2 isocratic; Flow: 40 mL/min; Temperature: 35° C.; back pressure: 1450 psi.

Example 63: Analytical SFC tR=7.00 min. $^1H$ NMR (400 MHz, DMSO-d6) δ 11.59 (s, 1H), 7.58-7.36 (m, 2H), 7.31-7.05 (m, 1H), 6.95-6.55 (m, 1H), 5.84-5.36 (m, 3H), 5.30-5.02 (m, 2H), 5.00-4.55 (m, 4H), 4.20-3.84 (m, 2H), 3.17-2.68 (m, 3H). LCMS $(M+H)^+$=443.2.

Example 64: Analytical SFC tR=8.07 min. $^1H$ NMR (400 MHz, DMSO-d6) δ 11.59 (s, 1H), 7.58-7.36 (m, 2H), 7.31-7.05 (m, 1H), 6.95-6.55 (m, 1H), 5.84-5.36 (m, 3H), 5.30-5.02 (m, 2H), 5.00-4.55 (m, 4H), 4.20-3.84 (m, 2H), 3.17-2.68 (m, 3H). LCMS $(M+H)^+$=443.2.

Example 65: 5-amino-N-cyclopentyl-N-((5-cyclopropyl-3-fluoropyridin-2-yl)methyl)-6,8-dihydro-1H-furo[3,4-d]pyrrolo[3,2-b]pyridine-2-carboxamide

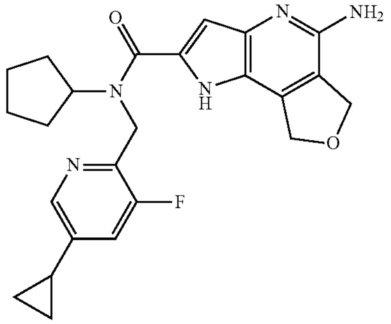 [SMILES: Nc1nc2cc(C(=O)N(Cc3ncc(C4CC4)cc3F)C3CCCC3)[nH]c2c2c1COC2]

Step 1: N-((5-cyclopropyl-3-fluoropyridin-2-yl)methyl)cyclopentanamine

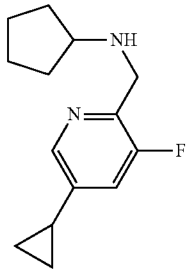 [SMILES: Fc1cc(C2CC2)cnc1CNC1CCCC1]

The title compound (60 mg, 85%) was prepared in a manner similar to that in Example 5 step 1 from 5-cyclopropyl-3-fluoropicolinaldehyde and cyclopentanamine. LC-MS $(M+H)^+$=235.2.

Step 2: 5-amino-N-cyclopentyl-N-((5-cyclopropyl-3-fluoropyridin-2-yl)methyl)-1-((2-(trimethylsilyl)ethoxy)methyl)-6,8-dihydro-1H-furo[3,4-d]pyrrolo[3,2-b]pyridine-2-carboxamide

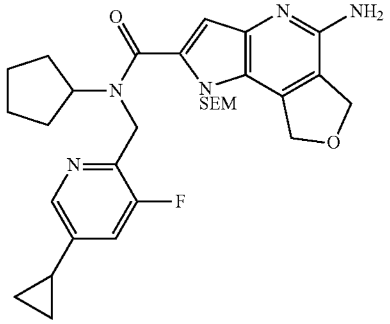 [SMILES: C[Si](C)(C)CCOCn1c(C(=O)N(Cc2ncc(C3CC3)cc2F)C2CCCC2)cc2nc(N)c3c(c21)COC3]

The title compound (120 mg, 83%) was prepared in a manner similar to that in Example 44 step 6 from 5-amino-1-((2-(trimethylsilyl)ethoxy)methyl)-6,8-dihydro-1H-furo[3,4-d]pyrrolo[3,2-b]pyridine-2-carboxylic acid and N-((5-cyclopropyl-3-fluoropyridin-2-yl)methyl)cyclopentanamine. LC-MS $(M+H)^+$=566.4.

Step 3: 5-amino-N-cyclopentyl-N-((5-cyclopropyl-3-fluoropyridin-2-yl)methyl)-6,8-dihydro-1H-furo[3,4-d]pyrrolo[3,2-b]pyridine-2-carboxamide Example 65 (62 mg, 67%) was prepared in a manner similar to that in Example 44 step 7 from 5-amino-N-cyclopentyl-N-((5-cyclopropyl-3-fluoropyridin-2-yl)methyl)-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.49 (s, 1H), 8.22 (s, 1H), 7.33 (d, J=11.6, 1H), 6.38 (s, 1H), 5.51 (s, 2H), 5.09 (s, 2H), 4.98-4.65 (m, 5H), 2.05-1.77 (m, 3H), 1.73-1.42 (m, 6H), 1.56 (d, J=55.7, 6H), 1.07-0.95 (m, 2H), 0.84-0.73 (m, 2H). LC-MS $(M+H)^+$=436.4.

Example 66: 5-amino-N-((5-cyclopropyl-3-fluoropyridin-2-yl)methyl)-N-isopropyl-6,8-dihydro-1H-furo[3,4-d]pyrrolo[3,2-b]pyridine-2-carboxamide

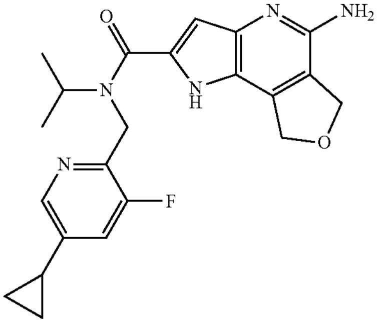 [SMILES: CC(C)N(Cc1ncc(C2CC2)cc1F)C(=O)c1cc2nc(N)c3c(c2[nH]1)COC3]

Step 1: N-((5-cyclopropyl-3-fluoropyridin-2-yl) methyl)propan-2-amine

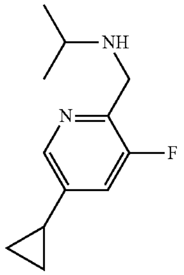

To a solution of 5-cyclopropyl-3-fluoropicolinaldehyde (60 mg, 0.36 mmol) and isopropylamine (32 mg, 0.54 mmol) in DCM (5 mL) was added $NaBH(OAc)_3$ (154 mg, 0.73 mmol). The mixture was stirred at room temperature for 2 h and then slowly added to sat. $NaHCO_3$ (10 mL). The mixture was extracted with EtOAc (10 mL). The organic layer was washed with brine (10 mL), dried over $Na_2SO_4$, filtered and concentrated under reduced pressure. The residue was purified by silica gel chromatograph (DCM: MeOH=10:1) to give the title compound (57 mg, 75%). $^1H$ NMR (400 MHz, DMSO-d6) δ 8.32-8.15 (m, 1H), 7.28 (dd, J=11.3, 1.6 Hz, 1H), 3.77 (d, J=1.8 Hz, 2H), 2.69 (hept, J=6.2 Hz, 1H), 2.05 (br s, 1H), 2.02-1.91 (m, 1H), 1.11-0.91 (m, 8H), 0.88-0.69 (m, 2H). LC-MS $(M+H)^+$=209.1.

Step 2: 5-amino-N-((5-cyclopropyl-3-fluoropyridin-2-yl)methyl)-N-isopropyl-1-((2-(trimethylsilyl) ethoxy)methyl)-6,8-dihydro-1H-furo[3,4-d]pyrrolo [3,2-b]pyridine-2-carboxamide

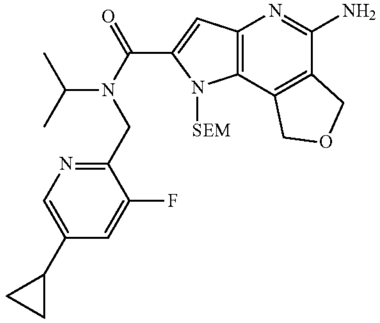 [SMILES: CC(C)N(Cc1ncc(C2CC2)cc1F)C(=O)c1cc2nc(N)c3c(c2n1COCC[Si](C)(C)C)COC3]

To a solution of N-((5-cyclopropyl-3-fluoropyridin-2-yl) methyl)propan-2-amine (57 mg, 0.27 mmol) in THF (5 mL) was added 5-amino-1-((2-(trimethylsilyl)ethoxy)methyl)-6, 8-dihydro-1H-furo[3,4-d]pyrrolo[3,2-b]pyridine-2-carboxylic acid (80 mg, 0.23 mmol), BOPCl (88 mg, 0.35 mmol) and DIPEA (148 mg, 1.15 mmol). The mixture was stirred for 2 h at 70° C. and then cooled to room temperature. The mixture was poured into water (20 mL) and extracted with EtOAc (10×2 mL). The combined organic layer was washed with brine (10 mL), dried over $Na_2SO_4$, filtered and concentrated under reduced pressure. The residue was purified by silica gel chromatography (DCM:MeOH=20:1) to give the title compound (60 mg, 41%). LC-MS $(M+H)^+$=540.3.

Step 3: 5-amino-N-((5-cyclopropyl-3-fluoropyridin-2-yl)methyl)-N-isopropyl-6,8-dihydro-1H-furo[3,4-d]pyrrolo[3,2-b]pyridine-2-carboxamide To a solution of 5-amino-N-((5-cyclopropyl-3-fluoropyridin-2-yl)methyl)-N-isopropyl-1-((2-(trimethylsilyl)ethoxy) methyl)-6,8-dihydro-1H-furo[3,4-d]pyrrolo[3,2-b]pyridine-2-carboxamide (60 mg, 0.11 mmol) in DCM (1 mL) was added TFA (1 mL). The mixture was stirred for 3 h at room temperature then concentrated under reduced pressure. The residue was re-dissolved in MeOH (1 mL) and $K_2CO_3$ (46 mg, 0.33 mmol) was added. The mixture was stirred at 40° C. for 1 h, and then cooled to room temperature. The mixture was concentrated under reduced pressure. The residue was purified by prep-HPLC to give Example 66 (28 mg, 61%). $^1H$ NMR (400 MHz, DMSO-d6) δ 11.47 (s, 1H), 8.23 (s, 1H), 7.33 (d, J=11.7 Hz, 1H), 6.64-6.17 (m, 1H), 5.58-5.41 (m, 2H), 5.17-5.06 (m, 2H), 4.95-4.49 (m, 5H), 2.07-1.91 (m, 1H), 1.36-1.08 (m, 6H), 1.07-0.94 (m, 2H), 0.83-0.73 (m, 2H). LC-MS $(M+H)^+$=410.4.

Example 67: (R)-5-amino-N-(sec-butyl)-N-((5-cyclopropyl-3-fluoropyridin-2-yl)methyl)-6,8-dihydro-1H-furo[3,4-d]pyrrolo[3,2-b]pyridine-2-carboxamide

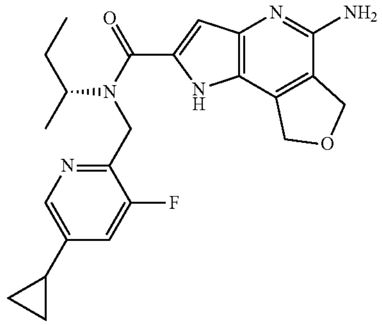 [SMILES: CC[C@@H](C)N(Cc1ncc(C2CC2)cc1F)C(=O)c1cc2nc(N)c3c(c2[nH]1)COC3]

Step 1: (R)—N-((5-cyclopropyl-3-fluoropyridin-2-yl)methyl)butan-2-amine

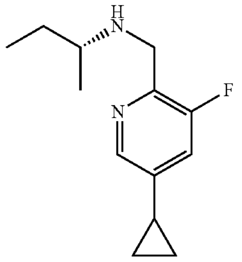 [SMILES: CC[C@@H](C)NCc1ncc(C2CC2)cc1F]

The title compound (118 mg, 73%) was prepared in a manner similar to that in Example 66 step 1 from 5-cyclopropyl-3-fluoropicolinaldehyde and (R)-butan-2-amine hydrochloride. LC-MS $(M+H)^+$=223.2.

Step 2: (R)-5-amino-N-(sec-butyl)-N-((5-cyclopropyl-3-fluoropyridin-2-yl)methy)-1-((2-(trimethylsilyl)ethoxy)methyl)-6,8-dihydro-1H-furo[3,4-d]pyrrolo[3,2-b]pyridine-2-carboxamide

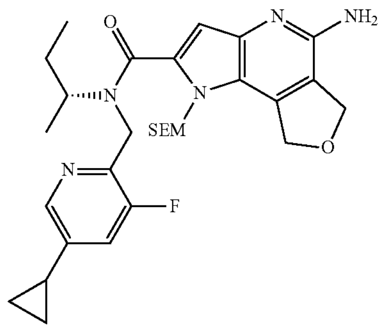 [SMILES: CC[C@@H](C)N(Cc1ncc(C2CC2)cc1F)C(=O)c1cc2nc(N)c3c(c2n1COCC[Si](C)(C)C)COC3]

The title compound (145 mg, 61%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and (R)—N-((5-cyclopropyl-3-fluoropyridin-2-yl)methyl)butan-2-anine. LC-MS $(M+H)^+$=554.3.

Step 3: (R)-5-amino-N-(sec-butyl)-N-((5-cyclopropyl-3-fluoropyridin-2-yl)methyl)-6,8-dihydro-1H-furo[3,4-d]pyrrolo[3,2-b]pyridine-2-carboxamide Example 67 (24 mg, 22%) was prepared in a manner similar to that in Example 66 step 3 from (R)-5-amino-N-(sec-butyl)-N-((5-cyclopropyl-3-fluoropyridin-2-yl)methyl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ: 11.48 (s, 1H), 8.22 (s, 1H), 7.32 (d, J=11.4 Hz, 1H), 6.42 (s, 1H), 5.51 (s, 2H), 5.10 (s, 2H), 4.98-4.35 (m, 5H), 2.02-1.92 (m, 1H), 1.75-1.40 (m, 2H), 1.30-1.05 (m, 3H), 1.05-0.95 (m, 2H), 0.85-0.73 (m, 5H). LC-MS $(M+H)^+$=424.4.

Example 68: (R)-5-amino-N,6-dimethyl-N—((S)-7-(trifluoromethyl)isochroman-4-yl)-6,8-dihydro-1H-furo[3,4-d]pyrrolo[3,2-b]pyridine-2-carboxamide

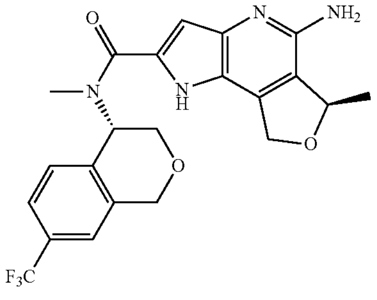 [SMILES: C[C@H]1OCc2c1c(N)nc1cc(C(=O)N(C)[C@@H]3COCc4cc(C(F)(F)F)ccc43)[nH]c21]

Step 1: tert-butyl (S)-(7-(trifluoromethyl)isochroman-4-yl)carbamate

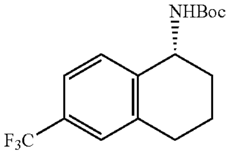

A racemate of tert-butyl (7-(trifluoromethyl)isochroman-4-yl)carbamate (13.0 g, 41.0 mmol) was separated by SFC to give the title compound (5.0 g, 38%).

Analytical chiral-SFC condition as below. Column: CHIRALPAK IC-3; Column size: 4.6×100 mm, 3 μm; Mobile phase: 14 mM $NH_3$ in methanol:$CO_2$, 1:9 for 0.2 min, 1:9 to 1:1 in 2.2 min, 1:1 for 1 min; Flow: 3.4 mL/min; Temperature: 35° C.; back pressure: 2000 psi.

tert-butyl (S)-(7-(trifluoromethyl)isochroman-4-yl)carbamate: Analytical SFC tR=1.18 min. 1H NMR (400 MHz, DMSO-d6) δ 7.59 (d, J=8.0 Hz, 1H), 7.60-7.44 (m, 1H), 7.35 (d, J=8.0 Hz, 1H), 4.82-4.64 (m, 3H), 3.93 (dd, J=5.2, 11.0 Hz, 1H), 3.63 (dd, J=7.6, 11.0 Hz, 1H), 1.43 (s, 9H). LC-MS $(M+H\text{-}t\text{-}Bu)^+$=262.0.

tert-butyl (R)-(7-(trifluoromethyl)isochroman-4-yl)carbamate: Analytical SFC tR=0.66 min.

Step 2: tert-butyl (S)-methyl(7-(trifluoromethyl)isochroman-4-yl)carbamate

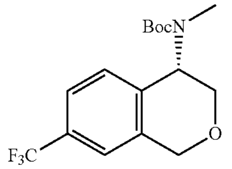 [SMILES: CN(C(=O)OC(C)(C)C)[C@@H]1COCc2cc(C(F)(F)F)ccc21]

The title compound (1.5 g, 72%) was prepared in a manner similar to that in Example 39 & 40 step 7 from tert-butyl (S)-(7-(trifluoromethyl)isochroman-4-yl)carbamate. LCMS $(M+H\text{-}tBu)^+$=276.1.

Step 3: (S)—N-methyl-7-(trifluoromethyl)isochroman-4-amine Hydrochloride

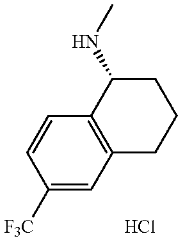 [SMILES: CN[C@@H]1CCCc2cc(C(F)(F)F)ccc21 ; Cl]

The title compound (1.4 g, 100%) was prepared in a manner similar to that in Example 39 & 40 step 8 from tert-butyl (S)-methyl(7-(trifluoromethyl)isochroman-4-yl) carbamate. LC-MS $(M+H)^+$=232.0.

Step 4: (R)-5-amino-N,6-dimethyl-N—((S)-7-(trifluoromethyl)isochroman-4-yl)-6,8-dihydro-1H-furo[3,4-d]pyrrolo[3,2-b]pyridine-2-carboxamide Example 68 (46 mg, 21%) was prepared in a manner similar to that in Example 2 step 3 from (S)—N-methyl-7-(trifluoromethyl)isochroman-4-amine hydrochloride and (R)-5-amino-6-methyl-6,8-dihydro-1H-furo[3,4-d]pyrrolo[3,2-b]pyridine-2-carboxylic acid. $^1$H NMR (400 MHz, DMSO-d6) δ 11.61 (s, 1H), 7.74-7.38 (m, 3H), 6.72 (brs, 1H), 5.80 (s, 1H), 5.50 (s, 2H), 5.37-5.30 (m, 1H), 5.17 (dd. J=13.9, 3.4 Hz, 1H), 5.06 (d, J=13.8 Hz, 1H), 4.91 (d, J=15.6 Hz, 1H), 4.74 (d, J=15.6 Hz, 1H), 4.10 (s, 2H), 3.06 (brs, 3H), 1.36 (d, J=6.1 Hz, 3H). LC-MS $(M+H)^+$=447.4.

Example 69: 5-amino-N-cyclobutyl-N-((5-cyclopropyl-3-fluoropyridin-2-yl)methyl)-6,8-dihydro-1H-furo[3,4-d]pyrrolo[3,2-b]pyridine-2-carboxamide

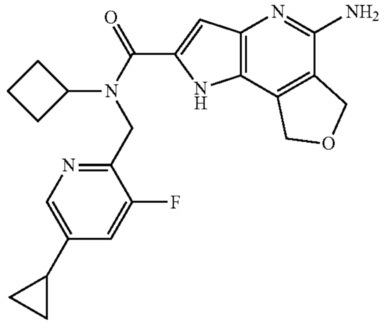 [SMILES: Nc1nc2cc(C(=O)N(Cc3ncc(C4CC4)cc3F)C3CCC3)[nH]c2c2c1COC2]

Step 1: N-((5-cyclopropyl-3-fluoropyridin-2-yl)methyl)cyclobutanamine

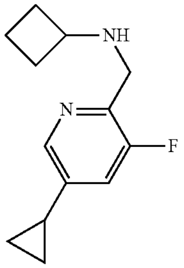 [SMILES: Fc1cc(C2CC2)cnc1CNC1CCC1]

The title compound (20 mg, 15%) was prepared in a manner similar to that in Example 66 step 1 from 5-cyclopropyl-3-fluoropicolinaldehyde and cyclobutylamine. LC-MS $(M+H)^+$=221.2.

Step 2: 5-amino-N-cyclobutyl-N-((5-cyclopropyl-3-fluoropyridin-2-yl)methyl)-1-((2-(trimethylsilyl)ethoxy)methyl)-6,8-dihydro-1H-furo[3,4-d]pyrrolo[3,2-b]pyridine-2-carboxamide

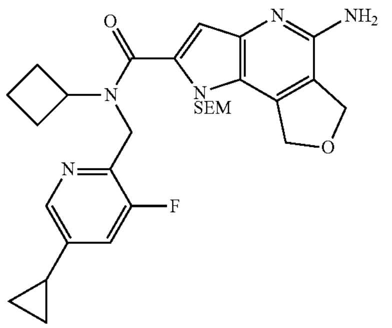 [SMILES: C[Si](C)(C)CCOCn1c(C(=O)N(Cc2ncc(C3CC3)cc2F)C2CCC2)cc2nc(N)c3c(c21)COC3]

The title compound (20 mg, 40%) was prepared in a manner similar to that in Example 66 step 2 from N-((5-cyclopropyl-3-fluoropyridin-2-yl)methyl)cyclobutanamine and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=552.3.

Step 3: 5-amino-N-cyclobutyl-N-((5-cyclopropyl-3-fluoropyridin-2-yl)methyl)-6,8-dihydro-1H-furo[3,4-d]pyrrolo[3,2-b]pyridine-2-carboxamide Example 69 (3 mg, 22%) was prepared in a manner similar to that in Example 66 step 3 from 5-amino-N-cyclobutyl-N-((5-cyclopropyl-3-fluoropyridin-2-yl)methyl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ 11.51 (s, 1H), 8.20 (s, 1H), 7.33 (d, J=11.6 Hz, 1H), 6.42 (s, 1H), 5.54 (s, 2H), 5.20-5.07 (m, 2H), 5.00-4.66 (m, 5H), 2.24-2.04 (m, 4H), 2.02-1.92 (m, 1H), 1.65-1.47 (m, 2H), 1.06-0.95 (m, 2H), 0.81-0.72 (m, 2H). LC-MS $(M+H)^+$=422.4.

Example 70: (R)-5-amino-N-((5-cyclopropyl-3-fluoropyridin-2-yl)methyl)-N-(3-methylbutan-2-yl)-6,8-dihydro-1H-furo[3,4-d]pyrrolo[3,2-b]pyridine-2-carboxamide

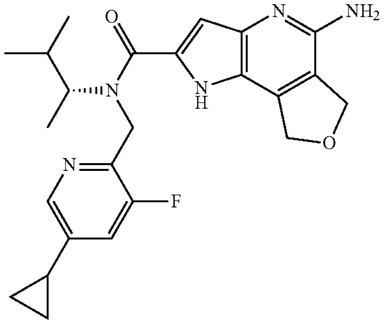 [SMILES: CC(C)[C@@H](C)N(Cc1ncc(C2CC2)cc1F)C(=O)c1cc2nc(N)c3c(c2[nH]1)COC3]

Step 1: (R)—N-((5-cyclopropyl-3-fluoropyridin-2-yl)methyl)-3-methylbutan-2-amine

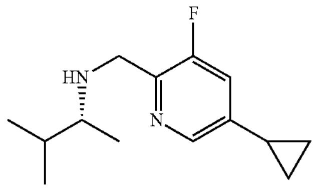 [SMILES: CC(C)[C@@H](C)NCc1ncc(C2CC2)cc1F]

The title compound (110 mg, 77%) was prepared in a manner similar to that in Example 66 step 1 from 5-cyclopropyl-3-fluoropicolinaldehyde and (R)-3-methylbutan-2-amine. LC-MS $(M+H)^+$=237.0.

Step 2: (R)-5-amino-N-((5-cyclopropyl-3-fluoropyridin-2-yl)methyl)-N-(3-methylbutan-2-yl)-1-((2-(trimethylsilyl)ethoxy)methyl)-6,8-dihydro-1H-furo[3,4-d]pyrrolo[3,2-b]pyridine-2-carboxamide

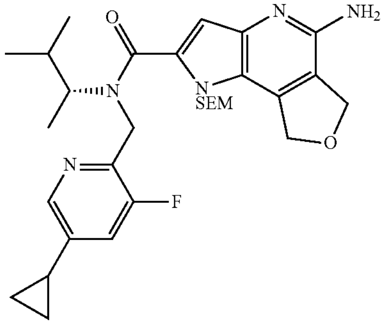 [SMILES: CC(C)[C@@H](C)N(Cc1ncc(C2CC2)cc1F)C(=O)c1cc2nc(N)c3c(c2n1COCC[Si](C)(C)C)COC3]

The title compound (40 mg, 33%) was prepared in a manner similar to that in Example 66 step 2 from (R)—N-((5-cyclopropyl-3-fluoropyridin-2-yl)methyl)-3-methylbutan-2-amine and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=568.3.

Step 3: (R)-5-amino-N-((5-cyclopropyl-3-fluoropyridin-2-yl)methyl)-N-(3-methylbutan-2-yl)-6,8-dihydro-1H-furo[3,4-d]pyrrolo[3,2-b]pyridine-2-carboxamide Example 70 (31 mg, 100%) was prepared in a manner similar to that in Example 66 step 3 from (R)-5-amino-N-((5-cyclopropyl-3-fluoropyridin-2-yl)methyl)-N-(3-methylbutan-2-yl)-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.46 (s, 1H), 8.21 (s, 1H), 7.30 (d, J=11.1 Hz, 1H), 6.58-6.34 (m, 1H), 5.50 (s, 2H), 5.20-3.87 (m, 7H), 2.06-1.86 (m, 2H), 1.45-0.94 (m, 5H), 0.91-0.73 (m, 8H). LC-MS $(M+H)^+$=438.4.

Example 71 & Example 72: (R)-5-amino-N—((R)-7-bromoisochroman-4-yl)-N,6-dimethyl-6,8-dihydro-1H-furo[3,4-d]pyrrolo[3,2-b]pyridine-2-carboxamide & (R)-5-amino-N—((S)-7-bromoisochroman-4-yl)-N,6-dimethyl-6,8-dihydro-1H-furo[3,4-d]pyrrolo[3,2-b]pyridine-2-carboxamide

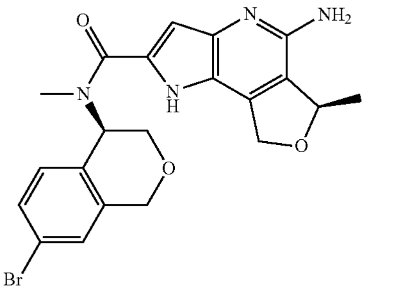

&

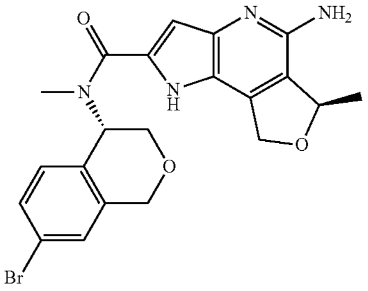

Example 71 (47 mg, 35%) and Example 72 (43 mg, 32%) were prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and 7-bromo-N-methylisochroman-4-amine, and the diastereomers were separated by chiral-HPLC.

Analytical chiral-HPLC condition as below. Column: YMC Cellulose-C; Column size: 4.6×250 mm, 5 μm; Mobile phase: (0.1% 2.0 M methanolic $NH_3$ in EtOH): hexane, 1:1 isocratic; Flow: 1.0 mL/min; Temperature: 25° C.

Example 71: Analytical chiral-HPLC tR=7.07 min. $^1H$ NMR (400 MHz, DMSO-d6) δ 11.59 (s, 1H), 7.56-7.36 (m, 2H), 7.29-7.08 (m, 1H), 6.70 (s, 1H), 5.70 (s, 1H), 5.49 (s, 2H), 5.4-5.29 (m, 1H), 5.22-5.02 (m, 2H), 4.90-4.57 (m, 2H), 4.65 (d, J=15.4 Hz, 1H), 4.06 (s, 2H), 3.16-2.66 (m, 3H), 1.36 (d, J=6.1 Hz, 3H). LCMS $(M+H)^+$=457.2.

Example 72: Analytical chiral-HPLC tR=8.84 min. $^1H$ NMR (400 MHz, DMSO-d6) δ 11.59 (s, 1H), 7.56-7.36 (m, 2H), 7.29-7.08 (m, 1H), 6.70 (s, 1H), 5.70 (s, 1H), 5.49 (s, 2H), 5.4-5.29 (m, 1H), 5.22-5.02 (m, 2H), 4.90-4.57 (m, 2H), 4.65 (d, J=15.4 Hz, 1H), 4.06 (s, 2H), 3.16-2.66 (m, 3H), 1.36 (d, J=6.1 Hz, 3H). LCMS $(M+H)^+$=457.2.

Example 73 & Example 74: (S)-5-amino-N-(7-chloroisochroman-4-yl)-N-ethyl-6,8-dihydro-1H-furo[3,4-d]pyrrolo[3,2-b]pyridine-2-carboxamide & (R)-5-amino-N-(7-chloroisochroman-4-yl)-N-ethyl-6,8-dihydro-1H-furo[3,4-d]pyrrolo[3,2-b]pyridine-2-carboxamide

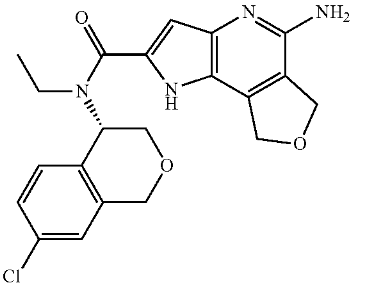

&

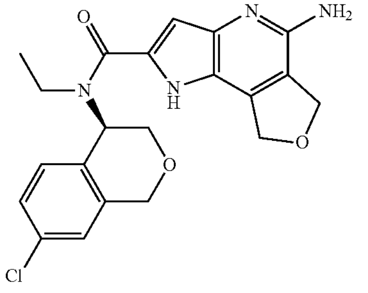

Step 1: methyl 2-(bromomethyl)-4-chlorobenzoate

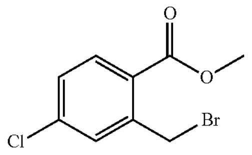

To a solution of methyl 4-chloro-2-methylbenzoate (5.0 g, 27.1 mmol) in $CCl_4$ (100 mL) was added NBS (5.3 g, 29.7 mmol) and AIBN (2.2 g, 13.5 mmol). The mixture was stirred at 80° C. under nitrogen overnight. The mixture was cooled to room temperature, diluted with DCM (100 mL), and washed with water (80 mL) and brine (60 mL). The organic layer was dried over $Na_2SO_4$, filtered and concentrated under vacuum. The residue was purified by purified by silica gel chromatography (PE:EtOAc=50:1) to give the title compound (6.3 g, 88%). LC-MS $(M+H)^+$=263.1.

Step 2: methyl 4-chloro-2-(2-methoxy-2-oxoethoxy)methyl)benzoate

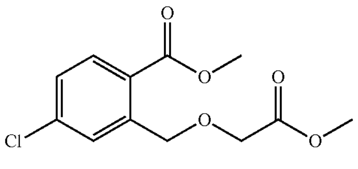 [SMILES: COC(=O)COCc1cc(Cl)ccc1C(=O)OC]

To a mixture of methyl 2-hydroxyacetate (4.3 g, 47.9 mmol) in DMF (100 mL) was added NaH (60%, 1.92 g, 47.9 mmol) at 0° C. The mixture was stirred for 30 min at room temperature and then cooled to 0° C. A solution of methyl 2-(bromomethyl)-4-chlorobenzoate (6.3 g, 23.9 mmol) in DMF (10 mL) was added and the mixture was stirred for 10 min at 0° C. Saturated $NH_4Cl$ (40 mL) was added dropwise, and then the mixture was partitioned between water (100 mL) and EtOAc (150 mL). The organic layer was washed with brine (2×60 mL), dried over $Na_2SO_4$, filtered and concentrated under vacuum. The residue was purified by silica gel chromatography (PE:EtOAc=4:1) to give the title compound (3.8 g, 58%). LC-MS $(M+Na)^+$=295.1.

Step 3: 2-((carboxymethoxy)methyl)-4-chlorobenzoic Acid

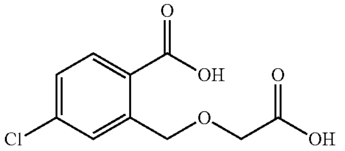 [SMILES: O=C(O)COCc1cc(Cl)ccc1C(=O)O]

To a solution of methyl 4-chloro-2-((2-methoxy-2-oxoethoxy)methyl)benzoate (3.8 g, 13.97 mmol) in EtOH (20 mL) was added a solution of NaOH (2.5 g, 62.5 mmol) in water (14 mL). The mixture was stirred for 1 h at room temperature. The pH of the mixture was adjusted to 3-4 with hydrochloric acid (1 M). The mixture was extracted with DCM (80 mL). The organic layer was washed with brine (60 mL), dried over $Na_2SO_4$, filtered and concentrated under vacuum to give the title compound (3.3 g, 97%). LC-MS $(M+H)^+$=245.1.

Step 4: Acetic 7-chloro-4-oxoisochromane-3-carboxylic Anhydride

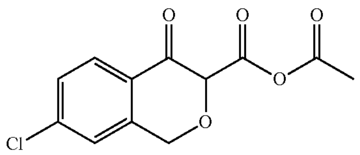 [SMILES: CC(=O)OC(=O)C1OCc2cc(Cl)ccc2C1=O]

To a mixture of 2-((carboxymethoxy)methyl)-4-chlorobenzoic acid (3.3 g, 13.5 mmol) in $Ac_2O$ (60 mL) was added KOAc (6.1 g, 62.2 mmol). The mixture was stirred for 3 h at 140° C. The mixture was cooled to room temperature and partitioned between iced water (100 mL) and EtOAc (120 mL). The aqueous phase was extracted with EtOAc (50 mL). The combined organic layer was washed with brine (60 mL), dried over $Na_2SO_4$, filtered and concentrated under vacuum to give the title compound (2.2 g, 61%).

Step 5: 7-chloroisochroman-4-one

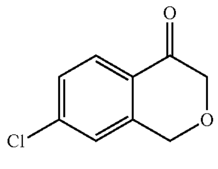 [SMILES: O=C1COCc2cc(Cl)ccc21]

To a solution of acetic 7-chloro-4-oxoisochromane-3-carboxylic anhydride (2.2 g, 8.21 mmol) in EtOH (60 mL) was added a solution of NaOH (1.64 g, 41.0 mmol) in water (20 mL). The mixture stirred for 15 min at room temperature and then partitioned between EtOAc (150 mL) and brine (70 mL). The organic layer was dried over $Na_2SO_4$, filtered and concentrated under vacuum. The residue was purified by silica gel chromatography (PE:EtOAc=10:1) to give the title compound (1.3 g, 87%). LC-MS $(M+H)^+$=183.1.

Step 6: 7-chloroisochroman-4-ol

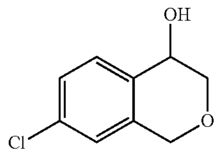 [SMILES: OC1COCc2cc(Cl)ccc21]

To a solution of 7-chloroisochroman-4-one (1.0 g, 5.49 mmol) in EtOH (25 mL) was added $NaBH_4$ (208 mg, 5.49 mmol) and the mixture was stirred for 1 h at room temperature. Saturated $NH_4Cl$ (30 mL) was added with stirring, and the mixture was successively extracted with and EA (80+50 mL). The combined organic layer was washed with brine (60 mL), dried over $Na_2SO_4$, filtered and concentrated under vacuum to give the title compound (950 mg, 94%). LC-MS $(M+H)^+$=185.1.

Step 7: 4,7-dichloroisochromane

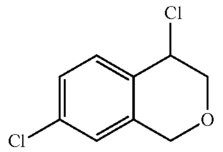 [SMILES: Clc1ccc2c(c1)COCC2Cl]

To a mixture of 7-chloroisochroman-4-ol (950 mg, 5.16 mmol) in THF (15 mL) was added $SOCl_2$ (1.96 g, 16.5 mmol) dropwise, and the mixture was stirred for 30 min at 80° C. The mixture was cooled to room temperature and concentrated under reduced pressure. The residue was re-dissolved in EtOAc (50 mL), successively washed with saturated $NaHCO_3$ (30 mL) and brine (20 mL). The organic layer was dried over $Na_2SO_4$, filtered and concentrated under vacuum to give the title compound (810 mg, 78%). LC-MS $(M+H)^+$=203.1.

Step 8: 7-chloro-N-ethylisochroman-4-amine

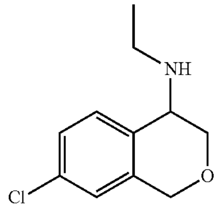

To a mixture of 4,7-dichloroisochromane (404 mg, 2.0 mmol) in DMA (10 mL) was added ethylamine hydrochloride (492 mg, 6.0 mmol), $K_2CO_3$ (1.1 g, 7.97 mmol) and KI (400 mg, 2.41 mmol). The mixture was stirred for overnight at 100° C. The mixture was cooled to room temperature, diluted with EtOAc (50 mL), successively washed with water (20 mL) and brine (20 mL). The organic layer was dried over $Na_2SO_4$, filtered and concentrated under vacuum. The residue was purified by prep-TLC (PE:EtOAc=1:1) to give the title compound (100 mg, 24%). LC-MS $(M+H)^+$=212.3.

Step 9: 5-amino-N-(7-chloroisochroman-4-yl)-N-ethyl-1-((2-(trimethylsilyl)ethoxy)methyl)-6,8-dihydro-1H-furo[3,4-d]pyrrolo[3,2-b]pyridine-2-carboxamide

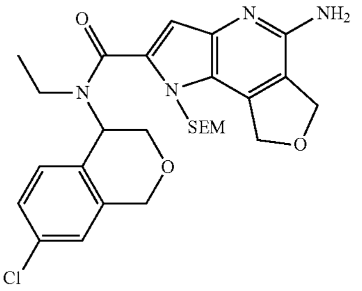 [SMILES: CCN(C(=O)c1cc2nc(N)c3c(c2n1COCC[Si](C)(C)C)COC3)C1COCc2cc(Cl)ccc21]

To a mixture of 5-amino-1-((2-(trimethylsilyl)ethoxy)methyl)-6,8-dihydro-1H-furo[3,4-d]pyrrolo[3,2-b]pyridine-2-carboxylic acid (166 mg, 0.47 mmol) and 7-chloro-N-ethylisochroman-4-amine (100 mg, 0.47 mmol) in THF (10 mL) was added DIPEA (303 mg, 3.0 mmol) and BOPCl (203 mg, 0.80 mmol). The mixture was stirred for 2 h at 60° C. The mixture was diluted with EtOAc (50 mL) and successively washed with water (20 mL) and brine (20 mL). The organic layer was dried over $Na_2SO_4$, filtered and concentrated under reduced pressure. The residue was purified by prep-TLC (MeOH:DCM=1:15) to give the title compound (160 mg, 62%). LC-MS $(M+H)^+$=543.3.

Step 10: (S)-5-amino-N-(7-chloroisochroman-4-yl)-N-ethyl-6,8-dihydro-1H-furo[3,4-d]pyrrolo[3,2-b]pyridine-2-carboxamide & (R)-5-amino-N-(7-chloroisochroman-4-yl)-N-ethyl-6,8-dihydro-1H-furo[3,4-d]pyrrolo[32-b]pyridine-2-carboxamide A mixture of 5-amino-N-(7-chloroisochroman-4-yl)-N-ethyl-1-((2-(trimethylsilyl)ethoxy)methyl)-6,8-dihydro-1H-furo[3,4-d]pyrrolo[3,2-b]pyridine-2-carboxamide (160 mg, 0.29 mmol) in TFA (5 mL) was stirred for 30 min at room temperature. The mixture was concentrated under reduced pressure. To the residue was added methanolic ammonia (7.0 M, 10 mL), and the mixture was stirred for 30 min at room temperature. The mixture was concentrated under reduced pressure. The residue was purified by prep-HPLC and further purified by SFC to give Example 73 (27 mg, 22%) and Example 74 (28 mg, 23%).

Analytical chiral-SFC condition as below. Column: CHIRALPAK IH; Column size: 4.6×100 mm, 5 μm; Mobile phase: 0.2% diethylamine in MeOH:$CO_2$, 1:9 to 4:6 in 3 min, 4:6 for 2 min, 4:6 to 1:9 in 0.1 min, 1:9 for 1.9 min; Flow: 2.0 mL/min; Temperature: 35° C.; back pressure: 1500 psi.

Example 73: Analytical SFC tR=3.82 min. $^1$H NMR (400 MHz, DMSO-d6) δ 11.58 (s, 1H), 7.32 (d, J=12.0 Hz, 1H), 7.28 (s, 1H), 7.23 (d, J=12.0 Hz, 1H), 6.59 (s, 1H), 6.66-6.55 (m, 1H), 5.53 (s, 2H), 5.14 (s, 2H), 4.92 (s, 2H), 4.83 (d, J=15.6 Hz, 1H), 4.66 (d, J=15.6 Hz, 1H), 4.12 (s, 2H), 3.31-3.30 (m, 2H), 1.11-1.01 (m, 3H). LCMS $(M+H)^+$= 413.4.

Example 74: Analytical SFC tR=4.09 min. $^1$H NMR (400 MHz, DMSO-d6) δ 11.58 (s, 1H), 7.32 (d, J=12.0 Hz, 1H), 7.28 (s, 1H), 7.23 (d, J=12.0 Hz, 1H), 6.59 (s, 1H), 6.66-6.55 (m, 1H), 5.53 (s, 2H), 5.14 (s, 2H), 4.92 (s, 2H), 4.83 (d, J=15.6 Hz, 1H), 4.66 (d, J=15.6 Hz, 1H), 4.12 (s, 2H), 3.31-3.30 (m, 2H), 1.11-1.01 (m, 3H). LCMS $(M+H)^+$= 413.3.

Example 75 & Example 76: (S)-5-amino-N-(5,7-difluoroisochroman-4-yl)-N-ethyl-6,8-dihydro-1H-furo[3,4-d]pyrrolo[3,2-b]pyridine-2-carboxamide & (R)-5-amino-N-(5,7-difluoroisochroman-4-yl)-N-ethyl-6,8-dihydro-1H-furo[3,4-d]pyrrolo[3,2-b]pyridine-2-carboxamide

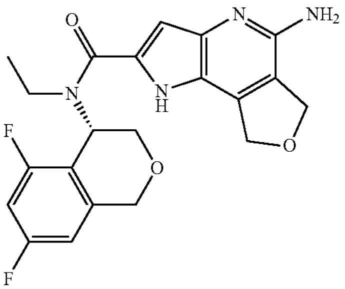

&

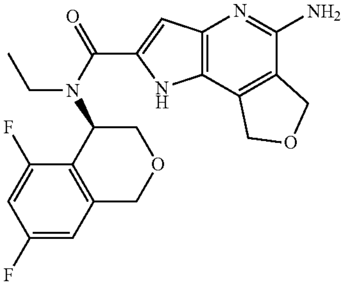

Step 1: (2-bromo-3,5-difluorophenyl)methanol

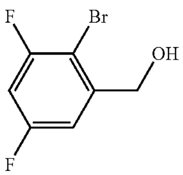 [SMILES: OCc1cc(F)cc(F)c1Br]

To a solution of 2-bromo-3,5-difluoro-benzaldehyde (5.0 g, 22.6 mmol) in MeOH (50 mL) was added $NaBH_4$ (942 mg, 24.9 mmol) at 0° C. under nitrogen. The mixture was stirred at 25° C. for 0.5 h. Saturated $NH_4Cl$ (10 mL) was added to the reaction mixture at 0° C., and the mixture was stirred at 25° C. for 1 h. The mixture was extracted with EtOAc (2×100 mL). The combined organic layer was washed with brine (50 mL), dried over $Na_2SO_4$, filtered and concentrated under reduced pressure. The residue was purified by silica gel chromatography (PE/EtOAc=1/0 to 5/1) to give the title compound (4.8 g, 95%). LCMS $(M+Na)^+$= 246.0.

Step 2: 1-((allyloxy)methyl)-2-bromo-3,5-difluorobenzene

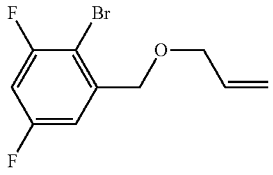

To a solution of (2-bromo-3,5-difluoro-phenyl)methanol (4.0 g, 17.9 mmol) in THF (40 mL) was added allyl bromide (2.82 g, 23.3 mmol) and NaH (60%, 861 mg, 21.5 mmol) at 0° C. under nitrogen. The mixture was stirred at 25° C. for 2 h. The mixture was poured into iced water (100 mL) and extracted with EtOAc (2×100 mL). The combined organic layer was washed with brine (50 mL), dried over $Na_2SO_4$, filtered and concentrated under reduced pressure. The residue was purified by silica gel chromatography (PE/EtOAc=1/0 to 5/1) to give the title compound (4.3 g, 91%). $^1$H NMR (400 MHz, $CD_3OD$) δ 7.20-7.12 (m, 1H), 7.09-7.00 (m, 1H), 6.06-5.92 (m, 1H), 5.35 (dd. J=17.2, 1.6 Hz, 1H), 5.23 (d, J=10.4 Hz, 1H), 4.58 (s, 2H), 4.14 (d, J=5.6 Hz, 2H).

Step 3: 5,7-difluoro-4-methyleneisochromane

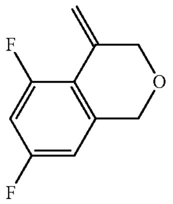

To a solution of 1-(allyloxymethyl)-2-bromo-3,5-difluoro-benzene (4.5 g, 17.1 mmol) in DMF (90 mL) was added $Cs_2CO_3$ (6.69 g, 20.5 mmol), $PPh_3$ (1.08 g, 4.11 mmol) and $Pd(OAc)_2$ (307 mg, 1.37 mmol), and the vessel was degassed and purged with $N_2$ for 3 times. The mixture was stirred at 90° C. for 16 h under nitrogen. The mixture was cooled to room temperature and diluted with water (100 mL). The mixture was extracted with EtOAc (2×100 mL). The combined organic layer was washed with brine (50 mL), dried with $Na_2SO_4$, filtered and concentrated under reduced pressure. The residue was purified by silica gel chromatography (PE/EtOAc=1/0 to 5/1) to give the title compound (1.5 g, 48%). $^1$H NMR (400 MHz, $CD_3OD$) δ 6.92-6.82 (m, 1H), 6.80-6.73 (m, 1H), 5.82 (s, 1H), 5.28 (d, J=4.4 Hz, 1H), 4.78 (s, 2H), 4.39-4.35 (m, 2H).

Step 4: 5,7-difluoroisochroman-4-one

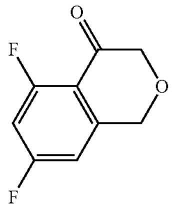 [SMILES: O=C1COCc2cc(F)cc(F)c21]

To a mixture of 5,7-difluoro-4-methylene-isochromane (1.5 g, 8.23 mmol) in dioxane (20 mL) and water (4 mL) was added potassium osmate (VI) dihydrate (303 mg, 823 μmol), 2,6-lutidine (1.76 g, 16.47 mmol) and sodium periodate (7.04 g, 32.9 mmol) at 25° C. under nitrogen. The mixture was stirred at 25° C. for 2 h. The mixture was quenched with saturated $Na_2S_2O_3$ (5 mL), diluted with water (100 mL) and extracted with EtOAc (3×100 mL). The combined organic layer was washed with brine (50 mL), dried over $Na_2SO_4$, filtered and concentrated under reduced pressure. The residue was purified by silica gel chromatography (PE/EtOAc=1/0 to 5/1) to give the title compound (1.0 g, 66%). $^1H$ NMR (400 MHz, $CD_3OD$) δ 7.10-6.96 (m, 2H), 5.88 (s, 2H), 4.29 (s, 2H).

Step 5: 5,7-difluoroisochroman-4-one Oxime

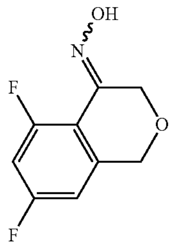 [SMILES: ON=C1COCc2cc(F)cc(F)c21]

The title compound (0.92 g, 85%) was prepared in a manner similar to that in Example 39 & Example 40 step 4 from 5,7-difluoroisochroman-4-one. LC-MS $(M+H)^+$= 200.2.

Step 6: 5,7-difluoroisochroman-4-amine

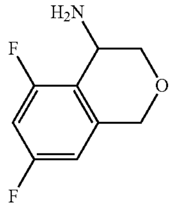 [SMILES: NC1COCc2cc(F)cc(F)c21]

The title compound (822 mg, 96%) was prepared in a manner similar to that in Example 39 & Example 40 step 5 from 5,7-difluoroisochroman-4-one oxime. LC-MS $(M+H)^+$= 186.1.

Step 7: tert-butyl (5,7-difluoroisochroman-4-yl)carbamate

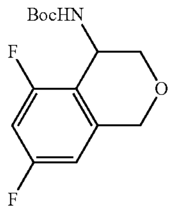 [SMILES: CC(C)(C)OC(=O)NC1COCc2cc(F)cc(F)c21]

The title compound (820 mg, 65%) was prepared in a manner similar to that in Example 39 & Example 40 step 6 from 5,7-difluoroisochroman-4-amine. LCMS $(M+H-tBu)^+$= 230.1.

Step 8: tert-butyl (5,7-difluoroisochroman-4-yl)(ethylcarbamate

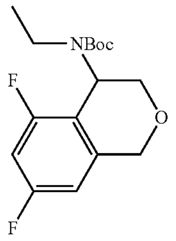 [SMILES: CCN(C(=O)OC(C)(C)C)C1COCc2cc(F)cc(F)c21]

The title compound (100 mg, 91%) was prepared in a manner similar to that in Example 39 & Example 40 step 7 from tert-butyl (5,7-difluoroisochroman-4-yl)carbamate and EtI. LCMS $(M+H-tBu)^+$=258.1.

Step 9: N-ethyl-5,7-difluoroisochroman-4-amine Hydrochloride

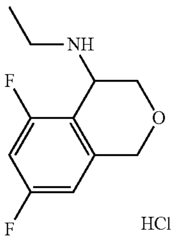

The title compound (125 mg, 100%) was prepared in a manner similar to that in Example 39 & Example 40 step 8 from tert-butyl (5,7-difluoroisochroman-4-yl)(ethyl)carbamate. LC-MS $(M+H)^+$=214.1.

Step 10: 5-amino-N-(5,7-difluoroisochroman-4-yl)-N-ethyl-1-((2-(trimethylsilyl)ethoxy)methyl)-6,8-dihydro-1H-furo[3,4-d]pyrrolo[3,2-b]pyridine-2-carboxamide

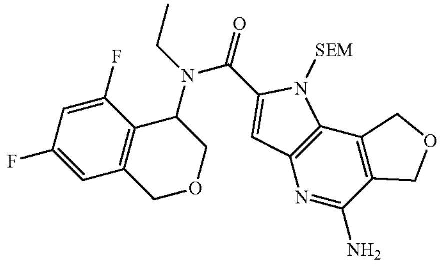 [SMILES: CCN(C(=O)c1cc2nc(N)c3c(c2n1COCC[Si](C)(C)C)COC3)C1COCc2cc(F)cc(F)c21]

The title compound (260 mg, 100%) was prepared in a manner similar to that in Example 73 & Example 74 step 9 from N-ethyl-5,7-difluoroisochroman-4-amine hydrochloride and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=545.3.

Step 11: (R)-5-amino-N-(5,7-difluoroisochroman-4-yl)-N-ethyl-6,8-dihydro-1H-furo[3,4-d]pyrrolo[3,2-b]pyridine-2-carboxamide & (S)-5-amino-N-(5,7-difluoroisochroman-4-yl)-N-ethyl-6,8-dihydro-1H-furo[3,4-d]pyrrolo[3,2-b]pyridine-2-carboxamide Example 75 (14 mg, 7%) and Example 76 (13 mg, 6%) were prepared in a manner similar to that in Example 73 & Example 74 step 10 from 5-amino-N-(5,7-difluoroisochroman-4-yl)-N-ethyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: ChiralPak IH; Column size: 4.6×100 mm, 3 μm; Mobile phase: (isopropanol containing 0.2% 7 M methanolic $NH_3$):$CO_2$ 1; 1:9 for 0.2 min, 1:9 to 1:1 in 2.4 min, 1:1 for min, 1:1 to 1:9 in 0.6 min; Flow: 3.4 mL/min; Temperature: 35° C.; back pressure: 2000 psi.

Example 75: Analytical SFC tR=2.10 min. $^1H$ NMR (400 MHz, DMSO-d6) δ 11.55 (s, 1H), 7.15 (t, J=8.8 Hz, 1H), 7.00 (d, J=8.8 Hz, 1H), 6.55 (s, 1H), 5.68 (s, 1H), 5.54 (s, 2H), 5.15 (d, J=2.4 Hz, 2H), 4.96-4.88 (m, 3H), 4.63 (d, J=15.6 Hz, 1H), 4.36-3.94 (m, 4H), 0.98 (t, J=6.8 Hz, 3H). LC-MS $(M+H)^+$=415.1.

Example 76: Analytical SFC tR=2.54 min. $^1H$ NMR (400 MHz, DMSO-d6) δ 11.55 (s, 1H), 7.15 (t, J=8.8 Hz, 1H), 7.00 (d, J=8.8 Hz, 1H), 6.55 (s, 1H), 5.68 (s, 1H), 5.54 (s, 2H), 5.15 (d, J=2.4 Hz, 2H), 4.96-4.88 (m, 3H), 4.63 (d, J=15.6 Hz, 1H), 4.36-3.94 (m, 4H), 0.98 (t, J=6.8 Hz, 3H). LC-MS $(M+H)^+$=415.1.

Example 77: (S)-5-amino-N-ethyl-N-(6-(trifluoromethyl)-2,3-dihydrobenzofuran-3-yl)-6,8-dihydro-1H-furo[3,4-d]pyrrolo[3,2-b]pyridine-2-carboxamide

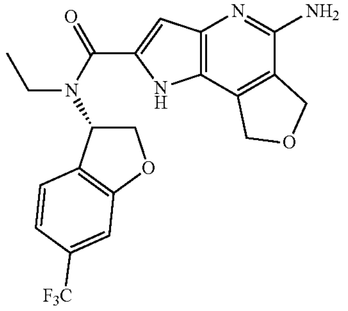 [SMILES: CCN(C(=O)c1cc2nc(N)c3c(c2[nH]1)COC3)[C@@H]1COc2cc(C(F)(F)F)ccc21]

Step 1: tert-butyl (S)-(6-(trifluoromethyl)-2,3-dihydrobenzofuran-3-yl)carbamate

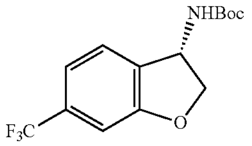

The title compound (300 mg, 99%) was prepared in a manner similar to that in Example 39 & Example 40 step 6 from (S)-6-(trifluoromethyl)-2,3-dihydrobenzofuran-3-amine hydrochloride. LC-MS $(M+Na)^+$=326.1.

Step 2: tert-butyl (S)-ethyl(6-(trifluoromethyl)-2,3-dihydrobenzofuran-3-yl)carbamate

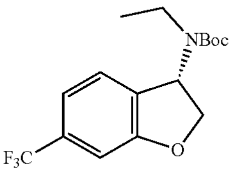 [SMILES: CCN(C(=O)OC(C)(C)C)[C@@H]1COc2cc(C(F)(F)F)ccc21]

The title compound (240 mg, 73%) was prepared in a manner similar to that in Example 39 & Example 40 step 7 from tert-butyl (S)-(6-(trifluoromethyl)-2,3-dihydrobenzofuran-3-yl)carbamate and EtI. LC-MS $(M+H-tBu)^+$=276.1.

Step 3: (S)—N-ethyl-6-(trifluoromethyl)-2,3-dihydrobenzofuran-3-amine

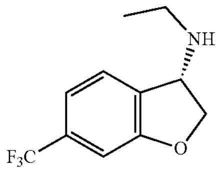

To tert-butyl (S)-ethyl(6-(trifluoromethyl)-2,3-dihydrobenzofuran-3-yl)carbamate (240 mg, 0.72 mmol) was added HCl (4.0 M in dioxane, 5 mL), and the mixture was stirred at room temperature for 2 h. The mixture was concentrated under reduced pressure. The residue was partitioned between saturated $NaHCO_3$ (50 mL) and EtOAc (40 mL). The aqueous layer was successively extracted with EtOAc (2×40 mL). The combined organic layer was dried over $Na_2SO_4$, filtered and concentrated under reduced pressure to give the title compound (120 mg, 79%). LC-MS $(M+H)^+$=232.1.

Step 4: (S)-5-amino-N-ethyl-N-(6-(trifluoromethyl)-2,3-dihydrobenzofuran-3-yl)-1-((2-(trimethylsilyl)ethoxy)methyl)-6,8-dihydro-1H-furo[3,4-d]pyrrolo[3,2-b]pyridine-2-carboxamide

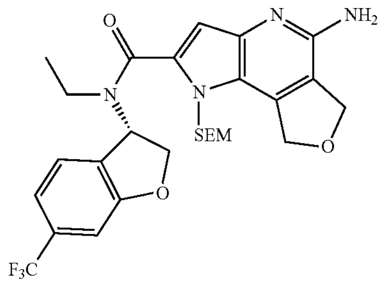 [SMILES: CCN(C(=O)c1cc2nc(N)c3c(c2n1COCC[Si](C)(C)C)COC3)[C@@H]1COc2cc(C(F)(F)F)ccc21]

The title compound (250 mg, 86%) was prepared in a manner similar to that in Example 73 & Example 74 step 9 from (S)—N-ethyl-6-(trifluoromethyl)-2,3-dihydrobenzofuran-3-amine and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=563.4.

Step 5: (S)-5-amino-N-ethyl-N-(6-(trifluoromethyl)-2,3-dihydrobenzofuran-3-yl)-6,8-dihydro-1H-furo[3,4-d]pyrrolo[3,2-b]pyridine-2-carboxamide Example 77 (103 mg, 60%) was prepared in a manner similar to that in Example 66 step 3 from (S)-5-amino-N-ethyl-N-(6-(trifluoromethyl)-2,3-dihydrobenzofuran-3-yl)-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.57 (s, 1H), 7.55 (d, J=7.6, 1 H), 7.38-7.11 (m, 2H), 6.60 (d, J=2.0 Hz, 1H), 6.12 (s, 1H), 5.58 (s, 2H), 5.12 (s, 2H), 4.98-4.78 (m, 3H), 4.72-4.61 (m, 1H), 3.65-3.35 (m, 2H), 1.05 (t, J=6.0 Hz, 3H). LC-MS $(M+H)^+$=433.3.

Example 78 & Example 79 & Example 80 & Example 81: 5-amino-N-((1S,4R)-7-bromo-1-methylisochroman-4-yl)-N-methyl-6,8-dihydro-1H-furo[3,4-d]pyrrolo[3,2-b]pyridine-2-carboxamide & 5-amino-N-((1R,4R)-7-bromo-1-methylisochroman-4-yl)-N-methyl-6,8-dihydro-1H-furo[3,4-d]pyrrolo[3,2-b]pyridine-2-carboxamide & 5-amino-N-((1S,4S)-7-bromo-1-methylisochroman-4-yl)-N-methyl-6,8-dihydro-1H-furo[3,4-d]pyrrolo[3,2-b]pyridine-2-carboxamide & 5-amino-N-((1R,4S)-7-bromo-1-methylisochroman-4-yl)-N-methyl-6,8-dihydro-1H-furo[3,4-d]pyrrolo[3,2-b]pyridine-2-carboxamide

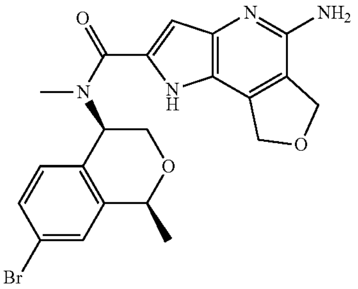

&

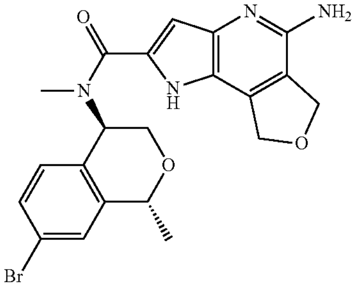

&

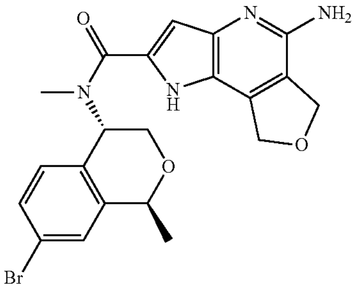

&

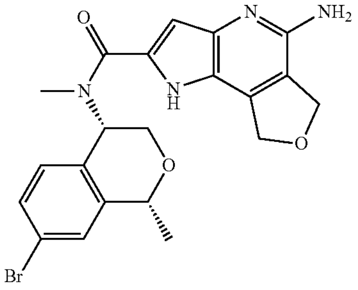

Step 1: 1-(5-bromo-2-iodophenyl)ethan-1-ol

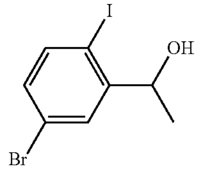

The title compound (22 g, 84%) was prepared in a manner similar to that in Example 57 & Example 58 & Example 59 & Example 60 step 1 from 5-bromo-2-iodo-benzaldehyde and MeMgBr. $^1$H NMR (400 MHz, $CDCl_3$) δ 7.72 (d, J=1.6 Hz, 1H), 7.64 (d, J=8.0 Hz, 1H), 7.11 (dd, J=8.4, 2.4 Hz, 1H), 5.01 (q, J=6.4 Hz, 1H), 1.99 (br s, 1H), 1.46 (d, J=6.4 Hz, 3H).

Step 2: 2-(1-(allyloxy)ethyl)-4-bromo-1-iodobenzene

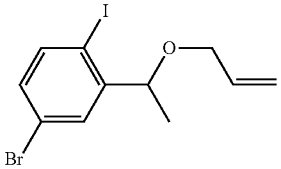

The title compound (19 g, 77%) was prepared in a manner similar to that in Example 39 & Example 40 step 1 from 1-(5-bromo-2-iodophenyl)ethan-1-ol and allyl bromide. $^1$H NMR (400 MHz, $CDCl_3$) δ 7.64 (d, J=8.4 Hz, 1H), 7.61 (d, J=2.4 Hz, 1H), 7.11 (dd, J=8.4, 2.8 Hz, 1H), 5.98-5.85 (m, 1H), 5.28-5.17 (m, 2H), 4.62 (q, J=6.4 Hz, 1H), 3.97-3.88 (m, 1H), 3.86-3.77 (m, 1H), 1.39 (d, J=6.4 Hz, 3H).

Step 3: 7-bromo-1-methyl-4-methyleneisochromane

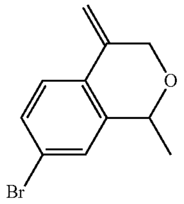

The title compound (2.6 g, 21%) was prepared in a manner similar to that in Example 39 & Example 40 step 2 from 2-(1-(allyloxy)ethyl)-4-bromo-1-iodobenzene. $^1$H NMR (400 MHz, $CDCl_3$) δ 7.53 (d, J=8.4 Hz, 1H), 7.37 (dd. J=8.0, 1.2 Hz, 1H), 7.29-7.26 (m, 1H), 5.59 (s, 1H), 5.04 (s, 1H), 4.84 (q, J=6.4 Hz, 1H), 4.54, 4.35 (ABq, J=13.2 Hz, 2H), 1.56 (d, J=6.8 Hz, 3H).

Step 4: 7-bromo-1-methylisochroman-4-one

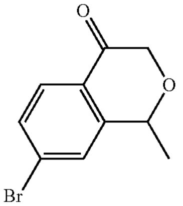

The title compound (2.2 g, 83%) was prepared in a manner similar to that in Example 39 & Example 40 step 3 from 7-bromo-1-methyl-4-methyleneisochromane. $^1$H NMR (400 MHz, $CDCl_3$) δ 7.91 (d, J=8.0 Hz, 1H), 7.57 (d, J=8.0 Hz, 1H), 7.43 (s, 1H), 4.91 (q, J=6.4 Hz, 1H), 4.51, 4.29 (ABq, J=17.2 Hz, 2H), 1.66 (d, J=6.8 Hz, 3H). LC-MS $(M+H)^+$=241.0.

Step 5: 7-bromo-1-methylisochroman-4-ol

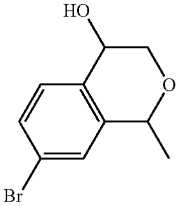

To a solution of 7-bromo-1-methylisochroman-4-one (2.2 g, 9.13 mmol) in MeOH (30 mL) was added $NaBH_4$ (449 mg, 11.9 mmol) at 0° C. The mixture was stirred at 25° C. for 1 h. The reaction mixture was quenched with saturated $NH_4Cl$ (10 mL) and extracted with EtOAc (3×30 mL). The combined organic layer was washed with brine (40 mL), dried over $Na_2SO_4$, filtered and concentrated under reduced pressure. The residue was purified by silica gel chromatography (PE/EtOAc=100/1 to 5/1) to give the title compound (1.9 g, 86%). LC-MS $(M+H—H_2O)^+$=225.0.

Step 6: 4-azido-7-bromo-1-methylisochromane

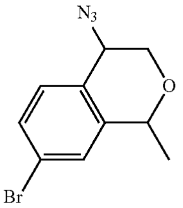

To a solution of 7-bromo-1-methylisochroman-4-ol (1.7 g, 6.99 mmol) in toluene (17 mL) at 0° C. was added DPPA (2.31 g, 8.39 mmol). A solution of DBU (1.60 g, 10.5 mmol) in toluene (4 mL) was added dropwise. The mixture was stirred at 25° C. for 12 h. The mixture was diluted with water (30 mL) and extracted with EtOAc (3×30 mL). The combined organic layer was washed with brine (40 mL), dried over $Na_2SO_4$, filtered and concentrated under reduced pressure to give a residue. The residue was purified by silica gel chromatography (PE/EtOAc=1/0 to 10/1) to give the title compound (1.4 g, 75%). LC-MS $(M+H—N_2)^+$=240.0.

Step 7: 7-bromo-1-methylisochroman-4-amine

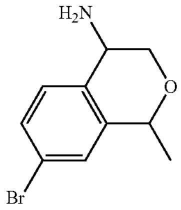

To a solution of 4-azido-7-bromo-1-methylisochromane (1.4 g, 5.22 mmol) in THF (15 mL) was added $PPh_3$ (2.74 g, 10.44 mmol) and a solution of KOH (732 mg, 13.0 mmol) in water (3 mL). The mixture was stirred at 50° C. for 1 h and 25° C. for 12 h. The pH of the mixture was adjusted to ~2 with hydrochloric acid (2 M), and the mixture was washed with EtOAc (3×10 mL). The pH of the aqueous layer was adjusted to ~11 with saturated KOH solution, and then the mixture was extracted with EtOAc (3×40 mL). The combined organic layer was washed with brine (40 mL), dried over $Na_2SO_4$, filtered and concentrated under reduced pressure to give the crude title compound (0.9 g, 71%). LC-MS $(M+H)^+$=242.0.

Step 8: tert-butyl (7-bromo-1-methylisochroman-4-yl)carbamate

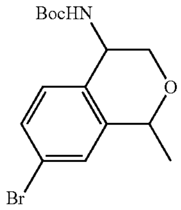

The title compound (1.2 g, 94%) was prepared in a manner similar to that in Example 39 & Example 40 step 6 from 7-bromo-1-methylisochroman-4-amine. LCMS $(M+H-tBu)^+$=286.1.

Step 9: tert-butyl (7-bromo-1-methylisochroman-4-yl)(methyl)carbamate

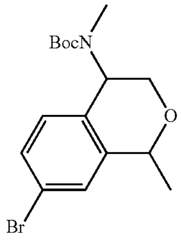

The title compound (900 mg, 72%) was prepared in a manner similar to that in Example 39 & Example 40 step 7 from tert-butyl (7-bromo-1-methylisochroman-4-yl)carbamate and MeI. LCMS $(M+H-tBu)^+$=300.0.

Step 10: 7-bromo-N,1-dimethylisochroman-4-amine Hydrochloride

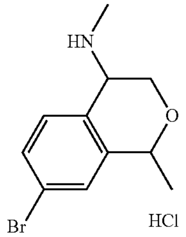

The title compound (650 mg, 88%) was prepared in a manner similar to that in Example 39 & Example 40 step 8 from tert-butyl (7-bromo-1-methylisochroman-4-yl)(methyl)carbamate. LC-MS $(M+H)^+$=256.1.

Step 11: 5-amino-N-(7-bromo-1-methylisochroman-4-yl)-N-methyl-1-((2-(trimethylsilyl)ethoxy)methyl)-6,8-dihydro-1H-furo[3,4-d]pyrrolo[3,2-b]pyridine-2-carboxamide

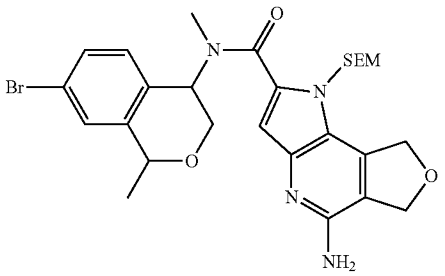 [SMILES: CC1OCC(N(C)C(=O)c2cc3nc(N)c4c(c3n2COCC[Si](C)(C)C)COC4)c2ccc(Br)cc21]

The title compound (0.6 g, 40%) was prepared in a manner similar to that in Example 73 & Example 74 step 9 from 5-amino-1-((2-(trimethylsilyl)ethoxy)methyl)-6,8-dihydro-1H-furo[3,4-d]pyrrolo[3,2-b]pyridine-2-carboxylic acid and 7-bromo-N,1-dimethylisochroman-4-amine hydrochloride. LC-MS $(M+H)^+$=587.3.

Step 12: 5-amino-N-((1S,4R)-7-bromo-1-methylisochroman-4-yl)-N-methyl-6,8-dihydro-1H-furo[3,4-d]pyrrolo[3,2-b]pyridine-2-carboxamide & 5-amino-N-((1R,4R)-7-bromo-1 -methylisochroman-4-yl-N-methyl-6,8-dihydro-1H-furo[3,4-d]pyrrolo[3,2-b]pyridine-2-carboxamide & 5-amino-N-(1S,4S)-7-bromo-1-methylisochroman-4-yl)-N-methyl-6,8-dihydro-1H-furo[3,4-d]pyrrolo[3,2-b]pyridine-2-carboxamide & 5-amino-N-((1R,4S)-7-bromo-1-methylisochroman-4-yl)-N-methyl-6,8-dihydro-1H-furo[3,4-d]pyrrolo[3,2-b]pyridine-2-carboxamide Example 78 (66 mg, 14%), Example 79 (16 mg, 3%), Example 80 (21 mg, 4%) and Example 81 (73 mg, 16%) were prepared in a manner similar to that in Example 73 & Example 74 step 10 from 5-amino-N-(7-bromo-1-methylisochroman-4-yl)-N-methyl-1-((2-(trimethylsilyl)ethoxy)

methyl)-6,8-dihydro-1H-furo[3,4-d]pyrrolo[3,2-b]pyridine-2-carboxamide, and the isomers were separated by chiral SFC.

Analytical chiral-SFC condition as below. Column: CHIRALPAK OJ-3; Column size: 4.6×50 mm, 3 μm; Mobile phase: (ethanol containing 0.2% 7 M methanolic $NH_3$):$CO_2$, 1:19 for 0.2 min, 1:19 to 1:1 in 1.0 min, 1:1 for 1 min, 1:1 to 1:19 in 0.4 min: 1:19 for 0.4 min; Flow: 3.4 mL/min; Temperature: 35° C.; back pressure: 1800 psi.

Example 78: Analytical SFC tR=1.45 min. $^1$H NMR (400 MHz, DMSO-d6) δ 11.57 (br s, 1H), 7.58-7.43 (m, 2H), 7.27-7.09 (m, 1H), 6.69 (br s, 1H), 5.71-5.50 (m, 3H), 5.15 (s, 2H), 4.93 (s, 2H), 4.73 (q, J=6.2 Hz, 1H), 4.27-4.11 (m, 1H), 4.08-3.97 (m, 1H), 3.19-2.71 (m, 3H), 1.54 (d, J=6.4 Hz, 3H). LC-MS $(M+H)^+$=457.0.

Example 79: Analytical SFC tR=1.52 min. $^1$H NMR (400 MHz, DMSO-d6) δ 11.60 (br s, 1H), 7.53-7.42 (m, 2H), 7.11 (d, J=8.4 Hz, 1H), 6.74 (br s, 1H), 5.85-5.66 (m, 1H), 5.57 (s, 2H), 5.15 (s, 2H), 4.97-4.86 (m, 3H), 4.30-4.07 (m, 1H), 3.96-3.77 (m, 1H), 3.09-2.62 (m, 3H), 1.46 (d, J=6.4 Hz, 3H). LC-MS $(M+H)^+$=457.0.

Example 80: Analytical SFC tR=1.87 min. $^1$H NMR (400 MHz, DMSO-d6) δ 11.60 (br s, 1H), 7.54-7.40 (m, 2H), 7.11 (d, J=8.4 Hz, 1H), 6.74 (br s, 1H), 5.85-5.66 (m, 1H), 5.57 (s, 2H), 5.15 (s, 2H), 4.98-4.85 (m, 3H), 4.30-4.07 (m, 1H), 3.96-3.77 (m, 1H), 3.09-2.63 (m, 3H), 1.46 (d, J=6.4 Hz, 3H). LC-MS $(M+H)^+$=457.0.

Example 81: Analytical SFC tR=2.23 min. $^1$H NMR (400 MHz, DMSO-d6) δ 11.57 (br s, 1H), 7.58-7.43 (m, 2H), 7.27-7.09 (m, 1H), 6.69 (br s, 1H), 5.71-5.50 (m, 3H), 5.15 (s, 2H), 4.93 (s, 2H), 4.73 (q, J=6.2 Hz, 1H), 4.27-4.11 (m, 1H), 4.08-3.97 (m, 1H), 3.19-2.71 (m, 3H), 1.54 (d, J=6.4 Hz, 3H). LC-MS $(M+H)^+$=457.0.

Example 82: (S)-5-amino-N-(5-fluoro-7-(trifluoromethyl)isochroman-4-yl)-N-methyl-6,8-dihydro-1H-furo[3,4-d]pyrrolo[3,2-b]pyridine-2-carboxamide

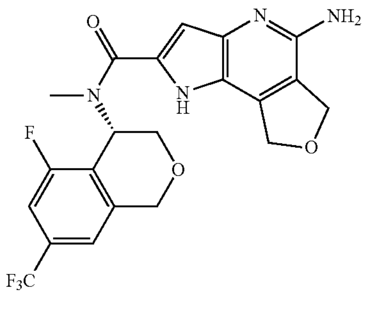 [SMILES: CN(C(=O)c1cc2nc(N)c3c(c2[nH]1)COC3)[C@@H]1COCc2cc(C(F)(F)F)cc(F)c21]

Step 1: 2-bromo-6-fluoro-4-(trifluoromethyl)aniline

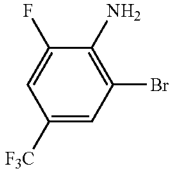

To a solution of 2-fluoro-4-(trifluoromethyl)aniline (25 g, 140 mmol) in DMF (200 mL) was added NBS (26.1 g, 146.6 mmol) at 0° C. The mixture was stirred at 25° C. for 12 h. The mixture was diluted with water (500 mL) and then extracted with ethyl acetate (3×150 mL). The combined organic layer was washed with brine (3×150 mL), dried over $Na_2SO_4$, filtered and concentrated under reduced pressure. The residue was purified by silica gel chromatography (PE/EtOAc=1/0 to 10/1) to give the title compound (29 g, 80%). $^1$H NMR (DMSO-d6, 400 MHz) δ 7.57 (s, 1H), 7.48 (dd, J=11.2, 0.8 Hz, 1H), 6.11 (s, 2H). LC-MS $(M+H)^+$=257.9.

Step 2: methyl 2-amino-3-fluoro-5-(trifluoromethyl)benzoate

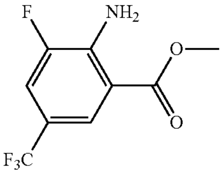 [SMILES: COC(=O)c1cc(C(F)(F)F)cc(F)c1N]

A mixture of 2-bromo-6-fluoro-4-(trifluoromethyl)aniline (29 g, 112.4 mmol), $PdCl_2$ (1.99 g, 11.2 mmol), BINAP (14.0 g, 22.5 mmol) and $Et_3N$ (22.8 g, 224.8 mmol) in MeOH (200 mL) was degassed and purged with CO for 3 times. The mixture was stirred at 80° C. for 24 h under CO. Solid was filtered off and the filtrate was concentrated under reduced pressure. The residue was purified by silica gel chromatography (PE/EtOAc=1/0 to 10/1) to give the title compound (15 g, 56%). $^1$H NMR (DMSO-d6, 400 MHz) δ 7.80 (s, 1H), 7.63 (dd, J=11.5, 1.9 Hz, 1H), 7.18 (br s, 2H), 3.84 (s, 3H). LC-MS $(M+H)^+$=238.0.

Step 3: methyl 2-bromo-3-fluoro-5-(trifluoromethyl)benzoate

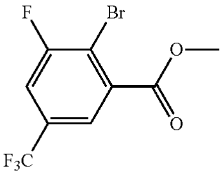 [SMILES: COC(=O)c1cc(C(F)(F)F)cc(F)c1Br]

To a solution of methyl 2-amino-3-fluoro-5-(trifluoromethyl)benzoate (15 g, 63.3 mmol) in MeCN (100 mL) was added $CuBr_2$ (18.4 g, 82.2 mmol), and the mixture was stirred at 25° C. for 1 h. tert-Butyl nitrite (7.83 g, 75.9 mmol) was added, and the mixture was stirred at 25° C. for 4 h. The mixture was diluted with water (100 mL) and extracted with EtOAc (100 mL× 2). The combined organic layer was washed with brine (50 mL), dried with $Na_2SO_4$, filtered and concentrated under reduced pressure. The residue was purified by silica gel chromatography (PE/EtOAc=1/0 to 100/1) to give the title compound (12.5 g, 66%). 1H NMR (DMSO-d6, 400 MHz) δ 8.10 (d, J=8.5 Hz, 1H), 7.96 (s, 1H), 3.91 (s, 3H).

Step 4: (2-bromo-3-fluoro-5-(trifluoromethyl)phenyl)methanol

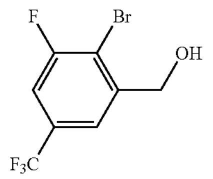 [SMILES: OCc1cc(C(F)(F)F)cc(F)c1Br]

To a solution of methyl 2-bromo-3-fluoro-5-(trifluoromethyl)benzoate (12.5 g, 41.5 mmol) in THF (120 mL) was added $LiBH_4$ in THF (2.0 M, 83.0 mL, 166 mmol) at 0° C. The mixture was stirred at 20° C. for 3 h under nitrogen. The mixture was quenched by saturated $NH_4Cl$ (150 mL) and then extracted with EtOAc (3×150 mL). The combined organic layer was washed with brine (50 mL), dried with $Na_2SO_4$, filtered and concentrated under reduced pressure. The residue was purified by silica gel chromatography (PE/EtOAc=1/0 to 10/1) to give the title compound (10.5 g, 93%). $^1$H NMR (DMSO-d6, 400 MHz) δ 7.77 (d, J=8.4 Hz, 1H), 7.66 (s, 1H), 5.80 (t, J=5.6 Hz, 1H), 4.59 (d, J=5.4 Hz, 2H).

Step 5: 1-((allyloxy)methyl)-2-bromo-3-fluoro-5-(trifluoromethyl)benzene

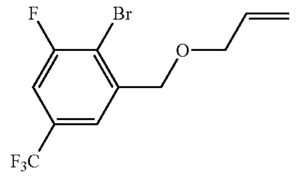 [SMILES: C=CCOCc1cc(C(F)(F)F)cc(F)c1Br]

To a solution of (2-bromo-3-fluoro-5-(trifluoromethyl)phenyl)methanol (10.5 g, 38.5 mmol) in DMF (100 mL) was added allyl bromide (9.31 g, 76.9 mmol) and NaH (60%, 3.08 g, 76.9 mmol) at 0° C. The mixture was stirred at 25° C. for 12 h under nitrogen. The mixture was poured into iced water (100 mL) and extracted with EtOAc (2×100 mL). The combined organic layer was washed with brine (50 mL), dried over $Na_2SO_4$, filtered and concentrated under reduced pressure. The residue was purified by silica gel chromatography (PE/EtOAc=1/0 to 10/1) to give the title compound (10.5 g, 87%). $^1$H NMR (DMSO-d6, 400 MHz) δ 7.82 (dd, J=8.5, 1.5 Hz, 1H), 7.63 (s, 1H), 6.00-5.93 (m, 1H), 5.35-5.30 (m, 1H), 5.23-5.20 (m, 1H), 4.60 (s, 2H), 4.13 (td, J=5.5, 1.4 Hz, 2H).

Step 6: 5-fluoro-4-methylene-7-(trifluoromethyl)isochromane

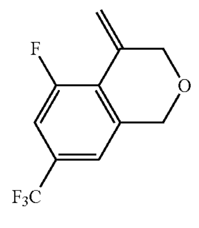 [SMILES: C=C1COCc2cc(C(F)(F)F)cc(F)c21]

To a solution of 1-((allyloxy)methyl)-2-bromo-3-fluoro-5-(trifluoromethyl)benzene (1.0 g, 3.19 mmol) in DMF (100 mL) was added $PPh_3$ (377 mg, 1.44 mmol), $Pd(OAc)_2$ (143 mg, 639 μmol) and $Cs_2CO_3$ (1.25 g, 3.83 mmol). The mixture was stirred at 90° C. for 12 h under nitrogen. The mixture was cooled to room temperature and diluted with water (100 mL). The mixture was extracted with EtOAc (2×100 mL). The combined organic layer was washed with brine (50 mL), dried with $Na_2SO_4$, filtered and concentrated under reduced pressure. The residue was purified by silica gel chromatograph (PE/EtOAc=1/0 to 10/1) to give the title compound (0.44 g, 59%). $^1$H NMR ($CDCl_3$, 400 MHz) δ 7.24 (d, J=11.6 Hz, 1H), 7.12 (s, 1H), 6.06 (s, 1H), 5.42 (d, J=3.0 Hz, 1H), 4.85 (s, 2H), 4.42 (s, 2H).

Step 7: 5-fluoro-7-(trifluoromethyl)isochroman-4-one

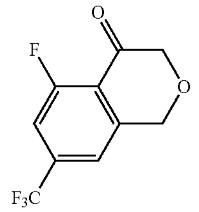

To a solution of 5-fluoro-4-methylene-7-(trifluoromethyl)isochromane (5.7 g, 24.6 mmol) in dioxane (150 mL) and water (30 mL) was added potassium osmate (VI) dihydrate (905 mg, 2.46 mmol), sodium periodate (21.0 g, 98.2 mmol) and 2,6-lutidine (5.26 g, 49.1 mmol). The mixture was stirred at 25° C. for 2 h under nitrogen. The mixture was quenched with saturated $Na_2S_2O_3$ (20 mL), diluted with water (50 mL) and extracted with EtOAc (3×50 mL). The combined organic layer was washed with brine (50 mL), dried over $Na_2SO_4$, filtered and concentrated under reduced pressure. The residue was purified by silica gel chromatography (PE/EtOAc=1/0 to 5/1) to give the title compound (4.4 g, 77%). $^1$H NMR (DMSO-d6, 400 MHz) δ 7.77 (d, J=10.9 Hz, 1H), 7.72 (s, 1H), 4.97 (s, 2H), 4.37 (s, 2H).

Step 8: (R)-5-fluoro-7-(trifluoromethyl)isochroman-4-ol

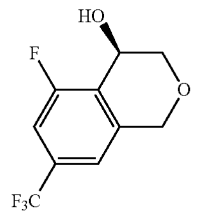 [SMILES: O[C@H]1COCc2cc(C(F)(F)F)cc(F)c21]

To a mixture of 5-fluoro-7-(trifluoromethyl)isochroman-4-one (4.4 g, 18.8 mmol) in formic acid-$Et_3N$ complex (5:2, 20 mL) in was added [(S,S)—N-(2-amino-1,2-diphenylethyl)-p-toluenesulfonamide]chloro(p-cymene)ruthenium (II) (599 mg, 940 μmol) under hydrogen. The mixture was stirred at 0° C. for 2 h, then slowly warmed to 25° C. and stirred for 12 h. The reaction mixture was diluted with water (50 mL) and extracted with EtOAc (3×30 mL). The combined organic layer was washed with brine (40 mL), dried over $Na_2SO_4$, filtered and concentrated under reduced pressure. The residue was purified by silica gel chromatography (PE/EtOAc=30/1 to 4/1) to give the title compound (4.1 g, 92%). $^1$H NMR ($CDCl_3$, 400 MHz) δ 7.18 (d, J=10.0 Hz, 1H), 7.05 (s, 1H), 4.82-4.73 (m, 2H), 4.60 (d, J=15.6 Hz, 1H), 4.15 (dd, J=12.4, 2.0 Hz, 1H), 3.75 (dd, J=12.4, 2.4 Hz, 1H), 2.53 (br s, 1H).

Step 9: (S)—N-(5-fluoro-7-(trifluoromethyl)isochroman-4-yl)-N-methyl-2-nitrobenzenesulfonamide

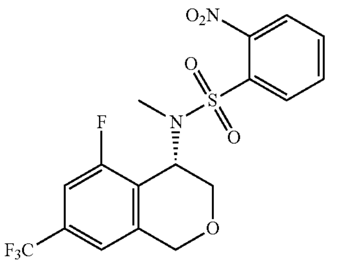 [SMILES: CN([C@@H]1COCc2cc(C(F)(F)F)cc(F)c21)S(=O)(=O)c1ccccc1[N+](=O)[O-]]

To a solution of (R)-5-fluoro-7-(trifluoromethyl)isochroman-4-ol (1.0 g, 4.23 mmol) and N-methyl-2-nitro-benzenesulfonamide (1.01 g, 4.66 mmol) in THF (16 mL) was added $PPh_3$ (1.22 g, 4.66 mmol) and DIAD (941.85 mg, 4.66 mmol) at 0° C. The mixture was stirred at 25° C. for 1 h. The reaction mixture was diluted with water (30 mL) and extracted with EtOAc (3×20 mL). The combined organic layer was washed with brine (40 mL), dried over $Na_2SO_4$, filtered and concentrated under reduced pressure. The residue was purified by silica gel chromatography (PE/EtOAc=5/1 to 1/1) to give the title compound (1.8 g, 98%). LC-MS $(M+Na)^+$=457.1.

Step 10: (S)-5-fluoro-N-methyl-7-(trifluoromethyl) isochroman-4-amine

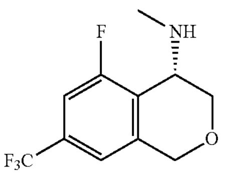

To a solution of (S)—N-(5-fluoro-7-(trifluoromethyl)isochroman-4-yl)-N-methyl-2-nitrobenzenesulfonamide (6.3 g, 14.5 mmol) in THF (63 mL) and DMF (6.3 mL) was added lithium hydroxide monohydrate (3.0 g, 72.5 mmol) and dodecane-1-thiol (14.7 g, 72.5 mmol) at 0° C. The mixture was stirred at 25° C. for 12 h. The pH of the mixture was adjusted to ~2 with hydrochloric acid (2 M), and the mixture was washed with EtOAc (3×50 mL). The pH of the aqueous layer was adjusted to ~13 with aqueous NaOH (2 M), and the mixture was extracted with EtOAc (3×50 mL). The combined organic layer was washed with brine (70 mL), dried over $Na_2SO_4$, filtered and concentrated under reduced pressure to give the title compound (1.1 g, 30%). LC-MS $(M+H)^+$=250.2.

Step 11: (S)-5-amino-N-(5-fluoro-7-(trifluoromethyl)isochroman-4-yl)-N-methyl-1-((2-(trimethylsilyl)ethoxy)methyl)-6,8-dihydro-1H-furo[3,4-d]pyrrolo[3,2-b]pyridine-2-carboxamide

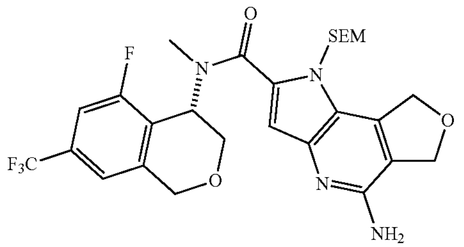 [SMILES: CN(C(=O)c1cc2nc(N)c3c(c2n1COCC[Si](C)(C)C)COC3)[C@@H]1COCc2cc(C(F)(F)F)cc(F)c21]

To a solution of (S)-5-fluoro-N-methyl-7-(trifluoromethyl)isochroman-4-amine (0.30 g, 1.20 mmol) and 5-amino-1-((2-(trimethylsilyl)ethoxy)methyl)-6,8-dihydro-1H-furo[3,4-d]pyrrolo[3,2-b]pyridine-2-carboxylic acid (463 mg, 1.32 mmol) in THF (10 mL) was added BOPCl (398 mg, 1.56 mmol) and DIPEA (467 mg, 3.61 mmol). The mixture was stirred at 40° C. for 2 h and cooled to room temperature. The mixture was diluted with water (30 mL) and extracted with EtOAc (3×30 mL). The combined organic layer was washed with brine (40 mL), dried over $Na_2SO_4$, filtered and concentrated under reduced pressure to give the title compound (0.55 g, 79%). LC-MS $(M+H)^+$=581.3.

Step 12: (S)-5-amino-N-(5-fluoro-7-(trifluoromethyl)isochroman-4-yl)-N-methyl-6,8-dihydro-1H-furo[3,4-d]pyrrolo[3,2-b]pyridine-2-carboxamide A solution of (S)-5-amino-N-(5-fluoro-7-(trifluoromethyl)isochroman-4-yl)-N-methyl-1-((2-(trimethylsilyl)ethoxy)methyl)-6,8-dihydro-1H-furo[3,4-d]pyrrolo[3,2-b]pyridine-2-carboxamide (0.55 g, 0.95 mmol) in TFA (4 mL) was stirred at 40° C. for 0.5 h. The mixture was cooled to room temperature and concentrated under reduced pressure. To the residue was added and methanolic ammonia (7.0 M, 4 mL) and the mixture was stirred at 25° C. for 0.5 h. The mixture was concentrated under reduced pressure. The residue was purified by prep-HPLC to give Example 82 (390 mg, 91%). $^1$H NMR (400 MHz, DMSO-d6) δ 11.58 (br s, 1H), 7.61 (d, J=9.2 Hz, 1H), 7.55 (s, 1H), 6.75-6.50 (m, 1H), 5.83 (br s, 1H), 5.58 (s, 2H), 5.22-5.10 (m, 2H), 5.05-4.91 (m, 3H), 4.72 (d, J=15.6 Hz, 1H), 4.24-3.99 (m, 2H), 3.19-2.69 (m, 3H). LC-MS $(M+H)^+$=451.0.

Example 83: (R)-5-amino-N,6-dimethyl-N-((1R, 4S)-1-methyl-7-(trifluoromethyl)isochroman-4-yl)-6, 8-dihydro-1H-furo[3,4-d]pyrrolo[3,2-b]pyridine-2-carboxamide

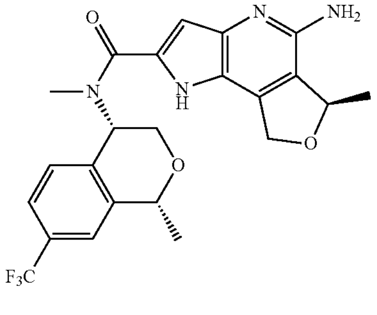 [SMILES: C[C@H]1OC[C@@H](N(C)C(=O)c2cc3nc(N)c4c(c3[nH]2)CO[C@@H]4C)c2ccc(C(F)(F)F)cc21]

Step 1: (R)-1-(2-bromo-5-(trifluoromethyl)phenyl) ethan-1-ol

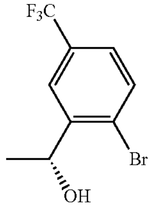

To a mixture of 1-(2-bromo-5-(trifluoromethyl)phenyl) ethan-1-one (11.2 g, 41.9 mmol) in formic acid-$Et_3N$ complex (5:2, 11 mL), was added [(R,R)—N-(2-amino-1,2-diphenylethyl)-p-toluenesulfonamide]chloro(p-cymene) ruthenium(II) (1.33 g, 2.1 mmol) at −18° C. under hydrogen. The mixture was stirred at 0° C. for 2 h and room temperature for 12 h. The mixture was partitioned between and saturated $NaHCO_3$ (150 mL) and EtOAc (250 mL). The organic layer was washed with brine (100 mL), dried over $Na_2SO_4$, filtered and concentrated under vacuum. The residue was purified by silica gel column chromatography (PE:EtOAc=20:1) to give the title compound (10.5 g, 93%). LC-MS $(M+H)^+$=269.1.

Step 2: (R)-2-(1-(allyloxy)ethyl)-1-bromo-4-(trifluoromethyl)benzene

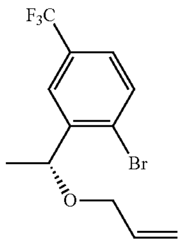 [SMILES: C=CCO[C@H](C)c1cc(C(F)(F)F)ccc1Br]

To a solution of (R)-1-(2-bromo-5-(trifluoromethyl)phenyl)ethan-1-ol (10.0 g, 37.2 mmol) in DMF (100 mL) was added NaH (60%, 1.78 g, 44.6 mmol) at 0° C. under nitrogen. After 30 min, allyl bromide (5.85 g, 48.3 mol) was added, and the mixture was stirred at 25° C. for 3 h. The reaction mixture was poured into water (150 mL) and then extracted with EtOAc (2×200 mL). The combined organic layer was washed with brine (2×100 mL), dried over $Na_2SO_4$, filtered and concentrated under vacuum. The residue was purified by silica gel chromatography (PE:EtOAc=20:1) to give the title compound (10.4 g, 90%). $^1$H NMR (400 MHz, $CDCl_3$) δ 7.80 (d, J=1.1 Hz, 1H), 7.64 (d, J=8.3 Hz, 1H), 7.38 (dd, J=8.2, 1.6 Hz, 1H), 6.00-5.84 (m, 1H), 5.32-5.23 (m, 1H), 5.19 (d, J=10.4 Hz, 1H), 4.88 (q, J=6.4 Hz, 1H), 3.92 (dd, J=12.6, 5.3 Hz, 1H), 3.85 (dd, J=12.6, 5.9 Hz, 1H), 1.43 (d, J=6.4 Hz, 3H). LC-MS $(M+H)^+$=309.1.

Step 3: (R)-1-methyl-4-methylene-7-(trifluoromethyl)isochromane

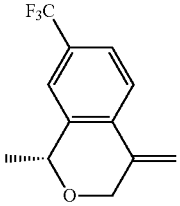

To a solution of (R)-2-(1-(allyloxy)ethyl)-1-bromo-4-(trifluoromethyl)benzene (10.4 g, 33.7 mmol) in DMF (250 mL) was added $Pd(OAc)_2$ (1.13 g, 5.1 mol), $Cs_2CO_3$ (13.2 g, 40.4 mol) and $PPh_3$ (5.3 g, 20.2 mol). The mixture solution was stirred for 16 h at 100° C. under nitrogen and cooled to room temperature. The mixture was poured into water (300 mL) and then extracted with EtOAc (2×400 mL). The combined organic layer was washed with brine (3×300 mL), dried over $Na_2SO_4$, filtered and concentrated under vacuum. The crude product was purified by silica gel chromatography (PE:EtOAc=30:1) to give the title compound (5.7 g, 74%). $^1$H NMR (400 MHz, $CDCl_3$) δ 7.76 (d, J=8.2 Hz, 1H), 7.48 (d, J=7.9 Hz, 1H), 7.37 (s, 1H), 5.69 (s, 1H), 5.13 (s, 1H), 4.89 (q, J=6.4 Hz, 1H), 4.57, 4.37 (ABq, J=13.4 Hz, 2H), 1.60 (d, J=6.5 Hz, 3H).

Step 4: (R)-1-methyl-7-(trifluoromethyl)isochroman-4-one

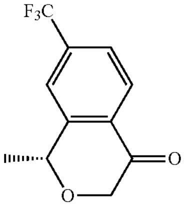 [SMILES: C[C@H]1OCC(=O)c2ccc(C(F)(F)F)cc21]

To a solution of (R)-1-methyl-4-methylene-7-(trifluoromethyl)isochromane (5.7 g, 25 mmol) in dioxane (150 mL) and water (30 mL) was added potassium osmate (VI) dihydrate (920 mg, 2.5 mmol), sodium periodate (21.4 g, 100 mmol) and 2,6-lutidine (5.4 g, 50 mmol). The mixture was stirred at 25° C. for 2 h. Solid was filtered off and the filtrate was diluted with water (250 mL) then extracted with EtOAc (2×350 mL). The combined organic layer was successively washed with saturated $Na_2S_2O_3$ (350 mL), hydrochloric acid (1 M, 300 mL) and brine (200 mL). The organic layer was dried over $Na_2SO_4$, filtered and concentrated under vacuum. The residue was purified by silica gel chromatography (PE:EtOAc=20:1) to give the title compound (5.6 g, 97%). $^1$H NMR (400 MHz, $CDCl_3$) δ 8.16 (d, J=8.1 Hz, 1H), 7.68 (d, J=8.0 Hz, 1H), 7.51 (s, 1H), 4.96 (q, J=6.4 Hz, 1H), 4.56, 4.33 (ABq, J=17.1 Hz, 2H), 1.70 (d, J=6.6 Hz, 3H). LC-MS $(M+H)^+$=231.3.

Step 5: (1R,4R)-1-methyl-7-(trifluoromethyl)isochroman-4-ol

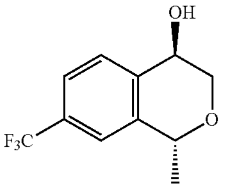 [SMILES: C[C@H]1OC[C@H](O)c2ccc(C(F)(F)F)cc21]

To a solution of (R)-1-methyl-3,3-diphenylhexahydropyrrolo[1,2-c][1,3,2]oxazaborole (674 mg, 2.43 mmol) in THF (10 mL), was added $BH_3$ in THF (1.0 M, 25.6 mmol, 25.6 mL) at −18° C. The mixture was stirred for 10 min, and a solution of (R)-1-methyl-7-(trifluoromethyl)isochroman-4-one (5.6 g, 24.3 mmol) in THF (70 mL) was added dropwise. The mixture was stirred for 1 h at −10° C. under nitrogen. MeOH (10 mL) was added dropwise and the mixture was stirred for 1 h at room temperature. The mixture was concentrated under reduced pressure. The residue was purified by silica gel chromatography (PE:EtOAc=4:1) to give the title compound (5.0 g, 89%). $^1$H NMR (400 MHz, $CDCl_3$) δ 7.64 (d, J=8.0 Hz, 1H), 7.53 (d, J=8.0 Hz, 1H), 7.31 (s, 1H), 4.93 (q, J=6.5 Hz, 1H), 4.81-4.71 (m, 1H), 4.20 (dd, J=11.5, 4.4 Hz, 1H), 3.67 (dd, J=11.5, 6.7 Hz, 1H), 2.15 (d, J=8.3 Hz, 1H), 1.53 (d, J=6.6 Hz, 3H). LC-MS $(M+H)^+$=233.3.

Step 6: N-methyl-N-((1R,4S)-1-methyl-7-(trifluoromethyl)isochroman-4-yl)-2-nitrobenzenesulfonamide

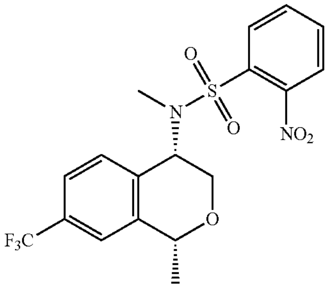 [SMILES: C[C@H]1OC[C@@H](N(C)S(=O)(=O)c2ccccc2[N+](=O)[O-])c2ccc(C(F)(F)F)cc21]

To a solution of (1R,4R)-1-methyl-7-(trifluoromethyl)isochroman-4-ol (5.0 g, 21.6 mmol), N-methyl-2-nitro-benzenesulfonamide (4.66 g, 21.6 mmol) and $PPh_3$ (6.2 g, 23.8 mmol) in THF (80 mL) was added DtBAD (5.47 g, 23.8 mmol) in portions at 0° C. under nitrogen. The mixture was stirred at 25° C. for 1 h and concentrated under reduced pressure. The residue was purified by silica gel chromatography (PE:EtOAc=2:1) to give the title compound (7.9 g, 86%). LC-MS $(M+H)^+$=431.3.

Step 7: (1R,4S)—N,1-dimethyl-7-(trifluoromethyl)isochroman-4-amine

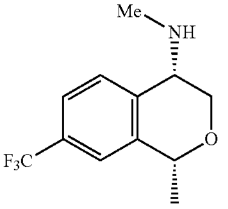 [SMILES: CN[C@@H]1CO[C@H](C)c2cc(C(F)(F)F)ccc21]

A mixture of N-methyl-N-((1R,4S)-1-methyl-7-(trifluoromethyl)isochroman-4-yl)-2-nitrobenzenesulfonamide (7.9 g, 18.4 mmol), dodecane-1-thiol (11.1 g, 55.1 mmol) and lithium hydroxide monohydrate (2.3 g, 55.1 mol) in DMF (10 mL) and THF (100 mL) was stirred at 25° C. for 16 h. The mixture was diluted with EtOAc (250 mL), washed with brine (100 mL), dried over $Na_2SO_4$, filtered and concentrated under vacuum. The residue was purified by silica gel chromatography (PE/EtOAc=1/1 to DCM:MeOH=10:1) to give the title compound (4.3 g, 96%). $^1$H NMR (400 MHz, $CDCl_3$) δ 7.48 (d, J=7.8 Hz, 1H), 7.41 (d, J=8.0 Hz, 1H), 7.35 (s, 1H), 4.78 (q, J=6.3 Hz, 1H), 4.28 (d, J=11.8 Hz, 1H), 3.73 (dd, J=11.8, 1.8 Hz, 1H), 3.47-3.39 (m, 1H), 2.52 (s, 3H), 1.58 (d, J=6.4 Hz, 3H). LC-MS $(M+H)^+$=246.3.

Step 8: 5-amino-N-methyl-N-((1R,4S)-1-methyl-7-(trifluoromethyl)isochroman-4-yl)-1-((2-(trimethylsilyl)ethoxy)methyl)-6,8-dihydro-1H-furo[3,4-d]pyrrolo[3,2-b]pyridine-2-carboxamide A mixture of (1R,4S)—N,1-dimethyl-7-(trifluoromethyl)isochroman-4-amine (2.85 g, 11.6 mol) and 5-amino-1-((2-(trimethylsilyl)ethoxy)methyl)-6,8-dihydro-1H-furo[3,4-d]pyrrolo[3,2-b]pyridine-2-carboxylic acid (4.25 g, 12.2 mmol) in THF (150 mL) was added DIPEA (3.0 g, 23.2 mmol) and BOPCl (3.83 g, 15.1 mmol) and the mixture was stirred at 50° C. for 4 h. The mixture was cooled to room temperature and concentrated under reduced pressure. The residue was treated with EtOAc (250 mL), successively washed with saturated $NaHCO_3$ (40 mL), water (80 mL), brine (60 mL), dried over $Na_2SO_4$, filtered and concentrated under vacuum. The residue was purified by silica gel chromatography (DCM:MeOH=25:1) to give the title compound (6.0 g, 86%). LC-MS $(M+H)^+$=577.2.

Step 9: 5-amino-N-methyl-N-((1R,4S)-1-methyl-7-(trifluoromethyl)isochroman-4-yl)-6,8-dihydro-1H-furo[3,4-d]pyrrolo[3,2-b]pyridine-2-carboxamide To a mixture of 5-amino-N-methyl-N-((1R,4S)-1-methyl-7-(trifluoromethyl)isochroman-4-yl)-1-((2-(trimethylsilyl)ethoxy)methyl)-6,8-dihydro-1H-furo[3,4-d]pyrrolo[3,2-b]pyridine-2-carboxamide (6.0 g, 10.4 mmol) in DCM (15 mL) was added TFA (60 mL), and the mixture was stirred at 25° C. for 1 h. The mixture was concentrated under reduced pressure. Methanolic ammonia (7 M, 40 mL) was added and the mixture was stirred at 25° C. for 30 min. The mixture was concentrated under reduced pressure. The residue was treated with EtOAc (250 mL), successive washed with aqueous $Na_2CO_3$ (0.5 M, 50 mL), water (80 mL), brine (80 mL), dried over $Na_2SO_4$, filtered and concentrated under vacuum. The residue was purified by silica gel chromatography (DCM:MeOH=20:1 to 10:1) to give 5-amino-N-methyl-N-((1R,4S)-1-methyl-7-(trifluoromethyl)isochroman-4-yl)-6,8-dihydro-1H-furo[3,4-d]pyrrolo[3,2-b] pyridine-2-carboxamide (2.6 g, 56%).

Step 10: (R)-5-amino-N,6-dimethyl-N-((1R,4S)-1-methyl-7-(trifluoromethyl)isochroman-4-yl)-6,8-dihydro-1H-furo[3,4-d]pyrrolo[3,2-b]pyridine-2-carboxamide To the mixture of (R)-5-amino-6-methyl-6,8-dihydro-1H-furo[3,4-d]pyrrolo[3,2-b]pyridine-2-carboxylic acid (200 mg, 0.86 mmol), (1R,4S)—N,1-dimethyl-7-(trifluoromethyl)isochroman-4-amine (210 mg, 0.86 mmol) and DIPEA (775 mg, 6.0 mmol) in anhydrous DMF (3 mL) under nitrogen was added T3P (1.36 g, 4.29 mmol) and the mixture was stirred at 60° C. for 16 h. The mixture was cooled to room temperature, hydrochloric acid (6 M, 9 mL) was added and the mixture was stirred for 3 h at 60° C. The mixture was cooled to room temperature, poured into saturated $NaHCO_3$ (100 mL) and extracted with EtOAc (100 mL). The combined organic layer was washed with brine (100 mL), dried over $Na_2SO_4$, filtered and concentrated under vacuum. The residue was purified by prep-HPLC to give Example 83 (141 mg, 36%). $^1$H NMR (400 MHz, DMSO-d6) δ 11.58 (s, 1H), 7.65 (s, 2H), 7.46 (s, 1H), 6.68 (s, 1H), 5.70 (s, 1H), 5.47 (s, 2H), 5.34 (s, 1H), 5.23-4.98 (m, 2H), 4.90-4.74 (m, 1H), 4.32-3.89 (m, 2H), 3.07 (s, 3H), 1.70-1.49 (m, 3H), 1.43-1.26 (m, 3H). LC-MS $(M+H)^+$=461.4.

Example 84: (S)-5-amino-N-(7-iodoisochroman-4-yl)-N-methyl-6,8-dihydro-1H-furo[3,4-d]pyrrolo[3,2-b]pyridine-2-carboxamide

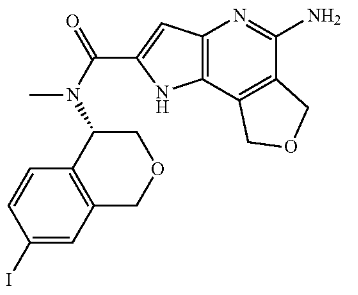 [SMILES: CN(C(=O)c1cc2nc(N)c3c(c2[nH]1)COC3)[C@@H]1COCc2cc(I)ccc21]

Step 1: (R)-7-chloroisochroman-4-ol

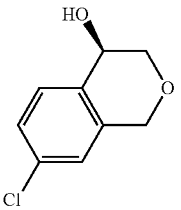 [SMILES: O[C@H]1COCc2cc(Cl)ccc21]

To a solution of (R)-1-methyl-3,3-diphenylhexahydropyrrolo[1,2-c][1,3,2]oxazaborole (607 mg, 2.19 mmol) in THF (10 mL) at 0° C. was added $BH_3{\cdot}Me_2S$ (1.31 mL, 13.8 mmol) under nitrogen. The mixture was stirred at 0° C. for 30 min. A solution of 7-chloroisochroman-4-one (2.0 g, 10.95 mmol) in THF (10 mL) was added dropwise into the reaction mixture over 10 min. The mixture was stirred at 25° C. for 12 h. MeOH (9 mL) was added dropwise. Upon cease of bubbling, the mixture was concentrated under reduced pressure. The residue was purified by silica gel chromatography (PE/EtOAc=5/1) to give the title compound (2.0 g, 99%). $^1$H NMR (400 MHz, DMSO-d6) δ 7.44 (d, J=8.0 Hz, 1H), 7.29 (d, J=8.0 Hz, 1H), 7.15 (s, 1H), 5.49 (d, J=6.0 Hz, 1H), 4.69, 4.60 (ABq, J=15.6 Hz, 2H), 4.55-4.46 (m, 1H), 3.93-3.82 (m, 1H), 3.66-3.56 (m, 1H).

Step 2: (S)-4-azido-7-chloroisochromane

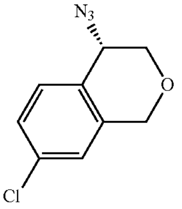 [SMILES: [N-]=[N+]=N[C@@H]1COCc2cc(Cl)ccc21]

The title compound (1.8 g, 79%) was prepared in a manner similar to that in Example 78 & Example 79 & Example 80 & Example 81 step 6 from (R)-7-chloroisochroman-4-ol. $^1$H NMR (400 MHz, DMSO-d6) δ 7.54-7.44 (m, 2H), 7.37 (s, 1H), 4.88, 4.70 (ABq, J=15.8 Hz, 2H), 4.54-4.49 (m, 1H), 4.18 (dd, J=12.4, 2.0 Hz, 1H), 3.95 (dd, J=12.4, 2.8 Hz, 1H).

Step 3: (S)-7-chloroisochroman-4-amine

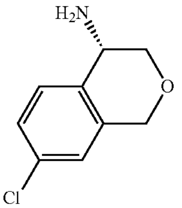 [SMILES: N[C@@H]1COCc2cc(Cl)ccc21]

The title compound (1.55 g, 97%) was prepared in a manner similar to that in Example 78 & Example 79 & Example 80 & Example 81 step 7 from (S)-4-azido-7-chloroisochromane. LC-MS $(M+H)^+$=184.1.

Step 4: tert-butyl (S)-(7-chloroisochroman-4-yl)carbamate

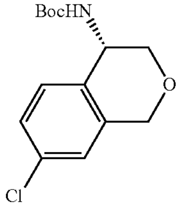 [SMILES: CC(C)(C)OC(=O)N[C@@H]1COCc2cc(Cl)ccc21]

The title compound (0.30 g, 87%) was prepared in a manner similar to that in Example 39 & Example 40 step 6 from (S)-7-chloroisochroman-4-amine. LCMS $(M+H-tBu)^+$ =228.0.

Step 5: tert-butyl (S)-(7-chloroisochroman-4-yl)(methyl)carbamate

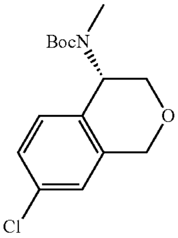 [SMILES: CN(C(=O)OC(C)(C)C)[C@@H]1COCc2cc(Cl)ccc21]

The title compound (1.0 g, 79%) was prepared in a manner similar to that in Example 39 & Example 40 step 7 from tert-butyl (S)-(7-chloroisochroman-4-yl)carbamate and MeI. LCMS $(M+H-tBu)^+$=242.1.

Step 6: tert-butyl (S)-methyl(7-(4,4,5,5-tetramethyl-1,3,2-dioxaborolan-2-yl)isochroman-4-yl)carbamate

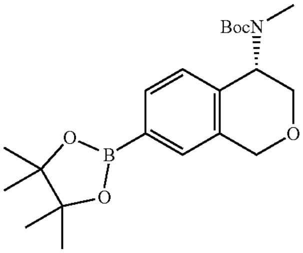

To a solution of tert-butyl (S)-(7-chloroisochroman-4-yl)(methyl)carbamate (700 mg, 2.35 mmol) and 4,4,5,5-tetramethyl-2-(4,4,5,5-tetramethyl-1,3,2-dioxaborolan-2-yl)-1,3,2-dioxaborolane (657 mg, 2.59 mmol) in dioxane (10 mL) was added XPhos (112 mg, 235 μmol), KOAc (692 mg, 7.05 mmol) and $Pd_2(dba)_3$ (215 mg, 235 μmol). The mixture was stirred at 100° C. for 16 h under nitrogen and then cooled to room temperature. The mixture was diluted with water (30 mL) and extracted with EtOAc (3×30 mL). The combined organic layers were washed with brine (40 mL), dried over $Na_2SO_4$, filtered and concentrated under reduced pressure. The residue was purified by silica gel chromatography (PE/EtOAc=1/0 to 5/1) to give the title compound (500 mg, 55%). LC-MS $(M+H-tBu)^+$=334.2.

Step 7: tert-butyl (S)-(7-iodoisochroman-4-yl)(methyl)carbamate

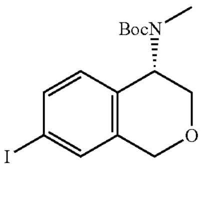 [SMILES: CN(C(=O)OC(C)(C)C)[C@@H]1COCc2cc(I)ccc21]

To a solution of tert-butyl (S)-methyl(7-(4,4,5,5-tetramethyl-1,3,2-dioxaborolan-2-yl)isochroman-4-yl)carbamate (500 mg, 1.28 mmol) in MeOH (5 mL) and water (0.5 mL) was added CuI (245 mg, 1.28 mmol) and NIS (289 mg, 1.28 mmol) under nitrogen. The mixture was stirred at 80° C. for 1 h and then cooled to room temperature. The reaction mixture was diluted with water (30 mL) and extracted with EtOAc (3×30 mL). The combined organic layer was washed with brine (40 mL), dried over $Na_2SO_4$, filtered and concentrated under reduced pressure. The residue was purified by silica gel chromatography (PE/EtOAc=1/0 to 5/1) to give the title compound (250 mg, 49%). LC-MS $(M+H-tBu)^+$= 334.1.

Step 8: (S)-7-iodo-N-methylisochroman-4-amine Hydrochloride

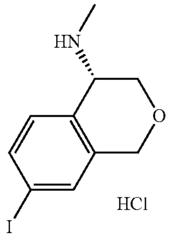

The title compound (66 mg, 99%) was prepared in a manner similar to that in Example 39 & Example 40 step 8 from tert-butyl (S)-(7-iodoisochroman-4-yl)(methyl)carbamate. LC-MS $(M+H)^+$=290.0.

Step 9: (S)-5-amino-N-(7-iodoisochroman-4-yl)-N-methyl-1-((2-(trimethylsilyl)ethoxy)methyl)-6,8-dihydro-1H-furo[3,4-d]pyrrolo[3,2-b]pyridine-2-carboxamide

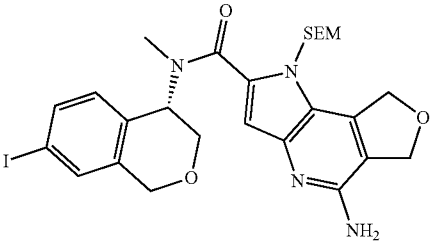 [SMILES: CN(C(=O)c1cc2nc(N)c3c(c2n1COCC[Si](C)(C)C)COC3)[C@@H]1COCc2cc(I)ccc21]

The title compound (100 mg, 79%) was prepared in a manner similar to that in Example 73 & Example 74 step 9 from (S)-7-iodo-N-methylisochroman-4-amine hydrochloride and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=621.2.

Step 10: (S)-5-amino-N-(7-iodoisochroman-4-yl)-N-methyl-6,8-dihydro-1H-furo[3,4-d]pyrrolo[3,2-b]pyridine-2-carboxamide Example 84 (50 mg, 58%) was prepared in a manner similar to that in Example 66 step 3 from (S)-5-amino-N-(7-iodoisochroman-4-yl)-N-methyl-1-((2-(trimethylsilyl)ethoxy)methyl)-6,8-dihydro-1H-furo[3,4-d]pyrrolo[3,2-b]

pyridine-2-carboxamide. $^{1}H$ NMR (400 MHz, DMSO-d6) δ 11.86 (br s, 1H), 7.65 (d, J=8.3 Hz, 1H), 7.59 (s, 1H), 7.03 (d, J=6.1 Hz, 1H), 6.74 (br s, 1H), 6.11 (br s, 2H), 5.69 (br s, 1H), 5.18 (s, 2H), 5.00-4.87 (m, 2H), 4.80 (d, J=15.4 Hz, 1H), 4.63 (d, J=15.4 Hz, 1H), 4.13-4.01 (m, 2H), 3.04 (s, 3H) LC-MS $(M+H)^+$=491.1.

Example 85 & Example 86: (S)-5-amino-N-methyl-N-(2-(trifluoromethyl)-5,8-dihydro-6H-pyrano[3,4-b]pyridin-5-yl)-6,8-dihydro-1H-furo[3,4-d]pyrrolo[3,2-b]pyridine-2-carboxamide & (R)-5-amino-N-methyl-N-(2-(trifluoromethyl)-5,8-dihydro-6H-pyrano[3,4-b]pyridin-5-yl)-6,8-dihydro-1H-furo[3,4-d]pyrrolo[3,2-b]pyridine-2-carboxamide

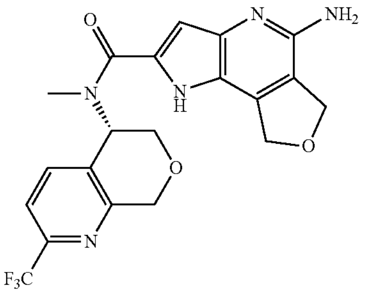

&

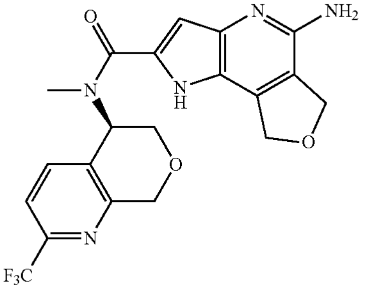

Step 1: (3-bromo-6-(trifluoromethyl)pyridin-2-yl)methanol

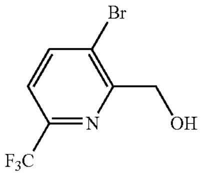 [SMILES: OCc1nc(C(F)(F)F)ccc1Br]

To a solution of methyl 3-bromo-6-(trifluoromethyl)picolinate (3.2 g, 11.3 mmol) in EtOH (100 mL) was added $NaBH_4$ (1.29 mg, 33.9 mmol) at 0° C. The mixture was stirred at room temperature for 11 h and then concentrated under reduced pressure. The residue was partitioned between EtOAc (100 mL) and saturated $NaHCO_3$ (100 mL). The aqueous phase was extracted with EtOAc (2×100 mL). The combined organic layer was washed with brine (50 mL), dried over $Na_2SO_4$, filtered and concentrated under reduced pressure. The residue was purified by silica gel chromatography (PE/EtOAc=10/1 to 1/1) to give the title compound (3.0 g, 100%). LC-MS $(M+Na)^+$=278.0.

Step 2: 2-((allyloxy)methyl)-3-bromo-6-(trifluoromethyl)pyridine

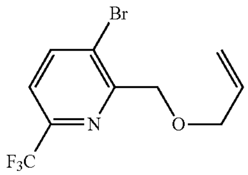 [SMILES: C=CCOCc1nc(C(F)(F)F)ccc1Br]

The title compound (1.74 g, 63%) was prepared in a manner similar to that in Example 82 step 5 from (3-bromo-6-(trifluoromethyl)pyridin-2-yl)methanol and allyl bromide. LC-MS $(M+H)^+$=296.0.

Step 3: 5-methylene-2-(trifluoromethyl)-5,8-dihydro-6H-pyrano[3,4-b]pyridine

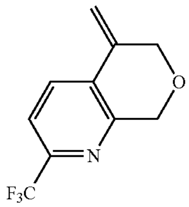

A mixture of 2-((allyloxy)methyl)-3-bromo-6-(trifluoromethyl)pyridine (1.74 g, 5.9 mmol), $Pd(PPh_3)_4$ (680 mg, 0.59 mmol), $Cs_2CO_3$ (2.88 g, 8.8 mmol) in DMF (50 mL) was degassed and purged with nitrogen for 3 times, and the mixture was stirred at 110° C. for 12 h. The mixture was cooled to room temperature and diluted with water (100 mL). The mixture was extracted with EtOAc (2×100 mL). The combined organic layer was washed with brine (50 mL), dried with $Na_2SO_4$, filtered and concentrated under reduced pressure. The residue was purified by silica gel chromatograph (PE/EtOAc=1/0 to 5/1) to give the title compound (892 mg, 71%). LC-MS $(M+H)^+$=216.1.

Step 4: 2-(trifluoromethyl)-6H-pyrano[3,4-b]pyridin-5(8H)-one

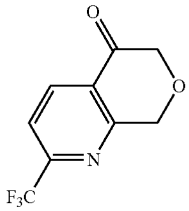 [SMILES: O=C1COCc2nc(C(F)(F)F)ccc21]

To a solution of 5-methylene-2-(trifluoromethyl)-5,8-dihydro-6H-pyrano[3,4-b]pyridine (892 mg, 4.1 mmol) in dioxane (100 mL) and water (20 mL) was added potassium osmate (VI) dihydrate (147 mg, 6.2 mmol), 2,6-lutidine (439 mg, 4.1 mmol) and sodium periodate (1.33 g, 6.2 mmol). The mixture was stirred at 25° C. for 4 h. The mixture was diluted with water (100 mL) and extracted with EtOAc (3×100 mL). The combined organic layer was washed with brine (50 mL), dried over $Na_2SO_4$, filtered and concentrated under reduced pressure. The residue was purified by silica gel chromatography (PE/EtOAc=1/0 to 3/1) to give the title compound (463 mg, 51%). LC-MS $(M+H)^+$=218.0.

Step 5: 2-(trifluoromethyl)-5,8-dihydro-6H-pyrano[3,4-b]pyridin-5-ol

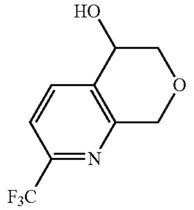 [SMILES: OC1COCc2nc(C(F)(F)F)ccc21]

To a solution of 2-(trifluoromethyl)-6H-pyrano[3,4-b]pyridin-5(8H)-one (100 mg, 0.46 mmol) in MeOH (1 mL) was added $NaBH_4$ (19 mg, 0.51 mmol) at 0° C. The mixture was stirred at room temperature for 2 h and then concentrated under reduced pressure. The residue was partitioned between EtOAc (30 mL) and saturated $NaHCO_3$ (30 mL). The aqueous phase was extracted with EtOAc (2×20 mL). The combined organic layer was washed with brine (30 mL), dried over $Na_2SO_4$, filtered and concentrated under reduced pressure. The residue was purified by silica gel chromatography (PE/EtOAc=10/1 to 1/1) to give the title compound (101 mg, 100%). LC-MS $(M+H)^+$=220.0.

Step 6: di-tert-butyl (2-(trifluoromethyl)-5,8-dihydro-6H-pyrano[3,4-b]pyridin-5-yl)iminodicarbonate

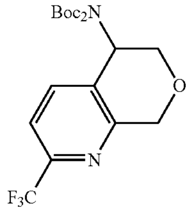

To a solution of 2-(trifluoromethyl)-5,8-dihydro-6H-pyrano[3,4-b]pyridin-5-ol (101 mg, 0.46 mmol), $PPh_3$ (181 mg, 0.69 mmol) and $Boc_2NH$ (150 mg, 0.69 mmol) in THF (3 mL) was added DIAD (139 mg, 0.69 mmol) at 0° C. The mixture was stirred at room temperature for 12 h and concentrated under reduced pressure. The residue was partitioned between EtOAc (30 mL) and saturated $NaHCO_3$ (30 mL). The aqueous phase was extracted with EtOAc (2×20 mL). The combined organic layer was washed with brine (30 mL), dried over $Na_2SO_4$, filtered and concentrated under reduced pressure. The residue was purified by silica gel chromatography (PE/EtOAc=1/0 to 5/1) to give the title compound (176 mg, 92%).

Step 7: tert-butyl (2-(trifluoromethyl)-5,8-dihydro-6H-pyrano[3,4-b]pyridin-5-yl)carbamate

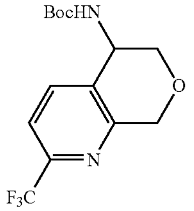

To a solution of di-tert-butyl (2-(trifluoromethyl)-5,8-dihydro-6H-pyrano[3,4-b]pyridin-5-yl)iminodicarbonate (176 mg, 0.42 mmol) in THF (1 mL), water (1 mL) and MeOH (1 mL) was added lithium hydroxide monohydrate (53 mg, 1.3 mmol). The mixture was stirred at 35° C. for 1.5 h, cooled to room temperature and then diluted with water (10 mL). The mixture was extracted with EtOAc (3×20 mL). The combined organic layer was washed with brine (5 mL), dried with $Na_2SO_4$, filtered and concentrated under reduced pressure. The residue was purified by silica gel chromatography (PE/EtOAc=1/0 to 3/1) to give the title compound (78 mg, 58%). LCMS $(M+H-tBu)^+$=263.1.

Step 8: tert-butyl methyl(2-(trifluoromethyl)-5,8-dihydro-6H-pyrano[3,4-b]pyridin-5-yl)carbamate

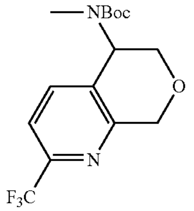

To the solution of tert-butyl (2-(trifluoromethyl)-5,8-dihydro-6H-pyrano[3,4-b]pyridin-5-yl)carbamate (780 mg, 2.45 mmol) in THF (20 mL) under nitrogen at 0° C. was added NaH (60%, 147 mg, 3.68 mmol) and stirred for 1 h. MeI (696 mg, 4.9 mmol) was added and the mixture was stirred at room temperature for 3 h. The reaction was quenched with saturated $NH_4Cl$ (20 mL). The mixture was extracted with EtOAc (3×20 mL). The combined organic layer was washed with brine (20 mL), dried over $Na_2SO_4$, filtered and concentrated under reduced pressure. The residue was purified by silica gel chromatography (PE/EtOAc=1/1) to give the title compound (220 mg, 27%). LCMS $(M+H)^+$=333.2.

Step 9: N-methyl-2-(trifluoromethyl)-5,8-dihydro-6H-pyrano[3,4-b]pyridin-5-amine hydrochloride

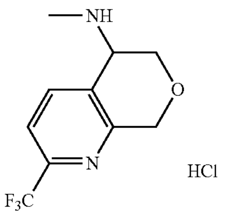 [SMILES: CNC1COCc2nc(C(F)(F)F)ccc21 ; Cl]

To a solution of tert-butyl methyl(2-(trifluoromethyl)-5,8-dihydro-6H-pyrano[3,4-b]pyridin-5-yl)carbamate (220 mg, 0.66 mmol) in DCM (5 mL) was added HCl in dioxane (4.0 M, 3 mL). The mixture was stirred at room temperature for 12 h. The mixture was concentrated under reduced pressure to give the title product (177 mg, 100%). LC-MS $(M+H)^+$=233.2.

Step 10: 5-amino-N-methyl-N-(2-(trifluoromethyl)-5,8-dihydro-6H-pyrano[3,4-b]pyridin-5-yl)-1-((2-(trimethylsilyl)ethoxy)methyl)-6,8-dihydro-1H-furo[3,4-d]pyrrolo[3,2-b]pyridine-2-carboxamide

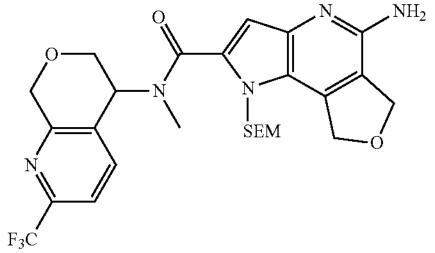 [SMILES: CN(C(=O)c1cc2nc(N)c3c(c2n1COCC[Si](C)(C)C)COC3)C1COCc2nc(C(F)(F)F)ccc21]

To a solution of N-methyl-2-(trifluoromethyl)-5,8-dihydro-6H-pyrano[3,4-b]pyridin-5-amine hydrochloride (177, 0.66 mmol) and 5-amino-1-((2-(trimethylsilyl)ethoxy)methyl)-6,8-dihydro-1H-furo[3,4-d]pyrrolo[3,2-b]pyridine-2-carboxylic acid (232 mg, 0.66 mmol) in THF (5 mL) was added DIPEA (170 mg, 1.32 mmol) and BOPCl (335 mg, 1.32 mmol). The mixture was stirred at room temperature for 1 h and then diluted with water (5 mL). The mixture was extracted with EtOAc (3×5 mL). The combined organic layer was washed with brine (5 mL), dried over $Na_2SO_4$, filtered and concentrated under reduced pressure to give the title compound (370 mg, 75%). LC-MS $(M+H)^+$=564.3.

Step 11: (R)-5-amino-N-methyl-N-(2-(trifluoromethyl)-5,8-dihydro-6H-pyrano[3,4-b]pyridin-5-yl)-6,8-dihydro-1H-furo[3,4-d]pyrrolo[3,2-b]pyridine-2-carboxamide & (S)-5-amino-N-methyl-N-(2-(trifluoromethyl)-5,8-dihydro-6H-pyrano[3,4-b]pyridin-5-yl)-6,8-dihydro-1H-furo[3,4-d]pyrrolo[3,2-b]pyridine-2-carboxamide To a solution of 5-amino-N-methyl-N-(2-(trifluoromethyl)-5,8-dihydro-6H-pyrano[3,4-b]pyridin-5-yl)-1-((2-(trimethylsilyl)ethoxy)methyl)-6,8-dihydro-1H-furo[3,4-d]pyrrolo[3,2-b]pyridine-2-carboxamide (370 mg, 0.65 mmol) in DCM (10 mL) was added TFA (1 mL) and the mixture was stirred at room temperature for 2 h. The mixture was concentrated under reduced pressure. The residue was dissolved in MeOH (5 mL) followed by addition of $K_2CO_3$ (179 mg, 1.3 mmol). The mixture was stirred at 50° C. for 2 h and then cooled to room temperature. The mixture was concentrated under reduced pressure and DCM (20 mL) was added. Solid was filtered off and the filtrate was concentrated under reduced pressure. The residue was purified by silica gel chromatography (DCM/MeOH=15/1) followed by chiral SFC to give Example 85 (15 mg, 5%) and Example 86 (15 mg, 5%).

Analytical chiral-SFC condition as below. Column: CHIRALPAK AS-H; Column size: 4.6×100 mm, 5 μm; Mobile phase: 0.1% diethylamine in methanol; Flow: 2.0 mL/min; Temperature: 35° C.; back pressure: 1800 psi.

Example 85: Analytical SFC tR=2.97 min. 1H NMR (400 MHz, DMSO-d6) δ 11.62 (s, 1H), 7.95 (d, J=8.0 Hz, 1H), 7.84 (d, J=8.1 Hz, 1H), 6.75 (s, 1H), 5.84 (s, 1H), 5.60 (s, 2H), 5.15 (s, 2H), 5.01-4.69 (m, 4H), 4.15 (s, 2H), 3.11 (s, 3H). LC-MS $(M+H)^+$=434.4.

Example 86: Analytical SFC tR=3.26 min. 1H NMR (400 MHz, DMSO-d6) δ 11.68 (s, 1H), 7.95 (d, J=8.1 Hz, 1H), 7.84 (d, J=8.1 Hz, 1H), 6.75 (s, 1H), 5.84 (s, 1H), 5.72 (s, 2H), 5.15 (s, 2H), 4.93-4.74 (m, 4H), 4.15 (s, 2H), 3.11 (s, 3H). LC-MS $(M+H)^+$=434.3.

Example 87 & Example 88: (S)-5-amino-N-(2-cyclopropyl-5,8-dihydro-6H-pyrano[3,4-b]pyridin-5-yl)-N-methyl-6,8-dihydro-1H-furo[3,4-d]pyrrolo[3,2-b]pyridine-2-carboxamide & (R)-5-amino-N-(2-cyclopropyl-5,8-dihydro-6H-pyrano[3,4-b]pyridin-5-yl)-N-methyl-6,8-dihydro-1H-furo[3,4-d]pyrrolo[3,2-b]pyridine-2-carboxamide

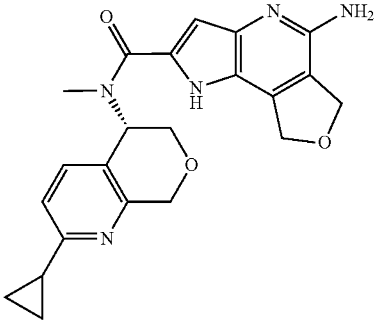

&

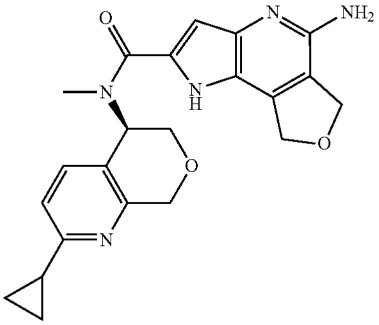

Step 1: N-methyl-5,8-dihydro-6H-pyrano[3,4-b]pyridin-5-amine

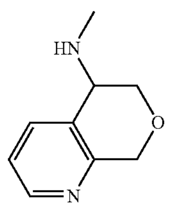

To a solution of 8H-pyrano[3,4-b]pyridin-5-one (1.0 g, 6.70 mmol) in $CF_3CH_2OH$ (10 mL) was added $MeNH_2$ in THF (2.0 M, 13.4 mL, 26.8 mmol). The mixture was stirred at 25° C. for 12 h followed by addition of $NaBH(OAc)_3$ (3.55 g, 16.8 mmol). The mixture was stirred at 25° C. for 1 h. The mixture was quenched with saturated $NaHCO_3$ (15 mL) and extracted with DCM (3×10 mL). The combined organic layer was washed with brine (15 mL), dried over $Na_2SO_4$, filtered and concentrated under reduced pressure to give the title compound (0.90 g, 82%). LC-MS $(M+H)^+=$ 165.2.

Step 2: tert-butyl (5,8-dihydro-6H-pyrano[3,4-b]pyridin-5-yl)(methyl)carbamate

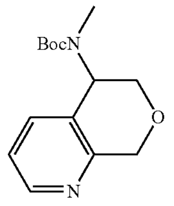 [SMILES: CN(C(=O)OC(C)(C)C)C1COCc2ncccc21]

The title compound (0.40 g, 28%) was prepared in a manner similar to that in Example 39 & Example 40 step 6 from N-methyl-5,8-dihydro-6H-pyrano[3,4-b]pyridin-5-amine. LC-MS $(M+H)^+=265.2$.

Step 3: 5-((tert-butoxycarbonyl)(methyl)amino)-5,8-dihydro-6H-pyrano[3,4-b]pyridine 1-oxide

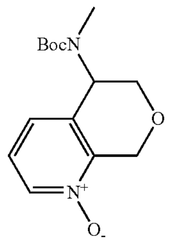

To a solution of tert-butyl (5,8-dihydro-6H-pyrano[3,4-b]pyridin-5-yl)(methyl)carbamate (0.40 g, 1.51 mmol) in DCM (4 mL) was added mCPBA (85%, 369 mg, 1.82 mmol). The mixture was stirred at 25° C. for 1 h. The mixture was quenched with saturated $Na_2SO_3$ (10 mL) and extracted with DCM (3×8 mL). The combined organic layer was washed with brine (12 mL), dried over $Na_2SO_4$, filtered and concentrated under reduced pressure. The residue was purified by silica gel chromatography (EtOAc/MeOH=1/0 to 10/1) to give the title compound (0.32 g, 75%). LC-MS $(M+H)^+=281.2$.

Step 4: tert-butyl (2-chloro-5,8-dihydro-6H-pyrano[3,4-b]pyridin-5-yl)(methyl)carbamate

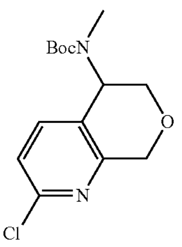 [SMILES: CN(C(=O)OC(C)(C)C)C1COCc2nc(Cl)ccc21]

A solution of 5-((tert-butoxycarbonyl)(methyl)amino)-5,8-dihydro-6H-pyrano[3,4-b]pyridine 1-oxide (0.32 g, 1.14 mmol) in $POCl_3$ (4 mL) was stirred at 50° C. for 1 h. The mixture was cooled to room temperature and concentrated under reduced pressure. To the residue was added saturated $Na_2CO_3$ (10 mL) at 0° C., and the mixture was extracted with EtOAc (3×5 mL). The combined organic layer was washed with brine (8 mL), dried over $Na_2SO_4$, filtered and concentrated under reduced pressure. The residue was re-dissolved in THF (2 mL) followed by addition of $Boc_2O$ (165 mg, 755 μmol) and DIPEA (130 mg, 1.01 mmol). The mixture was stirred at 25° C. for 12 h and then concentrated under reduced pressure. The residue was purified by silica gel chromatography (PE/EtOAc=10/1 to 1/1) to give the title compound (60 mg, 18%). LC-MS $(M+H)^+=299.2$.

Step 5: tert-butyl (2-cyclopropyl-5,8-dihydro-6H-pyrano[3,4-b]pyridin-5-yl)(methyl)carbamate

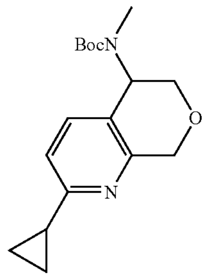 [SMILES: CN(C(=O)OC(C)(C)C)C1COCc2nc(C3CC3)ccc21]

To a solution of tert-butyl (2-chloro-5,8-dihydro-6H-pyrano[3,4-b]pyridin-5-yl)(methyl)carbamate (0.10 g, 335 μmol) and cyclopropylboronic acid (86 mg, 1.0 mmol) in dioxane (1 mL), toluene (1 mL) and water (0.5 mL) was added $Pd(dppf)Cl_2$ (24 mg, 33 μmol) and $K_3PO_4$ (142 mg, 669 μmol). The mixture was purged with $N_2$ for 3 times and stirred at 90° C. for 12 h. The mixture was cooled to room temperature, diluted with water (30 mL) and extracted with EtOAc (3×30 mL). The combined organic layer was washed with brine (40 mL), dried over $Na_2SO_4$, filtered and concentrated under reduced pressure. The residue was purified by prep-TLC (PE/EtOAc=3/1) to give the title compound (50 mg, 49%). LC-MS $(M+H)^+=305.2$.

Step 6: 2-cyclopropyl-N-methyl-5,8-dihydro-6H-pyrano[3,4-b]pyridin-5-amine hydrochloride

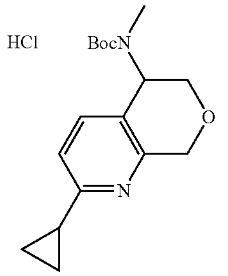 [SMILES: Cl ; CN(C(=O)OC(C)(C)C)C1COCc2nc(C3CC3)ccc21]

The title compound (40 mg, 100%) was prepared in a manner similar to that in Example 39 & Example 40 step 8 from tert-butyl (2-cyclopropyl-5,8-dihydro-6H-pyrano[3,4-b]pyridin-5-yl)(methyl)carbamate. LC-MS $(M+H)^+=205.2$.

Step 7: 5-amino-N-(2-cyclopropyl-5,8-dihydro-6H-pyrano[3,4-b]pyridin-5-yl)-N-methyl-1-((2-(trimethylsilyl)ethoxy)methyl)-6,8-dihydro-1H-furo[3,4-d]pyrrolo[3,2-b]pyridine-2-carboxamide

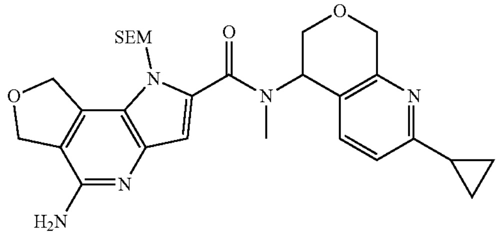 [SMILES: CN(C(=O)c1cc2nc(N)c3c(c2n1COCC[Si](C)(C)C)COC3)C1COCc2nc(C3CC3)ccc21]

The title compound (30 mg, 34%) was prepared in a manner similar to that in Example 73 & Example 74 step 9 from 2-cyclopropyl-N-methyl-5,8-dihydro-6H-pyrano[3,4-b]pyridin-5-amine hydrochloride and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+=536.4$.

Step 8: (S)-5-amino-N-(2-cyclopropyl-5,8-dihydro-6H-pyrano[3,4-b]pyridin-5-yl)-N-methyl-6,8-dihydro-1H-furo[3,4-d]pyrrolo[3,2-b]pyridine-2-carboxamide (R)-5-amino-N-(2-cyclopropyl-5,8-dihydro-6H-pyrano[3,4-b]pyridin-5-yl)-N-methyl-6,8-dihydro-1H-furo[3,4-d]pyrrolo[3,2-b]pyridine-2-carboxamide Example 87 (2 mg, 9%) and Example 88 (1.0 mg, 4%) were prepared in a manner similar to that in Example 73 & Example 74 step 10 from 5-amino-N-(2-cyclopropyl-5,8-dihydro-6H-pyrano[3,4-b]pyridin-5-yl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: ChiralPak IH; Column size: 4.6×100 mm, 3 μm Mobile phase: (isopropanol containing 0.2% 7 M methanolic $NH_3$):$CO_2$ 1; 1:9 for 0.2 min, 1:9 to 1:1 in 2.4 min, 1:1 for 1 min, 1:1 to 1:9 in 0.6 min; Flow: 3.4 mL/min; Temperature: 35° C.; back pressure: 2000 psi.

Example 87: Analytical SFC tR=2.301 min. $^1H$ NMR (400 MHz, DMSO-d6) δ 11.57 (br s, 1H), 7.48 (d, J=6.8 Hz, 1H), 7.22 (d, J=8.0 Hz, 1H), 6.70 (br s, 1H), 5.72 (br s, 1H), 5.56 (s, 2H), 5.15 (s, 2H), 4.93 (s, 2H), 4.74-4.65 (m, 1H), 4.61-4.51 (m, 1H), 4.07 (br s, 2H), 3.05 (br s, 3H), 2.13-2.04 (m, 1H), 1.00-0.82 (m, 4H). LC-MS $(M+H)^+=406.2$.

Example 88: Analytical SFC tR=2.478 min. $^1H$ NMR (400 MHz, DMSO-d6) δ 11.57 (br s, 1H), 7.48 (d, J=6.8 Hz, 1H), 7.22 (d, J=8.0 Hz, 1H), 6.70 (br s, 1H), 5.72 (br s, 1H), 5.56 (s, 2H), 5.15 (s, 2H), 4.93 (s, 2H), 4.74-4.65 (m, 1H), 4.61-4.51 (m, 1H), 4.07 (br s, 2H), 3.05 (br s, 3H), 2.13-2.04 (m, 1H), 1.00-0.82 (m, 4H). LC-MS $(M+H)^+=406.2$.

Example 89: 5-amino-N-ethyl-N-((1R,4S)-1-methyl-7-(trifluoromethyl)isochroman-4-yl)-6,8-dihydro-1H-furo[3,4-d]pyrrolo[3,2-b]pyridine-2-carboxamide

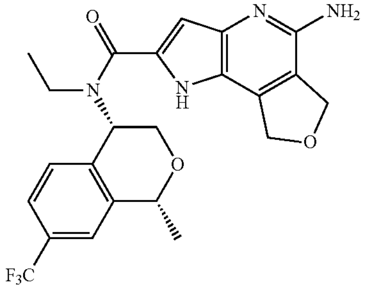 [SMILES: CCN(C(=O)c1cc2nc(N)c3c(c2[nH]1)COC3)[C@@H]1CO[C@H](C)c2cc(C(F)(F)F)ccc21]

Step 1: N-ethyl-N-((1R,4S)-1-methyl-7-(trifluoromethyl)isochroman-4-yl)-2-nitrobenzenesulfonamide

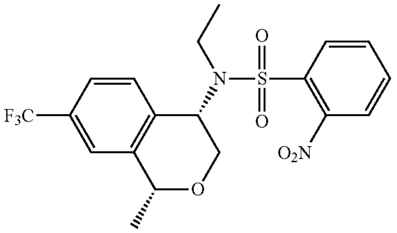 [SMILES: CCN([C@@H]1CO[C@H](C)c2cc(C(F)(F)F)ccc21)S(=O)(=O)c1ccccc1[N+](=O)[O-]]

The title compound (800 mg, 70%) was prepared in a manner similar to that in Example 83 step 6 from (1R,4R)-1-methyl-7-(trifluoromethyl)isochroman-4-ol and N-ethyl-2-nitrobenzenesulfonamide. LC-MS $(M+H)^+=445.2$.

Step 2: (1R,4S)—N-ethyl-1-methyl-7-(trifluoromethyl)isochroman-4-amine

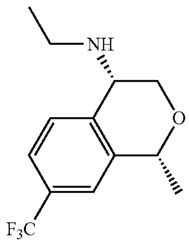 [SMILES: CCN[C@@H]1CO[C@H](C)c2cc(C(F)(F)F)ccc21]

The title compound (355 mg, 90%) was prepared in a manner similar to that in Example 83 step 7 from N-ethyl-N-((1R,4S)-1-methyl-7-(trifluoromethyl)isochroman-4-yl)-2-nitrobenzenesulfonamide. LC-MS $(M+H)^+$=260.2.

Step 3: 5-amino-N-ethyl-N-((1R,4S)-1-methyl-7-(trifluoromethyl)isochroman-4-yl)-1-((2-(trimethylsilyl)ethoxy)methyl)-6,8-dihydro-1H-furo[3,4-d]pyrrolo[3,2-b]pyridine-2-carboxamide

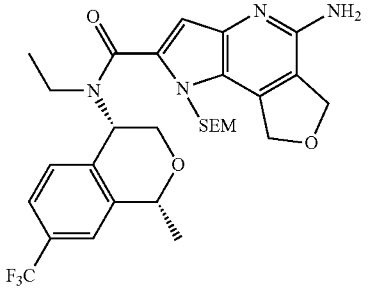 [SMILES: CCN(C(=O)c1cc2nc(N)c3c(c2n1COCC[Si](C)(C)C)COC3)[C@@H]1CO[C@H](C)c2cc(C(F)(F)F)ccc21]

The title compound (100 mg, 74%) was prepared in a manner similar to that in Example 82 step 11 from (1R,4S)—N-ethyl-1-methyl-7-(trifluoromethyl)isochroman-4-amine and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=591.2.

Step 4: 5-amino-N-ethyl-N-((1R,4S)-1-methyl-7-(trifluoromethyl)isochroman-4-yl)-6,8-dihydro-1H-furo[3,4-d]pyrrolo[3,2-b]pyridine-2-carboxamide Example 89 (54 mg, 58%) was prepared in a manner similar to that in Example 82 step 12 from 5-amino-N-ethyl-N-((1R,4S)-1-methyl-7-(trifluoromethyl)isochroman-4-yl)-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.59 (s, 1H), 7.70-7.55 (m, 2H), 7.51-7.35 (m, 1H), 6.62 (s, 1H), 5.60 (s, 1H), 5.56 (s, 2H), 5.19-5.11 (m, 2H), 4.93 (t, J=2.8 Hz, 2H), 4.89-4.82 (m, 1H), 4.35-4.24 (m, 1H), 4.15-4.01 (m, 1H), 3.87-3.44 (m, 2H), 1.60 (d, J=6.5 Hz, 3H), 1.14-1.00 (m, 3H). LC-MS $(M+H)^+$=461.2.

Example 90: (R)—N-(1-acetyl-7-(trifluoromethyl)-1,2,3,4-tetrahydroquinolin-4-yl)-5-amino-N-methyl-6,8-dihydro-1H-furo[3,4-d]pyrrolo[3,2-b]pyridine-2-carboxamide

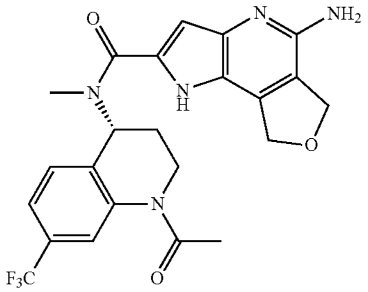 [SMILES: CC(=O)N1CC[C@@H](N(C)C(=O)c2cc3nc(N)c4c(c3[nH]2)COC4)c2ccc(C(F)(F)F)cc21]

Step 1: (R)—N-(1-acetyl-7-(trifluoromethyl)-1,2,3,4-tetrahydroquinolin-4-yl)-N-methyl-2-nitrobenzenesulfonamide

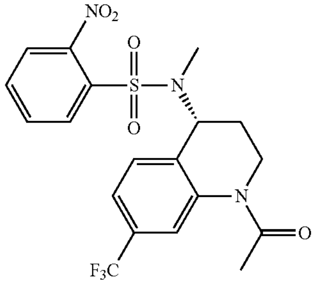 [SMILES: CC(=O)N1CC[C@@H](N(C)S(=O)(=O)c2ccccc2[N+](=O)[O-])c2ccc(C(F)(F)F)cc21]

To a solution of (R)—N-methyl-2-nitro-N-(7-(trifluoromethyl)-1,2,3,4-tetrahydroquinolin-2-yl)benzenesulfonamide (574 mg, 1.38 mmol) in DCM (10 mL) was added $Et_3N$ (419 mg, 4.15 mmol), and AcCl (162 mg, 2.08 mmol) at 0° C. The mixture was stirred for 3 h at 25° C. The mixture was partitioned between water (50 mL) and DCM (50 mL). The organic layers was washed with brine (50 mL), dried over $Na_2SO_4$, filtered and concentrated under vacuum. The residue was purified by silica gel chromatography (DCM: MeOH=30:1) to give the title compound (507 mg, 80%). LC-MS $(M+H)^+$=458.2.

Step 2: (R)-1-(4-(methylamino)-7-(trifluoromethyl)-3,4-dihydroquinolin-1(2H)-yl)ethan-1-one

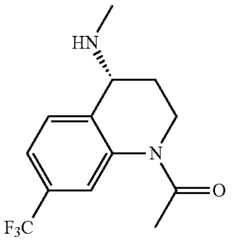 [SMILES: CN[C@@H]1CCN(C(C)=O)c2cc(C(F)(F)F)ccc21]

The title compound (200 mg, 66%) was prepared in a manner similar to that in Example 167 & Example 168 step 9 from (R)—N-(1-acetyl-7-(trifluoromethyl)-1,2,3,4-tetrahydroquinolin-4-yl)-N-methyl-2-nitrobenzenesulfonamide. LC-MS $(M+H)^+$=273.4.

Step 3: (R)—N-(1-acetyl-7-(trifluoromethyl)-1,2,3,4-tetrahydroquinolin-4-yl)-5-amino-N-methyl-1-((2-(trimethylsilyl)ethoxy)methyl)-6,8-dihydro-1H-furo[3,4-d]pyrrolo[3,2-b]pyridine-2-carboxamide

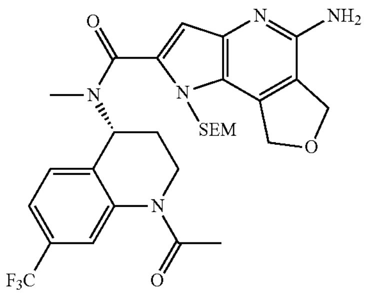 [SMILES: CC(=O)N1CC[C@@H](N(C)C(=O)c2cc3nc(N)c4c(c3n2COCC[Si](C)(C)C)COC4)c2ccc(C(F)(F)F)cc21]

The title compound (110 mg, 83%) was prepared in a manner similar to that in Example 167 & Example 168 step 10 from (R)-1-(4-(methylamino)-7-(trifluoromethyl)-3,4-dihydroquinolin-1(2H)-yl)ethan-1-one and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+=$ 604.3.

Step 4: (R)—N-(1-acetyl-7-(trifluoromethyl)-1,2,3,4-tetrahydroquinolin-4-yl)-5-amino-N-methyl-6,8-dihydro-1H-furo[3,4-d]pyrrolo[3,2-b]pyridine-2-carboxamide Example 90 (54 mg, 62%) was prepared in a manner similar to that in Example 167 & Example 168 step 11 from (R)—N-(1-acetyl-7-(trifluoromethyl)-1,2,3,4-tetrahydroquinolin-4-yl)-5-amino-N-methyl-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.58 (s, 1H), 8.08 (s, 1H), 7.59-7.12 (m, 2H), 6.92-6.44 (m, 1H), 5.92-5.68 (m, 1H), 5.56 (s, 2H), 5.10 (s, 2H), 4.88 (s, 2H), 4.18-3.88 (m, 1H), 3.75-3.61 (m, 1H), 3.12-2.64 (m, 3H), 2.30-2.00 (m, 5H). LC-MS $(M+H)^+=474.3$.

Example 91: (S)-5-amino-N-methyl-N-(7'-(trifluoromethyl)spiro[cyclopropane-1,1'-isochroman]-4'-yl)-6,8-dihydro-1H-furo[3,4-d]pyrrolo[3,2-b]pyridine-2-carboxamide

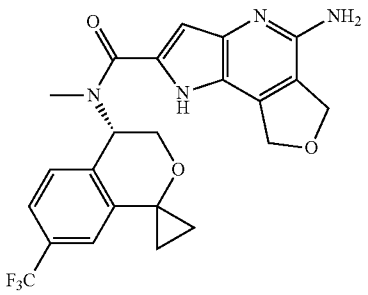 [SMILES: CN(C(=O)c1cc2nc(N)c3c(c2[nH]1)COC3)[C@@H]1COC2(CC2)c2cc(C(F)(F)F)ccc21]

Step 1: 1-(2-bromo-5-(trifluoromethyl)phenyl)cyclopropan-1-ol

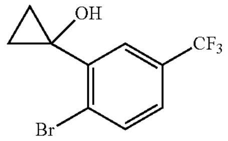 [SMILES: OC1(c2cc(C(F)(F)F)ccc2Br)CC1]

Bis(cyclopentadienyl)zirconium dichloride (4.1 g, 14.1 mmol) was suspended in toluene (30 mL) at 0° C. EtMgBr in THF (1.0 M, 15 mL, 15.0 mmol) was added dropwise. The mixture was stirred at 0° C. for 1 h, followed by addition of a solution of methyl 2-bromo-5-(trifluoromethyl)benzoate (2.0 g, 7.1 mmol) in toluene (10 mL) dropwise. The mixture was warmed to room temperature and stirred overnight. A solution of NaOH (1 g) in water (10 mL) was added, and the mixture was stirred at room temperature for 30 min. Solid was filtered off, and the solid was rinsed with EtOAc (20 mL). The organic layer of the filtrate was separated, and the aqueous layer was extracted with EtOAc (20 mL). The combined organic layer was washed with water (20 mL), dried with $Na_2SO_4$, filtered and concentrated under reduced pressure. The residue was purified by silica gel chromatography (PE/EtOAc=30:1) to give the title compound (760 mg, 38%). LC-MS $(M+H)^+=280.9$.

Step 2: 2-(1-(allyloxy)cyclopropyl)-1-bromo-4-(trifluoromethyl)benzene

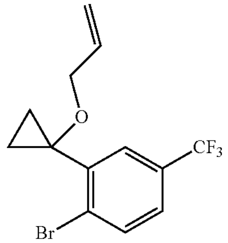 [SMILES: C=CCOC1(c2cc(C(F)(F)F)ccc2Br)CC1]

To a solution of 1-(2-bromo-5-(trifluoromethyl)phenyl)cyclopropan-1-ol (7.7 g, 27 mmol) and allyl bromide (6.6 g, 54 mmol) in DMF (50 mL) was added NaH (60%, 2.2 g, 54 mmol) at 0° C. The mixture was warmed to room temperature and stirred for 2 h. Water (200 mL) was added slowly. Upon cease of bubbling, the mixture was extracted with EtOAc (200 mL). The organic layer was washed with brine (100 mL), dried over $Na_2SO_4$, filtered and concentrated under reduced pressure. The residue was purified by silica gel chromatography (PE/EtOAc=50:1) to give the title compound (3.0 g, 34%).

Step 3: 4'-methylene-7'-(trifluoromethyl)spiro[cyclopropane-1,1'-isochromane]

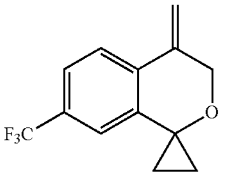 [SMILES: C=C1COC2(CC2)c2cc(C(F)(F)F)ccc21]

To a solution of 2-(1-(allyloxy)cyclopropyl)-1-bromo-4-(trifluoromethyl)benzene (850 mg, 25.5 mmol) in DMF (30 mL) was added $Pd(OAc)_2$ (90 mg, 3.8 mmol), $PPh_3$ (312 mg, 11.5 mmol) and $Cs_2CO_3$ (1.0 g, 30.7 mmol) under nitrogen. The mixture was stirred at 90° C. overnight and cooled to room temperature. The mixture was concentrated under reduced pressure and the residue was partitioned between water (20 mL) and EtOAc (30 mL). The organic layer was separated, dried over $Na_2SO_4$, filtered and concentrated under reduced pressure. The residue was purified by silica gel chromatography (PE/EtOAc=30:1) to give the title compound (500 mg, 79%).

Step 4: 7'-(trifluoromethyl)spiro[cyclopropane-1,1'-isochroman]-4'-one

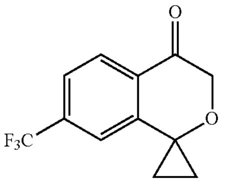 [SMILES: O=C1COC2(CC2)c2cc(C(F)(F)F)ccc21]

To a mixture of 4'-methylene-7'-(trifluoromethyl)spiro[cyclopropane-1,1'-isochromane](4.1 g, 17 mmol) in dioxane (100 mL) and water (20 mL) was added potassium osmate (VI) dihydrate (620 mg, 0.17 mmol), sodium periodate (14.6 g, 68 mmol) and 2,6-lutidine (3.6 g, 34 mmol). The mixture was stirred at room temperature for 2 h, and then solid was filtered off. The filtrate was extracted with EtOAc (20 mL). The organic layer was washed with water (20 mL), dried over $Na_2SO_4$, filtered and concentrated under reduced pressure. The residue was purified by silica gel chromatography (PE/EtOAc=10:1) to give the title compound (1.8 g, 43%). LC-MS $(M+H)^+$=243.0.

Step 5: (R)-7'-(trifluoromethyl)spiro[cyclopropane-1,1'-isochroman]-4'-ol

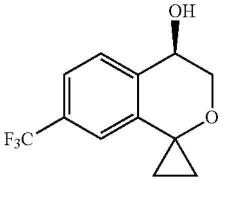 [SMILES: O[C@H]1COC2(CC2)c2cc(C(F)(F)F)ccc21]

To a solution of (R)-1-methyl-3,3-diphenylhexahydropyrrolo[1,2-c][1,3,2]oxazaborole (203 mg, 0.73 mmol) in THF (30 mL) was added and $BH_3$ in THF (1.0 M, 7.7 mL, 7.7 mmol) at 0° C. A solution of 7'-(trifluoromethyl)spiro[cyclopropane-1,1'-isochroman]-4'-one (1.77 g, 7.3 mmol) in THF (5 mL) was added dropwise under nitrogen. The mixture was stirred for 10 min at 0° C. MeOH (5 mL) was added dropwise. Upon cease of bubbling, the mixture was concentrated under reduced pressure. The residue was purified by silica gel chromatography (PE/EtOAc=10:1 to 5:1) to give the title compound (1.8 g, 100%). LC-MS $(M+H)^+$=245.0.

Step 6: (S)—N-methyl-2-nitro-N-(7'-(trifluoromethyl)spiro[cyclopropane-1,1'-isochroman]-4'-yl)benzenesulfonamide

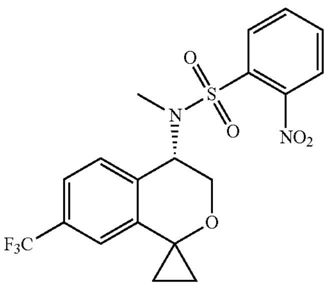 [SMILES: CN([C@@H]1COC2(CC2)c2cc(C(F)(F)F)ccc21)S(=O)(=O)c1ccccc1[N+](=O)[O-]]

To a mixture of (R)-7'-(trifluoromethyl)spiro[cyclopropane-1,1'-isochroman]-4'-ol (830 mg, 3.4 mmol) in THF (30 mL) was added N-methyl-2-nitro-benzenesulfonamide (735 mg, 3.4 mmol), DtBAD (860 mg, 3.7 mmol) and $PPh_3$ (980 mg, 3.7 mmol) under nitrogen. The mixture was stirred at room temperature for 1 h and then concentrated under reduced pressure. The residue was purified by silica gel chromatography (PE/EtOAc=10:1 to 5:1) to give the title compound, and the material (2.2 g) was used in step 7. LC-MS $(M+H)^+$=443.0.

Step 7: (S)—N-methyl-7'-(trifluoromethyl)spiro[cyclopropane-1,1'-isochroman]-4'-amine

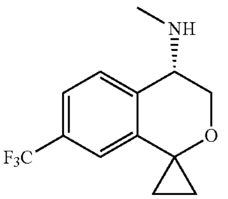 [SMILES: CN[C@@H]1COC2(CC2)c2cc(C(F)(F)F)ccc21]

A mixture of (S)—N-methyl-2-nitro-N-(7'-(trifluoromethyl)spiro[cyclopropane-1,1'-isochroman]-4'-yl)benzenesulfonamide (2.2 g from step 6), lithium hydroxide monohydrate (630 mg, 15 mmol) and dodecane-1-thiol (3.0 g, 15 mmol) in THF (40 mL) and DMF (10 mL) was stirred at room temperature for overnight. The mixture was concentrated under reduced pressure. The residue was partitioned between water (30 mL) and EtOAc (30 mL). The organic layer was dried over $Na_2SO_4$, filtered and concentrated under reduced pressure. The residue was purified by silica gel chromatography (PE/EtOAc=2:1 to 0:1) to give the title compound (630 mg, 70% over two steps). LC-MS $(M+H)^+$= 258.2.

Step 8: (S)-5-amino-N-methyl-N-(7'-(trifluoromethyl)spiro[cyclopropane-1,1'-isochroman]-4'-yl)-1-((2-(trimethylsilyl)ethoxy)methyl)-6,8-dihydro-1H-furo[3,4-d]pyrrolo[3,2-b]pyridine-2-carboxamide

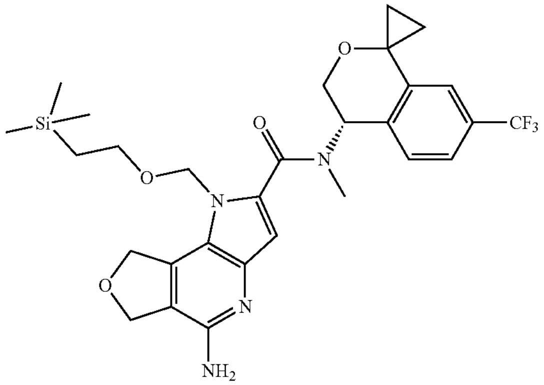 [SMILES: CN(C(=O)c1cc2nc(N)c3c(c2n1COCC[Si](C)(C)C)COC3)[C@@H]1COC2(CC2)c2cc(C(F)(F)F)ccc21]

To a mixture of 5-amino-1-((2-(trimethylsilyl)ethoxy)methyl)-6,8-dihydro-1H-furo[3,4-d]pyrrolo[3,2-b]pyridine-2-carboxylic acid (855 mg, 2.5 mmol) and (S)—N-methyl-7'-(trifluoromethyl)spiro[cyclopropane-1,1'-isochroman]-4'-amine (630 mg, 2.5 mmol) in THF (30 mL) was added BOPCl (810 mg, 3.2 mmol) and DIPEA (1.3 mL, 7.4 mmol). The mixture was stirred at 60° C. for 2 h and cooled to room temperature. The mixture was diluted with water (30 mL) and extracted with EtOAc (30 mL). The organic layer was dried over $Na_2SO_4$, filtered and concentrated under reduced pressure. The residue was purified by silica gel chromatography (DCM/MeOH=30:1) to give the title compound (1.4 g, 97%). LC-MS $(M+H)^+$=589.2.

Step 9: (S)-5-amino-N-methyl-N-(7'-(trifluoromethyl)spiro[cyclopropane-1,1'-isochroman]-4'-yl)-6,8-dihydro-1H-furo[3,4-d]pyrrolo[3,2-b]pyridine-2-carboxamide To a solution of (S)-5-amino-N-methyl-N-(7'-(trifluoromethyl)spiro[cyclopropane-1,1'-isochroman]-4'-yl)-1-((2-(trimethylsilyl)ethoxy)methyl)-6,8-dihydro-1H-furo[3,4-d]pyrrolo[3,2-b]pyridine-2-carboxamide (1.4 g, 2.4 mmol) in DCM (10 mL) was added TFA (5 mL). The mixture was stirred at room temperature for 1 h. The mixture was concentrated under reduced pressure. The residue was re-dissolved in MeOH (20 mL) followed by addition of strong ammonia solution (28%, 5 mL). The mixture was stirred at room temperature for 30 min. The mixture was concentrated under reduced pressure. The residue was partitioned between EtOAc (30 mL) and water (20 mL). The organic layer was concentrated under reduced pressure and the residue was purified by silica gel chromatography (DCM:MeOH=30:1) to give Example 91 (554 mg, 50%). $^1H$ NMR (400 MHz, DMSO-d6) δ 11.61 (s, 1H), 7.59 (d, J=8.1 Hz, 1H), 7.44 (br s, 1H), 7.15 (s, 1H), 6.81-6.49 (m, 1H), 5.89 (s, 1H), 5.59 (s, 2H), 5.14 (s, 2H), 4.91 (s, 2H), 4.48-3.94 (m, 2H), 3.19-2.67 (m, 3H), 1.43-1.06 (m, 4H). LC-MS $(M+H)^+$= 459.2.

Example 92: (S)-5-amino-3-cyano-N-methyl-N-(7-(trifluoromethyl)isochroman-4-yl)-6,8-dihydro-1H-furo[3,4-d]pyrrolo[3,2-b]pyridine-2-carboxamide

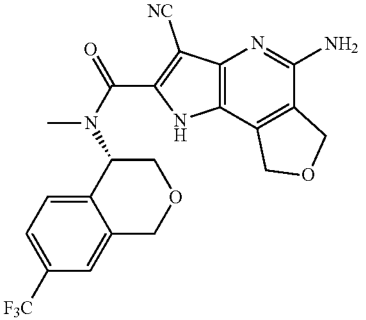 [SMILES: CN(C(=O)c1[nH]c2c3c(c(N)nc2c1C#N)COC3)[C@@H]1COCc2cc(C(F)(F)F)ccc21]

Step 1: ethyl 5-(bis(tert-butoxycarbonyl)amino)-1-((2-(trimethylsilyl)ethoxy)methyl)-6,8-dihydro-1H-furo[3,4-d]pyrrolo[3,2-b]pyridine-2-carboxylate

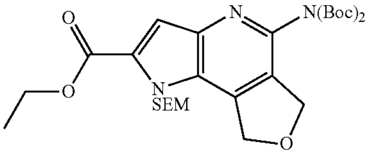

To a mixture of ethyl 5-amino-1-((2-(trimethylsilyl)ethoxy)methyl)-6,8-dihydro-1H-furo[3,4-d]pyrrolo[3,2-b]pyridine-2-carboxylate (2.2 g, 5.8 mmol) and $Et_3N$ (6.06 g, 60 mmol) and DMAP (73 mg, 0.6 mmol) in DCM (100 mL) was added $(Boc)_2O$ (13.0 g, 60 mmol). The mixture was stirred at room temperature for 12 h. Water (250 mL) was added and the organic layer was separated. The aqueous layer was extracted with DCM (2×100 mL). The combined organic layer was dried with $Na_2SO_4$, filtered and concentrated under reduced pressure. The residue was purified by silica gel chromatography (PE:EtOAc=20:1) to give the title compound (2.4 g, 71%).

Step 2: ethyl 5-(bis(tert-butoxycarbonyl)amino)-3-bromo-1-((2-(trimethylsilyl)ethoxy)methyl)-6,8-dihydro-1H-furo[3,4-d]pyrrolo[3,2-b]pyridine-2-carboxylate

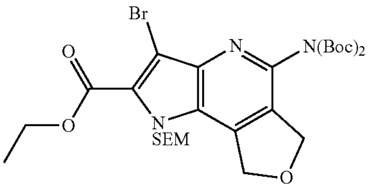

To a mixture of ethyl 5-(bis(tert-butoxycarbonyl)amino)-1-((2-(trimethylsilyl)ethoxy)methyl)-6,8-dihydro-1H-furo[3,4-d]pyrrolo[3,2-b]pyridine-2-carboxylate (2.4 g, 4.2 mmol) in MeCN (20 mL) was added NBS (756 mg, 4.2 mmol) and the mixture was stirred at 50° C. for 2 h. The mixture was cooled to room temperature and diluted with water (100 mL). The mixture was extracted with DCM (2×100 mL). The combined organic layer was dried with $Na_2SO_4$, filtered and concentrated under reduced pressure. The residue was purified by silica gel chromatography (PE:EtOAc=20:1) to give the title compound (2.4 g, 87%). LC-MS $(M+H)^+$=656.1.

Step 3: ethyl 5-amino-3-cyano-1-((2-(trimethylsilyl) ethoxy)methyl)-6,8-dihydro-1H-furo[3,4-d]pyrrolo [3,2-b]pyridine-2-carboxylate

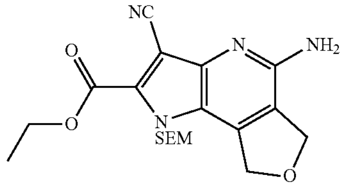 [SMILES: CCOC(=O)c1c(C#N)c2nc(N)c3c(c2n1COCC[Si](C)(C)C)COC3]

To a mixture of ethyl 5-(bis(tert-butoxycarbonyl)amino)-3-bromo-1-((2-(trimethylsilyl)ethoxy)methyl)-6,8-dihydro-1H-furo[3,4-d]pyrrolo[3,2-b]pyridine-2-carboxylate (1.7 g, 2.6 mmol) in NMP (15 mL) was added $Zn(CN)_2$ (620 mg, 5.3 mmol) and $Pd(PPh_3)_4$ (266 mg, 0.26 mmol) and the mixture was stirred at 140° C. for 3 h under nitrogen. The mixture was cooled to room temperature and diluted with water (150 mL). The mixture was extracted with EtOAc (3×50 mL). The combined organic layer was dried with $Na_2SO_4$, filtered and concentrated under reduced pressure to give the title compound (2(0) mg, 19%). LC-MS $(M+H)^+$=403.2.

Step 4: 5-amino-3-cyano-1-((2-(trimethylsilyl) ethoxy)methyl)-6,8-dihydro-1H-furo[3,4-d]pyrrolo [3,2-b]pyridine-2-carboxylic Acid

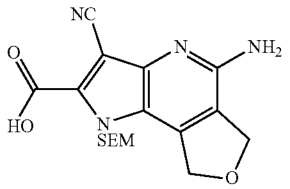 [SMILES: C[Si](C)(C)CCOCn1c(C(=O)O)c(C#N)c2nc(N)c3c(c21)COC3]

The title compound (350 mg, 96%) was prepared in a manner similar to that in Example 44 step 4 from ethyl 5-amino-3-cyano-1-((2-(trimethylsilyl)ethoxy)methyl)-6,8-dihydro-1H-furo[3,4-d]pyrrolo[3,2-b]pyridine-2-carboxylate. LC-MS $(M+H)^+$=375.2.

Step 5: (S)-5-amino-3-cyano-N-methyl-N-(7-(trifluoromethyl)isochroman-4-yl)-1-((2-(trimethylsilyl) ethoxy)methyl)-6,8-dihydro-1H-furo[3,4-d]pyrrolo [3,2-b]pyridine-2-carboxamide

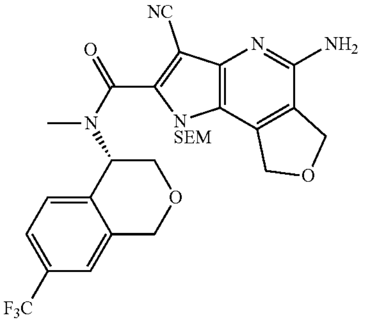 [SMILES: CN(C(=O)c1c(C#N)c2nc(N)c3c(c2n1COCC[Si](C)(C)C)COC3)[C@@H]1COCc2cc(C(F)(F)F)ccc21]

The title compound (50 mg, 64%) was prepared in a manner similar to that in Example 66 step 2 from 5-amino-3-cyano-1-((2-(trimethylsilyl)ethoxy)methyl)-6,8-dihydro-1H-furo[3,4-d]pyrrolo[3,2-b]pyridine-2-carboxylic acid and (S)—N-methyl-7-(trifluoromethyl)isochroman-4-amine hydrochloride. LC-MS $(M+H)^+$=588.4.

Step 6: (S)-5-amino-3-cyano-N-methyl-N-(7-(trifluoromethyl)isochroman-4-yl)-6,8-dihydro-1H-furo [3,4-d]pyrrolo[3,2-b]pyridine-2-carboxamide Example 92 (23 mg, 59%) was prepared in a manner similar to that in Example 66 step 3 from (S)-5-amino-3-cyano-N-methyl-N-(7-(trifluoromethyl)isochroman-4-yl)-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 12.69 (s, 1H), 7.75-7.42 (m, 3H), 6.12 (s, 2H), 5.68 (s, 1H), 5.15 (s, 2H), 4.98-4.62 (m, 4H), 4.13 (s, 2H), 2.86 (s, 3H). LC-MS $(M+H)^+$=458.4.

Example 93 & Example 94: 5-amino-N-((1S,4S)-1-ethyl-7-(trifluoromethyl)isochroman-4-yl)-N-methyl-6,8-dihydro-1H-furo[3,4-d]pyrrolo[3,2-b] pyridine-2-carboxamide & 5-amino-N-((1R,4S)-1-ethyl-7-(trifluoromethyl)isochroman-4-yl)-N-methyl-6,8-dihydro-1H-furo[3,4-d]pyrrolo[3,2-b] pyridine-2-carboxamide

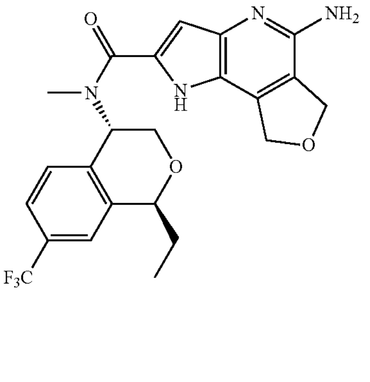

&

-continued

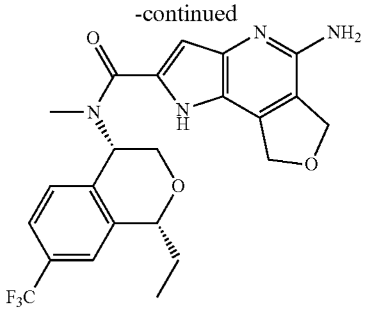

Step 1: 1-(2-bromo-5-(trifluoromethyl)phenyl)propan-1-ol

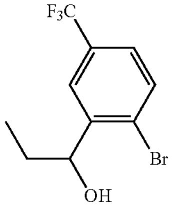

The title compound (4.8 g, 43%) was prepared in a manner similar to that in Example 57 & Example 58 & Example 59 & Example 60 step 1 from 2-bromo-5-(trifluoromethyl)benzaldehyde and EtMgBr. LC-MS $(M+H)^+$=283.3.

Step 2: 2-(1-(allyloxy)propyl)-1-bromo-4-(trifluoromethyl)benzene

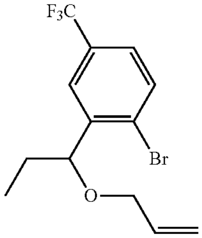 [SMILES: C=CCOC(CC)c1cc(C(F)(F)F)ccc1Br]

The title compound (5.4 g, 99%) was prepared in a manner similar to that in Example 39 & Example 40 step 1 from 1-(2-bromo-5-(trifluoromethyl)phenyl)propan-1-ol and allyl bromide. LC-MS $(M+H)^+$=323.1.

Step 3: 1-ethyl-4-methylene-7-(trifluoromethyl)isochromane

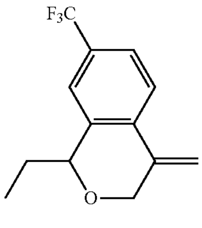 [SMILES: C=C1COC(CC)c2cc(C(F)(F)F)ccc21]

The title compound (2.5 g, 61%) was prepared in a manner similar to that in Example 39 & Example 40 step 2 from 2-(1-(allyloxy)propyl)-1-bromo-4-(trifluoromethyl)benzene. LC-MS $(M+H)^+$=243.3.

Step 4: 1-ethyl-7-trifluoromethyl)isochroman-4-one

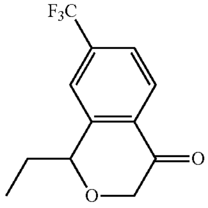 [SMILES: CCC1OCC(=O)c2ccc(C(F)(F)F)cc21]

The title compound (2.1 g, 84%) was prepared in a manner similar to that in Example 39 & Example 40 step 3 from 1-ethyl-4-methylene-7-(trifluoromethyl)isochromane. LC-MS $(M+H)^+$=245.4.

Step 5: (4R)-1-ethyl-7-(trifluoromethyl)isochroman-4-ol

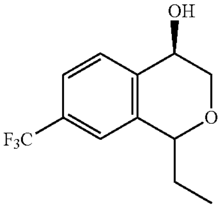 [SMILES: CCC1OC[C@H](O)c2ccc(C(F)(F)F)cc21]

The title compound (2.1 g, 100%) was prepared in a manner similar to that in Example 91 step 5 from 1-ethyl-7-(trifluoromethyl)isochroman-4-one. LC-MS $(M+H)^+$=247.1.

Step 6: N-((4S)-1-ethyl-7-(trifluoromethyl)isochroman-4-yl)-N-methyl-2-nitrobenzenesulfonamide

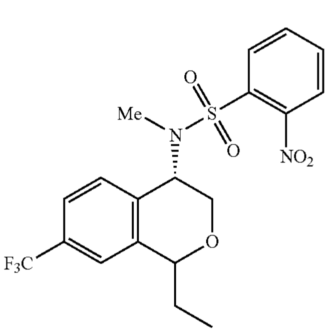 [SMILES: CCC1OC[C@@H](N(C)S(=O)(=O)c2ccccc2[N+](=O)[O-])c2ccc(C(F)(F)F)cc21]

The title compound (3.8 g, 100%) was prepared in a manner similar to that in Example 91 step 6 from (4R)-1-ethyl-7-(trifluoromethyl)isochroman-4-ol and N-methyl-2-nitro-benzenesulfonamide. LC-MS $(M+H)^+$=445.3.

Step 7: (4S)-1-ethyl-N-methyl-7-(trifluoromethyl)isochroman-4-amine

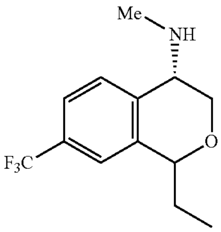 [SMILES: CCC1OC[C@@H](NC)c2ccc(C(F)(F)F)cc21]

The title compound (1.7 g, 77%) was prepared in a manner similar to that in Example 91 step 7 from N-((4S)-1-ethyl-7-(trifluoromethyl)isochroman-4-yl)-N-methyl-2-nitrobenzenesulfonamide. LC-MS $(M+H)^+$=260.2.

Step 8: 5-amino-N-((1S,4S)-1-ethyl-7-(trifluoromethyl)isochroman-4-yl)-N-methyl-6,8-dihydro-1H-furo[3,4-d]pyrrolo[3,2-b]pyridine-2-carboxamide & 5-amino-N-(1R,4S)-1-ethyl-7-(trifluoromethyl)isochroman-4-yl)-N-methyl-6,8-dihydro-1H-furo[3,4-d]pyrrolo[3,2-b]pyridine-2-carboxamide To a mixture of 5-amino-6,8-dihydro-1H-furo[3,4-d]pyrrolo[3,2-b]pyridine-2-carboxylic acid (120 mg, 0.54 mmol). (4S)-1-ethyl-N-methyl-7-(trifluoromethyl)isochroman-4-amine (141 mg, 0.54 mmol) and DIPEA (492 mg, 3.82 mmol) in anhydrous DMF (5 mL) under nitrogen was added T3P (867 mg, 2.73 mmol) and the mixture was stirred at 60° C. for 16 h. The mixture was cooled to room temperature followed by addition of hydrochloric acid HCl (6 M, 9 mL). The mixture was stirred for 3 h at 60° C. The mixture was cooled to room temperature and poured into saturated $NaHCO_3$ (100 mL). The mixture was extracted with EtOAc (100 mL). The organic layer was washed with brine (100 mL), dried over $Na_2SO_4$, filtered and concentrated under vacuum. The residue was purified by silica gel chromatography (DCM:MeOH=20:1), followed by chiral SFC to give Example 93 (34 mg, 13%) and Example 94 (36 mg, 14%).

Analytical chiral-SFC condition as below. Column: YMC Cellulose-C; Column size: 4.6×100 mm, 5 μm; Mobile phase: 4 mM methanolic $NH_3$:$CO_2$, 1:9 to 4:6 in 3 min. 4:6 for 2 min, 4:6 to 1:9 in 0.1 min, 1:9 for 1.9 min; Flow: 2.0 mL/min; Temperature: 35° C.; back pressure: 1500 psi.

Example 93: Analytical SFC tR=4.09 min. $^1H$ NMR (400 MHz, DMSO-d6) δ 11.60 (s, 1H), 7.62 (s, 2H), 7.48-7.33 (m, 1H), 6.75-6.50 (m, 1H), 5.91-5.46 (m, 3H), 5.14 (s, 2H), 5.01-4.77 (m, 3H), 4.25-4.12 (m, 1H), 4.01-3.81 (m, 1H), 3.02 (s, 3H), 2.04-1.75 (m, 2H), 0.98-0.83 (m, 3H). LCMS $(M+H)^+$=461.4.

Example 94: Analytical SFC tR=4.97 min. $^1H$ NMR (400 MHz, DMSO-d6) δ 11.56 (s, 1H), 7.65 (s, 2H), 7.46 (s, 1H), 6.70 (s, 1H), 5.85-5.47 (m, 3H), 5.14 (s, 2H), 4.91 (s, 2H), 4.75-4.57 (m, 1H), 4.32-3.91 (m, 2H), 3.09 (s, 3H), 2.21-2.02 (s, 1H), 1.97-1.83 (m, 1H), 1.00-0.89 (m, 3H). LCMS $(M+H)^+$=461.4.

Example 95: (S)-5-amino-N-(7-cyclopropyl-5-fluoroisochroman-4-yl)-N-methyl-6,8-dihydro-1H-furo[3,4-d]pyrrolo[3,2-b]pyridine-2-carboxamide

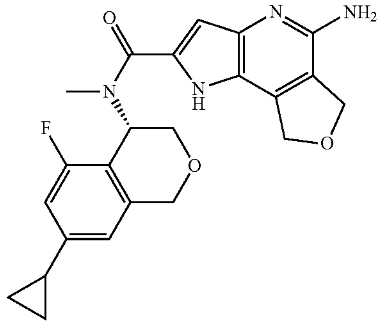 [SMILES: CN(C(=O)c1cc2nc(N)c3c(c2[nH]1)COC3)[C@@H]1COCc2cc(C3CC3)cc(F)c21]

Step 1: methyl 2-amino-5-cyclopropyl-3-fluorobenzoate

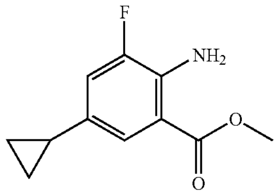

The title compound (22 g, 43%) was prepared in a manner similar to that in Example 87 & Example 88 step 5 from methyl 2-amino-5-bromo-3-fluoro-benzoate and cyclopropylboronic acid. LC-MS $(M+H)^+$=210.2.

Step 2: methyl 2-bromo-5-cyclopropyl-3-fluorobenzoate

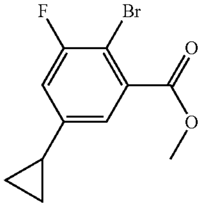

The title compound (22 g, 77%) was prepared in a manner similar to that in Example 82 step 3 from methyl 2-amino-5-cyclopropyl-3-fluorobenzoate. $^1H$ NMR (400 MHz, $CDCl_3$) δ 7.31-7.29 (m, 1H), 6.93 (dd, J=9.5, 2.1 Hz, 1H), 3.94 (s, 3H), 1.95-1.84 (m, 1H), 1.08-1.02 (m, 2H) 0.74-0.70 (m, 2H).

Step 3: (2-bromo-5-cyclopropyl-3-fluorophenyl)methanol

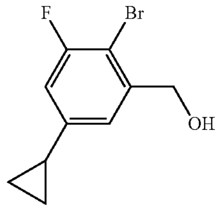 [SMILES: OCc1cc(C2CC2)cc(F)c1Br]

The title compound (3.55 g, 79%) was prepared in a manner similar to that in Example 82 step 4 from methyl 2-bromo-5-cyclopropyl-3-fluorobenzoate. $^1$H NMR (400 MHz, $CDCl_3$) δ 7.05-7.01 (m, 1H) 6.76 (dd, J=9.5, 2.0 Hz, 1H), 4.75-4.72 (m, 2H), 2.19-1.62 (m, 2H), 1.05-0.99 (m, 2H), 0.74-0.68 (m, 2H).

Step 4: 1-((allyloxy)methyl)-2-bromo-5-cyclopropyl-3-fluorobenzene

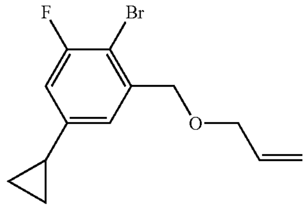 [SMILES: C=CCOCc1cc(C2CC2)cc(F)c1Br]

The title compound (3.37 g, 82%) was prepared in a manner similar to that in Example 82 step 5 from (2-bromo-5-cyclopropyl-3-fluorophenyl)methanol and allyl bromide. $^1$H NMR (400 MHz, $CDCl_3$) δ 7.07-7.02 (m, 1H), 6.74 (dd, J=9.7, 2.0 Hz, 1H), 6.05-5.94 (m, 1H), 5.36 (dd, J=17.3, 1.6 Hz, 1H), 5.25 (dd, J=10.4, 1.3 Hz, 1H), 4.56 (s, 2H), 4.14-4.10 (m, 2H), 1.92-1.85 (m, 1H), 1.05-0.98 (m, 2H), 0.73-0.67 (m, 2H).

Step 5: 7-cyclopropyl-5-fluoro-4-methyleneisochromane

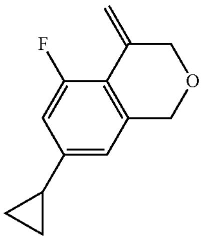

The title compound (3.9 g, 45%) was prepared in a manner similar to that in Example 82 step 6 from 1-((allyloxy)methyl)-2-bromo-5-cyclopropyl-3-fluorobenzene. LC-MS $(M+H)^+$=205.2.

Step 6: 7-cyclopropyl-5-fluoroisochroman-4-one

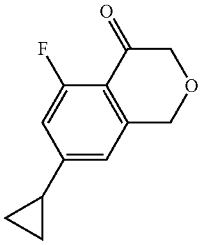 [SMILES: O=C1COCc2cc(C3CC3)cc(F)c21]

The title compound (1.6 g, 53%) was prepared in a manner similar to that in Example 82 step 7 from 7-cyclopropyl-5-fluoro-4-methyleneisochromane. $^1$H NMR (400 MHz, $CDCl_3$) δ 6.74-6.68 (m, 2H), 4.81 (s, 2H), 4.29 (s, 2H), 1.97-1.87 (m, 1H), 1.16-1.10 (m, 2H), 0.83-0.77 (m, 2H). LC-MS $(M+H)^+$=207.2.

Step 7: (R)-7-cyclopropyl-5-fluoroisochroman-4-ol

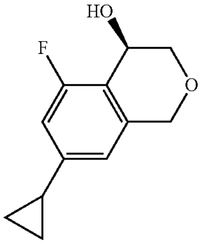 [SMILES: O[C@H]1COCc2cc(C3CC3)cc(F)c21]

The title compound (1.6 g, 53%) was prepared in a manner similar to that in Example 84 step 1 from 7-cyclopropyl-5-fluoroisochroman-4-one. $^1$H NMR (400 MHz, $CDCl_3$) δ 6.65 (d, J=10.9 Hz, 1H), 6.54 (s, 1H), 4.78-4.67 (m, 2H), 4.65-4.53 (m, 1H), 4.18 (dd. J=12.2, 1.1 Hz, 1H), 3.75 (dd, J=12.2, 2.2 Hz, 1H), 1.90-1.81 (m, 1H), 1.07-0.91 (m, 2H), 0.74-0.62 (m, 2H). LC-MS $(M+H—H_2O)^+$=191.2.

Step 8: (S)-4-azido-7-cyclopropyl-5-fluoroisochromane

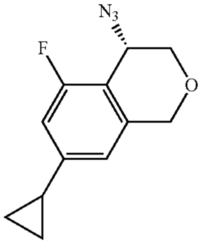 [SMILES: [N-]=[N+]=N[C@@H]1COCc2cc(C3CC3)cc(F)c21]

The title compound (1.18 g, 81%) was prepared in a manner similar to that in Example 78 & Example 79 & Example 80 & Example 81 step 6 from (R)-7-cyclopropyl-5-fluoroisochroman-4-ol. $^1$H NMR (400 MHz, $CDCl_3$) δ 6.62 (d, J=10.6 Hz, 1H), 6.53 (s, 1H), 4.77, 4.56 (ABq, J=15.4 Hz, 2H), 4.35-4.29 (m, 1H), 4.25-4.14 (m, 1H), 3.72-3.68 (m, 1H), 1.85-1.75 (m, 1H), 0.97-0.91 (m, 2H), 0.66-0.60 (m, 2H).

Step 9: (S)-7-cyclopropyl-5-fluoroisochroman-4-amine

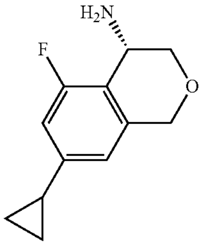 [SMILES: N[C@@H]1COCc2cc(C3CC3)cc(F)c21]

The title compound (1.5 g, 99%) was prepared in a manner similar to that in Example 78 & Example 79 & Example 80 & Example 81 step 7 from (S)-4-azido-7-cyclopropyl-5-fluoroisochromane. LC-MS $(M+H)^+$=208.2.

Step 10: tert-butyl (S)-(7-cyclopropyl-5-fluoroisochroman-4-yl)carbamate

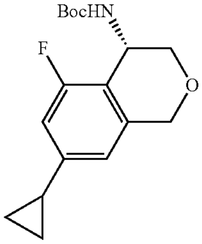 [SMILES: CC(C)(C)OC(=O)N[C@@H]1COCc2cc(C3CC3)cc(F)c21]

The title compound (1.4 g, 63%) was prepared in a manner similar to that in Example 39 & Example 40 step 6 from (S)-7-cyclopropyl-5-fluoroisochroman-4-amine. LCMS $(M+H\text{-}tBu)^+$=252.1.

Step 11: tert-butyl (S)-(7-cyclopropyl-5-fluoroisochroman-4-yl)(methyl)carbamate

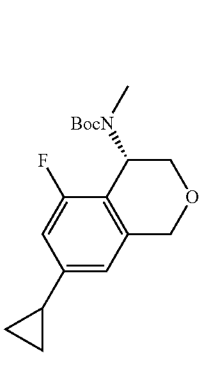 [SMILES: CN(C(=O)OC(C)(C)C)[C@@H]1COCc2cc(C3CC3)cc(F)c21]

The title compound (360 mg, 86%) was prepared in a manner similar to that in Example 39 & Example 40 step 7 from tert-butyl (S)-(7-cyclopropyl-5-fluoroisochroman-4-yl)carbamate and MeI. LCMS $(M+H\text{-}tBu)^+$=266.2.

Step 12: (S)-7-cyclopropyl-5-fluoro-N-methylisochroman-4-amine Hydrochloride

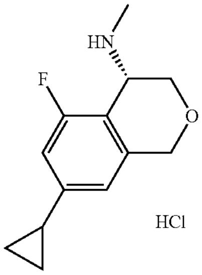 [SMILES: CN[C@@H]1COCc2cc(C3CC3)cc(F)c21 ; Cl]

The title compound (60 mg, 99%) was prepared in a manner similar to that in Example 39 & Example 40 step 8 from tert-butyl (S)-(7-cyclopropyl-5-fluoroisochroman-4-yl)(methyl)carbamate. LC-MS $(M+H)^+$=222.2.

Step 13: tert-butyl (S)-(2-((7-cyclopropyl-5-fluoroisochroman-4-yl)(methyl)carbamoyl)-6,8-dihydro-1H-furo[3,4-d]pyrrolo[3,2-b]pyridin-5-yl)carbamate

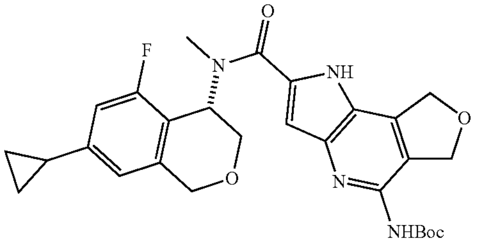

The title compound (110 mg, 78%) was prepared in a manner similar to that in Example 13 step 4 from (S)-7-cyclopropyl-5-fluoro-N-methylisochroman-4-amine hydrochloride and 5-((tert-butoxycarbonyl)amino)-6,8-dihydro-1H-furo[3,4-d]pyrrolo[3,2-b]pyridine-2-carboxylic acid. LC-MS $(M+H)^+$=523.3.

Step 14: (S)-5-amino-N-(7-cyclopropyl-5-fluoroisochroman-4-yl)-N-methyl-6,8-dihydro-1H-furo[3,4-d]pyrrolo[3,2-b]pyridine-2-carboxamide To a solution of tert-butyl (S)-(2-((7-cyclopropyl-5-fluoroisochroman-4-yl)(methyl)carbamoyl)-6,8-dihydro-1H-furo[3,4-d]pyrrolo[3,2-b]pyridin-5-yl)carbamate (90 mg, 172 μmol) in DCM (3 mL) was added $ZnBr_2$ (388 mg, 1.72 mmol). The mixture was stirred at 35° C. for 2 h. The mixture was concentrated under reduced pressure. The residue was purified by prep-HPLC to give Example 95 (30 mg, 41%). $^1H$ NMR (400 MHz, DMSO-d6) δ 11.54 (br s, 1H), 6.89-6.42 (m, 3H), 5.71 (br s, 1H), 5.55 (s, 2H), 5.15 (s, 2H), 4.93 (s, 2H), 4.86-4.80 (m, 1H), 4.62-4.55 (m, 1H), 4.15-3.90 (m, 2H), 3.20-2.70 (m, 3H), 1.98-1.85 (m, 1H), 0.99-0.87 (m, 2H), 0.76-0.62 (m, 2H). LC-MS $(M+H)^+$=423.2.

Example 96: (S)-5-amino-N-(7-bromo-5-fluoroisochroman-4-yl)-N-methyl-6,8-dihydro-1H-furo[3,4-d]pyrrolo[3,2-b]pyridine-2-carboxamide

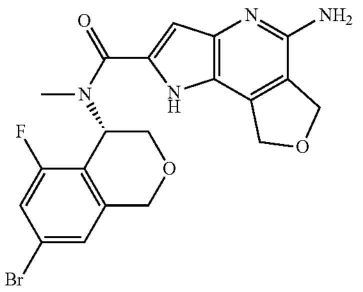 [SMILES: CN(C(=O)c1cc2nc(N)c3c(c2[nH]1)COC3)[C@@H]1COCc2cc(Br)cc(F)c21]

Step 1: methyl 4-bromo-2-(bromomethyl)-6-fluorobenzoate

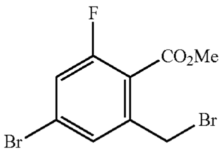 [SMILES: COC(=O)c1c(F)cc(Br)cc1CBr]

To a solution of methyl 4-bromo-2-fluoro-6-methyl-benzoate (50 g, 202.38 mmol) in $CCl_4$ (500 mL) was added AIBN (3.32 g, 20.2 mmol) and NBS (39.6 g, 223 mmol). The mixture was stirred at 100° C. for 24 h and then cooled to room temperature. The mixture was concentrated under reduced pressure. n-Hexane (300 mL) was added to the residue, and then the mixture was stirred at 25° C. for 30 min. Solid was filtered off and the filtrate was concentrated in vacuum to give the title compound (42 g, 64%). $^1$H NMR (400 MHz, $CDCl_3$) δ 7.35-7.29 (m, 1H), 7.21 (dd, J=9.0, 1.8 Hz, 1H), 4.53 (s, 2H), 3.90 (s, 3H).

Step 2: methyl 4-bromo-2-fluoro-6-((2-methoxy-2-oxoethoxy)methyl)benzoate

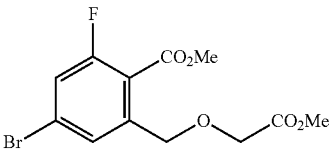 [SMILES: COC(=O)COCc1cc(Br)cc(F)c1C(=O)OC]

The title compound (22 g, 51%) was prepared in a manner similar to that in Example 73 & Example 74 step 2 from methyl 4-bromo-2-(bromomethyl)-6-fluorobenzoate and methyl 2-hydroxyacetate. $^1$H NMR (400 MHz, $CDCl_3$) δ 7.71 (dd, J=9.4, 1.8 Hz, 1H), 7.62-7.58 (m, 1H), 4.67 (s, 2H), 4.19 (s, 2H), 3.86 (s, 3H), 3.68 (s, 3H).

Step 3: methyl 7-bromo-5-fluoro-4-oxoisochromane-3-carboxylate

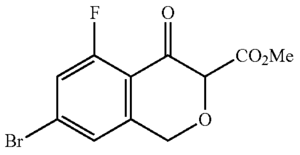 [SMILES: COC(=O)C1OCc2cc(Br)cc(F)c2C1=O]

A solution of LiHMDS in THF (1 M, 22.4 mL, 22.4 mmol) was diluted with THF (100 mL), and to the solution was added a solution of methyl 4-bromo-2-fluoro-6-((2-methoxy-2-oxoethoxy)methyl)benzoate (5.0 g, 15 mmol) in THF (100 mL). The mixture was stirred at 25° C. for 12 h. The reaction mixture was poured into iced water (50 mL) and extracted with EtOAc (3×50 mL). The combined organic layer was washed with brine (100 mL), dried over $Na_2SO_4$, filtered and concentrated under reduced pressure. The residue was purified by silica gel chromatography (PE/EtOAc=1/0 to 5/1) to give the title compound (3.25 g, 72%).

Step 4: 7-bromo-5-fluoroisochroman-4-one

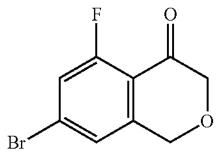 [SMILES: O=C1COCc2cc(Br)cc(F)c21]

To a solution of methyl 7-bromo-5-fluoro-4-oxoisochromane-3-carboxylate (13 g, 42.9 mmol) in HOAc (100 mL) was added concentrated HCl (33 mL) at 25° C. and the mixture was stirred at 25° C. for 12 h. The mixture was extracted with PE:EtOAc=10:1 (40 mL). The organic layer was concentrated in vacuum to give the title compound (6.0 g, 57%). LC-MS $(M+H)^+$=245.0.

Step 5: (R)-7-bromo-5-fluoroisochroman-4-ol

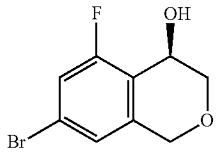 [SMILES: O[C@H]1COCc2cc(Br)cc(F)c21]

The title compound (1.0 g, 65%) was prepared in a manner similar to that in Example 84 step 1 from 7-bromo-5-fluoroisochroman-4-one. $^1$H NMR (400 MHz, DMSO-d6) δ 7.38 (d, J=9.2 Hz, 1H), 7.21 (s, 1H), 5.45 (d, J=6.4 Hz, 1H), 4.75 (d, J=15.6 Hz, 1H), 4.60-4.46 (m, 2H), 3.91 (dd, J=16.0, 2.0 Hz, 1H), 3.68 (dd, J=16.0, 2.0 Hz, 1H).

Step 6: (S)-4-azido-7-bromo-5-fluoroisochromane

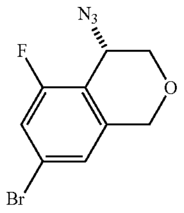

The title compound (0.54 g, 74%) was prepared in a manner similar to that in Example 78 & Example 79 & Example 80 & Example 81 step 6 from (R)-7-bromo-5-fluoroisochroman-4-ol. H NMR (40×0 MHz, DMSO-d6) δ 7.56 (d, J=9.2 Hz, 1H), 7.34 (s, 1H), 4.85 (d, J=16.0 Hz, 1H), 4.62 (d, J=16.0 Hz, 1H), 4.58-4.53 (m, 1H), 4.18 (d, J=12.4 Hz, 1H), 3.84 (dd, J=12.4, 2.6 Hz, 1H).

Step 7: (S)-7-bromo-5-fluoroisochroman-4-amine

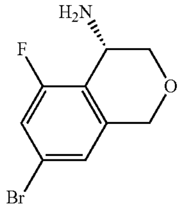

The title compound (1.5 g, 99%) was prepared in a manner similar to that in Example 78 & Example 79 & Example 80 & Example 81 step 7 from (S)-4-azido-7-bromo-5-fluoroisochromane. LCMS $(M+H)^+$=246.0.

Step 8: tert-butyl (S)-(7-bromo-5-fluoroisochroman-4-yl)carbamate

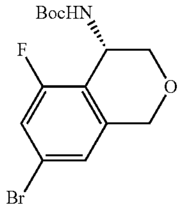

The title compound (0.15 g, 18%) was prepared in a manner similar to that in Example 39 & Example 40 step 6 from (S)-7-bromo-5-fluoroisochroman-4-amine. LCMS $(M+H\text{-}tBu)^+$=290.1.

Step 9: tert-butyl (S)-(7-bromo-5-fluoroisochroman-4-yl)(methyl)carbamate

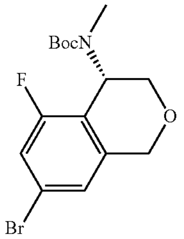

The title compound (0.10 g, 64%) was prepared in a manner similar to that in Example 39 & Example 40 step 7 from tert-butyl (S)-(7-bromo-5-fluoroisochroman-4-yl)carbamate and MeI. LCMS $(M+H\text{-}tBu)^+$=304.0.

Step 10: (S)-7-bromo-5-fluoro-N-methylisochroman-4-amine Hydrochloride

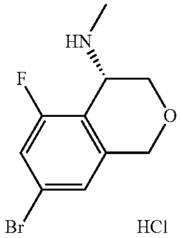

The title compound (130 mg, 99%) was prepared in a manner similar to that in Example 39 & Example 40 step 8 from tert-butyl (S)-(7-bromo-5-fluoroisochroman-4-yl)(methyl)carbamate. LC-MS $(M+H)^+$=260.0.

Step 11: (S)-5-amino-N-(7-bromo-5-fluoroisochroman-4-yl)-N-methyl-1-((2-(trimethylsilyl)ethoxy)methyl)-6,8-dihydro-1H-furo[3,4-d]pyrrolo[3,2-b]pyridine-2-carboxamide

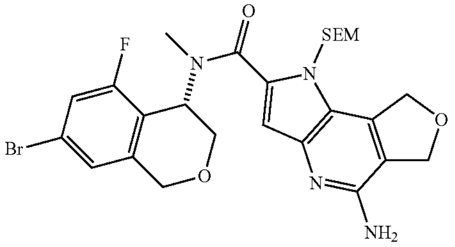 [SMILES: CN(C(=O)c1cc2nc(N)c3c(c2n1COCC[Si](C)(C)C)COC3)[C@@H]1COCc2cc(Br)cc(F)c21]

The title compound (100 mg, 34%) was prepared in a manner similar to that in Example 73 & Example 74 step 9 from (S)-7-bromo-5-fluoro-N-methylisochroman-4-amine hydrochloride and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=591.2.

Step 12: (S)-5-amino-N-(7-bromo-5-fluoroisochroman-4-yl)-N-methyl-6,8-dihydro-1H-furo[3,4-d]pyrrolo[3,2-b]pyridine-2-carboxamide Example 96 (34 mg, 42%) was prepared in a manner similar to that in Example 66 step 3 from (S)-5-amino-N-(7-bromo-5-fluoroisochroman-4-yl)-N-methyl-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ 11.55 (s, 1H), 7.47 (d, J=8.6 Hz, 1H), 7.35 (s, 1H), 6.73-6.47 (m, 1H), 5.74 (br s, 1H), 5.55 (s, 2H), 5.21-5.09 (m, 2H), 4.96-4.86 (m, 3H), 4.63 (d, J=15.4 Hz, 1H), 4.27-3.93 (m, 2H), 3.13-2.71 (m, 3H), LC-MS $(M+H)^+$= 461.1.

Example 97: (S)-5-amino-N-(7-cyano-5-fluoroisochroman-4-yl)-N-methyl-6,8-dihydro-1H-furo[3,4-d]pyrrolo[3,2-b]pyridine-2-carboxamide

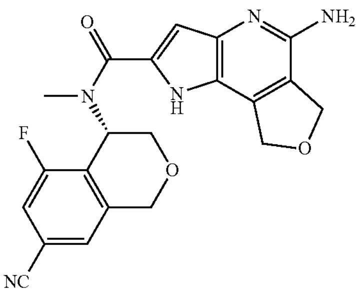 [SMILES: CN(C(=O)c1cc2nc(N)c3c(c2[nH]1)COC3)[C@@H]1COCc2cc(C#N)cc(F)c21]

Step 1: tert-butyl (S)-(7-cyano-5-fluoroisochroman-4-yl)(methyl)carbamate

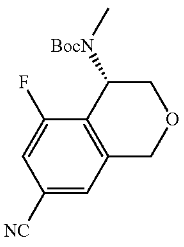 [SMILES: CN(C(=O)OC(C)(C)C)[C@@H]1COCc2cc(C#N)cc(F)c21]

To a solution of tert-butyl (S)-(7-bromo-5-fluoroisochroman-4-yl)(methyl)carbamate (0.10 g, 278 μmol) in DMF (1 mL) was added $Zn(CN)_2$ (49 mg, 416 μmol) and $Pd(PPh_3)_4$ (32 mg, 28 μmol). The mixture was stirred at 130° C. for 12 h and then cooled to room temperature. The mixture was poured into iced water (10 mL) and extracted with EtOAc (3×10 mL). The combined organic layer was washed with brine (10 mL), dried over $Na_2SO_4$, filtered and concentrated under reduced pressure to give the title compound (20 mg, 23%). LCMS $(M+H-tBu)^+$=251.1.

Step 2: (S)-5-fluoro-4-(methylamino)isochromane-7-carbonitrile Hydrochloride

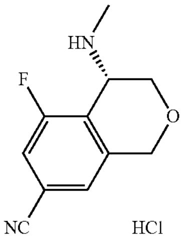

The title compound (37 mg, 79%) was prepared in a manner similar to that in Example 39 & Example 40 step 8 from tert-butyl (S)-(7-cyano-5-fluoroisochroman-4-yl)(methyl)carbamate. LC-MS $(M+H)^+$=207.2.

Step 3: (S)-5-amino-N-(7-cyano-5-fluoroisochroman-4-yl)-N-methyl-1-((2-(trimethylsilyl)ethoxy)methyl)-6,8-dihydro-1H-furo[3,4-d]pyrrolo[3,2-b]pyridine-2-carboxamide

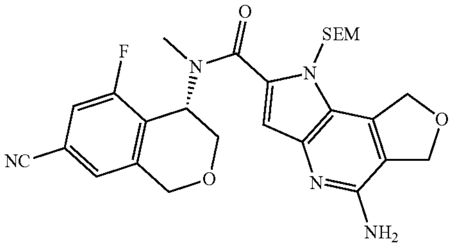 [SMILES: CN(C(=O)c1cc2nc(N)c3c(c2n1COCC[Si](C)(C)C)COC3)[C@@H]1COCc2cc(C#N)cc(F)c21]

The title compound (90 mg, 93%) was prepared in a manner similar to that in Example 73 & Example 74 step 9 from (S)-5-fluoro-4-(methylamino)isochromane-7-carbonitrile hydrochloride and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=538.3.

Step 4: (S)-5-amino-N-(7-cyano-5-fluoroisochroman-4-yl)-N-methyl-6,8-dihydro-1H-furo[3,4-d]pyrrolo[3,2-b]pyridine-2-carboxamide Example 97 (14 mg, 21%) was prepared in a manner similar to that in Example 66 step 3 from (S)-5-amino-N-(7-cyano-5-fluoroisochroman-4-yl)-N-methyl-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ 11.63 (br s, 1H), 7.81-7.72 (m, 1H), 7.64 (s, 1H), 6.71-6.46 (m, 1H), 5.84-5.75 (m, 1H), 5.56 (br s, 2H), 5.23-5.07 (m, 2H), 5.01-4.87 (m, 3H), 4.67 (d, J=16.0 Hz, 1H), 4.22-3.97 (m, 2H), 3.12-2.71 (m, 3H), LC-MS $(M+H)^+$= 408.1.

Example 98 and Example 99: (S)—N-(2-acetyl-7-(trifluoromethyl)-1,2,3,4-tetrahydroisoquinolin-4-yl)-5-amino-N-methyl-6,8-dihydro-1H-furo[3,4-d]pyrrolo[3,2-b]pyridine-2-carboxamide & (R)—N-(2-acetyl-7-(trifluoromethyl)-1,2,3,4-tetrahydroisoquinolin-4-yl)-5-amino-N-methyl-6,8-dihydro-1H-furo[3,4-d]pyrrolo[3,2-b]pyridine-2-carboxamide

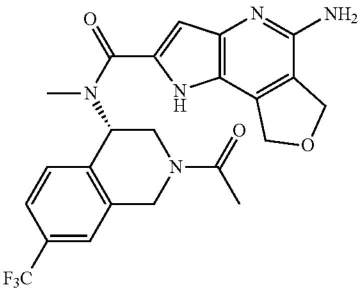

&

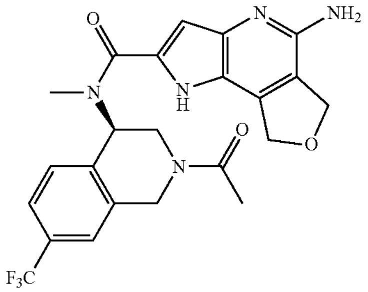

Step 1: ethyl 2-(bromomethyl)-4-(trifluoromethyl)benzoate

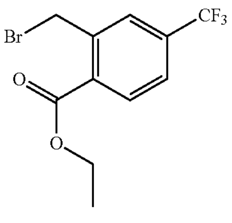 [SMILES: CCOC(=O)c1ccc(C(F)(F)F)cc1CBr]

To a solution of ethyl 2-methyl-4-(trifluoromethyl)benzoate (11 g, 47.4 mmol) in $CCl_4$ (150 mL) was added NBS (8.43 g, 47.4 mmol) and AIBN (200 mg, 1.2 mmol). The resulting mixture was heated to reflux and stirred for 16 h. The mixture was cooled to 0° C. and the solid was filtered off. The filtrate was diluted with DCM (200 mL) and successively washed with NaOH (1 M, 100 mL), saturated $NaHCO_3$ (100 mL) and brine (100 mL). The organic layer was dried over anhydrous $Na_2SO_4$, filtered and concentrated under reduced pressure. The residue was purified by silica gel chromatography (PE/EtOAc=10/1) to give the title compound (12 g, 82%). LC-MS $(M+H)^+$=311.2.

Step 2: ethyl 2-((benzyl(2-ethoxy-2-oxoethyl)amino)methyl)-4-(trifluoromethyl)benzoate

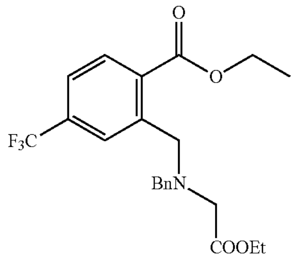 [SMILES: CCOC(=O)CN(Cc1ccccc1)Cc1cc(C(F)(F)F)ccc1C(=O)OCC]

To a mixture of ethyl 2-(bromomethyl)-4-(trifluoromethyl)benzoate (12 g, 38.7 mmol), ethyl benzylglycinate (11.2 g, 58 mmol) in THF (200 mL) was added $Et_3N$ (5.9 mL, 58 mmol) and the mixture was heated to reflux and stirred for 2 h. The mixture was cooled to room temperature and concentrated under reduced pressure. The residue was partitioned between EtOAc (200 mL) and saturated $NaHCO_3$. The aqueous layer was extracted with EtOAc (2×200 mL). The combined organic layer was concentrated under reduced pressure. The residue was purified by silica gel chromatography (PE/EtOAc=5/1) to give the title compound (10 g, 61%). LC-MS $(M+H)^+$=424.2.

Step 3: ethyl 2-benzyl-4-oxo-7-(trifluoromethyl)-1,2,3,4-tetrahydroisoquinoline-3-carboxylate

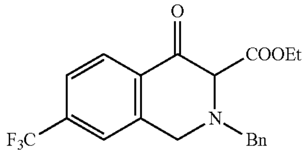 [SMILES: CCOC(=O)C1C(=O)c2ccc(C(F)(F)F)cc2CN1Cc1ccccc1]

To a solution of ethyl 2-((benzyl(2-ethoxy-2-oxoethyl)amino)methyl)-4-(trifluoromethyl)benzoate (10 g, 23.5 mmol) in toluene (50 mL) was added NaOEt in EtOH (20%, 12 g, 35.3 mmol). The mixture was stirred at refluxing temperature for 5 h. The mixture was cooled to room temperature and diluted with EtOAc (1(0) mL) and water (100 mL). The pH of the aqueous layer was adjusted to ~7 with hydrochloric acid (1 M). The organic layer was separated, dried over $Na_2SO_4$, filtered and concentrated under reduced pressure. The residue was purified by silica gel chromatography (PE/EtOAc=5/1) to give the title compound (8.5 g, 96%). LC-MS $(M+H)^+$=378.2.

Step 4: 2-benzyl-7-(trifluoromethyl)-2,3-dihydroisoquinolin-4(1H)-one

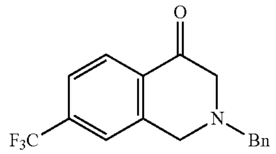 [SMILES: O=C1CN(Cc2ccccc2)Cc2cc(C(F)(F)F)ccc21]

To a mixture of ethyl 2-benzyl-4-oxo-7-(trifluoromethyl)-1,2,3,4-tetrahydroisoquinoline-3-carboxylate (8.5 g, 22.5 mmol) in EtOH (70 mL) was added concentrated hydrochloric acid (100 mL). The mixture was stirred at refluxing temperature for 24 h and then cooled to room temperature. The mixture was concentrated under reduced pressure. To the residue was added saturated $NaHCO_3$ (150 mL) and the mixture was extracted with DCM (2×150 mL). The combined organic layer was washed with brine (150 mL), dried over $Na_2SO_4$, filtered and concentrated under reduced pressure. The residue was purified by silica gel chromatography (PE/EtOAc=3/1) to give the title compound (3.5 g, 51%). LC-MS $(M+H)^+$=306.2.

Step 5: 7-(trifluoromethyl)-1,2,3,4-tetrahydroisoquinolin-4-ol

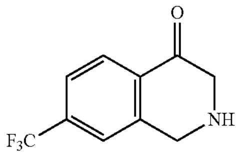

To a mixture of 2-benzyl-7-(trifluoromethyl)-2,3-dihydroisoquinolin-4(1H)-one (3.5 g, 11.5 mmol) in AcOH (10 mL) and EtOH (10 mL) was added 10% Pd/C (300 mg) under nitrogen. The mixture was purged with hydrogen and stirred under a hydrogen atmospheres for 5 h. Solid was filtered off and the filtrate was concentrated to give the title compound (2.2 g, 88%). LC-MS $(M+H)^+$=218.2.

Step 6: tert-butyl 4-hydroxy-7-(trifluoromethyl)-3,4-dihydroisoquinoline-2(1H)-carboxylate

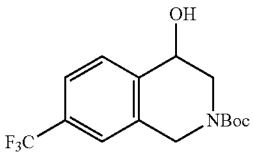 [SMILES: CC(C)(C)OC(=O)N1Cc2cc(C(F)(F)F)ccc2C(O)C1]

To a solution of 7-(trifluoromethyl)-1,2,3,4-tetrahydroisoquinolin-4-ol (2.2 g, 10.1 mmol) in DCM (40 mL) was added $Boc_2O$ (2.2 g, 10.1 mmol), $Et_3N$ (4.37 mL, 30.3 mmol). The reaction mixture was stirred room temperature for 5 h. The reaction mixture was concentrated and purified by silica gel chromatography (PE/EtOAc=4/1) to give the title compound (2.8 g, 87%). LC-MS $(M+H)^+$=318.2.

Step 7: tert-butyl 4-((N-methyl-2-nitrophenyl)sulfonamido)-7-(trifluoromethyl)-3,4-dihydroisoquinoline-2(1H)-carboxylate

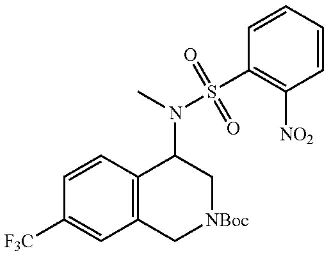 [SMILES: CN(C1CN(C(=O)OC(C)(C)C)Cc2cc(C(F)(F)F)ccc21)S(=O)(=O)c1ccccc1[N+](=O)[O-]]

To a solution of tert-butyl 4-hydroxy-7-(trifluoromethyl)-3,4-dihydroisoquinoline-2(1H)-carboxylate (2.8 g, 8.8 mmol), N-methyl-2-nitro-benzenesulfonamide (1.9 g, 8.8 mmol) and $PPh_3$ (2.99 g, 11.4 mmol) in THF (50 mL) was added DtBAD (2.64 g, 11.4 mmol) in portions at 0° C. under nitrogen. The final mixture was stirred at room temperature for 3 h. The mixture was concentrated under reduced pressure and the residue was purified by silica gel chromatography (PE/EtOAc=3/1) to give the title compound (4.2 g, 93%). LC-MS $(M+H)^+$=516.1.

Step 8: tert-butyl 4-(methylamino)-7-(trifluoromethyl)-3,4-dihydroisoquinoline-2(1H)-carboxylate

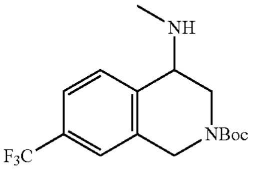

To a solution of tert-butyl 4-((N-methyl-2-nitrophenyl)sulfonamido)-7-(trifluoromethyl)-3,4-dihydroisoquinoline-2(1H)-carboxylate (4.2 g, 8.15 mmol) in DMF (10 mL) and THF (50 mL) was added dodecane-1-thiol (4.9 g, 24.4 mmol) and lithium hydroxide monohydrate (1.0 g, 24.4 mmol). The mixture was stirred at room temperature for 16 h. The mixture was concentrated under reduced pressure, and the residue was partitioned between water (100 mL) and EtOAc (100 mL). The organic layer was dried with $Na_2SO_4$, filtered and concentrated under reduced pressure. The residue was purified by silica gel chromatography (DCM:MeOH=10:1) to give the title compound (2.5 g, 93%). LC-MS $(M+H)^+$=331.1.

Step 9: tert-butyl 4-(5-amino-N-methyl-1-((2-(trimethylsilyl)ethoxy)methyl)-6,8-dihydro-1H-furo[3,4-d]pyrrolo[3,2-b]pyridine-2-carboxamido)-7-(trifluoromethyl)-3,4-dihydroisoquinoline-2(1H)-carboxylate

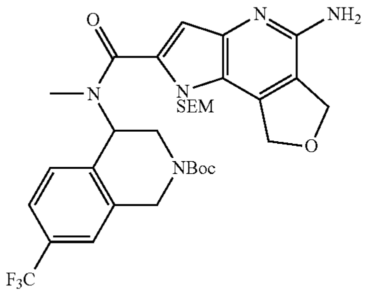 [SMILES: CN(C(=O)c1cc2nc(N)c3c(c2n1COCC[Si](C)(C)C)COC3)C1CN(C(=O)OC(C)(C)C)Cc2cc(C(F)(F)F)ccc21]

To a solution of tert-butyl 4-(methylamino)-7-(trifluoromethyl)-3,4-dihydroisoquinoline-2(1H)-carboxylate (2.0 g, 6.1 mmol) and 5-amino-1-((2-(trimethylsilyl)ethoxy)methyl)-6,8-dihydro-1H-furo[3,4-d]pyrrolo[3,2-b]pyridine-2-carboxylic acid (2.1 g, 6.0 mmol) in THF (50 mL) was added BOPCl (2.29 g, 9.0 mmol) and DIPEA (1.55 g, 12.0 mmol). The mixture was stirred at 60° C. for 16 h and cooled to room temperature. The residue was partitioned between water (50 mL) and EtOAc (50 mL). The organic layer was dried with $Na_2SO_4$, filtered and concentrated under reduced pressure. The residue was purified by silica gel chromatography (DCM:MeOH=20:1) to give the title compound (3.0 g, 76%). LC-MS $(M+H)^+$=662.2.

Step 10: 5-amino-N-methyl-N-(7-(trifluoromethyl)-1,2,3,4-tetrahydroisoquinolin-4-yl)-1-((2-(trimethylsilyl)ethoxy)methyl)-6,8-dihydro-1H-furo[3,4-d]pyrrolo[3,2-b]pyridine-2-carboxamide

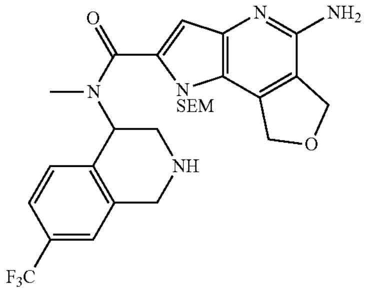 [SMILES: CN(C(=O)c1cc2nc(N)c3c(c2n1COCC[Si](C)(C)C)COC3)C1CNCc2cc(C(F)(F)F)ccc21]

To a solution of tert-butyl 4-(5-amino-N-methyl-1-((2-(trimethylsilyl)ethoxy)methyl)-6,8-dihydro-1H-furo[3,4-d]pyrrolo[3,2-b]pyridine-2-carboxamido)-7-(trifluoromethyl)-3,4-dihydroisoquinoline-2(1H)-carboxylate (1.0 g, 1.78 mmol) in dioxane (10 mL) was added HCl in dioxane (4.0 M, 10 mL). The mixture was stirred for 2 h at room temperature. The precipitate was collected by filtration. To the solid was added saturated $NaHCO_3$, and the mixture was extracted with DCM (2×30 mL). The combined organic layer was washed with brine (30 mL), dried over $Na_2SO_4$, filtered and concentrate under reduced pressure to give the title compound (850 mg, 85%). LC-MS $(M+H)^+$=562.2.

Step 11: N-(2-acetyl-7-(trifluoromethyl)-1,2,3,4-tetrahydroisoquinolin-4-yl)-5-amino-N-methyl-1-((2-(trimethylsilyl)ethoxy)methyl)-6,8-dihydro-1H-furo[3,4-d]pyrrolo[3,2-b]pyridine-2-carboxamide

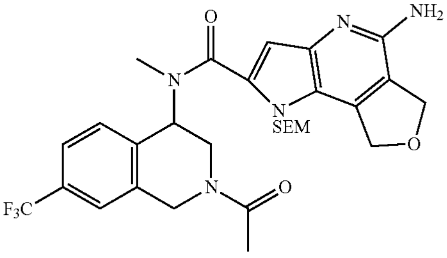 [SMILES: CC(=O)N1Cc2cc(C(F)(F)F)ccc2C(N(C)C(=O)c2cc3nc(N)c4c(c3n2COCC[Si](C)(C)C)COC4)C1]

To a mixture of 5-amino-N-methyl-N-(7-(trifluoromethyl)-1,2,3,4-tetrahydroisoquinolin-4-yl)-1-((2-(trimethylsilyl)ethoxy)methyl)-6,8-dihydro-1H-furo[3,4-d]pyrrolo[3,2-b]pyridine-2-carboxamide (200 mg, 0.356 mmol), HOAc (64 mg, 1.07 mmol) and DIPEA (92 mg, 0.71 mmol) in DMF (5 mL) was added HATU (203 mg, 0.53 mmol). The mixture was stirred at 25° C. for 16 h. The mixture was partitioned between water (20 mL) and EtOAc (20 mL). The organic layer was dried with $Na_2SO_4$, filtered and concentrated under reduced pressure. The residue was purified by prep-TLC (DCM:MeOH=20:1) to give the title compound (206 mg, 96%). LC-MS $(M+H)^+$=604.2.

Step 12: (S)—N-(2-acetyl-7-(trifluoromethyl)-1,2,3,4-tetrahydroisoquinolin-4-yl)-5-amino-N-methyl-6,8-dihydro-1H-furo[3,4-d]pyrrolo[3,2-b]pyridine-2-carboxamide & (R)—N-(2-acetyl-7-(trifluoromethyl)-1,2,3,4-tetrahydroisoquinolin-4-yl)-5-amino-N-methyl-6,8-dihydro-1H-furo[3,4-d]pyrrolo[3,2-b]pyridine-2-carboxamide To a mixture of N-(2-acetyl-7-(trifluoromethyl)-1,2,3,4-tetrahydroisoquinolin-4-yl)-5-amino-N-methyl-1-((2-(trimethylsilyl)ethoxy)methyl)-6,8-dihydro-1H-furo[3,4-d]pyrrolo[3,2-b]pyridine-2-carboxamide (206 mg, 0.34 mmol) in DCM (5 mL) was added and TFA (1 mL). The mixture was stirred at room temperature for 2 h. The mixture was concentrated under reduced pressure and the residue was re-dissolved in MeOH (5 mL). Strong ammonia solution (28%, 1 mL) was added and the mixture was stirred room temperature for 1 h. The mixture was concentrated under reduced pressure. The residue was purified by prep-HPLC and chiral SFC to give Example 98 (53 mg, 33%) and Example 99 (54 mg, 33%).

Analytical chiral-SFC condition as below. Column: CHIRALPAK IH; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 98: Analytical SFC tR=3.12 min. $^1$H NMR (400 MHz, DMSO-d6) δ 11.63 (s, 1H), 7.78-7.69 (m, 1H), 7.66-7.56 (m, 1H), 7.48-7.32 (m, 1H), 6.85-6.60 (m, 1H), 5.76 (s, 1H), 5.57 (s, 2H), 5.14 (s, 2H), 5.03-4.50 (m, 4H), 4.30-3.53 (m, 2H), 3.15-2.70 (m, 3H), 2.15-2.05 (m, 3H). LCMS $(M+H)^+$=474.3.

Example 99: Analytical SFC tR=3.73 min. $^1$H NMR (400 MHz, DMSO-d6) δ 11.63 (s, 1H), 7.78-7.69 (m, 1H), 7.66-7.56 (m, 1H), 7.48-7.32 (m, 1H), 6.85-6.60 (m, 1H), 5.76 (s, 1H), 5.57 (s, 2H), 5.14 (s, 2H), 5.03-4.50 (m, 4H), 4.30-3.53 (m, 2H), 3.15-2.70 (m, 3H), 2.15-2.05 (m, 3H). LCMS $(M+H)^+$=474.3.

Example 100 & Example 101: (S)-5-amino-N-(2-(cyclopropanecarbonyl)-7-(trifluoromethyl)-1,2,3,4-tetrahydroisoquinolin-4-yl)-N-methyl-6,8-dihydro-1H-furo[3,4-d]pyrrolo[3,2-b]pyridine-2-carboxamide & (R)-5-amino-N-(2-(cyclopropanecarbonyl)-7-(trifluoromethyl)-1,2,3,4-tetrahydroisoquinolin-4-yl)-N-methyl-6,8-dihydro-1H-furo[3,4-d]pyrrolo[3,2-b]pyridine-2-carboxamide

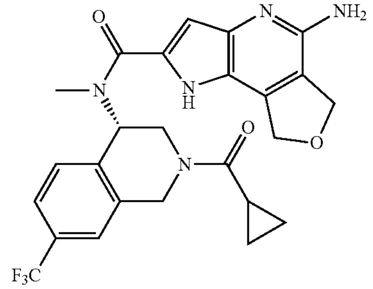

&

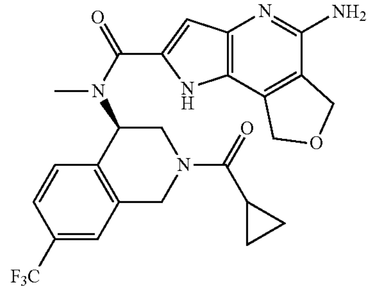

Step 1: 5-amino-N-(2-(cyclopropanecarbonyl)-7-(trifluoromethyl)-1,2,3,4-tetrahydroisoquinolin-4-yl)-N-methyl-1-((2-(trimethylsilyl)ethoxy)methyl)-6,8-dihydro-1H-furo[3,4-d]pyrrolo[3,2-b]pyridine-2-carboxamide

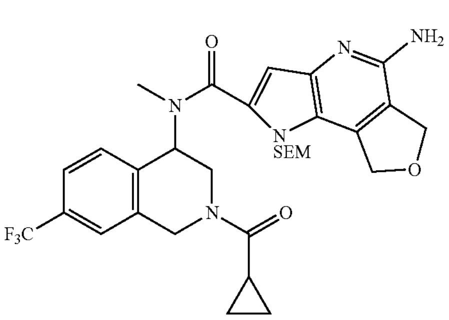 [SMILES: CN(C(=O)c1cc2nc(N)c3c(c2n1COCC[Si](C)(C)C)COC3)C1CN(C(=O)C2CC2)Cc2cc(C(F)(F)F)ccc21]

The title compound (80 mg, 71%) was prepared in a manner similar to that in Example 98 & Example 99 step 11 from (5-amino-N-methyl-N-(7-(trifluoromethyl)-1,2,3,4-tetrahydroisoquinolin-4-yl)-1-((2-(trimethylsilyl)ethoxy)methyl)-6,8-dihydro-1H-furo[3,4-d]pyrrolo[3,2-b]pyridine-2-carboxamide and cyclopropanecarboxylic acid. LC-MS $(M+H)^+$=630.2.

Step 2: (S)-5-amino-N-(2-(cyclopropanecarbonyl)-7-(trifluoromethyl)-1,2,3,4-tetrahydroisoquinolin-4-yl)-N-methyl-6,8-dihydro-1H-furo[3,4-d]pyrrolo[3,2-b]pyridine-2-carboxamide & (R)-5-amino-N-(2-(cyclopropanecarbonyl)-7-(trifluoromethyl)-1,2,3,4-tetrahydroisoquinolin-4-yl)-N-methyl-6,8-dihydro-1H-furo[3,4-d]pyrrolo[3,2-b]pyridine-2-carboxamide Example 100 (8 mg, 13%) and Example 101 (10 mg, 15%) was prepared in a manner similar to that in Example 98 & Example 99 step 12 from 5-amino-N-(2-(cyclopropanecarbonyl)-7-(trifluoromethyl)-1,2,3,4-tetrahydroisoquinolin-4-yl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: YMC Cellulose-C; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 100: Analytical SFC tR=3.96 min. $^1$H NMR (400 MHz, DMSO-d6) δ 11.63 (s, 1H), 7.80-7.70 (m, 1H), 7.63 (s, 1H), 7.46-7.36 (m, 1H), 6.73 (s, 1H), 5.90-5.70 (m, 1H), 5.58 (s, 2H), 5.30-5.00 (m, 3H), 4.95-4.60 (m, 3H), 4.40-3.59 (m, 2H), 3.10-2.65 (m, 3H), 2.20-1.98 (m, 1H), 0.90-0.60 (m, 4H). LCMS $(M+H)^+$=500.3.

Example 101: Analytical SFC tR=4.37 min. $^1$H NMR (400 MHz, DMSO-d6) δ 11.63 (s, 1H), 7.80-7.70 (m, 1H), 7.63 (s, 1H), 7.46-7.36 (m, 1H), 6.73 (s, 1H), 5.90-5.70 (m, 1H), 5.58 (s, 2H), 5.30-5.00 (m, 3H), 4.95-4.6) (m, 3H), 4.40-3.59 (m, 2H), 3.10-2.65 (m, 3H), 2.20-1.98 (m, 1H), 0.90-0.60 (m, 4H). LCMS $(M+H)^+$=500.3.

Example 102 & Example 103: (S)-5-amino-N-(2-isobutyryl-7-(trifluoromethyl)-1,2,3,4-tetrahydroisoquinolin-4-yl)-N-methyl-6,8-dihydro-1H-furo[3,4-d]pyrrolo[3,2-b]pyridine-2-carboxamide & (R)-5-amino-N-(2-isobutyryl-7-(trifluoromethyl)-1,2,3,4-tetrahydroisoquinolin-4-yl)-N-methyl-6,8-dihydro-1H-furo[3,4-d]pyrrolo[3,2-b]pyridine-2-carboxamide

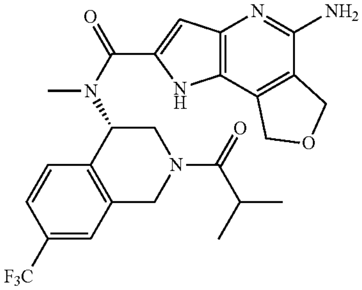

&

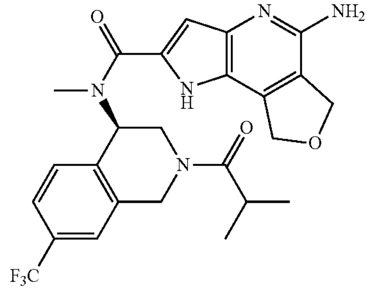

Step 1: 5-amino-N-(2-isobutyryl-7-(trifluoromethyl)-1,2,3,4-tetrahydroisoquinolin-4-yl-N-methyl-1-((2-(trimethylsilyl)ethoxy)methyl)-6,8-dihydro-1H-furo[3,4-d]pyrrolo[3,2-b]pyridine-2-carboxamide

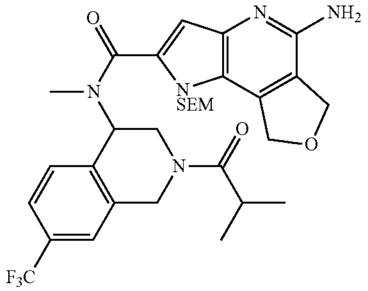 [SMILES: CC(C)C(=O)N1Cc2cc(C(F)(F)F)ccc2C(N(C)C(=O)c2cc3nc(N)c4c(c3n2COCC[Si](C)(C)C)COC4)C1]

The title compound (80 mg, 71%) was prepared in a manner similar to that in Example 98 & Example 99 step 11 from (5-amino-N-methyl-N-(7-(trifluoromethyl)-1,2,3,4-tetrahydroisoquinolin-4-yl)-1-((2-(trimethylsilyl)ethoxy)methyl)-6,8-dihydro-1H-furo[3,4-d]pyrrolo[3,2-b]pyridine-2-carboxamide and isobutyric acid. LC-MS $(M+H)^+$=632.2.

Step 2: (S)-5-amino-N-(2-isobutyryl-7-(trifluoromethyl)-1,2,3,4-tetrahydroisoquinolin-4-yl)-N-methyl-6,8-dihydro-1H-furo[3,4-d]pyrrolo[3,2-b]pyridine-2-carboxamide & (R)-5-amino-N-(2-isobutyryl-7-(trifluoromethyl)-1,2,3,4-tetrahydroisoquinolin-4-yl)-N-methyl-6,8-dihydro-1H-furo[3,4-d]pyrrolo[3,2-b]pyridine-2-carboxamide Example 102 (6 mg, 9%) and Example 103 (7 mg, 10%) was prepared in a manner similar to that in Example 98 & Example 99 step 12 from 5-amino-N-(2-isobutyryl-7-(trifluoromethyl)-1,2,3,4-tetrahydroisoquinolin-4-yl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: YMC Cellulose-C; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 102: Analytical SFC tR=3.52 min. $^1$H NMR (400 MHz, DMSO-d6) δ 11.75-11.50 (m, 1H), 7.80-7.73 (m, 1H), 7.70-7.58 (m, 1H), 7.50-7.30 (m, 1H), 6.82-6.60 (m, 1H), 5.76 (s, 1H), 5.59 (s, 2H), 5.26-4.43 (m, 6H), 4.37-3.58 (m, 3H), 3.16-2.70 (m, 4H), 1.12-0.92 (m, 6H). LCMS $(M+H)^+$=502.3.

Example 103: Analytical SFC tR=3.95 min. $^1$H NMR (400 MHz, DMSO-d6) δ 11.75-11.50 (m, 1H), 7.80-7.73 (m, 1H), 7.70-7.58 (m, 1H), 7.50-7.30 (m, 1H), 6.82-6.60 (m, 1H), 5.76 (s, 1H), 5.59 (s, 2H), 5.26-4.43 (m, 6H), 4.37-3.58 (m, 3H), 3.16-2.70 (m, 4H), 1.12-0.92 (m, 6H). LCMS $(M+H)^+$=502.3.

Example 104: (S)-5-amino-N-methyl-N-(7-(pyridin-3-yl)isochroman-4-yl)-6,8-dihydro-1H-furo[3,4-d]pyrrolo[3,2-b]pyridine-2-carboxamide

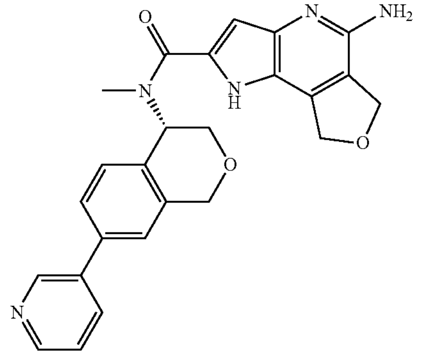 [SMILES: CN(C(=O)c1cc2nc(N)c3c(c2[nH]1)COC3)[C@@H]1COCc2cc(-c3cccnc3)ccc21]

Step 1: (S)—N-methyl-7-(pyridin-3-yl)isochroman-4-amine

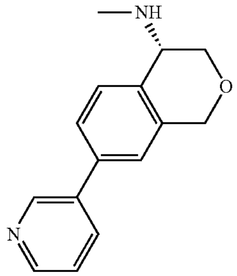 [SMILES: CN[C@@H]1COCc2cc(-c3cccnc3)ccc21]

The title compound (100 mg, 83%) was prepared in a manner similar to that in Example 87 & Example 88 step 5 from (S)-7-bromo-N-methylisochroman-4-amine and pyridin-3-ylboronic acid. LC-MS $(M+H)^+$=241.1.

Step 2: (S)-5-amino-N-methyl-N-(7-(pyridin-3-yl)isochroman-4-yl)-1-((2-(trimethylsilyl)ethoxy)methyl)-6,8-dihydro-1H-furo[3,4-d]pyrrolo[3,2-b]pyridine-2-carboxamide

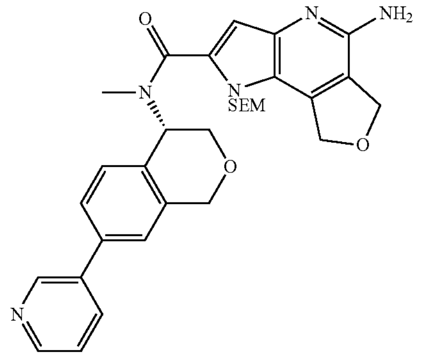 [SMILES: CN(C(=O)c1cc2nc(N)c3c(c2n1COCC[Si](C)(C)C)COC3)[C@@H]1COCc2cc(-c3cccnc3)ccc21]

The title compound (198 mg, 83%) was prepared in a manner similar to that in Example 73 & Example 74 step 9 from (S)—N-methyl-7-(pyridin-3-yl)isochroman-4-amine and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=572.4.

Step 3: (S)-5-amino-N-methyl-N-(7-(pyridin-3-yl)isochroman-4-yl)-6,8-dihydro-1H-furo[3,4-d]pyrrolo[3,2-b]pyridine-2-carboxamide Example 104 (114 mg, 75%) was prepared in a manner similar to that in Example 66 step 3 from (S)-5-amino-N-methyl-N-(7-(pyridin-3-yl)isochroman-4-yl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ 11.58 (s, 1H), 8.87 (d, J=1.6 Hz, 1H), 8.54 (dd, J=4.8, 1.2 Hz, 1H), 8.09-8.01 (m, 1H), 7.63 (d, J=7.6 Hz, 1H), 7.53 (s, 1H) 7.49-7.26 (m, 2H), 6.69 (s, 1H), 5.78 (s, 1H), 5.53 (s, 2H), 5.13 (s, 2H), 4.95-4.68 (m, 4H), 4.08 (s, 2H), 3.09-2.69 (m, 3H). LC-MS $(M+H)^+$=442.3.

Example 105: 5-amino-N-(4-cyclopropyl-2,6-difluorobenzyl)-N-(pentan-3-yl)-6,8-dihydro-1H-furo[3,4-d]pyrrolo[3,2-b]pyridine-2-carboxamide

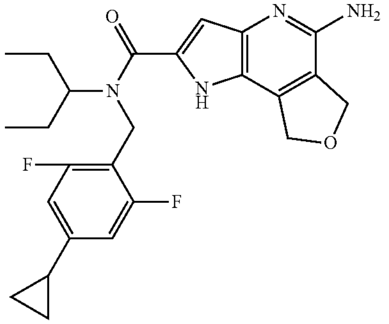 [SMILES: CCC(CC)N(Cc1c(F)cc(C2CC2)cc1F)C(=O)c1cc2nc(N)c3c(c2[nH]1)COC3]

Step 1: 4-cyclopropyl-2,6-difluorobenzaldehyde

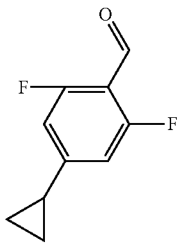 [SMILES: O=Cc1c(F)cc(C2CC2)cc1F]

The title compound (1.2 g, 61%) was prepared in a manner similar to that in Example 36 step 1 from 4-bromo-2,6-difluorobenzaldehyde and cyclopropylboronic acid. LC-MS $(M+H)^+$=183.1.

Step 2: N-(4-cyclopropyl-2,6-difluorobenzyl)pentan-3-amine

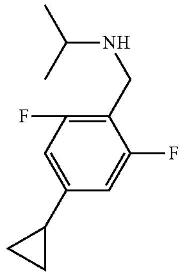 [SMILES: CC(C)NCc1c(F)cc(C2CC2)cc1F]

The title compound (230 mg, 92%) was prepared in a manner similar to that in Example 66 step 1 from 4-cyclopropyl-2,6-difluorobenzaldehyde and pentan-3-amine. LC-MS $(M+H)^+$=254.2.

Step 3: 5-amino-N-(4-cyclopropyl-2,6-difluorobenzyl)-N-(pentan-3-yl)-1-((2-(trimethylsilyl)ethoxy)methyl)-6,8-dihydro-1H-furo[3,4-d]pyrrolo[3,2-b]pyridine-2-carboxamide

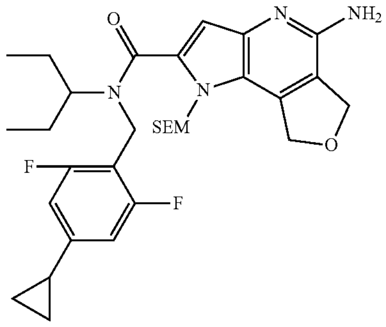 [SMILES: CCC(CC)N(Cc1c(F)cc(C2CC2)cc1F)C(=O)c1cc2nc(N)c3c(c2n1COCC[Si](C)(C)C)COC3]

The title compound (90 mg, 65%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and N-(4-cyclopropyl-2,6-difluorobenzyl)pentan-3-amine. LC-MS $(M+H)^+$=585.4.

Step 4: 5-amino-N-(4-cyclopropyl-2,6-difluorobenzyl)-N-(pentan-3-yl)-6,8-dihydro-1H-furo[3,4-d]pyrrolo[3,2-b]pyridine-2-carboxamide Example 105 (10 mg, 17%) was prepared in a manner similar to that in Example 66 step 3 from 5-amino-N-(4-cyclopropyl-2,6-difluorobenzyl)-N-(pentan-3-yl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ:11.50 (s, 1H), 6.80 (d, J=9.2 Hz, 2H), 6.47 (s, 1H), 5.53 (s, 2H), 5.12 (s, 2H), 4.92 (s, 2H), 4.88-3.62 (m, 3H), 1.97-1.88 (m, 1H), 1.72-1.43 (m, 4H), 1.02-0.91 (m, 2H), 0.82-0.67 (m, 8H). LC-MS $(M+H)^+$=455.2.

Example 106: (R)-5-amino-N-((5-cyclopropylpyridin-2-yl)methyl)-N-isopropyl-6-methyl-6,8-dihydro-1H-furo[3,4-d]pyrrolo[3,2-b]pyridine-2-carboxamide

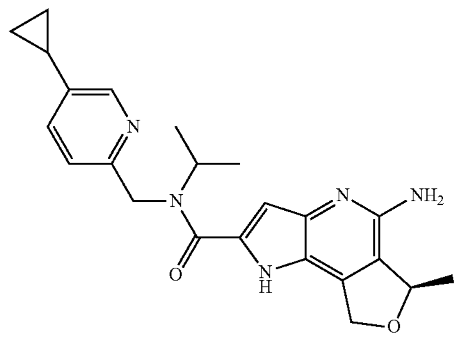 [SMILES: CC(C)N(Cc1ccc(C2CC2)cn1)C(=O)c1cc2nc(N)c3c(c2[nH]1)CO[C@@H]3C]

Step 1: N-((5-cycloproplpyridin-2-yl)methyl)propan-2-amine

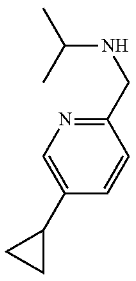

The title compound (70 mg, 90%) was prepared in a manner similar to that in Example 66 step 1 from 5-cyclopropylpicolinaldehyde and propan-2-amine. LC-MS $(M+H)^+$=191.2.

Step 2: (R)-5-amino-N-((5-cyclopropylpyridin-2-yl)methyl)-N-isopropyl-6-methyl-6,8-dihydro-1H-furo[3,4-d]pyrrolo[3,2-b]pyridine-2-carboxamide Example 106 (41 mg, 27%) was prepared in a manner similar to that in Example 2 step 3 from N-((5-cyclopropylpyridin-2-yl)methyl)propan-2-amine and (R)-5-amino-6-methyl-6,8-dihydro-1H-furo[3,4-d]pyrrolo[3,2-b]pyridine-2-carboxylic acid. $^1$H NMR (400 MHz, DMSO-d6) δ 11.56 (s, 1H), 8.38 (s, 1H), 7.46-7.33 (m, 1H), 7.28-7.14 (m, 1H), 6.66-5.97 (m, 1H), 5.42 (s, 2H), 5.36-5.28 (m, 1H), 5.22-4.98 (m, 2H), 4.74 (br s, 3H), 2.07-1.85 (m, 1H), 1.34 (d, J=6.1 Hz, 3H), 1.22-1.08 (m, 6H), 1.04-0.92 (m, 2H), 0.80-0.62 (m, 2H). LC-MS $(M+H)^+$=406.5.

Example 107: (R)-5-amino-N-(sec-butyl)-N-((5-cyclobutylpyridin-2-yl)methyl)-6,8-dihydro-1H-furo[3,4-d]pyrrolo[3,2-b]pyridine-2-carboxamide

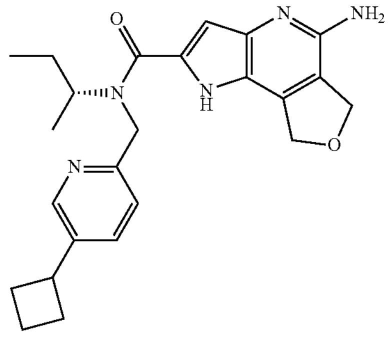 [SMILES: CC[C@@H](C)N(Cc1ccc(C2CCC2)cn1)C(=O)c1cc2nc(N)c3c(c2[nH]1)COC3]

Step 1: 5-bromo-2-(1,3-dioxolan-2-yl)pyridine

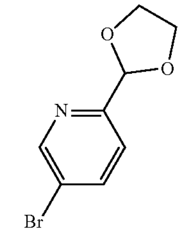 [SMILES: Brc1ccc(C2OCCO2)nc1]

To a solution of 5-bromopicolinaldehyde (5.0 g, 27 mmol) in toluene (250 mL) was added ethylene glycol (3.3 g, 54 mmol) and p-toluenesulfonic acid (465 mg, 2.7 mmol) at room temperature, and the mixture was stirred at 110° C. for 12 h equipped with a Dean-Stark trap. The mixture was cooled to room temperature, diluted with water (150 mL) and extracted with EtOAc (3×150 mL). The combined organic layer was washed with brine (100 mL), dried over $Na_2SO_4$, filtered and concentrated under reduced pressure. The residue was purified by silica gel chromatography (PE/EtOAc=1/0 to 5/1) to give the title compound (5.0 g, 81%). LC-MS $(M+H)^+$=230.0.

Step 2: 5-cyclobutyl-2-(1,3-dioxolan-2-yl)pyridine

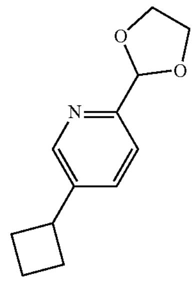 [SMILES: c1cc(C2OCCO2)ncc1C1CCC1]

Ten batches of the reaction described herein were set up. To a solution of 5-bromo-2-(1,3-dioxolan-2-yl)pyridine (0.10 g, 0.435 mmol) in DMA (1 mL) was added potassium cyclobutyltrifluoroborate (70 mg, 0.435 mmol), (4,4'-di-tert-butyl-2,2'-bipyridine)bis[3,5-difluoro-2-[5-trifluoromethyl-2-pyridinyl-under at blue light (34 W) at 25° C. for 12 h.

The ten batches of reaction mixture were combined and diluted with water (100 mL). The mixture was extracted with EtOAc (3×100 mL). The combined organic layers were washed with brine (10 mL), dried over $Na_2SO_4$, filtered and concentrated under reduced pressure. The residue was purified by silica gel chromatography (PE:EtOAc=10:1 to 0:1) to give the title compound (0.40 g, 45%). LC-MS $(M+H)^+$= 206.1.

Step 3: 5-cyclobutylpicolinaldehyde

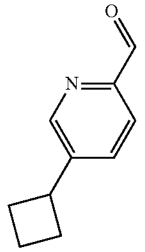 [SMILES: O=Cc1ccc(C2CCC2)cn1]

To a mixture of 5-cyclobutyl-2-(1,3-dioxolan-2-yl)pyridine (0.37 g, 1.8 mmol) in water (8.4 mL) was added concentrated HCl (1.6 mL) dropwise. The mixture was stirred at 80° C. for 2 h and then cooled to room temperature. The mixture was poured into aqueous NaOH solution (2 M, 12 mL), and the mixture was extracted with EtOAc (20 mL). The combined organic layer was washed with brine (20 mL), dried over $Na_2SO_4$, filtered and concentrated under reduced pressure to give the title compound (290 mg, 99%). LC-MS $(M+H)^+$=162.1.

Step 4: (R)—N-((5-cyclobutylpyridin-2-yl)methyl) butan-2-amine

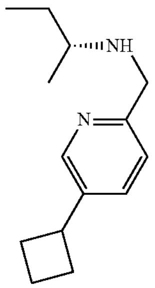 [SMILES: CC[C@@H](C)NCc1ccc(C2CCC2)cn1]

The title compound (100 mg, 92%) was prepared in a manner similar to that in Example 66 step 1 from 5-cyclobutylpicolinaldehyde and (R)-butan-2-amine. LC-MS $(M+H)^+$=219.2.

Step 5: (R)-5-amino-N-(sec-butyl)-N-((5-cyclobutylpyridin-2-yl)methyl)-1-((2-(trimethylsilyl)ethoxy)methyl)-6,8-dihydro-1H-furo[3,4-d]pyrrolo[3,2-b]pyridine-2-carboxamide

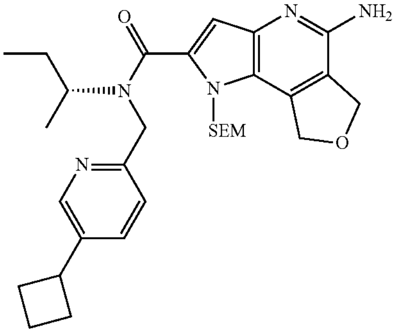 [SMILES: CC[C@@H](C)N(Cc1ccc(C2CCC2)cn1)C(=O)c1cc2nc(N)c3c(c2n1COCC[Si](C)(C)C)COC3]

The title compound (10 mg, 40%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and (R)—N-((5-cyclobutylpyridin-2-yl)methyl)butan-2-amine. LC-MS $(M+H)^+$=550.4.

Step 6: (R)-5-amino-N-(sec-butyl)-N-((5-cyclobutylpyridin-2-yl)methyl)-6,8-dihydro-1H-furo[3,4-d]pyrrolo[3,2-b]pyridine-2-carboxamide Example 107 (26 mg, 43%) was prepared in a manner similar to that in Example 66 step 3 from (R)-5-amino-N-(sec-butyl)-N-((5-cyclobutylpyridin-2-yl)methyl)-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.55 (s, 1H), 8.40 (s, 1H), 7.66 (d, J=8.0 Hz, 1H), 7.30 (d, J=8.0 Hz, 1H), 6.65-6.25 (m, 1H), 5.50 (s, 2H), 5.15-5.11 (m, 2H), 4.93-4.78 (m, 3H), 4.65-4.37 (m, 2H), 3.58-3.49 (m, 1H), 2.33-2.25 (m, 2H), 2.16-2.07 (m, 2H), 2.04-1.93 (m, 1H), 1.87-1.78 (m, 1H), 1.72-1.61 (m, 1H), 1.55-1.44 (m, 1H), 1.25-1.10 (m, 3H), 0.83-0.74 (m, 3H). LC-MS $(M+H)^+$=420.3.

Example 108: (R)-5-amino-N-(sec-butyl)-N-((5-cyclopropyl-6-methylpyridin-2-yl)methyl)-6,8-dihydro-1H-furo[3,4-d]pyrrolo[3,2-b]pyridine-2-carboxamide

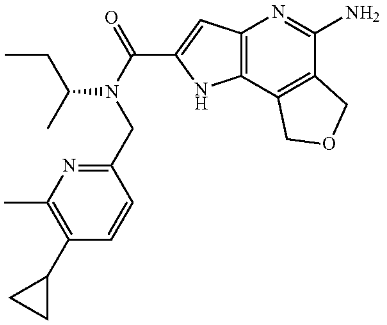 [SMILES: CC[C@@H](C)N(Cc1ccc(C2CC2)c(C)n1)C(=O)c1cc2nc(N)c3c(c2[nH]1)COC3]

Step 1: (R)—N-((5-bromo-6-methylpyridin-2-yl)methyl)butan-2-amine

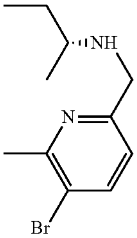

The title compound (490 mg, 95%) was prepared in a manner similar to that in Example 66 step 1 from 5-bromo-6-methylpicolinaldehyde and (R)-butan-2-amine. LC-MS $(M+H)^+$=257.1.

Step 2: (R)—N-((5-cyclopropyl-6-methylpyridin-2-yl)methyl)butan-2-amine

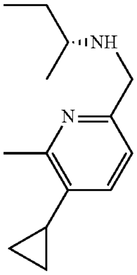 [SMILES: CC[C@@H](C)NCc1ccc(C2CC2)c(C)n1]

The title compound (350 mg, 94%) was prepared in a manner similar to that in Example 36 step 1 from (R)—N-((5-bromo-6-methylpyridin-2-yl)methyl)butan-2-amine and cyclopropylboronic acid. LC-MS $(M+H)^+$=219.2.

Step 3: (R)-5-amino-N-(sec-butyl)-N-((5-cyclopropyl-6-methylpyridin-2-yl)methyl)-1-((2-(trimethylsilyl)ethoxy)methyl)-6,8-dihydro-1H-furo[3,4-d]pyrrolo[3,2-b]pyridine-2-carboxamide

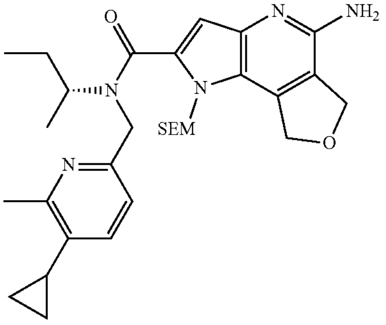 [SMILES: CC[C@@H](C)N(Cc1ccc(C2CC2)c(C)n1)C(=O)c1cc2nc(N)c3c(c2n1COCC[Si](C)(C)C)COC3]

The title compound (150 mg, 60%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and (R)—N-((5-cyclopropyl-6-methylpyridin-2-yl)methyl)butan-2-anine. LC-MS $(M+H)^+$=550.4.

Step 4: (R)-5-amino-N-(sec-butyl)-N-((5-cyclopropyl-6-methylpyridin-2-yl)methyl)-6,8-dihydro-1H-furo[3,4-d]pyrrolo[3,2-b]pyridine-2-carboxamide Example 108 (35 mg, 32%) was prepared in a manner similar to that in Example 66 step 3 from (R)-5-amino-N-(sec-butyl)-N-((5-cyclopropyl-6-methylpyridin-2-yl)methyl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ: 11.66 (br s, 1H), 8.19 (br s, 1H), 7.29 (br s, 1H), 7.08 (br s, 1H), 6.66-6.21 (m, 1H), 5.52 (br s, 2H), 5.12 (br s, 2H), 4.91 (br s, 2H), 4.76 (br s, 1H), 4.43 (br s, 2H), 2.57 (br s, 3H), 1.92 (br s, 1H), 1.65 (td, J=14.3, 7.4 Hz, 1H), 1.49 (td, J=14.0, 7.1 Hz, 1H), 1.17 (br s, 3H), 0.93 (br d, J=7.1 Hz, 2H), 0.81-0.73 (m, 3H), 0.60 (br d, J=2.7 Hz, 2H). LC-MS $(M+H)^+$=420.2.

Example 109: 5-amino-N-((5-cyclopropyl-4-methylpyridin-2-yl)methyl)-N-(pentan-3-yl)-6,8-dihydro-1H-furo[3,4-d]pyrrolo[3,2-b]pyridine-2-carboxamide

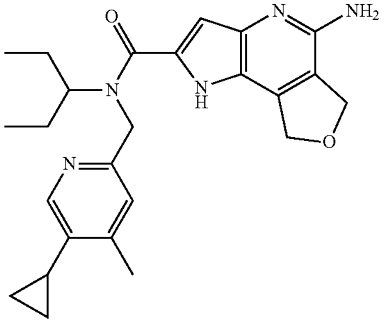 [SMILES: CCC(CC)N(Cc1cc(C)c(C2CC2)cn1)C(=O)c1cc2nc(N)c3c(c2[nH]1)COC3]

Step 1: 5-bromo-2-(1,3-dioxolan-2-yl)-4-methylpyridine

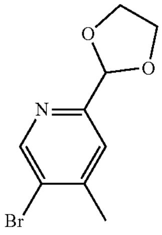

The title compound (1.9 g, 78%) was prepared in a manner similar to that in Example 107 step 1 from 5-bromo-4-methylpicolinaldehyde and ethylene glycol. LC-MS $(M+H)^+$=244.0.

Step 2: 5-cyclopropyl-2-(1,3-dioxolan-2-31)-4-methylpyridine

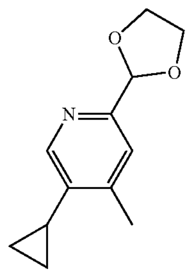

The title compound (1.6 g, 95%) was prepared in a manner similar to that in Example 36 step 1 from 5-bromo-2-(1,3-dioxolan-2-yl)-4-methylpyridine and cyclopropylboronic acid. LC-MS $(M+H)^+=206.1$.

Step 3: 5-cyclopropyl-4-methylpicolinaldehyde

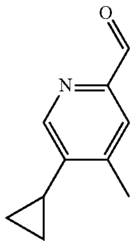

The title compound (1.0 g, 80%) was prepared in a manner similar to that in Example 107 step 3 from 5-cyclopropyl-2-(1,3-dioxolan-2-yl)-4-methylpyridine. LC-MS $(M+H)^+=162.1$.

Step 4: N-((5-cyclopropyl-4-methylpyridin-2-yl)methyl)pentan-3-amine

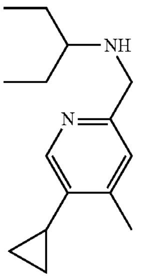 [SMILES: CCC(CC)NCc1cc(C)c(C2CC2)cn1]

The title compound (300 mg, 83%) was prepared in a manner similar to that in Example 66 step 1 from 5-cyclopropyl-4-methylpicolinaldehyde and pentan-3-amine. LC-MS $(M+H)^+=233.1$.

Step 5: 5-amino-N-((5-cyclopropyl-4-methylpyridin-2-yl)methyl)-N-(pentan-3-yl)-1-((2-(trimethylsilyl)ethoxy)methyl)-6,8-dihydro-1H-furo[3,4-d]pyrrolo[3,2-b]pyridine-2-carboxamide

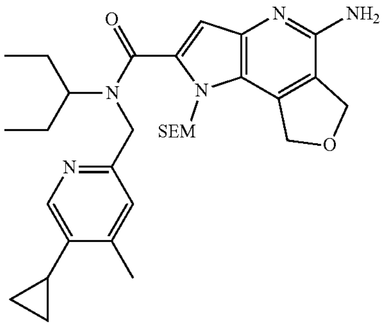 [SMILES: CCC(CC)N(Cc1cc(C)c(C2CC2)cn1)C(=O)c1cc2nc(N)c3c(c2n1COCC[Si](C)(C)C)COC3]

The title compound (240 mg, 33%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and N-((5-cyclopropyl-4-methylpyridin-2-yl)methyl)pentan-3-amine. LC-MS $(M+H)^+=564.3$.

Step 6: 5-amino-N-((5-cyclopropyl-4-methylpyridin-2-yl)methyl)-N-(pentan-3-yl)-6,8-dihydro-1H-furo[3,4-d]pyrrolo[3,2-b]pyridine-2-carboxamide Example 109 (60 mg, 33%) was prepared in a manner similar to that in Example 66 step 3 from 5-amino-N-((5-cyclopropyl-4-methylpyridin-2-yl)methyl)-N-(pentan-3-yl)-1-((2-(trimethylsilyl)ethoxy)methyl)-6,8-dihydro-1H-furo[3,4-d]pyrrolo[3,2-b]pyridine-2 -carboxamide. $^1H$ NMR (400 MHz, DMSO-d6) δ: 11.86-11.40 (m, 1H), 8.26-7.96 (m, 1H), 7.16 (s, 1H), 6.50 (s, 1H), 5.62-5.39 (m, 2H), 5.12 (s, 2H), 4.91 (s, 2H), 4.81-4.45 (m, 2H), 4.40-4.20 (m, 1H), 2.34 (s, 3H), 1.85 (s, 1H), 1.70-1.43 (m, 4H), 0.92 (d, J=7.6 Hz, 2H), 0.78 (t, J=7.3 Hz, 6H), 0.67 (s, 2H). LC-MS $(M+H)^+=434.0$.

Example 110 & Example 111: (R)-5-amino-N-ethyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide & (S)-5-amino-N-ethyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide

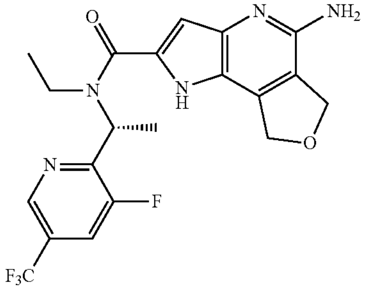 &

-continued

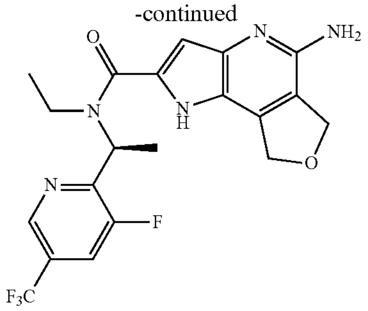

Step 1: 1-(3-fluoro-5-(trifluoromethyl)pyridin-2-yl)ethan-1-ol

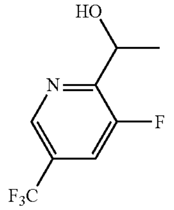

To a solution of 3-fluoro-5-(trifluoromethyl)picolinaldehyde (4.0 g, 20.7 mmol) in THF (40 mL) was added MeMgBr in diethyl ether (3.0 M, 8.29 mL, 24.9 mmol) at −78° C. under nitrogen. The mixture was slowly warmed to room temperature and stirred for 2 h. The reaction mixture was slowly added to saturated $NH_4Cl$ (50 mL) with stirring. The mixture was extracted with EtOAc (3×30 mL). The combined organic layer was washed with brine (100 mL), dried over $Na_2SO_4$, filtered and concentrated under reduced pressure. The residue was purified by silica gel chromatography (PE/EtOAc=100/0 to 20/1) to give the title compound (3.3 g, 76%). $^1H$ NMR (400 MHz, DMSO-d6) δ: 8.81 (s, 1H), 8.25 (d, J=10.0 Hz, 1H), 5.48 (d, J=5.7 Hz, 1H), 5.23-5.03 (m, 1H), 1.43 (d, J=6.5 Hz, 3H). LC-MS $(M+H)^+$=210.2.

Step 2: 2-(1-azidoethyl)-3-fluoro-5-(trifluoromethyl)pyridine

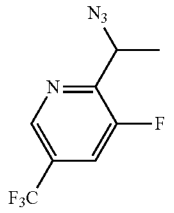

To a solution of 1-(3-fluoro-5-(trifluoromethyl)pyridin-2-yl)ethan-1-ol (3.3 g, 15.8 mmol) in toluene (45 mL) was added DBU (3.6 g 23.7 mmol) and DPPA (5.2 g, 18.9 mmol) at 0° C. The mixture was warmed to room temperature and stirred for 12 h. The mixture was diluted with water (50 mL) and extracted with EtOAc (3×40 mL). The combined organic layer was washed with brine (100 mL), dried over $Na_2SO_4$, filtered and concentrated under reduced pressure.

The residue was purified by silica gel chromatography (PE/EtOAc=100/0 to 20/1) to give the title compound (2.5 g, 68%). $^1H$ NMR (400 MHz, DMSO-d6) δ: 8.91 (s, 1H), 8.40 (d. J=9.8 Hz, 1H), 5.04 (q, J=6.8 Hz, 1H), 1.59 (d, J=6.8 Hz, 3H). LC-MS $(M+H)^+$=235.1.

Step 3: tert-butyl (1-(3-fluoro-5-(trifluoromethyl)pyridin-2-yl)ethyl)carbamate

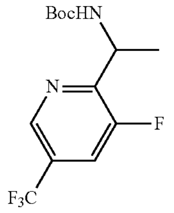 [SMILES: CC(NC(=O)OC(C)(C)C)c1ncc(C(F)(F)F)cc1F]

To a solution of 2-(1-azidoethyl)-3-fluoro-5-(trifluoromethyl)pyridine (2.5 g, 10.7 mmol) in MeOH (60 mL) was added $Boc_2O$ (3.77 g, 17.3 mmol) and 10% Pd/C (675 mg) under nitrogen. The mixture was degassed and purged with hydrogen for 3 times, then stirred under $H_2$ (30 psi) at 30° C. for 4 h. The mixture was filtered and concentrated under reduced pressure. The residue was purified by silica gel chromatography (PE/EtOAc=100/0 to 20/1) to give the title compound (3.0 g, 91%). $^1H$ NMR (400 MHz, DMSO-d6) δ: 8.80 (s, 1H), 8.25 (d, J=9.9 Hz, 1H), 7.41 (d, J=7.2 Hz, 1H), 5.04-4.93 (m, 1H), 1.49-1.25 (m, 12H). LC-MS $(M+H)^+$=309.2.

Step 4: tert-butyl ethyl(1-(3-fluoro-5-(trifluoromethyl)pyridin-2-yl)ethyl)carbamate

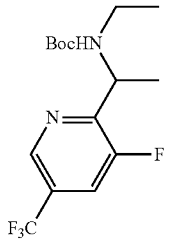

To a solution of tert-butyl (1-(3-fluoro-5-(trifluoromethyl)pyridin-2-yl)ethyl)carbamate (1.0 g, 3.24 mmol) in EtI (10.5 mL, 130 mmol) was added NaH (60%, 519 mg, 13.0 mmol) under nitrogen in a sealed tube. After cease of bubbling, the vessel was sealed and the mixture was stirred at 80° C. for 12 h. The mixture was cooled to room temperature and slowly added to saturated $NH_4Cl$ (20 mL). The mixture was extracted with EtOAc (3×15 mL). The combined organic layer was washed with brine (30 mL), dried over $Na_2SO_4$, filtered and concentrated under reduced pressure. The residue was purified by silica gel chromatography (PE/EtOAc=100/0 to 20/1) to give the title compound (440 mg, 40%). LC-MS $(M+H)^+$=337.3.

Step 5: N-ethyl-1-(3-fluoro-5-(trifluoromethyl)pyridin-2-yl)ethan-1-amine Hydrochloride

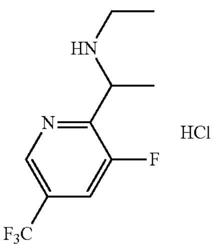 [SMILES: CCNC(C)c1ncc(C(F)(F)F)cc1F ; Cl]

To tert-butyl ethyl(1-(3-fluoro-5-(trifluoromethyl)pyridin-2-yl)ethyl)carbamate (240 mg, 0.71 mmol) was added HCl in MeOH (3.0 M, 3 mL). The mixture was stirred at room temperature for 3 h. The mixture was concentrated under reduced pressure to give the title compound (150 mg, 77%). LC-MS $(M+H)^+$=237.1.

Step 6: 5-amino-N-ethyl-N-(1-(3-fluoro-5-(trifluoromethyl)pyridin-2-yl)ethyl)-1-((2-(trimethylsilyl)ethoxy)methyl)-6,8-dihydro-1H-furo[3,4-d]pyrrolo[3,2-b]pyridine-2-carboxamide

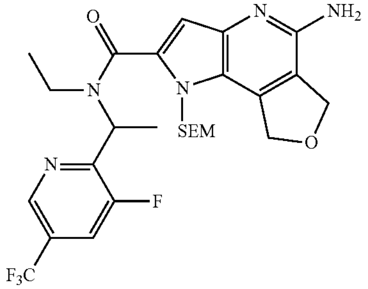

To a solution of N-ethyl-1-(3-fluoro-5-(trifluoromethyl)pyridin-2-yl)ethan-1-amine hydrochloride (127 mg, 466 μmol) and 5-amino-1-((2-(trimethylsilyl)ethoxy)methyl)-6,8-dihydro-1H-furo[3,4-d]pyrrolo[3,2-b]pyridine-2-carboxylic acid (163 mg, 466 μmol) in DMF (5 mL) was added DIPEA (150 mg, 1.16 mmol) and CMPI (131 mg, 512 μmol). The mixture was stirred at 40° C. for 6 h and then cooled to room temperature. The mixture was diluted with water (20 mL) and extracted with EtOAc (3×10 mL). The combined organic layer was washed with brine (3×20 mL), dried over $Na_2SO_4$, filtered and concentrated under reduced pressure. The residue was purified by silica gel chromatography (PE/EtOAc=100/0 to 1/4) to give the title compound (200 mg, 76%). LC-MS $(M+H)^+$=568.3.

Step 7: (R)-5-amino-N-ethyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide & (S)-5-amino-N-ethyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide To a solution of 5-amino-N-ethyl-N-(1-(3-fluoro-5-(trifluoromethyl)pyridin-2-yl)ethyl)-1-((2-(trimethylsilyl)ethoxy)methyl)-6,8-dihydro-1H-furo[3,4-d]pyrrolo[3,2-b]pyridine-2-carboxamide (180 mg, 317 μmol) in DCM (2 mL) was added TFA (2 mL). The mixture was stirred at room temperature for 1 h and then concentrated under reduced pressure. The residue was diluted with methanolic ammonia (7.0 M, 5 mL) and stirred at room temperature for 0.5 h. Solid was filtered off and the filtrate was concentrated under reduced pressure. The residue was purified by prep-HPLC and further separated by SFC to give Example 110 (7 mg, 5%) and Example 111 (10 mg, 7%).

Analytical chiral-SFC condition as below. Column: CHIRALPAK IH-3; Column size: 4.6×100 mm, 3 μm; Mobile phase: (ethanol containing 0.2% 7 M methanolic $NH_3$):$CO_2$, 1:9 for 0.2 min, 1:9 to 1:1 in 2.2 min, 1:1 for 1 min, 1:1 to 1:9 in 0.6 min; Flow: 3.5 mL/min, Temperature: 35° C.; back pressure: 2000 psi.

Example 110: Analytical SFC tR=1.39 min. $^1$H NMR (400 MHz, DMSO-d6) δ 11.53 (s, 1H), 8.88 (s, 1H), 8.29 (d, J=9.9 Hz, 1H), 6.60 (s, 1H), 6.04 (br s, 1H), 5.56 (s, 2H), 5.12 (s, 2H), 4.92 (s, 2H), 3.90-3.40 (m, 2H), 1.70 (d, J=6.5 Hz, 3H), 1.16-0.89 (m, 3H). LC-MS $(M+H)^+$=438.1.

Example 111: Analytical SFC tR=1.58 min. $^1$H NMR (400 MHz, DMSO-d6) δ 11.53 (s, 1H), 8.88 (s, 1H), 8.29 (d, J=9.9 Hz, 1H), 6.60 (s, 1H), 6.04 (br s, 1H), 5.56 (s, 2H), 5.12 (s, 2H), 4.92 (s, 2H), 3.85-3.40 (m, 2H), 1.70 (d, J=6.5 Hz, 3H), 1.15-0.89 (m, 3H). LC-MS $(M+H)^+$=438.2.

Example 110 can also be obtained through the next procedures:

Step 1: (S)-1-(3-fluoro-5-(trifluoromethyl)pyridin-2-yl)ethan-1-ol

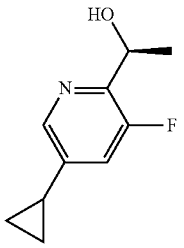

To a solution of 1-(3-fluoro-5-(trifluoromethyl)pyridin-2-yl)ethan-1-one (1.0 g, 4.8 mmol) in formic acid-$Et_3N$ complex (5:2, 20 mL) was added [(S,S)—N-(2-amino-1,2-diphenylethyl)-p-toluenesulfonamidelchloro(p-cymene) ruthenium(II) (156 mg, 0.24 mmol) at −18° C. under hydrogen. The mixture was stirred at 0° C. for 2 h and at room temperature for 12 h. The mixture was diluted with saturated $NaHCO_3$ (150 mL) and extracted with EtOAc (150 mL). The organic layer was washed with brine (150 mL), dried over $Na_2SO_4$, filtered and concentrated under reduced pressure. The residue was purified by silica gel chromatography (PE:EtOAc=10:1) to give the title compound (680 mg, 67%). LC-MS $(M+H)^+$=210.1.

Step 2: (R)—N-(1-(3-fluoro-5-(trifluoromethyl)pyridin-2-yl)ethyl)-N-ethyl-2-nitrobenzenesulfonamide

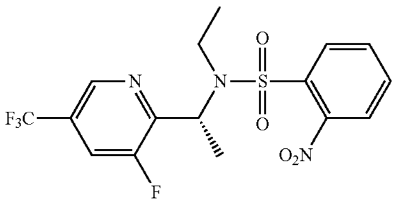 [SMILES: CCN([C@H](C)c1ncc(C(F)(F)F)cc1F)S(=O)(=O)c1ccccc1[N+](=O)[O-]]

To a mixture of (S)-1-(3-fluoro-5-(trifluoromethyl)pyridin-2-yl)ethan-1-ol (680 mg, 3.25 mmol), N-ethyl-2-nitrobenzenesulfonamide (748 mg, 3.25 mmol) and $PPh_3$ (936 mg, 3.58 mmol) in THF (30 mL) was added DtBAD (823 mg, 3.58 mmol) in portions at 0° C. under nitrogen. The mixture was stirred at room temperature for 3 h. The mixture was diluted water (100 mL) and then extracted with EtOAc (100 mL). The organic layer was washed with brine (100 mL), dried over $Na_2SO_4$, filtered and concentrated under reduced pressure. The residue was purified by silica gel chromatography (PE:EtOAc=3:1) to give the title compound (1.3 g, 95%). LC-MS $(M+H)^+$=422.1.

Step 3: (R)—N-ethyl-1-(3-fluoro-5-(trifluoromethyl)pyridin-2-yl)ethan-1-amine

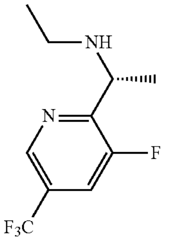 [SMILES: CCN[C@H](C)c1ncc(C(F)(F)F)cc1F]

To a mixture of (R)—N-(1-(3-fluoro-5-(trifluoromethyl)pyridin-2-yl)ethyl)-N-ethyl-2-nitrobenzenesulfonamide (1.3 g, 3.09 mmol), dodecane-1-thiol (1.94 g, 9.58 mmol) in DMF (4 mL) and THF (40 mL) was added LiOH—$H_2O$ (402 mg, 9.58 mmol), and the mixture was stirred at room temperature for 16 h. Volatiles were removed under reduced pressure and the residue was partitioned between water (50 mL) and EtOAc (50 mL). The organic layer was separated, dried with $Na_2SO_4$, filtered and concentrated under reduced pressure. The residue was purified by silica gel chromatography (PE/EtOAc=1/1 to DCM:MeOH=10:1) to give the title compound (560 mg, 76%). LC-MS $(M+H)^+$=237.1.

Step 4: (R)-5-amino-N-ethyl-N-(1-(3-fluoro-5-(trifluoromethyl)pyridin-2-yl)ethyl)-1-((2-(trimethylsilyl)ethoxy)methyl)-6,8-dihydro-1H-furo[3,4-d]pyrrolo[3,2-b]pyridine-2-carboxamide

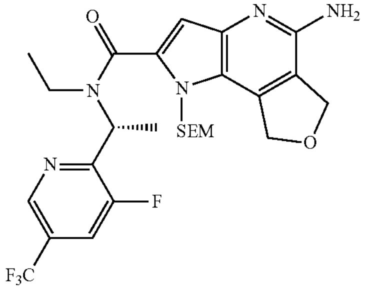

The title compound (105 mg, 59%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and 1-(5-cyclopropylpyridin-2-yl)-N-ethylethan-1-amine. LC-MS $(M+H)^+$=568.3.

Step 5: (R)-5-amino-N-ethyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide Example 110 (40 mg, 49%) was prepared in a manner similar to that in Example 110 & Example 111 step 7 from (R)-5-amino-N-ethyl-N-(1-(3-fluoro-5-(trifluoromethyl)pyridin-2-yl)ethyl)-1-((2-(trimethylsilyl)ethoxy)methyl)-6,8-dihydro-1H-furo[3,4-d]pyrrolo[3,2-b]pyridine-2-carboxamide.

Example 112 & Example 113: (R)-5-amino-N-(1-(5-cyclopropylpyridin-2-yl)ethyl)-N-ethyl-6,8-dihydro-1H-furo[3,4-d]pyrrolo[3,2-b]pyridine-2-carboxamide & (S)-5-amino-N-(1-(5-cyclopropylpyridin-2-yl)ethyl)-N-ethyl-6,8-dihydro-1H-furo[3,4-d]pyrrolo[3,2-b]pyridine-2-carboxamide

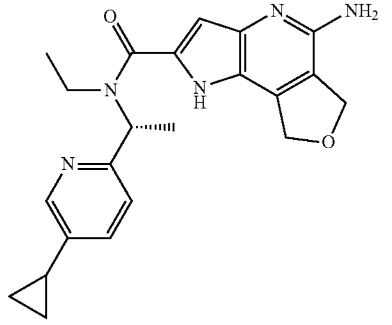

&

-continued

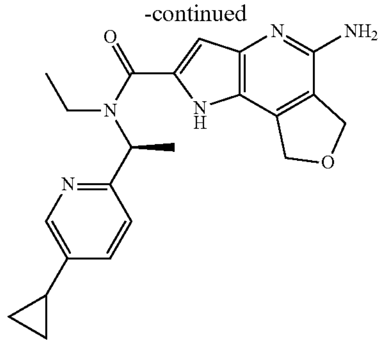

Step 1: 1-(5-cyclopropylpyridin-2-yl)ethan-1-one

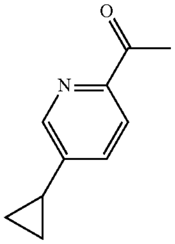

The title compound (990 mg, 61%) was prepared in a manner similar to that in Example 36 step 1 from 1-(5-bromopyridin-2-yl)ethan-1-one and cyclopropylboronic acid. LC-MS $(M+H)^+=162.2$.

Step 2: 1-(5-cyclopropylpyridin-2-yl)-N-ethylethan-1-amine

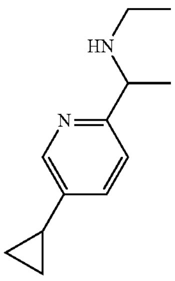

To a solution of 1-(5-cyclopropylpyridin-2-yl)ethan-1-one (0.30 g, 1.86 mmol) in ethylamine (2.10 g, 46.5 mmol) was added $Ti(OEt)_4$ (425 mg, 1.86 mmol) and the mixture was stirred at 60° C. for 12 h in a sealed tube. The mixture was cooled to room temperature and $NaBH_3CN$ (468 mg, 7.44 mmol) in THF (3 mL) was added. The tube was re-sealed and the mixture reacted with stirring at room temperature for 12 h. The reaction mixture was fully quenched with saturated $NaHCO_3$ (30 mL) and then extracted with DCM (3×5 mL). The combined organic layer was washed with brine (5 mL), dried over $Na_2SO_4$, filtered and concentrated under reduced pressure. The residue was purified by silica gel chromatography (PE/EtOAc=1/0 to 0/1) to give the title compound (267 mg, 75%). LC-MS $(M+H)^+=191.2$.

Step 3: 5-amino-N-(1-(5-cyclopropylpyridin-2-yl)ethyl)-N-ethyl-1-((2-(trimethylsilyl)ethoxy methyl)-6,8-dihydro-1H-furo[3,4-d]pyrrolo[3,2-b]pyridine-2-carboxamide

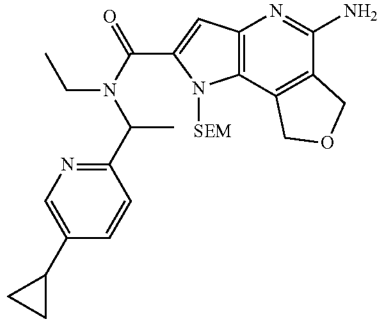 [SMILES: CCN(C(=O)c1cc2nc(N)c3c(c2n1COCC[Si](C)(C)C)COC3)C(C)c1ccc(C2CC2)cn1]

The title compound (66 mg, 16%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and 1-(5-cyclopropylpyridin-2-yl)-N-ethylethan-1-amine. LC-MS $(M+H)^+=522.2$.

Step 4: (R)-5-amino-N-(1-(5-cyclopropylpyridin-2-yl)ethyl)-N-ethyl-6,8-dihydro-1H-furo[3,4-d]pyrrolo[3,2-b]pyridine-2-carboxamide & (S)-5-amino-N-(1-5-cyclopropylpyridin-2-yl)ethyl)-N-ethyl-6,8-dihydro-1H-furo[3,4-d]pyrrolo[3,2-b]pyridine-2-carboxamide Example 112 (6 mg, 9%) and Example 113 (6 mg, 9%) were prepared in a manner similar to that in Example 110 & Example 111 step 7 from 5-amino-N-(1-(5-cyclopropylpyridin-2-yl)ethyl)-N-ethyl-1-((2-(trimethylsilyl)ethoxy) methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: Chiralcel OD-3; Column size: 4.6×50 mm, 3 μm; Mobile phase: 14 mM ammonia in MeOH:$CO_2$, 1:19 for 0.2 min, 1:19 to 1:1 in 1 min, 1:1 for 1 min, 1:1 to 1:19 in 0.4 min, 1:19 for 0.4 min; Flow: 3.4 mL/min; Temperature: 35° C.; back pressure: 1800 psi.

Example 112: Analytical SFC tR=1.49 min. $^1H$ NMR (400 MHz, DMSO-d6) δ 11.54 (s, 1H), 8.40 (d, J=1.9 Hz, 1H), 7.42 (dd, J=8.1, 2.1 Hz, 1H), 7.24 (d, J=8.1 Hz, 1H), 6.54 (s, 1H), 5.79-5.70 (m, 1H), 5.51 (s, 2H), 5.13 (s, 2H), 4.92 (s, 2H), 3.68-3.44 (m, 2H), 1.99-1.91 (m, 1H), 1.65 (d, J=7.0 Hz, 3H), 1.03-0.97 (m, 5H), 0.75-0.69 (m, 2H). LCMS $(M+H)^+=392.2$.

Example 113: Analytical SFC tR=1.68 min. $^1H$ NMR (400 MHz, DMSO-d6) δ 11.54 (s, 1H), 8.39 (d, J=1.8 Hz, 1H), 7.42 (dd, J=8.2, 1.9 Hz, 1H), 7.24 (d, J=8.3 Hz, 1H), 6.54 (s, 1H), 5.79-5.70 (m, 1H), 5.51 (s, 2H), 5.13 (s, 2H), 4.92 (s, 2H), 3.68-3.44 (m, 2H), 1.99-1.91 (m, 1H), 1.65 (d, J=7.0 Hz, 3H), 1.03-0.97 (m, 5H), 0.75-0.69 (m, 2H). LCMS $(M+H)^+=392.2$.

Example 114 & Example 115: (S)-5-amino-N-ethyl-N-(1-(5-(trifluoromethyl)pyridin-2-yl)ethyl)-6,8-dihydro-1H-furo[3,4-d]pyrrolo[3,2-b]pyridine-2-carboxamide & (R)-5-amino-N-ethyl-N-(1-(5-(trifluoromethyl)pyridin-2-yl)ethyl)-6,8-dihydro-1H-furo[3,4-d]pyrrolo[3,2-b]pyridine-2-carboxamide

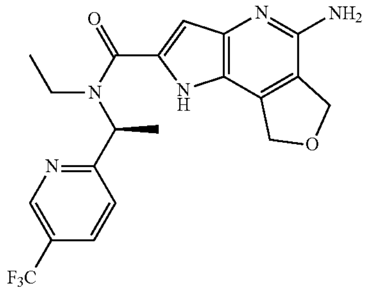

&

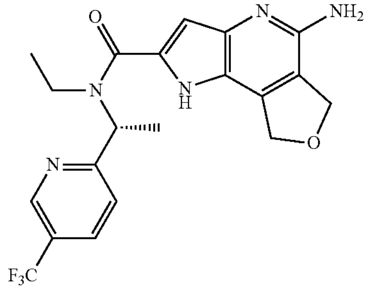

Step 1: 145-(trifluoromethyl)pyridin-2-yl)ethan-1-one Oxime

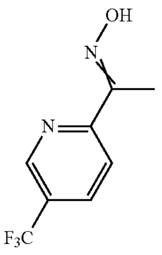

To a solution of 1-(5-(trifluoromethyl)pyridin-2-yl)ethan-1-one (2.0 g, 10.6 mmol) in pyridine (25 mL) was added hydroxylamine hydrochloride (1.84 g, 26.4 mmol). The mixture was stirred at 50° C. for 1.5 h. The mixture was diluted with water (50 mL) and extracted with EtOAc (3×40 mL). The combined organic layer was washed with saturated $NH_4Cl$ (3×100 mL), dried over $Na_2SO_4$, filtered and concentrated under reduced pressure. The residue was purified by silica gel chromatography (PE/EtOAc=100/0 to 50/1), to give the title compound (2.0 g, 93%). $^1H$ NMR (400 MHz, DMSO-d6) δ: 11.90 (s, 1H), 8.97 (s, 1H), 8.18 (dd, J=8.6, 2.1 Hz, 1H), 8.06 (d, J=8.5 Hz, 1H), 2.24 (s, 3H). LC-MS $(M+H)^+$=205.1.

Step 2: tert-butyl (1-(5-(trifluoromethyl)pyridin-2-yl)ethyl)carbamate

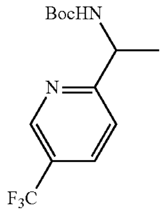 [SMILES: CC(NC(=O)OC(C)(C)C)c1ccc(C(F)(F)F)cn1]

To a solution of 1-(5-(trifluoromethyl)pyridin-2-yl)ethan-1-one oxime (2.0 g, 9.80 mmol) in MeOH (30 mL) was added $Boc_2O$ (4.3 g, 19.6 mmol) and Raney-Ni (84 mg, 0.98 mmol) under argon. The suspension was degassed and purged with hydrogen for 3 times. The mixture was stirred under hydrogen (40 psi) at 40° C. for 12 h. Solid was filtered off and the filtrate was concentrated under reduced pressure. The residue was purified by silica gel chromatography (PE/EtOAc=100/0 to 2/1) to give the title compound (2.3 g, 81%). $^1H$ NMR (400 MHz, DMSO-d6) δ: 8.88 (s, 1H), 8.19 (d, J=7.0 Hz, 1H), 7.58-7.47 (m, 2H), 4.79-4.65 (m, 1H), 1.43-1.28 (m, 12H). LC-MS $(M+H)^+$=291.1.

Step 3: tert-butyl ethyl(1-(5-(trifluoromethyl)pyridin-2-yl)ethyl)carbamate

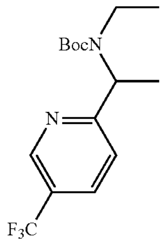 [SMILES: CCN(C(=O)OC(C)(C)C)C(C)c1ccc(C(F)(F)F)cn1]

The title compound (430 mg, 39%) was prepared in a manner similar to that in Example 110 & Example 111 step 4 from tert-butyl (1-(5-(trifluoromethyl)pyridin-2-yl)ethyl) carbamate and EtI. LC-MS $(M+H)^+$=319.1.

Step 4: N-ethyl-1-(5-(trifluoromethyl)pyridin-2-yl) ethan-1-amine Hydrochloride

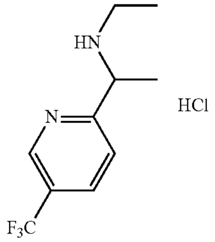

The title compound (300 mg, 87%) was prepared in a manner similar to that in Example 110 & Example 111 step 5 from tert-butyl ethyl(1-(5-(trifluoromethyl)pyridin-2-yl)ethyl)carbamate. LC-MS $(M+H)^+$=219.1.

Step 5: 5-amino-N-ethyl-N-(1-(5-(trifluoromethyl)pyridin-2-yl)ethyl)-1-((2-(trimethylsilyl)ethoxy)methyl)-6,8-dihydro-1H-furo[3,4-d]pyrrolo[3,2-b]pyridine-2-carboxamide

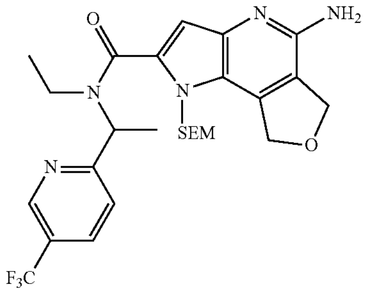 [SMILES: CCN(C(=O)c1cc2nc(N)c3c(c2n1COCC[Si](C)(C)C)COC3)C(C)c1ccc(C(F)(F)F)cn1]

The title compound (190 mg, 75%) was prepared in a manner similar to that in Example 110 & Example 111 step 6 from N-ethyl-1-(5-(trifluoromethyl)pyridin-2-yl)ethan-1-amine hydrochloride and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=550.3.

Step 5: (S)-5-amino-N-ethyl-N-(1-(5-(trifluoromethyl)pyridin-2-yl)ethyl)-6,8-dihydro-1H-furo[3,4-d]pyrrolo[3,2-b]pyridine-2-carboxamide & (R)-5-amino-N-ethyl-N-(1-(5-(trifluoromethylpyridin-2-yl)ethyl)-6,8-dihydro-1H-furo[3,4-d]pyrrolo[3,2-b]pyridine-2-carboxamide Example 114 (16 mg, 12%) and Example 115 (20 mg, 15%) were prepared in a manner similar to that in Example 110 & Example 111 step 7 from 5-amino-N-ethyl-N-(1-(5-(trifluoromethyl)pyridin-2-yl)ethyl)-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: Chiralpak IC-3; Column size: 4.6×100 mm, 3 μm; Mobile phase: (ethanol containing 0.2% 7 M methanolic $NH_3$):$CO_2$, 1:1 isocratic; Flow: 4 mL/min; Temperature: 35° C.; back pressure: 2000 psi.

Example 114: Analytical SFC tR=1.03 min. 1H NMR (400 MHz, DMSO-d6) δ 11.65-11.43 (m, 1H), 8.97 (s, 1H), 8.20 (d, J=7.1 Hz, 1H), 7.62 (d, J=8.4 Hz, 1H), 6.68-6.44 (m, 1H), 5.90-5.50 (m, 3H), 5.12 (s, 2H), 4.92 (s, 2H), 3.90-3.42 (m, 2H), 1.74 (d, J=7.0 Hz, 3H), 1.22-1.08 (m, 3H). LCMS $(M+H)^+$=420.2.

Example 115: Analytical SFC tR=1.29 min. $^1$H NMR (400 MHz, DMSO-d6) 11.65-11.43 (m, 1H), 8.97 (s, 1H), 8.20 (d, J=7.1 Hz, 1H), 7.62 (d, J=8.4 Hz, 1H), 6.68-6.44 (m, 1H), 5.90-5.50 (m, 3H), 5.12 (s, 2H), 4.92 (s, 2H), 3.90-3.42 (m, 2H), 1.74 (d, J=7.0 Hz, 3H), 1.22-1.08 (m, 3H). LCMS $(M+H)^+$=420.2.

Example 116: (R)-5-amino-N-(2,6-difluoro-4-(trifluoromethyl)benzyl)-6-methyl-N-(pentan-3-yl)-6,8-dihydro-1H-furo[3,4-d]pyrrolo[3,2-b]pyridine-2-carboxamide

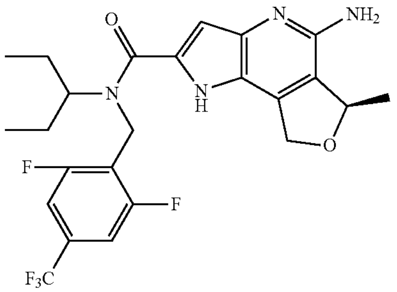 [SMILES: CCC(CC)N(Cc1c(F)cc(C(F)(F)F)cc1F)C(=O)c1cc2nc(N)c3c(c2[nH]1)CO[C@@H]3C]

Step 1: (2,6-difluoro-4-(trifluoromethyl)phenyl)methanol

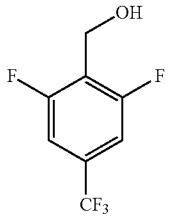 [SMILES: OCc1c(F)cc(C(F)(F)F)cc1F]

To a solution of 2,6-difluoro-4-(trifluoromethyl)benzoic acid (800 mg, 3.54 mmol) in THF (10 mL) was added borane in THF (1.0 M, 14.1 mL, 14.1 mmol) dropwise. The mixture was stirred at 60° C. for 3 h and then cooled to room temperature. The mixture was completely quenched with MeOH (10 mL) and then concentrated under vacuum. The residue was purified by silica gel chromatography (PE:EtOAc=2:1) to give the title compound (700 mg, 93%). LC-MS $(M+H)^+$=213.1.

Step 2: N-(2,6-difluoro-4-(trifluoromethyl)benzyl)pentan-3-amine

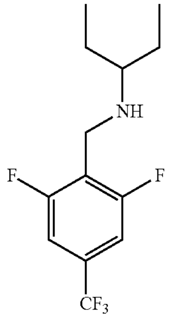 [SMILES: CCC(CC)NCc1c(F)cc(C(F)(F)F)cc1F]

To a solution of (2,6-difluoro-4-(trifluoromethyl)phenyl)methanol (700 mg, 3.3 mmol) in THF (10 mL) was added $SOCl_2$ (2.4 mL, 33 mmol). The mixture was stirred at refluxing temperature for 3 h and then cooled to room temperature. Volatiles were removed under reduced pressure. The residue was re-dissolved in MeCN (10 mL) in a sealed tube, followed by addition of pentan-3-amine (376 mg, 4.3 mmol) and DIPEA (0.8 mL, 4.3 mmol). The tube was sealed and the mixture was stirred at 100° C. for 12 h. The mixture was cooled to room temperature and diluted with water (20 mL). The mixture was extracted with EtOAc (50 mL). The organic laver was washed with brine (50 mL), dried over $Na_2SO_4$, filtered and concentrated under vacuum. The residue was purified by silica gel chromatography (DCM:MeOH=20:1) to give the title compound (50 mg, 5%). LC-MS $(M+H)^+$=281.2.

Step 3: (R)-5-amino-N-(2,6-difluoro-4-(trifluoromethyl)benzyl)-6-methyl-N-(pentan-3-yl)-6,8-dihydro-1H-furo[3,4-d]pyrrolo[3,2-b]pyridine-2-carboxamide To a mixture of (R)-5-amino-6-methyl-6,8-dihydro-1H-furo[3,4-d]pyrrolo[3,2-b]pyridine-2-carboxylic acid (72 mg, 0.31 mmol), N-(2,6-difluoro-4-(trifluoromethyl)benzyl)pentan-3-amine (87 mg, 0.31 mmol) and DIPEA (0.60 ml, 3.1 mmol) in anhydrous DMF (3 mL) under nitrogen was added T3P in EtOAc (50%, 1.0 g, 1.6 mmol) and the mixture was stirred at 60° C. for 16 h. After cooling to room temperature, hydrochloric acid (6 M, 9 mL) was added and the mixture was stirred for 3 h at 60° C. The mixture was cooled to room temperature and quenched with saturated $NaHCO_3$ (100 mL). The mixture was extracted with EtOAc (100 mL). The organic layer was washed with brine (100 mL), dried over $Na_2SO_4$, filtered and concentrated under vacuum. The residue was purified by prep-HPLC to give the title compound (40 mg, 26%). $^1$H NMR (400 MHz, DMSO-d6) δ 11.52 (s, 1H), 7.59-7.57 (m, 1H), 6.44 (s, 1H), 5.46 (s, 2H), 5.12 (s, 1H), 5.09-4.98 (m, 2H), 4.67 (s, 2H), 1.67-1.58 (m, 4H), 1.21 (s, 3H), 0.81-0.80 (m, 6H). LC-MS $(M+H)^+$=497.4.

Example 117: 5-amino-N-((3-fluoro-5-morpholinopyridin-2-yl)methyl)-N-(pentan-3-yl)-6,8-dihydro-1H-furo[3,4-d]pyrrolo[3,2-b]pyridine-2-carboxamide

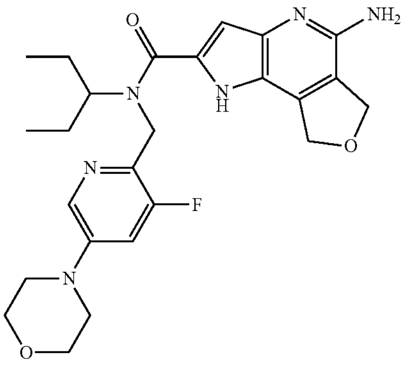 [SMILES: CCC(CC)N(Cc1ncc(N2CCOCC2)cc1F)C(=O)c1cc2nc(N)c3c(c2[nH]1)COC3]

Step 1: N-((5-bromo-3-fluoropyridin-2-yl)methyl)pentan-3-amine

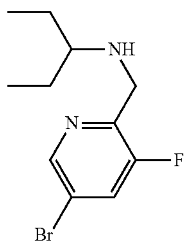

The title compound (11.5 g, 85%) was prepared in a manner similar to that in Example 66 step 1 from 5-bromo-3-fluoropicolinaldehyde and pentan-3-amine. LC-MS $(M+H)^+$=275.0.

Step 2: tert-butyl ((5-bromo-3-fluoropyridin-2-yl)methyl)(pentan-3-yl)carbamate

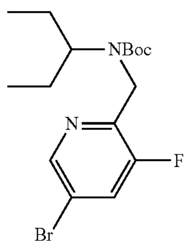 [SMILES: CCC(CC)N(Cc1ncc(Br)cc1F)C(=O)OC(C)(C)C]

The title compound (12.0 g 98%) was prepared in a manner similar to that in Example 39 & Example 40 step 6 from N-((5-bromo-3-fluoropyridin-2-yl)methyl)pentan-3-amine. LC-MS $(M+H)^+$=375.1.

Step 3: tert-butyl ((3-fluoro-5-morpholinopyridin-2-yl)methyl)(pentan-3-yl)carbamate

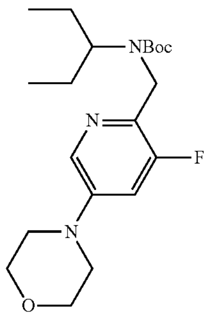 [SMILES: CCC(CC)N(Cc1ncc(N2CCOCC2)cc1F)C(=O)OC(C)(C)C]

To a solution of tert-butyl ((5-bromo-3-fluoropyridin-2-yl)methyl)(pentan-3-yl)carbamate (100 mg, 0.266 mmol) and morpholine (46 mg, 0.533 mmol) in toluene (2 mL) was added t-BuONa (38 mg, 0.40 mmol), Xantphos (31 mg, 53 μmol) and $Pd_2(dba)_3$ (24 mg, 27 μmol) under nitrogen and the mixture was stirred at 100° C. for 12 h. The mixture was cooled to room temperature, diluted with water (5 mL) and extracted with EtOAc (3×5 mL). The combined organic layer was washed with brine (10 mL), dried over $Na_2SO_4$, filtered and concentrated under reduced pressure to give the title compound (90 mg, 89%). LC-MS $(M+H)^+$=382.3.

Step 4: N-((3-fluoro-5-morpholinopyridin-2-yl) methyl)pentan-3-amine Hydrochloride

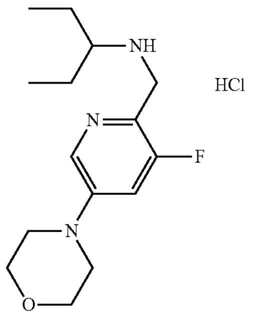 [SMILES: CCC(CC)NCc1ncc(N2CCOCC2)cc1F ; Cl]

The title compound (60 mg, 80%) was prepared in a manner similar to that in Example 110 & Example 111 step 5 from tert-butyl ((3-fluoro-5-morpholinopyridin-2-yl) methyl)(pentan-3-yl)carbamate. LC-MS $(M+H)^+$=282.3.

Step 5: 5-amino-N-((3-fluoro-5-morpholinopyridin-2-yl)methyl)-N-(pentan-3-yl)-1-((2-(trimethylsilyl) ethoxy)methyl)-6,8-dihydro-1H-furo[3,4-d]pyrrolo [3,2-b]pyridine-2-carboxamide

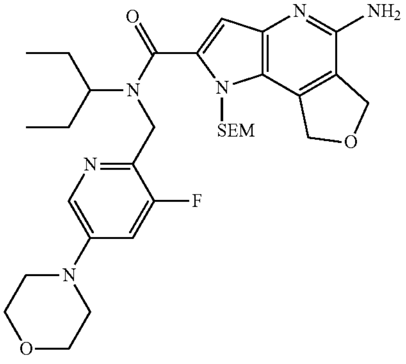 [SMILES: CCC(CC)N(Cc1ncc(N2CCOCC2)cc1F)C(=O)c1cc2nc(N)c3c(c2n1COCC[Si](C)(C)C)COC3]

The title compound (100 mg, 76%) was prepared in a manner similar to that in Example 66 step 2 from 5-amino-1-((2-(trimethylsilyl)ethoxy)methyl)-6,8-dihydro-1H-furo [3,4-d]pyrrolo[3,2-b]pyridine-2-carboxylic acid and N-((3-fluoro-5-morpholinopyridin-2-yl)methyl)pentan-3-amine hydrochloride. LC-MS $(M+H)^+$=613.3.

Step 6: 5-amino-N-((3-fluoro-5-morpholinopyridin-2-yl)methyl)-N-(pentan-3-yl)-6,8-dihydro-1H-furo [3,4-d]pyrrolo[3,2-b]pyridine-2-carboxamide Example 117 (34 mg, 48%) was prepared in a manner similar to that in Example 66 step 3 from 5-amino-N-((3-fluoro-5-morpholinopyridin-2-yl)methyl)-N-(pentan-3-yl)-1-((2-(trimethylsilyl)ethoxy)methyl)-6,8-dihydro-1H-furo [3,4-d]pyrrolo[3,2-b]pyridine-2-carboxamide. $^1$H NMR (400 MHz, DMSO-d6) δ: 11.71-11.30 (m, 1H), 8.28-8.00 (m, 1H), 7.32-7.16 (m, 1H), 6.80-6.35 (m, 1H), 5.61-5.42 (m, 2H), 5.20-5.04 (m, 2H), 4.94-4.47 (m, 4H), 4.39-4.02 (m, 1H), 3.81-3.61 (m, 4H), 3.28-3.10 (m, 4H), 1.80-1.32 (m, 4H), 0.95-0.68 (m, 6H). LC-MS $(M+H)^+$=483.3.

Example 118 & Example 119: (S)-5-amino-N-(1-(5-cyclopropyl-3-fluoropyridin-2-yl)ethyl)-N-methyl-6,8-dihydro-1H-furo[3,4-d]pyrrolo[3,2-b] pyridine-2-carboxamide & (R)-5-amino-N-(1-(5-cyclopropyl-3-fluoropyridin-2-yl)ethyl)-N-methyl-6, 8-dihydro-1H-furo[3,4-d]pyrrolo[3,2-b]pyridine-2-carboxamide

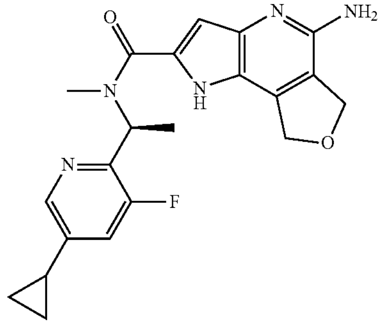

&

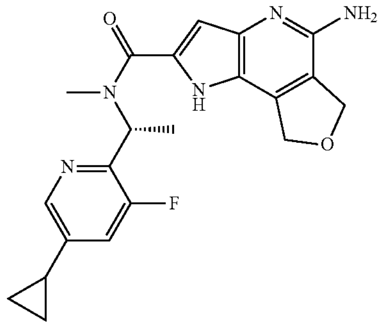

Step 1: 1-(5-bromo-3-fluoropyridin-2-yl)ethan-1-ol

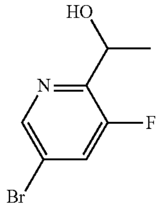

To a solution of 5-bromo-3-fluoropicolinaldehyde (10.0 g, 49.0 mmol) in THF (120 mL) was added MeMgBr in diethyl ether (3.0 M, 18.0 mL, 54.0 mmol) at −78° C. The mixture was stirred at 0° C. for 1 h and then quenched with water (120 mL). The mixture was extracted with EtOAc (3×50 mL). The combined organic layer was washed with brine (2×20 mL), dried over $Na_2SO_4$, filtered and concentrated under reduced pressure. The residue was purified by silica gel chromatography (PE/EtOAc=100/1 to 10/1). to give the title compound (7.53 g, 70%). LC-MS $(M+H)^+$=220.1.

Step 2: 2-(1-azidoethyl)-5-bromo-3-fluoropyridine

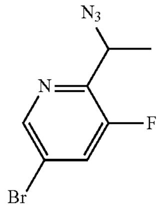

The title compound (5.0 g, 60%) was prepared in a manner similar to that in Example 110 & Example 111 step 2 from 1-(5-bromo-3-fluoropyridin-2-yl)ethan-1-ol. $^1$H NMR (400 MHz, $CDCl_3$) δ: 8.55-8.49 (m, 1H), 7.62 (dd, J=8.93, 1.83 Hz, 1H), 4.82 (q, J=6.8 Hz, 1H), 1.64 (d, J=6.8 Hz, 3H).

Step 3: tert-butyl (1-(5-bromo-3-fluoropyridin-2-yl) ethyl)carbamate

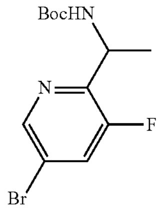 [SMILES: CC(NC(=O)OC(C)(C)C)c1ncc(Br)cc1F]

To a solution of 2-(1-azidoethyl)-5-bromo-3-fluoropyridine (2.5 g, 10.2 mmol) in THF (30 mL) and water (6 mL) was added KOH (1.43 g, 25.5 mmol) and $PPh_3$ (5.35 g, 20.4 mmol). The mixture was stirred at 50° C. for 1 h and room temperature for 11 h. The mixture was concentrated under reduced pressure. To the residue was added THF (20 mL), $Boc_2O$ (2.49 g, 11.4 mmol) and DIPEA (2.95 g, 22.8 mmol). The mixture was stirred at room temperature for 1 h and then concentrated under reduced pressure. The residue was purified by silica gel chromatography (PE/EtOAc=100/1 to 10/1) to give the title compound (2.4 g, 74%). $^1$H NMR (400 MHz, $CDCl_3$) δ: 8.47-8.41 (m, 1H), 7.57 (dd, J=8.7, 1.8 Hz, 1H), 5.78-5.58 (m, 1H), 5.23-5.11 (m, 1H), 1.50-1.35 (m, 12H).

Step 4: tert-butyl (1-(5-cyclopropyl-3-fluoropyridin-2-yl)ethyl)carbamate

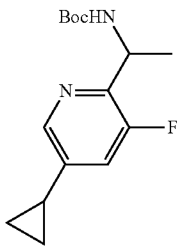 [SMILES: CC(NC(=O)OC(C)(C)C)c1ncc(C2CC2)cc1F]

The title compound (1.3 g, 62%) was prepared in a manner similar to that in Example 36 step 1 from tert-butyl (1-(5-bromo-3-fluoropyridin-2-yl)ethyl)carbamate and cyclopropylboronic acid. LC-MS $(M+H-tBu)^+$=225.0.

Step 5: tert-butyl (1-(5-cyclopropyl-3-fluoropyridin-2-yl)ethyl)(methyl)carbamate

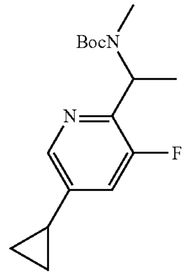 [SMILES: CC(c1ncc(C2CC2)cc1F)N(C)C(=O)OC(C)(C)C]

The title compound (0.30 g, 95%) was prepared in a manner similar to that in Example 39 & Example 40 step 7 from tert-butyl (1-(5-cyclopropyl-3-fluoropyridin-2-yl) ethyl)carbamate and MeI. LC-MS $(M+H)^+$=295.2.

Step 6: 1-(5-cyclopropyl-3-fluoropyridin-2-yl)-N-methylethan-1-amine Hydrochloride

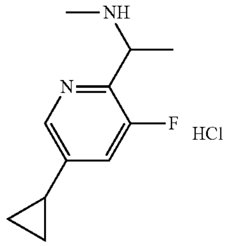

The title compound (0.20 g, 85%) was prepared in a manner similar to that in Example 110 & Example 111 step 5 from tert-butyl (1-(5-cyclopropyl-3-fluoropyridin-2-yl) ethyl)(methyl)carbamate. LC-MS $(M+H)^+$=195.3.

Step 7: 5-amino-N-(1-(5-cyclopropyl-3-fluoropyridin-2-yl)ethyl)-N-methyl-1-((2-(trimethylsilyl ethoxy)methyl)-6,8-dihydro-1H-furo[3,4-d]pyrrolo [3,2-b]pyridine-2-carboxamide

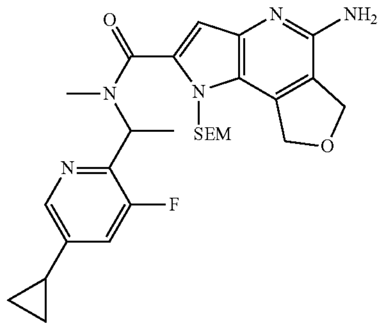 [SMILES: CC(c1ncc(C2CC2)cc1F)N(C)C(=O)c1cc2nc(N)c3c(c2n1COCC[Si](C)(C)C)COC3]

The title compound (0.20 g, 49%) was prepared in a manner similar to that in Example 66 step 2 from 5-amino- 1-((2-(trimethylsilyl)ethoxy)methyl)-6,8-dihydro-1H-furo[3,4-d]pyrrolo[3,2-b]pyridine-2-carboxylic acid and 1-(5-cyclopropyl-3-fluoropyridin-2-yl)-N-methylethan-1-amine hydrochloride. LC-MS $(M+H)^+$=526.4.

Step 8: (S)-5-amino-N-(1-(5-cyclopropyl-3-fluoropyridin-2-yl)ethyl)-N-methyl-6,8-dihydro-1H-furo[3,4-d]pyrrolo[3,2-b]pyridine-2-carboxamide & (R)-5-amino-N-(1-(5-cyclopropyl-3-fluoropyridin-2-yl)ethyl)-N-methyl-6,8-dihydro-1H-furo[3,4-d]pyrrolo[3,2-b]pyridine-2-carboxamide Example 118 (40 mg, 27%) and Example 119 (43 mg, 29%) were prepared in a manner similar to that in Example 110 & Example 111 step 7 from 5-amino-N-(1-(5-cyclopropyl-3-fluoropyridin-2-yl)ethyl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: Chiralpak IC-3; Column size: 4.6×50 mm, 3 μm Mobile phase: (0.1% isopropylamine in 1:1 v/v EtOH/MeCN):$CO_2$, 45:55 isocratic; Flow: 4 mL/min; Temperature: 35° C.; back pressure: 1800 psi.

Example 118: Analytical SFC tR=1.87 min. $^1$H NMR (400 MHz, DMSO-d6) δ 11.51 (s, 1H), 8.30 (s, 1H), 7.34 (dd, J=11.6, 1.6 Hz, 1H), 6.69-6.51 (m, 1H), 6.15-6.02 (m, 1H), 5.55 (s, 2H), 5.13 (s, 2H), 4.97-4.88 (m, 2H), 3.25-2.70 (m, 3H), 2.05-1.95 (m, 1H), 1.69-1.47 (m, 3H), 1.06-0.99 (m, 2H), 0.83-0.77 (m, 2H). LCMS $(M+H)^+$=396.2.

Example 119: Analytical SFC tR=2.49 min. $^1$H NMR (400 MHz, DMSO-d6) δ 11.51 (s, 1H), 8.30 (s, 1H), 7.34 (dd, J=11.6, 1.6 Hz, 1H), 6.69-6.51 (m, 1H), 6.15-6.02 (m, 1H), 5.55 (s, 2H), 5.13 (s, 2H), 4.97-4.88 (m, 2H), 3.25-2.70 (m, 3H), 2.05-1.95 (m, 1H), 1.69-1.47 (m, 3H), 1.06-0.99 (m, 2H), 0.83-0.77 (m, 2H). LCMS $(M+H)^+$=396.2.

Example 119 can also be obtained through the next procedures;

Step 1: (R)-5-amino-N-(1-(5-cyclopropyl-3-fluoropyridin-2-yl)ethyl)-N-methyl-1-((2-(trimethylsilyl)ethoxy)methyl)-6,8-dihydro-1H-furo[3,4-d]pyrrolo[3,2-b]pyridine-2-carboxamide

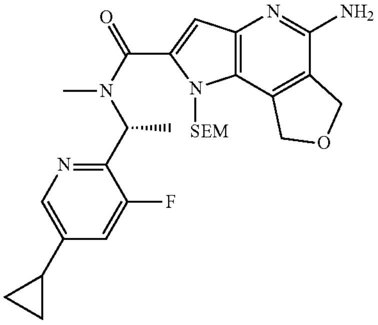 [SMILES: C[C@H](c1ncc(C2CC2)cc1F)N(C)C(=O)c1cc2nc(N)c3c(c2n1COCC[Si](C)(C)C)COC3]

The title compound (0.15 g, 86%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and (R)-1-(5-cyclopropyl-3-fluoropyridin-2-yl)-N-methylethan-1-amine. LC-MS $(M+H)^+$=526.4.

Step 2: (R)-5-amino-N-(1-(5-cyclopropyl-3-fluoropyridin-2-yl)ethyl)-N-methyl-6,8-dihydro-1H-furo[3,4-d]pyrrolo[3,2-b]pyridine-2-carboxamide Example 119 (49 mg, 43%) was prepared in a manner similar to that in Example 110 & Example 111 step 7 from (R)-5-amino-N-(1-(5-cyclopropyl-3-fluoropyridin-2-yl)ethyl)-N-methyl-1-((2-(trimethylsilyl)ethoxy)methyl)-6,8-dihydro-1H-furo[3,4-d]pyrrolo[3,2-b]pyridine-2-carboxamide.

Example 120 & Example 121: (R)-5-amino-N-(1-(5-cyclopropyl-3-fluoropyridin-2-yl)ethyl)-N-ethyl-6,8-dihydro-1H-furo[3,4-d]pyrrolo[3,2-b]pyridine-2-carboxamide & (S)-5-amino-N-(1-(5-cyclopropyl-3-fluoropyridin-2-yl)ethyl)-N-ethyl-6,8-dihydro-1H-furo[3,4-d]pyrrolo[3,2-b]pyridine-2-carboxamide

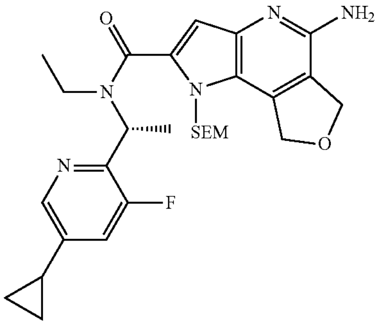

&

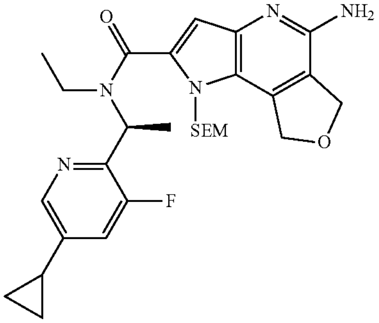

Step 1: tert-butyl (1-(5-cyclopropyl-3-fluoropyridin-2-yl)ethyl)(ethyl)carbamate

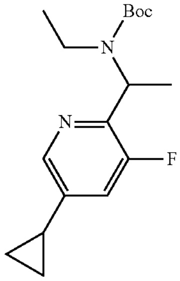 [SMILES: CCN(C(=O)OC(C)(C)C)C(C)c1ncc(C2CC2)cc1F]

The title compound (0.10 g, 23%) was prepared in a manner similar to that in Example 39 & Example 40 step 7 from tert-butyl (1-(5-cyclopropyl-3-fluoropyridin-2-yl) ethyl)carbamate and EtI. LC-MS $(M+H)^+$=309.3.

Step 2: 145-cyclopropyl-3-fluoropyridin-2-yl)-N-ethylethan-1-amine Hydrochloride

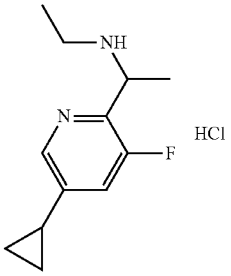

The title compound (54 mg, 100%) was prepared in a manner similar to that in Example 110 & Example 111 step 5 from tert-butyl (1-(5-cyclopropyl-3-fluoropyridin-2-yl) ethyl)ethyl)carbamate. LC-MS $(M+H)^+$=209.2.

Step 3: 5-amino-N-(1-(5-cyclopropyl-3-fluoropyridin-2-yl)ethyl)-N-ethyl-1-((2-(trimethylsilyl)ethoxy) methyl)-6,8-dihydro-1H-furo[3,4-d]pyrrolo[3,2-b] pyridine-2-carboxamide

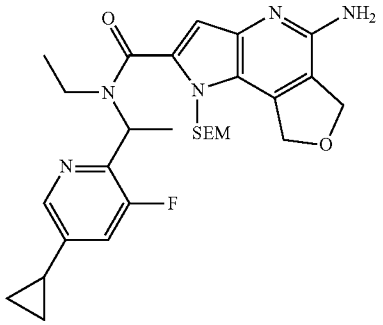 [SMILES: CCN(C(=O)c1cc2nc(N)c3c(c2n1COCC[Si](C)(C)C)COC3)C(C)c1ncc(C2CC2)cc1F]

The title compound (0.10 g, 48%) was prepared in a manner similar to that in Example 110 & Example 111 step 6 from 5-amino-1-((2-(trimethylsilyl)ethoxy)methyl)-6,8-dihydro-1H-furo[3,4-d]pyrrolo[3,2-b]pyridine-2-carboxylic acid and 1-(5-cyclopropyl-3-fluoropyridin-2-yl)-N-ethylethan-1-amine hydrochloride. LC-MS $(M+H)^+$=540.4.

Step 4: (R)-5-amino-N-(1-(5-cyclopropyl-3-fluoropyridin-2-yl)ethyl)-N-ethyl-6,8-dihydro-1H-furo[3,4-d]pyrrolo[3,2-b]pyridine-2-carboxamide & (S)-5-amino-N-(1-(5-cyclopropyl-3 -fluoropyridin-2-yl) ethyl)-N-ethyl-6,8-dihydro-1H-furo[3,4-d]pyrrolo[3,2-b]pyridine-2-carboxamide Example 120 (13 mg, 21%) and Example 121 (11 mg, 18%) were prepared in a manner similar to that in Example 110 & Example 111 step 7 from 5-amino-N-(1-(5-cyclopropyl-3-fluoropyridin-2-yl)ethyl)-N-ethyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: CHIRALPAK 1H-3; Column size: 4.6×100 mm, 3 μm; Mobile phase: (isopropanol containing 0.2% 7 M methanolic $NH_3$): $CO_2$, 1:9 for 0.2 min, 1:9 to 1:1 in 2.2 min, 1:1 for 1 min, 1:1 to 1:9 in 0.6 min, Flow: 3.4 mL/min; Temperature: 35° C.; back pressure: 2000 psi.

Example 120: Analytical SFC tR=2.23 min. $^1$H NMR (400 MHz, DMSO-d6) δ 11.52 (s, 1H), 8.33-8.29 (m, 1H) 7.33 (dd, J=11.6, 1.8 Hz, 1H), 6.58-6.55 (m, 1H), 6.07 (q, J=6.7 Hz, 1H), 5.54 (s, 2H), 5.17-5.10 (m, 2H), 4.96-4.89 (m, 2H), 3.75-3.40 (m, 2H), 2.05-1.96 (m, 1H), 1.73-1.57 (m, 3H), 1.06-0.99 (m, 2H), 0.90-0.81 (m, 5H). LCMS $(M+H)^+$=410.2.

Example 121: Analytical SFC tR=2.49 min. $^1$H NMR (400 MHz, DMSO-d6) δ 11.52 (s, 1H), 8.33-8.29 (m, 1H) 7.33 (dd, J=11.6, 1.8 Hz, 1H), 6.58-6.55 (m, 1H), 6.07 (q, J=6.7 Hz, 1H), 5.54 (s, 2H), 5.17-5.10 (m, 2H), 4.96-4.89 (m, 2H), 3.75-3.40 (m, 2H), 2.05-1.96 (m, 1H), 1.73-1.57 (m, 3H), 1.06-0.99 (m, 2H), 0.90-0.81 (m, 5H). LCMS $(M+H)^+$=410.2.

Example 122 & Example 123: (S)-5-amino-N-(1-(4-bromo-2,6-difluorophenyl)ethyl)-N-methyl-6,8-dihydro-1H-furo[3,4-d]pyrrolo[3,2-b]pyridine-2-carboxamide & (R)-5-amino-N-(1-(4-bromo-2,6-difluorophenyl)ethyl)-N-methyl-6,8-dihydro-1H-furo[3,4-d]pyrrolo[3,2-b]pyridine-2-carboxamide

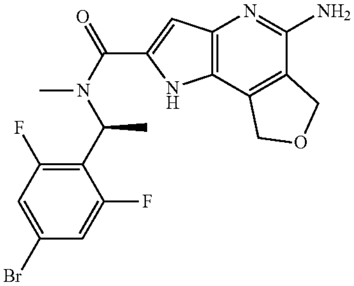

&

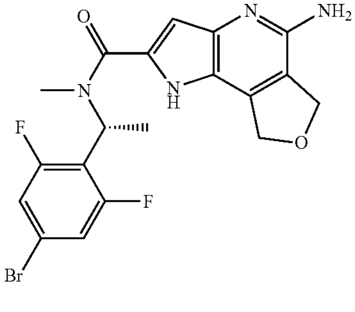

Step 1: tert-butyl (1-(4-bromo-2,6-difluorophenyl)ethyl)carbamate

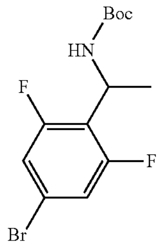 [SMILES: CC(NC(=O)OC(C)(C)C)c1c(F)cc(Br)cc1F]

The title compound (350 mg, 99%) was prepared in a manner similar to that in Example 4 step 2 from 1-(4-bromo-2,6-difluorophenyl)ethan-1-amine. $^1$H NMR (400 MHz, DMSO-d6) δ: 7.50-7.29 (m, 3H), 4.92-4.75 (m, 1H), 1.42-1.29 (m, 12H).

Step 2: tert-butyl (1-(4-bromo-2,6-difluorophenyl) ethyl)(methyl)carbamate

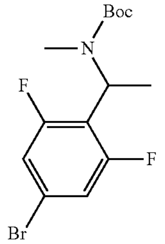 [SMILES: CC(c1c(F)cc(Br)cc1F)N(C)C(=O)OC(C)(C)C]

The title compound (104 mg, 100%) was prepared in a manner similar to that in Example 39 & Example 40 step 7 from tert-butyl (1-(4-bromo-2,6-difluorophenyl)ethyl)carbamate and MeI. LC-MS $(M+H-t-Bu)^+$=294.1.

Step 3: 1-(4-bromo-2,6-difluorophenyl)-N-methyl-ethan-1-amine Hydrochloride

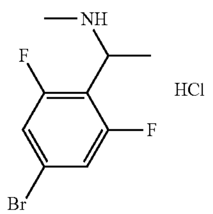

The title compound (95 mg, 100%) was prepared in a manner similar to that in Example 110 & Example 111 step 5 from tert-butyl (1-(4-bromo-2,6-difluorophenyl)ethyl)(methyl)carbamate. LC-MS $(M+H)^+$=250.0.

Step 4: 5-amino-N-(1-(4-bromo-2,6-difluorophenyl) ethyl)-N-methyl-1-((2-(trimethylsilyl)ethoxy) methyl)-6,8-dihydro-1H-furo[3,4-d]pyrrolo[3,2-b] pyridine-2-carboxamide

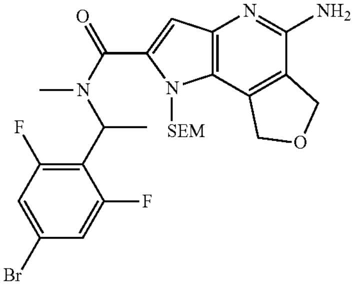 [SMILES: CC(c1c(F)cc(Br)cc1F)N(C)C(=O)c1cc2nc(N)c3c(c2n1COCC[Si](C)(C)C)COC3]

The title compound (150 mg, 87%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and 1-(4-bromo-2,6-difluorophenyl)-N-methylethan-1-amine hydrochloride. LC-MS $(M+H)^+$=581.2.

Step 4: (S)-5-amino-N-(1-(4-bromo-2,6-difluoro-phenyl)ethyl)-N-methyl-6,8-dihydro-1H-furo[3,4-d] pyrrolo[3,2-b]pyridine-2-carboxamide & (R)-5-amino-N-(1-(4-bromo-2,6-difluorophenyl)ethyl)-N-methyl-6,8-dihydro-1H-furo[3,4-d]pyrrolo[3,2-b] pyridine-2-carboxamide Example 122 (24 mg, 13%) and Example 123 (23 mg, 12%) were prepared in a manner similar to that in Example 110 & Example 111 step 7 from 5-amino-N-(1-(4-bromo-2,6-difluorophenyl)ethyl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: Chiralcel OD-3; Column size: 4.6×50 mm, 3 μm; Mobile phase: (isopropanol containing 0.2% 7 M methanolic $NH_3$):$CO_2$, 1:19 for 0.2 min, 1:19 to 1:1 in 1 min, 1:1 for 1 min, 1:1 to 1:19 in 0.4 min, 1:19 for 0.4 min; Flow: 3.4 mL/min; Temperature: 35° C.; back pressure: 1800 psi.

Example 122: Analytical SFC tR=1.48 min. 1H NMR (400 MHz, DMSO-d6) δ 11.51 (s, 1H), 7.55-7.42 (m, 2H), 6.70-6.57 (m, 1H), 6.01-5.86 (m, 1H), 5.56 (s, 2H), 5.20-5.03 (m, 2H), 4.98-4.85 (m, 2H), 3.22-3.00 (m, 3H), 1.64 (d, J=7.2 Hz, 3H). LCMS $(M+H)^+$=451.0.

Example 123: Analytical SFC tR=1.67 min. $^1$H NMR (400 MHz, DMSO-d6) δ 11.52 (s, 1H), 7.55-7.42 (m, 2H), 6.70-6.57 (m, 1H), 6.01-5.86 (m, 1H), 5.58 (s, 2H), 5.20-5.03 (m, 2H), 4.98-4.85 (m, 2H), 3.22-3.00 (m, 3H), 1.64 (d, J=7.2 Hz, 3H). LCMS $(M+H)^+$=451.0.

Example 124 & Example 125: (R)-5-amino-N—((R)-1-(4-bromo-2-fluorophenyl)ethyl)-N-ethyl-6-methyl-6,8-dihydro-1H-furo[3,4-d]pyrrolo[3,2-b]pyridine-2-carboxamide & ((R)-5-amino-N—((S)-1-(4-bromo-2-fluorophenyl)ethyl)-N-ethyl-6-methyl-6,8-dihydro-1H-furo[3,4-d]pyrrolo[3,2-b]pyridine-2-carboxamide

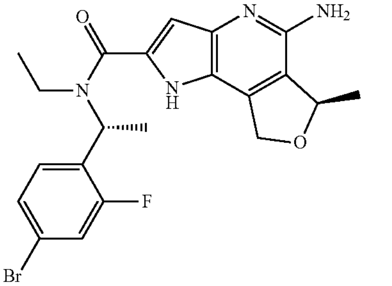

&

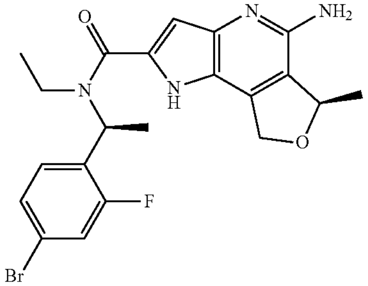

Step 1: 1-(4-bromo-2-fluorophenyl)-N-ethylethan-1-amine

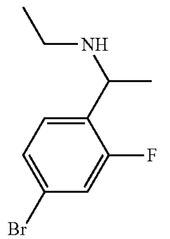

To a solution of 1-(4-bromo-2-fluorophenyl)ethan-1-one (500 mg, 2.31 mmol) in MeOH (10 mL) was added ethylamine in THF (2.0 M, 2.3 mL, 4.62 mmol) and $NaBH_3CN$ (291 mg, 4.62 mmol). The mixture was stirred for 16 h at 60° C. and then cooled to room temperature. The mixture was quenched with saturated $NaHCO_3$ (50 mL) and then extracted with EtOAc (50 mL). The organic layer was washed with brine (50 mL), dried over $Na_2SO_4$, filtered and concentrated under reduced pressure. The residue was purified by silica gel chromatography (DCM:MeOH=20:1) to give the title compound (300 mg, 53%). LC-MS $(M+H)^+$=246.3.

Step 2: (R)-5-amino-N—((R)-1-(4-bromo-2-fluorophenyl)ethyl)-N-ethyl-6-methyl-6,8-dihydro-1H-furo[3,4-d]pyrrolo[3,2-b]pyridine-2-carboxamide & ((R)-5-amino-N—((S)-1-(4-bromo-2-fluorophenyl)ethyl)-N-ethyl-6-methyl-6,8-dihydro-1H-furo[3,4-d]pyrrolo[3,2-b]pyridine-2-carboxamide To a mixture of (R)-5-amino-6-methyl-6,8-dihydro-1H-furo[3,4-d]pyrrolo[3,2-b]pyridine-2-carboxylic acid (40 mg, 0.17 mmol), 1-(4-bromo-2-fluorophenyl)-N-ethylethan-1-amine (42 mg, 0.17 mmol) and DIPEA (155 mg, 1.2 mmol) in anhydrous DMF (3 mL) under nitrogen was added T3P in EtOAc (50%, 546 mg, 0.86 mmol) and the mixture was stirred at 60° C. for 16 h. After cooling to room temperature, 6 M HCl (9 mL) was added and the mixture was stirred for 3 h at 60° C. The mixture was cooled to room temperature and quenched with saturated $NaHCO_3$ (100 mL). The mixture was extracted with EtOAc (100 mL). The organic layer was washed with brine (100 mL), dried over $Na_2SO_4$, filtered and concentrated under vacuum. The residue was purified by prep-HPLC and further separated by SFC to give Example 124 (12 mg, 16%) and Example 125 (12 mg, 16%).

Analytical chiral-SFC condition as below. Column: YMC Cellulose-C; Column size: 4.6×100 mm, 5 μm; Mobile phase: 4 mM methanolic $NH_3$:$CO_2$, 1:9 to 4:6 in 3 min, 4:6 for 2 min, 4:6 to 1:9 in 0.1 min, 1:9 for 1.9 min; Flow: 2.0 mL/min; Temperature: 35° C.; back pressure: 1500 psi.

Example 124: Analytical SFC tR=4.20 min. $^1H$ NMR (400 MHz, DMSO-d6) δ 11.52 (s, 1H), 7.66-7.39 (m, 3H), 6.51 (s, 1H), 5.96-5.81 (m, 1H), 5.44 (s, 2H), 5.32 (s, 1H), 5.21-5.08 (m, 1H), 5.06-4.95 (m, 1H), 3.52-3.34 (m, 2H), 1.75-1.58 (m, 3H), 1.40-1.30 (m, 3H), 0.97-0.85 (m, 3H). LC-MS $(M+H)^+$=461.3.

Example 125: Analytical SFC tR=4.60 min. $^1H$ NMR (400 MHz, DMSO-d6) δ 11.52 (s, 1H), 7.59-7.33 (m, 3H), 6.51 (s, 1H), 5.97-5.79 (m, 1H), 5.44 (s, 2H), 5.32 (s, 1H), 5.19-5.06 (m, 1H), 5.07-4.89 (m, 1H), 3.63-3.32 (m, 2H), 1.73-1.52 (m, 3H), 1.39-1.28 (m, 3H), 0.98-0.87 (m, 3H). LC-MS $(M+H)^+$=461.3.

Example 126 & Example 127: (R)-5-amino-N-ethyl-N—((R)-1-(2-fluoro-4-(trifluoromethyl)phenyl)ethyl)-6-methyl-6,8-dihydro-1H-furo[3,4-d]pyrrolo[3,2-b]pyridine-2-carboxamide & (R)-5-amino-N-ethyl-N—((S)-1-(2-fluoro-4-(trifluoromethyl)phenyl)ethyl)-6-methyl-6,8-dihydro-1H-furo[3,4-d]pyrrolo[3,2-b]pyridine-2-carboxamide

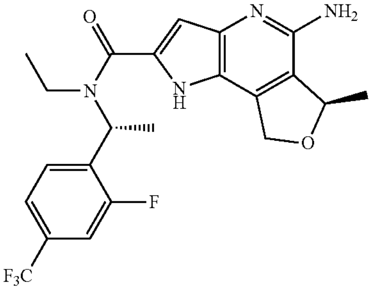

&

-continued

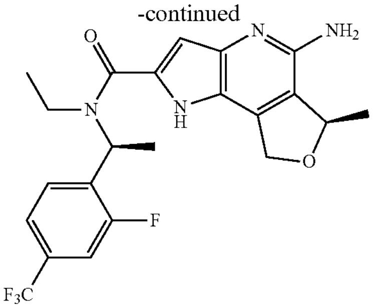

Step 1: N-ethyl-1-(2-fluoro-4-(trifluoromethyl)phenyl)ethan-1-amine

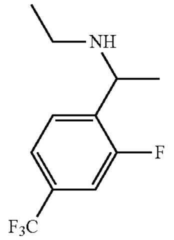 [SMILES: CCNC(C)c1ccc(C(F)(F)F)cc1F]

The title compound (400 mg, 70%) was prepared in a manner similar to that in Example 124 & Example 125 step 1 from 1-(2-fluoro-4-(trifluoromethyl)phenyl)ethan-1-one and ethylamine. LC-MS $(M+H)^+$=236.2.

Step 2: (R)-5-amino-N-ethyl-N—((R)-1-(2-fluoro-4-(trifluoromethyl)phenyl)ethyl)-6-methyl-6,8-dihydro-1H-furo[3,4-d]pyrrolo[3,2-b]pyridine-2-carboxamide & (R)-5-amino-N-ethyl-N—((S)-1-(2-fluoro-4-(trifluoromethyl)phenyl)ethyl)-6-methyl-6,8-dihydro-1H-furo[3,4-d]pyrrolo[3,2-b]pyridine-2-carboxamide Example 126 (6 mg, 7%) and Example 127 (8 mg, 11%) were prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and N-ethyl-1-(2-fluoro-4-(trifluoromethyl)phenyl)ethan-1-amine, and the diastereomers were separated by chiral SFC.

Analytical chiral-SFC condition as below. Column: YMC Cellulose-C; Column size: 4.6×100 mm, 5 μm; Mobile phase: 4 mM methanolic $NH_3$:$CO_2$, 1:9 to 4:6 in 3 min, 4:6 for 2 min, 4:6 to 1:9 in 0.1 min, 1:9 for 1.9 min; Flow: 2.0 mL/min: Temperature: 35° C.; back pressure: 1500 psi.

Example 126: Analytical SFC tR=3.06 min. $^1H$ NMR (400 MHz, DMSO-d6) δ 11.54 (s, 1H), 7.86-7.73 (m, 1H), 7.70-7.53 (m, 2H), 6.52 (s, 1H), 5.96-5.88 (m, 1H), 5.47 (s, 2H), 5.36-5.28 (m, 1H), 5.19-5.07 (m, 1H), 5.06-4.97 (m, 1H), 3.62-3.33 (m, 2H), 1.74-1.60 (m, 3H), 1.37-1.31 (m, 3H), 1.02-0.89 (m, 3H). LCMS $(M+H)^+$=451.3.

Example 127: Analytical SFC tR=3.32 min. H NMR (400 MHz, DMSO-d6) δ 11.53 (s, 1H), 7.89-7.72 (m, 1H), 7.71-7.51 (m, 2H), 6.52 (s, 1H), 5.97-5.87 (m, 1H), 5.45 (s, 2H), 5.35-5.28 (m, 1H), 5.19-5.08 (m, 1H), 5.07-4.89 (m, 1H), 3.59-3.32 (m, 2H), 1.76-1.61 (m, 3H), 1.38-1.27 (m, 3H), 1.02-0.89 (m, 3H). LCMS $(M+H)^+$=451.3.

Example 128 & Example 129: (R)-5-amino-N—((R)-1-(5-bromo-3-fluoropyridin-2-yl)ethyl)-N-ethyl-6-methyl-6,8-dihydro-1H-furo[3,4-d]pyrrolo[3,2-b]pyridine-2-carboxamide & (R)-5-amino-N—((S)-1-(5-bromo-3-fluoropyridin-2-yl)ethyl)-N-ethyl-6-methyl-6,8-dihydro-1H-furo[3,4-d]pyrrolo[3,2-b]pyridine-2-carboxamide

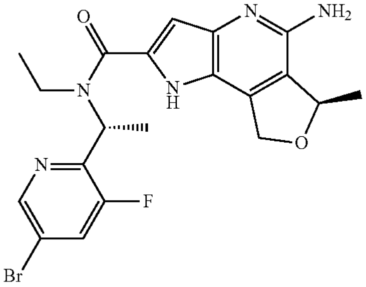

&

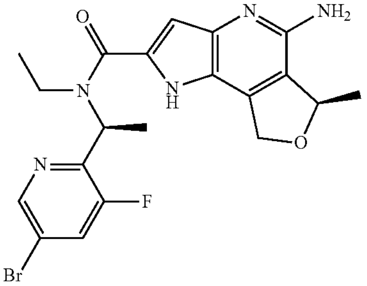

Step 1: 1-(5-bromo-3-fluoropyridin-2-yl)-N-ethylethan-1-amine

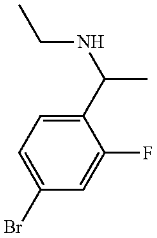

To a solution of 1-(5-bromo-3-fluoropyridin-2-yl)ethan-1-one (3(0) mg, 1.38 mmol) in MeOH (10 mL) was added $EtNH_2$ in THF (2.0 M, 1.37 mL, 2.76 mmol) and $NaBH_3CN$ (174 mg, 2.76 mmol). The mixture was stirred for 16 h at 60° C. The reaction mixture was cooled to room temperature and quenched with saturated $NaHCO_3$ (50 mL). The mixture was extracted with EtOAc (50 mL). The organic laver was washed with brine (50 mL), dried over $Na_2SO_4$, filtered and concentrated under vacuum. The residue was purified by silica gel chromatography (DCM:MeOH=20:1) to give the title compound (150 mg, 44%). LC-MS $(M+H)^+$=247.1.

Step 2: (R)-5-amino-N—((R)-1-(5-bromo-3-fluoro-pyridin-2-yl)ethyl)-N-ethyl-6-methyl-6,8-dihydro-1H-furo[3,4-d]pyrrolo[3,2-b]pyridine-2-carboxamide & (R)-5-amino-N—((S)-1-(5-bromo-3-fluoropyridin-2-yl)ethyl)-N-ethyl-6-methyl-6,8-dihydro-1H-furo[3,4-d]pyrrolo[3,2-b]pyridine-2-carboxamide Example 129 (16 mg, 16%) and Example 130 (19 mg, 19%) were prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and 1-(5-bromo-3-fluoropyridin-2-yl)-N-ethylethan-1-amine, and the diastereomers were separated by chiral SFC.

Analytical chiral-SFC condition as below. Column: Lux Cellulose-4; Column size: 4.6×100 mm, 5 μm; Mobile phase: 4 mM methanolic $NH_3$:$CO_2$, 45:55 for 5 min, 45:55 to 1:1 in 0.1 min, 1:1 for 1.9 min; Flow: 2.0 mL/min; Temperature: 35° C.; back pressure: 1500 psi.

Example 129: Analytical SFC tR=3.83 min. $^1$H NMR (400 MHz, DMSO-d6) δ 11.53 (s, 1H), 8.60 (s, 1H), 8.29-8.05 (m, 1H), 6.55 (s, 1H), 6.04-5.96 (m, 1H), 5.46 (s, 2H), 5.35-5.28 (m, 1H), 5.19-5.10 (m, 1H), 5.08-4.97 (m, 1H), 3.73-3.32 (m, 2H), 1.63 (br s, 3H), 1.41-1.28 (m, 3H), 0.90 (br s, 3H). LCMS $(M+H)^+$=462.3.

Example 130: Analytical SFC tR=4.92 min. $^1$H NMR (400 MHz, DMSO-d6) δ11.54 (s, 1H), 8.61 (s, 1H), 8.24-7.93 (m, 1H), 6.56 (s, 1H), 6.03-5.96 (m, 1H), 5.49 (s, 2H), 5.36-5.28 (m, 1H), 5.17-4.93 (m, 2H), 3.54-3.39 (m, 2H), 1.63 (br s, 3H), 1.37-1.29 (m, 3H), 0.91 (br s, 3H). LCMS $(M+H)^+$=462.2.

Example 130 & Example 131: (R)-5-amino-N-ethyl-N—((R)-1-(3-fluoro-5-(trifluoromethyl)pyridin-2-yl)ethyl)-6-methyl-6,8-dihydro-1H-furo[3,4-d]pyrrolo[3,2-b]pyridine-2-carboxamide & (R)-5-amino-N-ethyl-N—((S)-1-(3-fluoro-5-(trifluoromethyl)pyridin-2-yl)ethyl)-6-methyl-6,8-dihydro-1H-furo[3,4-d]pyrrolo[3,2-b]pyridine-2-carboxamide

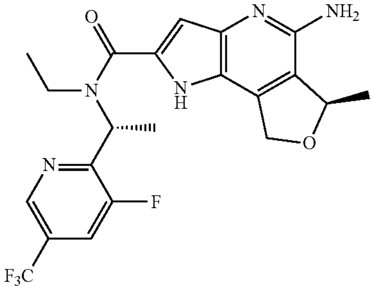

&

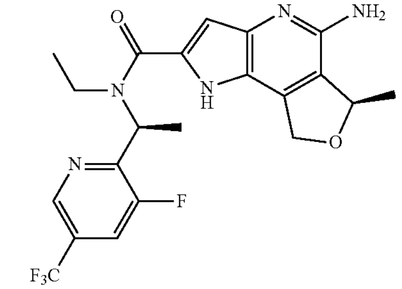

Step 1: N-ethyl-1-(3-fluoro-5-(trifluoromethyl)pyridin-2-yl)ethan-1-amine

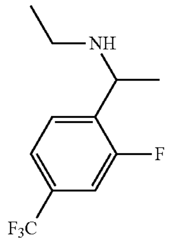 [SMILES: CCNC(C)c1ccc(C(F)(F)F)cc1F]

The title compound (100 mg, 35%) was prepared in a manner similar to that in Example 124 & Example 125 step 1 from 1-(3-fluoro-5-(trifluoromethyl)pyridin-2-yl)ethan-1-one and ethylamine. LC-MS $(M+H)^+$=237.4.

Step 2: (R)-5-amino-N-ethyl-N—((R)-1-(3-fluoro-5-(trifluoromethyl)pyridin-2-yl)ethyl)-6-methyl-6,8-dihydro-1H-furo[3,4-d]pyrrolo[3,2-b]pyridine-2-carboxamide & (R)-5-amino-N-ethyl-N—((S)-1-(3-fluoro-5-(trifluoromethyl)pyridin-2-yl)ethyl)-6-methyl-6,8-dihydro-1H-furo[3,4-d]pyrrolo[3,2-b]pyridine-2-carboxamide Example 130 (17 mg, 18%) and Example 131 (18 mg, 18%) were prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and N-ethyl-1-(3-fluoro-5-(trifluoromethyl)pyridin-2-yl)ethan-1-amine, and the diastereomers were separated by chiral SFC.

Analytical chiral-SFC condition as below. Column: Lux Cellulose-4; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min: Flow: 2.0 mL/min: Temperature: 35° C.; back pressure: 1500 psi.

Example 130: Analytical SFC tR=3.33 min. $^1$H NMR (400 MHz, DMSO-d6) δ 11.60 (s, 1H), 8.87 (s, 1H), 8.36-8.16 (m, 1H), 6.57 (s, 1H), 6.06-5.94 (m, 1H), 5.60 (s, 2H), 5.36-5.28 (m, 1H), 5.21-5.06 (m, 1H), 5.06-4.91 (m, 1H), 3.78-3.32 (m, 2H), 1.75-1.59 (m, 3H), 1.39-1.27 (m, 3H), 1.05-0.92 (m, 3H). LCMS $(M+H)^+$=452.3.

Example 131: Analytical SFC tR=3.64 min. $^1$H NMR (400 MHz, DMSO-d6) δ 11.85 (s, 1H), 8.87 (s, 1H), 8.38-8.22 (m, 1H), 6.61 (s, 1H), 6.31-5.76 (m, 3H), 5.39-5.31 (m, 1H), 5.21-4.94 (m, 2H), 3.75-3.46 (m, 2H), 1.72-1.63 (m, 3H), 1.39-1.25 (m, 3H), 1.09-0.86 (m, 3H). LCMS $(M+H)^+$=452.4.

Example 130 can also be obtained through the next procedures.

Step 1: (R)-5-amino-N-ethyl-N—((R)-1-(3-fluoro-5-(trifluoromethyl)pyridin-2-yl)ethyl)-6-methyl-6,8-dihydro-1H-furo[3,4-d]pyrrolo[3,2-b]pyridine-2-carboxamide Example 130 (60 mg, 57%) was prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and (R)—N-ethyl-1-(3-fluoro-5-(trifluoromethyl)pyridin-2-yl)ethan-1-amine.

Example 132: 5-amino-N-ethyl-N-(1-(3-fluoro-5-morpholinopyridin-2-yl)ethyl)-6,8-dihydro-1H-furo[3,4-d]pyrrolo[3,2-b]pyridine-2-carboxamide

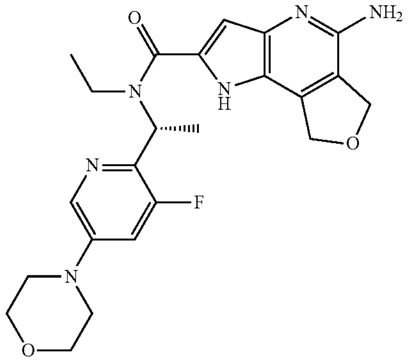 [SMILES: CCN(C(=O)c1cc2nc(N)c3c(c2[nH]1)COC3)[C@H](C)c1ncc(N2CCOCC2)cc1F]

Step 1: N-ethyl-1-(3-fluoro-5-morpholinopyridin-2-yl)ethan-1-amine

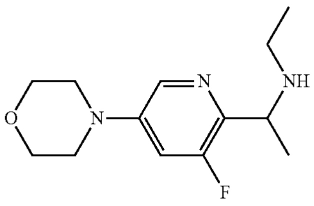 [SMILES: CCNC(C)c1ncc(N2CCOCC2)cc1F]

The title compound (20 mg, 36%) was prepared in a manner similar to that in Example 124 & Example 125 step 1 from 1-(3-fluoro-5-morpholinopyridin-2-yl)ethan-1-one and ethylamine. LC-MS $(M+H)^+$=254.2.

Step 2: 5-amino-N-ethyl-N-(1-(3-fluoro-5-morpholinopyridin-2-yl)ethyl)-1-((2-(trimethylsilyl)ethoxy)methyl)-6,8-dihydro-1H-furo[3,4-d]pyrrolo[3,2-b]pyridine-2-carboxamide

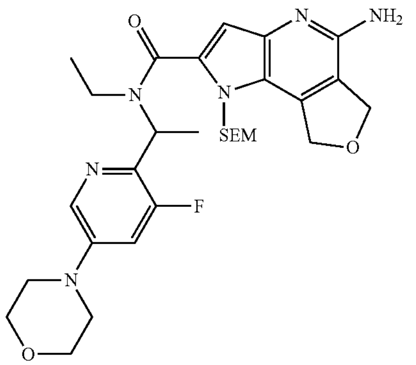 [SMILES: CCN(C(=O)c1cc2nc(N)c3c(c2n1COCC[Si](C)(C)C)COC3)C(C)c1ncc(N2CCOCC2)cc1F]

The title compound (10 mg, 21%) was prepared in a manner similar to that in Example 66 step 2 from 5-amino-1-((2-(trimethylsilyl)ethoxy)methyl)-6,8-dihydro-1H-furo[3,4 -d]pyrrolo[3,2-b]pyridine-2-carboxylic acid and N-ethyl-1-(3-fluoro-5-morpholinopyridin-2-yl)ethan-1-amine. LC-MS $(M+H)^+$=585.4.

Step 3: 5-amino-N-ethyl-N-(1-(3-fluoro-5-morpholinopyridin-2-yl)ethyl)-6,8-dihydro-1H-furo[3,4-d]pyrrolo[3,2-b]pyridine-2-carboxamide Example 132 (3 mg, 38%) was prepared in a manner similar to that in Example 66 step 3 from 5-amino-N-ethyl-N-(1-(3-fluoro-5-morpholinopyridin-2-yl)ethyl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ 11.52 (s, 1H), 7.25-7.22 (m, 1H), 6.55 (s, 1H), 6.03 (s, 1H), 5.54 (s, 2H), 5.12 (s, 2H), 4.91 (s, 2H), 3.71 (s, 4H), 3.20 (s, 4H), 1.61 (s, 3H), 0.83-0.80 (m, 3H). LC-MS $(M+H)^+$=455.4.

Example 133 & Example 134: (R)-5-amino-N-(1-(4-bromo-2-fluorophenyl)ethyl)-N-ethyl-6,8-dihydro-1H-furo[3,4-d]pyrrolo[3,2-b]pyridine-2-carboxamide & (S)-5-amino-N-(1-(4-bromo-2-fluorophenyl)ethyl)-N-ethyl-6,8-dihydro-1H-furo[3,4-d]pyrrolo[3,2-b]pyridine-2-carboxamide

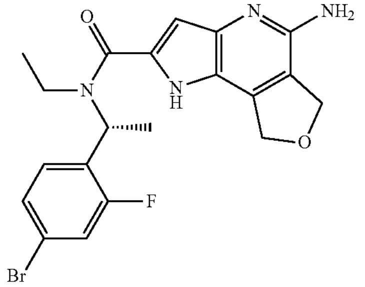

&

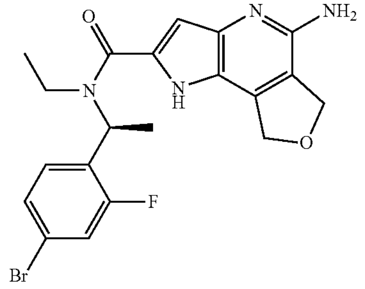

Example 133 (6 mg, 8%) and Example 134 (6 mg, 7%) were prepared in a manner similar to that in Example 124 & Example 125 step 2 from 5-amino-6,8-dihydro-1H-furo[3,4-d]pyrrolo[3,2-b]pyridine-2-carboxylic acid and 1-(5-bromo-3-fluoropyridin-2-yl)-N-ethylethan-1-amine, and the enantiomers were separated by chiral SFC.

Analytical chiral-SFC condition as below. Column: CHIRALPAK AS-H; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 133: Analytical SFC tR=2.74 min. $^1$H NMR (400 MHz, DMSO-d6) δ 11.51 (s, 1H), 7.57-7.32 (m, 3H), 6.52 (s, 1H), 5.98-5.76 (m, 1H), 5.53 (s, 2H), 5.11 (s, 2H), 4.90 (s, 2H), 3.45-3.36 (m, 2H), 1.74-1.52 (m, 3H), 1.00-0.85 (m, 3H). LCMS $(M+H)^+$=447.3.

Example 134: Analytical SFC tR=3.07 min. $^1$H NMR (400 MHz, DMSO-d6) δ 11.51 (s, 1H), 7.57-7.26 (m, 3H), 6.52 (s, 1H), 5.97-5.78 (m, 1H), 5.53 (s, 2H), 5.11 (s, 2H), 4.90 (s, 2H), 3.56-3.31 (m, 2H), 1.74-1.58 (m, 3H), 0.97-0.88 (m, 3H). LCMS $(M+H)^+$=447.3.

Example 135 & Example 136: (R)-5-amino-N-ethyl-N-(1-(2-fluoro-4-(trifluoromethyl)phenyl)ethyl)-6,8-dihydro-1H-furo[3,4-d]pyrrolo[3,2-b]pyridine-2-carboxamide & (S)-5-amino-N-ethyl-N-(1-(2-fluoro-4-(trifluoromethyl)phenyl)ethyl)-6,8-dihydro-1H-furo[3,4-d]pyrrolo[3,2-b]pyridine-2-carboxamide

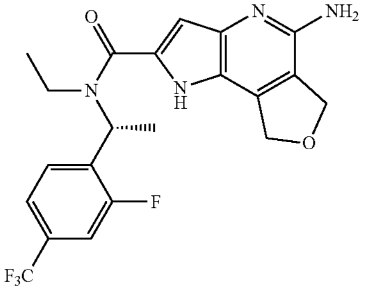

&

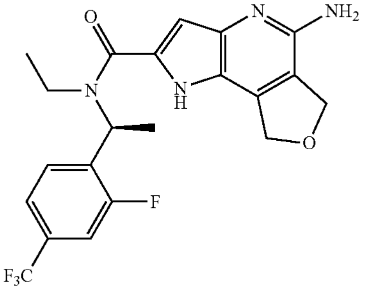

Example 135 (13 mg, 17%) and Example 136 (11 mg, 14%) were prepared in a manner similar to that in Example 124 & Example 125 step 2 from 5-amino-6,8-dihydro-1H-furo[3,4-d]pyrrolo[3,2-b]pyridine-2-carboxylic acid and 1-(4-bromo-2-fluorophenyl)-N-ethylethan-1-amine, and the enantiomers were separated by chiral SFC.

Analytical chiral-SFC condition as below. Column: CHIRALPAK AS-H; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 135: Analytical SFC tR=1.96 min. $^1$H NMR (400 MHz, DMSO-d6) δ 11.53 (s, 1H), 7.83-7.71 (m, 1H), 7.71-7.56 (m, 2H), 6.54 (s, 1H), 5.96-5.88 (m, 1H), 5.55 (s, 2H), 5.11 (s, 2H), 4.90 (s, 2H), 3.57-3.42 (m, 2H), 1.76-1.59 (m, 3H), 1.02-0.91 (m, 3H). LCMS $(M+H)^+$=437.3.

Example 136: Analytical SFC tR=2.21 min. $^1$H NMR (400 MHz, DMSO-d6) δ 11.56 (s, 1H), 7.86-7.75 (m, 1H), 7.70-7.49 (m, 2H), 6.54 (s, 1H), 5.97-5.88 (m, 1H), 5.59 (s, 2H), 5.11 (s, 2H), 4.90 (s, 2H), 3.55-3.41 (m, 2H), 1.78-1.59 (m, 3H), 0.99-0.91 (m, 3H). LCMS $(M+H)^+$=437.3.

Example 137 & Example 138: (R)-5-amino-N-(1-(4-bromo-2-fluorophenyl)ethyl)-N-methyl-6,8-dihydro-1H-furo[3,4-d]pyrrolo[3,2-b]pyridine-2-carboxamide & (S)-5-amino-N-(1-(4-bromo-2-fluorophenyl)ethyl)-N-methyl-6,8-dihydro-1H-furo[3,4-d]pyrrolo[3,2-b]pyridine-2-carboxamide

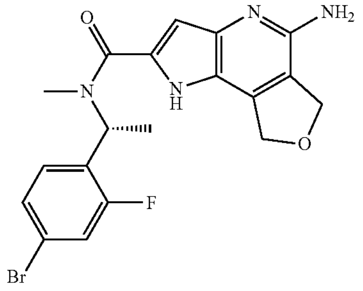

&

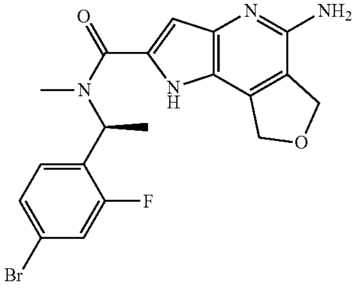

Step 1: 1-(4-bromo-2-fluorophenyl)-N-methylethan-1-amine

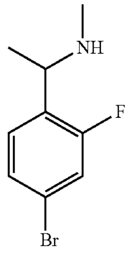

To a solution of 1-(4-bromo-2-fluorophenyl)ethan-1-one (4.32 g, 20.0 mmol), $MeNH_2$ in THF (2.0 M, 20 mL, 40.0 mmol) in DCM (80 mL) was added $NaH(OAc)_3$ (8.44 g, 40.0 mmol) in portions. The mixture was stirred at room temperature for 48 h and then quenched with saturated $NaHCO_3$ (200 mL). The mixture was extracted with DCM (3×50 mL). The combined organic layer was dried with $Na_2SO_4$, filtered and concentrated under reduced pressure. The residue was purified by silica gel chromatography (DCM:MeOH=30:1) to give the title compound (820 mg, 18%). LC-MS $(M+H)^+$=232.1.

Step 2: 5-amino-N-(1-(4-bromo-2-fluorophenyl)ethyl)-N-methyl-1-((2-(trimethylsilyl)ethoxy)methyl)-6,8-dihydro-1H-furo[3,4-d]pyrrolo[3,2-b]pyridine-2-carboxamide

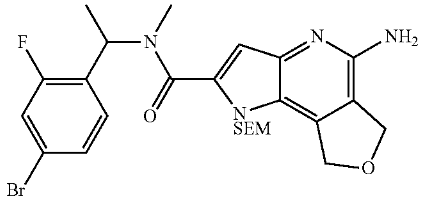 [SMILES: CC(c1ccc(Br)cc1F)N(C)C(=O)c1cc2nc(N)c3c(c2n1COCC[Si](C)(C)C)COC3]

The title compound (170 mg, 76%) was prepared in a manner similar to that in Example 110 & Example 111 step 6 from 5-amino-1-((2-(trimethylsilyl)ethoxy)methyl)-6,8-dihydro-1H-furo[3,4-d]pyrrolo[3,2-b]pyridine-2-carboxylic acid and 1-(4-bromo-2-fluorophenyl)-N-methylethan-1-amine. LC-MS $(M+H)^+$=563.4.

Step 3: (R)-5-amino-N-(1-(4-bromo-2-fluorophenyl)ethyl)-N-methyl-6,8-dihydro-1H-furo[3,4-d]pyrrolo[3,2-b]pyridine-2-carboxamide & (S)-5-amino-N-(0-(4-bromo-2-fluorophenyl)ethyl)-N-methyl-6,8-dihydro-1H-furo[3,4-d]pyrrolo[3,2-b]pyridine-2-carboxamide Example 137 (43 mg, 33%) and Example 138 (44 mg, 34%) were prepared in a manner similar to that in Example 110 & Example 111 step 7 from 5-amino-N-(1-(4-bromo-2-fluorophenyl)ethyl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: CHIRALPAK AS-H; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min: Temperature: 35° C.; back pressure: 1500 psi.

Example 137: Analytical SFC tR=2.88 min. $^1$H NMR (400 MHz, DMSO-d6) δ 11.50 (s, 1H), 7.63-7.37 (m, 3H), 6.57 (s, 1H), 6.01-5.87 (m, 1H), 5.54 (s, 2H), 5.12 (s, 2H), 4.90 (s, 2H), 2.92 (s, 3H), 1.57 (d, J=5.2 Hz, 3H). LCMS $(M+H)^+$=433.3.

Example 138: Analytical SFC tR=3.17 min. $^1$H NMR (400 MHz, DMSO-d6) δ 11.50 (s, 1H), 7.70-7.33 (m, 3H), 6.57 (s, 1H), 6.03-5.89 (m, 1H), 5.54 (s, 2H), 5.12 (s, 2H), 4.90 (s, 2H), 2.92 (s, 3H), 1.57 (d, J=5.2 Hz, 3H). LCMS $(M+H)^+$=433.3.

Example 139 & Example 140: (R)-5-amino-N—((R)-1-(4-bromo-2-fluorophenyl)ethyl)-N,6-dimethyl-6,8-dihydro-1H-furo[3,4-d]pyrrolo[3,2-b]pyridine-2-carboxamide & (R)-5-amino-N—((S)-1-(4-bromo-2-fluorophenyl)ethyl)-N,6-dimethyl-6,8-dihydro-1H-furo[3,4-d]pyrrolo[3,2-b]pyridine-2-carboxamide

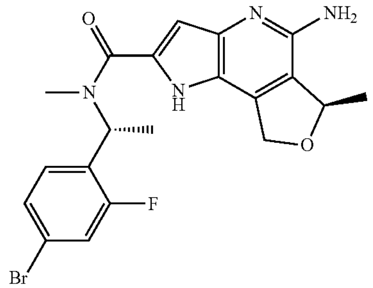

&

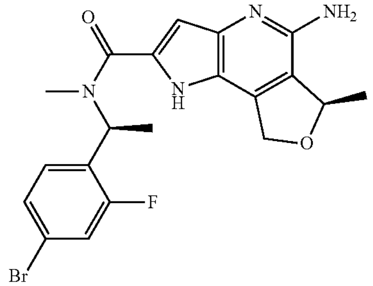

To a mixture of (R)-5-amino-6-methyl-6,8-dihydro-1H-furo[3,4-d]pyrrolo[3,2-b]pyridine-2-carboxylic acid (117 mg, 0.50 mmol), 1-(4-bromo-2-fluorophenyl)-N-methylethan-1-amine (116 mg, 0.50 mmol) and DIPEA (516 mg, 4.0 mmol) in anhydrous DMF (6 mL) under nitrogen was added T3P in DMF (50%, 1.59 g, 2.5 mmol) and the mixture was stirred at 60° C. for 2 h. After cooling to room temperature, HCl in MeOH (4.0 M, 6 mL) was added and the mixture was stirred for 6 h at 60° C. The mixture was cooled to room temperature and quenched with saturated $NaHCO_3$ (100 mL). The mixture was extracted with EtOAc (4×50 mL). The combined organic layer was washed with brine (100 mL), dried over $Na_2SO_4$, filtered and concentrated under vacuum. The residue was purified by silica gel chromatography (DCM:MeOH=15:1) and further separated by SFC to give Example 139 (35 mg, 16%) and Example 140 (36 mg, 16%).

Analytical chiral-SFC condition as below. Column: CHIRALPAK AS-H; Column size: 4.6×100 mm, 5 μm; Mobile phase: 4 mM methanolic $NH_4$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 139: Analytical SFC tR=2.71 min. $^1$H NMR (400 MHz, DMSO-d6) δ 11.53 (s, 1H), 7.54 (d, J=10.1 Hz, 1H), 7.50-7.41 (m, 2H), 6.70-6.46 (m, 1H), 6.02-5.86 (m, 1H), 5.60-5.39 (m, 2H), 5.38-5.27 (m, 1H), 5.14 (dd. J=14.0, 3.2 Hz, 1H), 5.02 (d, J=13.9 Hz, 1H), 3.16-2.71 (m, 3H), 1.57 (d, J=5.0 Hz, 3H), 1.34 (d, J=6.1 Hz, 3H). LCMS $(M+H)^+$=447.3.

Example 140: Analytical SFC tR=2.93 min. $^1$H NMR (400 MHz, DMSO-d6) δ 11.50 (s, 1H), 7.53 (d, J=9.8 Hz, 1H), 7.49-7.38 (m, 2H), 6.56 (s, 1H), 5.94 (q, J=6.7 Hz, 1H), 5.45 (s, 2H), 5.37-5.26 (m, 1H), 5.13 (dd, J=13.9, 3.3 Hz, 1H), 5.03 (d, J=14.0 Hz, 1H), 3.14-2.62 (m, 3H), 1.57 (d, J=5.0 Hz, 3H), 1.34 (d, J=6.1 Hz, 3H). LCMS $(M+H)^+$= 447.3.

Example 141: (S)-(5-amino-6,8-dihydro-1H-furo[3,4-d]pyrrolo[3,2-b]pyridin-2-yl)(3-(4-(trifluoromethyl)phenyl)morpholino)methanone

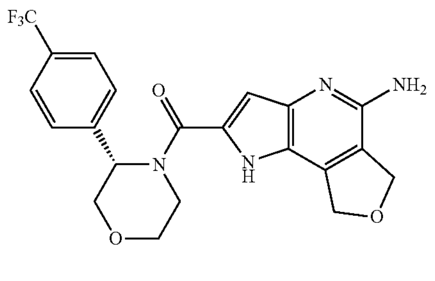 [SMILES: Nc1nc2cc(C(=O)N3CCOC[C@@H]3c3ccc(C(F)(F)F)cc3)[nH]c2c2c1COC2]

Step 1: (S)-(5-amino-1-((2-(trimethylsilyl)ethoxy)methyl)-6,8-dihydro-1H-furo[3,4-d]pyrrolo[3,2-b]pyridin-2-yl)(3-(4-(trifluoromethyl)phenyl)morpholino)methanone

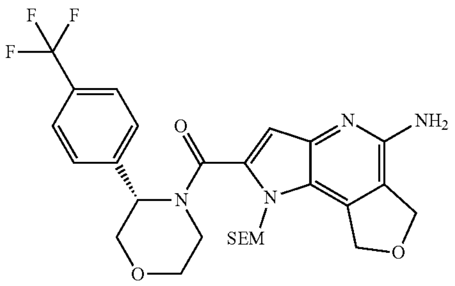 [SMILES: C[Si](C)(C)CCOCn1c(C(=O)N2CCOC[C@@H]2c2ccc(C(F)(F)F)cc2)cc2nc(N)c3c(c21)COC3]

To a mixture of 5-amino-1-((2-(trimethylsilyl)ethoxy)methyl)-6,8-dihydro-1H-furo[3,4-d]pyrrolo[3,2-b]pyridine-2-carboxylic acid (151 mg, 0.43 mmol) and DIPEA (0.23 ml, 1.29 mmol) in THF (10 mL) was added BOPCl (164 mg, 0.65 mmol) and (S)-3-(4-(trifluoromethyl)phenyl)morpholine (100 mg, 0.43 mmol). The mixture was stirred at 60° C. for 2 h and then cooled to room temperature. The mixture was diluted with water (10 mL) and then extracted with EtOAc (50 mL). The organic layer was washed with brine (10 mL), dried over $Na_2SO_4$, filtered and concentrated under reduced pressure. The residue was purified by prep-TLC to give the title compound (100 mg, 41%). LC-MS $(M+H)^+$= 563.3.

Step 2: (S)-(5-amino-6,8-dihydro-1H-furo[3,4-d]pyrrolo[3,2-b]pyridin-2-yl)(3-(4-(trifluoromethyl)phenyl)morpholino)methanone To (S)-(5-amino-1-((2-(trimethylsilyl)ethoxy)methyl)-6,8-dihydro-1H-furo[3,4-d]pyrrolo[3,2-b]pyridin-2-yl)(3-(4-(trifluoromethyl)phenyl)morpholino)methanone (100 mg, 0.18 mmol) was added TFA (2 mL), and the mixture was stirred at room temperature for 0.5 h. The mixture was concentrated under reduced pressure, and the residue was re-dissolved in THF (4 mL), and then strong ammonia solution (28%, 1 mL) was added. The mixture was stirred at room temperature for 2 h and concentrated under reduced pressure. The residue was purified by prep-HPLC to give Example 141 (30 mg, 39%). $^1H$ NMR (400 MHz, DMSO-d6) δ 12.16 (s, 1H), 7.77-7.75 (m, 2H), 7.65-7.63 (m, 2H), 6.65 (s, 2H), 5.66 (s, 1H), 5.17 (s, 2H), 4.92 (s, 2H), 4.48 (s, 1H), 4.25 (s, 1H), 3.83-3.85 (m, 2H), 3.56-3.54 (m, 1H). LC-MS $(M+H)^+$=433.4.

Example 142: (R)-5-amino-N—((R)-1-(5-cyclopropyl-3-fluoropyridin-2-yl)ethyl)-N,6-dimethyl-6,8-dihydro-1H-furo[3,4-d]pyrrolo[3,2-b]pyridine-2-carboxamide

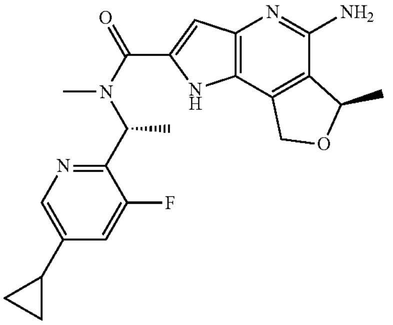 [SMILES: C[C@H](c1ncc(C2CC2)cc1F)N(C)C(=O)c1cc2nc(N)c3c(c2[nH]1)CO[C@@H]3C]

Step 1: 1-(5-cyclopropyl-3-fluoropyridin-2-yl)ethan-1-one

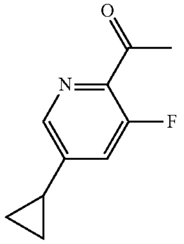

To a solution of 1-(5-bromo-3-fluoropyridin-2-yl)ethan-1-one (5.0 g, 22.9 mmol) in dioxane (100 mL) and water (20 mL) was added cyclopropylboronic acid (2.% g, 34.4 mmol), $K_2CO_3$ (6.32 g, 45.8 mmol) and $Pd(dppf)Cl_2$ (1.68 g, 2.29 mmol). The mixture was stirred for 16 h at 100° C. under nitrogen and then cooled to room temperature. The mixture was diluted with water (150 mL) and then extracted with EtOAc (150 mL). The organic layer was washed with brine (2×150 mL), dried over $Na_2SO_4$, filtered and concentrated under reduced pressure. The residue was purified by silica gel chromatography (PE:EtOAc=10:1) to give the title compound (1.0 g, 24%). LC-MS $(M+H)^+$=180.3.

Step 2: (S)-1-(5-cyclopropyl-3-fluoropyridin-2-yl) ethan-1-ol

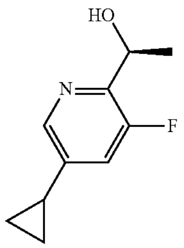

To a solution of 1-(5-cyclopropyl-3-fluoropyridin-2-yl) ethan-1-one (440 mg, 2.46 mmol) in formic acid-$Et_3N$ complex (5:2, 10 mL) was added [(S,S)—N-(2-amino-1,2-diphenylethyl)-p-toluenesulfonamidelchloro(p-cymene)ruthenium(II) (78 mg, 0.12 mmol) at −18° C. under hydrogen. The mixture was stirred at 0° C. for 2 h and at room temperature for 12 h. The mixture was diluted with saturated $NaHCO_3$ (150 mL) and extracted with EtOAc (150 mL). The organic layer was washed with brine (150 mL), dried over $Na_2SO_4$, filtered and concentrated under reduced pressure. The residue was purified by silica gel chromatography (PE:EtOAc=10:1) to give the title compound (382 mg, 86%). LC-MS $(M+H)^+$=182.1.

Step 3: (R)—N-(1-(5-cyclopropyl-3-fluoropyridin-2-yl)ethyl)-N-methyl-2-nitrobenzenesulfonamide

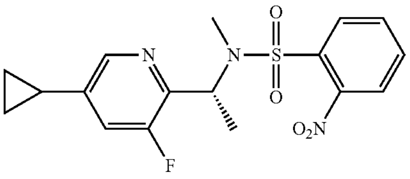 [SMILES: C[C@H](c1ncc(C2CC2)cc1F)N(C)S(=O)(=O)c1ccccc1[N+](=O)[O-]]

To a mixture of (S)-1-(5-cyclopropyl-3-fluoropyridin-2-yl)ethan-1-ol (350 mg, 1.92 mmol), N-methyl-2-nitro-benzenesulfonamide (415 mg, 1.92 mmol) and $PPh_3$ (604 mg, 2.30 mmol) in THF (15 mL) was added DtBAD (529 mg, 2.30 mmol) in portions at 0° C. under nitrogen. The mixture was stirred at room temperature for 3 h. The mixture was diluted water (100 mL) and then extracted with EtOAc (100 mL). The organic layer was washed with brine (100 mL), dried over $Na_2SO_4$, filtered and concentrated under reduced pressure. The residue was purified by silica gel chromatography (PE:EtOAc=3:1) to give the title compound (720 mg, 100%). LC-MS $(M+H)^+$=380.4.

Step 4: (R)-1-(5-cyclopropyl-3-fluoropyridin-2-yl)-N-methylethan-1-amine

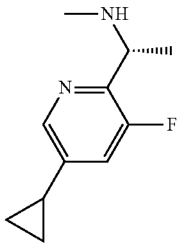

To a mixture of (R)—N-(1-(5-cyclopropyl-3-fluoropyridin-2-yl)ethyl)-N-methyl-2-nitrobenzenesulfonamide (720 mg, 1.92 mmol), dodecane-1-thiol (1.23 g, 6.09 mmol) in DMF (2 mL) and THF (20 mL) was added $LiOH{\cdot}H_2O$ (256 mg, 6.09 mmol), and the mixture was stirred at room temperature for 16 h. Volatiles were removed under reduced pressure and the residue was partitioned between water (50 mL) and EtOAc (50 mL). The organic layer was separated, dried with $Na_2SO_4$, filtered and concentrated under reduced pressure. The residue was purified by silica gel chromatography (PE/EtOAc=1/1 to DCM:MeOH=10:1) to give the title compound (300 mg, 81%). LC-MS $(M+H)^+$=195.1.

Step 5: (R)-5-amino-N—((R)-1-(5-cyclopropyl-3-fluoropyridin-2-yl)ethyl)-N,6-dimethyl-6,8-dihydro-1H-furo[3,4-d]pyrrolo[3,2-b]pyridine-2-carboxamide To a mixture of (R)-5-amino-6-methyl-6,8-dihydro-1H-furo[3,4-d]pyrrolo[3,2-b]pyridine-2-carboxylic acid (50 mg, 0.21 mmol), (R)-1-(5-cyclopropyl-3-fluoropyridin-2-yl)-N-methylethan-1-amine (42 mg, 0.21 mmol) and DIPEA (194 mg, 1.5 mmol) in anhydrous DMF (3 mL) under nitrogen was added T3P in EtOAc (50%, 682 mg, 1.07 mmol) and the mixture was stirred at 60° C. for 16 h. After cooling to room temperature, 6 M HCl (9 mL) was added and the mixture was stirred for 3 h at 60° C. The mixture was cooled to room temperature and quenched with saturated $NaHCO_3$ (100 mL). The mixture was extracted with EtOAc (100 mL). The organic layer was washed with brine (100 mL), dried over $Na_2SO_4$, filtered and concentrated under reduced pressure. The residue was purified by prep-HPLC and SFC to give Example 142 (23 mg, 27%). $^1H$ NMR (400 MHz, DMSO-d6) δ 11.51 (s, 1H), 8.29 (s, 1H), 7.33 (d, J=11.5 Hz, 1H), 6.79-6.43 (m, 1H), 6.20-5.93 (m, 1H), 5.56-5.40 (m, 2H), 5.38-5.26 (m, 1H), 5.13 (dd, J=14.0, 2.9 Hz, 1H), 5.02 (d, J=13.6 Hz, 1H), 3.21-2.61 (m, 3H), 2.05-1.91 (m, 1H), 1.72-1.40 (m, 3H), 1.34 (d, J=6.1 Hz, 3H), 1.10-0.90 (m, 2H), 0.83-0.67 (m, 2H). LC-MS $(M+H)^+$=410.4.

Example 143 & Example 144: (R)-5-amino-N-(1-(5-bromo-3-fluoropyridin-2-yl)ethyl)-N-ethyl-6,8-dihydro-1H-furo[3,4-d]pyrrolo[3,2-b]pyridine-2-carboxamide & (S)-5-amino-N-(1-(5-bromo-3-fluoropyridin-2-yl)ethyl)-N-ethyl-6,8-dihydro-1H-furo[3,4-d]pyrrolo[3,2-b]pyridine-2-carboxamide

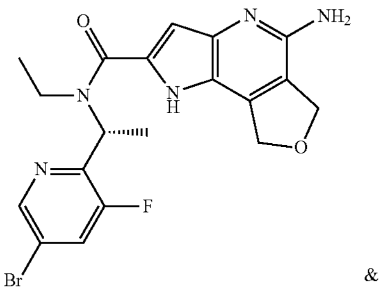

&

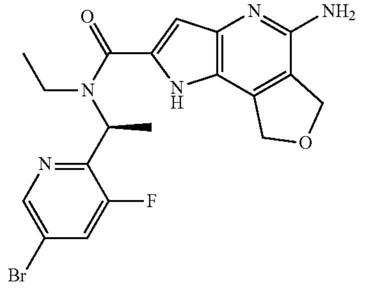

Step 1: 5-amino-N-(1-(5-bromo-3-fluoropyridin-2-yl)ethyl)-N-ethyl-1-((2-(trimethylsilyl)ethoxy)methyl)-6,8-dihydro-H-furo[3,4-d]pyrrolo[3,2-b]pyridine-2-carboxamide

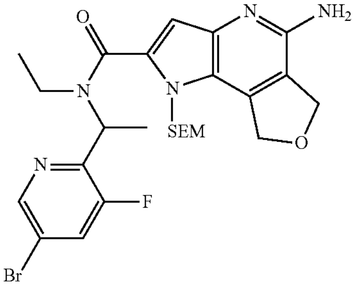 [SMILES: CCN(C(=O)c1cc2nc(N)c3c(c2n1COCC[Si](C)(C)C)COC3)C(C)c1ncc(Br)cc1F]

The title compound (2.0 g, 43%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and 1-(5-bromo-3-fluoropyridin-2-yl)-N-ethylethan-1-amine. LC-MS $(M+H)^+$=578.3.

Step 2: (R)-5-amino-N-(1-(5-bromo-3-fluoropyridin-2-yl)ethyl)-N-ethyl-6,8-dihydro-1H-furo[3,4-d]pyrrolo[3,2-b]pyridine-2-carboxamide & (S)-5-amino-N-(1-(5-bromo-3-fluoropyridin-2-yl)ethyl)-N-ethyl-6,8-dihydro-1H-furo[3,4-d]pyrrolo[3,2-b]pyridine-2-carboxamide Example 143 (78 mg, 5%) and Example 144 (91 mg, 6%) were prepared in a manner similar to that in Example 110 & Example 111 step 7 from 5-amino-N-(1-(5-bromo-3-fluoropyridin-2-yl)ethyl)-N-ethyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: Chiralcel OZ-3; Column size: 4.6×50 mm, 3 μm; Mobile phase: 14 mM $NH_3$ in MeOH:$CO_2$, 1:19 for 0.2 min, 1:19 to 1:1 in 1 min, 1:1 for 1 min, 1:1 to 1:19 in 0.4 min, 1:19 for 0.4 min; Flow: 3.4 mL/min; Temperature: 35° C.; back pressure: 1800 psi.

Example 143: Analytical SFC tR=1.89 min. $^1H$ NMR (400 MHz, DMSO-d6) δ 11.53 (s, 1H), 8.75-8.69 (m, 1H), 8.17 (dd. J=9.6, 2.0 Hz, 1H), 6.64-6.55 (m, 1H), 6.12-5.96 (m, 1H), 5.54 (s, 2H), 5.18-5.08 (m, 2H), 4.99-4.88 (m, 2H), 3.70-3.36 (m, 2H), 1.65 (d, J=6.0 Hz, 3H), 1.00-0.97 (m, 3H). LCMS $(M+H)^+$=448.1.

Example 144: Analytical SFC tR=2.10 min. $^1H$ NMR (400 MHz, DMSO-d6) δ 11.54 (s, 1H), 8.75-8.69 (m, 1H), 8.17 (dd, J=9.6, 2.0 Hz, 1H), 6.64-6.55 (m, 1H), 6.12-5.96 (m, 1H), 5.57 (s, 2H), 5.18-5.08 (m, 2H), 4.99-4.88 (m, 2H), 3.70-3.36 (m, 2H), 1.65 (d, J=6.0 Hz, 3H), 1.00-0.97 (m, 3H). LCMS $(M+H)^+$=448.1.

Example 145 & Example 146: (R)-5-amino-N-(1-(2-fluoro-4-(trifluoromethyl)phenyl)ethyl)-N-methyl-6,8-dihydro-1H-furo[3,4-d]pyrrolo[3,2-b]pyridine-2-carboxamide & (S)-5-amino-N-(1-(2-fluoro-4-(trifluoromethyl)phenyl)ethyl)-N-methyl-6,8-dihydro-1H-furo[3,4-d]pyrrolo[3,2-b]pyridine-2-carboxamide

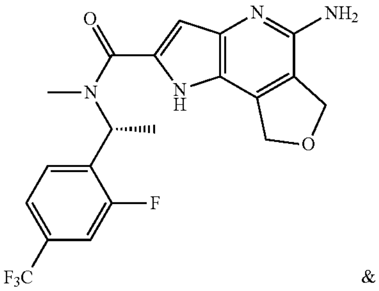

&

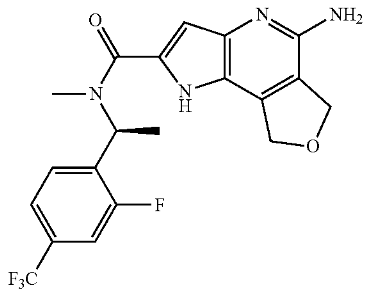

Step 1: 1-(2-fluoro-4-(trifluoromethyl)phenyl)-N-methylethan-1-amine

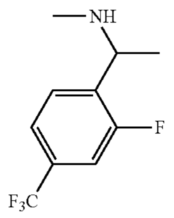

The title compound (420 mg, 16%) was prepared in a manner similar to that in Example 137 & Example 138 step 1 from 1-(2-fluoro-4-(trifluoromethyl)phenyl)ethan-1-one and $MeNH_2$. LC-MS $(M+H)^+$=222.1

Step 2: 5-amino-N-(1-(2-fluoro-4-(trifluoromethyl)phenyl)ethyl)-N-methyl-1-((2-(trimethylsilyl)ethoxy)methyl)-6,8-dihydro-1H-furo[3,4-d]pyrrolo[3,2-b]pyridine-2-carboxamide

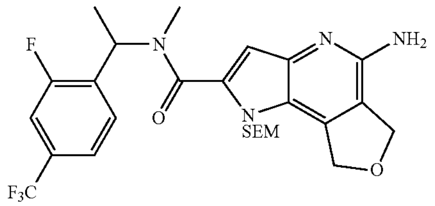 [SMILES: CC(c1ccc(C(F)(F)F)cc1F)N(C)C(=O)c1cc2nc(N)c3c(c2n1COCC[Si](C)(C)C)COC3]

The title compound (173 mg, 78%) was prepared in a manner similar to that in Example 110 & Example 111 step 6 from 5-amino-1-((2-(trimethylsilyl)ethoxy)methyl)-6,8-dihydro-1H-furo[ 3,4-d]pyrrolo[3,2-b]pyridine-2-carboxylic acid and 1-(2-fluoro-4-(trifluoromethyl)phenyl)-N-methylethan-1-amine. LC-MS $(M+H)^+$=553.2.

Step 3: (R)-5-amino-N-(1-(2-fluoro-4-(trifluoromethyl)phenyl)ethyl)-N-methyl-6,8-dihydro-1H-furo[3,4-d]pyrrolo[3,2-b]pyridine-2-carboxamide & (S)-5-amino-N-(1-(2-fluoro-4-(trifluoromethyl)phenyl)ethyl)-N-methyl-6,8-dihydro-1H-furo[3,4-d]pyrrolo[3,2-b]pyridine-2-carboxamide Example 145 (48 mg, 37%) and Example 146 (49 mg, 37%) were prepared in a manner similar to that in Example 110 & Example 111 step 7 from 5-amino-N-(1-(2-fluoro-4-(trifluoromethyl)phenyl)ethyl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: CHIRALPAK AS-H; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 145: Analytical SFC tR=2.02 min. $^1H$ NMR (400 MHz, DMSO-d6) δ 11.56 (s, 1H), 7.83-7.51 (m, 3H), 6.69-6.45 (m, 1H), 6.13-5.86 (m, 1H), 5.63 (s, 2H), 5.12 (s, 2H), 4.91 (s, 2H), 3.14-2.62 (m, 3H), 1.81-1.45 (m, 3H). LCMS $(M+H)^+$=423.4.

Example 146: Analytical SFC tR=2.24 min. $^1H$ NMR (400 MHz, DMSO-d6) δ 11.56 (s, 1H), 7.83-7.51 (m, 3H), 6.69-6.45 (m, 1H), 6.13-5.86 (m, 1H), 5.63 (s, 2H), 5.12 (s, 2H), 4.91 (s, 2H), 3.14-2.62 (m, 3H), 1.81-1.45 (m, 3H). LCMS $(M+H)^+$=423.4.

Example 145 can also be obtained through the next procedures:

Step 1: (R)—N-(1-(3-fluoro-5-(trifluoromethyl)pyridin-2-yl)ethyl)-N-methyl-2-nitrobenzenesulfonamide

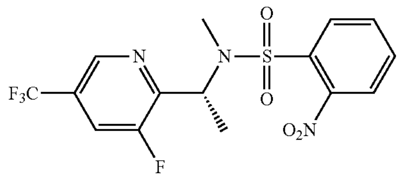 [SMILES: C[C@H](c1ncc(C(F)(F)F)cc1F)N(C)S(=O)(=O)c1ccccc1[N+](=O)[O-]]

The title compound (730 mg, 99%) was prepared in a manner similar to that in Example 110 & Example 111 step 9 from (S)-1-(3-fluoro-5-(trifluoromethyl)pyridine-2-yl)ethan-1-ol and N-methyl-2-nitro-benzenesulfonamide. LC-MS $(M+H)^+$=408.1.

Step 2: (R)-1-(3-fluoro-5-(trifluoromethyl)pyridin-2-yl)-N-methylethan-1-amine

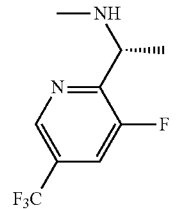

The title compound (250 mg, 63%) was prepared in a manner similar to that in Example 110 & Example 111 step 10 from (R)—N-(1-(3-fluoro-5-(trifluoromethyl)pyridin-2-yl)ethyl)-N-methyl-2-nitrobenzenesulfonamide. LC-MS $(M+H)^+$=223.1.

Step 3: (R)-5-amino-N-(1-(3-fluoro-5-(trifluoromethyl)pyridin-2-yl)ethyl)-N-methyl-1-((2-(trimethylsilyl)ethoxy)methyl)-6,8-dihydro-1H-furo[3,4-d]pyrrolo[3,2-b]pyridine-2-carboxamide

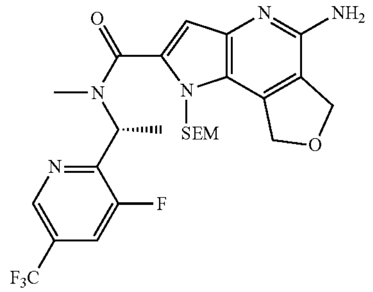 [SMILES: C[C@H](c1ncc(C(F)(F)F)cc1F)N(C)C(=O)c1cc2nc(N)c3c(c2n1COCC[Si](C)(C)C)COC3]

The title compound (90 mg, 52%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and (R)-1-(3-fluoro-5-(trifluoromethyl)pyridin-2-yl)-N-methylethan-1-amine. LC-MS $(M+H)^+$=554.3.

Step 4: (R)-5-amino-N-(1-(2-fluoro-4-(trifluoromethyl)phenyl)ethyl)-N-methyl-6,8-dihydro-1H-furo[3,4-d]pyrrolo[3,2-b]pyridine-2-carboxamide Example 145 (33 mg, 48%) was prepared in a manner similar to that in Example 110 & Example 111 step 7 from (R)-5-amino-N-(l-(3-fluoro-5-(trifluoromethyl)pyridin-2-yl)ethyl)-N-methyl-1-((2-(trimethylsilyl)ethoxy)methyl)-6,8-dihydro-1H-furo[3,4-d]pyrrolo[3,2-b]pyridine-2-carboxamide.

Example 147 & Example 148: (R)-5-amino-N—((S)-1-(2-fluoro-4-(trifluoromethyl)phenyl)ethyl)-N,6-dimethyl-6,8-dihydro-1H-furo[3,4-d]pyrrolo[3,2-b]pyridine-2-carboxamide & (R)-5-amino-N—((R)-1-(2-fluoro-4-(trifluoromethyl)phenyl)ethyl)-N,6-dimethyl-6,8-dihydro-1H-furo[3,4-d]pyrrolo[3,2-b]pyridine-2-carboxamide

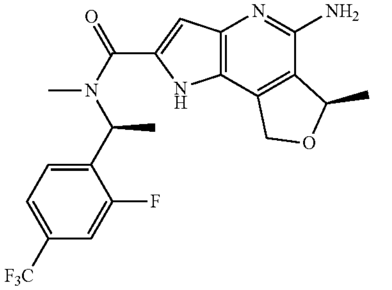

&

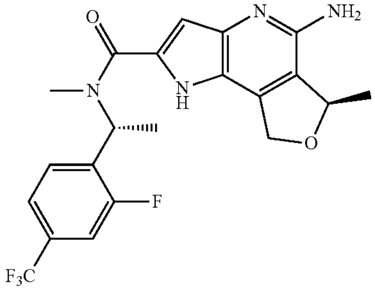

Example 147 (24 mg, 18%) and Example 148 (24 mg, 18%) were prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and 1-(2-fluoro-4-(trifluoromethyl)phenyl)-N-methylethan-1-amine, and the diastereomers were separated by chiral SFC.

Analytical chiral-SFC condition as below. Column: CHIRALPAK AD-H; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 147: Analytical SFC tR=4.03 min. $^1$H NMR (400 MHz, DMSO-d6) δ 11.51 (s, 1H), 7.85-7.58 (m, 3H), 6.72-6.45 (m, 1H), 6.11-5.91 (m, 1H), 5.45 (s, 2H), 5.39-5.27 (m, 1H), 5.13 (dd. J=13.9, 3.2 Hz, 1H), 5.03 (d, J=13.8 Hz, 1H), 3.16-2.65 (m, 3H), 1.62 (d, J=6.3 Hz, 3H), 1.34 (d, J=6.1 Hz, 3H). LCMS $(M+H)^+$=437.4.

Example 148: Analytical SFC tR=4.98 min. $^1$H NMR (400 MHz, DMSO-d6) δ 11.51 (s, 1H), 7.83-7.55 (m, 3H), 6.74-6.43 (m, 1H), 6.00 (q, J=6.7 Hz, 1H), 5.45 (s, 2H), 5.38-5.26 (m, 1H), 5.14 (dd, J=13.9.3.2 Hz, 1H), 5.02 (d, J=13.8 Hz, 1H), 3.15-2.68 (m, 3H), 1.62 (d, J=6.3 Hz, 3H), 1.34 (d, J=6.1 Hz, 3H). LCMS $(M+H)^+$=437.4.

Example 149 & Example 150: (S)-5-amino-N-(1-(2,6-difluoro-4-(trifluoromethyl)phenyl)ethyl)-N-methyl-6,8-dihydro-1H-furo[3,4-d]pyrrolo[3,2-b]pyridine-2-carboxamide & (R)-5-amino-N-(1-(2,6-difluoro-4-(trifluoromethyl)phenyl)ethyl)-N-methyl-6,8-dihydro-1H-furo[3,4-d]pyrrolo[3,2-b]pyridine-2-carboxamide

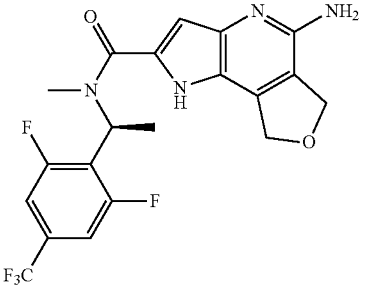

&

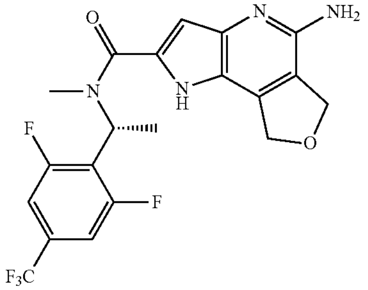

Step 1: N-(2,6-difluoro-4-(trifluoromethyl)benzylidene)-2-methylpropane-2-sulfinamide

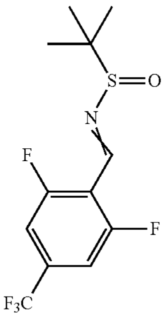 [SMILES: CC(C)(C)S(=O)N=Cc1c(F)cc(C(F)(F)F)cc1F]

To a solution of 2,6-difluoro-4-iodobenzaldehyde (0.50 g, 1.87 mmol) in DMF (5 mL) was added methyl 2,2-difluoro-2-(fluorosulfonyl)acetate (2.15 g, 11.19 mmol) and CuI (533 mg, 2.80 mmol). The mixture was stirred at 100° C. for 16 h and then cooled to room temperature. The mixture was diluted with water (15 mL) and extracted with DCM (3×5 mL). The combined organic layer was washed with brine (3×5 mL), dried over $Na_2SO_4$, filtered and concentrated under reduced pressure. The residue was re-dissolved in DCM (5 mL) followed by addition of tert-butanesulfinamide (577 mg, 4.76 mmol), PPTS (30 mg, 119 μmol) and $CuSO_4$ (1.90 g, 11.9 mmol). The mixture was stirred at 30° C. for 12 h. Water (15 mL) was added and the mixture was extracted with DCM (3×5 mL). The combined organic layer was washed with brine (5 mL), dried over $Na_2SO_4$, filtered and concentrated under reduced pressure to give the title compound. The residue was purified by silica gel chromatography (PE/EtOAc=1/0 to 50/1) to give the title compound (122 mg, 21%) $^1H$ NMR (400 MHz, $CDCl_3$) δ 8.82 (s, 1H), 7.30 (d, 2H, J=8.0 Hz), 1.30 (s, 9H).

Step 2: N-(1-(2,6-difluoro-4-(trifluoromethyl)phenyl)ethyl)-2-methylpropane-2-sulfinamide

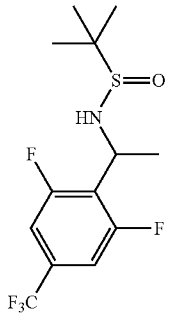 [SMILES: CC(NS(=O)C(C)(C)C)c1c(F)cc(C(F)(F)F)cc1F]

To a solution of N-(2,6-difluoro-4-(trifluoromethyl)benzylidene)-2-methylpropane-2-sulfinamide (122 mg, 390 μmol) in DCM (2 mL) was added MeMgBr in $Et_2O$ (3.0 M, 207 μL, 0.62 mmol) at −20° C. The mixture was stirred at −20° C. for 2 h and then saturated $NH_4Cl$ (6 mL) was added. The mixture was extracted with DCM (3×2 mL). The combined organic layer was washed with brine (2 mL), dried over $Na_2SO_4$, filtered and concentrated under reduced pressure. The residue was purified by prep-TLC (PE:EtOAc=3:1) to give the title compound (0.10 g, 77%). LCMS $(M+H)^+$= 330.0.

Step 3: N-(1-(2,6-difluoro-4-(trifluoromethyl)phenyl)ethyl)-N,2-dimethylpropane-2-sulfinamide

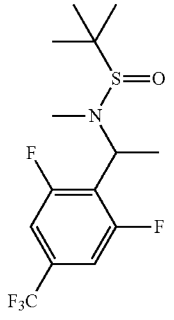 [SMILES: CC(c1c(F)cc(C(F)(F)F)cc1F)N(C)S(=O)C(C)(C)C]

To a solution of N-(1-(2,6-difluoro-4-(trifluoromethyl)phenyl)ethyl)-2-methylpropane-2-sulfinamide (0.10 g, 304 μmol) in THF (2 mL) was added NaH (60%, 24 mg, 607 μmol) at 0° C. The mixture was stirred at 25° C. for 30 min followed by addition of MeI (86 mg, 607 μmol). The mixture was stirred at 25° C. for 3 h and then diluted with water (8 mL). The mixture was extracted with EtOAc (3×3 mL). The combined organic layer was washed with brine (3 mL), dried over $Na_2SO_4$, filtered and concentrated under reduced pressure. The residue was purified by prep-TLC (PE:EtOAc=3:1) to give the title compound (80 mg, 76%). LC-MS $(M+H)^+$=344.1.

Step 4: 1-(2,6-difluoro-4-(trifluoromethyl)phenyl)-N-methylethan-1-amine Hydrochloride

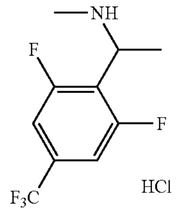 [SMILES: CNC(C)c1c(F)cc(C(F)(F)F)cc1F ; Cl]

To a flask charged with N-(1-(2,6-difluoro-4-(trifluoromethyl)phenyl)ethyl)-N,2-dimethylpropane-2-sulfinamide (80 mg, 233 μmol) was added HCl in MeOH (3.0 M, 2 mL). The mixture was stirred at room temperature for 1 h and then concentrated under reduced pressure to give the title compound (64 mg, 100%). LC-MS $(M+H)^+$=240.0.

Step 5: 5-amino-N-(1-(2,6-difluoro-4-(trifluoromethyl)phenyl)ethyl)-N-methyl-1-((2-(trimethylsilyl)ethoxy)methyl)-6,8-dihydro-1H-furo[3,4-d]pyrrolo[3,2-b]pyridine-2-carboxamide

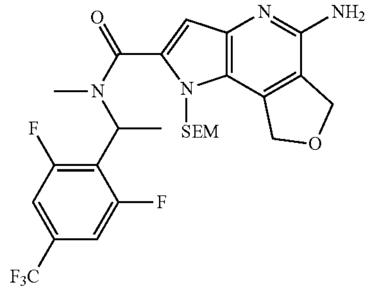 [SMILES: CC(c1c(F)cc(C(F)(F)F)cc1F)N(C)C(=O)c1cc2nc(N)c3c(c2n1COCC[Si](C)(C)C)COC3]

The title compound (150 mg, 95%) was prepared in a manner similar to that in Example 66 step 2 from 5-amino-1-((2-(trimethylsilyl)ethoxy)methyl)-6,8-dihydro-1H-furo[3,4-d]pyrrolo[3,2-b]pyridine-2-carboxylic acid and 1-(2,6-difluoro-4-(trifluoromethyl)phenyl)-N-methylethan-1-amine hydrochloride. LC-MS $(M+H)^+$=571.2.

Step 6: (S)-5-amino-N-(1-(2,6-difluoro-4-(trifluoromethyl)phenyl)ethyl)-N-methyl-6,8-dihydro-1H-furo[3,4-d]pyrrolo[3,2-b]pyridine-2-carboxamide & (R)-5-amino-N-(1-(2,6-difluoro-4-(trifluoromethyl)phenyl)ethyl)-N-methyl-6,8-dihydro-1H-furo[3,4-d]pyrrolo[3,2-b]pyridine-2-carboxamide Example 149 (12 mg, 10%) and Example 150 (10 mg, 9%) were prepared in a manner similar to that in Example 110 & Example 111 step 7 from 5-amino-N-(1-(2,6-difluoro-4-(trifluoromethyl)phenyl)ethyl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: Chiralpak AD-3; Column size: 4.6×50 mm, 3 μm; Mobile phase: 14 mM $NH_3$ in MeOH:$CO_2$, 1:19 for 0.2 min, 1:19 to 1:1 in 1 min. 1:1 for 1 min, 1:1 to 1:19 in 0.4 min, 1:19 for 0.4 min: Flow: 3.4 mL/min; Temperature: 35° C.; back pressure: 1800 psi.

Example 149: Analytical SFC tR=1.44 min. $^1$H NMR (400 MHz, DMSO-d6) δ 11.51 (s, 1H), 7.67-7.61 (m, 2H), 6.67 (s, 1H), 5.98-5.88 (m, 1H), 5.57 (s, 2H), 5.13-5.08 (m, 2H), 4.96-4.87 (m, 2H), 3.28-3.20 (m, 3H), 1.68 (d, J=7.2 Hz, 3H). LCMS $(M+H)^+$=441.2.

Example 150: Analytical SFC tR=1.65 min. $^1$H NMR (400 MHz, DMSO-d6) δ 11.51 (s, 1H), 7.67-7.61 (m, 2H), 6.67 (s, 1H), 5.98-5.88 (m, 1H), 5.57 (s, 2H), 5.13-5.08 (m, 2H), 4.96-4.87 (m, 2H), 3.28-3.20 (m, 3H), 1.68 (d, J=7.2 Hz, 3H). LCMS $(M+H)^+$=441.2.

Example 151 & Example 152: (R)-5-amino-N-(1-(4-cyclopropyl-2-fluoro-5-methylphenyl)ethyl)-N-methyl-6,8-dihydro-1H-furo[3,4-d]pyrrolo[3,2-b]pyridine-2-carboxamide & (S)-5-amino-N-(1-(4-cyclopropyl-2-fluoro-5-methylphenyl)ethyl)-N-methyl-6,8-dihydro-1H-furo[3,4-d]pyrrolo[3,2-b]pyridine-2-carboxamide

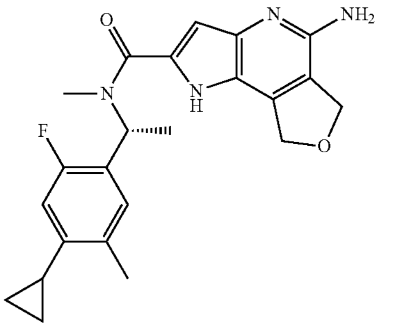

&

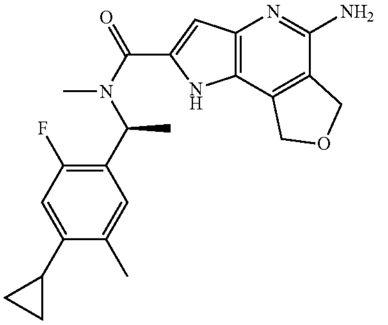

Step 1: 1-(4-bromo-2-fluoro-5-methylphenyl)ethan-1-one

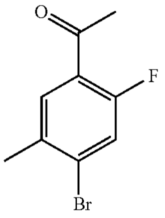

To a solution of 2-bromo-4-fluoro-1-methylbenzene (2.0 g, 10.6 mmol) in DCM (20 mL) was added $AlCl_3$ (1.55 g, 11.6 mmol) at room temperature. The mixture was stirred for 30 min, and then AcCl (878 mg, 11.1 mmol) was added dropwise at 0° C. The mixture was warmed to room temperature and stirred overnight. The mixture was slowly quenched with addition of water (1 mL) dropwise at 0° C., and the mixture was concentrated under reduced pressure. The residue was purified by silica gel chromatography (PE/EtOAc=30:1) to give the title compound (280 mg, 12%). LC-MS $(M+H)^+$=230.9.

Step 2: 1-(4-cyclopropyl-2-fluoro-5-methylphenyl)ethan-1-one

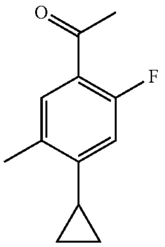

The title compound (220 mg, 95%) was prepared in a manner similar to that in Example 36 step 1 from 1-(4-bromo-2-fluoro-5-methylphenyl)ethan-1-one and cyclopropylboronic acid. LC-MS $(M+H)^+$=193.1.

Step 3: 1-(4-cyclopropyl-2-fluoro-5-methylphenyl)-N-methylethan-1-amine

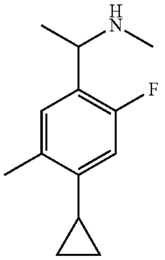

The title compound (90 mg, 38%) was prepared in a manner similar to that in Example 137 & Example 138 step 1 from 1-(4-cyclopropyl-2-fluoro-5-methylphenyl)ethan-1-one and $MeNH_2$. LC-MS $(M+H)^+$=208.1

Step 4: 5-amino-N-(1-(4-cyclopropyl-2-fluoro-5-methylphenyl)ethyl)-N-methyl-1-((2-(trimethylsilyl)ethoxy)methyl)-6,8-dihydro-1H-furo[3,4-d]pyrrolo[3,2-b]pyridine-2-carboxamide

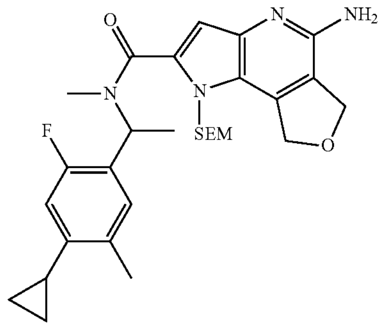 [SMILES: Cc1cc(C(C)N(C)C(=O)c2cc3nc(N)c4c(c3n2COCC[Si](C)(C)C)COC4)c(F)cc1C1CC1]

The title compound (200 mg, 78%) was prepared in a manner similar to that in Example 110 & Example 111 step 6 from 5-amino-1-((2-(trimethylsilyl)ethoxy)methyl)-6,8-dihydro-1H-furo[3,4-d]pyrrolo[3,2-b]pyridine-2-carboxylic acid and 1-(4-cyclopropyl-2-fluoro-5-methylphenyl)-N-methylethan-1-amine. LC-MS $(M+H)^+$=539.2.

Step 5: (R)-5-amino-N-(1-(4-cyclopropyl-2-fluoro-5-methylphenyl)ethyl)-N-methyl-6,8-dihydro-1H-furo[3,4-d]pyrrolo[3,2-b]pyridine-2-carboxamide & (S)-5-amino-N-(1-(4-cyclopropyl-2-fluoro-5-methylphenyl)ethyl)-N-methyl-6,8-dihydro-1H-furo[3,4-d]pyrrolo[3,2-b]pyridine-2-carboxamide Example 151 (12 mg, 8%) and Example 152 (12 mg, 8%) were prepared in a manner similar to that in Example 110 & Example 111 step 7 from 5-amino-N-(1-(4-cyclopropyl-2-fluoro-5-methylphenyl)ethyl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: CHIRALPAK AS-H; Column size: 4.6×100 mm, 5 μm Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 151: Analytical SFC tR=2.72 min. $^1$H NMR (400 MHz, DMSO-d6) δ 11.49 (s, 1H), 7.22 (d, J=7.9 Hz, 1H), 6.69 (d, J=12.0 Hz, 1H), 6.54 (s, 1H), 5.93 (d, J=6.5 Hz, 1H), 5.53 (s, 2H), 5.11 (s, 2H), 4.90 (s, 2H), 2.89 (s, 3H), 2.35 (s, 3H), 1.88 (s, 1H), 1.55 (s, 3H), 0.91 (d, J=8.6 Hz, 2H), 0.63-0.59 (m, 2H). LCMS $(M+H)^+$=409.2.

Example 152: Analytical SFC tR=3.06 min. $^1$H NMR (400 MHz, DMSO-d6) δ 11.49 (s, 1H), 7.22 (d, J=7.9 Hz, 1H), 6.70-6.67 (m, 1H), 6.54 (s, 1H), 5.93 (d, J=6.8 Hz, 1H), 5.53 (s, 2H), 5.11 (s, 2H), 4.90 (s, 2H), 2.89 (s, 3H), 2.35 (s, 3H), 1.88 (s, 1H), 1.55 (s, 3H), 0.92-0.89 (m, 2H), 0.63-0.59 (m, 2H). LCMS $(M+H)^+$=409.2.

Example 153 & Example 154: (R)-5-amino-N-cyclobutyl-N-(1-(5-cyclopropyl-3-fluoropyridin-2-yl)ethyl)-6,8-dihydro-1H-furo[3,4-d]pyrrolo[3,2-b]pyridine-2-carboxamide & (S)-5-amino-N-cyclobutyl-N-(1-(5-cyclopropyl-3-fluoropyridin-2-yl)ethyl)-6,8-dihydro-1H-furo[3,4-d]pyrrolo[3,2-b]pyridine-2-carboxamide

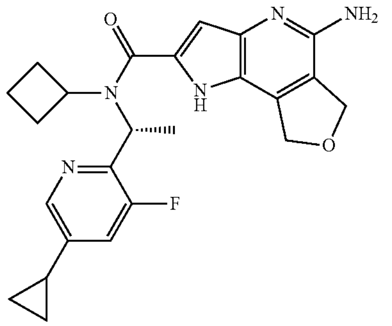

&

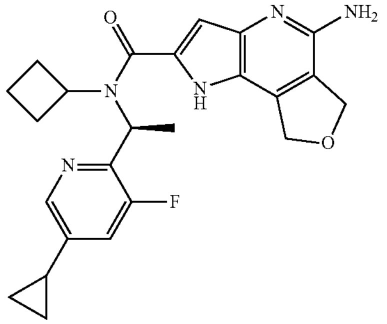

Step 1: N-(1-(5-cyclopropyl-3-fluoropyridin-2-yl)ethyl)cyclobutanamine

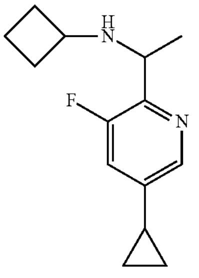 [SMILES: CC(NC1CCC1)c1ncc(C2CC2)cc1F]

The title compound (200 mg, 77%) was prepared in a manner similar to that in Example 124 & Example 125 step 1 from 1-(5-cyclopropyl-3-fluoropyridin-2-yl)ethan-1-one and cyclobutanamine. LC-MS $(M+H)^+$=235.2.

Step 2: 5-amino-N-cyclobutyl-N-(1-(5-cyclopropyl-3-fluoropyridin-2-yl)ethyl)-1-((2-(trimethylsilyl)ethoxy)methyl)-6,8-dihydro-1H-furo[3,4-d]pyrrolo[3,2-b]pyridine-2-carboxamide

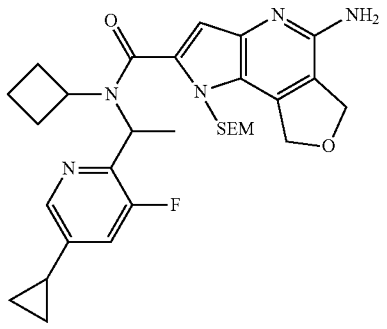 [SMILES: CC(c1ncc(C2CC2)cc1F)N(C(=O)c1cc2nc(N)c3c(c2n1COCC[Si](C)(C)C)COC3)C1CCC1]

The title compound (100 mg, 20%) was prepared in a manner similar to that in Example 110 & Example 111 step 6 from N-(1-(5-cyclopropyl-3-fluoropyridin-2-yl)ethyl)cyclobutanamine and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=566.2.

Step 3: (R)-5-amino-N-cyclobutyl-N-(1-(5-cyclopropyl-3-fluoropyridin-2-yl)ethyl)-6,8-dihydro-1H-furo[3,4-d]pyrrolo[3,2-b]pyridine-2-carboxamide & (S)-5-amino-N-cyclobutyl-N-(1-(5-cyclopropyl-3-fluoropyridin-2-yl)ethyl)-6,8-dihydro-1H-furo[3,4-d]pyrrolo[3,2-b]pyridine-2-carboxamide Example 153 (17 mg, 22%) and Example 154 (18 mg, 23%) were prepared in a manner similar to that in Example 110 & Example 111 step 7 from 5-amino-N-cyclobutyl-N-(1-(5-cyclopropyl-3-fluoropyridin-2-yl)ethyl)-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: YMC Cellulose-C; Column size: 4.6×100 mm, 5 μm Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 153: Analytical SFC tR=3.76 min. $^1$H NMR (400 MHz, DMSO-d6) δ 11.51 (s, 1H), 8.26 (s, 1H), 7.28-7.20 (m, 1H), 6.48 (d, J=1.7 Hz, 1H), 5.70-5.58 (m, 1H), 5.53 (s, 2H), 5.10 (s, 2H), 4.90 (s, 2H), 4.35-4.06 (m, 1H), 2.71-2.55 (m, 2H), 2.05-1.90 (m, 2H), 1.71 (d, J=6.8 Hz, 3H), 1.68-1.40 (m, 4H), 1.11-0.93 (m, 2H), 0.89-0.59 (m, 2H). LC-MS $(M+H)^+$=436.4.

Example 154: Analytical SFC tR=4.12 min. $^1$H NMR (400 MHz, DMSO-d6) δ 11.51 (s, 1H), 8.26 (s, 1H), 7.28-7.20 (m, 1H), 6.48 (d, J=1.7 Hz, 1H), 5.70-5.58 (m, 1H), 5.53 (s, 2H), 5.10 (s, 2H), 4.90 (s, 2H), 4.35-4.06 (m, 1H), 2.71-2.55 (m, 2H), 2.05-1.90 (m, 2H), 1.71 (d, J=6.8 Hz, 3H), 1.68-1.40 (m, 4H), 1.11-0.93 (m, 2H), 0.89-0.59 (m, 2H). LC-MS $(M+H)^+$=436.4.

Example 155 & Example 156: (R)-5-amino-N-cyclobutyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide & (S)-5-amino-N-cyclobutyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide

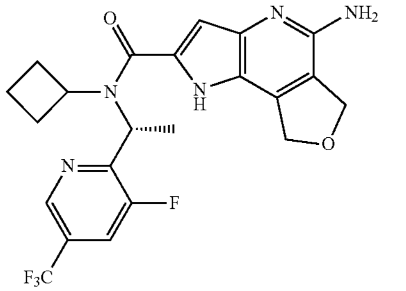

&

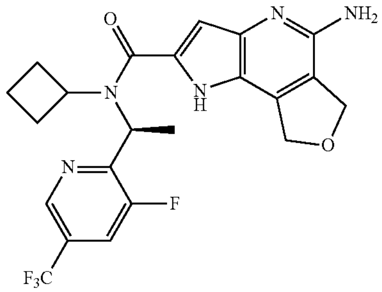

Step 1: N-(1-(3-fluoro-5-(trifluoromethyl)pyridin-2-yl)ethyl)cyclobutanamine

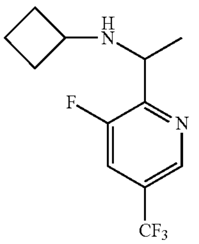 [SMILES: CC(NC1CCC1)c1ncc(C(F)(F)F)cc1F]

The title compound (150 mg, 47%) was prepared in a manner similar to that in Example 124 & Example 125 step 1 from 1-(3-fluoro-5-(trifluoromethyl)pyridin-2-yl)ethan-1-one and cyclobutanamine. LC-MS $(M+H)^+$=263.2.

Step 2: 5-amino-N-cyclobutyl-N-(1-(3-fluoro-5-(trifluoromethyl)pyridin-2-yl)ethyl)-1-((2-(trimethylsilyl)ethoxy)methyl)-6,8-dihydro-1H-furo[3,4-d]pyrrolo[3,2-b]pyridine-2-carboxamide

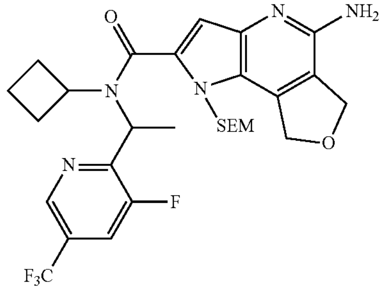 [SMILES: CC(c1ncc(C(F)(F)F)cc1F)N(C(=O)c1cc2nc(N)c3c(c2n1COCC[Si](C)(C)C)COC3)C1CCC1]

The title compound (100 mg, 20%) was prepared in a manner similar to that in Example 110 & Example 111 step 6 from N-(l-(3-fluoro-5-(trifluoromethyl)pyridin-2-yl)ethyl) cyclobutanamine and 5-amino-1-((2-(trimethylsilyl)ethoxy) methyl)-6,8-dihydro-1H-furo[3,4-d]pyrrolo[3,2-b]pyridine-2-carboxylic acid. LC-MS $(M+H)^+$=594.2.

Step 3: (R)-5-amino-N-cyclobutyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide & (S)-5-amino-N-cyclobutyl-N-(1-(3-fluoro-5-(trifluoromethyl)pyridin-2-yl)ethyl)-6,8-dihydro-1H-furo[3,4-d]pyrrolo[3,2-b]pyridine-2-carboxamide Example 155 (7 mg, 9%) and Example 156 (7 mg, 8%) were prepared in a manner similar to that in Example 110 & Example 111 step 7 from 5-amino-N-cyclobutyl-N-(1-(3-fluoro-5-(trifluoromethyl)pyridin-2-yl)ethyl)-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: YMC Cellulose-C; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min: Flow: 2.0 mL/min: Temperature: 35° C.; back pressure: 1500 psi.

Example 155: Analytical SFC tR=2.94 min. $^1H$ NMR (400 MHz, DMSO-d6) δ 11.49 (s, 1H), 8.82 (s, 1H), 8.21-8.13 (m, 1H), 6.54-6.49 (m, 1H), 5.55 (s, 3H), 5.07 (s, 2H), 4.90 (s, 2H), 4.75-4.50 (m, 1H), 2.74-2.58 (m, 2H), 2.20-1.85 (m, 2H), 1.77 (d, J=6.5 Hz, 3H), 1.72-1.44 (m, 2H). LC-MS $(M+H)^+$=464.3.

Example 156: Analytical SFC tR=3.12 min. $^1H$ NMR (400 MHz, DMSO-d6) δ 11.49 (s, 1H), 8.82 (s, 1H), 8.21-8.13 (m, 1H), 6.54-6.49 (m, 1H), 5.55 (s, 3H), 5.07 (s, 2H), 4.90 (s, 2H), 4.75-4.50 (m, 1H), 2.74-2.58 (m, 2H), 2.20-1.85 (m, 2H), 1.77 (d, J=6.5 Hz, 3H), 1.72-1.44 (m, 2H). LC-MS $(M+H)^+$=464.3.

Example 157 and Example 158: (R)-5-amino-N-(1-(3-fluoro-5-(trifluoromethyl)pyridin-2-yl)ethyl)-N-(2-methoxyethyl)-6,8-dihydro-1H-furo[3,4-d]pyrrolo[3,2-b]pyridine-2-carboxamide & (S)-5-amino-N-(1-(3-fluoro-5-(trifluoromethyl)pyridin-2-yl)ethyl)-N-(2-methoxyethyl)-6,8-dihydro-1H-furo[3,4-d]pyrrolo[3,2-b]pyridine-2-carboxamide

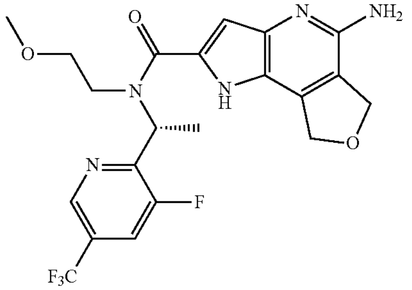

&

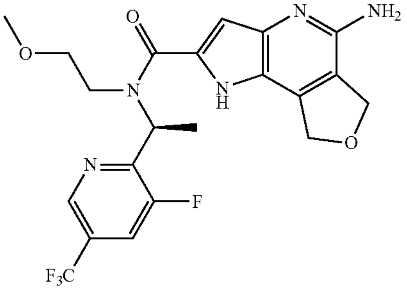

Step 1: 1-(3-fluoro-5-(trifluoromethyl)pyridin-2-yl) ethan-1-amine Hydrochloride

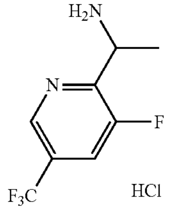

The title compound (1.02 g, 100%) was prepared in a manner similar to that in Example 110 & Example 111 step 5 from tert-butyl (1-(3-fluoro-5-(trifluoromethyl)pyridin-2-yl)ethyl)carbamate. LC-MS $(M+H)^+$=209.1.

Step 2: 1-(3-fluoro-5-(trifluoromethyl)pyridin-2-yl)-N-(2-methoxyethyl)ethan-1-amine

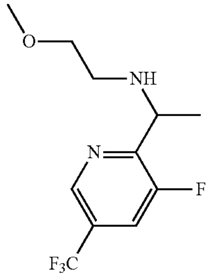 [SMILES: COCCNC(C)c1ncc(C(F)(F)F)cc1F]

To a solution of 1-(3-fluoro-5-(trifluoromethyl)pyridin-2-yl)ethan-1-amine hydrochloride (1.02 g, 3.64 mmol) in DMF (20 mL) was added $K_2CO_3$ (1.24 g, 8.99 mmol), 1-bromo-2-methoxyethane (688 mg, 4.95 mmol) and KI (149 mg, 0.90 mmol). The mixture was stirred at 90° C. for 12 h and then cooled to room temperature. The mixture was diluted with water (50 mL) and extracted with EtOAc (3×30 mL). The combined organic layer was washed with brine (30 mL), dried over $Na_2SO_4$, filtered and concentrated under reduced pressure. The residue was purified by prep-HPLC to give the title compound (300 mg, 31%). LC-MS $(M+H)^+$=267.0.

Step 3: 5-amino-N-(1-(3-fluoro-5-(trifluoromethyl)pyridin-2-yl)ethyl)-N-(2-methoxyethyl)-1-((2-(trimethylsilyl)ethoxy)methyl)-6,8-dihydro-1H-furo[3,4-d]pyrrolo[3,2-b]pyridine-2-carboxamide

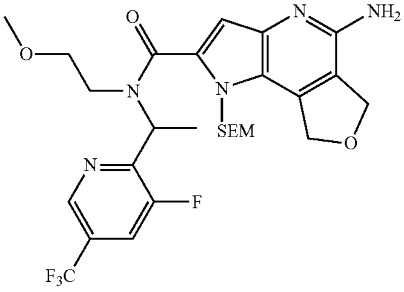 [SMILES: COCCN(C(=O)c1cc2nc(N)c3c(c2n1COCC[Si](C)(C)C)COC3)C(C)c1ncc(C(F)(F)F)cc1F]

The title compound (200 mg, 36%) was prepared in a manner similar to that in Example 110 & Example 111 step 6 from 5-amino-1-((2-(trimethylsilyl)ethoxy)methyl)-6,8-dihydro-1H-furo[3,4-d]pyrrolo[3,2-b]pyridine-2-carboxylic acid and 1-(3-fluoro-5-(trifluoromethyl)pyridin-2-yl)-N-(2-methoxyethyl)ethan-1-amine. LC-MS $(M+H)^+$=598.2.

Step 4: (R)-5-amino-N-(1-(3-fluoro-5-(trifluoromethyl)pyridin-2-yl)ethyl)-N-(2-methoxyethyl)-6,8-dihydro-1H-furo[3,4-d]pyrrolo[3,2-b]pyridine-2-carboxamide & (S)-5-amino-N-(0-(3-fluoro-5-(trifluoromethyl)pyridin-2-yl)ethyl)-N-(2-methoxyethyl)-6,8-dihydro-1H-furo[3,4-d]pyrrolo[3,2-b]pyridine-2-carboxamide Example 157 (25 mg, 16%) and Example 158 (26 mg, 16%) were prepared in a manner similar to that in Example 110 & Example 111 step 7 from 5-amino-N-(1-(3-fluoro-5-(trifluoromethyl)pyridin-2-yl)ethyl)-N-(2-methoxyethyl)-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: Chiralcel OX-3; Column size: 4.6×50 mm, 5 μm; Mobile phase: (EtOH containing 0.2% 7 M methanolic $NH_3$):$CO_2$, 1:19 for 0.2 min, 1:19 to 1:1 in 1 min, 1:1 for 1 min, 1:1 to 1:19 in 0.4 min, 1:9 for 0.4 min; Flow: 3.4 mL/min; Temperature: 35° C.; back pressure: 1800 psi.

Example 157: Analytical SFC tR=1.43 min. $^1$H NMR (400 MHz, DMSO-d6) δ 11.54 (s, 1H), 8.87 (s, 1H) 8.28 (d, J=8.0 Hz, 1H), 6.65 (d, J=1.6 Hz, 1H), 6.11-5.83 (m, 1H), 5.58 (s, 2H), 5.12 (s, 2H), 4.96-4.84 (m, 2H), 3.98-3.37 (m, 3H), 3.31-3.21 (m, 1H), 3.14 (s, 3H), 1.69 (d, J=6.8 Hz, 3H). LC-MS $(M+H)^+$=468.2.

Example 158: Analytical SFC tR=1.51 min. $^1$H NMR (400 MHz, DMSO-d6) δ 11.54 (s, 1H), 8.87 (s, 1H) 8.28 (d, J=8.0 Hz, 1H), 6.65 (d, J=1.6 Hz, 1H), 6.11-5.83 (m, 1H), 5.58 (s, 2H), 5.12 (s, 2H), 4.96-4.84 (m, 2H), 3.98-3.37 (m, 3H), 3.31-3.21 (m, 1H), 3.14 (s, 3H), 1.69 (d, J=6.8 Hz, 3H). LC-MS $(M+H)^+$=468.2.

Example 159 & Example 160: (R)-5-amino-N-cyclobutyl-N-(1-(5-cyclopropylpyridin-2-yl)ethyl)-6,8-dihydro-1H-furo[3,4-d]pyrrolo[3,2-b]pyridine-2-carboxamide & (S)-5-amino-N-cyclobutyl-N-( 1-(5-cyclopropylpyridin-2-yl)ethyl)-6,8-dihydro-1H-furo[3,4-d]pyrrolo[3,2-b]pyridine-2-carboxamide

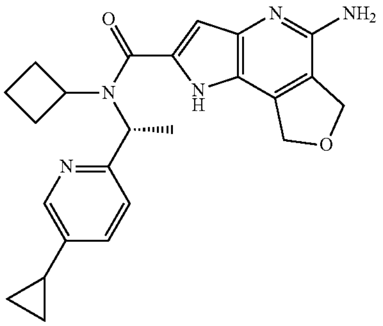

&

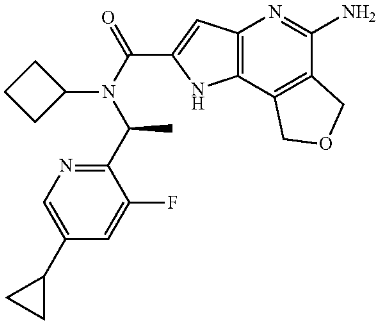

Step 1: N-(1-(5-cyclopropylpyridin-2-yl)ethyl)cyclobutanamine

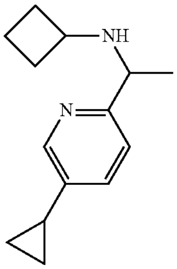 [SMILES: CC(NC1CCC1)c1ccc(C2CC2)cn1]

The title compound (160 mg, 29%) was prepared in a manner similar to that in Example 124 & Example 125 step 1 from 1-(5-cyclopropylpyridin-2-yl)ethan-1-one and cyclobutanamine. LC-MS $(M+H)^+$=217.3.

Step 2: 5-amino-N-cyclobutyl-N-(1-(5-cyclopropylpyridin-2-yl)ethyl)-1-((2-(trimethylsilyl)ethoxy)methyl)-6,8-dihydro-1H-furo[3,4-d]pyrrolo[3,2-b]pyridine-2-carboxamide

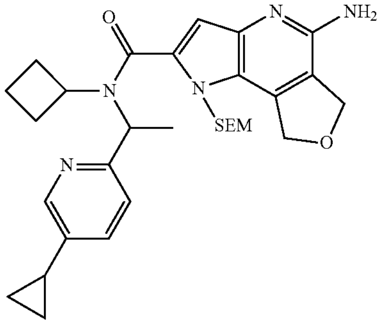 [SMILES: CC(c1ccc(C2CC2)cn1)N(C(=O)c1cc2nc(N)c3c(c2n1COCC[Si](C)(C)C)COC3)C1CCC1]

The title compound (90 mg, 14%) was prepared in a manner similar to that in Example 110 & Example 111 step 6 from N-(1-(5-cyclopropylpyridin-2-yl)ethyl)cyclobutanamine and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=548.3.

Step 3: (R)-5-amino-N-cyclobutyl-N-(1-(5-cyclopropylpyridin-2-yl)ethyl)-6,8-dihydro-1H-furo[3,4-d]pyrrolo[3,2-b]pyridine-2-carboxamide & (S)-5-amino-N-cyclobutyl-N-(1-(5-cyclopropylpyridin-2-yl)ethyl)-6,8-dihydro-1H-furo[3,4-d]pyrrolo[3,2-b]pyridine-2-carboxamide Example 159 (19 mg, 28%) and Example 160 (18 mg, 27%) were prepared in a manner similar to that in Example 110 & Example 111 step 7 from 5-amino-N-cyclobutyl-N-(1-(5-cyclopropylpyridin-2-yl)ethyl)-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: CHIRALPAK Cellulose-C; Column size: 4.6×100 mm, 5 μm; Mobile phase: 4 mM methanolic $NH_2$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 159: Analytical SFC tR=3.82 min. $^1$H NMR (400 MHz, DMSO-d6) δ 11.54 (s, 1H), 8.35 (s, 1H), 7.36 (d, J=8.0 Hz, 1H), 7.20 (d, J=8.0 Hz, 1H), 6.45 (s, 1H), 5.54 (s, 2H), 5.31-5.19 (m, 1H), 5.09 (s, 2H), 4.89 (s, 2H), 4.68-4.40 (m, 1H), 2.19-1.86 (m, 4H), 1.70 (d. J=3.6 Hz, 3H), 1.66-1.45 (m, 3H), 0.99-0.93 (m, 2H), 0.73-0.66 (m, 2H). LC-MS $(M+H)^+$=418.4.

Example 160: Analytical SFC tR=4.18 min. $^1$H NMR (400 MHz, DMSO-d6) δ 11.54 (s, 1H), 8.35 (s, 1H), 7.36 (d, J=8.0 Hz, 1H), 7.20 (d, J=8.0 Hz, 1H), 6.45 (s, 1H), 5.54 (s, 2H), 5.31-5.19 (m, 1H), 5.09 (s, 2H), 4.89 (s, 2H), 4.68-4.40 (m, 1H), 2.19-1.86 (m, 4H), 1.70 (d, J=3.6 Hz, 3H), 1.66-1.45 (m, 3H), 0.99-0.93 (m, 2H), 0.73-0.66 (m, 2H). LC-MS $(M+H)^+$=418.4.

Example 161: (S)-5-amino-N-ethyl-N-(7'-(trifluoromethyl)spiro[cyclopropane-1,1'-isochroman]-4'-yl)-6,8-dihydro-1H-furo[3,4-d]pyrrolo[3,2-b]pyridine-2-carboxamide

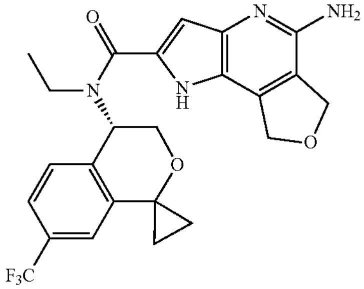 [SMILES: CCN(C(=O)c1cc2nc(N)c3c(c2[nH]1)COC3)[C@@H]1COC2(CC2)c2cc(C(F)(F)F)ccc21]

Step 1: (S)—N-ethyl-2-nitro-N-(7'-(trifluoromethyl)spiro[cyclopropane-1,1'-isochroman]-4'-yl)benzenesulfonamide

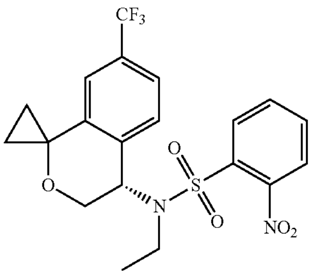 [SMILES: CCN([C@@H]1COC2(CC2)c2cc(C(F)(F)F)ccc21)S(=O)(=O)c1ccccc1[N+](=O)[O-]]

The title compound (100 mg, 67%) was prepared in a manner similar to that in Example 91 step 6 from (R)-7'-(trifluoromethyl)spiro[cyclopropane-1,1'-isochroman]-4'-ol and N-ethyl-2-nitro-benzenesulfonamide. LC-MS $(M+H)^+$=457.1.

Step 2: (S)—N-ethyl-7'-(trifluoromethyl)spiro[cyclopropane-1,1'-isochroman]-4'-amine

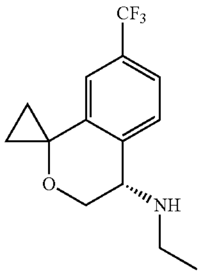 [SMILES: CCN[C@@H]1COC2(CC2)c2cc(C(F)(F)F)ccc21]

The title compound (100 mg, 84%) was prepared in a manner similar to that in Example 91 step 7 from (S)—N-ethyl-2-nitro-N-(7'-(trifluoromethyl)spiro[cyclopropane-1,1'-isochroman]-4'-yl)benzenesulfonamide. LC-MS $(M+H)^+$= 272.2.

Step 3: (S)-5-amino-N-ethyl-N-(7'-(trifluoromethyl)spiro[cyclopropane-1,1'-isochroman]-4'-yl)-1-((2-(trimethylsilyl)ethoxy)methyl)-6,8-dihydro-1H-furo[3,4-d]pyrrolo[3,2-b]pyridine-2-carboxamide

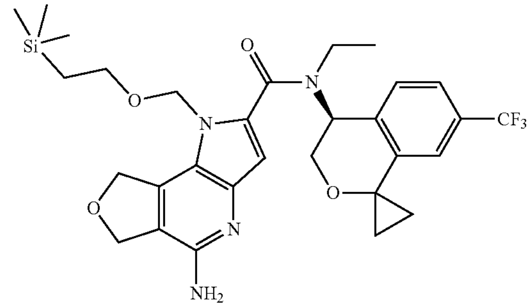 [SMILES: CCN(C(=O)c1cc2nc(N)c3c(c2n1COCC[Si](C)(C)C)COC3)[C@@H]1COC2(CC2)c2cc(C(F)(F)F)ccc21]

The title compound (50 mg, 90%) was prepared in a manner similar to that in Example 91 step 8 from 5-amino-1-((2-(trimethylsilyl)ethoxy)methyl)-6,8-dihydro-1H-furo[3,4-d]pyrrolo[3,2-b]pyridine-2-carboxylic acid and (S)—N-ethyl-7'-(trifluoromethyl)spiro[cyclopropane-1,1'-isochroman]-4'-amine. LC-MS $(M+H)^+$=603.2.

Step 4: (S)-5-amino-N-ethyl-N-(7'-(trifluoromethyl)spiro[cyclopropane-1,1'-isochroman]-4'-yl)-6,8-dihydro-1H-furo[3,4-d]pyrrolo[3,2-b]pyridine-2-carboxamide Example 161 (12 mg, 31%) was prepared in a manner similar to that in Example 91 step 9 from (S)-5-amino-N-ethyl-N-(7'-(trifluoromethyl)spiro[cyclopropane-1,1'-isochroman]-4'-yl)-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.60 (s, 1H), 7.56 (d, J=7.5 Hz, 1H), 7.41 (d, J=7.6 Hz, 1H), 7.11 (s, 1H), 6.62 (s, 1H), 5.70 (s, 1H), 5.56 (s, 2H), 5.12 (s, 2H), 4.91 (s, 2H), 4.19 (s, 2H), 4.00-3.50 (m, 2H), 1.35-1.20 (m, 4H), 1.12 (s, 3H). LC-MS $(M+H)^+$=473.1.

Example 162: (R)-5-amino-N-methyl-N-(7-(trifluoromethyl)chroman-4-yl)-6,8-dihydro-1H-furo[3,4-d]pyrrolo[3,2-b]pyridine-2-carboxamide

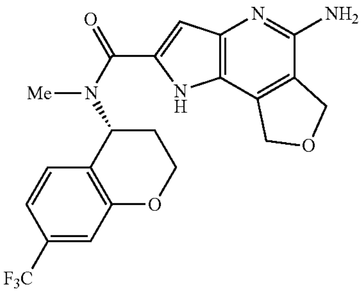 [SMILES: CN(C(=O)c1cc2nc(N)c3c(c2[nH]1)COC3)[C@@H]1CCOc2cc(C(F)(F)F)ccc21]

Step 1: (S)-7-(trifluoromethyl)chroman-4-ol

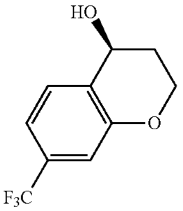 [SMILES: O[C@H]1CCOc2cc(C(F)(F)F)ccc21]

The title compound (600 mg, 99%) was prepared in a manner similar to that in Example 83 step 5 from 7-(trifluoromethyl)chroman-4-one.

Step 2: (R)—N-methyl-2-nitro-N-(7-(trifluoromethyl)chroman-4-yl)benzenesulfonamide

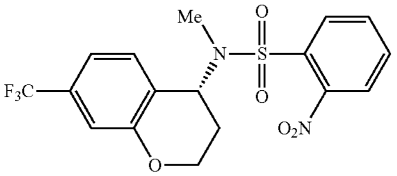 [SMILES: CN([C@@H]1CCOc2cc(C(F)(F)F)ccc21)S(=O)(=O)c1ccccc1[N+](=O)[O-]]

The title compound (1.1 g, 88%) was prepared in a manner similar to that in Example 82 step 9 from (S)-7-(trifluoromethyl)chroman-4-ol and N-methyl-2-nitro-benzenesulfonamide. LC-MS $(M+Na)^+$=439.1.

Step 3: (R)—N-methyl-7-(trifluoromethyl)chroman-4-amine

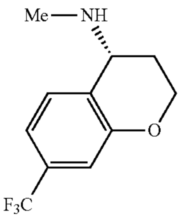 [SMILES: CN[C@@H]1CCOc2cc(C(F)(F)F)ccc21]

The title compound (458 mg, 76%) was prepared in a manner similar to that in Example 82 step 10 from (R)—N-methyl-2-nitro-N-(7-(trifluoromethyl)chroman-4-yl)benzenesulfonamide. LC-MS $(M+H)^+$=232.1.

Step 4: (R)-5-amino-N-methyl-N-(7-(trifluoromethyl)chroman-4-yl)-1-((2-(trimethylsilyl)ethoxy)methyl)-6,8-dihydro-1H-furo[3,4-d]pyrrolo[3,2-b]pyridine-2-carboxamide

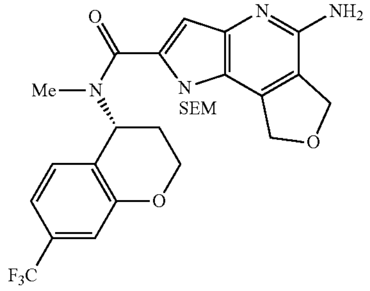 [SMILES: CN(C(=O)c1cc2nc(N)c3c(c2[nH]1)COC3)[C@@H]1CCOc2cc(C(F)(F)F)ccc21]

The title compound (332 mg, 84%) was prepared in a manner similar to that in Example 73 & Example 74 step 9 from 5-amino-1-((2-(trimethylsilyl)ethoxy)methyl)-6,8-dihydro-1H-furo[3,4-d]pyrrolo[3,2-b]pyridine-2-carboxylic acid and (R)—N-methyl-7-(trifluoromethyl)chroman-4-amine. LC-MS $(M+H)^+$=563.4.

Step 5: (R)-5-amino-N-methyl-N-(7-(trifluoromethyl)chroman-4-yl)-6,8-dihydro-1H-furo[3,4-d]pyrrolo[3,2-b]pyridine-2-carboxamide Example 162 (214 mg, 84%) prepared in a manner similar to that in Example 66 step 3 from (R)-5-amino-N-methyl-N-(7-(trifluoromethyl)chroman-4-yl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ 11.62 (s, 1H), 7.37-7.11 (m, 3H), 6.76 (s, 1H), 5.97 (s, 1H), 5.58 (s, 2H), 5.14 (s, 2H), 4.91 (s, 2H), 4.51-4.28 (m, 2H), 3.15-2.68 (m, 3H), 2.31-2.05 (m, 2H). LC-MS $(M+H)^+$=433.3

Example 163 & Example 164: (R)-5-amino-N-methyl-N-(3-(trifluoromethyl)-7,8-dihydro-5H-pyrano[4,3-b]pyridin-8-yl)-6,8-dihydro-1H-furo[3,4-d]pyrrolo[3,2-b]pyridine-2-carboxamide & (S)-5-amino-N-methyl-N-(3-(trifluoromethyl)-7,8-dihydro-5H-pyrano[4,3-b]pyridin-8-yl)-6,8-dihydro-1H-furo[3,4-d]pyrrolo[3,2-b]pyridine-2-carboxamide

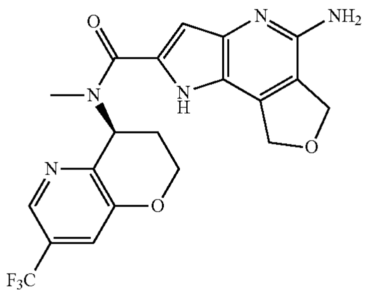

&

-continued

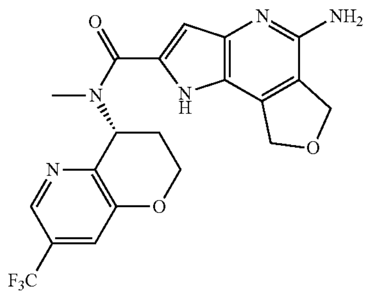

Step 1: (2-chloro-5-(trifluoromethyl)pyridin-3-yl)methanol

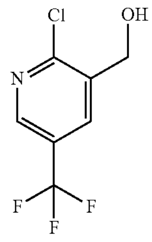 [SMILES: OCc1cc(C(F)(F)F)cnc1Cl]

The title compound (2.0 g, 95%) was prepared in a manner similar to that in Example 75 & Example 76 step 1 from 2-chloro-5-(trifluoromethyl)nicotinaldehyde. LC-MS $(M+H)^+$=212.2

Step 2: 3-((allyloxy)methyl)-2-chloro-5-(trifluoromethyl)pyridine

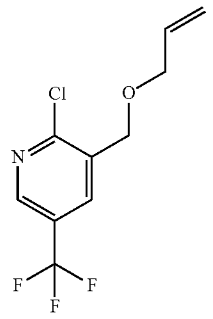 [SMILES: C=CCOCc1cc(C(F)(F)F)cnc1Cl]

The title compound (1.6 g, 71%) was prepared in a manner similar to that in Example 39 & Example 40 step 1 from (2-chloro-5-(trifluoromethyl)pyridin-3-yl)methanol and allyl bromide. LC-MS $(M+H)^+$=252.2.

Step 3: 8-methylene-3-(trifluoromethyl)-7,8-dihydro-5H-pyrano[4,3-b]pyridine

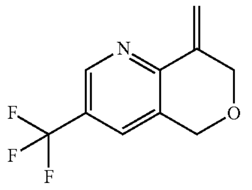

The title compound (630 mg, 46%) was prepared in a manner similar to that in Example 39 & Example 40 step 2 from 3-((allyloxy)methyl)-2-chloro-5-(trifluoromethyl)pyridine. LC-MS $(M+H)^+$=216.3.

Step 4: 3-(trifluoromethyl)-5H-pyrano[4,3-b]pyridin-8(7H)-one

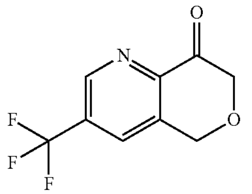 [SMILES: O=C1COCc2cc(C(F)(F)F)cnc21]

The title compound (308 mg, 49%) was prepared in a manner similar to that in Example 39 & Example 40 step 3 from 8-methylene-3-(trifluoromethyl)-7,8-dihydro-5H-pyrano[4,3-b]pyridine. LC-MS $(M+H)^+$=218.0

Step 5: 3-(trifluoromethyl)-7,8-dihydro-5H-pyrano[4,3-b]pyridin-8-ol

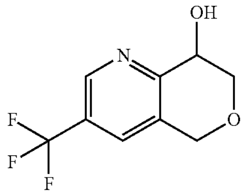 [SMILES: OC1COCc2cc(C(F)(F)F)cnc21]

To a solution of 3-(trifluoromethyl)-5H-pyrano[4,3-b]pyridin-8(7H)-one (88 mg, 0.41 mmol) in THF (3 mL) was added $BH_3$ in THF (1.0 M, 0.50 mL, 0.50 mmol) dropwise at 0° C. The mixture was stirred at room temperature for 0.5 h, and then MeOH (0.5 mL) was added. Upon cease of bubbling, the mixture was concentrated under reduced pressure. The residue was purified by silica gel chromatography to give the title compound (80 mg, 91%). LC-MS $(M+H)^+$=220.1.

Step 6: N-methyl-2-nitro-N-(3-(trifluoromethyl)-7,8-dihydro-5H-pyrano[4,3-b]pyridin-8-yl)benzenesulfonamide

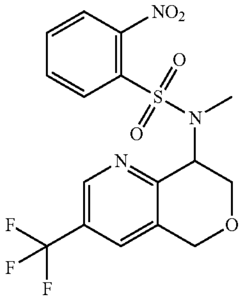 [SMILES: CN(C1COCc2cc(C(F)(F)F)cnc21)S(=O)(=O)c1ccccc1[N+](=O)[O-]]

The title compound (142 mg, 93%) was prepared in a manner similar to that in Example 91 step 6 from 3-(trifluoromethyl)-7,8-dihydro-5H-pyrano[4,3-b]pyridin-8-ol and N-methyl-2-nitro-benzenesulfonamide. LC-MS $(M+H)^+$=418.1.

Step 7: N-methyl-3-(trifluoromethyl)-7,8-dihydro-5H-pyrano[4,3-b]pyridin-8-amine

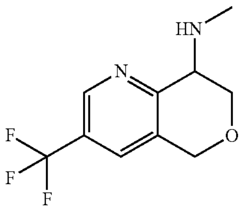 [SMILES: CNC1COCc2cc(C(F)(F)F)cnc21]

The title compound (69 mg, 88%) was prepared in a manner similar to that in Example 91 step 7 from N-methyl-2-nitro-N-(3-(trifluoromethyl)-7,8-dihydro-5H-pyrano[4,3-b]pyridin-8-yl)benzenesulfonamide. LC-MS $(M+H)^+$=233.1.

Step 8: 5-amino-N-methyl-N-(3-(trifluoromethyl)-7,8-dihydro-5H-pyrano[4,3-b]pyridin-8-yl)-1-((2-(trimethylsilyl)ethoxy)methyl)-6,8-dihydro-1H-furo[3,4-d]pyrrolo[3,2-b]pyridine-2-carboxamide

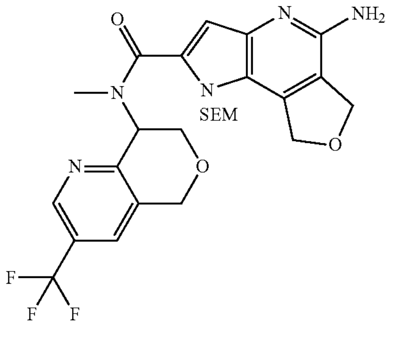 [SMILES: CN(C(=O)c1cc2nc(N)c3c(c2[nH]1)COC3)C1COCc2cc(C(F)(F)F)cnc21]

The title compound (142 mg, 84%) was prepared in a manner similar to that in Example 91 step 8 from 5-amino- 1-((2-(trimethylsilyl)ethoxy)methyl)-6,8-dihydro-1H-furo[3,4-d]pyrrolo[3,2-b]pyridine-2-carboxylic acid and N-methyl-3-(trifluoromethyl)-7,8-dihydro-5H-pyrano[4,3-b]pyridin-8-amine. LC-MS $(M+H)^+$=564.4.

Step 9: (R)-5-amino-N-methyl-N-(3-(trifluoromethyl)-7,8-dihydro-5H-pyrano[4,3-b]pyridin-8-yl)-6,8-dihydro-1H-furo[3,4-d]pyrrolo[3,2-b]pyridine-2-carboxamide & (S)-5-amino-N-methyl-N-(3-(trifluoromethyl)-7,8-dihydro-5H-pyrano[4,3-b]pyridin-8-yl)-6,8-dihydro-1H-furo[3,4-d]pyrrolo[3,2-b]pyridine-2-carboxamide Example 163 (20 mg, 15%) and Example 164 (22 mg, 17%) were prepared in a manner similar to that in Example 110 & Example 111 step 7 from 5-amino-N-methyl-N-(3-(trifluoromethyl)-7,8-dihydro-5H-pyrano[4,3-b]pyridin-8-yl)-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: Lux Cellulose-3; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 163: Analytical SFC tR=2.95 min. $^1H$ NMR (400 MHz, DMSO-d6) δ 11.56 (s, 1H), 8.88 (s, 1H), 8.10 (s, 1H), 6.69 (s, 1H), 5.78-5.51 (m, 3H), 5.12 (s, 2H), 4.99-4.70 (m, 4H), 4.43-4.05 (m, 2H), 3.18-2.62 (m, 3H). LC-MS $(M+H)^+$=434.4.

Example 164: Analytical SFC tR=3.52 min. $^1H$ NMR (400 MHz, DMSO-d6) δ 11.55 (s, 1H), 8.88 (s, 1H), 8.10 (s, 1H), 6.69 (s, 1H), 5.77-5.48 (m, 3H), 5.12 (s, 2H), 4.98-4.74 (m, 4H), 4.43-4.09 (m, 2H), 3.18-2.65 (m, 3H). LC-MS $(M+H)^+$=434.3.

Example 165: (R)-5-amino-N,6-dimethyl-N—((S)-7'-(trifluoromethyl)spiro[cyclopropane-1,1'-isochroman]-4'-yl)-6,8-dihydro-1H-furo[3,4-d]pyrrolo[3,2-b]pyridine-2-carboxamide

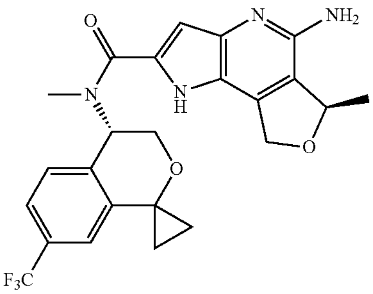 [SMILES: C[C@H]1OCc2c1c(N)nc1cc(C(=O)N(C)[C@@H]3COC4(CC4)c4cc(C(F)(F)F)ccc43)[nH]c21]

Example 165 (37 mg, 37%) was prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and (S)—N-methyl-7'-(trifluoromethyl)spiro[cyclopropane-1,1'-isochroman]-4'-amine. $^1H$ NMR (400 MHz, DMSO-d6) δ 11.61 (s, 1H), 7.60 (d, J=7.8 Hz, 1H), 7.51-7.31 (m, 1H), 7.15 (s, 1H), 6.82-6.47 (m, 1H), 6.00-5.66 (m, 1H), 5.49 (s, 2H), 5.40-5.29 (m, 1H), 5.22-5.11 (m, 1H), 5.11-5.01 (m, 1H), 4.32-3.94 (m, 2H), 3.19-2.69 (m, 3H), 1.40-1.15 (m, 7H). LC-MS $(M+H)^+$=473.3.

Example 166: (R)-5-amino-N-ethyl-6-methyl-N—((S)-7'-(trifluoromethyl)spiro[cyclopropane-1,1'-isochroman]-4'-yl)-6,8-dihydro-1H-furo[3,4-d]pyrrolo[3,2-b]pyridine-2-carboxamide

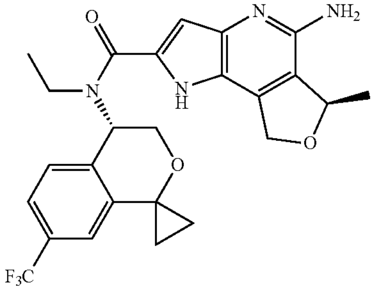 [SMILES: CCN(C(=O)c1cc2nc(N)c3c(c2[nH]1)CO[C@@H]3C)[C@@H]1COC2(CC2)c2cc(C(F)(F)F)ccc21]

Example 166 (55 mg, 53%) was prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and (S)—N-ethyl-7'-(trifluoromethyl)spiro[cyclopropane-1,1'-isochroman]-4'-amine. $^1H$ NMR (400 MHz, DMSO-d6) δ 11.59 (s, 1H), 7.56 (d, J=7.5 Hz, 1H), 7.41 (d, J=7.9 Hz, 1H), 7.11 (s, 1H), 6.76-6.45 (m, 1H), 5.87-5.54 (m, 1H), 5.47 (s, 2H), 5.37-5.26 (m, 1H), 5.21-5.08 (m, 1H), 5.08-4.99 (m, 1H), 4.33-4.02 (m, 2H), 3.95-2.75 (m, 2H), 1.34 (d, J=6.0 Hz, 3H), 1.31-0.97 (m, 7H). LC-MS $(M+H)^+$=487.3.

Example 167 & Example 168: (R)-5-amino-N-(5'-fluoro-7'-(trifluoromethyl)spiro[cyclopropane-1,1'-isochroman]-4'-yl)-N-methyl-6,8-dihydro-1H-furo[3,4-d]pyrrolo[3,2-b]pyridine-2-carboxamide & (S)-5-amino-N-(5'-fluoro-7'-(trifluoromethyl)spiro[cyclopropane-1,1'-isochroman]-4'-yl)-N-methyl-6,8-dihydro-1H-furo[3,4-d]pyrrolo[3,2-b]pyridine-2-carboxamide

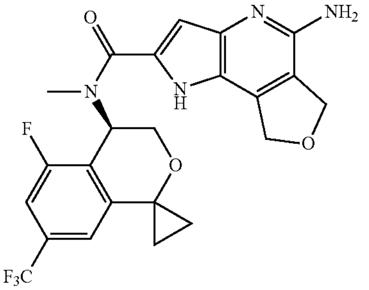

&

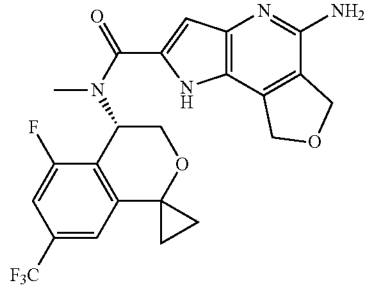

Step 1: methyl 2-amino-3-fluoro-5-(trifluoromethyl)benzoate

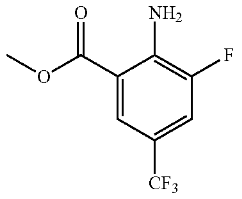 [SMILES: COC(=O)c1cc(C(F)(F)F)cc(F)c1N]

To a solution of 2-fluoro-4-(trifluoromethyl)aniline (24.9 g, 139 mmol) in DMF (130 mL) was added NBS (25.0 g, 146 mmol) at room temperature and the mixture was stirred for 2 h. The mixture was partitioned between water (300 mL) and EtOAc (300 mL). The organic layer was washed with brine (200 mL), dried over $Na_2SO_4$, filtered and concentrated under reduced pressure. The residue was re-dissolved in MeOH (400 mL) followed by addition of $Pd(dppf)Cl_2$ (5.7 g, 7.8 mmol) and $Et_3N$ (47.0 g, 465 mmol). The vessel was flushed with CO and the mixture was stirred at 100° C. under CO (20 bar) overnight. The mixture was cooled to room temperature and concentrated under reduced pressure. The crude was purified by silica gel chromatography (PE/EtOAc=5:1) to give the title compound (21.4 g, 65%). LC-MS $(M+H)^+$=238.0.

Step 2: methyl 2-bromo-3-fluoro-5-(trifluoromethyl)benzoate

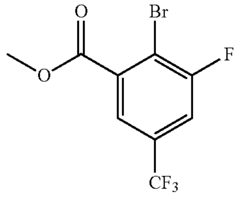 [SMILES: COC(=O)c1cc(C(F)(F)F)cc(F)c1Br]

A mixture of methyl 2-amino-3-fluoro-5-(trifluoromethyl)benzoate (21.4 g, 90 mmol), t-BuONO (10.2 g, 99 mmol) and $CuBr_2$ (22.1 g, 99 mmol) in MeCN (200 mL) was stirred for 2 h at room temperature. The mixture was concentrated under reduced pressure. The residue was purified by silica gel chromatography (PE/EtOAc=10:1) to give the title compound (24.0 g, 88%).

Step 3: 1-(2-bromo-3-fluoro-5-(trifluoromethyl)phenyl)cyclopropan-1-ol

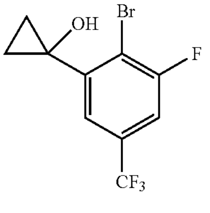 [SMILES: OC1(c2cc(C(F)(F)F)cc(F)c2Br)CC1]

Bis(cyclopentadienyl)zirconium dichloride (3.9 g, 13.3 mmol) was suspended in toluene (20 mL) at 0° C., EtMgBr in $Et_2O$ (3.0 M, 6.6 mL, 19.9 mmol) was added dropwise. The mixture was stirred at 0° C. for 1 h, followed by addition of methyl 2-bromo-3-fluoro-5 -(trifluoromethyl)benzoate (2.0 g, 6.6 mmol) in toluene (10 mL) dropwise. The mixture was warmed to room temperature and stirred overnight. A solution of NaOH (1 g) in water (10 mL) was added, and the mixture was stirred at room temperature for 30 min. Solid was filtered off, and the solid was rinsed with EtOAc (20 mL). The organic layer of the filtrate was separated, and the aqueous layer was extracted with EtOAc (20 mL). The combined organic layer was washed with water (20 mL), dried with $Na_2SO_4$, filtered and concentrated under reduced pressure. The residue was purified by silica gel chromatography (PE/EtOAc=30:1) to give the title compound (660 mg, 33%). $^1H$ NMR (400 MHz, DMSO-d6) δ 7.81 (d, J=8.4 Hz, 1H), 7.55 (s, 1H), 6.03 (s, 1H), 1.10-1.02 (m, 2H), 0.95-0.89 (m, 2H). LC-MS $(M+H)^+$=298.9.

Step 4: 1-(1-(allyloxy)cyclopropyl)-2-bromo-3-fluoro-5-(trifluoromethyl)benzene

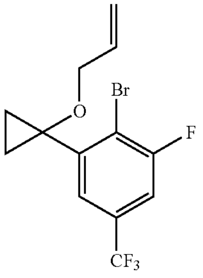 [SMILES: C=CCOC1(c2cc(C(F)(F)F)cc(F)c2Br)CC1]

To a solution of 1-(2-bromo-3-fluoro-5-(trifluoromethyl)phenyl)cyclopropan-1-ol (660 mg, 2.2 mmol) and allyl bromide (534 mg, 4.4 mmol) in DMF (10 mL) was added NaH (60%, 176 mg, 4.4 mmol) at 0° C. The mixture was warmed to room temperature and stirred at room temperature for 2 h. Water (50 mL) was added, and the mixture was extracted with EtOAc (50 mL). The organic layer was washed with brine (50 mL), dried over $Na_2SO_4$, filtered and concentrated under reduced pressure. The residue was purified by silica gel chromatography (PE/EtOAc=50:1) to give the title compound (610 mg, 81%).

Step 5: 5'-fluoro-4'-methylene-7'-(trifluoromethyl)spiro[cyclopropane-1,1'-isochromane]

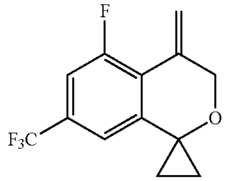 [SMILES: C=C1COC2(CC2)c2cc(C(F)(F)F)cc(F)c21]

To a mixture of 1-(1-(allyloxy)cyclopropyl)-2-bromo-3-fluoro-5-(trifluoromethyl)benzene (2.1 g, 6.2 mmol) in DMF (50 mL) was added $Pd(OAc)_2$ (138 mg, 0.62 mmol), Xant-Phos (710 mg, 1.24 mmol) and $Cs_2CO_3$ (2.4 g, 7.4 mmol) under nitrogen. The mixture was heated to 100° C. overnight. The mixture was cooled to room temperature and concentrated under reduced pressure. The residue was partitioned between water (20 mL) and EtOAc (30 mL). The organic layer was dried over $Na_2SO_4$, filtered and concentrated under reduced pressure. The residue was purified by silica gel chromatography (PE/EtOAc=30:1) to the title compound (1.5 g, 94%). LC-MS $(M+H)^+$=259.1.

Step 6: 5'-fluoro-7'-(trifluoromethyl)spiro[cyclopropane-1,1'-isochroman]-4'-one

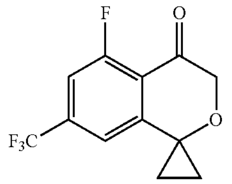 [SMILES: O=C1COC2(CC2)c2cc(C(F)(F)F)cc(F)c21]

To a mixture of 5'-fluoro-4'-methylene-7'-(trifluoromethyl)spiro[cyclopropane-1,1'-isochromane] (580 mg, 2.2 mmol) in dioxane (10 mL) and water (2 mL) was added potassium osmate (VI) dihydrate (82 mg, 0.22 mmol), 2,6-lutidine (480 mg, 4.4 mmol) and sodium periodate (1.9 g, 8.8 mmol). The mixture was stirred at room temperature for 2 h. Solid was filtered off, then the filtrate was diluted with EtOAc (20 mL). The organic layer was washed with water (20 mL), dried over $Na_2SO_4$, filtered and concentrated under reduced pressure. The residue was purified by silica gel chromatography (PE/EtOAc=10:1) to give the title compound (84 mg, 14%). LC-MS $(M+H)^+$=261.0.

Step 7: 5'-fluoro-7'-(trifluoromethyl)spiro[cyclopropane-1,1'-isochroman]-4'-ol

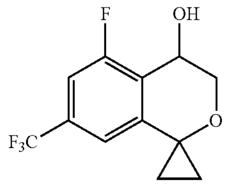 [SMILES: OC1COC2(CC2)c2cc(C(F)(F)F)cc(F)c21]

To a solution of 5'-fluoro-7'-(trifluoromethyl)spiro[cyclopropane-1,1'-isochroman]-4'-one (84 mg, 0.32 mmol) in methanol (5 mL) was added $NaBH_4$ (25 mg, 0.64 mmol) at 0° C. The mixture was warmed to room temperature and stirred for 1 h. The mixture was concentrated under reduced pressure and purified by silica gel chromatography (PE/EtOAc=5:1) to give the title compound (80 mg, 95%). LC-MS $(M+H)^+$=263.0.

Step 8: N-(5'-fluoro-7'-(trifluoromethyl)spiro[cyclopropane-1,1'-isochroman]-4'-yl)-N-methyl-2-nitrobenzenesulfonamide

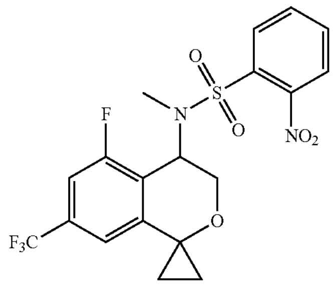 [SMILES: CN(C1COC2(CC2)c2cc(C(F)(F)F)cc(F)c21)S(=O)(=O)c1ccccc1[N+](=O)[O-]]

To a solution of 5'-fluoro-7'-(trifluoromethyl)spiro[cyclopropane-1,1'-isochroman]-4'-ol (80 mg, 0.31 mmol) and N-methyl-2-nitro-benzenesulfonamide (66 mg, 0.34 mmol) in THF (5 mL) was added DtBAD (77 mg, 0.34 mmol) and $PPh_3$ (88 mg, 0.34 mmol) under nitrogen, and the mixture was stirred at room temperature for 1 h. The mixture was concentrated under reduced pressure, and the residue was purified by silica gel chromatography (PE/EtOAc=10:1 to 5:1) to give the title compound (130 mg, 92%). LC-MS $(M+H)^+$=461.0.

Step 9: 5'-fluoro-N-methyl-7'-(trifluoromethyl)spiro[cyclopropane-1,1'-isochroman]-4'-amine

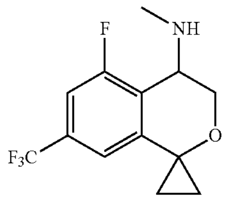 [SMILES: CNC1COC2(CC2)c2cc(C(F)(F)F)cc(F)c21]

To a mixture of N-(5'-fluoro-7'-(trifluoromethyl)spiro[cyclopropane-1,1'-isochroman]-4'-yl)-N-methyl-2-nitrobenzenesulfonamide (130 mg, 0.28 mmol) in THF (4 mL) and DMF (1 mL) was added lithium hydroxide monohydrate (36 mg, 0.86 mmol) and dodecane-1-thiol (171 mg, 0.86 mmol), and the mixture was stirred at room temperature overnight. The mixture was concentrated under reduced pressure, and the residue was partitioned between water (10 mL) and EtOAc (10 mL). The organic layer was separated and concentrated under reduced pressure. The residue was purified by silica gel chromatography (PE/EtOAc=2:1 to 0:1) to give the title compound (46 mg, 59%). LC-MS $(M+H)^+$=276.0.

Step 10: 5-amino-N-(5'-fluoro-7'-(trifluoromethyl)spiro[cyclopropane-1,1'-isochroman]-4'-yl)-N-methyl-1-((2-(trimethylsilyl)ethoxy)methyl)-6,8-dihydro-1H-furo[3,4-d]pyrrolo[3,2-b]pyridine-2-carboxamide

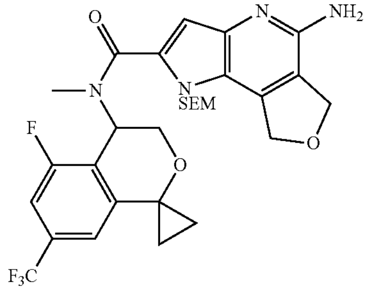 [SMILES: CN(C(=O)c1cc2nc(N)c3c(c2n1COCC[Si](C)(C)C)COC3)C1COC2(CC2)c2cc(C(F)(F)F)cc(F)c21]

To a mixture of 5-amino-1-((2-(trimethylsilyl)ethoxy)methyl)-6,8-dihydro-1H-furo[3,4-d]pyrrolo[3,2-b]pyridine-2-carboxylic acid (34 mg, 0.10 mmol) and 5'-fluoro-N-methyl-7'-(trifluoromethyl)spiro[cyclopropane-1,1'-isochroman]-4'-amine (24 mg, 0.09 mmol) in THF (5 mL) was added BOPCl (29 mg, 0.13 mmol) and DIPEA (34 mg, 0.26 mmol). The mixture was stirred at 60° C. for 2 h. The mixture was cooled to room temperature and concentrated under reduced pressure. The residue was partitioned between water (10 mL) and EtOAc (10 mL). The organic layer was separated, dried over $Na_2SO_4$, filtered and concentrated under reduced pressure. The residue was purified by silica gel chromatography (DCM/MeOH=30:1) to give the title compound (50 mg, 94%). LC-MS $(M+H)^+$=607.2.

Step 11: (R)-5-amino-N-(5'-fluoro-7'-(trifluoromethyl)spiro[cyclopropane-1,1'-isochroman]-4'-yl)-N-methyl-6,8-dihydro-1H-furo[3,4-d]pyrrolo[3,2-b]pyridine-2-carboxamide & (S)-5-amino-N-(5'-fluoro-7'-(trifluoromethyl)spiro[cyclopropane-1,1'-isochroman]-4'-yl)-N-methyl-6,8-dihydro-1H-furo[3,4-d]pyrrolo[3,2-b]pyridine-2-carboxamide To a solution of 5-amino-N-(5'-fluoro-7'-(trifluoromethyl)spiro[cyclopropane-1,1'-isochroman]-4'-yl)-N-methyl-1-((2-(trimethylsilyl)ethoxy)methyl)-6,8-dihydro-1H-furo[3,4-d]pyrrolo[3,2-b]pyridine-2-carboxamide (50 mg, 0.083 mmol) in DCM (2 mL) was added TFA (1 mL) and the mixture was stirred at room temperature for 1 h. The mixture was concentrated under reduced pressure. The residue was dissolved in MeOH (5 mL) followed by addition of strong ammonia solution (28%, 1 mL). The mixture was stirred at room temperature for 30 min and concentrated under reduced pressure. The residue was purified by silica gel chromatography (DCM/MeOH=30/1) followed by chiral SFC to give Example 167 (5 mg, 13%) and Example 168 (10 mg, 25%).

Analytical chiral-SFC condition as below. Column: YMC Cellulose-C; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min: Flow: 2.0 mL/min: Temperature: 35° C.; back pressure: 1500 psi.

Example 167: Analytical SFC tR=3.46 min. $^1H$ NMR (400 MHz, DMSO-d6) δ 11.55 (s, 1H), 7.62-7.38 (m, 1H), 7.06 (s, 1H), 6.79-6.40 (m, 1H), 5.98-5.73 (m, 1H), 5.55 (s, 2H), 5.20-5.04 (m, 2H), 4.89 (s, 2H), 4.52-3.92 (m, 2H), 3.21-2.68 (m, 3H), 1.69-1.50 (m, 1H), 1.45-1.31 (m, 1H), 1.29-1.17 (m, 1H), 1.12-0.93 (m, 1H). LC-MS $(M+H)^+$=477.2.

Example 168: Analytical SFC tR=3.92 min. $^1H$ NMR (400 MHz, DMSO-d6) δ 11.55 (s, 1H), 7.62-7.38 (m, 1H), 7.06 (s, 1H), 6.79-6.40 (m, 1H), 5.98-5.73 (m, 1H), 5.55 (s, 2H), 5.20-5.04 (m, 2H), 4.89 (s, 2H), 4.52-3.92 (m, 2H), 3.21-2.68 (m, 3H), 1.69-1.50 (m, 1H), 1.45-1.31 (m, 1H), 1.29-1.17 (m, 1H), 1.12-0.93 (m, 1H). LC-MS $(M+H)^+$=477.2.

Example 169 & Example 170: (R)-5-amino-N—((R)-5'-fluoro-7'-(trifluoromethyl)spiro[cyclopropane-1,1'-isochroman]-4'-yl)-N,6-dimethyl-6,8-dihydro-1H-furo[3,4-d]pyrrolo[3,2-b]pyridine-2-carboxamide & (R)-5-amino-N—((S)-5'-fluoro-7-(trifluoromethyl)spiro[cyclopropane-1,1'-isochroman]-4'-yl)-N,6-dimethyl-6,8-dihydro-1H-furo[3,4-d]pyrrolo[3,2-b]pyridine-2-carboxamide

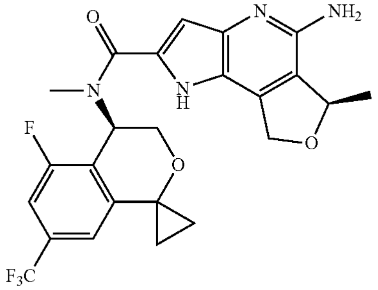

&

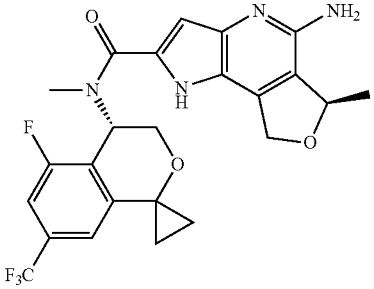

To the mixture of (R)-5-amino-6-methyl-6,8-dihydro-1H-furo[3,4-d]pyrrolo[3,2-b]pyridine-2-carboxylic acid (23 mg, 0.10 mmol), 5'-fluoro-N-methyl-7'-(trifluoromethyl)spiro[cyclopropane-1,1'-isochroman]-4'-amine (25 mg, 0.11 mmol) and DIPEA (79 mg, 0.46 mmol) in anhydrous DMF (3 mL) under nitrogen was added T3P (289 mg, 0.49 mmol, 50% in DMF) and the mixture was stirred at 60° C. for 16 h. The mixture was cooled to room temperature, hydrochloric acid (6 M, 9 mL) was added and the mixture was stirred for 3 h at 60° C. The mixture was cooled to room temperature, poured into saturated $NaHCO_3$ (100 mL) and extracted with EtOAc (100 mL). The combined organic layer was washed with brine (100 mL), dried over $Na_2SO_4$, filtered and concentrated under vacuum. The residue was purified by silica gel chromatography (DCM/MeOH=30:1) followed by chiral SFC to give Example 169 (4 mg, 8%) and Example 170 (8 mg, 16%).

Analytical chiral-SFC condition as below. Column: YMC Cellulose-C; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 169: Analytical SFC tR=3.17 min. $^{1}$H NMR (400 MHz, DMSO-d6) δ 11.55 (s, 1H), 7.64-7.42 (m, 1H), 7.07 (s, 1H), 6.72-6.43 (m, 1H), 5.97-5.70 (m, 1H), 5.54-5.42 (m, 2H), 5.36-5.25 (m, J=5.2 Hz, 1H), 5.19-4.98 (m, 2H), 4.55-3.95 (m, 2H), 3.17-2.66 (m, 3H), 1.66-1.52 (m, 1H), 1.42-1.28 (m, 4H), 1.28-1.19 (m, 1H), 1.09-0.94 (m, 1H). LC-MS $(M+H)^+$=491.1.

Example 170: Analytical SFC tR=3.72 min. $^{1}$H NMR (400 MHz, DMSO-d6) δ 11.55 (s, 1H), 7.63-7.41 (m, 1H), 7.07 (s, 1H), 6.72-6.44 (m, 1H), 5.96-5.73 (m, 1H), 5.46 (s, 2H), 5.36-5.25 (m, 1H), 5.14 (dd, J=14.0, 3.3 Hz, 1H), 5.01 (d, J=13.4 Hz, 1H), 4.49-3.98 (m, 2H), 3.19-2.67 (m, 3H), 1.66-1.51 (m, 1H), 1.47-1.27 (m, 4H), 1.27-1.18 (m, 1H), 1.09-0.90 (m, 1H). LC-MS $(M+H)^+$=491.1.

Example 171: (R)-5-amino-N—((S)-7'-cyclopropyl-spiro[cyclopropane-1,1'-isochroman]-4'-yl)-N,6-dimethyl-6,8-dihydro-1H-furo[3,4-d]pyrrolo[3,2-b]pyridine-2-carboxamide

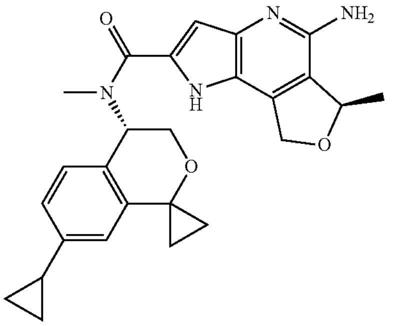 [SMILES: C[C@H]1OCc2c1c(N)nc1cc(C(=O)N(C)[C@@H]3COC4(CC4)c4cc(C5CC5)ccc43)[nH]c21]

Step 1: 1-(2-bromo-5-cycloproplphenyl)cyclopropan-1-ol

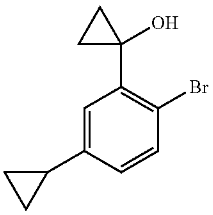 [SMILES: OC1(c2cc(C3CC3)ccc2Br)CC1]

The title compound (1.5 g, 45%) was prepared in a manner similar to that in Example 167 & Example 168 step 3 from methyl 2-bromo-5-cyclopropylbenzoate. LC-MS $(M+H)^+$=253.0.

Step 2: 2-(1-(allyloxy)cyclopropyl)-1-bromo-4-cyclopropylbenzene

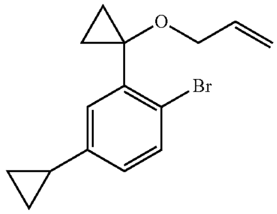 [SMILES: C=CCOC1(c2cc(C3CC3)ccc2Br)CC1]

The title compound (1.35 g, 79%) was prepared in a manner similar to that in Example 167 & Example 168 step 4 from 1-(2-bromo-5-cyclopropylphenyl)cyclopropan-1-ol and allyl bromide.

Step 3: 7'-cyclopropyl-4'-methylenespiro[cyclopropane-1,1'-isochromane]

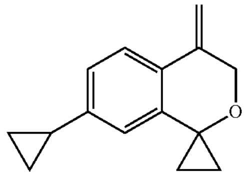 [SMILES: C=C1COC2(CC2)c2cc(C3CC3)ccc21]

The title compound (630 mg, 64%) was prepared in a manner similar to that in Example 167 & Example 168 step 5 from 2-(1-(allyloxy)cyclopropyl)-1-bromo-4-cyclopropylbenzene.

Step 4: 7'-cyclopropylspiro[cyclopropane-1,1'-isochroman]-4'-one

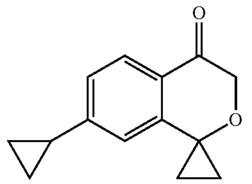 [SMILES: O=C1COC2(CC2)c2cc(C3CC3)ccc21]

The title compound (285 mg, 45%) was prepared in a manner similar to that in Example 167 & Example 168 step 6 from 7'-cyclopropyl-4'-methylenespiro[cyclopropane-1,1'-isochromane]. LC-MS $(M+H)^+$=215.1.

Step 5: (R)-7'-cyclopropylspiro[cyclopropane-1,1'-isochroman]-4'-ol

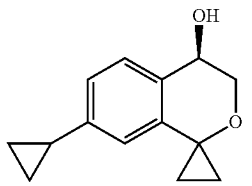 [SMILES: O[C@H]1COC2(CC2)c2cc(C3CC3)ccc21]

The title compound (186 mg, 65%) was prepared in a manner similar to that in Example 84 step 1 from 7'-cyclopropylspiro[cyclopropane-1,1'-isochroman]-4'-one. LC-MS $(M+H)^+$=217.1.

Step 6: (S)—N-(7'-cyclopropylspiro[cyclopropane-1,1'-isochroman]-4'-yl)-N-methyl-2-nitrobenzenesulfonamide

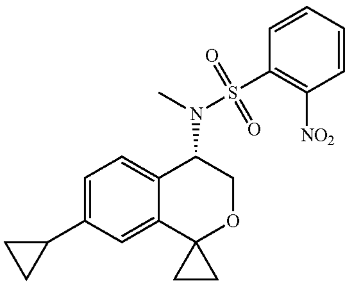 [SMILES: CN([C@@H]1COC2(CC2)c2cc(C3CC3)ccc21)S(=O)(=O)c1ccccc1[N+](=O)[O-]]

The title compound (355 mg, 100%) was prepared in a manner similar to that in Example 167 & Example 168 step 8 from (R)-7'-cyclopropylspiro[cyclopropane-1,1'-isochroman]-4'-ol and N-methyl-2-nitro-benzenesulfonamide. LC-MS $(M+H)^+$=415.1.

Step 7: (S)-7'-cyclopropyl-N-methylspiro[cyclopropane-1,1'-isochroman]-4'-amine

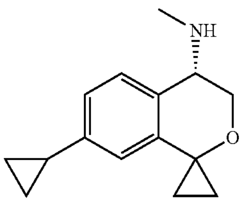 [SMILES: CN[C@@H]1COC2(CC2)c2cc(C3CC3)ccc21]

The title compound (124 mg, 56%) was prepared in a manner similar to that in Example 167 & Example 168 step 9 from (S)—N-(7'-cyclopropylspiro[cyclopropane-1,1'-isochroman]-4'-yl)-N-methyl-2-nitrobenzenesulfonamide. LC-MS $(M+H)^+$=230.1.

Step 8: (R)-5-amino-N—((S)-7'-cyclopropylspiro[cyclopropane-1,1'-isochroman]-4'-yl)-N,6-dimethyl-6,8-dihydro-1H-furo[3,4-d]pyrrolo[3,2-b]pyridine-2-carboxamide Example 171 (5 mg, 5%) was prepared in a manner similar to that in Example 169 & Example 170 from (S)-7'-cyclopropyl-N-methylspiro[cyclopropane-1,1'-isochroman]-4'-amine and (R)-5-amino-6-methyl-6,8-dihydro-1H-furo[3,4-d]pyrrolo[3,2-b]pyridine-2-carboxylic acid. $^1$H NMR (400 MHz, DMSO-d6) δ 11.67 (s, 1H), 7.04 (s, 1H), 6.87 (d, J=8.1 Hz, 1H), 6.67 (s, 1H), 6.48 (s, 1H), 5.74-5.67 (m, 2H), 5.33 (d, J=3.7 Hz, 1H), 5.20-5.00 (m, 2H), 4.03 (s, 2H), 3.01 (s, 3H), 1.87-1.81 (m, 1H), 1.33 (d, J=6.1 Hz, 3H), 1.30-1.07 (m, 4H), 0.98 (s, 1H), 0.88 (td, J=6.1, 4.0 Hz, 2H), 0.64 (t, J=4.5 Hz, 2H). LC-MS $(M+H)^+$=445.2.

Example 172: (S)-5-amino-N-(7'-cyclopropylspiro[cyclopropane-1,1'-isochroman]-4'-yl)-N-methyl-6,8-dihydro-1H-furo[3,4-d]pyrrolo[3,2-b]pyridine-2-carboxamide

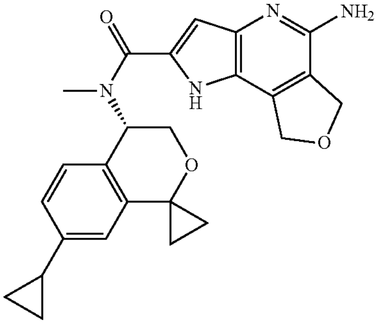 [SMILES: CN(C(=O)c1cc2nc(N)c3c(c2[nH]1)COC3)[C@@H]1COC2(CC2)c2cc(C3CC3)ccc21]

Step 1: (S)-5-amino-N-(7'-cyclopropylspiro[cyclopropane-1,1'-isochroman]-4'-yl)-N-methyl-1-((2-(trimethylsilyl)ethoxy)methyl)-6,8-dihydro-1H-furo[3,4-d]pyrrolo[3,2-b]pyridine-2-carboxamide

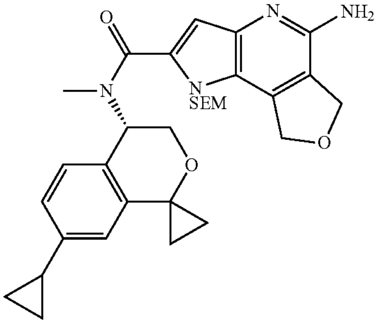 [SMILES: CN(C(=O)c1cc2nc(N)c3c(c2n1COCC[Si](C)(C)C)COC3)[C@@H]1COC2(CC2)c2cc(C3CC3)ccc21]

The title compound (100 mg, 60%) was prepared in a manner similar to that in Example 167 & Example 168 step 10 from 5-amino-1-((2-(trimethylsilyl)ethoxy)methyl)-6,8-dihydro-1H-furo[3,4-d]pyrrolo[3,2-b]pyridine-2-carboxylic acid and (S)-7'-cyclopropyl-N-methylspiro[cyclopropane-1,1'-isochroman]-4'-amine. LC-MS $(M+H)^+$=561.2.

Step 2: (S)-5-amino-N-(7'-cyclopropylspiro[cyclopropane-1,1'-isochroman]-4'-yl)-N-methyl-6,8-dihydro-1H-furo[3,4-d]pyrrolo[3,2-b]pyridine-2-carboxamide Example 172 (10 mg, 7%) was prepared in a manner similar to that in Example 167 & Example 168 step 11 from (S)-5-amino-N-(7'-cyclopropylspiro[cyclopropane-1,1'-isochroman]-4'-yl)-N-methyl-1-((2-(trimethylsilyl)ethoxy)methyl)-6,8-dihydro-1H-furo[3,4-d]pyrrolo[3,2 -b]pyridine-2-carboxamide. $^1$H NMR (400 MHz, DMSO-d6) δ 11.59 (s, 1H), 7.03 (s, 1H), 6.86 (d, J=8.0 Hz, 1H), 6.66 (s, 1H), 6.47 (s, 1H), 5.80-5.70 (m, 1H), 5.63 (s, 2H), 5.11 (s, 2H), 4.88 (s, 2H), 4.10-3.95 (m, 2H), 3.01 (s, 3H), 1.81 (dd, J=9.1, 4.1 Hz, 1H), 1.14 (d, J=3.2 Hz, 3H), 1.01-0.91 (m, 1H), 0.87-0.75 (m, 2H), 0.65-0.49 (m, 2H). LC-MS $(M+H)^+$=431.2.

Example 173 & Example 174: (R)-5-amino-N-(1-(4-cyclopropyl-2-fluorophenyl)ethyl)-N-methyl-6,8-dihydro-1H-furo[3,4-d]pyrrolo[3,2-b]pyridine-2-carboxamide & (S)-5-amino-N-(1-(4-cyclopropyl-2-fluorophenyl)ethyl)-N-methyl-6,8-dihydro-1H-furo[3,4-d]pyrrolo[3,2-b]pyridine-2-carboxamide

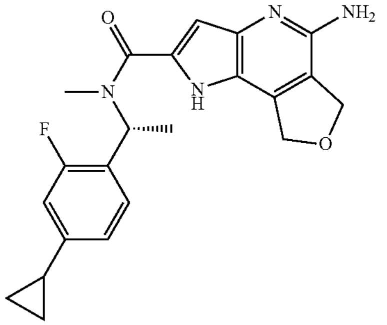

&

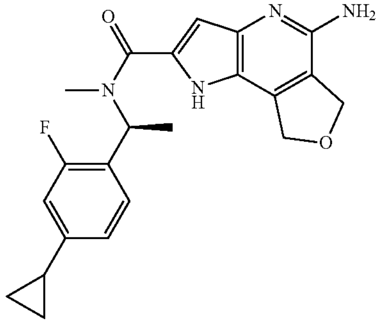

Step 1: 1-(4-cyclopropyl-2-fluorophenyl)ethan-1-one

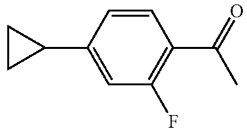

The title compound (730 mg, 89%) was prepared in a manner similar to that in Example 36 step 1 from 1-(4-bromo-2-fluorophenyl)ethan-1-one and cyclopropylboronic acid. LC-MS $(M+H)^+$=179.2.

Step 2: 1-(4-cyclopropyl-2-fluorophenyl)-N-methylethan-1-amine

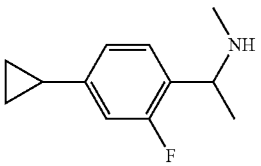

The title compound (90 mg, 28%) was prepared in a manner similar to that in Example 137 & Example 138 step 1 from 1-(4-cyclopropyl-2-fluorophenyl)ethan-1-one and $MeNH_2$. LC-MS $(M+H)^+$=194.1.

Step 3: 5-amino-N-(1-(4-cyclopropyl-2-fluorophenyl)ethyl)-N-methyl-1-((2-(trimethylsilyl)ethoxy)methyl)-6,8-dihydro-1H-furo[3,4-d]pyrrolo[3,2-b]pyridine-2-carboxamide

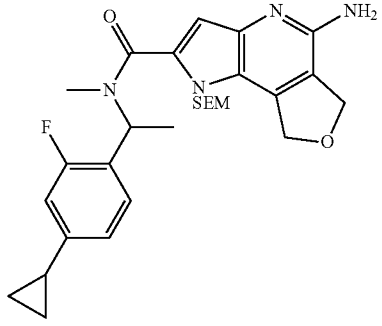 [SMILES: CC(c1ccc(C2CC2)cc1F)N(C)C(=O)c1cc2nc(N)c3c(c2n1COCC[Si](C)(C)C)COC3]

The title compound (220 mg, 76%) was prepared in a manner similar to that in Example 110 & Example 111 step 6 from 5-amino-1-((2-(trimethylsilyl)ethoxy)methyl)-6,8-dihydro-1H-furo[ 3,4-d]pyrrolo[3,2-b]pyridine-2-carboxylic acid and 1-(4-cyclopropyl-2-fluorophenyl)-N-methylethan-1-amine. LC-MS $(M+H)^+$=525.2.

Step 4: (R)-5-amino-N-(1-(4-cyclopropyl-2-fluorophenyl)ethyl)-N-methyl-6,8-dihydro-1H-furo[3,4-d]pyrrolo[3,2-b]pyridine-2-carboxamide & (S)-5-amino-N-(1-(4-cyclopropyl-2-fluorophenyl)ethyl)-N-methyl-6,8-dihydro-1H-furo[3,4-d]pyrrolo[3,2-b]pyridine-2-carboxamide Example 173 (4 mg, 2%) and Example 174 (8 mg, 5%) were prepared in a manner similar to that in Example 110 & Example 111 step 7 from 5-amino-N-(1-(4-cyclopropyl-2-fluorophenyl)ethyl)-N-methyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: CHIRALPAK AS-H; Column size: 4.6×100 mm, 5 μm; Mobile phase: 4 mM methanolic $NH_3$:$CO_2$, 1:9 to 1:1 in 3 min, 1:1 for 2 min, 1:1 to 1:9 in 0.1 min, 1:9 for 1.9 min; Flow: 2.0 mL/min; Temperature: 35° C.; back pressure: 1500 psi.

Example 173: Analytical SFC tR=2.83 min. $^1H$ NMR (400 MHz, DMSO-d6) δ 11.51 (s, 1H), 7.34 (t, J=8.1 Hz, 1H), 6.95 (d, J=8.1 Hz, 1H), 6.88-6.85 (m, 1H), 6.54 (s, 1H), 5.95 (d. J=6.1 Hz, 1H), 5.55 (s, 2H), 5.12 (s, 2H), 4.90 (s, 2H), 2.87 (s, 3H), 1.92 (s, 1H), 1.55 (s, 3H), 0.95 (d, J=6.4 Hz, 2H), 0.68 (d, J=3.1 Hz, 2H). LCMS $(M+H)^+$=395.1.

Example 174: Analytical SFC tR=3.12 min. $^1H$ NMR (400 MHz, DMSO-d6) δ 11.51 (s, 1H), 7.34 (t, J=8.0 Hz, 1H), 6.95 (d, J=8.0 Hz, 1H), 6.88-6.85 (m, 1H), 6.55 (s, 1H), 5.95 (d, J=6.4 Hz, 1H), 5.55 (s, 2H), 5.12 (s, 2H), 4.90 (s, 2H), 2.88 (s, 3H), 1.92 (s, 1H), 1.55 (s, 3H), 0.95 (d, J=6.3 Hz, 2H), 0.68 (d, J=3.1 Hz, 2H). LCMS $(M+H)^+$=395.1.

Example 175 & Example 176: (R)-5-amino-N—((R)-1-(4-cyclopropyl-2-fluorophenyl)ethyl)-N-ethyl-6-methyl-6,8-dihydro-1H-furo[3,4-d]pyrrolo[3,2-b]pyridine-2-carboxamide & (R)-5-amino-N—((S)-1-(4-cyclopropyl-2-fluorophenyl)ethyl)-N-ethyl-6-methyl-6,8-dihydro-1H-furo[3,4-d]pyrrolo[3,2-b]pyridine-2-carboxamide

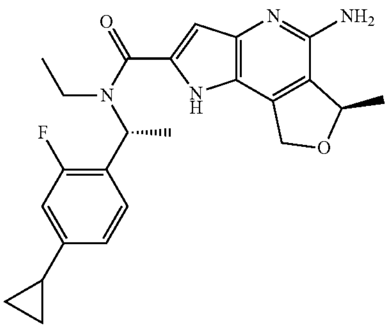

&

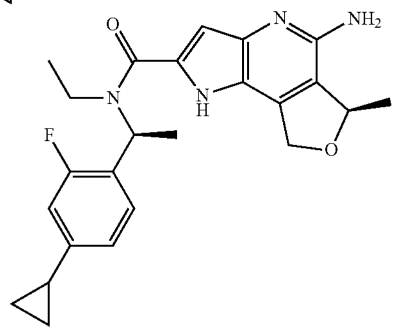

Step 1: 1-(4-cyclopropyl-2-fluorophenyl)-N-ethylethan-1-amine

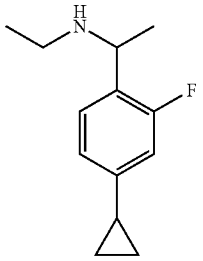

The title compound (300 mg, 52%) was prepared in a manner similar to that in Example 137 & Example 138 step 1 from 1-(4-cyclopropyl-2-fluorophenyl)ethan-1-one and $EtNH_2$. LC-MS $(M+H)^+$=208.2.

Step 2: (R)-5-amino-N—((R)-1-(4-cyclopropyl-2-fluorophenyl)ethyl)-N-ethyl-6-methyl-6,8-dihydro-1H-furo[3,4-d]pyrrolo[3,2-b]pyridine-2-carboxamide & (R)-5-amino-N—((S)-1-(4-cyclopropyl-2-fluorophenyl)ethyl)-N-ethyl-6-methyl-6,8-dihydro-1H-furo[3,4-d]pyrrolo[3,2-b]pyridine-2-carboxamide Example 175 (7 mg, 7%) and Example 176 (4 mg, 4%) were prepared in a manner similar to that in Example 124 & Example 125 step 2 from (R)-5-amino-6-methyl-6,8-dihydro-1H-furo[3,4-d]pyrrolo[3,2-b]pyridine-2-carboxylic acid and 1-(4-cyclopropyl-2-fluorophenyl)-N-ethylethan-1-amine, and the diastereomers were separated by chiral SFC.

Analytical chiral-SFC condition as below. Column: CHIRALPAK Cellulose-3; Column size: 4.6×100 mm, 5 μm; Mobile phase: 4 mM methanolic $NH_3$:$CO_2$, 1:9 to 1:1 in 3 min, 1:1 for 2 min. 1:1 to 1:9 in 0.1 min. 1:9 for 1.9 min; Flow: 2.0 mL/min; Temperature: 35° C.; back pressure: 1500 psi.

Example 175: Analytical SFC tR=2.71 min. $^1H$ NMR (400 MHz, DMSO-d6) δ 11.51 (s, 1H), 7.47-7.33 (m, 1H), 6.95 (d, J=8.0 Hz, 1H), 6.85 (d, J=12.0 Hz, 1H), 6.49 (s, 1H), 6.00-5.86 (m, 1H), 5.44 (s, 2H), 5.37-5.25 (m, 1H), 5.20-5.09 (m, 1H), 5.02 (d, J=13.9 Hz, 1H), 3.55-3.23 (m, 2H), 2.03-1.85 (m, 1H), 1.70-1.51 (m, 3H), 1.34 (d, J=6.1 Hz, 3H), 1.01-0.91 (m, 2H), 0.86 (t, J=6.8 Hz, 3H), 0.74-0.62 (m, 2H). LCMS $(M+H)^+$=423.5.

Example 176: Analytical SFC tR=3.62 min. $^1H$ NMR (400 MHz, DMSO-d6) δ 11.51 (s, 1H), 7.39 (t, J=8.1 Hz, 1H), 6.95 (d, J=7.9 Hz, 1H), 6.85 (d, J=12.2 Hz, 1H), 6.50 (s, 1H), 6.00-5.82 (m, 1H), 5.44 (s, 2H), 5.39-5.28 (m, 1H), 5.13 (dd, J=13.9, 3.2 Hz, 1H), 5.04 (d, J=13.9 Hz, 1H), 3.42-3.06 (m, 2H), 2.01-1.86 (m, 1H), 1.69-1.52 (m, 3H), 1.34 (d, J=6.1 Hz, 3H), 0.98-0.90 (m, 2H), 0.86 (t, J=6.8 Hz, 3H), 0.72-0.63 (m, 2H). LCMS $(M+H)^+$=423.5.

Example 177 & Example 178: (R)-5-amino-N-(1-(4-cyclopropyl-2-fluorophenyl)ethyl)-N-ethyl-6,8-dihydro-1H-furo[3,4-d]pyrrolo[3,2-b]pyridine-2-carboxamide & (S)-5-amino-N-(1-(4-cyclopropyl-2-fluorophenyl)ethyl)-N-ethyl-6,8-dihydro-1H-furo[3,4-d]pyrrolo[3,2-b]pyridine-2-carboxamide

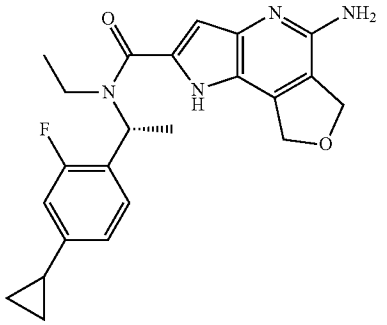

&

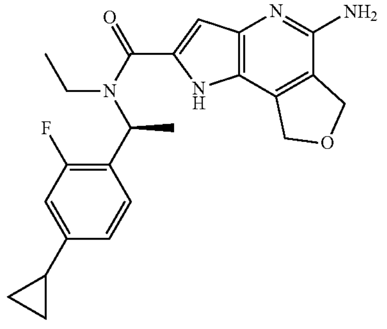

Step 1: 5-amino-N-(1-(4-cyclopropyl-2-fluorophenyl)ethyl)-N-ethyl-1-((2-(trimethylsilyl)ethoxy)methyl)-6,8-dihydro-1H-furo[3,4-d]pyrrolo[3,2-b]pyridine-2-carboxamide

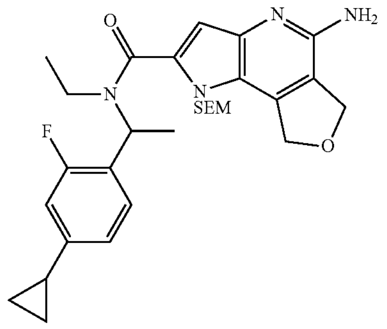 [SMILES: CCN(C(=O)c1cc2nc(N)c3c(c2n1COCC[Si](C)(C)C)COC3)C(C)c1ccc(C2CC2)cc1F]

The title compound (30 mg, 39%) was prepared in a manner similar to that in Example 110 & Example 111 step 6 from 5-amino-1-((2-(trimethylsilyl)ethoxy)methyl)-6,8-dihydro-1H-furo[3,4-d]pyrrolo[3,2-b]pyridine-2-carboxylic acid and 1-(4-cyclopropyl-2-fluorophenyl)-N-ethylethan-1-amine. LC-MS $(M+H)^+=538.2$.

Step 2: (R)-5-amino-N-(1-(4-cyclopropyl-2-fluorophenyl)ethyl)-N-ethyl-6,8-dihydro-1H-furo[3,4-d]pyrrolo[3,2-b]pyridine-2-carboxamide & (S)-5-amino-N-(1-(4-cyclopropyl-2-fluorophenyl)ethyl)-N-ethyl-6,8-dihydro-1H-furo[3,4-d]pyrrolo[3,2-b]pyridine-2-carboxamide Example 177 (1 mg, 3%) and Example 178 (1 mg, 3%) were prepared in a manner similar to that in Example 110 & Example 111 step 7 from 5-amino-N-(1-(4-cyclopropyl-2-fluorophenyl)ethyl)-N-ethyl-1-((2-(trimethylsilyl)ethoxy)methyl)-6,8-dihydro-1H-furo[3,4-d]pyrrolo[3,2-b]pyridine-2-carboxamide, and the enantiomers were separated by chiral SFC.

Analytical chiral-SFC condition as below. Column: CHIRALPAK AS-H; Column size: 4.6×100 mm, 5 μm; Mobile phase: 4 mM methanolic $NH_3$:$CO_2$, 1:9 to 1:1 in 3 min, 1:1 for 2 min. 1:1 to 1:9 in 0.1 min, 1:9 for 1.9 min; Flow: 2.0 mL/min; Temperature: 35° C.; back pressure: 1500 psi.

Example 177: Analytical SFC tR=2.66 min. $^1$H NMR (400 MHz, DMSO-d6) δ 11.48 (s, 1H), 7.50-7.31 (m, 1H), 6.95 (d, J=7.9 Hz, 1H), 6.85 (d, J=11.4 Hz, 1H), 6.50 (s, 1H), 6.00-5.83 (m, 1H), 5.50 (s, 2H), 5.12 (s, 2H), 4.91 (s, 2H), 3.50-3.20 (m, 2H), 1.98-1.88 (m, 1H), 1.61 (d, J=6.2 Hz, 3H), 0.99-0.92 (m, 2H), 0.91-0.83 (m, 3H), 0.72-0.64 (m, 2H). LCMS $(M+H)^+=409.4$.

Example 178: Analytical SFC tR=2.93 min. $^1$H NMR (400 MHz, DMSO-d6) δ 11.48 (s, 1H), 7.50-7.31 (m, 1H), 6.95 (d, J=7.9 Hz, 1H), 6.85 (d, J=11.4 Hz, 1H), 6.50 (s, 1H), 6.00-5.83 (m, 1H), 5.50 (s, 2H), 5.12 (s, 2H), 4.91 (s, 2H), 3.50-3.20 (m, 2H), 1.98-1.88 (m, 1H), 1.61 (d, J=6.2 Hz, 3H), 0.99-0.92 (m, 2H), 0.91-0.83 (m, 3H), 0.72-0.64 (m, 2H). LCMS $(M+H)^+=409.4$.

Example 179: (S)-5-amino-N-(7'-bromospiro[cyclopropane-1,1'-isochroman]-4'-yl)-N-methyl-6,8-dihydro-1H-furo[3,4-d]pyrrolo[3,2-b]pyridine-2-carboxamide

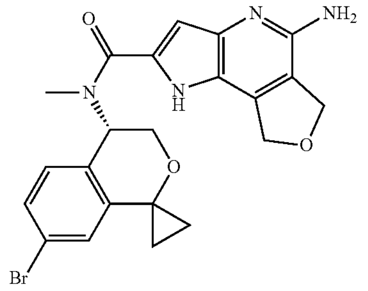 [SMILES: CN(C(=O)c1cc2nc(N)c3c(c2[nH]1)COC3)[C@@H]1COC2(CC2)c2cc(Br)ccc21]

Step 1: 1-(5-bromo-2-iodophenyl)cyclopropan-1-ol

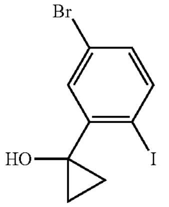 [SMILES: OC1(c2cc(Br)ccc2I)CC1]

The title compound (8.5 g, 29%) was prepared in a manner similar to that in Example 167 & Example 168 step 3 from methyl 5-bromo-2-iodobenzoate. LC-MS $(M+H)^+=338.8$.

Step 2: 2-(1-(allyloxy)cyclopropyl)-4-bromo-1-iodobenzene

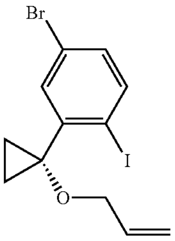

The title compound (9.4 g, 99%) was prepared in a manner similar to that in Example 167 & Example 168 step 4 from 1-(5-bromo-2-iodophenyl)cyclopropan-1-ol and allyl bromide. LC-MS $(M+H)^+=379.1$.

Step 3: 7'-bromo-4'-methylenespiro[cyclopropane-1, 1'-isochromane]

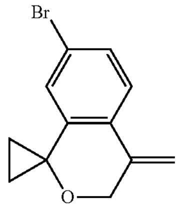

The title compound (4.6 g, 72%) was prepared in a manner similar to that in Example 167 & Example 168 step 5 from 2-(1-(allyloxy)cyclopropyl)-4-bromo-1-iodobenzene.

Step 4: 7'-bromospiro[cyclopropane-1,1'-isochroman]-4'-one

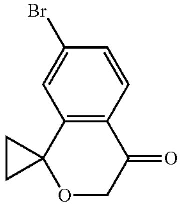 [SMILES: O=C1COC2(CC2)c2cc(Br)ccc21]

The title compound (3.5 g, 75%) was prepared in a manner similar to that in Example 167 & Example 168 step 6 from 7'-bromo-4'-methylenespiro[cyclopropane-1,1'-isochromane]. $^1$H NMR (400 MHz, DMSO-d6) δ 7.88-7.82 (m, 1H), 7.70-7.63 (m, 1H), 7.38 (d, J=1.7 Hz, 1H), 4.43 (s, 2H), 1.45-1.31 (m, 4H). LC-MS $(M+H)^+$=253.1.

Step 5: (R)-7'-bromospiro[cyclopropane-1,1'-isochroman]-4'-ol

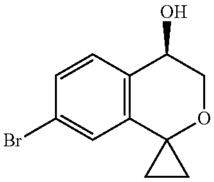

The title compound (2.4 g, 95%) was prepared in a manner similar to that in Example 84 step 1 from 7'-bromospiro[cyclopropane-1,1'-isochroman]-4'-one. LC-MS $(M+H)^+$=255.1.

Step 6: (S)—N-(7'-bromospiro[cyclopropane-1,1'-isochroman]-4'-yl)-N-methyl-2-nitrobenzenesulfonamide

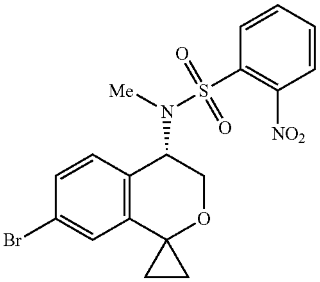 [SMILES: CN([C@@H]1COC2(CC2)c2cc(Br)ccc21)S(=O)(=O)c1ccccc1[N+](=O)[O-]]

The title compound (1.0 g, 93%) was prepared in a manner similar to that in Example 167 & Example 168 step 8 from (R)-7'-bromospiro[cyclopropane-1,1'-isochroman]-4'-ol and N-methyl-2-nitro-benzenesulfonamide. LC-MS $(M+H)^+$=453.1.

Step 7: (S)-7'-bromo-N-methylspiro[cyclopropane-1,1'-isochroman]-4'-amine

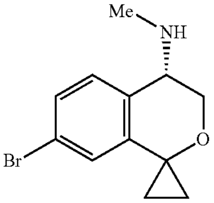 [SMILES: CN[C@@H]1COC2(CC2)c2cc(Br)ccc21]

The title compound (550 mg, 93%) was prepared in a manner similar to that in Example 167 & Example 168 step 9 from (S)—N-(7'-bromospiro[cyclopropane-1,1'-isochroman]-4'-yl)-N-methyl-2-nitrobenzenesulfonamide. LC-MS $(M+H)^+$=268.1.

Step 8: (S)-5-amino-N-(7'-bromospiro[cyclopropane-1,1'-isochroman]-4'-yl)-N-methyl-1-((2-(trimethylsilyl)ethoxy methyl)-6,8-dihydro-1H-furo[3,4-d]pyrrolo[3,2-b]pyridine-2-carboxamide

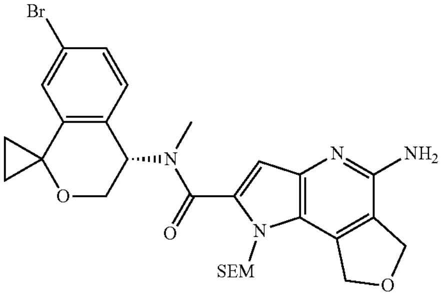 [SMILES: CN(C(=O)c1cc2nc(N)c3c(c2n1COCC[Si](C)(C)C)COC3)[C@@H]1COC2(CC2)c2cc(Br)ccc21]

The title compound (130 mg, 84%) was prepared in a manner similar to that in Example 167 & Example 168 step 10 from (S)-7'-bromo-N-methylspiro[cyclopropane-1,1'-isochroman]-4'-amine and 5-amino-1-((2-(trimethylsilyl) ethoxy)methyl)-6,8-dihydro-1H-furo[3,4-d]pyrrolo[3,2-b] pyridine-2-carboxylic acid. LC-MS $(M+H)^+$=599.1.

Step 9: (S)-5-amino-N-(7'-bromospiro[cyclopropane-1,1'-isochroman]-4'-yl)-N-methyl-6,8-dihydro-1H-furo[3,4-d]pyrrolo[3,2-b]pyridine-2-carboxamide Example 179 (53 mg, 52%) was prepared in a manner similar to that in Example 167 & Example 168 step 11 from (S)-5-amino-N-(7'-bromospiro[cyclopropane-1,1'-isochroman]-4'-yl)-N-methyl-1-((2-(trimethylsilyl)ethoxy)methyl)-6,8-dihydro-1H-furo[3,4-d]pyrrolo[3,2-b]pyridine-2-carboxamide. $^1H$ NMR (400 MHz, DMSO-d6) δ 11.56 (s, 1H), 7.39 (dd, J=8.3, 1.7 Hz, 1H), 7.17-7.04 (m, 1H), 7.01 (d, J=1.7 Hz, 1H), 6.72-6.43 (m, 1H), 5.83-5.59 (m, 1H), 5.54 (s, 2H), 5.10 (s, 2H), 4.88 (s, 2H), 4.26-3.88 (m, 2H), 3.15-2.64 (m, 3H), 1.33-1.00 (m, 4H). LC-MS $(M+H)^+$= 469.1.

Example 180: (R)-5-amino-N—((S)-7'-bromospiro[cyclopropane-1,1'-isochroman]-4'-yl)-N,6-dimethyl-6,8-dihydro-1H-furo[3,4-d]pyrrolo[3,2-b]pyridine-2-carboxamide

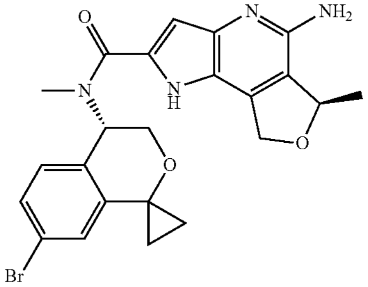 [SMILES: C[C@H]1OCc2c1c(N)nc1cc(C(=O)N(C)[C@@H]3COC4(CC4)c4cc(Br)ccc43)[nH]c21]

Example 180 (54 mg, 50%) was prepared in a manner similar to that in Example 124 & Example 125 step 2 from (S)-7'-bromo-N-methylspiro[cyclopropane-1,1'-isochroman]-4'-amine and (R)-5-amino-6-methyl-6,8-dihydro-1H-furo[3,4-d]pyrrolo[3,2-b]pyridine-2-carboxylic acid. $^1H$ NMR (400 MHz, DMSO-d6) δ 11.55 (s, 1H), 7.40 (dd, J=8.3, 1.8 Hz, 1H), 7.21-7.06 (m, 1H), 7.01 (d, J=1.7 Hz, 1H), 6.79-6.38 (m, 1H), 5.86-5.52 (m, 1H), 5.44 (s, 2H), 5.36-5.23 (m, 1H), 5.12 (dd. J=13.9, 3.4 Hz, 1H), 5.02 (d, J=13.0 Hz, 1H), 4.30-3.85 (m, 2H), 3.13-2.57 (m, 3H), 1.32 (d, J=6.1 Hz, 3H), 1.30-1.10 (m, 4H). LC-MS $(M+H)^+$= 483.1.

Example 181: (R)-5-amino-N-methyl-N-(1-methyl-7-(trifluoromethyl)-1,2,3,4-tetrahydroquinolin-4-yl)-6,8-dihydro-1H-furo[3,4-d]pyrrolo[3,2-b]pyridine-2-carboxamide

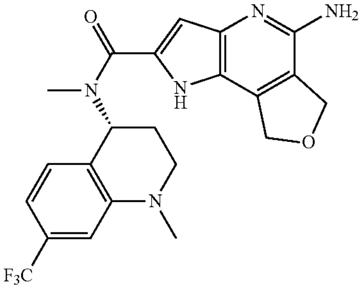 [SMILES: CN1CC[C@@H](N(C)C(=O)c2cc3nc(N)c4c(c3[nH]2)COC4)c2ccc(C(F)(F)F)cc21]

Step 1: tert-butyl 7-iodo-4-oxo-3,4-dihydroquinoline-1(2H)-carboxylate

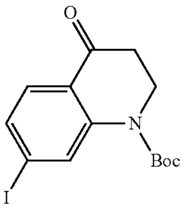 [SMILES: CC(C)(C)OC(=O)N1CCC(=O)c2ccc(I)cc21]

To a solution of tert-butyl 7-bromo-4-oxo-3,4-dihydroquinoline-1(2H)-carboxylate (3 g, 9.2 mmol) in 1,4-dioxane (100 mL) was added NaI (5.52 g, 36.8 mmol), CuI (876 mg, 4.6 mmol) and trans-N,N'-dimethylcyclohexane-1,2-diamine (654 mg, 4.6 mmol). The mixture was stirred at 100° C. for 16 h under nitrogen, then cooled to room temperature. Solid was filtered off and the filtrate was concentrated under vacuum. The residue was partitioned between water (200 mL) and EtOAc (200 mL). The organic layer was washed with brine (2×100 mL), dried over $Na_2SO_4$, filtered and concentrated under reduced pressure. The residue was purified by silica gel chromatography (PE:EtOAc=10:1) to give the title compound (2.2 g, 64%). LC-MS $(M+H)^+$=374.1.

Step 2: tert-butyl 4-oxo-7-(trifluoromethyl)-3,4-dihydroquinoline-1(2H)-carboxylate

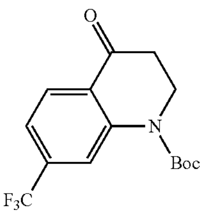 [SMILES: CC(C)(C)OC(=O)N1CCC(=O)c2ccc(C(F)(F)F)cc21]

To a solution of tert-butyl 7-iodo-4-oxo-3,4-dihydroquinoline-1(2H)-carboxylate (2.2 g, 5.9 mmol) in DMF (50 mL) was added CuI (1.13 g, 5.9 mmol) and methyl 2,2-difluoro-2-(fluorosulfonyl)acetate (4.53 g, 23.6 mmol). The mixture was stirred for 16 h at 100° C. under nitrogen and cooled to room temperature. The mixture was filtered off and the filtrate was partitioned between saturated $NaHCO_3$ solution (100 mL) and EtOAc (100 mL). The organic layer was washed with brine (2×100 mL), dried over $Na_2SO_4$, filtered and concentrated under vacuum. The residue was purified by silica gel chromatography (PE:EtOAc=10:1) to give the title compound (1.5 g, 81%). LC-MS $(M+H)^+$=316.4.

Step 3: tert-butyl (S)-4-hydroxy-7-(trifluoromethyl)-3,4-dihydroquinoline-1(2H)-carboxylate

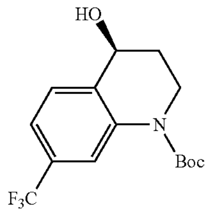 [SMILES: CC(C)(C)OC(=O)N1CC[C@H](O)c2ccc(C(F)(F)F)cc21]

The title compound (1.5 g, 99%) was prepared in a manner similar to that in Example 84 step 1 from tert-butyl 4-oxo-7-(trifluoromethyl)-3,4-dihydroquinoline-1(2H)-carboxylate. LC-MS $(M+H)^+$=318.2.

Step 4: tert-butyl (R)-4-((N-methyl-2-nitrophenyl)sulfonamido)-7-(trifluoromethyl)-3,4-dihydroquinoline-1(2H)-carboxylate

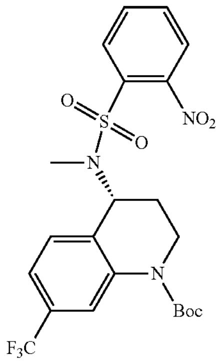 [SMILES: CN([C@@H]1CCN(C(=O)OC(C)(C)C)c2cc(C(F)(F)F)ccc21)S(=O)(=O)c1ccccc1[N+](=O)[O-]]

The title compound (3.0 g, 100%) was prepared in a manner similar to that in Example 91 step 6 from tert-butyl (S)-4-hydroxy-7-(trifluoromethyl)-3,4-dihydroquinoline-1(2H)-carboxylate and N-methyl-2-nitro-benzenesulfonamide. LC-MS $(M+H)^+$=516.3.

Step 5: (R)—N-methyl-2-nitro-N-(7-(trifluoromethyl)-1,2,3,4-tetrahydroquinolin-4-yl)benzenesulfonamide

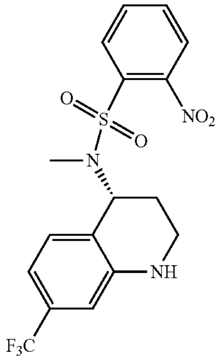 [SMILES: CN([C@@H]1CCNc2cc(C(F)(F)F)ccc21)S(=O)(=O)c1ccccc1[N+](=O)[O-]]

To a solution of tert-butyl (R)-4-((N-methyl-2-nitrophenyl)sulfonamido)-7-(trifluoromethyl)-3,4-dihydroquinoline-1(2H)-carboxylate (3.0 g, 5.82 mmol) in DCM (20 mL) was added HCl in dioxane (4 M, 20 mL). The mixture was stirred at 25° C. for 3 h. The mixture was concentrated under vacuum. The residue was partitioned between saturated $NaHCO_3$ solution (100 mL) and EtOAc (100 mL). The organic layer was washed with brine (100 mL), dried over $Na_2SO_4$, filtered and concentrated under vacuum. The residue was purified by silica gel chromatography (DCM:MeOH=20:1) to give the title compound (1.4 g, 58%). LC-MS $(M+H)^+$=416.1.

Step 6: (R)—N-methyl-N-(1-methyl-7-(trifluoromethyl)-1,2,3,4-tetrahydroquinolin-4-yl)-2-nitrobenzenesulfonamide

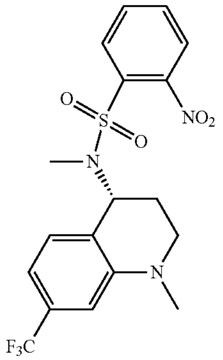 [SMILES: CN1CC[C@@H](N(C)S(=O)(=O)c2ccccc2[N+](=O)[O-])c2ccc(C(F)(F)F)cc21]

To a solution of (R)—N-methyl-2-nitro-N-(7-(trifluoromethyl)-1,2,3,4-tetrahydroquinolin-4-yl)benzenesulfonamide (520 mg, 1.25 mmol) in MeOH (10 mL) was added paraformaldehyde (188 mg, 6.26 mmol), $NaBH_3CN$ (237 mg, 3.76 mmol) and AcOH (376 mg, 6.26 mmol). The mixture was stirred for 16 h at 60° C. then cooled to room temperature. The reaction was quenched with saturated $NaHCO_3$ solution (100 mL) and then extracted with EtOAc (100 mL). The organic layer was washed with brine (100 mL), dried over $Na_2SO_4$, filtered and concentrated under reduced pressure. The residue was purified by silica gel chromatography (DCM:MeOH=30:1) to give the title compound (535 mg, 100%). LC-MS $(M+H)^+$=430.3.

Step 7: (R)—N,1-dimethyl-7-(trifluoromethyl)-1,2,3,4-tetrahydroquinolin-4-amine

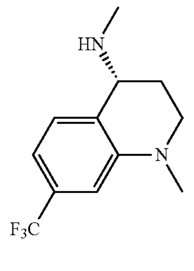 [SMILES: CN[C@@H]1CCN(C)c2cc(C(F)(F)F)ccc21]

The title compound (150 mg, 49%) was prepared in a manner similar to that in Example 167 & Example 168 step 9 from (R)—N-methyl-N-(1-methyl-7-(trifluoromethyl)-1,2,3,4-tetrahydroquinolin-4-yl)-2-nitrobenzenesulfonamide LC-MS $(M+H)^+$=245.1.

Step 8: (R)-5-amino-N-methyl-N-(1-methyl-7-(trifluoromethyl)-1,2,3,4-tetrahydroquinolin-4-yl)-1-((2-(trimethylsilyl)ethoxy)methyl)-6,8-dihydro-1H-furo[3,4-d]pyrrolo[3,2-b]pyridine-2-carboxamide

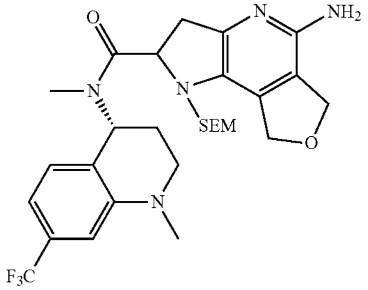 [SMILES: CN1CC[C@@H](N(C)C(=O)C2Cc3nc(N)c4c(c3N2COCC[Si](C)(C)C)COC4)c2ccc(C(F)(F)F)cc21]

The title compound (105 mg, 69%) was prepared in a manner similar to that in Example 167 & Example 168 step 10 from (R)—N,1-dimethyl-7-(trifluoromethyl)-1,2,3,4-tetrahydroquinolin-4-amine and 5-amino-1-((2-(trimethylsilyl)ethoxy)methyl)-6,8-dihydro-1H-furo[3,4-d]pyrrolo[3,2-b]pyridine-2-carboxylic acid. LC-MS $(M+H)^+$=576.2.

Step 9: (R)-5-amino-N-methyl-N-(1-methyl-7-(trifluoromethyl)-1,2,3,4-tetrahydroquinolin-4-yl)-6,8-dihydro-1H-furo[3,4-d]pyrrolo[3,2-b]pyridine-2-carboxamide Example 181 (51 mg, 63%) was prepared in a manner similar to that in Example 167 & Example 168 step 11 from (R)-5-amino-N-methyl-N-(1-methyl-7-(trifluoromethyl)-1,2,3,4-tetrahydroquinolin-4-yl)-1-((2-(trimethylsilyl)ethoxy)methyl)-6,8-dihydro-1H-furo[3,4-d]pyrrolo[3,2-b]pyridine-2-carboxamide. $^1$H NMR (400 MHz, DMSO-d6) δ 11.59 (s, 1H), 7.18-6.78 (m, 2H), 6.80-6.23 (m, 2H), 5.94-5.68 (m, 1H), 5.58 (s, 2H), 5.20-5.03 (m, 2H), 4.88 (s, 2H), 3.57-3.31 (m, 2H), 3.14-2.69 (m, 6H), 2.27-1.94 (m, 2H). LC-MS $(M+H)^+$=446.37.

Cell Killing in HCT116 Isogenic Pair

HCT116 cell line (ATCC, CCL-247) was isolated from the colon of an adult male with colon cancer. It has a mutation in codon 13 of the ras proto-oncogene and can be used as a positive control for PCR assays of mutation in this codon. HCT116-MTAP-KO was knocked-out-MTAP-gene based HCT116, and a single clone was passed for this assay. HCT116-mock-RNA-KO was knocked-out-mock-gene based HCT116 with MTAP wildtype genotype. The base medium for HCT116 isogenic pair is RPMI 1640, HEPES (Gibco, 22400105). To make the complete growth medium, added the following components to the base medium: fetal bovine serum to a final concentration of 10% (Gibco, 10099-141C). The cell line was grown in a humidified 5% $CO_2$ atmosphere at 37° C. and regularly tested for the presence of *mycoplasma* with MpcoAlert™ PLUS *Mycoplasma* Detection Kit (Lonzak LT07-710).

Experimental

Seeded HCT116-mock-RNA-KO (4E2/well) or HCT116-MTAP-KO (4E2/well) cells into a 96-well plate (Greiner: 655090), 100 μL/well.

Incubated at 37° C., 5% $CO_2$, overnight.

Added 50 μL fresh growth medium containing serial dilution of test compounds for a final test compound concentration of 0-10 μM to each well.

Incubated at 37° C., 5% $CO_2$, 6 days.

The cell viability was detected by Cell Titer-Glo (Promega, G7573). Added 70 μL of CellTiter-Glo® reagent in each well.

Incubated at room temperature for 10 minutes to stabilize luminescent signal.

Analyzed with Microplate Reader (TECAN, SPARK) and fit $IC_{50}$ using Prism® 9.

The compounds disclosed herein showed cell killing activity values as in Table 1.

TABLE 1

Cell killing $IC_{50}$ (nM) for the compounds disclosed herein

| Example | Cell killing $IC_{50}$ (nM) in HCT116-MTAP-KO | Cell killing $IC_{50}$ (nM) in HCT116-mock-RNA-KO | Example | Cell killing $IC_{50}$ (nM) in HCT116-MTAP-KO | Cell killing $IC_{50}$ (nM) in HCT116-mock-RNA-KO |
|---|---|---|---|---|---|
| 1 | <1.5* | 4.6 | 2 | 3.3 | 23 |
| 3 | 2.4 | 221 | 4 | 2.3 | 99 |
| 5 | 4.0 | 76 | 6 | 11 | 40 |
| 7 | 30 | 3143 | 8 | 34 | 2746 |
| 9 | 46 | 3445 | 10 | 4.6 | 247 |
| 11 | 3.8 | 69 | 12 | 29 | 1906 |
| 13 | 4.6 | 251 | 14 | <1.5* | 554 |

TABLE 1-continued

Cell killing $IC_{50}$ (nM) for the compounds disclosed herein

| Example | Cell killing $IC_{50}$ (nM) in HCT116-MTAP-KO | Cell killing $IC_{50}$ (nM) in HCT116-mock-RNA-KO | Example | Cell killing $IC_{50}$ (nM) in HCT116-MTAP-KO | Cell killing $IC_{50}$ (nM) in HCT116-mock-RNA-KO |
|---|---|---|---|---|---|
| 15 | 8.1 | 225 | 16 | 1.0 | 165 |
| 17 | 8.2 | 1054 | 18 | 1.8 | 96 |
| 19 | <1.5* | 185 | 20 | 658 | 4004 |
| 21 | <1.5* | 7.0 | 22 | <1.5* | 11 |
| 23 | 4.8 | 81 | 24 | 103 | 8538 |
| 25 | 96 | 2002 | 26 | 14 | 1873 |
| 27 | 2.4 | 284 | 28 | 11 | 1903 |
| 29 | 1.3 | 81 | 30 | 0.8 | 22 |
| 31 | 1.2 | 7.1 | 32 | 3.9 | 451 |
| 33 | 210 | >10000 | 34 | 7.4 | 1346 |
| 35 | 11 | 1530 | 36 | 5.8 | 445 |
| 37 | 13 | 1685 | 38 | 6.3 | 665 |
| 39 | 1174 | >10000 | 40 | 13 | 2491 |
| 41 | 6.6 | 586 | 42 | 24 | 2498 |
| 43 | 2.9 | 207 | 44 | 8.2 | 568 |
| 45 | 7.2 | 856 | 46 | 9.0 | 854 |
| 47 | 4.4 | 605 | 48 | 8.4 | 625 |
| 49 | 6.1 | 835 | 50 | 8.6 | 1360 |
| 51 | 7.8 | 558 | 52 | 4.6 | 419 |
| 53 | 34 | >10000 | 54 | 12 | 1362 |
| 55 | 1643 | >10000 | 56 | 5.0 | 146 |
| 57 | 958 | >10000 | 58 | 1077 | >10000 |
| 59 | 110 | >10000 | 60 | 7.3 | 857 |
| 61 | 808 | >10000 | 62 | 17 | 2084 |
| 63 | 22 | 2502 | 64 | 362 | >10000 |
| 65 | 17 | 2455 | 66 | 20 | 2519 |
| 67 | 4.2 | 453 | 68 | 9.0 | 1693 |
| 69 | 26 | 2704 | 70 | 12 | 1184 |
| 71 | 728 | 6155 | 72 | 8.2 | 1007 |
| 73 | 34 | 2490 | 74 | 1066 | >10000 |
| 75 | 41 | >10000 | 76 | 2108 | >10000 |
| 77 | 51 | >10000 | 78 | 624 | 2931 |
| 79 | 525 | 3280 | 80 | 351 | >10000 |
| 81 | 9.7 | 1025 | 82 | 13 | 1841 |
| 83 | 7.2 | 556 | 84 | 10 | 2202 |
| 85 | 113 | >10000 | 86 | 1903 | >10000 |
| 87 | 67 | >10000 | 88 | 1412 | >10000 |
| 89 | 4.1 | 446 | 90 | 29 | 5446 |
| 91 | 32 | 3877 | 92 | 49 | 2049 |
| 93 | 165 | >10000 | 94 | 3.8 | 578 |
| 95 | 18 | 1779 | 96 | 7.2 | 1933 |
| 97 | 17 | 2886 | 98 | 11 | 1858 |
| 99 | 722 | >10000 | 100 | 1.4 | 136 |
| 101 | 339 | 2091 | 102 | 1.1 | 77 |
| 103 | 272 | 2448 | 104 | 18 | 2730 |
| 105 | 13 | 930 | 106 | 11 | 2631 |
| 107 | 20 | 1094 | 108 | 31 | 3422 |
| 109 | 24 | 1790 | 110 | 12 | 2488 |
| 111 | 2200 | >10000 | 112 | 59 | >10000 |
| 113 | 1609 | >10000 | 114 | 3629 | >10000 |
| 115 | 43 | 6815 | 116 | 6.9 | 269 |
| 117 | 6.5 | 609 | 118 | 2246 | >10000 |
| 119 | 9.8 | 1591 | 120 | 5.6 | 992 |
| 121 | 586 | >10000 | 122 | 2224 | 5780 |
| 123 | 46 | 4912 | 124 | 22 | 2472 |
| 125 | 365 | 7457 | 126 | 11 | 1719 |
| 127 | 236 | 5896 | 128 | 6.0 | 1054 |
| 129 | 1182 | >10000 | 130 | 8.5 | 1093 |
| 131 | 1834 | >10000 | 132 | 45 | >10000 |
| 133 | 13 | 1337 | 134 | 336 | 2883 |
| 135 | 26 | 2133 | 136 | 245 | 3518 |
| 137 | 44 | 3023 | 138 | 913 | 3240 |
| 139 | 12 | 2397 | 140 | 270 | 3026 |
| 141 | 149 | >10000 | 142 | 2.6 | 477 |
| 143 | 11 | 1381 | 144 | 543 | >10000 |
| 145 | 26 | 3426 | 146 | 316 | >10000 |
| 147 | 1229 | 5422 | 148 | 19 | 2437 |
| 149 | 2678 | >10000 | 150 | 32 | 2793 |
| 151 | 85 | >10000 | 152 | 1277 | >10000 |
| 153 | 10 | 610 | 154 | 1626 | 8516 |
| 155 | 19 | 2253 | 156 | 523 | >10000 |
| 157 | 64 | >10000 | 158 | 2018 | >10000 |

TABLE 1-continued

Cell killing $IC_{50}$ (nM) for the compounds disclosed herein

| Example | Cell killing $IC_{50}$ (nM) in HCT116-MTAP-KO | Cell killing $IC_{50}$ (nM) in HCT116-mock-RNA-KO | Example | Cell killing $IC_{50}$ (nM) in HCT116-MTAP-KO | Cell killing $IC_{50}$ (nM) in HCT116-mock-RNA-KO |
|---|---|---|---|---|---|
| 159 | 36 | 2577 | 160 | 598 | >10000 |
| 161 | 39 | 2799 | 162 | 186 | >10000 |
| 163 | >10000 | >10000 | 164 | 145 | >10000 |
| 165 | 17 | 2573 | 166 | 19 | 2150 |
| 167 | 697 | 3325 | 168 | 8.4 | 2108 |
| 169 | 565 | 2112 | 170 | 4.4 | 1012 |
| 171 | 39 | 3034 | 172 | 33 | 5050 |
| 173 | 67 | 5920 | 174 | 478 | 6070 |
| 175 | 14 | 704 | 176 | 452 | 1785 |
| 177 | 74 | 2687 | 178 | 1039 | 3269 |
| 179 | 24 | 4388 | 180 | 20 | 3567 |
| 181 | 15 | 1796 | | | |

*More than 50% viability inhibition at tested concentration without a full curve for $IC_{50}$ determination The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

What is claimed is:

1. A compound or pharmaceutically acceptable salt thereof selected from:

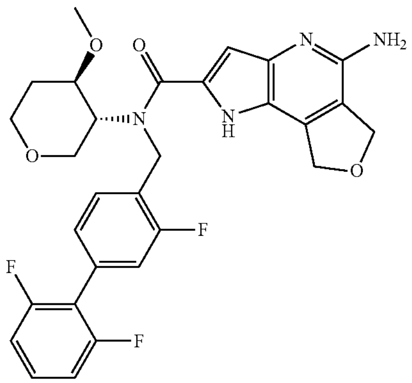

-continued

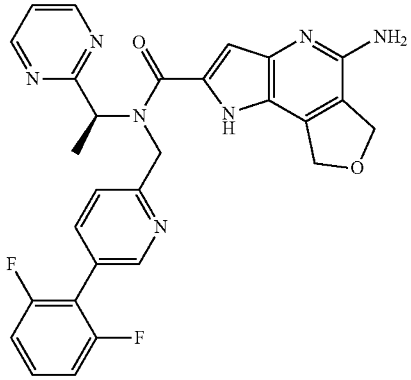

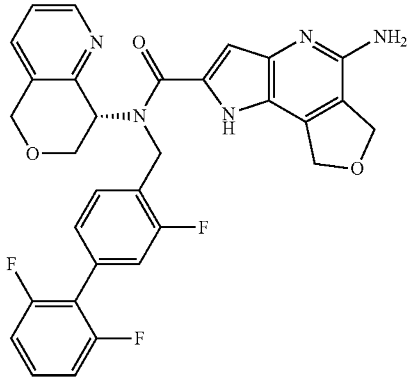

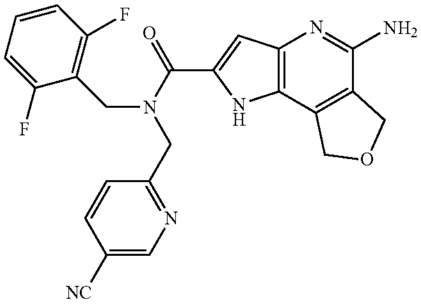

-continued
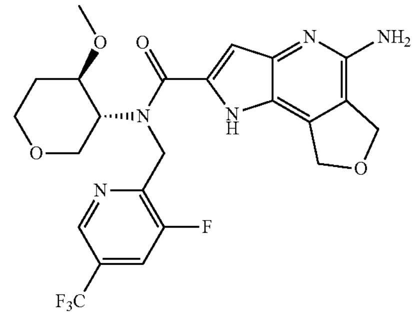
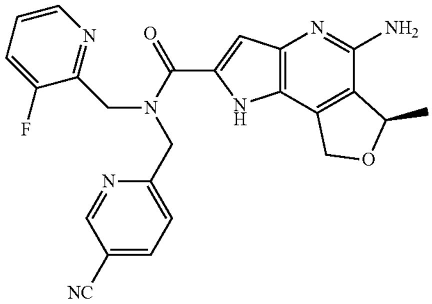
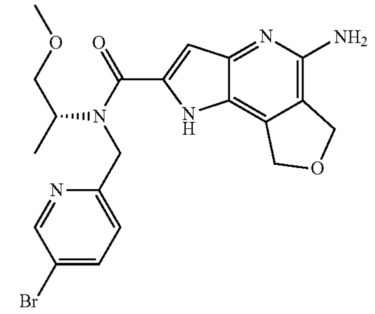
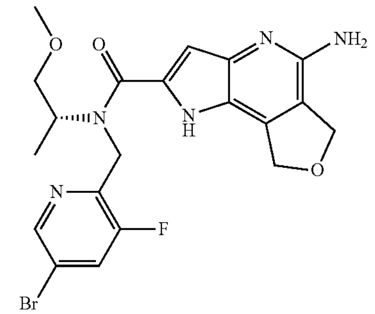
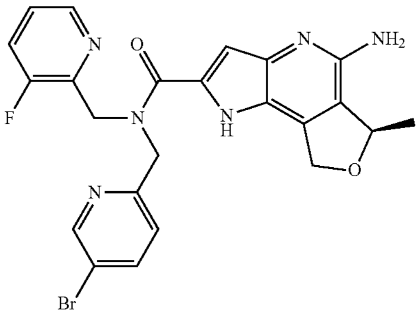
-continued
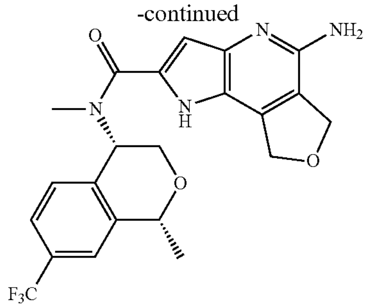
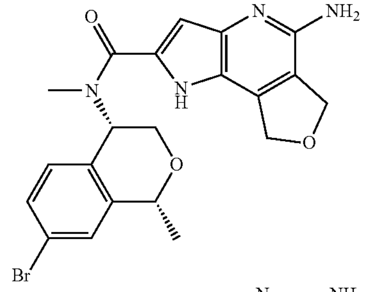
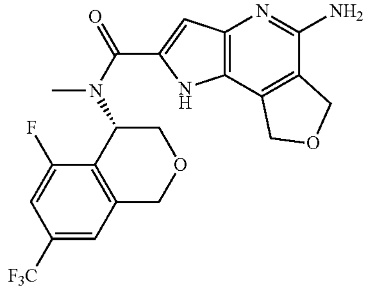
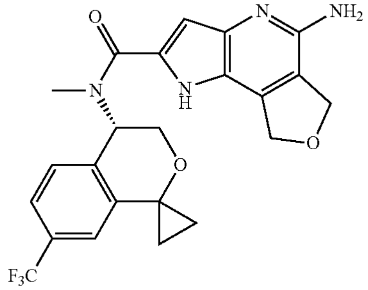
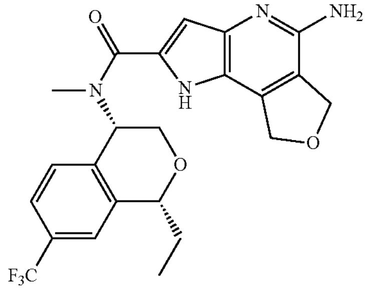
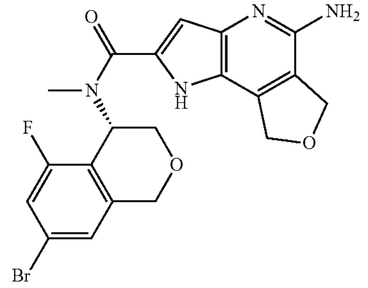

-continued

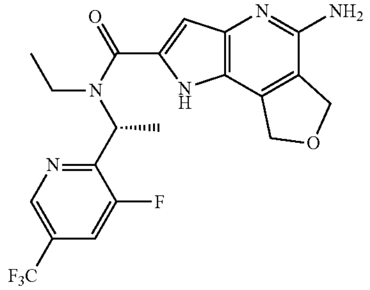

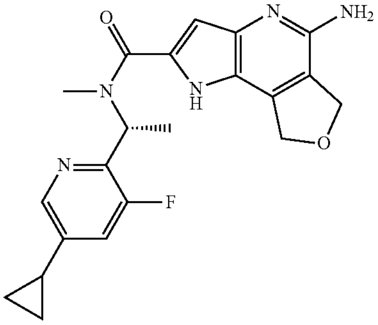

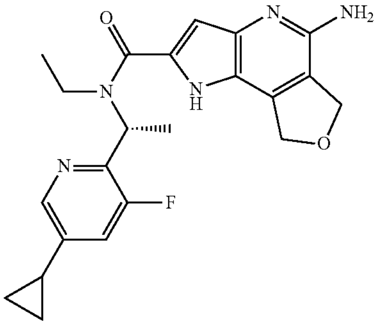

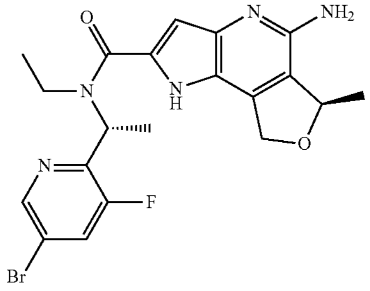

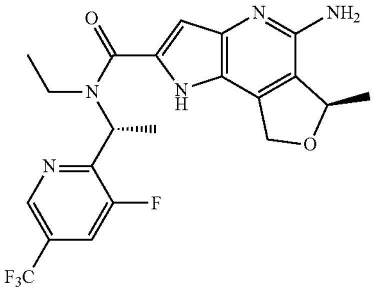

-continued

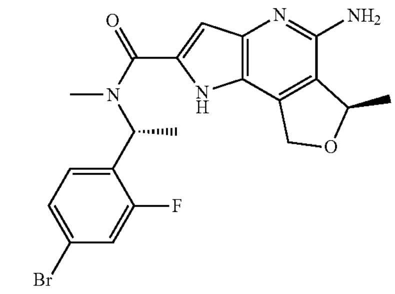

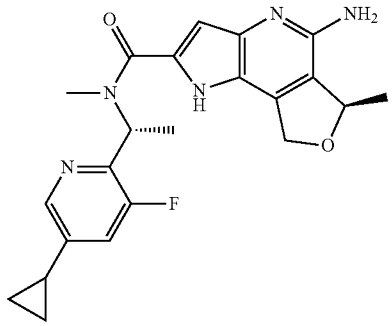

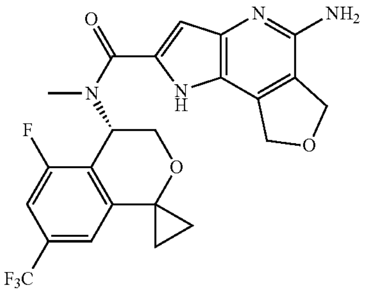

and

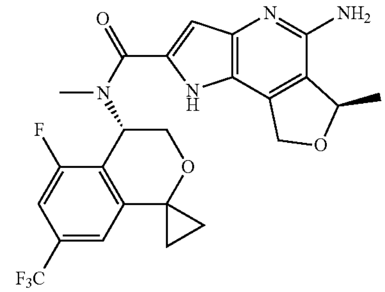

.

2. A method of inhibiting PRMT5 activity or treating a disease modulated by PRMT5, comprising administering to a subject in need thereof an effective amount of a compound of claim 1, or a pharmaceutically acceptable salt thereof.

3. A method of treating cancer, comprising administering to a subject in need thereof an effective amount of a compound of claim 1, or a pharmaceutically acceptable salt thereof.

4. A pharmaceutical composition comprising a compound of claim 1, or a pharmaceutically acceptable salt thereof, and a pharmaceutically acceptable excipient.

5. The compound of claim 1, wherein the compound is:

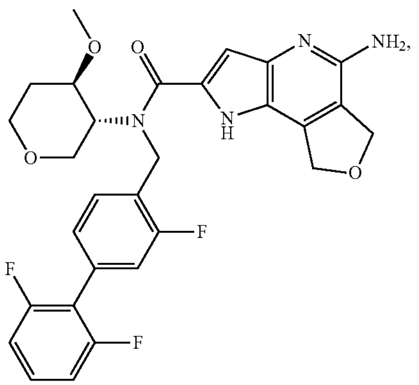 [SMILES: CO[C@@H]1CCOC[C@H]1N(Cc1ccc(-c2c(F)cccc2F)cc1F)C(=O)c1cc2nc(N)c3c(c2[nH]1)COC3]

or a pharmaceutically acceptable salt thereof.

6. The compound of claim 1, wherein the compound is:

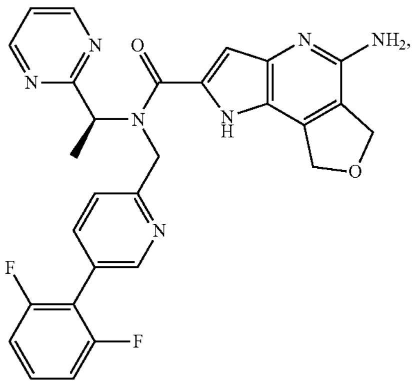 [SMILES: C[C@@H](c1ncccn1)N(Cc1ccc(-c2c(F)cccc2F)cn1)C(=O)c1cc2nc(N)c3c(c2[nH]1)COC3]

or a pharmaceutically acceptable salt thereof.

7. The compound of claim 1, wherein the compound is:

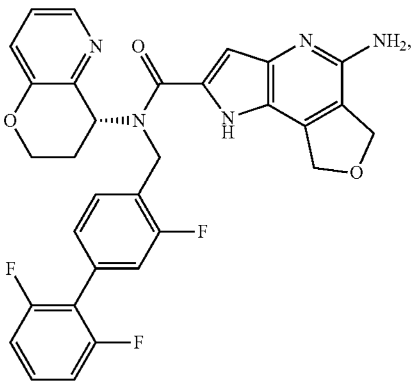 [SMILES: Nc1nc2cc(C(=O)N(Cc3ccc(-c4c(F)cccc4F)cc3F)[C@@H]3CCOc4cccnc43)[nH]c2c2c1COC2]

or a pharmaceutically acceptable salt thereof.

8. The compound of claim 1, wherein the compound is:

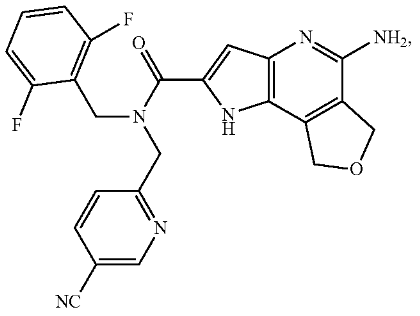 [SMILES: N#Cc1ccc(CN(Cc2c(F)cccc2F)C(=O)c2cc3nc(N)c4c(c3[nH]2)COC4)nc1]

or a pharmaceutically acceptable salt thereof.

9. The compound of claim 1, wherein the compound is:

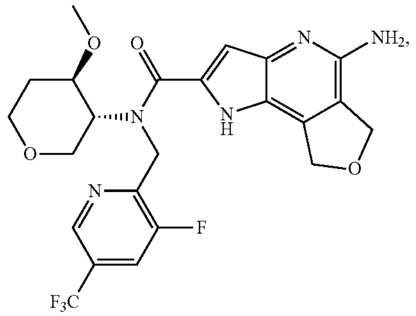 [SMILES: CO[C@@H]1CCOC[C@H]1N(Cc1ncc(C(F)(F)F)cc1F)C(=O)c1cc2nc(N)c3c(c2[nH]1)COC3]

or a pharmaceutically acceptable salt thereof.

10. The compound of claim 1, wherein the compound is:

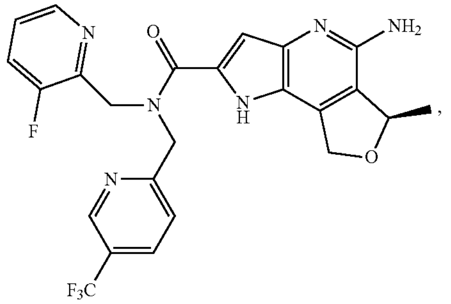 [SMILES: C[C@H]1OCc2c1c(N)nc1cc(C(=O)N(Cc3ccc(C(F)(F)F)cn3)Cc3ncccc3F)[nH]c21]

or a pharmaceutically acceptable salt thereof.

11. The compound of claim 1, wherein the compound is:

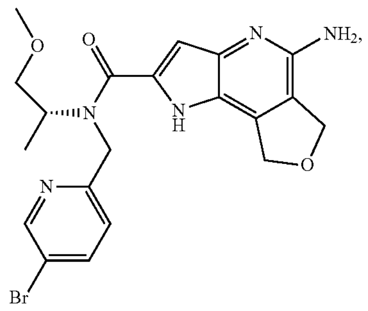 [SMILES: COC[C@@H](C)N(Cc1ccc(Br)cn1)C(=O)c1cc2nc(N)c3c(c2[nH]1)COC3]

or a pharmaceutically acceptable salt thereof.

12. The compound of claim 1, wherein the compound is:

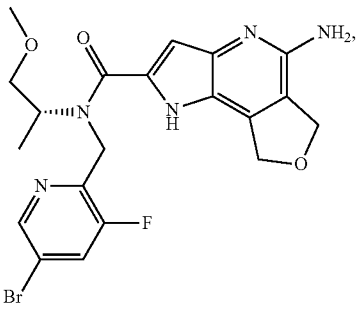 [SMILES: COC[C@@H](C)N(Cc1ncc(Br)cc1F)C(=O)c1cc2nc(N)c3c(c2[nH]1)COC3]

or a pharmaceutically acceptable salt thereof.

13. The compound of claim 1, wherein the compound is:

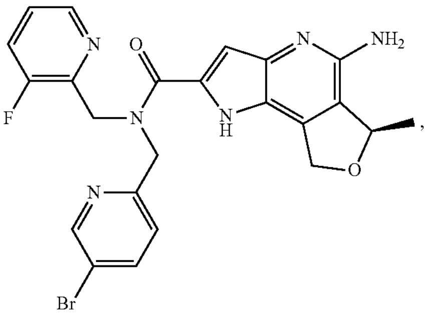 [SMILES: C[C@H]1OCc2c1c(N)nc1cc(C(=O)N(Cc3ccc(Br)cn3)Cc3ncccc3F)[nH]c21]

or a pharmaceutically acceptable salt thereof.

14. The compound of claim 1, wherein the compound is:

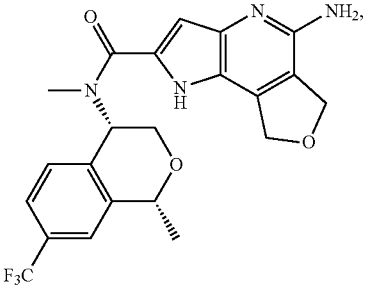 [SMILES: C[C@H]1OC[C@@H](N(C)C(=O)c2cc3nc(N)c4c(c3[nH]2)COC4)c2ccc(C(F)(F)F)cc21]

or a pharmaceutically acceptable salt thereof.

15. The compound of claim 1, wherein the compound is:

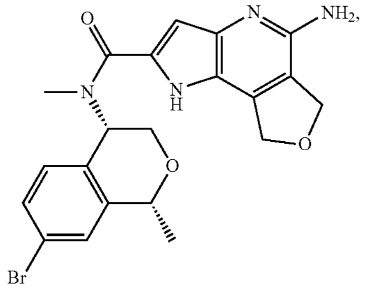 [SMILES: C[C@H]1OC[C@@H](N(C)C(=O)c2cc3nc(N)c4c(c3[nH]2)COC4)c2ccc(Br)cc21]

or a pharmaceutically acceptable salt thereof.

16. The compound of claim 1, wherein the compound is:

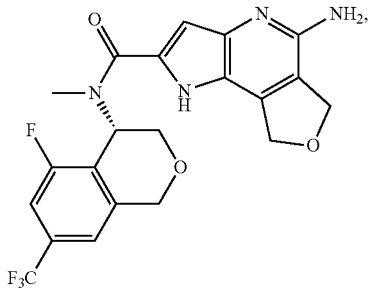 [SMILES: CN(C(=O)c1cc2nc(N)c3c(c2[nH]1)COC3)[C@@H]1COCc2cc(C(F)(F)F)cc(F)c21]

or a pharmaceutically acceptable salt thereof.

17. The compound of claim 1, wherein the compound is:

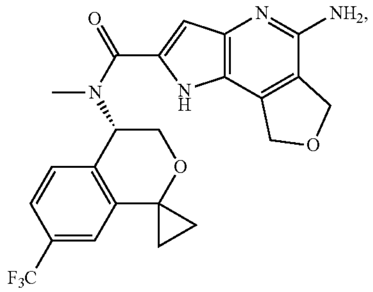

or a pharmaceutically acceptable salt thereof.

18. The compound of claim 1, wherein the compound is:

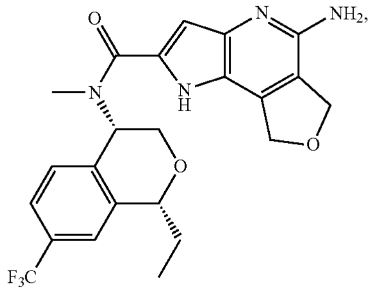 [SMILES: CC[C@H]1OC[C@@H](N(C)C(=O)c2cc3nc(N)c4c(c3[nH]2)COC4)c2ccc(C(F)(F)F)cc21]

or a pharmaceutically acceptable salt thereof.

19. The compound of claim 1, wherein the compound is:

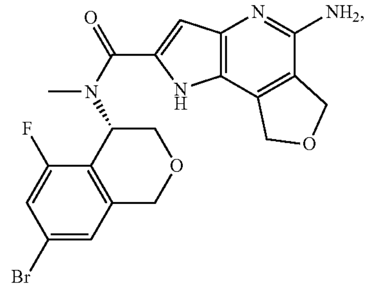 [SMILES: CN(C(=O)c1cc2nc(N)c3c(c2[nH]1)COC3)[C@@H]1COCc2cc(Br)cc(F)c21]

or a pharmaceutically acceptable salt thereof.

20. The compound of claim 1, wherein the compound is:

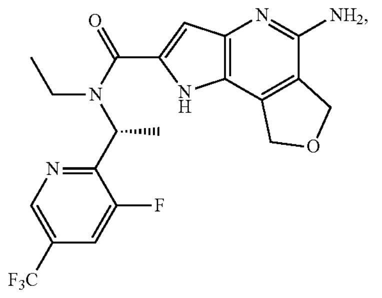 [SMILES: CCN(C(=O)c1cc2nc(N)c3c(c2[nH]1)COC3)[C@H](C)c1ncc(C(F)(F)F)cc1F]

or a pharmaceutically acceptable salt thereof.

21. The compound of claim 1, wherein the compound is:

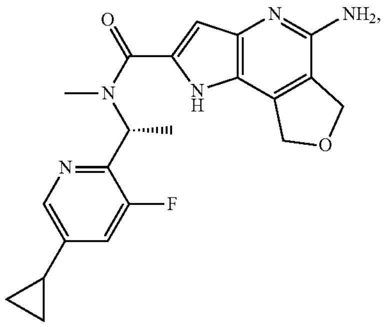 [SMILES: C[C@H](c1ncc(C2CC2)cc1F)N(C)C(=O)c1cc2nc(N)c3c(c2[nH]1)COC3]

or a pharmaceutically acceptable salt thereof.

22. The compound of claim 1, wherein the compound is:

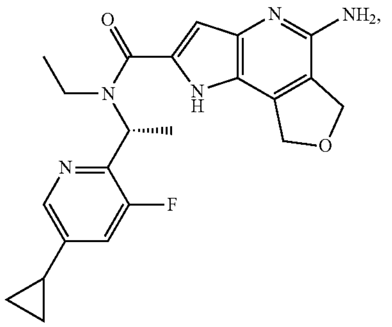 [SMILES: CCN(C(=O)c1cc2nc(N)c3c(c2[nH]1)COC3)[C@H](C)c1ncc(C2CC2)cc1F]

or a pharmaceutically acceptable salt thereof.

23. The compound of claim 1, wherein the compound is:

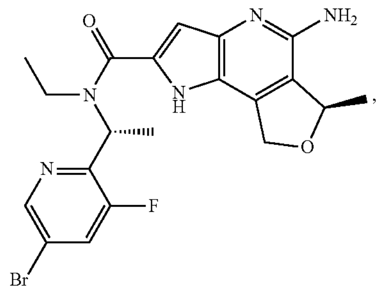 [SMILES: CCN(C(=O)c1cc2nc(N)c3c(c2[nH]1)CO[C@@H]3C)[C@H](C)c1ncc(Br)cc1F]

or a pharmaceutically acceptable salt thereof.

24. The compound of claim 1, wherein the compound is:

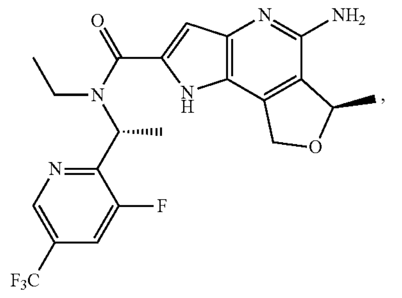 [SMILES: CCN(C(=O)c1cc2nc(N)c3c(c2[nH]1)CO[C@@H]3C)[C@H](C)c1ncc(C(F)(F)F)cc1F]

or a pharmaceutically acceptable salt thereof.

25. The compound of claim 1, wherein the compound is:

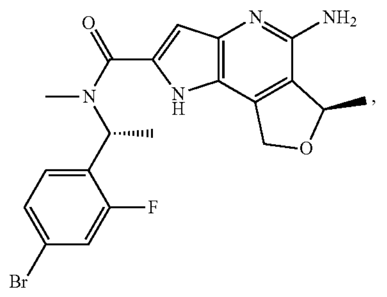 [SMILES: C[C@H](c1ccc(Br)cc1F)N(C)C(=O)c1cc2nc(N)c3c(c2[nH]1)CO[C@@H]3C]

or a pharmaceutically acceptable salt thereof.

26. The compound of claim 1, wherein the compound is:

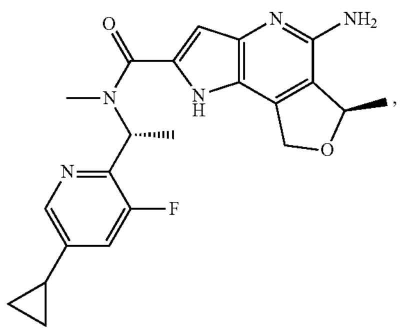 [SMILES: C[C@H](c1ncc(C2CC2)cc1F)N(C)C(=O)c1cc2nc(N)c3c(c2[nH]1)CO[C@@H]3C]

or a pharmaceutically acceptable salt thereof.

27. The compound of claim 1, wherein the compound is:

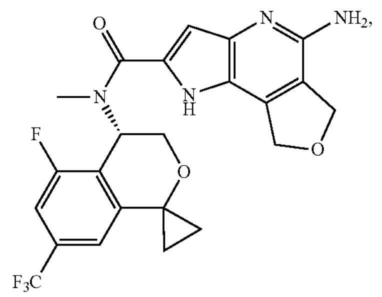 [SMILES: CN(C(=O)c1cc2nc(N)c3c(c2[nH]1)COC3)[C@@H]1COC2(CC2)c2cc(C(F)(F)F)cc(F)c21]

or a pharmaceutically acceptable salt thereof.

28. The compound of claim 1, wherein the compound is:
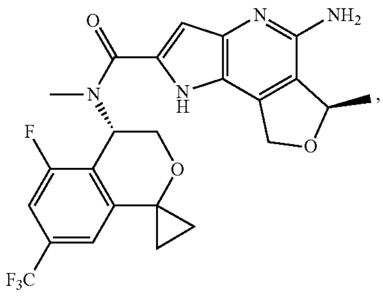 [SMILES: C[C@H]1OCc2c1c(N)nc1cc(C(=O)N(C)[C@@H]3COC4(CC4)c4cc(C(F)(F)F)cc(F)c43)[nH]c21]
,
or a pharmaceutically acceptable salt thereof.
* * * * *